US009084420B2

(12) United States Patent
Kobayashi et al.

(10) Patent No.: US 9,084,420 B2
(45) Date of Patent: *Jul. 21, 2015

(54) AMIDE DERIVATIVE, PEST CONTROL AGENT CONTAINING THE AMIDE DERIVATIVE, AND PEST CONTROLLING METHOD

(71) Applicant: Mitsui Chemicals Agro, Inc., Tokyo (JP)

(72) Inventors: Yumi Kobayashi, Chiba (JP); Hiroyuki Katsuta, Chiba (JP); Michikazu Nomura, Chiba (JP); Hidetaka Tsukada, Fukuoka (JP); Atsushi Hirabayashi, Fukuoka (JP); Hidenori Daido, Shiga (JP); Yusuke Takahashi, Fukuoka (JP); Shinichi Banba, Chiba (JP)

(73) Assignee: Mitsui Chemicals Agro, Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/102,930

(22) Filed: Dec. 11, 2013

(65) Prior Publication Data

US 2014/0107368 A1    Apr. 17, 2014

Related U.S. Application Data

(62) Division of application No. 13/056,895, filed as application No. PCT/JP2009/061864 on Jun. 29, 2009, now Pat. No. 8,633,228.

(30) Foreign Application Priority Data

Aug. 1, 2008    (JP) ................................ 2008-200114

(51) Int. Cl.
*C07C 237/40*    (2006.01)
*C07D 213/81*    (2006.01)
(Continued)

(52) U.S. Cl.
CPC ................ *A01N 37/34* (2013.01); *A01N 37/22* (2013.01); *A01N 37/24* (2013.01); *A01N 37/30* (2013.01); *A01N 37/44* (2013.01); *A01N 37/46* (2013.01); *A01N 37/48* (2013.01); *A01N 43/40* (2013.01); *A01N 43/78* (2013.01); *C07C 237/40* (2013.01); *C07C 237/42* (2013.01); *C07C 251/38* (2013.01); *C07C 255/57* (2013.01); *C07C 255/58* (2013.01); *C07C 259/06* (2013.01); *C07C 271/22* (2013.01); *C07C 279/36* (2013.01); *C07C 311/32* (2013.01); *C07C 311/46* (2013.01); *C07C 317/28* (2013.01); *C07C 323/42* (2013.01); *C07D 213/81* (2013.01); *C07D 277/20* (2013.01); *C07D 277/56* (2013.01)

(58) Field of Classification Search
None
See application file for complete search history.

(56) References Cited

U.S. PATENT DOCUMENTS 5,631,280 A    5/1997    Ciccarone et al.
8,633,228 B2 *    1/2014    Kobayashi et al. ........... 514/352
(Continued)

FOREIGN PATENT DOCUMENTS

CA    2537124    3/2005
CA    2554437    8/2005
(Continued)

OTHER PUBLICATIONS

Japanese Office Action dated Jul. 15, 2014 in the corresponding Japanese patent application No. 2013-096071; English translation thereof.

(Continued)

*Primary Examiner* — Zinna Northington Davis
(74) *Attorney, Agent, or Firm* — Rankin, Hill & Clark LLP

(57) ABSTRACT

A pest control agent containing a compound represented by the following Formula (1), wherein A represents a carbon atom, a nitrogen atom, or the like, K represents a non-metal atom group necessary for forming a cyclic linking group derived from a 5- or 6-membered aromatic ring, in combination with A and two carbon atoms to which A bonds, X represents a hydrogen atom, a halogen atom, or the like, n represents an integer of from 0 to 4, T represents —C(=$G_1$)-$Q_1$ (wherein $G_1$ and $G_2$ represent an oxygen atom or the like, $Q_1$ represents a phenyl group which may have a substituent, a heterocyclic group which may have a substituent, or the like), or the like, $Q_2$ represents a phenyl group or the like, $G_3$ represents an oxygen atom or the like, and $R_1$ and $R_2$ each independently represent a hydrogen atom, a C1-C6 alkyl group, or a group represented by -L-D, or the like (provided that at least either $R_1$ or $R_2$ represents a group represented by -L-D); as an active ingredient exhibits an excellent effect.

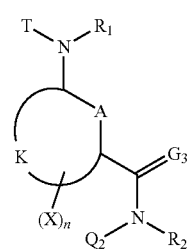

Formula (1)

3 Claims, No Drawings

(51) Int. Cl.
| | | |
|---|---|---|
| C07D 277/56 | (2006.01) | |
| A01N 37/34 | (2006.01) | |
| A01N 37/22 | (2006.01) | |
| A01N 37/24 | (2006.01) | |
| A01N 37/44 | (2006.01) | |
| A01N 37/46 | (2006.01) | |
| A01N 37/48 | (2006.01) | |
| A01N 43/40 | (2006.01) | |
| A01N 43/78 | (2006.01) | |
| C07C 237/42 | (2006.01) | |
| C07C 251/38 | (2006.01) | |
| C07C 255/57 | (2006.01) | |
| C07C 255/58 | (2006.01) | |
| C07C 259/06 | (2006.01) | |
| C07C 271/22 | (2006.01) | |
| C07C 279/36 | (2006.01) | |
| C07C 311/32 | (2006.01) | |
| C07C 311/46 | (2006.01) | |
| C07C 317/28 | (2006.01) | |
| C07C 323/42 | (2006.01) | |
| C07D 277/20 | (2006.01) | |
| A01N 37/30 | (2006.01) | |

(56) References Cited

U.S. PATENT DOCUMENTS

| | | |
|---|---|---|
| 2007/0275980 A1 | 11/2007 | Yoshida et al. |
| 2009/0099204 A1 | 4/2009 | Yoshida et al. |
| 2009/0162453 A1 | 6/2009 | Kawahara et al. |

FOREIGN PATENT DOCUMENTS

| | | |
|---|---|---|
| EP | 298803 | 1/1989 |
| EP | 936212 | 8/1999 |
| GB | 740307 | 11/1955 |
| JP | 2006-306771 | 11/2006 |
| JP | 2007-031395 | 2/2007 |
| JP | 2007-099761 | 4/2007 |
| JP | 2007-302617 | 11/2007 |
| JP | 2008-137992 | 6/2008 |
| JP | 2011-506504 | 3/2011 |
| WO | 96/30014 | 10/1996 |
| WO | 03/002518 | 1/2003 |
| WO | 2004/037810 | 5/2004 |
| WO | 2005/021488 | 10/2005 |
| WO | 2005/073165 | 11/2005 |
| WO | 2006/137376 | 12/2006 |
| WO | 2006/137395 | 12/2006 |
| WO | 2007/013150 | 2/2007 |
| WO | 2007/013332 | 2/2007 |
| WO | 2007/083394 | 7/2007 |
| WO | 2007/128410 | 11/2007 |
| WO | 2008/000438 | 1/2008 |
| WO | 2008/012027 | 1/2008 |
| WO | 2008/074427 | 6/2008 |
| WO | 2008/075453 | 6/2008 |
| WO | 2008/075454 | 6/2008 |
| WO | 2008/075459 | 6/2008 |
| WO | 2009/049845 | 4/2009 |
| WO | 2009/080203 | 7/2009 |

OTHER PUBLICATIONS

V. E. Platonov et al. "Polyfluorinated arylnitramines," Journal of Fluorine Chemistry 109, 2001, pp. 131-139.; Cited in Japanese Office Action.
International Search Report dated Aug. 11, 2009.
Berichte der Deutschen Chemischen Gesellschaft, 49, pp. 2179-2203, 1916; discussed in Canadian Examiner's Report issued Dec. 6, 2012, partial English explanation included.
Canadian Examiner's Report issued Dec. 6, 2012 (Canadian Patent Application No. 2794350).
Canadian Examiner's Report issued Jan. 10, 2013 (Canadian Patent Application No. 2737348).
Japanese Office Action dated Feb. 26, 2013 issued in corresponding Japanese Patent Application No. 2010-522662; English translation thereof.
Canadian Office Action dated Jul. 4, 2013 filed in the corresponding Canadian application No. 2794350.
Canadian Office Action dated Oct. 22, 2013 filed in the corresponding Canadian patent application No. 2737348.
Okumura, Kentaro et al., "4-Oxo-1,2,3,4-tetrahydroquinazolines. II. Synthesis of 1-Alkyl- and 1-[2-(Disubstituted amino)ethyl]-2-methyl-3-aryl-4-oxo-1,2,3,4-tetrahydroquinazolines," Journal of Medicinal Chemistry, 1968, vol. 11, pp. 788-792.; Cited in Canadian Office Action dated Oct. 22, 2013.
Kovac, T. et al., "New Synthesis of 11-Acyl-5, 11-dihydro-6H-pyrido[2,3-b][1,4]-benzodiazepin-6-ones and Related Studies," Journal of Heterocyclic Chemistry, 1983, 20(5), pp. 1339-1349.; Cited in Canadian Office Action dated Oct. 22, 2013.
Office Action dated Jan. 9, 2013 filed in related U.S. Appl. No. 13/056,895.
Office Action dated Apr. 4, 2013 filed in related U.S. Appl. No. 13/056,895.
Indian Office Action dated Nov. 22, 2014 issued in the corresponding Indian patent application No. 1454/DELNP/2011.
Bellezza et al., "Nucleus- and side-chain fluorinated 3-substituted indoles by a suitable combination of organometalic and radical chemistry", Journal of Fluorine Chemistry, Elsevier, NL, vol. 129, No. 2, Jan. 14, 2008, pp. 97-107.; Cited in Indian Office Action.

* cited by examiner

AMIDE DERIVATIVE, PEST CONTROL AGENT CONTAINING THE AMIDE DERIVATIVE, AND PEST CONTROLLING METHOD

CONTINUING DATA

This application is a divisional of 13/056,895 filed Jan. 31, 2011 now U.S. Pat. No. 8,633,228 which is a 371 of PCT/JP2009/061864 filed Jun. 29, 2009.

TECHNICAL FIELD

The present invention relates to an amide derivative, a pest control agent containing the amide derivative, and a pest controlling method.

BACKGROUND ART

Various amide derivatives are described in the pamphlets of International Publication WO 2005/21488, International Publication WO 2005/73165, International Publication WO 2006/137376, and International Publication WO 2006/137395.

DISCLOSURE OF INVENTION

Problems to be Solved by the Invention

In the production of, for example, agricultural and horticultural crops, due to causes such as currently-occurring large scale damage due to pests or the like, and the propagation of pests having resistance to existing chemicals, it is desirable to develop a novel agricultural/horticultural pesticide. Furthermore, there is a demand for various labor-saving methods due to increases in the age of farmers, and the like, and there is also a demand for creation of an agricultural/horticultural pesticide having characteristics suitable for such application methods.

It is an object of the present invention to provide an amide derivative exhibiting a pesticidal effect against various agricultural pests, having an effect of protection of useful crops, and greatly contributing to reduction in an environmental impact owing to the use at a low dose, a pest control agent containing the amide derivative, and a pest controlling method.

Means for Solving the Problems

The present inventors have conducted intensive studies to develop a novel agricultural/horticultural pesticide, and as a result, have found that the amide derivative represented by the Formula (1) according to the present invention is a novel compound unknown in the literature, and it is also a pesticide exhibiting an excellent pesticidal effect by exhibiting a high uptake and migration action from a plant root, and also exhibiting an excellent pesticidal effect by a spray treatment to stems, leaves and the like, thereby completing the present invention.

Furthermore, the present inventors have found a novel method for producing and a useful intermediate for producing the amide derivative according to the present invention, and as a result, they have completed the present invention.

That is, the present invention is as follows.

<1> An amide derivative represented by the following Formula (1):

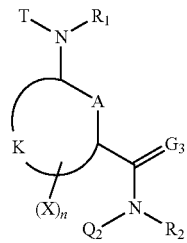

Formula (1)

Wherein, A represents a carbon atom, an oxygen atom, a nitrogen atom, an oxidized nitrogen atom, or a sulfur atom.

K represents a non-metal atom group necessary for forming a cyclic linking group derived from benzene, pyridine, pyridine-N-oxide, pyrimidine, pyrazine, pyridazine, triazine, pyrrole, pyrazole, imidazole, oxazole, isoxazole, thiazole, isothiazole, furan, thiophene, oxadiazole, thiodiazole, or triazole, in combination with A and two carbon atoms to which A bonds.

X represents a hydrogen atom, a halogen atom, a C1-C6 alkyl group which may have a substituent, a C1-C6 haloalkyl group which may have a substituent, a C3-C9 cycloalkyl group which may have a substituent, a C3-C9 halocycloalkyl group which may have a substituent, a C2-C6 alkenyl group which may have a substituent, a C2-C6 haloalkenyl group which may have a substituent, a C2-C6 alkynyl group which may have a substituent, a C2-C6 haloalkynyl group which may have a substituent, a C1-C6 alkoxy group which may have a substituent, a C1-C6 haloalkoxy group which may have a substituent, a C1-C6 alkylthio group which may have a substituent, a C1-C6 haloalkylthio group which may have a substituent, a C1-C6 alkylsulfinyl group which may have a substituent, a C1-C6 haloalkylsulfinyl group which may have a substituent, a C1-C6 alkylsulfonyl group which may have a substituent, a C1-C6 haloalkylsulfonyl group which may have a substituent, a C1-C6 alkylsulfonyloxy group which may have a substituent, a C1-C6 haloalkylsulfonyloxy group which may have a substituent, a C2-C7 alkylcarbonyl group which may have a substituent, a C2-C7 haloalkylcarbonyl group which may have a substituent, a C2-C7 alkylcarbonyloxy group which may have a substituent, a C2-C7 haloalkylcarbonyloxy group which may have a substituent, an arylcarbonyloxy group which may have a substituent, a C2-C7 alkoxycarbonyl group which may have a substituent, a C2-C7 haloalkoxycarbonyl group which may have a substituent, a C2-C7 alkylcarbonylamino group which may have a substituent, a C2-C7 haloalkylcarbonylamino group which may have a substituent, a C2-C7 alkoxycarbonylamino group which may have a substituent, a C2-C7 haloalkoxycarbonylamino group which may have a substituent, a C2-C7 alkoxycarbonyloxy group which may have a substituent, a C2-C7 haloalkoxycarbonyloxy group which may have a substituent, an arylcarbonylamino group which may have a substituent, an amino group, a carbamoyl group which may have a substituent, a cyano group, a nitro group, a hydroxy group, a pentafluorosulfanyl group, a C1-C6 alkylamino group which may have a substituent, a C1-C6 haloalkylamino group which may have a substituent, a C2-C6 alkenylamino group which may have a substituent, a C2-C6 haloalkenylamino group which may have a substituent, a C2-C6 alkynylamino group which may have a substituent, a C2-C6 haloalkynylamino group which may have a substituent, a C3-C9 cycloalkylamino group which may have a substituent, a C3-C9 halocycloalkylamino group which may have a substituent, a C2-C7 alkylaminocarbonyl group which may have a substituent, a C2-C7 haloalkylaminocarbonyl group which may have a substituent, a C3-C7 alkenylaminocarbonyl group which may have a substituent, a C3-C7 haloalkenylaminocarbonyl group which may have a substituent, a C3-C7 alkynylaminocarbonyl group which may have a substituent, a C3-C7 haloalkynylaminocarbonyl group which may have a substituent, a C4-C10 cycloalkylaminocarbonyl group which may have a substituent, a C4-C10 halocycloalkylaminocarbonyl group which may have a substituent, a phenyl group which may have a substituent, or a heterocyclic group which may have a substituent, and when there are plural X's, each X may be the same as or different from each other.

The heterocyclic group in X represents a pyridyl group, a pyridine-N-oxide group, a pyrimidinyl group, a pyrazinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrolyl group, an imidazolyl group, a triazolyl group, a pyrazolyl group, or a tetrazolyl group.

n represents an integer of from 0 to 4.

T represents —C(=$G_1$)-$Q_1$ or —C(=$G_1$)-$G_2Q_3$, wherein $G_1$ and $G_2$ each independently represent an oxygen atom or a sulfur atom, $Q_1$ and $Q_3$ each independently represent a hydrogen atom, a C1-C6 alkyl group which may have a substituent, a C1-C6 haloalkyl group which may have a substituent, a C2-C6 alkenyl group which may have a substituent, a C2-C6 haloalkenyl group which may have a substituent, a C2-C6 alkynyl group which may have a substituent, a C2-C6 haloalkynyl group which may have a substituent, a C3-C9 cycloalkyl group which may have a substituent, a C3-C9 halocycloalkyl group which may have a substituent, a benzyl group which may have a substituent, a phenyl group which may have a substituent, a naphthyl group which may have a substituent, or a heterocyclic group which may have a substituent.

$Q_2$ represents a phenyl group which may have a substituent, a naphthyl group which may have a substituent, a heterocyclic group which may have a substituent, or a tetrahydronaphthalene group which may have a substituent.

Further, in $Q_1$, $Q_3$, and $Q_2$, the substituent of a benzyl group which may have a substituent, a phenyl group which may have a substituent, a naphthyl group which may have a substituent, and a heterocyclic group which may have a substituent, and the substituent of a tetrahydronaphthalene group which may have a substituent represents one or more substituent selected from a group consisting of a halogen atom, a C1-C6 alkyl group, a C1-C6 haloalkyl group, a C3-C9 cycloalkyl group, a C3-C9 halocycloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C2-C7 alkylcarbonyl group, a C2-C7 haloalkylcarbonyl group, a C2-C7 alkylcarbonyloxy group, a C2-C7 haloalkylcarbonyloxy group, a C1-C6 alkylsulfonyloxy group, a C1-C6 haloalkylsulfonyloxy group, a C2-C7 alkoxycarbonyl group, a C2-C7 haloalkoxycarbonyl group, a C2-C7 alkylcarbonylamino group, a C2-C7 haloalkylcarbonylamino group, a C2-C7 alkoxycarbonylamino group, a C2-C7 haloalkoxycarbonylamino group, a C1-C6 alkylamino group, a C1-C6 haloalkylamino group, an amino group, a carbamoyl group, a sulfamoyl group, a cyano group, a nitro group, a hydroxy group, a carboxy group, a pentafluorosulfanyl group, a benzyloxy group which may have a substituent, a benzyloxycarbonyl group which may have a substituent, a phenyl group which may have a substituent, a heterocyclic group which may have a substituent, a benzoyl group which may have a substituent, a phenylcarbamoyl group which may have a substituent, and a phenylamino group which may have a substituent, and when there are two or more substituents, the substituents may be the same as or different from each other.

The heterocyclic group in $Q_1$, $Q_3$, and $Q_2$ has the same definition as the heterocyclic group in X.

$G_3$ represents an oxygen atom or a sulfur atom.

$R_1$ and $R_2$ each independently represent a hydrogen atom, a C1-C6 alkyl group which may have a substituent, a C1-C6 haloalkyl group which may have a substituent, a C2-C6 alkenyl group which may have a substituent, a C2-C6 haloalkenyl group which may have a substituent, a C2-C6 alkynyl group which may have a substituent, a C2-C6 haloalkynyl group which may have a substituent, a C3-C9 cycloalkyl group which may have a substituent, a C3-C9 halocycloalkyl group which may have a substituent, a C1-C6 alkoxy group which may have a substituent, a C1-C6 haloalkoxy group which may have a substituent, a C2-C6 alkenyloxy group which may have a substituent, a C2-C6 haloalkenyloxy group which may have a substituent, a C2-C6 alkynyloxy group which may have a substituent, a C2-C6 haloalkynyloxy group which may have a substituent, a C3-C9 cycloalkoxy group which may have a substituent, a C3-C9 halocycloalkoxy group which may have a substituent, a C2-C7 alkylcarbonyl group which may have a substituent, a C2-C7 haloalkylcarbonyl group which may have a substituent, a C3-C7 alkenylcarbonyl group which may have a substituent, a C3-C7 haloalkenylcarbonyl group which may have a substituent, a C3-C7 alkynylcarbonyl group which may have a substituent, a C3-C7 haloalkynylcarbonyl group which may have a substituent, a C4-C10 cycloalkylcarbonyl group which may have a substituent, a C4-C10 halocycloalkylcarbonyl group which may have a substituent, a C2-C7 alkoxycarbonyl group which may have a substituent, a C2-C7 haloalkoxycarbonyl group which may have a substituent, a C3-C7 alkenyloxycarbonyl group which may have a substituent, a C3-C7 haloalkenyloxycarbonyl group which may have a substituent, a C3-C7 alkynyloxycarbonyl group which may have a substituent, a C3-C7 haloalkynyloxycarbonyl group which may have a substituent, a C4-C10 cycloalkyloxycarbonyl group which may have a substituent, a C4-C10 halocycloalkyloxycarbonyl group which may have a substituent, or a group represented by -L-D, wherein provided that at least either $R_1$ or $R_2$ represents a group represented by -L-D.

Wherein L represents
—C($M_1$)($M_2$)-,
—C($M_1$)($M_2$)-C($M_3$)($M_4$)-,
—C($M_1$)=C($M_3$)-, —C≡C—,
—C($M_1$)($M_2$)-C($M_3$)($M_4$)-C($M_5$)($M_6$)-,
—C($M_1$)=C($M_3$)-C($M_5$)($M_6$)-,
—C($M_1$)($M_2$)-C($M_3$)=C($M_5$)-,
—C≡C—C($M_5$)($M_6$)-, —C($M_1$)($M_2$)-C≡C—,
—C($M_1$)($M_2$)-C($M_3$)($M_4$)-C($M_5$)($M_6$)-C($M_7$)($M_8$)-,
—C($M_1$)=C($M_3$)-C($M_5$)($M_6$)-C($M_7$)($M_8$)-,
—C($M_1$)($M_2$)-C($M_3$)=C($M_5$)-C($M_7$)($M_8$)-,
—C($M_1$)($M_2$)-C($M_3$)($M_4$)-C($M_5$)=C($M_7$)-,
—C($M_1$)=C($M_3$)-C($M_5$)=C($M_7$)-,
—C($M_1$)=C($M_3$)-C≡C—,
—C≡C—C($M_5$)($M_6$)-C($M_7$)($M_8$)-,
—C($M_1$)($M_2$)-C≡C—C($M_7$)($M_8$)-,
—C($M_1$)($M_2$)-C($M_3$)($M_4$)-C≡C—,
—C≡C—C($M_5$)=C($M_7$)-, or
—C≡C—C≡C—.

$M_1$ to $M_8$ each independently represent a hydrogen atom, a halogen atom, a cyano group, a nitro group, an amino group, a carboxy group, a hydroxy group, a carbamoyl group, a C1-C6 alkyl group which may have a substituent, a C1-C6 haloalkyl group which may have a substituent, a C2-C6 alkenyl group which may have a substituent, a C2-C6 haloalkenyl group which may have a substituent, a C2-C6 alkynyl group which may have a substituent, a C2-C6 haloalkynyl group which may have a substituent, a C3-C9 cycloalkyl group which may have a substituent, a C3-C9 halocycloalkyl group which may have a substituent, a C1-C6 alkoxy group which may have a substituent, a C1-C6 haloalkoxy group which may have a substituent, a C2-C6 alkenyloxy group which may have a substituent, a C2-C6 haloalkenyloxy group which may have a substituent, a C2-C6 alkynyloxy group which may have a substituent, a C2-C6 haloalkynyloxy group which may have a substituent, a C3-C9 cycloalkoxy group which may have a substituent, a C3-C9 halocycloalkoxy group which may have a substituent, a C1-C6 alkylthio group which may have a substituent, a C1-C6 haloalkylthio group which may have a substituent, a C2-C6 alkenylthio group which may have a substituent, a C2-C6 haloalkenylthio group which may have a substituent, a C2-C6 alkynylthio group which may have a substituent, a C2-C6 haloalkynylthio group which may have a substituent, a C1-C6 alkylsulfinyl group which may have a substituent, a C1-C6 haloalkylsulfinyl group which may have a substituent, a C2-C6 alkenylsulfinyl group which may have a substituent, a C2-C6 haloalkenylsulfinyl group which may have a substituent, a C2-C6 alkynylsulfinyl group which may have a substituent, a C2-C6 haloalkynylsulfinyl group which may have a substituent, a C3-C9 cycloalkylsulfinyl group which may have a substituent, a C3-C9 halocycloalkylsulfinyl group which may have a substituent, a C1-C6 alkylsulfonyl group which may have a substituent, a C1-C6 haloalkylsulfonyl group which may have a substituent, a C2-C6 alkenylsulfonyl group which may have a substituent, a C2-C6 haloalkenylsulfonyl group which may have a substituent, a C2-C6 alkynylsulfonyl group which may have a substituent, a C2-C6 haloalkynylsulfonyl group which may have a substituent, a C3-C9 cycloalkylsulfonyl group which may have a substituent, a C3-C9 halocycloalkylsulfonyl group which may have a substituent, a C2-C7 alkylcarbonyl group which may have a substituent, a C2-C7 haloalkylcarbonyl group which may have a substituent, a C3-C7 alkenylcarbonyl group which may have a substituent, a C3-C7 haloalkenylcarbonyl group which may have a substituent, a C3-C7 alkynylcarbonyl group which may have a substituent, a C3-C7 haloalkynylcarbonyl group which may have a substituent, a C4-C10 cycloalkylcarbonyl group which may have a substituent, a C4-C10 halocycloalkylcarbonyl group which may have a substituent, a C2-C7 alkoxycarbonyl group which may have a substituent, a C2-C7 haloalkoxycarbonyl group which may have a substituent, a C3-C7 alkenyloxycarbonyl group which may have a substituent, a C3-C7 haloalkenyloxycarbonyl group which may have a substituent, a C3-C7 alkynyloxycarbonyl group which may have a substituent, a C3-C7 haloalkynyloxycarbonyl group which may have a substituent, a C4-C10 cycloalkyloxycarbonyl group which may have a substituent, a C4-C10 halocycloalkyloxycarbonyl group which may have a substituent, a C1-C6 alkylamino group which may have a substituent, a C1-C6 haloalkylamino group which may have a substituent, a C2-C6 alkenylamino group which may have a substituent, a C2-C6 haloalkenylamino group which may have a substituent, a C2-C6 alkynylamino group which may have a substituent, a C2-C6 haloalkynylamino group which may have a substituent, a C3-C9 cycloalkylamino group which may have a substituent, a C3-C9 halocycloalkylamino group which may have a substituent, a C2-C7 alkylaminocarbonyl group which may have a substituent, a C2-C7 haloalkylaminocarbonyl group which may have a substituent, a C3-C7 alkenylaminocarbonyl group which may have a substituent, a C3-C7 haloalkenylaminocarbonyl group which may have a substituent, a C3-C7 alkynylaminocarbonyl group which may have a substituent, a C3-C7 haloalkynylaminocarbonyl group which may have a substituent, a C4-C10 cycloalkylaminocarbonyl group which may have a substituent, a C4-C10 halocycloalkylaminocarbonyl group which may have a substituent, a phenyl group which may have a substituent, a naphthyl group which may have a substituent, or a heterocyclic group which may have a substituent.

Further, in $M_1$ to $M_8$, the substituent of a phenyl group which may have a substituent and a heterocyclic group which may have a substituent has the same definition as the substituent of a phenyl group which may have a substituent, a naphthyl group which may have a substituent, and a heterocyclic group which may have a substituent, in $Q_1$, $Q_3$, and $Q_2$.

Moreover, the heterocyclic group in $M_1$ to $M_8$ has the same definition as the heterocyclic group in $Q_1$, $Q_3$, and $Q_2$.

D represents —C(=O)O$U_1$, —C(=O)$U_2$, —C(=O)N$U_3U_4$, —N$U_5$C(=O)$U_6$, —S—$U_7$, —S(=O)$U_8$, —S(=O)(=O)$U_9$, —S(=O)(=O)N$U_{10}U_{11}$, —O$U_{12}$, —N$U_{13}U_{14}$, —C(=N$U_{15}$)$U_{16}$, —N$U_{17}$-C(=N$U_{18}$)$U_{19}$, or —C≡N.

$U_1$ to $U_{19}$ each independently represent a hydrogen atom, a hydroxy group, an amino group, a cyano group, a nitro group, a C1-C6 alkyl group which may have a substituent, a C1-C6 haloalkyl group which may have a substituent, a C2-C6 alkenyl group which may have a substituent, a C2-C6 haloalkenyl group which may have a substituent, a C2-C6 alkynyl group which may have a substituent, a C2-C6 haloalkynyl group which may have a substituent, a C3-C9 cycloalkyl group which may have a substituent, a C3-C9 halocycloalkyl group which may have a substituent, a C2-C7 alkoxycarbonyl group which may have a substituent, a C2-C7 haloalkoxycarbonyl group which may have a substituent, a C2-C7 alkylcarbonyl group which may have a substituent, a C2-C7 haloalkylcarbonyl group which may have a substituent, a C1-C3 alkylamino group which may have a substituent, a C1-C3 haloalkylamino group which may have a substituent, a phenyl group which may have a substituent, a naphthyl group which may have a substituent, or a heterocyclic group which may have a substituent, $U_3$ and $U_4$, $U_5$ and $U_6$, $U_{10}$ and $U_{11}$, $U_{12}$ and L, $U_{13}$ and $U_{14}$, $U_{15}$ and $U_{16}$, and from $U_{17}$ to $U_{19}$ may be linked with each other to form a saturated heterocyclic group.

In a case where D represents —O$U_{12}$ and L represents a methylene group, $U_{12}$ represents a hydrogen atom, a hydroxy group, an amino group, a cyano group, a nitro group, a C2-C6 alkyl group which may have a substituent, a C1-C6 haloalkyl group which may have a substituent, a C2-C6 alkenyl group which may have a substituent, a C2-C6 haloalkenyl group which may have a substituent, a C2-C6 alkynyl group which may have a substituent, a C2-C6 haloalkynyl group which may have a substituent, a C3-C9 cycloalkyl group which may have a substituent, a C3-C9 halocycloalkyl group which may have a substituent, a C2-C7 alkoxycarbonyl group which may have a substituent, a C2-C7 haloalkoxycarbonyl group which may have a substituent, a C2-C7 alkylcarbonyl group which may have a substituent, a C2-C7 haloalkylcarbonyl group which may have a substituent, a C1-C3 alkylamino group which may have a substituent, a C1-C3 haloalkylamino group which may have a substituent, a phenyl group which may have a substituent, a naphthyl group which may have a substituent, or a heterocyclic group which may have a substituent.

Further, in $U_1$ to $U_{19}$, the substituent of a phenyl group which may have a substituent and a heterocyclic group which may have a substituent have the same definition as the substituent of a phenyl group which may have a substituent, a naphthyl group which may have a substituent, and a heterocyclic group which may have a substituent, in $Q_1$, $Q_3$ and $Q_2$.

Moreover, the heterocyclic group in $U_1$ to $U_{19}$ have the same definition as the heterocyclic group in $Q_1$, $Q_3$ and $Q_2$}.

<2> The amide derivative according to <1>, wherein in the Formula (1),

A represents a carbon atom, a nitrogen atom, an oxidized nitrogen atom, or a sulfur atom, K represents a non-metal atom group necessary for forming a cyclic linking group derived from benzene, pyridine, pyridine-N-oxide, pyrrole, furan, thiophene, or thiazole, in combination with A and two carbon atoms to which A bonds, X represents a hydrogen atom, a halogen atom, a nitro group, or a cyano group, n represents an integer of from 1 to 4, T represents —C(=$G_1$)-$Q_1$ (wherein $G_1$ represents an oxygen atom, $Q_1$ represents a phenyl group which may have a substituent, a naphthyl group which may have a substituent, or a heterocyclic group which may have a substituent), and $Q_2$ is represented by the following Formula (2) or the following Formula (3):

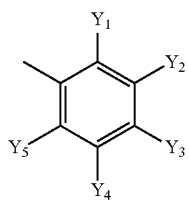

Formula (2)

Wherein $Y_1$ and $Y_5$ each independently represent a halogen atom, a C1-C4 alkyl group, a C1-C4 haloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, or a cyano group, $Y_3$ represents a C1-C6 haloalkyl group, a C1-C6 haloalkoxy group, a C1-C6 haloalkylthio group, a C1-C6 haloalkylsulfinyl group, or a C1-C6 haloalkylsulfonyl group, $Y_2$ and $Y_4$ each independently represent a hydrogen atom, a halogen atom, or a C1-C4 alkyl group.

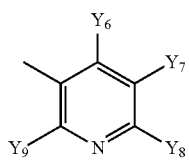

Formula (3)

Wherein $Y_6$ and $Y_9$ each independently represent a halogen atom, a C1-C4 alkyl group, a C1-C4 haloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, or a cyano group, $Y_8$ represents a C1-C6 haloalkyl group, a C1-C6 haloalkoxy group, a C1-C6 haloalkylthio group, a C1-C6 haloalkylsulfinyl group, or a C1-C6 haloalkylsulfonyl group, and $Y_7$ represents a hydrogen atom, a halogen atom, or a C1-C4 alkyl group.

<3> The amide derivative according to <2>, wherein in the Formula (1), A represents a carbon atom, a nitrogen atom, an oxidized nitrogen atom, or a sulfur atom, K represents a non-metal atom group necessary for forming a cyclic linking group derived from benzene, pyridine, pyridine-N-oxide, or thiazole, in combination with A and two carbon atoms to which A bonds.

<4> The amide derivative according to <3>, wherein in the Formula (1), $R_1$ and $R_2$ each independently represent a hydrogen atom, a C1-C4 alkyl group which may have a substituent, or a group represented by -L-D, wherein any one of $R_1$ and $R_2$ represents a group represented by -L-D, wherein L representing —C($M_1$)($M_2$)-, —C($M_1$)($M_2$)-C($M_3$)($M_4$)-, or —C($M_1$)($M_2$)-C($M_3$)($M_4$)-C($M_5$)($M_6$)-, $M_1$ to $M_6$ representing a hydrogen atom, a halogen atom, a cyano group, a carboxy group, a hydroxy group, a carbamoyl group, a C1-C4 alkyl group which may have a substituent, a C1-C4 haloalkyl group which may have a substituent, a C2-C4 alkenyl group which may have a substituent, a C2-C4 haloalkenyl group which may have a substituent, a C2-C4 alkynyl group which may have a substituent, a C2-C4 haloalkynyl group which may have a substituent, a C3-C9 cycloalkyl group which may have a substituent, or a C3-C9 halocycloalkyl group which may have a substituent, and D representing —C(=O)N$U_3U_4$, —S—$U_7$, —S(=O)$U_8$, —S(=O)(=O)$U_9$, —S(=O)(=O)N$U_{10}U_{11}$, or —C≡N.

<5> The amide derivative according to <4>, wherein in the Formula (1), $R_1$ represents a group represented by -L-D, $R_2$ represents a hydrogen atom or a C1-C4 alkyl group which may have a substituent.

D represents —C(=O)N$U_3U_4$, —S(=O)$U_8$, —S(=O)(=O)$U_9$, or —S(=O)(=O)N$U_{10}U_{11}$, and $U_3$, $U_4$, $U_8$, $U_9$, $U_{10}$, and $U_{11}$ each independently represent a hydrogen atom, a hydroxy group, a C1-C4 alkyl group which may have a substituent, a C1-C4 haloalkyl group which may have a substituent, a C2-C4 alkenyl group which may have a substituent, a C2-C4 haloalkenyl group which may have a substituent, a C2-C4 alkynyl group which may have a substituent, a C2-C4 haloalkynyl group which may have a substituent, a C3-C9 cycloalkyl group which may have a substituent, a C3-C9 halocycloalkyl group which may have a substituent, a C2-C7 alkoxycarbonyl group which may have a substituent, or a C2-C7 haloalkoxycarbonyl group which may have a substituent.

<6> The amide derivative according to <5>, wherein the compound represented by the Formula (1) is represented by the following Formula (4a):

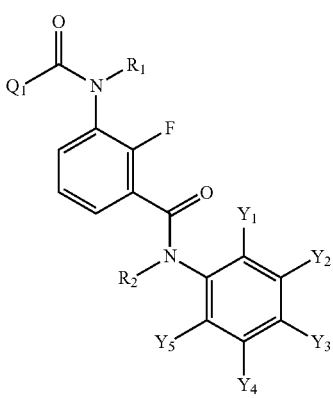

Formula (4a)

Wherein, in the Formula (4a), $Q_1$ represents a phenyl group which may have a substituent, or a heterocyclic group which may have a substituent, $Y_1$ and $Y_5$ each independently represent a halogen atom or a C1-C3 haloalkyl group, $Y_2$ and $Y_4$ represent a hydrogen atom, and $Y_3$ represents a C3-C4 perfluoroalkyl group. $R_1$ and $R_2$ have the same definitions as $R_1$ and $R_2$, respectively, in the Formula (1).

<7> The amide derivative according to <5>, wherein D in the Formula (1) represents —C(=O)NU$_3$U$_4$ or —S(=O)(=O)NU$_{10}$U$_{11}$.

<8> The amide derivative according to <7>, wherein the compound represented by the Formula (1) is represented by the following Formula (4b):

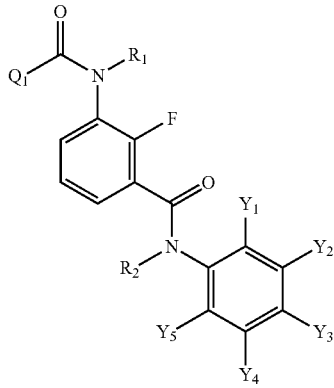

Formula (4b)

Wherein, in the Formula (4b), $Q_1$ represents a phenyl group which may have a substituent, or a heterocyclic group which may have a substituent, $Y_1$ and $Y_5$ each independently represent a halogen atom or a C1-C3 haloalkyl group, $Y_2$ and $Y_4$ represent a hydrogen atom, and $Y_3$ represents a C3-C4 perfluoroalkyl group. $R_1$ and $R_2$ have the same definitions as $R_1$ and $R_2$, respectively, in the Formula (1).

<9> An aniline derivative represented by the following Formula (6d):

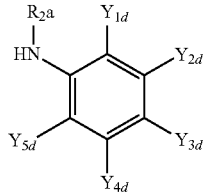

Formula (6d)

wherein $Y_{5d}$ represents a C1-C3 haloalkyl group. $Y_{1d}$ represents a hydrogen atom, a halogen atom, a C1-C4 alkyl group, a C1-C4 haloalkyl group, a C1-C4 alkoxy group, a C1-C4 haloalkoxy group, a C1-C4 alkylthio group, a C1-C4 haloalkylthio group, a C1-C4 alkylsulfinyl group, a C1-C4 haloalkylsulfinyl group, a C1-C4 alkylsulfonyl group, a C1-C4 haloalkylsulfonyl group, or a cyano group.

$Y_{3d}$ represents a C1-C6 haloalkyl group, a C1-C6 haloalkoxy group, a C1-C6 haloalkylthio group, a C1-C6 haloalkylsulfinyl group, or a C1-C6 haloalkylsulfonyl group.

$Y_{2d}$ and $Y_{4d}$ each independently represent a hydrogen atom, a halogen atom, or a C1-C4 alkyl group.

$R_{2a}$ represents a hydrogen atom, an oxygen atom, a halogen atom, a hydroxy group, a nitro group, a nitroso group, a trimethylsilyl group, a t-butyldimethylsilyl group, a cyano group, an amino group, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C9 cycloalkyl group, a C3-C9 halocycloalkyl group, a C1-C6 alkoxy group, a C1-C6 haloalkoxy group, a C2-C6 alkenyloxy group, a C2-C6 haloalkenyloxy group, a C2-C6 alkynyloxy group, a C2-C6 haloalkynyloxy group, a C3-C9 cycloalkoxy group, a C3-C9 halocycloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a benzenesulfonyl group, a benzylsulfonyl group, a C2-C7 alkylcarbonyl group, a C2-C7 haloalkylcarbonyl group, a C3-C7 alkenylcarbonyl group, a C3-C7 haloalkenylcarbonyl group, a C3-C7 alkynylcarbonyl group, a C3-C7 haloalkynylcarbonyl group, a C4-C10 cycloalkylcarbonyl group, a C4-C10 halocycloalkylcarbonyl group, a C2-C7 alkoxycarbonyl group, a C2-C7 haloalkoxycarbonyl group, a C3-C7 alkenyloxycarbonyl group, a C3-C7 haloalkenyloxycarbonyl group, a C3-C7 alkynyloxycarbonyl group, a C3-C7 haloalkynyloxycarbonyl group, a phenoxycarbonyl group, a C2-C7 alkylaminocarbonyl group, a C2-C7 haloalkylaminocarbonyl group, a C2-C7 alkylcarbonyloxy group, a C2-C7 haloalkylcarbonyloxy group, a C4-C10 cycloalkyloxycarbonyl group, a C4-C10 halocycloalkyloxycarbonyl group, a benzoyl group, a benzyl group, —C(=O)C(=O)R$_7$, wherein R$_7$ represents a C1-C6 alkyl group, a C1-C6 haloalkyl group, a C1-C6 alkoxy group, or a C1-C6 haloalkoxy group, or a group represented by -L-D, wherein L and D have the same definition as L and D respectively, in R$_2$.

<10> The amide derivative according to <9>, wherein in Formula (6d) according to <9>, $Y_{1d}$ represents a halogen atom.

<11> A method for producing the amide derivative according to <10>, including a compound represented by Formula (6d) according to <9>, in which $Y_{1d}$ represents halogen atom reacting with a halogenating agent.

<12> An amide derivative represented by the following Formula (6a):

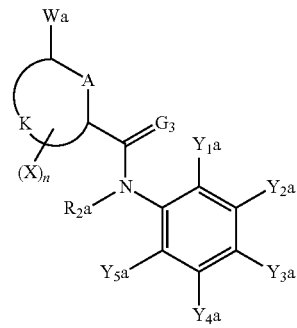

Formula (6a)

Wherein A, K, X, n, and $G_3$ have the same definitions as A, K, X, n, and $G_3$, respectively, in the Formula (1).

$R_{2a}$ has the same definition as $R_{2a}$ in the Formula (6d).

$W_a$ represents a nitro group, an amino group, or —NH—$R_{1a}$.

$R_{1a}$ represents an oxygen atom, a halogen atom, a hydroxy group, a nitro group, a nitroso group, a trimethylsilyl group, a t-butyldimethylsilyl group, a cyano group, an amino group, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C9 cycloalkyl group, a C3-C9 halocycloalkyl group, a C1-C6 alkoxy group, a C1-C6 haloalkoxy group, a C2-C6 alkenyloxy group, a C2-C6 haloalkenyloxy group, a C2-C6 alkynyloxy group, a C2-C6 haloalkynyloxy group, a C3-C9 cycloalkoxy group, a C3-C9 halocycloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a benzenesulfonyl group, a benzylsulfonyl group, a C2-C7 alkylaminocarbonyl group, a C2-C7 haloalkylaminocarbonyl group, a C2-C7 alkylcarbonyloxy group, a C2-C7 haloalkylcarbonyloxy group, a benzyl group, —C(=O)C(=O)R$_7$, wherein R$_7$ represents a C1-C6 alkyl group, a C1-C6 haloalkyl group, a C1-C6 alkoxy group, or a C1-C6 haloalkoxy group, or a group represented by -L-D, wherein L and D have the same definitions as L and D, respectively, in R$_2$.

Y$_{1a}$ and Y$_{5a}$ each independently represent a halogen atom, a C1-C6 haloalkoxy group, or a C1-C3 haloalkyl group.

In a case where K is combined with A and two carbon atoms to which A bonds to form a benzene ring, X's are all hydrogen atoms, R$_{2a}$ is a hydrogen atom, and Y$_{3a}$ is a C3 perfluoroalkyl group, Y$_{5a}$ is a C1-C3 haloalkyl group. Further, in a case where K is combined with A and two carbon atoms to which A bonds to form a benzene ring, and X is a cyano group, Y$_{5a}$ is a C1-C6 haloalkoxy group or a C1-C3 haloalkyl group.

Y$_{2a}$ and Y$_{4a}$ each independently represent a hydrogen atom, a halogen atom, or a C1-C4 alkyl group, and Y$_{3a}$ represents a C2-C5 haloalkyl group.

<13> The amide derivative according to <12>, wherein the compound represented by the Formula (6a) is represented by the following Formula (41):

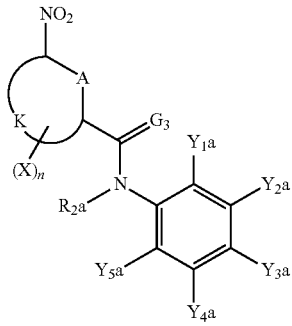

Wherein A, K, X, n, G$_3$, R$_{2a}$, Y$_{1a}$, Y$_{2a}$, Y$_{3a}$, Y$_{4a}$, and Y$_{5a}$ have the same definitions as A, K, X, n, G$_3$, R$_{2a}$, Y$_{1a}$, Y$_{2a}$, Y$_{3a}$, Y$_{4a}$, and Y$_{5a}$, respectively, in the Formula (6a).

<14> A method for producing the amide derivative according to <13>, including reacting a compound represented by the following Formula (40) with a compound represented by the following Formula (6f):

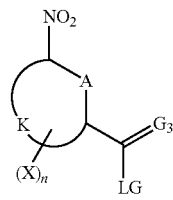

Wherein LG represents a functional group having a leaving ability, such as a halogen atom, a hydroxy group, and the like, and A, K, X, n, and G$_3$ have the same definitions as A, K, X, n, and G$_3$, respectively, in the Formula (1).

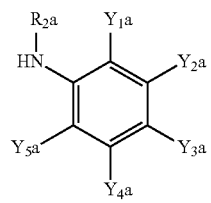

Wherein R$_{2a}$, Y$_{1a}$, Y$_{2a}$, Y$_{3a}$, Y$_{4a}$, and Y$_{5a}$ have the same definitions as R$_{2a}$, Y$_{1a}$, Y$_{2a}$, Y$_{3a}$, Y$_{4a}$, and Y$_{5a}$, respectively, in the Formula (6a).

<15> The amide derivative according to <12>, wherein the compound represented by the Formula (6a) is represented by the following Formula (42):

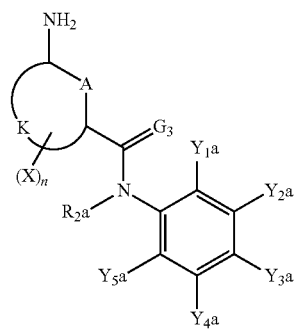

Wherein A, K, X, n, G$_3$, R$_{2a}$, Y$_{1a}$, Y$_{2a}$, Y$_{3a}$, Y$_{4a}$, and Y$_{5a}$ have the same definitions as A, K, X, n, G$_3$, R$_{2a}$, Y$_{1a}$, Y$_{2a}$, Y$_{3a}$, Y$_{4a}$, and Y$_{5a}$, respectively, in the Formula (6a).

<16> A method for producing the amide derivative represented by the Formula (42) according to <15>, including reacting a compound represented by the Formula (41) according to <13> in the presence of a reducing agent.

<17> A method for producing the amide derivative represented by the following Formula (41c), including reacting a compound represented by the following Formula (43) with a compound represented by the following Formula (49a):

Formula (43)

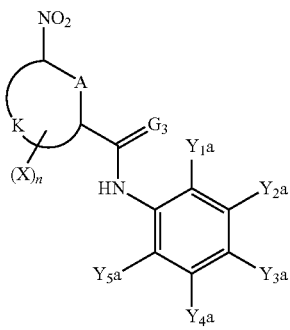

Wherein A, K, X, n, $G_3$, $Y_{1a}$, $Y_{2a}$, $Y_{3a}$, $Y_{4a}$, and $Y_{5a}$ have the same definitions as A, K, X, n, $G_3$, $Y_{1a}$, $Y_{2a}$, $Y_{3a}$, $Y_{4a}$, and $Y_{5a}$, respectively, in the Formula (6a).

$R_{2a}$-LG  Formula (49a)

Wherein LG represents a functional group having a leaving ability, such as a halogen atom, a hydroxy group, or the like, and $R_{2a}$ represents a trimethylsilyl group, a t-butyldimethylsilyl group, a cyano group, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C9 cycloalkyl group, a C3-C9 halocycloalkyl group, a C1-C6 alkylsulfinyl group, a C1-C6 haloalkylsulfinyl group, a C1-C6 alkylsulfonyl group, a C1-C6 haloalkylsulfonyl group, a benzenesulfonyl group, a benzylsulfonyl group, a C2-C7 alkylcarbonyl group, a C2-C7 haloalkylcarbonyl group, a C3-C7 alkenylcarbonyl group, a C3-C7 haloalkenylcarbonyl group, a C3-C7 alkynylcarbonyl group, a C3-C7 haloalkynylcarbonyl group, a C4-C10 cycloalkylcarbonyl group, a C4-C10 halocycloalkylcarbonyl group, a C2-C7 alkoxycarbonyl group, a C2-C7 haloalkoxycarbonyl group, a C3-C7 alkenyloxycarbonyl group, a C3-C7 haloalkenyloxycarbonyl group, a C3-C7 alkynyloxycarbonyl group, a C3-C7 haloalkynyloxycarbonyl group, a phenoxycarbonyl group, a C2-C7 alkylaminocarbonyl group, a C2-C7 haloalkylaminocarbonyl group, a C4-C10 cycloalkyloxycarbonyl group, a C4-C10 halocycloalkyloxycarbonyl group, a benzoyl group, a benzyl group, —C(=O)C(=O)$R_7$, wherein $R_7$ represents a C1-C6 alkyl group, a C1-C6 haloalkyl group, a C1-C6 alkoxy group, or a C1-C6 haloalkoxy group, or a group represented by -L-D, wherein L and D have the same definitions as L and D, respectively, in $R_2$.

Formula (41c)

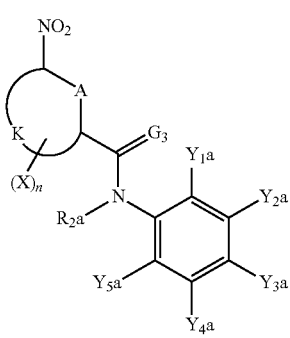

Wherein $R_{2a}$ has the same definition as $R_{2a}$ in the Formula (49a), and A, K, X, n, $G_3$, $Y_{1a}$, $Y_{2a}$, $Y_{3a}$, $Y_{4a}$, and $Y_{5a}$ have the same definitions as A, K, X, n, $G_3$, $Y_{1a}$, $Y_{2a}$, $Y_{3a}$, $Y_{4a}$, and $Y_{5a}$, respectively, in the Formula (6a).

<18> The amide derivative according to <12>, wherein the compound represented by the Formula (6a) is represented by the following Formula (44):

Formula (44)

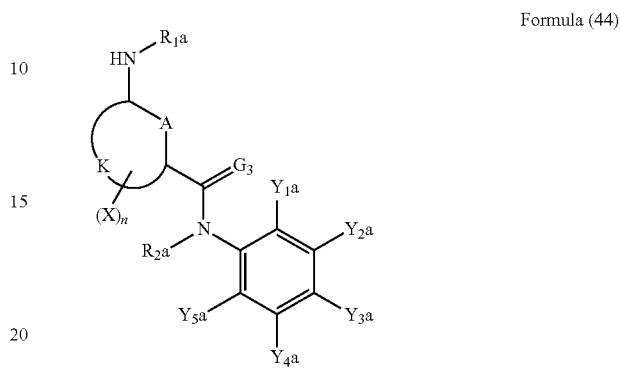

Wherein A, K, X, n, $G_3$, $Y_{1a}$, $Y_{2a}$, $Y_{3a}$, $Y_{4a}$, $Y_{5a}$, $R_{1a}$, and $R_{2a}$, have the same definitions as A, K, X, n, $G_3$, $Y_{1a}$, $Y_{2a}$, $Y_{3a}$, $Y_{4a}$, $Y_{5a}$, $R_{1a}$, and $R_{2a}$, respectively, in the Formula (6a).

<19> A method for producing the amide derivative represented by the following Formula (44a), including reacting a compound represented by the following Formula (42a) with a compound represented by the following Formula (47a):

Formula (42a)

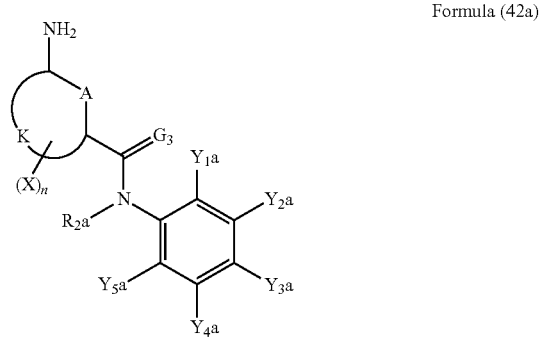

Wherein $R_{2a}$ represents an oxygen atom, a halogen atom, a hydroxy group, a nitro group, a nitroso group, a trimethylsilyl group, a t-butyldimethylsilyl group, a cyano group, an amino group, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C9 cycloalkyl group, a C3-C9 halocycloalkyl group, a C1-C6 alkoxy group, a C1-C6 haloalkoxy group, a C2-C6 alkenyloxy group, a C2-C6 haloalkenyloxy group, a C2-C6 alkynyloxy group, a C2-C6 haloalkynyloxy group, a C3-C9 cycloalkoxy group, a C3-C9 halocycloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a benzenesulfonyl group, a benzylsulfonyl group, a C2-C7 alkylcarbonyl group, a C2-C7 haloalkylcarbonyl group, a C3-C7 alkenylcarbonyl group, a C3-C7 haloalkenylcarbonyl group, a C3-C7 alkynylcarbonyl group, a C3-C7 haloalkynylcarbonyl group, a C4-C10 cycloalkylcarbonyl group, a C4-C10 halocycloalkylcarbonyl group, a C2-C7 alkoxycarbonyl group, a C2-C7 haloalkoxycarbonyl group, a C3-C7 alkenyloxycarbonyl group, a C3-C7 haloalkenyloxycarbonyl group, a C3-C7 alkynyloxycarbonyl group, a C3-C7 haloalkynyloxycarbonyl group, a phenoxycarbonyl group, a C2-C7 alkylaminocarbonyl group, a C2-C7 haloalkylaminocarbonyl group, a C2-C7 alkylcarbonyloxy group, a C2-C7 haloalkylcarbonyloxy group, a C4-C10 cycloalkyloxycarbonyl group, a C4-C10 halocycloalkyloxycarbonyl group, a benzoyl group, a benzyl group, —C(=O)C(=O)R$_7$ (wherein R$_7$ represents a C1-C6 alkyl group which may have a substituent, a C1-C6 haloalkyl group, or a C1-C6 alkoxy group or a C1-C6 haloalkoxy group which may have a substituent), or a group represented by -L-D (wherein L and D have the same definitions as L and D, respectively, in R$_2$), and A, K, X, n, G$_3$, Y$_{1a}$, Y$_{2a}$, Y$_{3a}$, Y$_{4a}$, and Y$_{5a}$ have the same definitions as A, K, X, n, G$_3$, Y$_{1a}$, Y$_{2a}$, Y$_{3a}$, Y$_{4a}$, and Y$_{5a}$, respectively, in the Formula (6a).

R$_{1a}$-LG            Formula (47a)

Wherein LG represents a functional group having a leaving ability, such as a halogen atom, a hydroxy group, or the like, and R$_{1a}$ represents a trimethylsilyl group, a t-butyldimethylsilyl group, a cyano group, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C9 cycloalkyl group, a C3-C9 halocycloalkyl group, a C1-C6 alkylsulfinyl group, a C1-C6 haloalkylsulfinyl group, a C1-C6 alkylsulfonyl group, a C1-C6 haloalkylsulfonyl group, a benzenesulfonyl group, a benzylsulfonyl group, a C2-C7 alkylaminocarbonyl group, a C2-C7 haloalkylaminocarbonyl group, a benzyl group, —C(=O)C(=O)R$_7$, wherein R$_7$ represents a C1-C6 alkyl group, a C1-C6 haloalkyl group, a C1-C6 alkoxy group, or a C1-C6 haloalkoxy group, or a group represented by -L-D, wherein L and D have the same definitions as L and D, respectively, in R$_2$.

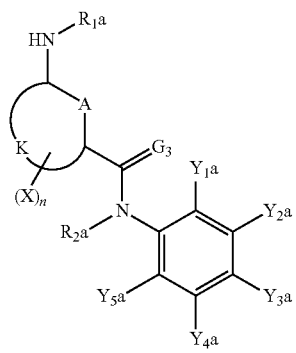

Formula (44a)

Wherein R$_{1a}$ has the same definition as R$_{1a}$ in the Formula (47a), R$_{2a}$ has the same definition as R$_{2a}$ in the Formula (42a), and A, K, X, n, G$_3$, Y$_{1a}$, Y$_{2a}$, Y$_{3a}$, Y$_{4a}$, and Y$_{5a}$ have the same definitions as A, K, X, n, G$_3$, Y$_{1a}$, Y$_{2a}$, Y$_{3a}$, Y$_{4a}$, and Y$_{5a}$, respectively, in the Formula (6a).

<20> A method for producing the amide derivative represented by the following Formula (44c), including reacting the compound represented by the Formula (42) according to <15> with an aldehyde:

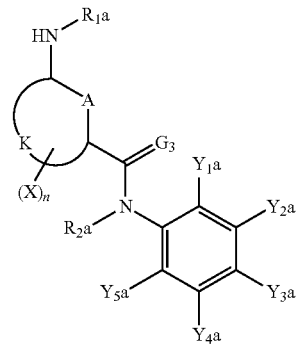

Formula (44c)

Wherein R$_{1a}$ represents a C1-C6 alkyl group, a C1-C6 haloalkyl group, or a benzyl group, and A, K, X, n, G$_3$, R$_{2a}$, Y$_{1a}$, Y$_{2a}$, Y$_{3a}$, Y$_{4a}$, and Y$_{5a}$ have the same definitions as A, K, X, n, G$_3$, R$_{2a}$, Y$_{1a}$, Y$_{2a}$, Y$_{3a}$, Y$_{4a}$, and Y$_{5a}$, respectively, in the Formula (6a).

<21> The amide derivative according to <12>, wherein the compound represented by the Formula (6a) is represented by the following Formula (6b):

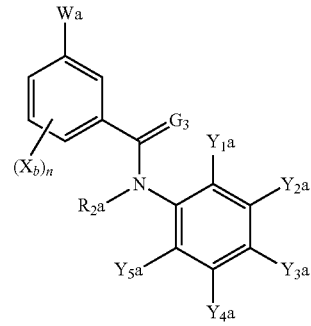

Formula (6b)

Wherein Xb represents a hydrogen atom, a halogen atom, a cyano group, or a nitro group, n is 4, and W$_a$, G$_3$, R$_{2a}$, Y$_{1a}$, Y$_{2a}$, Y$_{3a}$, Y$_{4a}$, and Y$_{5a}$ have the same definitions as W$_a$, G$_3$, R$_{2a}$, Y$_{1a}$, Y$_{2a}$, Y$_{3a}$, Y$_{4a}$, and Y$_{5a}$, respectively, in the Formula (6a).

<22> The compound according to <21>, wherein the compound represented by the Formula (6b) is represented by the following Formula (41b):

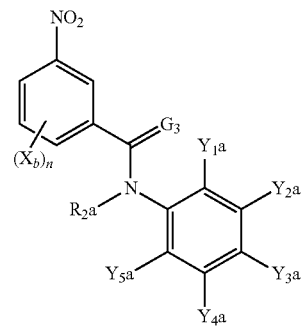

Formula (41b)

Wherein Xb, n, G$_3$, R$_{2a}$, Y$_{1a}$, Y$_{2a}$, Y$_{3a}$, Y$_{4a}$, and Y$_{5a}$ have the same definitions as Xb, n, G$_3$, R$_{2a}$, Y$_{1a}$, Y$_{2a}$, Y$_{3a}$, Y$_{4a}$, and Y$_{5a}$, respectively, in the Formula (6b).

<23> A method for producing the amide derivative represented by the Formula (41b) according to <22>, including reacting a compound represented by the following Formula (40b) with the compound represented by the following Formula (60 according to <14>:

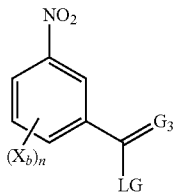

Formula (40b)

Wherein LG represents a functional group having a leaving ability, such as a halogen atom, a hydroxy group, and the like, and G$_3$ has the same definition as G$_3$ in the Formula (1). n and Xb have the same definitions as n and Xb, respectively, in the Formula (6b).

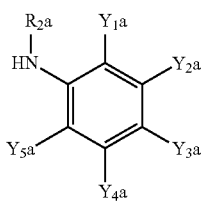

Formula (6f)

Wherein R$_{2a}$, Y$_{1a}$, Y$_{2a}$, Y$_{3a}$, Y$_{4a}$, and Y$_{5a}$ have the same definitions as R$_{2a}$, Y$_{1a}$, Y$_{2a}$, Y$_{3a}$, Y$_{4a}$, and Y$_{5a}$, respectively, in the Formula (6a).

<24> The amide derivative according to <21>, wherein the compound represented by the Formula (6b) is represented by the following Formula (42b):

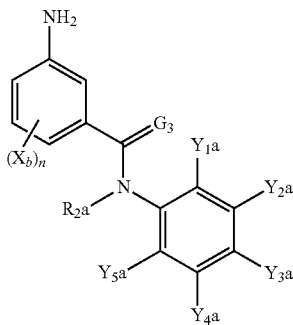

Formula (42b)

Wherein Xb, n, G$_3$, R$_{2a}$, Y$_{1a}$, Y$_{2a}$, Y$_{3a}$, Y$_{4a}$, and Y$_{5a}$ have the same definitions as Xb, n, G$_3$, R$_{2a}$, Y$_{1a}$, Y$_{2a}$, Y$_{3a}$, Y$_{4a}$, and Y$_{5a}$, respectively, in the Formula (6b).

<25> The method for producing the amide derivative according to <24>, including reacting the compound represented by the Formula (41b) according to <22> in the presence of a reducing agent.

<26> A method for producing the following Formula (41d), including reacting a compound represented by the following Formula (43b) with a compound represented by the following Formula (49a) according to <17>:

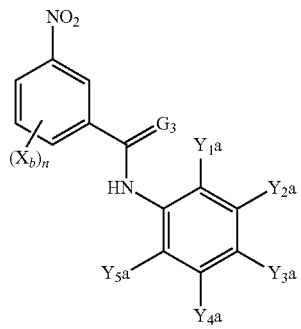

Formula (43b)

Wherein Xb, n, G$_3$, Y$_{1a}$, Y$_{2a}$, Y$_{3a}$, Y$_{4a}$, and Y$_{5a}$ have the same definitions as Xb, n, G$_3$, Y$_{1a}$, Y$_{2a}$, Y$_{3a}$, Y$_{4a}$, and Y$_{5a}$, respectively, in the Formula (6b).

R$_{2a}$-LG    Formula (49a)

Wherein LG represents a functional group having a leaving ability, such as a halogen atom, a hydroxy group, or the like, and R$_{2a}$ represents a trimethylsilyl group, a t-butyldimethylsilyl group, a cyano group, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C9 cycloalkyl group, a C3-C9 halocycloalkyl group, a C1-C6 alkylsulfonyl group, a C1-C6 haloalkylsulfinyl group, a C1-C6 alkylsulfonyl group, a C1-C6 haloalkylsulfonyl group, a benzenesulfonyl group, a benzylsulfonyl group, a C2-C7 alkylcarbonyl group, a C2-C7 haloalkylcarbonyl group, a C3-C7 alkenylcarbonyl group, a C3-C7 haloalkenylcarbonyl group, a C3-C7 alkynylcarbonyl group, a C3-C7 haloalkynylcarbonyl group, a C4-C10 cycloalkylcarbonyl group, a C4-C10 halocycloalkylcarbonyl group, a C2-C7 alkoxycarbonyl group, a C2-C7 haloalkoxycarbonyl group, a C3-C7 alkenyloxycarbonyl group, a C3-C7 haloalkenyloxycarbonyl group, a C3-C7 alkynyloxycarbonyl group, a C3-C7 haloalkynyloxycarbonyl group, a phenoxycarbonyl group, a C2-C7 alkylaminocarbonyl group, a C2-C7 haloalkylaminocarbonyl group, a C4-C10 cycloalkyloxycarbonyl group, a C4-C10 halocycloalkyloxycarbonyl group, a benzoyl group, a benzyl group, —C(=O)C(=O)R$_7$, wherein R$_7$ represents a C1-C6 alkyl group, a C1-C6 haloalkyl group, a C1-C6 alkoxy group, or a C1-C6 haloalkoxy group, or a group represented by -L-D, wherein L and D have the same definitions as L and D, respectively, in R$_2$.

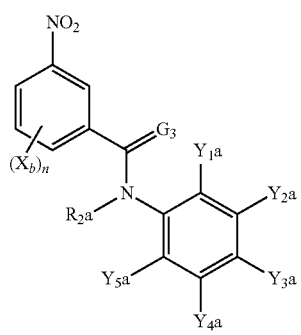

Formula (41d)

Wherein $R_{2a}$ has the same definition as $R_{2a}$ in the Formula (49a), and Xb, n, $G_3$, $Y_{1a}$, $Y_{2a}$, $Y_{3a}$, $Y_{4a}$, and $Y_{5a}$ have the same definitions as Xb, n, $G_3$, $Y_{1a}$, $Y_{2a}$, $Y_{3a}$, $Y_{4a}$, and $Y_{5a}$, respectively, in the Formula (6b).

<27> The amide derivative according to <21>, wherein the compound represented by the Formula (6b) is represented by the following Formula (44b):

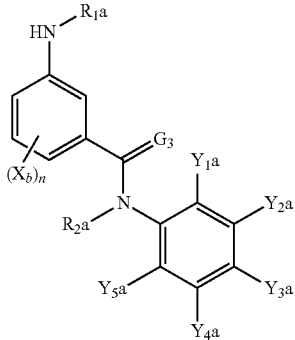

Formula (44b)

Wherein Xb, n, $G_3$, $Y_{1a}$, $Y_{2a}$, $Y_{3a}$ $Y_{4a}$, $Y_{5a}$, $R_{1a}$, and $R_{2a}$ have the same definitions as Xb, n, $G_3$, $Y_{1a}$, $Y_{2a}$, $Y_{3a}$, $Y_{4a}$, $Y_{5a}$, $R_{1a}$, and $R_{2a}$, respectively, in the Formula (6b).

<28> A method for producing the amide derivative represented by the following Formula (44d) according to <27>, including reacting a compound represented by the following Formula (42c) with a compound represented by the following Formula (47a) according to <19>:

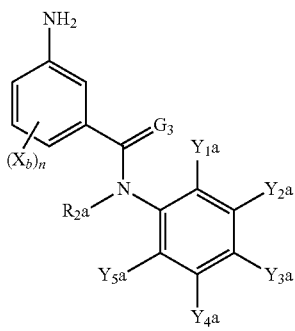

Formula (42c)

Wherein $R_{2a}$ has the same definition as in the Formula (42a), and Xb, n, $G_3$, $Y_{1a}$, $Y_{2a}$, $Y_{3a}$, $Y_{4a}$ and $Y_{5a}$ have the same definitions as Xb, n, $G_3$, $Y_{1a}$, $Y_{2a}$, $Y_{3a}$, $Y_{4a}$ and $Y_{5a}$, respectively, in the Formula (6b).

$R_{1a}$-LG    Formula (47a)

Wherein LG represents a functional group having a leaving ability, such as a halogen atom, a hydroxy group, or the like, and $R_{1a}$ represents a trimethylsilyl group, a t-butyldimethylsilyl group, a cyano group, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C9 cycloalkyl group, a C3-C9 halocycloalkyl group, a C1-C6 alkylsulfinyl group, a C1-C6 haloalkylsulfinyl group, a C1-C6 alkylsulfonyl group, a C1-C6 haloalkylsulfonyl group, a benzenesulfonyl group, a benzylsulfonyl group, a C2-C7 alkylaminocarbonyl group, a C2-C7 haloalkylaminocarbonyl group, a benzyl group, —C(=O)C(=O)$R_7$ (wherein $R_7$ represents a C1-C6 alkyl group, a C1-C6 haloalkyl group, a C1-C6 alkoxy group, or a C1-C6 haloalkoxy group), or a group represented by -L-D (wherein L and D have the same definitions as L and D, respectively, in $R_2$.

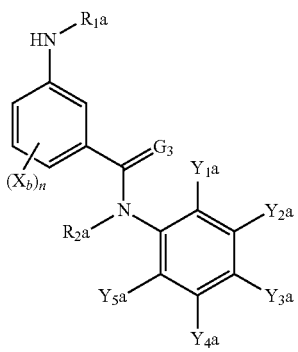

Formula (44d)

Wherein $R_{1a}$ has the same definition as $R_{1a}$ in the Formula (47a), $R_{2a}$ has the same definition as $R_{2a}$ in the Formula (42a), and Xb, n, $G_3$, $Y_{1a}$, $Y_{2a}$, $Y_{3a}$, $Y_{4a}$, and $Y_{5a}$ have the same definitions as Xb, n, $G_3$, $Y \rightarrow Y_{2a}$, $Y_{3a}$, $Y_{4a}$, and $Y_{5a}$, respectively, in the Formula (6b).

<29> A method for producing the amide derivative represented by the following Formula (44e), including reacting a compound represented by the Formula (42b) according to <24> with an aldehyde:

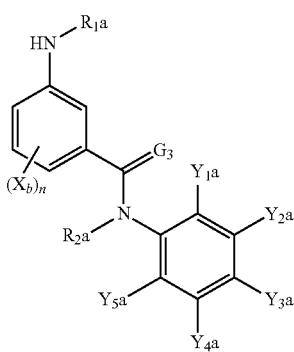

Formula (44e)

Wherein $R_{1a}$ has the same definition as $R_{1a}$ in the Formula (44c), and $R_{2a}$, Xb, n, $G_3$, $Y_{1a}$, $Y_{2a}$, $Y_{3a}$, $Y_{4a}$, and $Y_{5a}$ have the same definitions as $R_{2a}$, Xb, n, $G_3$, $Y_{1a}$, $Y_{2a}$, $Y_{3a}$, $Y_{4a}$, and $Y_{5a}$ in the Formula (6b).

<30> An amide derivative represented by the following Formula (6g):

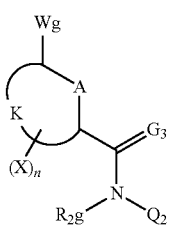

Formula (6g)

Wherein A, K, X, n, G₃, and Q₂ have the same definitions as A, K, X, n, G₃, and Q₂, respectively, in the Formula (1). Wg represents a nitro group, an amino group, or —NH-T. T has the same definition as T in the Formula (1). R$_{2g}$ represents a group represented by -L-D (wherein L and D have the same definitions as L and D, respectively, in R₂ in the Formula (1).

<31> The amide derivative according to <30>, wherein the compound represented by the Formula (6g) is represented by the following Formula (41g):

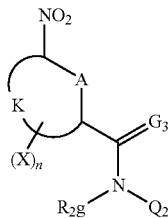

Formula (41g)

Wherein A, K, X, n, G₃, R$_{2g}$, and Q₂ have the same definitions as A, K, X, n, G₃, R$_{2g}$, and Q₂, respectively, in the Formula (6g).

<32> A method for producing an aniline derivative represented by the following Formula (48g), including reacting a compound represented by the following Formula (48) with a compound represented by the following Formula (49g):

H₂N-Q₂    Formula (48)

Wherein Q₂ has the same definition as Q₂ in the Formula (1).

R$_{2g}$-LG    Formula (49g)

Wherein LG represents a functional group having a leaving ability, such as a halogen atom, a hydroxy group, or the like, and R$_{2g}$ has the same definition as R$_{2g}$ in the Formula (6g).

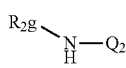

Formula (48g)

Wherein Q₂ has the same definition as Q₂ in the Formula (1), and R$_{2g}$ has the same definition as R$_{2g}$ in the Formula (6g).

<33> A method for producing an aniline derivative represented by the following Formula (48h), including reacting the compound represented by the Formula (48) according to <32> with an aldehyde:

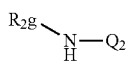

Formula (48h)

Wherein Q₂ has the same definition as Q₂ in the Formula (1). R$_{2g}$ represents -L-D, wherein L represents —C(M₁)(M₂)-, —C(M₁)(M₂)-C(M₃)(M₄)-, —C(M₁)(M₂)-C(M₃)(M₄)-C(M₅)(M₆)-, —C(M₁)(M₂)-C(M₃)=C(M₅)-, —C(M₁)(M₂)-C≡C—, —C(M₁)(M₂)-C(M₃)(M₄)-C(M₅)(M₆)-C(M₇)(M₈)-, —C(M₁)(M₂)-C(M₃)=C(M₅)-C(M₇)(M₈)-, —C(M₁)(M₂)-C(M₃)(M₄)-C(M₅)=C(M₇)-, —C(M₁)(M₂)-C≡C—C(M₇)(M₈)-, or —C(M₁)(M₂)-C(M₃)(M₄)-C≡C—, M₁ to M₈ have the same definitions as M₁ to M₈, respectively, in the Formula (1), and D has the same definition as R₂ in L and D in the Formula (1).

<34> A method for producing the amide derivative represented by the following Formula (41g) according to <31>, including reacting a compound represented by the following Formula (40) according to <14> with a compound represented by the following Formula (48g):

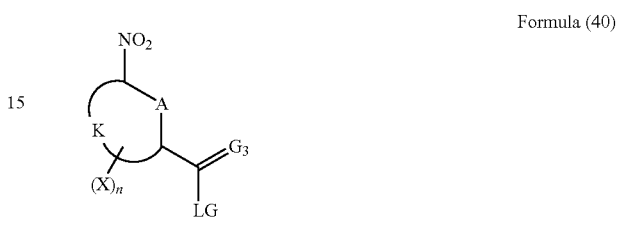

Formula (40)

Wherein LG represents a functional group having a leaving ability, such as a halogen atom, a hydroxy group, and the like, and A, K, X, n, and G₃ have the same definitions as A, K, X, n, and G₃, respectively, in the Formula (1).

Formula (48g)

Wherein Q₂ has the same definition as Q₂ in the Formula (1), and R$_{2g}$ has the same definition as R$_{2g}$ in the Formula (6g).

<35> The amide derivative according to <30>, wherein the compound represented by the Formula (6g) is represented by the following Formula (42g):

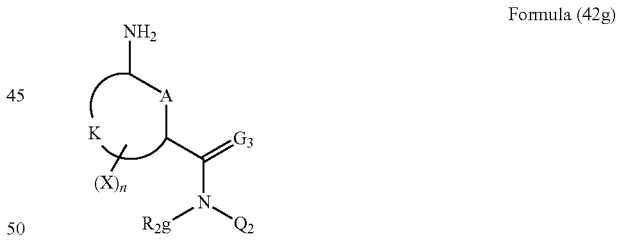

Formula (42g)

Wherein A, K, X, n, G₃, R$_{2g}$, and Q₂ have the same definitions as A, K, X, n, G₃, R$_{2g}$, and Q₂, respectively, in the Formula (6g).

<36> A method for producing the amide derivative represented by the Formula (42g) according to <35>, including reacting the compound represented by the Formula (41g) according to <31> in the presence of a reducing agent.

<37> A method for producing the amide derivative represented by the Formula (41g) according to <31>, including reacting a compound represented by the following Formula (43g) with the compound represented by the following Formula (49g) according to <32>:

Formula (43g)

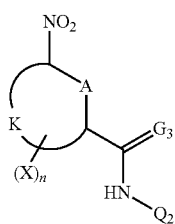

Wherein A, K, X, n, G$_3$, and Q$_2$ have the same definitions as A, K, X, n, G$_3$, and Q$_2$, respectively, in the Formula (1).

R$_{2g}$-LG                                                Formula (49g)

Wherein LG represents a functional group having a leaving ability, such as a halogen atom, a hydroxy group, or the like, R$_{2g}$ has the same definition as R$_{2g}$ in the Formula (6g).

<38> The amide derivative according to <30>, wherein the compound represented by the Formula (6g) is represented by the following Formula (46g):

Formula (46g)

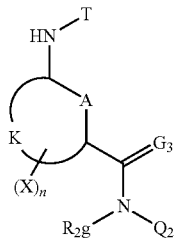

Wherein T, A, K, X, n, G$_3$, R$_{2g}$, and Q$_2$ have the same definitions as T, A, K, X, n, G$_3$, R$_{2g}$, and Q$_2$, respectively, in the Formula (6g).

<39> A method for producing the amide derivative represented by the Formula (46g) according to <38>, including reacting a compound represented by the following Formula (42g) according to <35> with a compound represented by the following Formula (45):

Formula (42g)

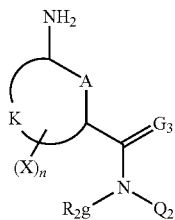

Wherein A, K, X, n, G$_3$, R$_{2g}$, and Q$_2$ have the same definitions as A, K, X, n, G$_3$, R$_{2g}$, and Q$_2$, respectively, in the Formula (6g).

T-LG                                                     Formula (45)

Wherein LG represents a functional group having a leaving ability, such as a halogen atom, a hydroxy group, or the like, T has the same definition as T in the Formula (1).

<40> A method for producing the amide derivative represented by the following Formula (1g), including reacting a compound represented by the following Formula (50) with a compound represented by the following Formula (47g):

Formula (50)

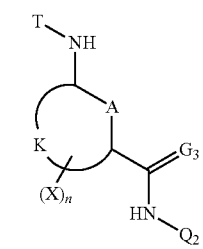

Wherein T, A, K, X, n, G$_3$, and Q$_2$ have the same definitions as T, A, K, X, n, G$_3$, and Q$_2$, respectively, in the Formula (1).

R$_{1g}$-LG                                                Formula (47g)

Wherein LG represents a functional group having a leaving ability, such as a halogen atom, a hydroxy group, or the like, and R$_{1g}$ represents -L-D (wherein L and D have the same definitions as L and D in R$_1$, respectively, in the Formula (1).

Formula (1g)

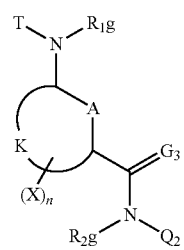

Wherein R$_{1g}$ has the same definition as R$_{1g}$ in the Formula (47g), and T, A, K, X, n, G$_3$, and Q$_2$ have the same definitions as T, A, K, X, n, G$_3$, and Q$_2$, respectively, in the Formula (1).

<41> A method for producing the amide derivative represented by the Formula (1) according to <1>, including reacting a compound represented by the following Formula (52) with a compound represented by the following Formula (47):

Formula (52)

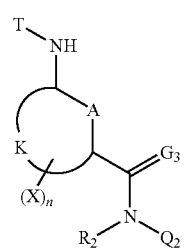

Wherein T, R$_2$, A, K, X, n, G$_3$, and Q$_2$ have the same definitions as T, R$_2$, A, K, X, n, G$_3$, and Q$_2$, respectively, in the Formula (1).

R$_1$-LG                                                  Formula (47)

Wherein LG represents a functional group having a leaving ability, such as a halogen atom, a hydroxy group, or the like, and R$_1$ has the same definition as R$_1$ in the Formula (1).

<42> An amide derivative represented by the following Formula (55a):

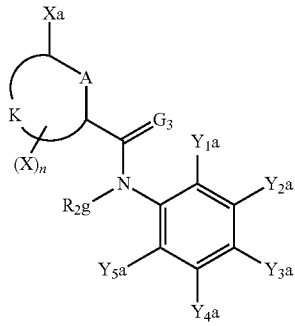

Formula (55a)

Wherein $X_a$ represents a halogen atom. A, K, X, n, and $G_3$ have the same definitions as A, K, X, n, and $G_3$, respectively, in the Formula (1), and $R_{2a}$, $Y_{1a}$, $Y_{2a}$, $Y_{3a}$, $Y_{4a}$, and $Y_{5a}$ have the same definitions as $R_{2a}$, $Y_{1a}$, $Y_{2a}$, $Y_{3a}$, $Y_{4a}$, and $Y_{5a}$, respectively, in the Formula (6a).

<43> A method for producing the amide derivative represented by the Formula (55a) according to <42>, including reacting a compound represented by the following Formula (54) with a compound represented by the following Formula (6f) according to <14>:

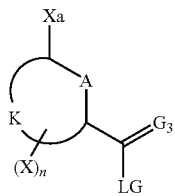

Formula (54)

Wherein $X_a$ represents a halogen atom, LG represents a functional group having a leaving ability, such as a halogen atom, a hydroxy group, and the like, and A, K, X, n, and $G_3$ have the same definitions as A, K, X, n, and $G_3$, respectively, in the Formula (1).

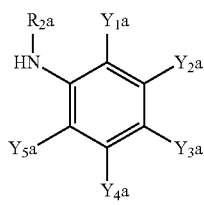

Formula (6f)

Wherein $R_{2a}$, $Y_{1a}$, $Y_{2a}$, $Y_{3a}$, $Y_{4a}$, and $Y_{5a}$ have the same definitions as $R_{2a}$, $Y_{1a}$, $Y_{2a}$, $Y_{3a}$, $Y_{4a}$, and $Y_{5a}$, respectively, in the Formula (6a).

<44> A method for producing the amide derivative represented by the Formula (55b), including reacting a compound represented by the following Formula (56a) with a compound represented by the following Formula (49a) according to <17>:

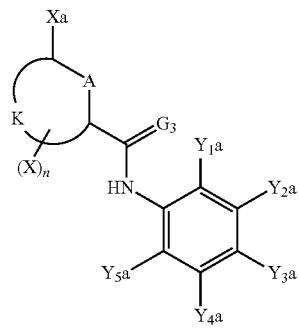

Formula (56a)

Wherein $X_a$ represents a halogen atom. A, K, X, n, and $G_3$ have the same definitions as A, K, X, n, and $G_3$, respectively, in the Formula (1), and $Y_{1a}$, $Y_{2a}$, $Y_{3a}$, $Y_{4a}$, and $Y_{5a}$ have the same definitions as $Y_{1a}$, $Y_{2a}$, $Y_{3a}$, $Y_{4a}$, and $Y_{5a}$, respectively, in the Formula (6a).

$$R_{2a}\text{-LG} \qquad \text{Formula (49a)}$$

Wherein LG represents a functional group having a leaving ability, such as a halogen atom, a hydroxy group, or the like, and $R_{2a}$ represents a trimethylsilyl group, a t-butyldimethylsilyl group, a cyano group, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C9 cycloalkyl group, a C3-C9 halocycloalkyl group, a C1-C6 alkylsulfinyl group, a C1-C6 haloalkylsulfinyl group, a C1-C6 alkylsulfonyl group, a C1-C6 haloalkylsulfonyl group, a benzenesulfonyl group, a benzylsulfonyl group, a C2-C7 alkylcarbonyl group, a C2-C7 haloalkylcarbonyl group, a C3-C7 alkenylcarbonyl group, a C3-C7 haloalkenylcarbonyl group, a C3-C7 alkynylcarbonyl group, a C3-C7 haloalkynylcarbonyl group, a C4-C10 cycloalkylcarbonyl group, a C4-C10 halocycloalkylcarbonyl group, a C2-C7 alkoxycarbonyl group, a C2-C7 haloalkoxycarbonyl group, a C3-C7 alkenyloxycarbonyl group, a C3-C7 haloalkenyloxycarbonyl group, a C3-C7 alkynyloxycarbonyl group, a C3-C7 haloalkynyloxycarbonyl group, a phenoxycarbonyl group, a C2-C7 alkylaminocarbonyl group, a C2-C7 haloalkylaminocarbonyl group, a C4-C10 cycloalkyloxycarbonyl group, a C4-C10 halocycloalkyloxycarbonyl group, a benzoyl group, a benzyl group, —C(=O)C(=O)$R_7$, wherein $R_7$ represents a C1-C6 alkyl group, a C1-C6 haloalkyl group, a C1-C6 alkoxy group, or a C1-C6 haloalkoxy group, or a group represented by -L-D, wherein L and D have the same definitions as L and D, respectively, in $R_2$.

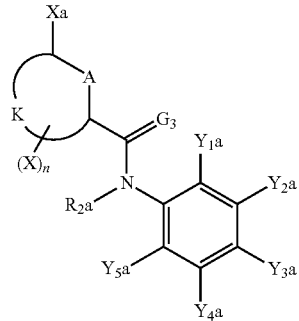

Formula (55b)

Wherein $R_{2a}$ has the same definition as $R_{2a}$ in the Formula (49a). X, represents a halogen atom. A, K, X, n, and $G_3$ have the same definitions as A, K, X, n, and $G_3$, respectively, in the Formula (1). $Y_{1a}$, $Y_{2a}$, $Y_{3a}$, $Y_{4a}$, and $Y_{5a}$ have the same definitions as $Y_{1a}$, $Y_{2a}$, $Y_{3a}$, $Y_{4a}$, and $Y_{5a}$, respectively, in the Formula (6a).

<45> A method for producing the amide derivative represented by the following Formula (53a), including reacting a compound represented by the Formula (55a) according to <42> with an aminating agent:

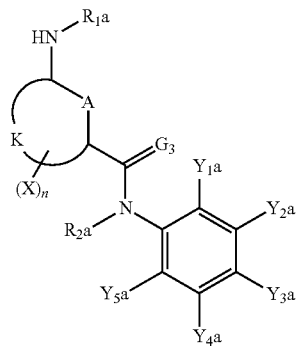

Formula (53a)

Wherein $R_{1a}$ represents a hydrogen atom, an oxygen atom, a halogen atom, a hydroxy group, a nitro group, a nitroso group, a trimethylsilyl group, a t-butyldimethylsilyl group, a cyano group, an amino group, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C9 cycloalkyl group, a C3-C9 halocycloalkyl group, a C1-C6 alkoxy group, a C1-C6 haloalkoxy group, a C2-C6 alkenyloxy group, a C2-C6 haloalkenyloxy group, a C2-C6 alkynyloxy group, a C2-C6 haloalkynyloxy group, a C3-C9 cycloalkoxy group, a C3-C9 halocycloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a benzenesulfonyl group, a benzylsulfonyl group, a C2-C7 alkylaminocarbonyl group, a C2-C7 haloalkylaminocarbonyl group, a C2-C7 alkylcarbonyloxy group, a C2-C7 haloalkylcarbonyloxy group, a benzyl group, —C(=O)C(=O)R$_7$ (wherein $R_7$ represents a C1-C6 alkyl group, a C1-C6 haloalkyl group, a C1-C6 alkoxy group, or a C1-C6 haloalkoxy group), or a group represented by -L-D (wherein L and D have the same definitions as L and D, respectively, in $R_2$). A, K, X, n, and $G_3$ have the same definitions as A, K, X, n, and $G_3$, respectively, in the Formula (1). $R_{2a}$, $Y_{1a}$, $Y_{2a}$, $Y_{3a}$, $Y_{4a}$, and $Y_{5a}$ have the same definitions as $R_{2a}$, $Y_{1a}$, $Y_{2a}$, $Y_{3a}$, $Y_{4a}$, and $Y_{5a}$, respectively, in the Formula (6a).

<46> An amide derivative represented by the following Formula (55g):

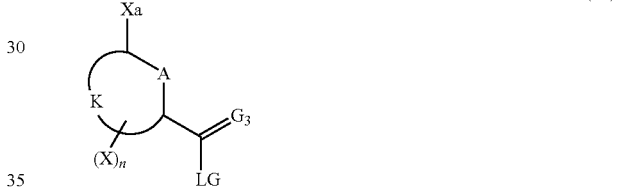

Formula (55g)

Wherein $X_a$ represents a halogen atom. A, K, X, n, $G_3$, and $Q_2$ have the same definitions as A, K, X, n, $G_3$, and $Q_2$, respectively, in the Formula (1). $R_{2g}$ represents -L-D (wherein L and D have the same definitions as L and D, respectively, in $R_2$.

<47> A method for producing the amide derivative represented by the Formula (55g) according to <46>, including reacting a compound represented by the following Formula (54) according to <43> with a compound represented by the following Formula (48g) according to <32>:

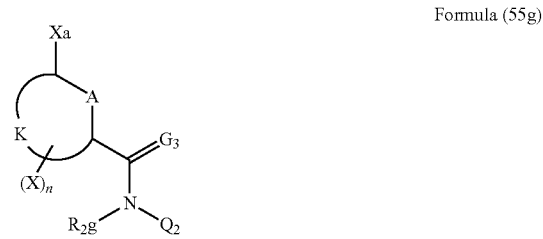

Formula (54)

Wherein $X_a$ represents a halogen atom, LG represents a functional group having a leaving ability, such as a halogen atom, a hydroxy group, and the like, and A, K, X, n, and $G_3$ have the same definitions as A, K, X, n, and $G_3$, respectively, in the Formula (1).

Formula (48g)

Wherein $Q_2$ has the same definition as $Q_2$ in the Formula (1). $R_{2g}$ has the same definition as $R_{2g}$ in the Formula (6g).

<48> A method for producing the amide derivative represented by the following Formula (53g), including reacting the compound according to <46> with an aminating agent:

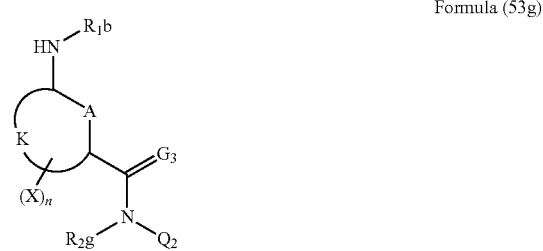

Formula (53g)

Wherein A, K, X, n, $G_3$, and $Q_2$ have the same definitions as A, K, X, n, $G_3$, and $Q_2$, respectively, in the Formula (1). $R_{2g}$ has the same definition as $R_{2g}$ in the Formula (6g). $R_{1b}$ represents a hydrogen atom, an oxygen atom, a halogen atom, a hydroxy group, a nitro group, a nitroso group, a trimethylsilyl group, a t-butyldimethylsilyl group, a cyano group, an amino group, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C9 cycloalkyl group, a C3-C9 halocycloalkyl group, a C1-C6 alkoxy group, a C1-C6 haloalkoxy group, a C2-C6 alkenyloxy group, a C2-C6 haloalkenyloxy group, a C2-C6 alkynyloxy group, a C2-C6 haloalkynyloxy group, a C3-C9 cycloalkoxy group, a C3-C9 halocycloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a benzenesulfonyl group, a benzylsulfonyl group, a C2-C7 alkylcarbonyl group, a C2-C7 haloalkylcarbonyl group, a C3-C7 alkenylcarbonyl group, a C3-C7 haloalkenylcarbonyl group, a C3-C7 alkynylcarbonyl group, a C3-C7 haloalkynylcarbonyl group, a C4-C10 cycloalkylcarbonyl group, a C4-C10 halocycloalkylcarbonyl group, a C2-C7 alkoxycarbonyl group, a C2-C7 haloalkoxycarbonyl group, a C3-C7 alkenyloxycarbonyl group, a C3-C7 haloalkenyloxycarbonyl group, a C3-C7 alkynyloxycarbonyl group, a C3-C7 haloalkynyloxycarbonyl group, a phenoxycarbonyl group, a C2-C7 alkylaminocarbonyl group, a C2-C7 haloalkylaminocarbonyl group, a C2-C7 alkylcarbonyloxy group, a C2-C7 haloalkylcarbonyloxy group, a C4-C10 cycloalkyloxycarbonyl group, a C4-C10 halocycloalkyloxycarbonyl group, a benzoyl group, a benzyl group, —C(=O)C(=O)$R_7$, wherein $R_7$ represents a C1-C6 alkyl group, a C1-C6 haloalkyl group, a C1-C6 alkoxy group, or a C1-C6 haloalkoxy group, or a group represented by -L-D, wherein L and D have the same definitions as L and D in $R_1$.

<49> The amide derivative according to <13>, wherein the compound represented by the Formula (41) is represented by the following Formula (58a):

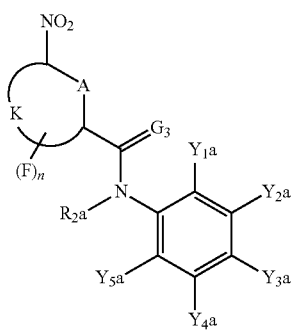

Formula (58a)

Wherein n represents an integer of from 1 to 4. A, K, $G_3$, $R_{2a}$, $Y_{1a}$, $Y_{2a}$, $Y_{3a}$, $Y_{4a}$, and $Y_{5a}$ have the same definitions as A, K, $G_3$, $R_{2a}$, $Y_{1a}$, $Y_{2a}$, $Y_{3a}$, $Y_{4a}$, and $Y_{5a}$, respectively, in the Formula (6a).

<50> A method for producing the amide derivative represented by the Formula (58a) according to <49>, including reacting the compound represented by the Formula (41) according to <13>, in which X represents a chlorine atom, a bromine atom, or an iodine atom, with a fluorinating agent.

<51> The amide derivative according to <31>, wherein the compound represented by the Formula (41g) is represented by the following Formula (58g):

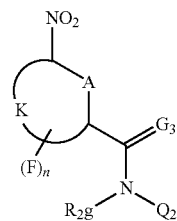

Formula (58g)

Wherein n represents an integer of from 1 to 4. A, K, $G_3$ and $Q_2$ have the same definitions as A, K, $G_3$ and $Q_2$, respectively, in the Formula (1). $R_{2g}$ has the same definition as $R_{2g}$ in the Formula (6g).

<52> A method for producing the amide derivative according to <51>, including reacting the compound represented by the Formula (41g) according to <31>, in which X represents a chlorine atom, a bromine atom, or an iodine atom, with a fluorinating agent.

<53> The amide derivative according to <13>, wherein the compound represented by the Formula (41) is represented by the following Formula (60a):

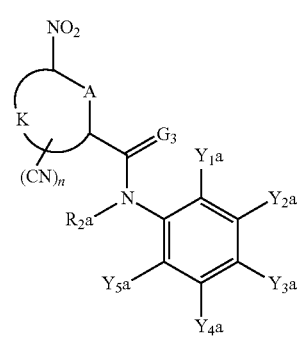

Formula (60a)

Wherein n represents an integer of from 1 to 4. A, K, $G_3$, $R_{2a}$, $Y_{1a}$, $Y_{2a}$, $Y_{3a}$, $Y_{4a}$, and $Y_{5a}$ have the same definitions as A, K, $G_3$, $R_{2a}$, $Y_{1a}$, $Y_{2a}$, $Y_{3a}$, $Y_{4a}$, and $Y_{5a}$, respectively, in the Formula (6a).

<54> A method for producing the amide derivative represented by the Formula (60a) according to <53>, including reacting the compound represented by the Formula (41) according to <13>, in which X represents a halogen atom with a cyanating agent.

<55> The amide derivative according to <31>, wherein the compound represented by the Formula (41g) is represented by the following Formula (60g):

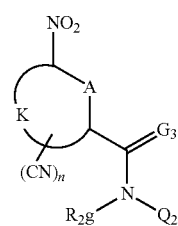

Formula (60g)

Wherein n represents an integer of from 1 to 4. A, K, $G_3$ and $Q_2$ have the same definitions as A, K, $G_3$ and $Q_2$, respectively, in the Formula (1). $R_{2g}$ has the same definition as $R_{2g}$ in the Formula (6g).

<56> A method for producing the amide derivative represented by the Formula (60g) according to <55>, including reacting the compound represented by the Formula (41g) according to <31>, in which X represents a halogen atom with a cyanating agent.

<57> An amide derivative represented by the following Formula (6h):

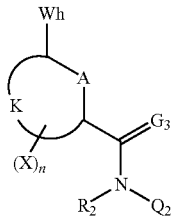

Formula (6h)

Wherein A, K, X, n, $G_3$, $R_2$ and $Q_2$ have the same definitions as A, K, X, n, $G_3$, $R_2$ and $Q_2$, respectively, in the Formula (1).

$W_h$ represents —NH—$R_1$ or —N(T)-$R_1$. $R_1$ and T have the same definitions as $R_1$ and T, respectively, in the Formula (1), provided that at least either $R_1$ or $R_2$ represents a group represented by -L-D.

<58> The amide derivative according to <57>, wherein the compound represented by the Formula (6h) is represented by the following Formula (6c):

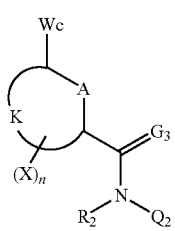

Formula (6c)

Wherein $W_c$ represents —NH—C($M_1$)($M_2$)-C($M_3$)-D, —N(T)-C($M_1$)($M_2$)-C($M_3$)-D, —N(T)-L-C(=O)-LG, or —N(T)-L-C(=O)—N$U_3U_4$. $M_1$, $M_2$, $M_3$, D, L, $U_3$, and $U_4$ have the same definitions as $M_1$, $M_2$, $M_3$, D, L, $U_3$, and $U_4$, respectively, in $R_2$. LG represents a functional group having a leaving ability, such as a halogen atom, a hydroxy group, and the like. T, A, K, X, n, $G_3$, $R_2$ and $Q_2$ have the same definitions as T, A, K, X, n, $G_3$, $R_2$ and $Q_2$, respectively, in the Formula (1).

<59> The amide derivative according to <58>, which is represented by the Formula (61):

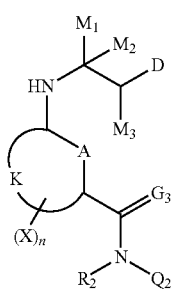

Formula (61)

Wherein $M_1$, $M_2$, $M_3$, D, A, K, X, n, $G_3$, $R_2$ and $Q_2$ have the same definitions as $M_2$, $M_3$, D, A, K, X, n, $G_3$, $R_2$ and $Q_2$, respectively, in the Formula (6c).

<60> A method for producing the amide derivative represented by the Formula (61) according to <59>, including reacting a compound represented by the following Formula (51) with a compound represented by the following Formula (62):

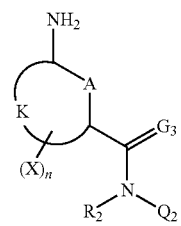

Formula (51)

Wherein $R_2$, A, K, X, n, $G_3$, and $Q_2$ have the same definitions as $R_2$, A, K, X, n, $G_3$, and $Q_2$, respectively, in the Formula (1).

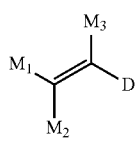

Formula (62)

Wherein $M_1$, $M_2$, $M_3$, and D have the same definitions as $M_1$, $M_2$, $M_3$, and D, respectively, in the Formula (1).

<61> The amide derivative according to <58>, wherein the compound represented by the Formula (6c) is represented by the following Formula (63):

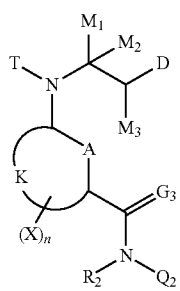

Formula (63)

Wherein T, $M_1$, $M_2$, $M_3$, D, A, K, X, n, $G_3$, $R_2$ and $Q_2$ have the same definitions as T, $M_1$, $M_2$, $M_3$, D, A, K, X, n, $G_3$, $R_2$ and $Q_2$, respectively, in the Formula (6c).

<62> A method for producing the amide derivative represented by the Formula (63) according to <61>, including reacting the compound represented by the following Formula (61) according to <59> with the compound represented by the following Formula (45) according to <39>:

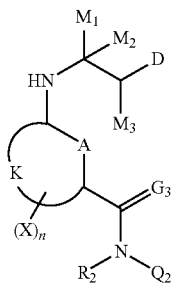

Formula (61)

Wherein A, K, $Q_2$, $R_2$, $G_3$, X, n, $M_1$, $M_2$, $M_3$ and D have the same definitions as A, K, $Q_2$, $R_2$, $G_3$, X, n, $M_1$, $M_2$, $M_3$ and D, respectively, in the Formula (6c).

T-LG    Formula (45)

Wherein LG represents a functional group having a leaving ability, such as a halogen atom, a hydroxy group, or the like, and T has the same definition as T in the Formula (1).

<63> The amide derivative according to <58>, wherein the compound represented by the Formula (6c) is represented by the following Formula (64):

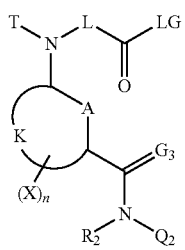

Formula (64)

Wherein LG represents a functional group having a leaving ability, such as a halogen atom, a hydroxy group, or the like, and T, A, K, $Q_2$, $R_2$, $G_3$, X, n, and L have the same definitions as T, A, K, $Q_2$, $R_2$, $G_3$, X, n, and L, respectively, in the Formula (6c).

<64> The amide derivative according to <58>, wherein the compound represented by the Formula (6c) is represented by the following Formula (65):

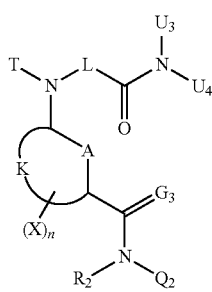

Formula (65)

Wherein T, L, $U_3$, $U_4$, A, K, X, n, $G_3$, $R_2$ and $Q_2$ have the same definitions as T, L, $U_3$, $U_4$, A, K, X, n, $G_3$, $R_2$ and $Q_2$, respectively, in the Formula (6c).

<65> A method for producing the amide derivative represented by the Formula (65) according to <64>, including reacting the compound represented by the following Formula (64) according to <63> with the compound represented by the following Formula (66):

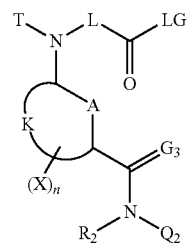

Formula (64)

Wherein LG represents a functional group having a leaving ability, such as a halogen atom, a hydroxy group, or the like, and T, A, K, $Q_2$, $R_2$, $G_3$, X, n, and L have the same definitions as T, A, K, $Q_2$, $R_2$, $G_3$, X, n, and L, respectively, in the Formula (6c).

Formula (66)

Wherein $U_3$ and $U_4$ have the same definitions as $U_3$ and $U_4$, respectively, in the Formula (1).

<66> The amide derivative according to <64>, wherein in the Formula (65), $U_4$ is a C2-C7 alkoxycarbonyl group which may have a substituent, a C2-C7 haloalkoxycarbonyl group which may have a substituent, a C2-C7 alkylcarbonyl group which may have a substituent, or a C2-C7 haloalkylcarbonyl group which may have a substituent.

<67> A method for producing the amide derivative represented by the Formula (65) according to <66>, including reacting the compound according to <64>, in which the compound represented by the Formula (65) is represented by the following Formula (68), with a compound represented by the following Formula (67):

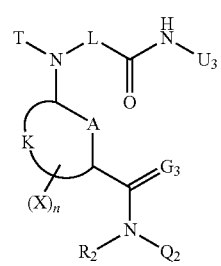

Formula (68)

Wherein T, L, $U_3$, A, K, X, n, $G_3$, $R_2$ and $Q_2$ have the same definitions as T, L, $U_3$, A, K, X, n, $G_3$, $R_2$ and $Q_2$, respectively, in the Formula (6c).

$U_4$-LG    Formula (67)

Wherein $U_4$ has the same definition as $U_4$ in <66>.

<68> A method for producing the aniline derivative represented by the following Formula (6e), including reacting the compound of the Formula (6d) in which $R_{2a}$ is a hydrogen atom, with the compound represented by the following Formula (49a) according to <17>:

$R_2a$-LG    Formula (49a)

Wherein LG represents a functional group having a leaving ability, such as a halogen atom, a hydroxy group, or the like, and $R_{2a}$ represents a trimethylsilyl group, a t-butyldimethylsilyl group, a cyano group, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C9 cycloalkyl group, a C3-C9 halocycloalkyl group, a C1-C6 alkylsulfinyl group, a C1-C6 haloalkylsulfinyl group, a C1-C6 alkylsulfonyl group, a C1-C6 haloalkylsulfonyl group, a benzenesulfonyl group, a benzylsulfonyl group, a C2-C7 alkylcarbonyl group, a C2-C7 haloalkylcarbonyl group, a C3-C7 alkenylcarbonyl group, a C3-C7 haloalkenylcarbonyl group, a C3-C7 alkynylcarbonyl group, a C3-C7 haloalkynylcarbonyl group, a C4-C10 cycloalkylcarbonyl group, a C4-C10 halocycloalkylcarbonyl group, a C2-C7 alkoxycarbonyl group, a C2-C7 haloalkoxycarbonyl group, a C3-C7 alkenyloxycarbonyl group, a C3-C7 haloalkenyloxycarbonyl group, a C3-C7 alkynyloxycarbonyl group, a C3-C7 haloalkynyloxycarbonyl group, a phenoxycarbonyl group, a C2-C7 alkylaminocarbonyl group, a C2-C7 haloalkylaminocarbonyl group, a C4-C10 cycloalkyloxycarbonyl group, a C4-C10 halocycloalkyloxycarbonyl group, a benzoyl group, a benzyl group, —C(=O)C(=O)$R_7$, wherein $R_7$ represents a C1-C6 alkyl group, a C1-C6 haloalkyl group, a C1-C6 alkoxy group, or a C1-C6 haloalkoxy group, or a group represented by -L-D, wherein L and D have the same definitions as L and D, respectively, in $R_2$.

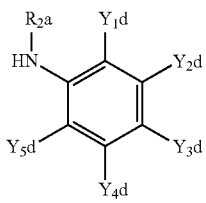

Formula (6e)

Wherein $R_{2a}$ has the same definition as $R_{2a}$ in the Formula (49a), and $Y_{1d}, Y_{2d}, Y_{3d}, Y_{4d}$, and $Y_{5d}$ have the same definitions as $Y_{1d}, Y_{2d}, Y_{3d}, Y_{4d}$, and $Y_{5d}$, respectively, in the Formula (6a).

<69> A method for producing the aniline derivative represented by the following Formula (6i), including reacting the compound of the Formula (6d) in which $R_{2a}$ is a hydrogen atom with an aldehyde:

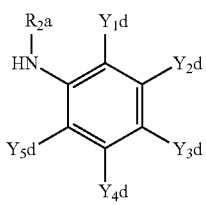

Formula (6i)

Wherein $R_{2a}$ represents a C1-C6 alkyl group, a C1-C6 haloalkyl group, or a benzyl group, and $Y_{1d}, Y_{2d}, Y_{3d}, Y_{4d}$ and $Y_{5d}$ have the same definitions as $Y_{1d}, Y_{2d}, Y_{3d}, Y_{4d}$, and $Y_{5d}$, respectively, in the Formula (6a).

<70> A pest control agent containing at least one kind of the amide derivative according to any one of <1> to <8> as an active ingredient.

<71> A pest controlling method including applying the pest control agent according to <70>.

Effects of the Invention

According to the present invention, an amide derivative exhibiting a pesticidal effect against various agricultural pests, having an effect of protection of useful crops, greatly contributing to reduction in an environmental impact owing to the use at a low dose, a pest control agent containing the amide derivative, and a pest controlling method can be provided.

BEST MODE FOR CARRYING OUT THE INVENTION

The amide derivative according to the present invention is a compound represented by the following Formula (1). It has a specific structure and thus exhibits an excellent pest control effect.

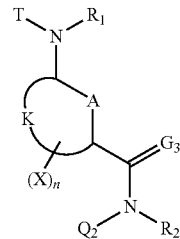

Formula (1)

In the formula, A represents a carbon atom, an oxygen atom, a nitrogen atom, an oxidized nitrogen atom, or a sulfur atom.

K represents a non-metal atom group necessary for forming a cyclic linking group derived from benzene, pyridine, pyridine-N-oxide, pyrimidine, pyrazine, pyridazine, triazine, pyrrole, pyrazole, imidazole, oxazole, isoxazole, thiazole, isothiazole, furan, thiophene, oxadiazole, thiodiazole, or triazole, in combination with A and two carbon atoms to which A bonds.

X represents a hydrogen atom, a halogen atom, a C1-C6 alkyl group, a C1-C6 haloalkyl group, a C3-C9 cycloalkyl group, a C3-C9 halocycloalkyl group, a C2-C6 alkenyl group, a C2-C6 haloalkenyl group, a C2-C6 alkynyl group, a C2-C6 haloalkynyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C1-C6 alkylsulfonyloxy group, a C1-C6 haloalkylsulfonyloxy group, a C2-C7 alkylcarbonyl group, a C2-C7 haloalkylcarbonyl group, a C2-C7 alkylcarbonyloxy group, a C2-C7 haloalkylcarbonyloxy group, an arylcarbonyloxy group, a C2-C7 alkoxycarbonyl group, a C2-C7 haloalkoxycarbonyl group, a C2-C7 alkylcarbonylamino group, a C2-C7 haloalkylcarbonylamino group, a C2-C7 alkoxycarbonylamino group, a C2-C7 haloalkoxycarbonylamino group, a C2-C7 alkoxycarbonyloxy group, a C2-C7 haloalkoxycarbonyloxy group, an arylcarbonylamino group, an amino group, a carbamoyl group, a cyano group, a nitro group, a hydroxy group, a pentafluorosulfanyl group, a C1-C6 alkylamino group, a C1-C6 haloalkylamino group, a C2-C6 alkenylamino group, a C2-C6 haloalkenylamino group, a C2-C6 alkynylamino group, a C2-C6 haloalkynylamino group, a C3-C9 cycloalkylamino group, a C3-C9 halocycloalkylamino group, a C2-C7 alkylaminocarbonyl group, a C2-C7 haloalkylaminocarbonyl group, a C3-C7 alkynylaminocarbonyl group, a C3-C7 haloalkenylaminocarbonyl group, a C3-C7 alkynylaminocarbonyl group, a C3-C7 haloalkynylaminocarbonyl group, a C4-C10 cycloalkylaminocarbonyl group, a C4-C10 halocycloalkylaminocarbonyl group, a phenyl group, or a heterocyclic group, and when there are plural X's, each X may be the same as or different from each other.

The heterocyclic group in X represents a pyridyl group, a pyridine-N-oxide group, a pyrimidinyl group, a pyrazinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrolyl group, an imidazolyl group, a triazolyl group, a pyrazolyl group, or a tetrazolyl group.

n represents an integer of from 0 to 4. Further, n represents a number of substituents which is not hydrogen atom.

T represents —C(=$G_1$)-$Q_1$ or —C(=$G_1$)-$G_2Q_3$.

In the formula, $G_1$ and $G_2$ each independently represent an oxygen atom or a sulfur -atom.

$Q_1$ and $Q_3$ each independently represent a hydrogen atom, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C9 cycloalkyl group, a C3-C9 halocycloalkyl group, a benzyl group, a phenyl group which may have a substituent, a naphthyl group which may have a substituent, or a heterocyclic group which may have a substituent.

$Q_2$ represents a phenyl group which may have a substituent, a naphthyl group which may have a substituent, a heterocyclic group which may have a substituent, or a tetrahydronaphthalene group which may have a substituent.

Further, in $Q_1$, $Q_3$, and $Q_2$, the substituent of a phenyl group which may have a substituent, a naphthyl group which may have a substituent, and a heterocyclic group which may have a substituent, and the substituent of a tetrahydronaphthalene group which may have a substituent represents one or more substituent selected from a group consisting of a halogen atom, a C1-C6 alkyl group, a C1-C6 haloalkyl group, a C3-C9 cycloalkyl group, a C3-C9 halocycloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C2-C7 alkylcarbonyl group, a C2-C7 haloalkylcarbonyl group, a C2-C7 alkylcarbonyloxy group, a C2-C7 haloalkylcarbonyloxy group, a C1-C6 alkylsulfonyloxy group, a C1-C6 haloalkylsulfonyloxy group, a C2-C7 alkoxycarbonyl group, a C2-C7 haloalkoxycarbonyl group, a C2-C7 alkylcarbonylamino group, a C2-C7 haloalkylcarbonylamino group, a C2-C7 alkoxycarbonylamino group, a C2-C7 haloalkoxycarbonylamino group, a C1-C6 alkylamino group, a C1-C6 haloalkylamino group, an amino group, a carbamoyl group, a sulfamoyl group, a cyano group, a nitro group, a hydroxy group, a carboxy group, a pentafluorosulfanyl group, a benzyloxy group, a benzyloxycarbonyl group, a phenyl group, a heterocyclic group, a benzoyl group, a phenylcarbamoyl group, and a phenylamino group, and when there are two or more substituents, the substituents may be the same as or different from each other.

Moreover, the heterocyclic group in $Q_1$, $Q_3$, and $Q_2$ has the same definition as the heterocyclic group in X.

$G_3$ represents an oxygen atom or a sulfur atom.

$R_1$ and $R_2$ each independently represent a hydrogen atom, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C9 cycloalkyl group, a C3-C9 halocycloalkyl group, a C1-C6 alkoxy group, a C1-C6 haloalkoxy group, a C2-C6 alkenyloxy group, a C2-C6 haloalkenyloxy group, a C2-C6 alkynyloxy group, a C2-C6 haloalkynyloxy group, a C3-C9 cycloalkoxy group, a C3-C9 halocycloalkoxy group, a C2-C7 alkylcarbonyl group, a C2-C7 haloalkylcarbonyl group, a C3-C7 alkenylcarbonyl group, a C3-C7 haloalkenylcarbonyl group, a C3-C7 alkynylcarbonyl group, a C3-C7 haloalkynylcarbonyl group, a C4-C10 cycloalkylcarbonyl group, a C4-C10 halocycloalkylcarbonyl group, a C2-C7 alkoxycarbonyl group, a C2-C7 haloalkoxycarbonyl group, a C3-C7 alkenyloxycarbonyl group, a C3-C7 haloalkenyloxycarbonyl group, a C3-C7 alkynyloxycarbonyl group, a C3-C7 haloalkynyloxycarbonyl group, a C4-C10 cycloalkyloxycarbonyl group, a C4-C10 halocycloalkyloxycarbonyl group, or, a group represented by -L-D, provided that at least either $R_1$ or $R_2$ represents a group represented by -L-D.

Wherein L represents —C($M_1$)($M_2$)—, —C($M_1$)($M_2$)-C($M_3$)($M_4$)—, —C($M_1$)=C($M_3$)—, —C≡C—, —C($M_1$)($M_2$)-C($M_3$)($M_4$)-C($M_5$)($M_6$)—, —C($M_1$)=C($M_3$)-C($M_5$)($M_6$)—, —C($M_1$)($M_2$)-C($M_3$)=C($M_5$)—, —C≡C—C($M_5$)($M_6$)—, —C($M_1$)($M_2$)-C≡C—, —C($M_1$)($M_2$)-C($M_3$)($M_4$)-C($M_5$)($M_6$)-C($M_7$)($M_8$)—, —C($M_1$)=C($M_3$)-C($M_5$)($M_6$)-C($M_7$)($M_8$)—, —C($M_1$)($M_2$)-C($M_3$)=C($M_5$)-C($M_7$)($M_8$)—, —C($M_1$)($M_2$)-C($M_3$)($M_4$)-C($M_5$)=C($M_7$)—, —C($M_1$)=C($M_3$)-C($M_5$)=C($M_7$)—, —C($M_1$)=C($M_3$)—C≡C—, —C≡C—C($M_5$)=C($M_7$)—, —C($M_1$)($M_2$)-C≡C—C($M_7$)($M_8$)—, —C($M_1$)($M_2$)-C($M_3$)($M_4$)-C≡C—, —C≡C—C($M_5$)=C($M_7$)—, or —C≡C—C≡C—.

$M_1$ to $M_8$ each independently represent a hydrogen atom, a halogen atom, a cyano group, a nitro group, an amino group, a carboxy group, a hydroxy group, a carbamoyl group, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C9 cycloalkyl group, a C3-C9 halocycloalkyl group, a C1-C6 alkoxy group, a C1-C6 haloalkoxy group, a C2-C6 alkenyloxy group, a C2-C6 haloalkenyloxy group, a C2-C6 alkynyloxy group, a C2-C6 haloalkynyloxy group, a C3-C9 cycloalkoxy group, a C3-C9 halocycloalkoxy group, a C1-C6 alkylthio group, a C1-C6 haloalkylthio group, a C2-C6 alkenylthio group, a C2-C6 haloalkenylthio group, a C2-C6 alkynylthio group, a C2-C6 haloalkynylthio group, a C1-C6 alkylsulfinyl group, a C1-C6 haloalkylsulfinyl group, a C2-C6 alkynylsulfinyl group, a C2-C6 haloalkenylsulfinyl group, a C2-C6 alkynylsulfinyl group, a C2-C6 haloalkynylsulfinyl group, a C3-C9 cycloalkylsulfinyl group, a C3-C9 halocycloalkylsulfinyl group, a C1-C6 alkylsulfonyl group, a C1-C6 haloalkylsulfonyl group, a C2-C6 alkenylsulfonyl group, a C2-C6 haloalkenylsulfonyl group, a C2-C6 alkynylsulfonyl group, a C2-C6 haloalkynylsulfonyl group, a C3-C9 cycloalkylsulfonyl group, a C3-C9 halocycloalkylsulfonyl group, a C2-C7 alkylcarbonyl group, a C2-C7 haloalkylcarbonyl group, a C3-C7 alkenylcarbonyl group, a C3-C7 haloalkenylcarbonyl group, a C3-C7 alkynylcarbonyl group, a C3-C7 haloalkynylcarbonyl group, a C4-C10 cycloalkylcarbonyl group, a C4-C10 halocycloalkylcarbonyl group, a C2-C7 alkoxycarbonyl group, a C2-C7 haloalkoxycarbonyl group, a C3-C7 alkenyloxycarbonyl group, a C3-C7 haloalkenyloxycarbonyl group, a C3-C7 alkynyloxycarbonyl group, a C3-C7 haloalkynyloxycarbonyl group, a C4-C10 cycloalkyloxycarbonyl group, a C4-C10 halocycloalkyloxycarbonyl group, a C1-C6 alkylamino group, a C1-C6 haloalkylamino group, a C2-C6 alkenylamino group, a C2-C6 haloalkenylamino group, a C2-C6 alkynylamino group, a C2-C6 haloalkynylamino group, a C3-C9 cycloalkylamino group, a C3-C9 halocycloalkylamino group, a C2-C7 alkylaminocarbonyl group, a C2-C7 haloalkylaminocarbonyl group, a C3-C7 alkenylaminocarbonyl group, a C3-C7 haloalkenylaminocarbonyl group, a C3-C7 alkynylaminocarbonyl group, a C3-C7 haloalkynylaminocarbonyl group, a C4-C10 cycloalkylaminocarbonyl group, a C4-C10 halocycloalkylaminocarbonyl group, a phenyl group, a naphthyl group, or a heterocyclic group.

D represents —C(=O)OU$_1$, —C(=O)U$_2$, —C(=O)NU$_3$U$_4$, —NU$_5$C(=O)U$_6$, —S—U$_7$, —S(=O)U$_8$, —S(=O)(=O)U$_9$, —S(=O)(=O)NU$_{10}$U$_{11}$, —OU$_{12}$, —NU$_{13}$U$_{14}$, —C(=NU$_{15}$)U$_{16}$, —NU$_{17}$—C(=NU$_{18}$)U$_{19}$, or —C≡N.

U$_1$ to U$_{19}$ each independently represent a hydrogen atom, a hydroxy group, an amino group, a cyano group, a nitro group, a C1-C6 alkyl group which may have a substituent, a C1-C6 haloalkyl group, a C2-C6 alkenyl group, a C2-C6 haloalkenyl group, a C2-C6 alkynyl group, a C2-C6 haloalkynyl group, a C3-C9 cycloalkyl group, a C3-C9 halocycloalkyl group, a C2-C7 alkoxycarbonyl group, a C2-C7 haloalkoxycarbonyl group, a C2-C7 alkylcarbonyl group, a C2-C7 haloalkylcarbonyl group, a C1-C3 alkylamino group, a C1-C3 haloalkylamino group, a phenyl group, a naphthyl group, or a heterocyclic group.

U$_3$ and U$_4$, U$_5$ and U$_6$, U$_{10}$ and U$_{11}$, U$_{12}$ and L, U$_{13}$ and U$_{14}$, U$_{15}$ and U$_{16}$, and U$_{17}$ to U$_{19}$ may be linked with each other to form a saturated heterocyclic group.

However, in a case where D represents —OU$_{12}$ and L represents a methylene group, U$_{12}$ represents a hydrogen atom, a hydroxy group, an amino group, a cyano group, a nitro group, a C2-C6 alkyl group which may have a substituent, a C1-C6 haloalkyl group, a C2-C6 alkenyl group, a C2-C6 haloalkenyl group, a C2-C6 alkynyl group, a C2-C6 haloalkynyl group, a C3-C9 cycloalkyl group, a C3-C9 halocycloalkyl group, a C2-C7 alkoxycarbonyl group, a C2-C7 haloalkoxycarbonyl group, a C2-C7 alkylcarbonyl group, a C2-C7 haloalkylcarbonyl group, a C1-C3 alkylamino group, a C1-C3 haloalkylamino group, a phenyl group, a naphthyl group, or a heterocyclic group The terms used in the formulae including the Formula (1) and the like according to the present invention have the same meanings as described below in the definitions.

The "halogen atom" represents a fluorine atom, a chlorine atom, a bromine atom, or an iodine atom.

The expression "Ca-Cb (wherein a and b represent an integer of 1 or more)", for example, "C1-C3" means the number of carbon atoms of from 1 to 3, the "C2-C6" means the number of carbon atoms of from 2 to 6, and the "C1-C4" means the number of carbon atoms of from 1 to 4.

"n-" means normal, "i-" means iso, "s-" means secondary, and "t-" means tertiary.

The "C1-C6 alkyl group" in the present invention represents, for example, a linear or branched alkyl group having from 1 to 6 carbon atoms such as methyl, ethyl, n-propyl, propyl, n-butyl, s-butyl, t-butyl, n-pentyl, 2-pentyl, neopentyl, 4-methyl-2-pentyl, n-hexyl, 3-methyl-n-pentyl, and the like.

Furthermore, in a case where only the number of carbon atoms constituting the same substituent is different, specific examples in which there is a matching number of carbon atoms among the specific examples of the substituent shown below become the corresponding specific examples.

The "C1-C6 haloalkyl group" represents, for example, a linear or branched alkyl group having from 1 to 6 carbon atoms, that is substituted with one or more halogen atoms which may be the same as or different from each other, such as trifluoromethyl, pentafluoroethyl, heptafluoro-n-propyl, heptafluoro-1-propyl, 2,2-difluoroethyl, 2,2-dichloroethyl, 2,2,2-trifluoroethyl, 2-fluoroethyl, 2-chloroethyl, 2-bromoethyl, 2-iodoethyl, 2,2,2-trichloroethyl, 2,2,2-tribromoethyl, 1,3-difluoro-2-propyl, 1,3-dichloro-2-propyl, 1-chloro-3-fluoro-2-propyl, 1,1,1-trifluoro-2-propyl, 2,3,3,3-trifluoro-n-propyl, 4,4,4-trifluoro-n-butyl, 1,1,1,3,3,3-hexafluoro-2-propyl, 1,1,1,3,3,3-hexafluoro-2-chloro-2-propyl, 1,1,1,3,3,3-hexafluoro-2-bromo-2-propyl, 1,1,2,3,3,3-hexafluoro-2-chloro-n-propyl, 1,1,2,3,3,3-hexafluoro-2-bromo-n-propyl, 1,1,2,3,3,3-hexafluoro-1-bromo-2-propyl, 2,2,3,3,3-pentafluoro-n-propyl, 3-fluoro-n-propyl, 3-chloro-n-propyl, 3-bromo-n-propyl, 3,3,4,4,4-pentafluoro-2-butyl, nonafluoro-n-butyl, nonafluoro-2-butyl, 5,5,5-trifluoro-n-pentyl, 4,4,5,5,5-pentafluoro-2-pentyl, 3-chloro-n-pentyl, 4-bromo-2-pentyl, and the like.

The "C3-C9 cycloalkyl group" represents, for example, a cycloalkyl group having from 3 to 9 carbon atoms, that has a cyclic structure, such as cyclopropyl, cyclobutyl, cyclopentyl, 2-methylcyclopentyl, 3-methylcyclopentyl, cyclohexyl, 2-methylcyclohexyl, 3-methylcyclohexyl, 4-methylcyclohexyl, and the like.

The "C3-C9 halocycloalkyl group" represents, for example, a cycloalkyl group having from 3 to 9 carbon atoms, that is substituted with one or more halogen atoms which may be the same as or different from each other and has a cyclic structure, such as, 2,2,3,3-tetrafluorocyclobutyl, 2-chlorocyclohexyl, 4-chlorocyclohexyl, and the like.

The "C2-C6 alkenyl group" represents, for example, an alkenyl group having from 2 to 6 carbon atoms, that has a double bond in the carbon chain, such as vinyl, allyl, 2-butenyl, 3-butenyl, and the like.

The "C2-C6 haloalkenyl group" represents, for example, a linear or branched alkenyl group having from 2 to 6 carbon atoms, that is substituted with one or more halogen atoms which may be the same as or different from each other and has a double bond in the carbon chain, such as 3,3-difluoro-2-propenyl, 3,3-dichloro-2-propenyl, 3,3-dibromo-2-propenyl, 2,3-dibromo-2-propenyl, 4,4-difluoro-3-butenyl, 3,4,4-tribromo-3-butenyl, and the like.

The "C2-C6 alkynyl group" represents, for example, an alkynyl group having from 2 to 6 carbon atoms, that has a triple bond in the carbon chain, such as propargyl, 1-butyn-3-yl, 1-butyn-3-methyl-3-yl, and the like.

The "C2-C6 haloalkynyl group" represents, for example, a linear or branched alkynyl group having from 2 to 6 carbon atoms, that is substituted with one or more halogen atoms which may be the same as or different from each other and has a triple bond in the carbon chain, such as fluoroethynyl, chloroethynyl, bromoethynyl, 3,3,3-trifluoro-1-propynyl, 3,3,3-trichloro-1-propynyl, 3,3,3-tribromo-1-propynyl, 4,4,4-trifluoro-1-butynyl, 4,4,4-trichloro-1-butynyl, 4,4,4-tribromo-1-butynyl, and the like.

The "C1-C6 alkoxy group" represents, for example, a linear, branched, or cyclic alkoxy group having from 1 to 6 carbon atoms, such as methoxy, ethoxy, n-propyloxy, i-propyloxy, cyclopropoxy, n-butoxy, s-butoxy, i-butoxy, t-butoxy, n-pentyloxy, i-pentyloxy, n-hexyloxy, cyclohexyloxy, and the like.

The "C1-C6 haloalkoxy group" represents, for example, a linear, branched, or cyclic alkoxy group having from 1 to 6 carbon atoms, that is substituted with one or more halogen atoms which may be the same as or different from each other, such as trifluoromethoxy, pentafluoroethoxy, 2-chloroethoxy, 2,2,2-trifluoroethoxy, heptafluoro-n-propoxy, heptafluoro-1-propoxy, 1,1,1,3,3,3-hexafluoro-2-propoxy, 3-fluoro-n-propoxy, 1-chlorocyclopropoxy, 2-bromocyclopropoxy, 3,3,4,4,4-pentafluoro-2-butoxy, nonafluoro-n-butoxy, nonafluoro-2- butoxy, 5,5,5-trifluoro-n-pentyloxy, 4,4,5,5,5-pentafluoro-2-pentyloxy, 3-chloro-n-pentyloxy, 4-bromo-2-pentyloxy, 4-chlorobutyloxy, 2-iodo-n-propyloxy, and the like.

The "C1-C6 alkylthio group" represents, for example, a linear, branched, or cyclic alkylthio group having from 1 to 6 carbon atoms, such as methylthio, ethylthio, n-propylthio, i-propylthio, cyclopropylthio, n-butylthio, s-butylthio, i-butylthio, t-butylthio, n-pentylthio, i-pentylthio, n-hexylthio, cyclohexylthio, and the like.

The "C1-C6 haloalkylthio group" represents, for example, a linear, branched, or cyclic alkylthio group having from 1 to 6 carbon atoms, that is substituted with one or more halogen atoms which may be the same as or different from each other, such as trifluoromethylthio, pentafluoroethylthio, 2-chloroethylthio, 2,2,2-trifluoroethylthio, heptafluoro-n-propylthio, heptafluoro-1-propylthio, 1,1,1,3,3,3-hexafluoro-2-propylthio, 3-fluoro-n-propylthio, 1-chlorocyclopropylthio, 2-bromocyclopropylthio, 3,3,4,4,4-pentafluoro-2-butylthio, nonafluoro-n-butylthio, nonafluoro-2-butylthio, 5,5,5-trifluoro-n-pentylthio, 4,4,5,5,5-pentafluoro-2-pentylthio, 3-chloro-n-pentylthio, 4-bromo-2-pentylthio, 4-chlorobutylthio, 2-iodo-n-propylthio, and the like.

The "C1-C6 alkylsulfinyl group" represents, for example, a linear, branched, or cyclic alkylsulfinyl group having from 1 to 6 carbon atoms, such as methylsulfinyl, ethylsulfinyl, n-propylsulfinyl, i-propylsulfinyl, cyclopropylsulfinyl, n-butylsulfinyl, s-butylsulfinyl, i-butylsulfinyl, t-butylsulfinyl, n-pentylsulfinyl, i-pentylsulfinyl, n-hexylsulfinyl, cyclohexylsulfinyl, and the like.

The "C1-C6 haloalkylsulfinyl group" represents, for example, a linear, branched, or cyclic alkylsulfinyl group having from 1 to 6 carbon atoms, that is substituted with one or more halogen atoms which may be the same as or different from each other, such as trifluoromethylsulfinyl, pentafluoroethylsulfinyl, 2-chloroethylsulfinyl, 2,2,2-trifluoroethylsulfinyl, heptafluoro-n-propylsulfinyl, heptafluoro-1-propylsulfinyl, 1,1,1,3,3,3-hexafluoro-2-propylsulfinyl, 3-fluoro-n-propylsulfinyl, 1-chlorocyclopropylsulfinyl, 2-bromocyclopropylsulfinyl, 3,3,4,4,4-pentafluoro-2-butylsulfinyl, nonafluoro-n-butylsulfinyl, nonafluoro-2-butylsulfinyl, 5,5,5-trifluoro-n-pentylsulfinyl, 4,4,5,5,5-pentafluoro-2-pentylsulfinyl, 3-chloro-n-pentylsulfinyl, 4-bromo-2-pentylsulfinyl, 4-chlorobutylsulfinyl, 2-iodo-n-propylsulfinyl, and the like.

The "C1-C6 alkylsulfonyl group" represents, for example, a linear, branched, or cyclic alkylsulfonyl group having from 1 to 6 carbon atoms, such as methylsulfonyl, ethylsulfonyl, n-propylsulfonyl, i-propylsulfonyl, cyclopropylsulfonyl, n-butylsulfonyl, s-butylsulfonyl, i-butylsulfonyl, t-butylsulfonyl, n-pentylsulfonyl, i-pentylsulfonyl, n-hexylsulfonyl, cyclohexylsulfonyl, and the like.

The "C1-C6 haloalkylsulfonyl group" represents, for example, a linear, branched, or cyclic alkylsulfonyl group having from 1 to 6 carbon atoms, that is substituted with one or more halogen atoms which may be the same as or different from each other, such as trifluoromethylsulfonyl, pentafluoroethylsulfonyl, 2-chloroethylsulfonyl, 2,2,2-trifluoroethylsulfonyl, heptafluoro-n-propylsulfonyl, heptafluoro-1-propylsulfonyl, 1,1,1,3,3,3-hexafluoro-2-propylsulfonyl, 3-fluoro-n-propylsulfonyl, 1-chlorocyclopropylsulfonyl, 2-bromocyclopropylsulfonyl, 3,3,4,4,4-pentafluoro-2-butylsulfonyl, nonafluoro-n-butylsulfonyl, nonafluoro-2-butylsulfonyl, 5,5,5-trifluoro-n-pentylsulfonyl, 4,4,5,5,5-pentafluoro-2-pentylsulfonyl, 3-chloro-n-pentylsulfonyl, 4-bromo-2-pentylsulfonyl, 4-chlorobutylsulfonyl, 2-iodo-n-propylsulfonyl, and the like.

The "C1-C6 alkylsulfonyloxy group" represents, for example, a linear, branched, or cyclic alkylsulfonyloxy group having from 1 to 6 carbon atoms, such as methanesulfonyloxy, ethanesulfonyloxy, n-propanesulfonyloxy, i-propanesulfonyloxy, cyclopropanesulfonyloxy, n-butanesulfonyloxy, s-butanesulfonyloxy, i-butanesulfonyloxy, t-butanesulfonyloxy, n-pentanesulfonyloxy, i-pentanesulfonyloxy, n-hexanesulfonyloxy, cyclohexanesulfonyloxy, and the like.

The "C1-C6 haloalkylsulfonyloxy group" represents, for example, a linear, branched, or cyclic alkylsulfonyloxy group having from 1 to 6 carbon atoms, that is substituted with one or more halogen atoms which may be the same as or different from each other, such as trifluoromethanesulfonyloxy, pentafluoropropanesulfonyloxy, 2-chloropropanesulfonyloxy, 2,2,2-trifluoropropanesulfonyloxy, heptafluoro-n-propanesulfonyloxy, heptafluoro-1-propanesulfonyloxy, 1,1,1,3,3,3-hexafluoro-2-propanesulfonyloxy, 3-fluoro-n-propanesulfonyloxy, 1-chlorocyclopropanesulfonyloxy, 2-bromocyclopropanesulfonyloxy, 3,3,4,4,4-pentafluoro-2-butanesulfonyloxy, nonafluoro-n-butanesulfonyloxy, nonafluoro-2-butanesulfonyloxy, 5,5,5-trifluoro-n-pentanesulfonyloxy, 4,4,5,5,5-pentafluoro-2-pentanesulfonyloxy, 3-chloro-n-pentanesulfonyloxy, 4-bromo-2-pentanesulfonyloxy, 4-chlorobutanesulfonyloxy, 2-iodo-n-propanesulfonyloxy, and the like.

The "C2-C7 alkylcarbonyl group" represents, for example, a linear, branched, or cyclic alkylcarbonyl group having from 2 to 7 carbon atoms, such as acetyl, propionyl, propylcarbonyl, cyclopropylcarbonyl, n-butylcarbonyl, s-butylcarbonyl, t-butylcarbonyl, n-pentylcarbonyl, 2-pentylcarbonyl, neopentylcarbonyl, cyclopentylcarbonyl, and the like.

The "C2-C7 haloalkylcarbonyl group" represents, for example, a linear, branched, or cyclic alkylcarbonyl group having from 2 to 7 carbon atoms, that is substituted with one or more halogen atoms which may be the same as or different from each other, such as trifluoroacetyl, pentafluoropropionyl, 2-chloropropionyl, 2,2,2-trifluoropropionyl, heptafluoro-n-propylcarbonyl, heptafluoro-1-propylcarbonyl, 1,1,1,3,3,3-hexafluoro-2-propylcarbonyl, 3-fluoro-n-propylcarbonyl, 1-chlorocyclopropylcarbonyl, 2-bromocyclopropylcarbonyl, 3,3,4,4,4-pentafluoro-2-butylcarbonyl, nonafluoro-n-butylcarbonyl, nonafluoro-2-butylcarbonyl, 5,5,5-trifluoro-n-pentylcarbonyl, 4,4,5,5,5-pentafluoro-2-pentylcarbonyl, 3-chloro-n-pentylcarbonyl, 4-bromo-2-pentylcarbonyl, 4-chlorobutylcarbonyl, 2-iodo-n-propylcarbonyl, and the like.

The "C2-C7 alkylcarbonyloxy group" represents, for example, a linear, branched, or cyclic alkylcarbonyloxy group having from 2 to 7 carbon atoms, such as acetyloxy, propionyloxy, i-propylcarbonyloxy, cyclopropylcarbonyloxy, n-butylcarbonyloxy, s-butylcarbonyloxy, t-butylcarbonyloxy, n-pentylcarbonyloxy, 2-pentylcarbonyloxy, neopentylcarbonyloxy, cyclopentylcarbonyloxy, and the like.

The "C2-C7 haloalkylcarbonyloxy group" represents, for example, a linear, branched, or cyclic alkylcarbonyloxy group having from 2 to 7 carbon atoms, that is substituted with one or more halogen atoms which may be the same as or different from each other, such as trifluoroacetyloxy, pentafluoropropionyloxy, 2-chloropropionyloxy, 2,2,2-trifluoropropionyloxy, heptafluoro-n-propylcarbonyloxy, heptafluoro-1-propylcarbonyloxy, 1,1,1,3,3,3-hexafluoro-2-propylcarbonyloxy, 3-fluoro-n-propylcarbonyloxy, 1-chlorocyclopropylcarbonyloxy, 2-bromocyclopropylcarbonyloxy, 3,3,4,4,4-pentafluoro-2-butylcarbonyloxy, nonafluoro-n-butylcarbonyloxy, nonafluoro-2-butylcarbonyloxy, 5,5,5-trifluoro-n-pentylcarbonyloxy, 4,4,5,5,5-pentafluoro-2-pentylcarbonyloxy, 3-chloro-n- pentylcarbonyloxy, 4-bromo-2-pentylcarbonyloxy, 4-chlorobutylcarbonyloxy, 2-iodo-n-propylcarbonyloxy, and the like.

The "C2-C7 alkoxycarbonyl group" represents, for example, a linear, branched, or cyclic alkoxycarbonyl group having from 2 to 7 carbon atoms, such as methoxycarbonyl, ethoxycarbonyl, isopropoxycarbonyl, cyclopropoxycarbonyl, n-butoxycarbonyl, s-butoxycarbonyl, t-butoxycarbonyl, n-pentyloxycarbonyl, 2-pentyloxycarbonyl, neopentyloxycarbonyl, cyclopentyloxycarbonyl, and the like.

The "C2-C7 haloalkoxycarbonyl group" represents, for example, a linear, branched, or cyclic alkoxycarbonyl group having from 2 to 7 carbon atoms, that is substituted with one or more halogen atoms which may be the same as or different from each other, such as trifluoromethoxycarbonyl, pentafluoroethoxycarbonyl, 2-chloroethoxycarbonyl, 2,2,2-trifluoroethoxycarbonyl, heptafluoro-n-propoxycarbonyl, heptafluoro-1-propoxycarbonyl, 1,1,1,3,3,3-hexafluoro-2-propoxycarbonyl, 3-fluoro-n-propoxycarbonyl, 1-chlorocyclopropoxycarbonyl, 2-bromocyclopropoxycarbonyl, 3,3,4,4,4-pentafluoro-2-butoxycarbonyl, nonafluoro-n-butoxycarbonyl, nonafluoro-2-butoxycarbonyl, 5,5,5-trifluoro-n-pentyloxycarbonyl, 4,4,5,5,5-pentafluoro-2-pentyloxycarbonyl, 3-chloro-n-pentyloxycarbonyl, 4-bromo-2-pentyloxycarbonyl, 4-chlorobutyloxycarbonyl, 2-iodo-n-propyloxycarbonyl, and the like.

The aryl group in the "arylcarbonyloxy group" and the "arylcarbonylamino group" represents, for example, a phenyl group, a naphthyl group, or the like.

The "C2-C7 alkylcarbonylamino group" represents, thr example, a linear, branched, or cyclic alkylcarbonylamino group having from 2 to 7 carbon atoms, such as acetylamino, propionylamino, n-propylcarbonylamino, i-propylcarbonylamino, cyclopropylcarbonylamino, n-butylcarbonylamino, s-butylcarbonylamino, i-butylcarbonylamino, t-butylcarbonylamino, n-pentylcarbonylamino, i-pentylcarbonylamino, n-hexylcarbonylamino, cyclohexylcarbonylamino, and the like.

The "C2-C7 haloalkylcarbonylamino group" represents, for example, a linear, branched, or cyclic alkylcarbonylamino group having from 2 to 7 carbon atoms, that is substituted with one or more halogen atoms which may be the same as or different from each other, such as trifluoroacetylamino, pentafluoropropionylamino, 2-chloropropionylamino, 2,2,2-trifluoropropionylamino, heptafluoro-n-propylcarbonylamino, heptafluoro-1-propylcarbonylamino, 1,1,1,3,3,3-hexafluoro-2-propylcarbonylamino, 3-fluoro-n-propylcarbonylamino, 1-chlorocyclopropylcarbonylamino, 2-bromocyclopropylcarbonylamino, 3,3,4,4,4-pentafluoro-2-butylcarbonylamino, nonafluoro-n-butylcarbonylamino, nonafluoro-2-butylcarbonylamino, 5,5,5-trifluoro-n-pentylcarbonylamino, 4,4,5,5,5-pentafluoro-2-pentylcarbonylamino, 3-chloro-n-pentylcarbonylamino, 4-bromo-2-pentylcarbonylamino, 4-chlorobutylcarbonylamino, 2-iodo-n-propylcarbonylamino, and the like.

The "C2-C7 alkoxycarbonylamino group" represents, for example, a linear, branched, or cyclic alkoxycarbonylamino group having from 2 to 7 carbon atoms, such as methoxycarbonylamino, ethoxycarbonylamino, n-propyloxycarbonylamino, i-propyloxycarbonylamino, cyclopropoxycarbonylamino, n-butoxycarbonylamino, s-butoxycarbonylamino, i-butoxycarbonylamino, t-butoxycarbonylamino, n-pentyloxycarbonylamino, i-pentyloxycarbonylamino, n-hexyloxycarbonylamino, cyclohexyloxycarbonylamino, and the like.

The "C2-C7 haloalkoxycarbonylamino group" represents, for example, a linear, branched, or cyclic alkoxycarbonylamino group having from 2 to 7 carbon atoms, that is substituted with one or more halogen atoms which may be the same as or different from each other, such as trifluoromethoxycarbonylamino, pentafluoroethoxycarbonylamino, 2-chloroethoxycarbonylamino, 2,2,2-trifluoroethoxycarbonylamino, heptafluoro-n-propoxycarbonylamino, heptafluoro-1-propoxycarbonylamino, 1,1,1,3,3,3-hexafluoro-2-propoxycarbonylamino, 3-fluoro-n-propoxycarbonylamino, 1-chlorocyclopropoxycarbonylamino, 2-bromocyclopropoxycarbonylamino, 3,3,4,4,4-pentafluoro-2-butoxycarbonylamino, nonafluoro-n-butoxycarbonylamino, nonafluoro-2-butoxycarbonylamino, 5,5,5-trifluoro-n-pentyloxycarbonylamino, 4,4,5,5,5-pentafluoro-2-pentyloxycarbonylamino, 3-chloro-n-pentyloxycarbonylamino, 4-bromo-2-pentyloxycarbonylamino, 4-chlorobutyloxycarbonylamino, 2-iodo-n-propyloxycarbonylamino, and the like.

The "C2-C7 alkoxycarbonyloxy group" represents, for example, a linear, branched, or cyclic alkoxycarbonyloxy group having from 2 to 7 carbon atoms, such as methoxycarbonyloxy, ethoxycarbonyloxy, n-propyloxycarbonyloxy, i-propyloxycarbonyloxy, cyclopropoxycarbonyloxy, n-butoxycarbonyloxy, s-butoxycarbonyloxy, i-butoxycarbonyloxy, t-butoxycarbonyloxy, n-pentyloxycarbonyloxy, i-pentyloxycarbonyloxy, n-hexyloxycarbonyloxy, cyclohexyloxycarbonyloxy, and the like.

The "C2-C7 haloalkoxycarbonyloxy group" represents, for example, a linear, branched, or cyclic alkoxycarbonyloxy group having from 2 to 7 carbon atoms, that is substituted with one or more halogen atoms which may be the same as or different from each other, such as trifluoromethoxycarbonyloxy, pentafluoroethoxycarbonyloxy, 2-chloroethoxycarbonyloxy, 2,2,2-trifluoroethoxycarbonyloxy, heptafluoro-n-propoxycarbonyloxy, heptafluoro-1-propoxycarbonyloxy, 1,1,1,3,3,3-hexafluoro-2-propoxycarbonyloxy, 3-fluoro-n-propoxycarbonyloxy, 1-chlorocyclopropoxycarbonyloxy, 2-bromocyclopropoxycarbonyloxy, 3,3,4,4,4-pentafluoro-2-butoxycarbonyloxy, nonafluoro-n-butoxycarbonyloxy, nonafluoro-2-butoxycarbonyloxy, 5,5,5-trifluoro-n-pentyloxycarbonyloxy, 4,4,5,5,5-pentafluoro-2-pentyloxycarbonyloxy, 3-chloro-n-pentyloxycarbonyloxy, 4-bromo-2-pentyloxycarbonyloxy, 4-chlorobutyloxycarbonyloxy, 2-iodo-n-propyloxycarbonyloxy, and the like.

The "C1-C6 alkylamino group" represents, for example, a linear, branched, or cyclic alkylamino group having from 1 to 6 carbon atoms, such as methylamino, dimethylamino, ethylamino, diethylamino, n-propylamino, i-propylamino, cyclopropylamino, n-butylamino, s-butylamino, i-butylamino, t-butylamino, n-pentylamino, i-pentylamino, n-hexylamino, cyclohexylamino, and the like.

The "C1-C6 haloalkylamino group" represents, for example, a linear, branched, or cyclic alkylamino group having from 1 to 6 carbon atoms substituted with one or more halogen atoms which may be the same as or different from each other, such as trifluoromethylamino, ditrifluoromethylamino, pentafluoroethylamino, dipentafluoroethylamino, 2-chloroethylamino, 2,2,2-trifluoroethylamino, heptafluoro-n-propylamino, heptafluoro-1-propylamino, 1,1,1,3,3,3-hexafluoro-2-propylamino, 3-fluoro-n-propylamino, 1-chlorocyclopropylamino, 2-bromocyclopropylamino, 3,3,4,4,4-pentafluoro-2-butylamino, nonafluoro-n-butylamino, nonafluoro-2-butylamino, 5,5,5-trifluoro-n-pentylamino, 4,4,5,5,5-pentafluoro-2-pentylamino, 3-chloro-n-pentylamino, 4-bromo-2-pentylamino, 4-chlorobutylamino, 2-iodo-n-propylamino, and the like.

The "C2-C6 alkenyloxy group" represents, for example, an alkenyloxy group having from 2 to 6 carbon atoms, that has a double bond in the carbon chain, such as vinyloxy, allyloxy, 2-butenyloxy, 3-butenyloxy, and the like.

The "C2-C6 haloalkenyloxy group" represents, for example, a linear or branched alkenyloxy group having from 2 to 6 carbon atoms, that is substituted with one or more halogen atoms which may be the same as or different from each other and has a double bond in the carbon chain, such as 3,3-difluoro-2-propenyloxy, 3,3-dichloro-2-propenyloxy, 3,3-dibromo-2-propenyloxy, 2,3-dibromo-2-propenyloxy, 4,4-difluoro-3-butenyloxy, 3,4,4-tribromo-3-butenyloxy, and the like.

The "C2-C6 alkynyloxy group" represents, for example, an alkynyloxy group having from 2 to 6 carbon atoms, that has a triple bond in the carbon chain, such as propargyloxy, 1-butyn-3-yloxy, 1-butyn-3-methyl-3-yloxy, and the like.

The "C2-C6 haloalkynyloxy group" represents, for example, a linear or branched alkynyloxy group having from 2 to 6 carbon atoms, that is substituted with one or more halogen atoms which may be the same as or different from each other and has a triple bond in the carbon chain, such as fluoroethynyloxy, chloroethynyloxy, bromoethynyloxy, 3,3,3-trifluoro-1-propynyloxy, 3,3,3-trichloro-1-propynyloxy, 3,3,3-tribromo-1-propynyloxy, 4,4,4-trifluoro-1-butynyloxy, 4,4,4-trichloro-1-butynyloxy, 4,4,4-tribromo-1-butynyloxy, and the like.

The "C3-C9 cycloalkoxy group" represents, for example, a cycloalkyloxy group having from 3 to 9 carbon atoms, that has a cyclic structure, such as cyclopropyloxy, cyclobutyloxy, cyclopentyloxy, 2-methylcyclopentyloxy, 3-methylcyclopentyloxy, cyclohexyloxy, 2-methylcyclohexyloxy, 3-methylcyclohexyloxy, 4-methylcyclohexyloxy, and the like.

The "C3-C9 halocycloalkoxy group" represents, for example, a cycloalkyloxy group having from 3 to 9 carbon atoms, that is substituted with one or more halogen atoms which may be the same as or different from each other and has a cyclic structure, such as 2,2,3,3-tetrafluorocyclobutyloxy, 2-chlorocyclohexyloxy, 4-chlorocyclohexyloxy, and the like.

The "C2-C6 alkenylthio group" represents, for example, an alkenylthio group having from 2 to 6 carbon atoms, that has a double bond in the carbon chain, such as vinylthio, allylthio, 2-butenylthio, 3-butenylthio, and the like.

The "C2-C6 haloalkenylthio group" represents, for example, a linear or branched alkenylthio group having from 2 to 6 carbon atoms, that is substituted with one or more halogen atoms which may be the same as or different from each other and has a double bond in the carbon chain, such as 3,3-difluoro-2-propenylthio, 3,3-dichloro-2-propenylthio, 3,3-dibromo-2-propenylthio, 2,3-dibromo-2-propenylthio, 4,4-difluoro-3-butenylthio, 3,4,4-tribromo-3-butenylthio, and the like.

The "C2-C6 alkynylthio group" represents, for example, an alkynylthio group having from 2 to 6 carbon atoms, that has a triple bond in the carbon chain, such as propargylthio, 1-butyn-3-ylthio, 1-butyn-3-methyl-3-ylthio, and the like.

The "C2-C6 haloalkynylthio group" represents, for example, a linear or branched alkynylthio group having from 2 to 6 carbon atoms, that is substituted with one or more halogen atoms which may be the same as or different from each other and has a triple bond in the carbon chain.

The "C2-C6 alkenylsulfinyl group" represents, for example, an alkenylsulfinyl group having from 2 to 6 carbon atoms, that has a double bond in the carbon chain, such as vinylsulfinyl, allylsulfinyl, 2-butenylsulfinyl, 3-butenylsulfinyl, and the like.

The "C2-C6 haloalkenylsulfinyl group" represents, for example, a linear or branched alkenylsulfinyl group having from 2 to 6 carbon atoms, that is substituted with one or more halogen atoms which may be the same as or different from each other and has a double bond in the carbon chain, such as 3,3-difluoro-2-propenylsulfinyl, 3,3-dichloro-2-propenylsulfinyl, 3,3-dibromo-2-propenylsulfinyl, 2,3-dibromo-2-propenylsulfinyl, 4,4-difluoro-3-butenylsulfinyl, 3,4,4-tribromo-3-butenylsulfinyl, and the like.

The "C2-C6 alkynylsulfinyl group" represents, for example, an alkynylsulfinyl group having from 2 to 6 carbon atoms, that has a triple bond in the carbon chain, such as propargylsulfinyl, 1-butyn-3-ylsulfinyl, 1-butyn-3-methyl-3-ylsulfinyl, and the like.

The "C2-C6 haloalkynylsulfinyl group" represents, for example, a linear or branched alkynylsulfinyl group having from 2 to 6 carbon atoms, that is substituted with one or more halogen atoms which may be the same as or different from each other and has a triple bond in the carbon chain.

The "C3-C9 cycloalkylsulfinyl group" represents, for example, a cycloalkylsulfinyl group having from 3 to 9 carbon atoms, that has a cyclic structure, such as cyclopropylsulfinyl, cyclobutylsulfinyl, cyclopentylsulfinyl, 2-methylcyclopentylsulfinyl, 3-methylcyclopentylsulfinyl, cyclohexylsulfinyl, 2-methylcyclohexylsulfinyl, 3-methylcyclohexylsulfinyl, 4-methylcyclohexylsulfinyl, and the like.

The "C3-C9 halocycloalkylsulfinyl group" represents, for example, a cycloalkylsulfinyl group having from 3 to 9 carbon atoms, that is substituted with one or more halogen atoms which may be the same as or different from each other and has a cyclic structure, such as 2,2,3,3-tetrafluorocyclobutylsulfinyl, 2-chlorocyclohexylsulfinyl, 4-chlorocyclohcxylsulfinyl, and the like.

The "C2-C6 alkenylsulfonyl group" represents, for example, an alkenylsulfonyl group having from 2 to 6 carbon atoms, that has a double bond in the carbon chain, such as vinylsulfonyl, allylsulfonyl, 2-butenylsulfonyl, 3-butenylsulfonyl, and the like.

The "C2-C6 haloalkenylsulfonyl group" represents, for example, a linear or branched alkenylsulfonyl group having from 2 to 6 carbon atoms, that is substituted with one or more halogen atoms which may be the same as or different from each other and has a double bond in the carbon chain, such as 3,3-difluoro-2-propenylsulfonyl, 3,3-dichloro-2-propenylsulfonyl, 3,3-dibromo-2-propenylsulfonyl, 2,3-dibromo-2-propenylsulfonyl, 4,4-difluoro-3-butenylsulfonyl, 3,4,4-tribromo-3-butenylsulfonyl, and the like.

The "C2-C6 alkynylsulfonyl group" represents, for example, an alkynylsulfonyl group having from 2 to 6 carbon atoms, that has a triple bond in the carbon chain, such as propargylsulfonyl, 1-butyn-3-ylsulfonyl, 1-butyn-3-methyl-3-ylsulfonyl, and the like.

The "C2-C6 haloalkynylsulfonyl group" represents, for example, a linear or branched alkynylsulfonyl group having from 2 to 6 carbon atoms, that is substituted with one or more halogen atoms which may be the same as or different from each other and has a triple bond in the carbon chain.

The "C3-C9 cycloalkylsulfonyl group" represents, for example, a cycloalkylsulfonyl group having from 3 to 9 carbon atoms, that has a cyclic structure, such as cyclopropylsulfonyl, cyclobutylsulfonyl, cyclopentylsulfonyl, 2-methylcyclopentylsulfonyl, 3-methylcyclopentylsulfonyl, cyclohexylsulfonyl, 2-methylcyclohexylsulfonyl, 3-methylcyclohexylsulfonyl, 4-methylcyclohexylsulfonyl, and the like.

The "C3-C9 halocycloalkylsulfonyl group" represents, for example, a cycloalkylsulfonyl group having from 3 to 9 carbon atoms, that is substituted with one or more halogen atoms which may be the same as or different from each other and has a cyclic structure, such as 2,2,3,3-tetrafluorocyclobutylsulfonyl, 2-chlorocyclohexylsulfonyl, 4-chlorocyclohexylsulfonyl, and the like.

The "C3-C7 alkenylcarbonyl group" represents, for example, an alkenylcarbonyl group having from 3 to 7 carbon atoms, that has a double bond in the carbon chain, such as vinylcarbonyl, allylcarbonyl, 2-butenylcarbonyl, 3-butenylcarbonyl, and the like.

The "C3-C7 haloalkynylcarbonyl group" represents an alkenylcarbonyl group having from 3 to 7 carbon atoms, that is substituted with one or more halogen atoms which may be the same as or different from each other and has a double bond in the carbon chain, such as 3,3-difluoro-2-propenylcarbonyl, 3,3-dichloro-2-propenylcarbonyl, 3,3-dibromo-2-propenylcarbonyl, 2,3-dibromo-2-propenylcarbonyl, 4,4-difluoro-3-butenylcarbonyl, 3,4,4-tribromo-3-butenylcarbonyl, and the like.

The "C3-C7 alkynylcarbonyl group" represents an alkynylcarbonyl group having from 3 to 7 carbon atoms and has a triple bond in the carbon chain, such as propargylcarbonyl, 1-butyn-3-ylcarbonyl, 1-butyn-3-methyl-3-ylcarbonyl, and the like.

The "C3-C7 haloalkynylcarbonyl group" represents, for example, a linear or branched alkynylcarbonyl group having from 3 to 7 carbon atoms, that is substituted with one or more halogen atoms which may be the same as or different from each other and has a triple bond in the carbon chain, such as fluoroethynylcarbonyl, chloroethynylcarbonyl, bromoethynylcarbonyl, 3,3,3-trifluoro-1-propynylcarbonyl, 3,3,3-trichloro-1-propynylcarbonyl, 3,3,3-tribromo-1-propynylcarbonyl, 4,4,4-trifluoro-1-butynylcarbonyl, 4,4,4-trichloro-1-butynylcarbonyl, 4,4,4-tribromo-1-butynylcarbonyl, and the like.

The "C4-C10 cycloalkylcarbonyl group" represents, for example, a cycloalkylcarbonyl group having from 4 to 10 carbon atoms, that has a cyclic structure, such as cyclopropylcarbonyl, cyclobutylcarbonyl, cyclopentylcarbonyl, 2-methylcyclopentylcarbonyl, 3-methylcyclopentylcarbonyl, cyclohexylcarbonyl, 2-methylcyclohexylcarbonyl, 3-methylcyclohexylcarbonyl, 4-methylcyclohexylcarbonyl, and the like.

The "C4-C10 halocycloalkylcarbonyl group" represents, for example, a cycloalkylcarbonyl group having from 4 to 10 carbon atoms, that is substituted with one or more halogen atoms which may be the same as or different from each other and has a cyclic structure, such as 2,2,3,3-tetrafluorocyclobutylcarbonyl, 2-chlorocyclohexyl carbonyl, 4-chlorocyclohexyl carbonyl, and the like.

The "C3-C7 alkenyloxycarbonyl group" represents an alkenyloxycarbonyl group having from 3 to 7 carbon atoms, that has a double bond in the carbon chain, such as vinyloxycarbonyl, allyloxycarbonyl, 2-butenyloxycarbonyl, 3-butenyloxycarbonyl, and the like.

The "C3-C7 haloalkenyloxycarbonyl group" represents, for example, a linear or branched alkenyloxycarbonyl group having from 3 to 7 carbon atoms, that is substituted with one or more halogen atoms which may be the same as or different from each other and has a double bond in the carbon chain, such as 3,3-difluoro-2-propenyloxycarbonyl, 3,3-dichloro-2-propenyloxycarbonyl, 3,3-dibromo-2-propenyloxycarbonyl, 2,3-dibromo-2-propenyloxycarbonyl, 4,4-difluoro-3-butenyloxycarbonyl, 3,4,4-tribromo-3-butenyloxycarbonyl, and the like.

The "C3-C7 alkynyloxycarbonyl group" represents, for example, an alkynyloxycarbonyl group having from 3 to 7 carbon atoms, that has a triple bond in the carbon chain, such as propargyloxycarbonyl, 1-butyn-3-yloxycarbonyl, 1-butyn-3-methyl-3-yloxycarbonyl, and the like.

The "C3-C7 haloalkynyloxycarbonyl group" represents, for example, a linear or branched alkynyloxycarbonyl group having from 3 to 7 carbon atoms, that is substituted with one or more halogen atoms which may be the same as or different from each other and has a triple bond in the carbon chain, such as fluoroethynyloxycarbonyl, chloroethynyloxycarbonyl, bromoethynyloxycarbonyl, 3,3,3-trifluoro-1-propynyloxycarbonyl, 3,3,3-trichloro-1-propynyloxycarbonyl, 3,3,3-tribromo-1-propynyloxycarbonyl, 4,4,4-trifluoro-1-butynyloxycarbonyl, 4,4,4-trichloro-1-butynyloxycarbonyl, 4,4,4-tribromo-1-butynyloxycarbonyl, and the like.

The "C4-C10 cycloalkyloxycarbonyl group" represents, for example, a cycloalkyloxycarbonyl group having from 4 to 10 carbon atoms, that has a cyclic structure, such as cyclopropyloxycarbonyl, cyclobutyloxycarbonyl, cyclopentyloxycarbonyl, 2-methylcyclopentyloxycarbonyl, 3-methylcyclopentyloxycarbonyl, cyclohexyloxycarbonyl, 2-methylcyclohexyloxycarbonyl, 3-methylcyclohexyloxycarbonyl, 4-methylcyclohexyloxycarbonyl, and the like.

The "C4-C10 halocycloalkyloxycarbonyl group" represents, for example, a cycloalkyloxycarbonyl group having from 4 to 10 carbon atoms, that is substituted with one or more halogen atoms which may be the same as or different from each other and has a cyclic structure, such as 2,2,3,3-tetrafluorocyclobutyloxycarbonyl, 2-chlorocyclohexyloxycarbonyl, 4-chlorocyclohexyloxycarbonyl, and the like.

The "C2-C6 alkenylamino group" represents, for example, an alkenylamino group having from 2 to 6 carbon atoms, that has a double bond in the carbon chain, such as vinylamino, allylamino, 2-butenylamino, 3-butenylamino, and the like.

The "C2-C6 haloalkenylamino group" represents a linear or branched alkenylamino group having from 2 to 6 carbon atoms, that is substituted with one or more halogen atoms which may be the same as or different from each other and has a double bond in the carbon chain, such as 3,3-difluoro-2-propenylamino, 3,3-dichloro-2-propenylamino, 3,3-dibromo-2-propenylamino, 2,3-dibromo-2-propenylamino, 4,4-difluoro-3-butenylamino, 3,4,4-tribromo-3-butenylamino, and the like.

The "C2-C6 alkynylamino group" represents, for example, an alkynylamino group having from 2 to 6 carbon atoms, that has a triple bond in the carbon chain, such as propargylamino, 1-butyn-3-ylamino, 1-butyn-3-methyl-3-ylamino, and the like.

The "C2-C6 haloalkynylamino group" represents, for example, a linear or branched alkynylamino group having from 2 to 6 carbon atoms, that is substituted with one or more halogen atoms which may be the same as or different from each other and has a triple bond in the carbon chain, such as fluoroethynylamino, chloroethynylamino, bromoethynylamino, 3,3,3-trifluoro-1-propynylamino, 3,3,3-trichloro-1-propynylamino, 3,3,3-tribromo-1-propynylamino, 4,4,4-trifluoro-1-butynylamino, 4,4,4-trichloro-1-butynylamino, 4,4,4-tribromo-1-butynylamino, and the like.

The "C3-C9 cycloalkylamino group" represents, for example, a cycloalkyl group amino having from 3 to 9 carbon atoms, that has a cyclic structure, such as cyclopropylamino, cyclobutylamino, cyclopentylamino, 2-methylcyclopentylamino, 3-methylcyclopentylamino, cyclohexylamino, 2-methylcyclohexylamino, 3-methylcyclohexylamino, 4-methylcyclohexylamino, and the like.

The "C3-C9 halocycloalkylamino group" represents, for example, a cycloalkylamino group having from 3 to 9 carbon atoms, that is substituted with one or more halogen atoms which may be the same as or different from each other and has a cyclic structure, such as 2,2,3,3-tetrafluorocyclobutylamino, 2-chlorocyclohexylamino, 4-chlorocyclohexylamino, and the like.

The "C2-C7 alkylaminocarbonyl group" represents, for example, a linear or branched alkylaminocarbonyl group having from 2 to 7 carbon atoms, such as methylaminocarbonyl, ethylaminocarbonyl, n-propylaminocarbonyl, i-propylaminocarbonyl, n-butylaminocarbonyl, s-butylaminocarbonyl, t-butylaminocarbonyl, n-pentylaminocarbonyl, 2-pentylaminocarbonyl, neopentylaminocarbonyl, 4-methyl-2-pentylaminocarbonyl, n-hexylaminocarbonyl, 3-methyl-n-pentylaminocarbonyl, and the like.

The "C2-C7 haloalkylaminocarbonyl group" represents, for example, a linear or branched alkylaminocarbonyl group having from 2 to 7 carbon atoms, that is substituted with one or more halogen atoms which may be the same as or different from each other, such as trifluoromethylaminocarbonyl, pentafluoroethylaminocarbonyl, heptafluoro-n-propylaminocarbonyl, heptafluoro-1-propylaminocarbonyl, 2,2-difluoroethylaminocarbonyl, 2,2-dichloroethylaminocarbonyl, 2,2,2-trifluoroethylaminocarbonyl, 2-fluoroethylaminocarbonyl, 2-chloroethylaminocarbonyl, 2-bromoethylaminocarbonyl, 2-iodoethylaminocarbonyl, 2,2,2-trichloroethylaminocarbonyl, 2,2,2-tribromoethylaminocarbonyl, 1,3-difluoro-2-propylaminocarbonyl, 1,3-dichloro-2-propylaminocarbonyl, 1-chloro-3-fluoro-2-propylaminocarbonyl, 1,1,1-trifluoro-2-propylaminocarbonyl, 2,3,3,3-trifluoro-n-propylaminocarbonyl, 4,4,4-trifluoro-n-butylaminocarbonyl, 1,1,1,3,3,3-hexafluoro-2-propylaminocarbonyl, 1,1,1,3,3,3-hexafluoro-2-chloro-2-propylaminocarbonyl, 1,1,1,3,3,3-hexafluoro-2-bromo-2-propylaminocarbonyl, 1,1,2,3,3,3-hexafluoro-2-chloro-n-propylaminocarbonyl, 1,1,2,3,3,3-hexafluoro-2-bromo-n-propylaminocarbonyl, 1,1,2,3,3,3-hexafluoro-1-bromo-2-propylaminocarbonyl, 2,2,3,3,3-pentafluoro-n-propylaminocarbonyl, 3-fluoro-n-propylaminocarbonyl, 3-chloro-n-propylaminocarbonyl, 3-bromo-n-propylaminocarbonyl, 3,3,4,4,4-pentafluoro-2-butylaminocarbonyl, nonafluoro-n-butylaminocarbonyl, nonafluoro-2-butylaminocarbonyl, 5,5,5-trifluoro-n-pentylaminocarbonyl, 4,4,5,5,5-pentafluoro-2-pentylaminocarbonyl, 3-chloro-n-pentylaminocarbonyl, 4-bromo-2-pentylaminocarbonyl, and the like.

The "C3-C7 alkenylaminocarbonyl group" represents, for example, an alkenylaminocarbonyl group having from 3 to 7 carbon atoms, that has a double bond in the carbon chain, such as vinylaminocarbonyl, allylaminocarbonyl, 2-butenylaminocarbonyl, 3-butenylaminocarbonyl, and the like.

The "C3-C7 haloalkenylaminocarbonyl group" represents, for example, a linear or branched alkenylaminocarbonyl group having from 3 to 7 carbon atoms, that is substituted with one or more halogen atoms which may be the same as or different from each other and has a double bond in the carbon chain, such as 3,3-difluoro-2-propenylaminocarbonyl, 3,3-dichloro-2-propenylaminocarbonyl, 3,3-dibromo-2-propenylaminocarbonyl, 2,3-dibromo-2-propenylaminocarbonyl, 4,4-difluoro-3-butenylaminocarbonyl, 3,4,4-tribromo-3-butenylaminocarbonyl, and the like.

The "C3-C7 alkynylaminocarbonyl group" represents, for example, an alkynylaminocarbonyl group having from 3 to 7 carbon atoms, that has a triple bond in the carbon chain, such as propargylaminocarbonyl, 1-butyn-3-ylaminocarbonyl, 1-butyn-3-methyl-3-ylaminocarbonyl, and the like.

The "C3-C7 haloalkynylaminocarbonyl group" represents, for example, a linear or branched alkynylaminocarbonyl group having from 3 to 7 carbon atoms, that is substituted with one or more halogen atoms which may be the same as or different from each other and has a triple bond in the carbon chain, such as fluoroethynylaminocarbonyl, chloroethynylaminocarbonyl, bromoethynylaminocarbonyl, 3,3,3-trifluoro-1-propynylaminocarbonyl, 3,3,3-trichloro-1-propynylaminocarbonyl, 3,3,3-tribromo-1-propynylaminocarbonyl, 4,4,4-trifluoro-1-butynylaminocarbonyl, 4,4,4-trichloro-1-butynylaminocarbonyl, 4,4,4-tribromo-1-butynylaminocarbonyl, and the like.

The "C4-C10 cycloalkylaminocarbonyl group" represents, for example, a cycloalkylaminocarbonyl group having from 4 to 10 carbon atoms, that has a cyclic structure, such as cyclopropylaminocarbonyl, cyclobutylaminocarbonyl, cyclopentylaminocarbonyl, 2-methylcyclopentylaminocarbonyl, 3-methylcyclopentylaminocarbonyl, cyclohexylaminocarbonyl, 2-methylcyclohexylaminocarbonyl, 3-methylcyclohexylaminocarbonyl, 4-methylcyclohexylaminocarbonyl, and the like.

The "C4-C10 halocycloalkylaminocarbonyl group" represents, for example, a cycloalkylaminocarbonyl group having from 4 to 10 carbon atoms that is substituted with one or more halogen atoms which may be the same as or different from each other and has a cyclic structure, such as 2,3,3-tetrafluorocyclobutylaminocarbonyl, 2-chlorocyclohexylaminocarbonyl, 4-chlorocyclohexylaminocarbonyl, and the like.

The substituents of the "C1-C6 alkyl group which may have a substituent", the "C1-C6 haloalkyl group which may have a substituent", the "C3-C9 cycloalkyl group which may have a substituent", the "C3-C9 halocycloalkyl group which may have a substituent", the "C2-C6 alkenyl group which may have a substituent", the "C2-C6 haloalkenyl group which may have a substituent", the "C2-C6 alkynyl group which may have a substituent", the "C2-C6 haloalkynyl group which may have a substituent", the "C1-C6 alkoxy group which may have a substituent", the "C1-C6 haloalkoxy group which may have a substituent", the "C1-C6 alkylthio group which may have a substituent", the "C1-C6 haloalkylthio group which may have a substituent", the "C2-C6 alkenylthio group which may have a substituent", the "C2-C6 haloalkenylthio group which may have a substituent", the "C2-C6 alkynylthio group which may have a substituent", the "C2-C6 haloalkynylthio group which may have a substituent", the "C1-C6 alkylsulfinyl group which may have a substituent", the "C1-C6 haloalkylsulfinyl group which may have a substituent", the "C2-C6 alkenylsulfinyl group which may have a substituent", the "C2-C6 haloalkenylsulfinyl group which may have a substituent", the "C2-C6 alkynylsulfinyl group which may have a substituent", the "C2-C6 haloalkynylsulfinyl group which may have a substituent", the "C3-C9 cycloalkylsulfinyl group which may have a substituent", the "C3-C9 halocycloalkylsulfinyl group which may have a substituent", the "C1-C6 alkylsulfonyl group which may have a substituent", the "C1-C6 haloalkylsulfonyl group which may have a substituent", the "C2-C6 alkenylsulfonyl group which may have a substituent", the "C2-C6 haloalkenylsulfonyl group which may have a substituent", the "C2-C6 alkynylsulfonyl group which may have a substituent", the "C2-C6 haloalkynylsulfonyl group which may have a substituent", the "C3-C9 cycloalkylsulfonyl group which may have a substituent", the "C3-C9 halocycloalkylsulfonyl group which may have a substituent", the "C1-C6 alkylsulfonyloxy group which may have a substituent", the "C1-C6 haloalkylsulfonyloxy group which may have a substituent", the "C2-C7 alkylcarbonyl group which may have a substituent", the "C2-C7 haloalkylcarbonyl group which may have a substituent", the "C2-C7 alkoxycarbonyl group which may have a substituent", the "C2-C7 haloalkoxycarbonyl group which may have a substituent", the "C2-C7 alkylcarbonylamino group which may have a substituent", the "C2-C7 haloalkylcarbonylamino group which may have a substituent", the "C2-C7 alkoxycarbonylamino group which may have a substituent", the "C2-C7 haloalkoxycarbonylamino group which may have a substituent", the "C2-C6 alkenyloxy group which may have a substituent", the "C2-C6 haloalkenyloxy group which may have a substituent", the "C2-C6 alkynyloxy group which may have a substituent", the "C2-C6 haloalkynyloxy group which may have a substituent", the "C3-C9 cycloalkoxy group which may have a substituent", the "C3-C9 halocycloalkoxy group which may have a substituent", the "C3-C7 alkenylcarbonyl group which may have a substituent", the "C3-C7 haloalkenylcarbonyl group which may have a substituent", the "C3-C7 alkynylcarbonyl group which may have a substituent", the "C3-C7 haloalkynylcarbonyl group which may have a substituent", the "C4-C10 cycloalkylcarbonyl group which may have a substituent", the "C4-C10 halocycloalkylcarbonyl group which may have a substituent", the "C3-C7 alkenyloxycarbonyl group which may have a substituent", the "C3-C7 haloalkenyloxycarbonyl group which may have a substituent", the "C3-C7 alkynyloxycarbonyl group which may have a substituent", the "C3-C7 haloalkynyloxycarbonyl group which may have a substituent", the "C4-C10 cycloalkyloxycarbonyl group which may have a substituent", the "C4-C10 halocycloalkyloxycarbonyl group which may have a substituent", the "C1-C6 alkylamino group which may have a substituent", the "C1-C6 haloalkylamino group which may have a substituent", the "C2-C6 alkenylamino group which may have a substituent", the "C2-C6 haloalkenylamino group which may have a substituent", the "C2-C6 alkynylamino group which may have a substituent", the "C2-C6 haloalkynylamino group which may have a substituent", the "C3-C9 cycloalkylamino group which may have a substituent", the "C3-C9 halocycloalkylamino group which may have a substituent", the "C2-C7 alkylaminocarbonyl group which may have a substituent", the "C2-C7 haloalkylaminocarbonyl group which may have a substituent", the "C3-C7 alkenylaminocarbonyl group which may have a substituent", the "C3-C7 haloalkenylaminocarbonyl group which may have a substituent", the "C3-C7 alkynylaminocarbonyl group which may have a substituent", the "C3-C7 haloalkynylaminocarbonyl group which may have a substituent", the "C4-C10 cycloalkylaminocarbonyl group which may have a substituent", and the "C4-C10 halocycloalkylaminocarbonyl group which may have a substituent" each represents one or more substituents selected from a group consisting of:

a halogen atom, a C1-C6 alkyl group, a C1-C6 haloalkyl group, a C3-C9 cycloalkyl group, a C3-C9 halocycloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C2-C7 alkylcarbonyl group, a C2-C7 haloalkylcarbonyl group, a C2-C7 alkylcarbonyloxy group, a C2-C7 haloalkylcarbonyloxy group, a C1-C6 alkylsulfonyloxy group, a C1-C6 haloalkylsulfonyloxy group, a C2-C7 alkoxycarbonyl group, a C2-C7 haloalkoxycarbonyl group, a C2-C7 alkylcarbonylamino group, a C2-C7 haloalkylcarbonylamino group, a C2-C7 alkylaminocarbonyl group, a C2-C7 haloalkylaminocarbonyl group, a C2-C7 alkoxycarbonylamino group, a C2-C7 haloalkoxycarbonylamino group, a C1-C6 alkylamino group, a C1-C6 haloalkylamino group, an amino group, a carbamoyl group, a sulfamoyl group, a cyano group, a nitro group, a hydroxy group, a carboxyl group, a pentafluorosulfanyl group, a benzyloxy group which may have a substituent, a benzyloxycarbonyl group which may have a substituent, a phenyl group which may have a substituent, a heterocyclic group which may have a substituent, a benzyl group which may have a substituent, a phenylcarbonyl group which may have a substituent, and a phenylamino group which may have a substituent, and in a case where there are two or more substituents, each substituent may be the same as or different from each other.

Furthermore, the substituent in the present invention may have a further substituent, and examples of the substituent include those as described above.

The compound represented by the Formula (1) according to the present invention may include one or plural chiral carbon atoms or chiral centers in their structural Formulae, and thus two or more optical isomers may exist. However, the present invention includes each of the optical isomers and a mixture thereof at any proportions. Further, the compounds represented by the Formula (1) according to the present invention may include two or more kinds of geometrical isomers derived from carbon-carbon double bonds in the structural Formula e. However, the present invention includes each of the geometrical isomers and a mixture thereof at any proportions.

The preferred substituents and the like for the compounds represented by the Formula (1) and the like according to the present invention are as follows.

T is preferably —C(=$G_1$)-$Q_1$, $G_1$ is preferably an oxygen atom, $Q_1$ is preferably a phenyl group which may have a substituent, or a pyridyl group which may have a substituent, and $Q_1$ more preferably has one or more substituents selected from a group consisting of a halogen atom, a C1 haloalkyl group, a nitro group, and a cyano group, and in a case where there are two or more substituents, each substituent is a phenyl group or a pyridyl group, which may be the same as or different from each other.

A represents preferably a carbon atom, K is preferably a non-metal atom group, that forms benzene together with A and two carbon atoms to which A bonds.

X represents preferably a hydrogen atom, a halogen atom, a nitro group, or a cyano group, and more preferably a hydrogen atom or a fluorine atom.

n represents preferably 4.

$Q_2$ represents preferably a phenyl group which may have a substituent, represented by the Formula (2).

$G_3$ represents preferably an oxygen atom.

The representative methods for producing the compound according to the present invention are shown below, and according to them, the compound according to the present invention can be prepared, but the pathways for the preparation methods are not limited to the preparation methods below.

In the Formulae shown in the following preparation method, A, K, X, n, $R_2$, $Q_2$, T, and $R_1$ have the same definitions as A, K, X, n, $R_2$, $Q_2$, T, and $R_1$, respectively, in the Formula (1).

Furthermore, LG represents a functional group having a leaving ability, such as a halogen atom, a hydroxy group, or the like.

Also, each of $R_3$, $R_4$, $R_5$, $R_6$, $R_7$, and $R_8$ represents a hydrogen atom, a C1-C6 alkyl group which may have a substituent, a C1-C6 haloalkyl group which may have a substituent, a C2-C6 alkenyl group which may have a substituent, a C2-C6 haloalkenyl group which may have a substituent, a C2-C6 alkynyl group which may have a substituent, a C2-C6 haloalkynyl group which may have a substituent, a C3-C9 cycloalkyl group which may have a substituent, a C3-C9 halocycloalkyl group which may have a substituent, a phenyl group which may have a substituent, a naphthyl group which may have a substituent, or a heterocyclic group which may have a substituent.

PREPARATION METHOD 1

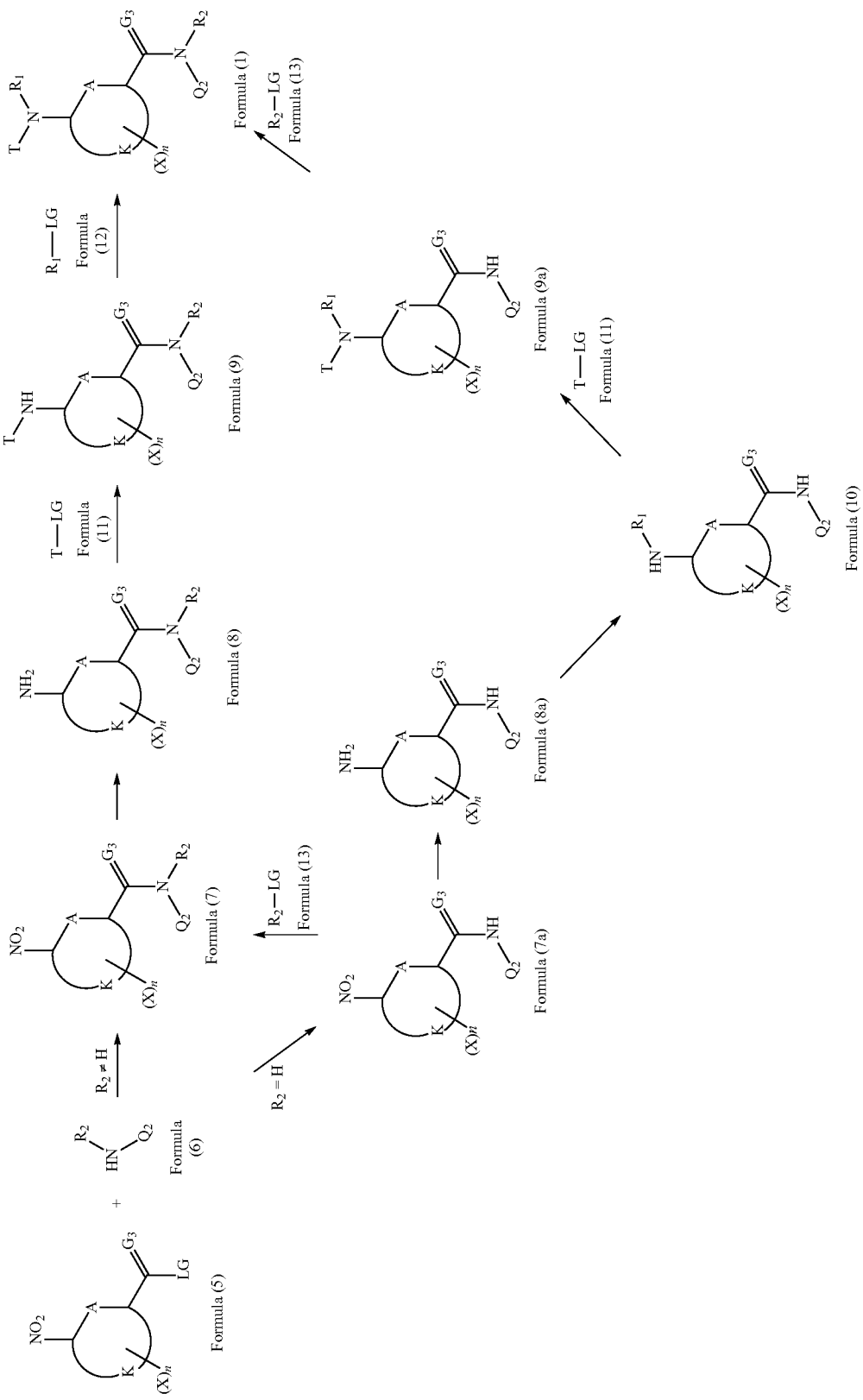

Step 1-(i): Formula (5)+Formula (6)→Formula (7)
Formula (5)+Formula (6)→Formula (7a)

A nitro aromatic carboxamide derivative represented by the Formula (7) or the Formula (7a) can be prepared by reacting a nitro aromatic carboxylic acid derivative represented by the Formula (5) with an aromatic amine derivative represented by the Formula (6) in a suitable solvent. In the present step, a suitable base can be used. The solvent may be any of those which do not inhibit the reaction significantly, and examples thereof may include aromatic hydrocarbons such as benzene, toluene, xylene, and the like, halogenated hydrocarbons such as dichloromethane, chloroform, carbon tetrachloride, and the like, chained or cyclic ethers such as diethyl ether, dioxane, tetrahydrofuran, 1,2-dimethoxy ethane, and the like, esters such as ethyl acetate, butyl acetate, and the like, ketones such as acetone, methyl isobutyl ketone, cyclohexanone, and the like, amides such as dimethyl formamide, dimethylacetamide, and the like, nitriles such as acetonitrile and the like, and inert solvents such as 1,3-dimethyl-2-imidazolidinone and the like. These solvents may be used alone or as a mixture of two or more kinds thereof.

Furthermore, examples of the base may include organic bases such as triethylamine, tri-n-butyl amine, pyridine, 4-dimethylamino pyridine, and the like, alkali metal hydroxides such as sodium hydroxide, potassium hydroxide, and the like, carbonates such as sodium hydrogen carbonate, potassium carbonate, and the like, phosphates such as dipotassium monohydrogen phosphate, trisodium phosphate, and the like, alkali metal hydride salts such as sodium hydride and the like, alkali metal alkoxides such as sodium methoxide, sodium ethoxide, and the like, and lithium amides such as lithium diisopropyl amide, and the like. These bases may be appropriately used in an amount in the range from 0.01-fold molar equivalent to 5-fold molar equivalents with respect to the compound represented by the Formula (6). The reaction temperature may be appropriately selected from −20° C. to the reflux temperature of the solvent used. Further, the reaction time may be appropriately selected within the range from several minutes to 96 hours.

Among the Formula (5), the nitro aromatic carboxyl chloride derivative can be prepared easily by a usual method using a halogenating agent from the nitro aromatic carboxylic acid derivative. Examples of the halogenating agent include thionyl chloride, thionyl bromide, phosphorus oxychloride, oxalyl chloride, phosphorus trichloride, and the like.

Meanwhile, examples of the method for producing the compound represented by the Formula (7) or the Formula (7a) from the nitro aromatic carboxylic acid derivative and the compound represented by the Formula (6) without using a halogenating agent may include a method described in Chem. Ber. p. 788 (1970), in which a condensing agent such as N,N-dicyclohexylcarbodiimide and the like is appropriately used, suitably with a use of an additive such as 1-hydroxybenzotriazole and the like.

Examples of other condensing agents may include 1-ethyl-3-(3-dimethylaminopropyl)carbodiimide, 1,1'-carbonylbis-1H-imidazole, and the like.

Furthermore, examples of other methods above may include a mixed anhydride method using chloroformic acid esters, and a method described in J. Am. Chem. Soc., p. 5012 (1967), whereby the compound represented by the Formula (7) or the Formula (7a) can be used. Examples of the chloroformic acid esters may include isobutyl chloroformate, isopropyl chloroformate and the like. In addition to chloroformic acid esters, diethylacetyl chloride, trimethylacetyl chloride and the like may also be included. Both the method using a condensing agent and the mixed anhydride method are not limited to the solvent, the reaction temperature, and the reaction time according to the literature above. An inert solvent may be used which does not inhibit the appropriate reaction significantly, and the reaction temperature and the reaction time may also be selected appropriately according to the proceeding of the reaction.

Step 1-(ii): Formula (7)→Formula (8)
Formula (7a)→Formula (8a)

An aromatic carboxamide derivative having an amino group represented by the Formula (8) or the Formula (8a) can be derived from the aromatic carboxamide derivative having a nitro group represented by the Formula (7) or the Formula (7a) by means of reduction. Examples of such reduction include a method using a hydrogenation reaction and a method using stannous chloride (anhydride) and the like. The reaction of the former method can be carried out in a suitable solvent in the presence of a catalyst at atmospheric pressure or a higher pressure under a hydrogen atmosphere. Examples of the catalyst may include palladium catalysts such as palladium-carbon and the like, nickel catalysts such as Raney-nickel and the like, cobalt catalysts, ruthenium catalysts, rhodium catalysts, platinum catalysts, and the like, and examples of the solvent may include water, alcohols such as methanol, ethanol, and the like, aromatic hydrocarbons such as benzene, toluene, and the like, chained or cyclic ethers such as ether, dioxane, tetrahydrofuran, and the like, and esters such as ethyl acetate and the like. The reaction temperature may be appropriately selected within a range of −20° C. to the reflux temperature of the solvent used, and the reaction time may be appropriately selected within a range of several minutes to 96 hours, whereby the compound of the Formula (8) or the Formula (8a) can be prepared.

For the latter method, although not being limited to the condition, by using the conditions described in, for example, "Organic Syntheses" Coll. Vol. III, P. 453, the compound of the Formula (8) or the Formula (8a) can be prepared.

Step 1-(iii): Formula (8)+Formula (11)→Formula (9)

An aromatic carboxamide or carbamate derivative represented by the Formula (9) can be prepared by reacting the aromatic amine derivative represented by the Formula (8) with the carboxylic acid derivative or the carbonate ester derivative having a leaving group represented by the Formula (11) in a suitable solvent. In the present step, a suitable base or solvent can be used, and as the base or solvent, those exemplified in 1-(i) can be used. Examples of the reaction temperature, the reaction time, and the like may include those exemplified in 1-(i).

In the Formula (11), the carboxylic acid chloride derivative can be prepared easily from a carboxylic acid derivative by a usual method using a halogenating agent. Examples of the halogenating agent may include those exemplified in 1-(i).

Examples of this method include a method for producing a compound represented by the Formula (9) from the carboxylic acid derivative (11) and the compound represented by the Formula (8) without the use of a halogenating agent, and the preparation can be conducted according to the method exemplified in 1-(i).

Step 1-(iv): Formula (9)+Formula (12)→Formula (1)

The compound represented by the Formula (1) according to the present invention can be prepared by reacting the amide compound represented by the Formula (9) with the compound having a leaving group such as halogen and the like, represented by the Formula (12) in a solvent or without a solvent. In the present step, a suitable base or solvent can be used, and as the base or solvent, those exemplified in 1-(i) can be used. Examples of the reaction temperature, the reaction time, and the like may include those exemplified in 1-(i).

Step 1-(v): Formula (7a)+Formula (13)→Formula (7)

A compound represented by the Formula (7) can be prepared by reacting the amide compound represented by the Formula (7a) with the compound having a leaving group such as halogen and the like, represented by the Formula (13) in a solvent or without a solvent. In the present step, a suitable base or solvent can be used, and as the base or solvent, those exemplified in 1-(i) can be used. Examples of the reaction temperature, the reaction time, and the like may include those exemplified in 1-(i).

Step 1-(vi): Formula (8a)→Formula (10)

(Method A)

A compound represented by the Formula (10) can be prepared by reacting the compound represented by the Formula (8a) with an aldehyde or a ketone in a suitable solvent, and reacting them under a hydrogen atmosphere with the addition of a suitable catalyst.

The solvent may be any of those which do not inhibit the reaction significantly, and examples thereof may include aliphatic hydrocarbons such as hexane, cyclohexane, methylcyclohexane, and the like, aromatic hydrocarbons such as benzene, xylene, toluene, and the like, halogenated hydrocarbons such as dichloromethane, chloroform, carbon tetrachloride, 1,2-dichloroethane, and the like, ethers such as diethyl ether, dioxane, tetrahydrofuran, 1,2-dimethoxy ethane, and the like, amides such as dimethyl formamide, dimethylacetamide, and the like, nitriles such as acetonitrile, propionitrile, and the like, esters such as ethyl acetate, butyl acetate, and the like, alcohols such as 1,3-dimethyl-2-imidazolidinone, methanol, ethanol, and the like, and water. These solvents may be used alone or as a mixture of two or more kinds thereof.

Examples of the catalyst may include palladium catalysts such as palladium-carbon, palladium hydroxide-carbon, and the like, nickel catalysts such as Raney-nickel and the like, cobalt catalysts, platinum catalysts, ruthenium catalysts, rhodium catalysts, and the like.

Examples of the aldehyde may include formaldehyde, acetaldehyde, propionaldehyde, trifluoroacetaldehyde, difluoroacetaldehyde, fluoroacetaldehyde, chloroacetaldehyde, dichloroacetaldehyde, trichloroacetaldehyde, bromoacetaldehyde, and the like.

Examples of the ketone may include acetone, perfluoroacetone, methyl ethyl ketone, and the like.

The reaction pressure may be appropriately selected within the range of 1 atm to 100 atm. The reaction temperature may be appropriately selected within the range from −20° C. to the reflux temperature of the solvent used. Further, the reaction time may be appropriately selected within the range from several minutes to 96 hours.

(Method B)

A compound represented by the Formula (10) can be prepared by reacting the compound represented by the Formula (8a) with an aldehyde or a ketone in a suitable solvent, and treating the product with a suitable reducing agent.

The solvent may be any of those which do not inhibit the reaction significantly, and examples thereof may include aliphatic hydrocarbons such as hexane, cyclohexane, methylcyclohexane, and the like, aromatic hydrocarbons such as benzene, xylene, toluene, and the like, halogenated hydrocarbons such as dichloromethane, chloroform, carbon tetrachloride, 1,2-dichloroethane, and the like, ethers such as diethyl ether, dioxane, tetrahydrofuran, 1,2-dimethoxy ethane, and the like, amides such as dimethyl formamide, dimethylacetamide, and the like, nitriles such as acetonitrile, propionitrile, and the like, esters such as ethyl acetate, butyl acetate, and the like, alcohols such as 1,3-dimethyl-2-imidazolidinone, methanol, ethanol, and the like, water, and the like. These solvents may be used alone or as a mixture of two or more kinds thereof.

Examples of the reducing agent may include borohydrides such as sodium borohydride, sodium cyanoborohydride, sodium triacetate borohydride, and the like.

Examples of the aldehydes may include formaldehyde, acetaldehyde, propionaldehyde, trifluoroacetaldehyde, difluoroacetaldehyde, fluoroacetaldehyde, chloroacetaldehyde, dichloroacetaldehyde, trichloroacetaldehyde, bromoacetaldehyde, and the like.

Examples of the ketones may include acetone, perfluoroacetone, methyl ethyl ketone, and the like.

The reaction temperature may be appropriately selected within the range from −20° C. to the reflux temperature of the solvent used. Further, the reaction time may be appropriately selected within the range from several minutes to 96 hours.

(Method C)

A compound of the Formula (10) can be prepared by reacting the compound represented by the Formula (8a) with an aldehyde in a solvent or without a solvent.

The solvent may be any of those which do not inhibit the reaction significantly, and examples thereof may include aliphatic hydrocarbons such as hexane, cyclohexane, methylcyclohexane, and the like, aromatic hydrocarbons such as benzene, xylene, toluene, and the like, halogenated hydrocarbons such as dichloromethane, chloroform, carbon tetrachloride, 1,2-dichloroethane, and the like, ethers such as diethyl ether, dioxane, tetrahydrofuran, 1,2-dimethoxy ethane, and the like, amides such as dimethyl formamide, dimethylacetamide, and the like, nitriles such as acetonitrile, propionitrile, and the like, ketones such as acetone, methyl isobutyl ketone, cyclohexanone, methyl ethyl ketone, and the like, esters such as ethyl acetate, butyl acetate, and the like, alcohols such as methanol, ethanol, and the like, 1,3-dimethyl-2-imidazolidinone, sulfolane, dimethylsulfoxide, inorganic acids such as sulfuric acid, hydrochloric acid, and the like, organic acids such as formic acid, acetic acid, and the like, water, and the like. These solvents may be used alone or as a mixture of two or more kinds thereof.

Examples of the aldehydes may include formaldehyde, acetaldehyde, propionaldehyde, and the like.

The reaction temperature may be appropriately selected within the range from −20° C. to the reflux temperature of the solvent used, and the reaction time may be appropriately selected within the range from several minutes to 96 hours.

Step 1-(vii): Formula (10)+Formula (11)→Formula (9a)

An aromatic carboxamide or carbamate derivative represented by the Formula (9a) can be prepared by reacting the aromatic amine derivative represented by the Formula (10) with the carboxylic acid derivative or the carbonate ester derivative having a leaving group represented by the Formula (11) in a suitable solvent. In the present step, a suitable base or solvent can be used, and as the base or solvent, those exemplified in 1-(i) can be used. Examples of the reaction temperature, the reaction time, and the like may include those exemplified in 1-(i).

In the Formula (11), the carboxylic acid chloride derivative can be prepared easily from a carboxylic acid derivative by a usual method using a halogenating agent. Examples of the halogenating agent may include those exemplified in 1-(i).

Examples of this method include a method for producing a compound represented by the Formula (9a) from the carboxylic acid derivative (11) and the compound represented by the Formula (10) without the use of a halogenating agent, and the preparation can be conducted according to the method exemplified in 1-(i).

Step 1-(viii): Formula (9a)+Formula (13)→Formula (1)

The compound represented by the Formula (1) according to the present invention can be prepared by reacting the amide compound represented by the Formula (9a) with the compound having a leaving group such as halogen and the like, represented by the Formula (13) in a solvent or without a solvent. In the present step, a suitable base or solvent can be used, and as the base or solvent, those exemplified in 1-(i) can be used. Examples of the reaction temperature, the reaction time, and the like may include those exemplified in 1-(i).

PREPARATION METHOD 2

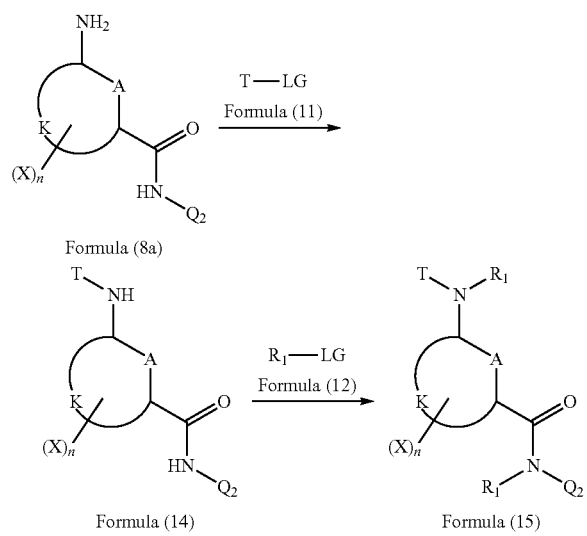

Step 2-(i): Formula (8a)+Formula (11)→Formula (14)

An aromatic carboxamide or carbamate derivative represented by the Formula (14) can be prepared by reacting the aromatic amine derivative represented by the Formula (8a) with the carboxylic acid derivative or the carbonate ester derivative having a leaving group represented by the Formula (11) in a suitable solvent. In the present step, a suitable base or solvent can be used, and as the base or solvent, those exemplified in 1-(i) can be used. Examples of the reaction temperature, the reaction time, and the like may include those exemplified in 1-(i).

In the Formula (11), the carboxylic acid chloride derivative can be prepared easily from a carboxylic acid derivative by a usual method using a halogenating agent. Examples of the halogenating agent may include those exemplified in 1-(i).

Examples of this method include a method for producing a compound represented by the Formula (14) from the carboxylic acid derivative (11) and the compound represented by the Formula (8a) without the use of a halogenating agent, and the preparation can be conducted according to the method exemplified in 1-(i).

Step 2-(ii): Formula (14)+Formula (12)→Formula (15)

The compound represented by the Formula (15) according to the present invention can be prepared by reacting the amide compound represented by the Formula (14) with the compound having a leaving group such as halogen and the like, represented by the Formula (12) in a solvent or without a solvent. In the present step, a suitable base or solvent can be used, and as the base or solvent, those exemplified in 1-(i) can be used. Examples of the reaction temperature, the reaction time, and the like may include those exemplified in 1-(i).

PREPARATION METHOD 3

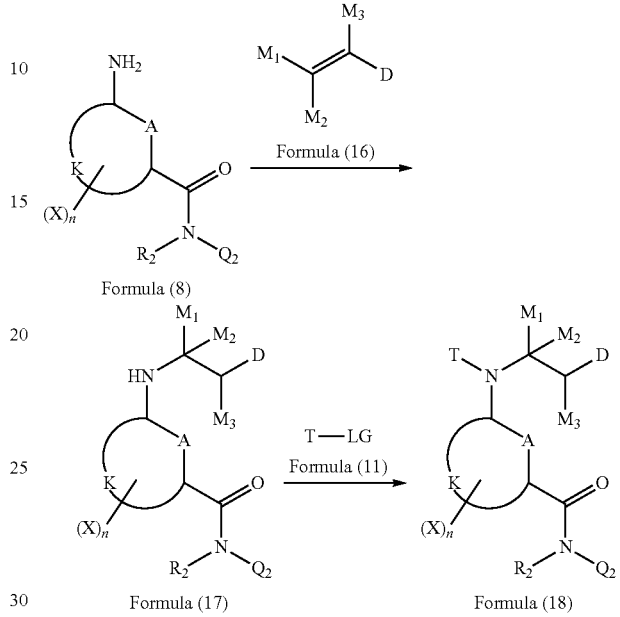

Step 3-(i): Formula (8)+Formula (16)→Formula (17)

A compound represented by the Formula (17) can be prepared by reacting the aromatic amine derivative represented by the Formula (8) with an olefin derivative represented by the Formula (16) in a solvent or without a solvent.

The solvent used in the present reaction may be any of those which do not inhibit the present reaction significantly, and examples thereof may include aromatic hydrocarbons such as benzene, toluene, xylene, and the like, halogenated hydrocarbons such as dichloromethane, chloroform, carbon tetrachloride, and the like, chained or cyclic ethers such as diethyl ether, dioxane, tetrahydrofuran, 1,2-dimethoxy ethane, and the like, esters such as ethyl acetate, butyl acetate, and the like, ketones such as acetone, methyl isobutyl ketone, cyclohexanone, and the like, amides such as dimethyl formamide, dimethylacetamide, and the like, nitriles such as acetonitrile and the like, inert solvents such as 1,3-dimethyl-2-imidazolidinone, and the like, organic acids such as formic acid, acetic acid, propionic acid, butyric acid, and the like, and mineral acids such as hydrochloric acid, phosphoric acid, sulfuric acid, and the like. These solvents may be used alone or as a mixture of two or more kinds thereof.

A catalyst may be added in the present reaction, and examples of the catalyst used include organic bases such as triethylamine, tri-n-butyl amine, pyridine, 4-dimethylamino pyridine, N-benzyl trimethyl ammonium hydroxide (Triton B), and the like, alkali metal hydroxides such as sodium hydroxide, potassium hydroxide, and the like, carbonates such as sodium hydrogen carbonate, potassium carbonate, and the like, phosphates such as dipotassium monohydrogen phosphate, trisodium phosphate, and the like, organic acids such as acetic acid, propionic acid, butyric acid, and the like, mineral acids such as hydrochloric acid, phosphoric acid, sulfuric acid, and the like, Lewis acids such as aluminum trichloride, boron trifluoride, boron trichloride, boron tribromide, tin tetrachloride, titanium tetrachloride, and the like, radical initiators such as an organic peroxide, an azo compound, and the like, fluoride ion-containing compounds such as tetra-n-butyl ammonium fluoride, and the like, and noble metal catalysts such as a palladium catalyst, a ruthenium catalyst, and the like.

These catalysts may be appropriately used in an amount in the range from 0.001-fold molar equivalent to 5-fold molar equivalents with respect to the compound represented by the Formula (8). The reaction temperature may be appropriately selected within the range from −70° C. to 200° C., and the reaction time may be appropriately selected within the range from several minutes to 96 hours.

The compound represented by the Formula (16) may be appropriately used in an amount selected within the range from 0.2-fold molar equivalent to 10.0-fold molar equivalents with respect to the compound represented by the Formula (8).

Step 3-(ii): Formula (17)+Formula (11)→Formula (18)

An aromatic carboxamide or carbamate derivative represented by the Formula (18) can be prepared by reacting the aromatic amine derivative represented by the Formula (17) with the carboxylic acid derivative or the carbonate ester derivative having a leaving group represented by the Formula (11) in a suitable solvent. In the present step, a suitable base or solvent can be used, and as the base or solvent, those exemplified in 1-(i) can be used. Examples of the reaction temperature, the reaction time, and the like may include those exemplified in 1-(i).

In the Formula (11), the carboxylic acid chloride derivative can be prepared easily from a carboxylic acid derivative by a usual method using a halogenating agent. Examples of the halogenating agent may include those exemplified in 1-(i).

Examples of this method include a method for producing a compound represented by the Formula (18) from the carboxylic acid derivative (11) and the compound represented by the Formula (17) without the use of a halogenating agent, and the preparation can be conducted according to the method exemplified in 1-(i).

PREPARATION METHOD 4

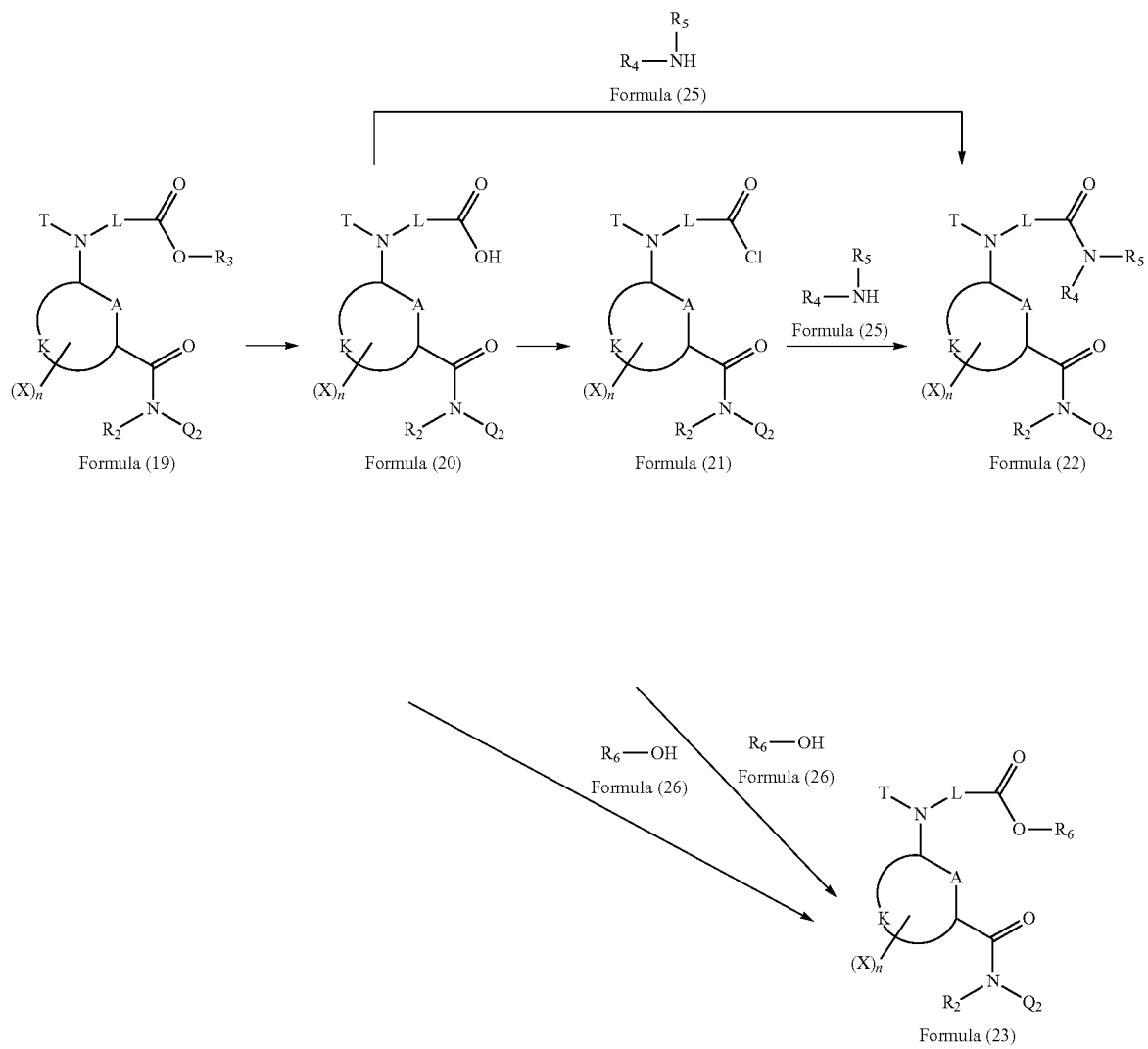

Step 4-(i): Formula (19)→Formula (20)

A carboxylic acid represented by the Formula (20) can be prepared by hydrolyzing an ester derivative represented by the Formula (19). Examples of the hydrolysis method include a method using an acid described in "Shin Jikken Kagaku Kooza" (Maruzen), Vol. 14-II, pp. 931-935, a method using an alkali described in pp. 935-938 in the same literature, a method under a neutralized condition described in pp. 938-941 in the same literature, and the like.

Step 4-(ii): Formula (20)→Formula (21)

An acid halogen derivative represented by the Formula (21) can be easily prepared from a carboxylic acid derivative represented by the Formula (20) by a usual method using a halogenating agent. The halogenating agent may include those exemplified in 1-(i).

Step 4-(iii): Formula (21)+Formula (25)→Formula (22)

An amide derivative of the Formula (22) can be prepared by reacting the acid halogen derivative represented by the Formula (21) with an amine derivative represented by the Formula (25). The present preparation step can be conducted according to the method exemplified in 1-i.

Step 4-(iv): Formula (20)+Formula (25) Formula (22)

The amide derivative of the Formula (22) can be prepared by reacting the carboxylic acid represented by the Formula (20) with an amine represented by the Formula (25). The present preparation step can be conducted according to the method exemplified in 1-i.

Step 4-(v): Formula (21)+Formula (26)→Formula (23)

An ester derivative represented by the Formula (23) can be prepared by reacting the acid halogen derivative represented by the Formula (21) with an alcohol derivative represented by the Formula (26) in a suitable solvent. In the present step, a suitable base can be used. The solvent may be any of those which do not inhibit the reaction significantly, and examples thereof may include aromatic hydrocarbons such as benzene, toluene, xylene, and the like, halogenated hydrocarbons such as dichloromethane, chloroform, carbon tetrachloride, and the like, chained or cyclic ethers such as diethyl ether, dioxane, tetrahydrofuran, 1,2-dimethoxy ethane, and the like, esters such as ethyl acetate, butyl acetate, and the like, ketones such as acetone, methyl isobutyl ketone, cyclohexanone, and the like, amides such as dimethyl formamide, dimethylacetamide, and the like, nitriles such as acetonitrile and the like, and inert solvents such as 1,3-dimethyl-2-imidazolidinone and the like. These solvents may be used alone or as a mixture of two or more kinds thereof.

Furthermore, examples of the base may include organic bases such as triethylamine, tri-n-butyl amine, pyridine, 4-dimethylamino pyridine, and the like, alkali metal hydroxides such as sodium hydroxide, potassium hydroxide, and the like, carbonates such as sodium hydrogen carbonate, potassium carbonate, and the like, phosphates such as dipotassium monohydrogen phosphate, trisodium phosphate, and the like, alkali metal hydride salts such as sodium hydride and the like, alkali metal alkoxides such as sodium methoxide, sodium ethoxide, and the like, and lithium amides such as lithium diisopropyl amide, and the like. These bases may be appropriately used in an amount in the range from 0.01-fold molar equivalent to 5-fold molar equivalents with respect to the compound represented by the Formula (26). The reaction temperature may be appropriately selected from −20° C. to the reflux temperature of the solvent used, and the reaction time may be appropriately selected within the range from several minutes to 96 hours.

Step 4-(vi): Formula (20)+Formula (26)→Formula (23)

The ester derivative represented by the Formula (23) can be prepared by reacting the carboxylic acid derivative represented by the Formula (20) with the alcohol derivative represented by the Formula (26). Examples of the preparation method of the present reaction include a synthesis method using an acid catalyst described in "Shin Jikken Kagaku Kooza" (Maruzen), Vol. 14-II, pp. 1002-1004, and the like.

PREPARATION METHOD 5

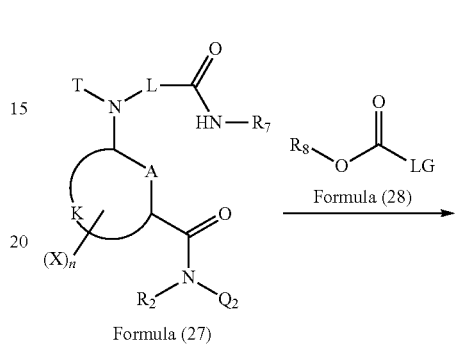

Formula (27)

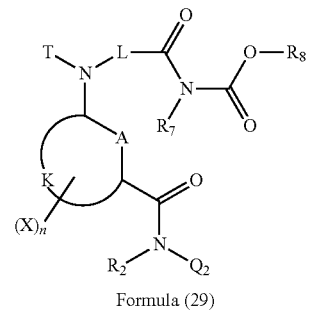

Formula (29)

Step 5: Formula (27)+Formula (28)→Formula (29)

The compound represented by the Formula (29) according to the present invention can be prepared by reacting the amide compound represented by the Formula (27) with a formate ester derivative represented by the Formula (28) in a solvent or without a solvent. In the present step, a suitable base or solvent can be used, and as the base or solvent, those exemplified in 1-(i) can be used. Examples of the reaction temperature, the reaction time, and the like may include those exemplified in 1-(i).

In the Formula (28), the formate chloride derivative can be prepared easily from a formic acid derivative by a usual method using a halogenating agent. The halogenating agent may include those exemplified in 1-(i).

Examples of this method include a method for producing a compound represented by the Formula (29) from the formate ester derivative (28) and the compound represented by the Formula (27) without the use of a halogenating agent, and the preparation can be conducted according to the method exemplified in 1-(i).

PREPARATION METHOD 6

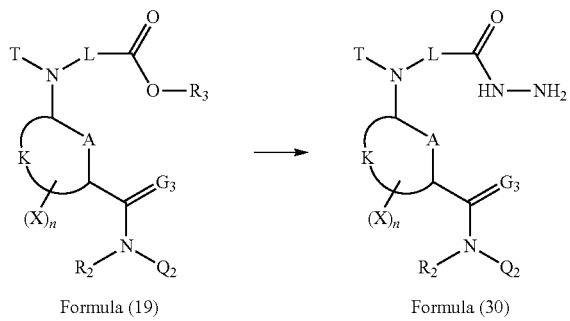

Formula (19)        Formula (30)

Step 6: Formula (19)→Formula (30)

The compound represented by the Formula (30) according to the present invention can be prepared by reacting the ester compound represented by the Formula (19) with a hydrazine in a solvent or without a solvent.

In the present step, a suitable solvent can be used. The solvent may be any of those which do not inhibit the reaction significantly, examples thereof may include aliphatic hydrocarbons such as hexane, cyclohexane, methylcyclohexane, and the like, aromatic hydrocarbons such as benzene, xylene, toluene, and the like, halogenated hydrocarbons such as dichloromethane, chloroform, carbon tetrachloride, 1,2-dichloroethane, and the like, ethers such as diethyl ether, dioxane, tetrahydrofuran, 1,2-dimethoxy ethane, and the like, amides such as dimethyl formamide, dimethylacetamide, and the like, nitriles such as acetonitrile, propionitrile, and the like, alcohols such as methanol, ethanol, and the like, 1,3-dimethyl-2-imidazolidinone, sulfolane, dimethylsulfoxide, water, and the like. These solvents may be used alone or as a mixture of two or more kinds thereof.

The reaction temperature may be appropriately selected within the range from −20° C. to the reflux temperature of the solvent used, and the reaction time may be appropriately selected within the range from several minutes to 96 hours.

PREPARATION METHOD 7

Formula (31)        Formula (9a)

Step 7: Formula (31)+Formula (12)→Formula (9a)

The compound represented by the Formula (9a) according to the present invention can be prepared by reacting the amide compound represented by the Formula (31) with the compound having a leaving group such as halogen and the like, represented by the Formula (12) in a solvent or without a solvent. In the present step, a suitable base or solvent can be used, and as the base or solvent, those exemplified in 1-(i) can be used. Examples of the reaction temperature, the reaction time, and the like may include those exemplified in 1-(i).

PREPARATION METHOD 8

Formula (32)        Formula (6)

Formula (33)

Formula (10a)        Formula (1)

8-(i): Formula (32)+Formula (6)→Formula (33)

A compound represented by the Formula (33) can be prepared by reacting the compound represented by the Formula (32) with a compound represented by the Formula (6) under the condition described in 1-(i).

8-(ii): Formula (33)→Formula (10a)

A compound represented by the Formula (10a) can be prepared by carrying out an amination reaction using ammonia according to the conditions described, for example, in J. Org. Chem. p. 280 (1958). However, the conditions such as a reaction solvent and the like are not restricted to those described in the literature, and an inert solvent which does not inhibit the proper progress of the reaction significantly may be used appropriately. The reaction temperature and reaction time may be suitably selected as the reaction proceeds. Further, examples of the amination agent include methylamine, ethylamine or the like, in addition to ammonia.

8-(iii): Formula (10a)+Formula (11)→Formula (1)

The compound represented by the Formula (1) according to the present invention can be prepared by reacting the compound represented by the Formula (10a) with a compound represented by the Formula (11) according to the conditions described in 1-(i).

PREPARATION METHOD 9

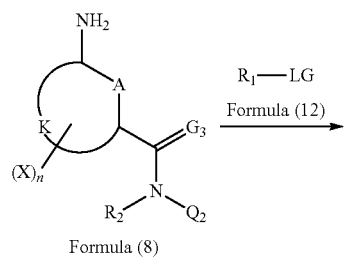

Formula (8)

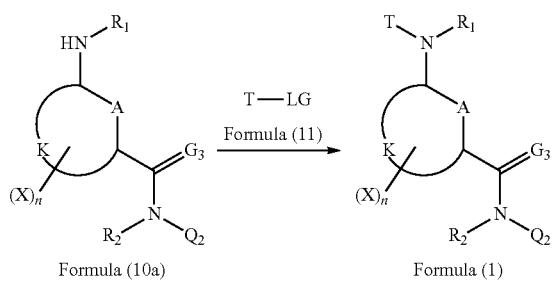

Formula (10a)   Formula (1)

9-(i): Formula (8)→Formula (10a)

The compound represented by the Formula (10a) can be prepared by reacting the compound represented by the Formula (8) as a starting material according to the conditions of (Method A), (Method B), or (Method C) described in 1-(vi).

9-(i'): Formula (8)+Formula (12)→Formula (10a)

An aromatic carboxamide represented by the Formula (10a) can be prepared by reacting the aromatic amine derivative represented by the Formula (8) with the carboxylic acid derivative or the carbonate ester derivative having a leaving group represented by the Formula (12) in a suitable solvent. In the present step, a suitable base or solvent can be used, and as the base or solvent, those exemplified in 1-(i) can be used. Examples of the reaction temperature, the reaction time, and the like may include those exemplified in 1-(i).

In the Formula (12), the carboxylic acid chloride derivative can be prepared easily from a carboxylic acid derivative by a usual method using a halogenating agent. Examples of the halogenating agent may include those exemplified in 1-(i).

Examples of this method include a method for producing a compound represented by the Formula (10a) from the carboxylic acid derivative (12) and the compound represented by the Formula (8) without the use of a halogenating agent, and the preparation can be conducted according to the method exemplified in 1-(i).

9-(ii): Formula (10a)+Formula (11)→Formula (1)

A compound represented by the Formula (1) can be prepared by reacting the compound represented by the Formula (10a) and the compound represented by the Formula (11) as starting materials according to the conditions described in 1-(i).

PREPARATION METHOD 10

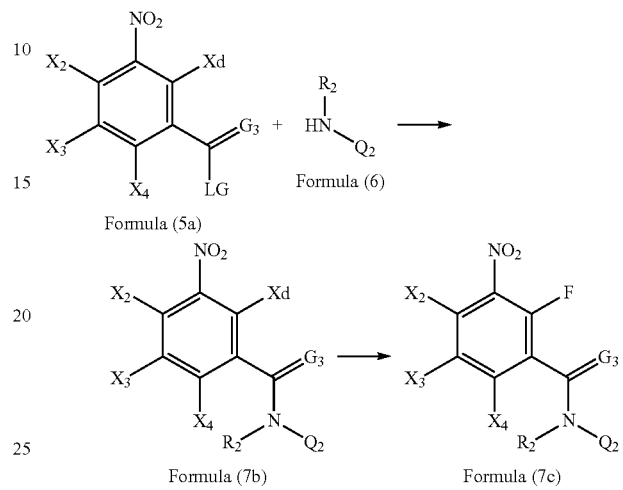

Formula (5a)

Formula (7b)   Formula (7c)

10-(i): Formula (5a)+Formula (6)→Formula (7b)

A compound represented by the Formula (7b) can be prepared by reacting the compound represented by the Formula (5a) and the compound represented by the Formula (6) according to the conditions described in 1-(i).

10-(ii): Formula (7b)→Formula (7c)

A compound represented by the Formula (7c) can be prepared by reacting the nitro aromatic carboxamide derivative represented by the Formula (7b) with a suitable fluorinating agent in a suitable solvent or without a solvent.

The solvent may be any of those which do not inhibit the reaction significantly, and examples thereof may include aliphatic hydrocarbons such as hexane, cyclohexane, methylcyclohexane, and the like, aromatic hydrocarbons such as benzene, toluene, xylene, and the like, halogenated hydrocarbons such as dichloromethane, chloroform, carbon tetrachloride, 1,2-dichloroethane, and the like, chained or cyclic ethers such as diethyl ether, dioxane, tetrahydrofuran, 1,2-dimethoxy ethane, and the like, esters such as ethyl acetate, butyl acetate, and the like, ketones such as acetone, methyl isobutyl ketone, cyclohexanone, methyl ethyl ketone, and the like, nitriles such as acetonitrile, propionitrile, and the like, and aprotic polar solvents such as 1,3-dimethyl-2-imidazolidinone, sulfolane, dimethylsulfoxide, N,N-dimethyl formamide, N-methylpyrrolidone, N,N-dimethylacetamide, and the like. These solvents may be used alone or as a mixture of two or more kinds thereof.

Examples of the fluorinating agent may include 1,1,2,2-tetrafluoroethyl diethylamine, 2-chloro-1,1,2-trifluoroethyl diethylamine, trifluorodiphenylphospholane, difluorotriphenylphospholane, fluoroformic acid esters, sulfur tetrafluoride, potassium fluoride, potassium hydrogen fluoride, cesium fluoride, rubidium fluoride, sodium fluoride, lithium fluoride, antimony (III) fluoride, antimony (V) fluoride, zinc fluoride, cobalt fluoride, lead fluoride, copper fluoride, mercury (II) fluoride, silver fluoride, silver fluoroborate, thallium (I) fluoride, molybdenum (VI) fluoride, arsenic (ITT) fluoride, bromine fluoride, selenium tetrafluoride, tris(dimethylamino)sulfonium difluorotrimethylsilicate, sodium hexafluorosilicate, quaternary ammonium fluorides, (2-chloroethyl) diethylamine, diethylaminosulfur trifluoride, morpholinosulfur trifluoride, silicon tetrafluoride, hydrogen fluoride, hydrofluoric acid, hydrogen fluoride-pyridine complex, hydrogen fluoride-triethylamine complex, hydrogen fluoride salts, bis(2-methoxyethyl)amino sulfurtrifluoride, 2,2-difluoro-1,3-dimethyl-2-imidazolidinone, iodine pentafluoride, tris(diethylamino)phosphonium 2,2,3,3,4,4-hexafluorocyclobutanilide, triethylammonium hexafluorocylcobutanilide, hexafluoropropene, and the like. These fluorinating agents may be used alone or as a mixture of two or more kinds thereof.

The fluorinating agent may be used as a solvent in an amount appropriately selected within the range of 1-fold molar equivalent to 10-fold molar equivalents with respect to the nitro aromatic carboxamide derivative represented by the Formula (7b).

Additives may be used, and examples thereof may include crown ethers such as 18-crown-6 and the like, phase transfer catalysts such as a tetraphenylphosphonium salt and the like, inorganic salts such as calcium fluoride, calcium chloride, and the like, metal oxides such as mercury oxide and the like, ion exchange resins, and the like. These additives may not only be added to the reaction system but also used as a pretreating agent for the fluorinating agent.

The reaction temperature may be appropriately selected within the range from −80° C. to the reflux temperature of the solvent used, and the reaction time may be appropriately selected within the range from several minutes to 96 hours.

PREPARATION METHOD 11

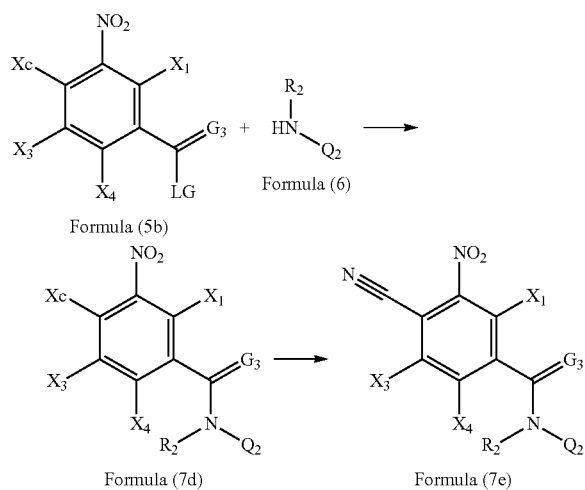

Formula (5b)

Formula (6)

Formula (7d)

Formula (7e)

11-(i): Formula (5b)+Formula (6)→Formula (7d)

A compound represented by the Formula (7d) can be prepared by reacting the compound represented by the Formula (5b) with a compound represented by the Formula (6) according to the conditions described in 1-(i).

11-(ii): Formula (7d)→Formula (7e)

A compound represented by the Formula (7e) can be prepared by reacting the halogen aromatic carboxamide derivative represented by the Formula (7d) with a suitable cyanating agent in a suitable solvent or without a solvent.

The solvent may be any of those which do not inhibit the progress of the present reaction significantly. Examples thereof may include aliphatic hydrocarbons such as hexane, cyclohexane, methylcyclohexane, and the like, aromatic hydrocarbons such as benzene, toluene, xylene, and the like, halogenated hydrocarbons such as dichloromethane, chloroform, carbon tetrachloride, 1,2-dichloroethane, and the like, chained or cyclic ethers such as diethyl ether, dioxane, tetrahydrofuran, 1,2-dimethoxy ethane, and the like, esters such as ethyl acetate, butyl acetate, and the like, ketones such as acetone, methyl isobutyl ketone, cyclohexanone, methyl ethyl ketone, and the like, nitriles such as acetonitrile, propionitrile, and the like, and aprotic polar solvents such as 1,3-dimethyl-2-imidazolidinone, sulfolane, dimethylsulfoxide, N,N-dimethyl formamide, N-methylpyrrolidone, N,N-dimethylacetamide, and the like. These solvents may be used alone or as a mixture of two or more kinds thereof.

Examples of the cyanating agent include cyanide salts such as sodium cyanide, potassium cyanide, sodium cyanoborohydride, and the like, metal cyanides such as copper cyanide, silver cyanide, lithium cyanide, and the like, hydrogen cyanide, tetraethylammonium cyanide, and the like.

These cyanating agents may be used as a solvent in an amount appropriately selected within the range of 1-fold molar equivalent to 10-fold molar equivalents with respect to the halogen aromatic carboxamide derivative represented by the Formula (7d).

Additives may be used, and examples thereof may include crown ethers such as 18-crown-6 and the like, phase transfer catalysts such as a tetraphenylphosphonium salt and the like, inorganic salts such as sodium iodide and the like.

The reaction temperature may be appropriately selected within the range from −20° C. to the reflux temperature of the solvent used. Further, the reaction time may be appropriately selected within the range from several minutes to 96 hours.

PREPARATION METHOD 12

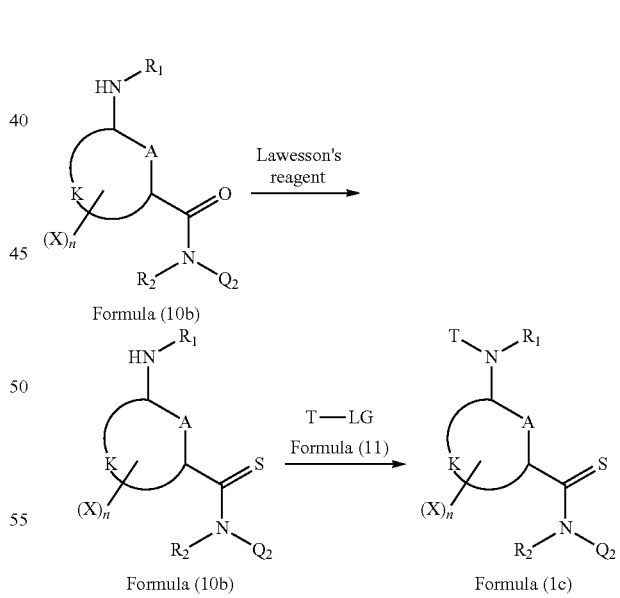

Formula (10b)

Formula (10b)

Formula (1c)

12-(i): Formula (10b)→Formula (10c)

A compound represented by the Formula (10c) can be prepared by reacting the compound represented by the Formula (10b) with a Lawesson's reagent according to the known conditions described in Synthesis p. 463 (1993), Synthesis p. 829 (1984) and the like. The conditions such as a solvent, reaction temperature and the like are not restricted to those described in the literature.

12-(ii): Formula (10c)+Formula (11)→Formula (1c)

A compound represented by the Formula (1c) can be prepared by reacting the compound represented by the Formula (10c) with a compound represented by the Formula (11) according to the conditions described in 1-(i).

PREPARATION METHOD 13

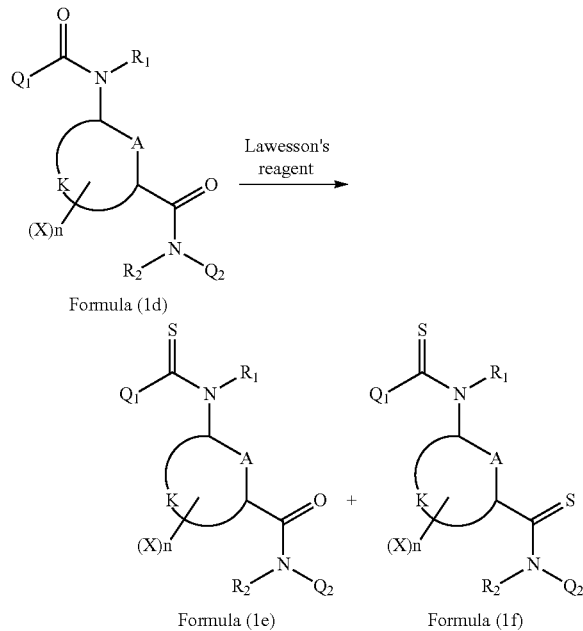

Formula (1d)

Formula (1e)    Formula (1f)

13: Formula (1d)→Formula (1e)+the Formula (1f)

The compounds represented by the Formula (1e) and the Formula (1f) can be prepared from a compound represented by the Formula (1d) according to the conditions described in 12-(i). The conditions such as a solvent, a reaction temperature, and the like are not restricted to those described in the literature. These two compounds can be easily separated and purified by a known separation and purification technique such as silica gel column chromatography and the like.

In all of the preparation methods as described above, a desired product may be isolated from the reaction system after the reaction is completed according to a usual method, but optionally, purification can be carried out by operations such as recrystallization, column chromatography, distillation, and the like. In addition, the desired product can be also provided to the subsequent reaction method without being separated from the reaction system.

Hereinbelow, examples of the representative compounds of the compound represented by the Formula (1) as an active ingredient for the pesticide according to the present invention will be given in Table 1 to Table 8 below, but the present invention is not limited thereto.

Furthermore, examples of the representative compounds of the compounds represented by the Formula (6a), the Formula (6b), the Formula (6c), and the Formula (6d), which are intermediates of the compounds according to the present invention will be given in Table 11 to Table 21 below, but the present invention is not limited thereto.

In addition, in the tables, "n-" represents normal, "Me" represents a methyl group, "Et" represents an ethyl group, "nPr" represents a normal propyl group, "nPr" represents a normal propyl group, "iPr" represents an isopropyl group, "nBu" represents a normal butyl group, "iBu" represents an isobutyl group, "sBu" represents a secondary butyl group, "tBu" represents a tertiary butyl group, "Ph" represents a phenyl group, "H" represents a hydrogen atom, "O" represents an oxygen atom, "S" represents a sulfur atom, "C" represents a carbon atom, "N" represents a nitrogen atom, "F" represents a fluorine atom, "Cl" represents a chlorine atom, "Br" represents a bromine atom, "I" represents an iodine atom, "CF3" represents a trifluoromethyl group, "C2F5" represents a pentafluoroethyl group, "OCF3" represents a trifluoromethoxy group, "MeS" represents a methylthio group, "MeSO" represents a methylsulfinyl group, "MeSO2" represents a methylsulfonyl group, "MeO" represents a methoxy group, "NH2" represents an amino group, "MeNH" represents a methylamino group, "Me2N" represents a dimethylamino group, "OH" represents a hydroxy group, "CN" represents a cyano group, "NO2" represents a nitro group, and "Ac" represents an acetyl group.

Further, n in the tables represents the substitution number in the case of X being other than a hydrogen atom. In addition, the expression "2-F" in the X column indicates that a fluorine atom is substituted at the 2-position, which shall apply in other descriptions.

TABLE 1

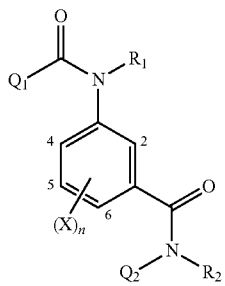

| compound number | $R_1$ | $R_2$ | L | D | X | n | $Q_1$ | $Q_2$ |
|---|---|---|---|---|---|---|---|---|
| 1-1 | —L—D | H | —CH2CH2— | CONH2 | H | 0 | phenyl | 2,6-dimethyl-4-(1,2,2,2-tetrafluoro-1-trifluoromethyl-ethyl)-phenyl |
| 1-2 | —L—D | H | —CH2CH2— | CONH2 | H | 0 | 4-cyanophenyl | 2,6-dimethyl-4-(1,2,2,2-tetrafluoro-1-trifluoromethyl-ethyl)-phenyl |
| 1-3 | —L—D | H | —CH2CH2— | CONH2 | H | 0 | 3-cyanophenyl | 2,6-dimethyl-4-(1,2,2,2-tetrafluoro-1-trifluoromethyl-ethyl)-phenyl |

TABLE 1-continued

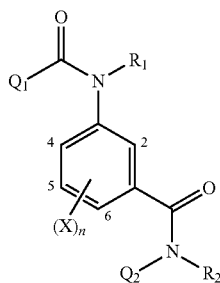

| compound number | R₁ | R₂ | L | D | X | n | Q₁ | Q₂ |
|---|---|---|---|---|---|---|---|---|
| 1-4 | —L—D | H | —CH2CH2— | CONH2 | H | 0 | 3,5-dicyanophenyl | 2,6-dimethyl-4-(1,2,2,2-tetrafluoro-1-trifluoromethyl-ethyl)-phenyl |
| 1-5 | —L—D | H | —CH2CH2— | CONH2 | H | 0 | 2-fluorophenyl | 2,6-dimethyl-4-(1,2,2,2-tetrafluoro-1-trifluoromethyl-ethyl)-phenyl |
| 1-6 | —L—D | H | —CH2CH2— | CONH2 | H | 0 | 4-fluorophenyl | 2,6-dimethyl-4-(1,2,2,2-tetrafluoro-1-trifluoromethyl-ethyl)-phenyl |
| 1-7 | —L—D | H | —CH2CH2— | CONH2 | H | 0 | 2,6-difluorophenyl | 2,6-dimethyl-4-(1,2,2,2-tetrafluoro-1-trifluoromethyl-ethyl)-phenyl |
| 1-8 | —L—D | H | —CH2CH2— | CONH2 | H | 0 | 2-fluoro-4-cyanophenyl | 2,6-dimethyl-4-(1,2,2,2-tetrafluoro-1-trifluoromethyl-ethyl)-phenyl |
| 1-9 | —L—D | H | —CH2CH2— | CONH2 | H | 0 | 2-chlorophenyl | 2,6-dimethyl-4-(1,2,2,2-tetrafluoro-1-trifluoromethyl-ethyl)-phenyl |
| 1-10 | —L—D | H | —CH2CH2— | CONH2 | H | 0 | 4-chlorophenyl | 2,6-dimethyl-4-(1,2,2,2-tetrafluoro-1-trifluoromethyl-ethyl)-phenyl |
| 1-11 | —L—D | H | —CH2CH2— | CONH2 | H | 0 | 4-nitrophenyl | 2,6-dimethyl-4-(1,2,2,2-tetrafluoro-1-trifluoromethyl-ethyl)-phenyl |
| 1-12 | —L—D | H | —CH2CH2— | CONH2 | H | 0 | 2-methylphenyl | 2,6-dimethyl-4-(1,2,2,2-tetrafluoro-1-trifluoromethyl-ethyl)-phenyl |
| 1-13 | —L—D | H | —CH2CH2— | CONH2 | H | 0 | pyridin-2-yl | 2,6-dimethyl-4-(1,2,2,2-tetrafluoro-1-trifluoromethyl-ethyl)-phenyl |
| 1-14 | —L—D | H | —CH2CH2— | CONH2 | H | 0 | pyridin-3-yl | 2,6-dimethyl-4-(1,2,2,2-tetrafluoro-1-trifluoromethyl-ethyl)-phenyl |
| 1-15 | —L—D | H | —CH2CH2— | CONH2 | H | 0 | pyridin-4-yl | 2,6-dimethyl-4-(1,2,2,2-tetrafluoro-1-trifluoromethyl-ethyl)-phenyl |
| 1-16 | —L—D | H | —CH2CH2— | CONH2 | H | 0 | 2-chloropyridin-3-yl | 2,6-dimethyl-4-(1,2,2,2-tetrafluoro-1-trifluoromethyl-ethyl)-phenyl |
| 1-17 | —L—D | H | —CH2CH2— | CONH2 | H | 0 | 6-chloropyridin-3-yl | 2,6-dimethyl-4-(1,2,2,2-tetrafluoro-1-trifluoromethyl-ethyl)-phenyl |
| 1-18 | —L—D | H | —CH2CH2— | CONH2 | H | 0 | 2-chloropyridin-4-yl | 2,6-dimethyl-4-(1,2,2,2-tetrafluoro-1-trifluoromethyl-ethyl)-phenyl |
| 1-19 | —L—D | H | —CH2CH2— | CONH2 | H | 0 | pyrazin-2-yl | 2,6-dimethyl-4-(1,2,2,2-tetrafluoro-1-trifluoromethyl-ethyl)-phenyl |
| 1-20 | —L—D | H | —CH2CH2— | CONH2 | H | 0 | pyrimidin-5-yl | 2,6-dimethyl-4-(1,2,2,2-tetrafluoro-1-trifluoromethyl-ethyl)-phenyl |
| 1-21 | —L—D | H | —CH2CH2— | CONH2 | 2-F | 1 | phenyl | 2,6-dimethyl-4-(1,2,2,2-tetrafluoro-1-trifluoromethyl-ethyl)-phenyl |
| 1-22 | —L—D | H | —CH2CH2— | CONH2 | 2-F | 1 | 4-cyanophenyl | 2,6-dimethyl-4-(1,2,2,2-tetrafluoro-1-trifluoromethyl-ethyl)-phenyl |
| 1-23 | —L—D | H | —CH2CH2— | CONH2 | 2-F | 1 | 3-cyanophenyl | 2,6-dimethyl-4-(1,2,2,2-tetrafluoro-1-trifluoromethyl-ethyl)-phenyl |
| 1-24 | —L—D | H | —CH2CH2— | CONH2 | 2-F | 1 | 3,5-dicyanophenyl | 2,6-dimethyl-4-(1,2,2,2-tetrafluoro-1-trifluoromethyl-ethyl)-phenyl |
| 1-25 | —L—D | H | —CH2CH2— | CONH2 | 2-F | 1 | 2-fluorophenyl | 2,6-dimethyl-4-(1,2,2,2-tetrafluoro-1-trifluoromethyl-ethyl)-phenyl |
| 1-26 | —L—D | H | —CH2CH2— | CONH2 | 2-F | 1 | 4-fluorophenyl | 2,6-dimethyl-4-(1,2,2,2-tetrafluoro-1-trifluoromethyl-ethyl)-phenyl |
| 1-27 | —L—D | H | —CH2CH2— | CONH2 | 2-F | 1 | 2,6-difluorophenyl | 2,6-dimethyl-4-(1,2,2,2-tetrafluoro-1-trifluoromethyl-ethyl)-phenyl |
| 1-28 | —L—D | H | —CH2CH2— | CONH2 | 2-F | 1 | 2-fluoro-4-cyanophenyl | 2,6-dimethyl-4-(1,2,2,2-tetrafluoro-1-trifluoromethyl-ethyl)-phenyl |
| 1-29 | —L—D | H | —CH2CH2— | CONH2 | 2-F | 1 | 2-chlorophenyl | 2,6-dimethyl-4-(1,2,2,2-tetrafluoro-1-trifluoromethyl-ethyl)-phenyl |
| 1-30 | —L—D | H | —CH2CH2— | CONH2 | 2-F | 1 | 4-chlorophenyl | 2,6-dimethyl-4-(1,2,2,2-tetrafluoro-1-trifluoromethyl-ethyl)-phenyl |
| 1-31 | —L—D | H | —CH2CH2— | CONH2 | 2-F | 1 | 4-nitrophenyl | 2,6-dimethyl-4-(1,2,2,2-tetrafluoro-1-trifluoromethyl-ethyl)-phenyl |
| 1-32 | —L—D | H | —CH2CH2— | CONH2 | 2-F | 1 | 2-methylphenyl | 2,6-dimethyl-4-(1,2,2,2-tetrafluoro-1-trifluoromethyl-ethyl)-phenyl |
| 1-33 | —L—D | H | —CH2CH2— | CONH2 | 2-F | 1 | pyridin-2-yl | 2,6-dimethyl-4-(1,2,2,2-tetrafluoro-1-trifluoromethyl-ethyl)-phenyl |
| 1-34 | —L—D | H | —CH2CH2— | CONH2 | 2-F | 1 | pyridin-3-yl | 2,6-dimethyl-4-(1,2,2,2-tetrafluoro-1-trifluoromethyl-ethyl)-phenyl |

TABLE 1-continued

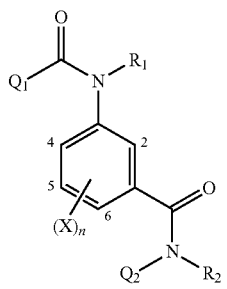

| compound number | R₁ | R₂ | L | D | X | n | Q₁ | Q₂ |
|---|---|---|---|---|---|---|---|---|
| 1-35 | —L—D | H | —CH2CH2— | CONH2 | 2-F | 1 | pyridin-4-yl | 2,6-dimethyl-4-(1,2,2,2-tetrafluoro-1-trifluoromethyl-ethyl)-phenyl |
| 1-36 | —L—D | H | —CH2CH2— | CONH2 | 2-F | 1 | 2-chloropyridin-3-yl | 2,6-dimethyl-4-(1,2,2,2-tetrafluoro-1-trifluoromethyl-ethyl)-phenyl |
| 1-37 | —L—D | H | —CH2CH2— | CONH2 | 2-F | 1 | 6-chloropyridin-3-yl | 2,6-dimethyl-4-(1,2,2,2-tetrafluoro-1-trifluoromethyl-ethyl)-phenyl |
| 1-38 | —L—D | H | —CH2CH2— | CONH2 | 2-F | 1 | 2-chloropyridin-4-yl | 2,6-dimethyl-4-(1,2,2,2-tetrafluoro-1-trifluoromethyl-ethyl)-phenyl |
| 1-39 | —L—D | H | —CH2CH2— | CONH2 | 2-F | 1 | pyrazin-2-yl | 2,6-dimethyl-4-(1,2,2,2-tetrafluoro-1-trifluoromethyl-ethyl)-phenyl |
| 1-40 | —L—D | H | —CH2CH2— | CONH2 | 2-F | 1 | pyrimidin-5-yl | 2,6-dimethyl-4-(1,2,2,2-tetrafluoro-1-trifluoromethyl-ethyl)-phenyl |
| 1-41 | —L—D | H | —CH2CH2— | CONH2 | 4-F | 1 | phenyl | 2,6-dimethyl-4-(1,2,2,2-tetrafluoro-1-trifluoromethyl-ethyl)-phenyl |
| 1-42 | —L—D | H | —CH2CH2— | CONH2 | 4-F | 1 | 4-cyanophenyl | 2,6-dimethyl-4-(1,2,2,2-tetrafluoro-1-trifluoromethyl-ethyl)-phenyl |
| 1-43 | —L—D | H | —CH2CH2— | CONH2 | 4-F | 1 | 3-cyanophenyl | 2,6-dimethyl-4-(1,2,2,2-tetrafluoro-1-trifluoromethyl-ethyl)-phenyl |
| 1-44 | —L—D | H | —CH2CH2— | CONH2 | 4-F | 1 | 2-chloropyridin-3-yl | 2,6-dimethyl-4-(1,2,2,2-tetrafluoro-1-trifluoromethyl-ethyl)-phenyl |
| 1-45 | —L—D | H | —CH2CH2— | CONH2 | 4-F | 1 | 2-fluorophenyl | 2,6-dimethyl-4-(1,2,2,2-tetrafluoro-1-trifluoromethyl-ethyl)-phenyl |
| 1-46 | —L—D | H | —CH2CH2— | CONH2 | 4-CN | 1 | phenyl | 2,6-dimethyl-4-(1,2,2,2-tetrafluoro-1-trifluoromethyl-ethyl)-phenyl |
| 1-47 | —L—D | H | —CH2CH2— | CONH2 | 4-CN | 1 | 4-cyanophenyl | 2,6-dimethyl-4-(1,2,2,2-tetrafluoro-1-trifluoromethyl-ethyl)-phenyl |
| 1-48 | —L—D | H | —CH2CH2— | CONH2 | 4-CN | 1 | 3-cyanophenyl | 2,6-dimethyl-4-(1,2,2,2-tetrafluoro-1-trifluoromethyl-ethyl)-phenyl |
| 1-49 | —L—D | H | —CH2CH2— | CONH2 | 4-CN | 1 | 2-chloropyridin-3-yl | 2,6-dimethyl-4-(1,2,2,2-tetrafluoro-1-trifluoromethyl-ethyl)-phenyl |
| 1-50 | —L—D | H | —CH2CH2— | CONH2 | 4-CN | 1 | 2-fluorophenyl | 2,6-dimethyl-4-(1,2,2,2-tetrafluoro-1-trifluoromethyl-ethyl)-phenyl |
| 1-51 | —L—D | H | —CH2CH2— | CONH2 | H | 0 | 4-cyanophenyl | 2,6-dibromo-4-pentafluoroethyl-phenyl |
| 1-52 | —L—D | H | —CH2CH2— | CONH2 | H | 0 | 4-cyanophenyl | 2,6-diiodo-4-pentafluoroethyl-phenyl |
| 1-53 | —L—D | H | —CH2CH2— | CONH2 | H | 0 | 4-cyanophenyl | 2-bromo-6-trifluoromethyl-4-pentafluoroethyl-phenyl |
| 1-54 | —L—D | H | —CH2CH2— | CONH2 | H | 0 | 4-cyanophenyl | 2-iodo-6-trifluoromethyl-4-pentafluoroethyl-phenyl |
| 1-55 | —L—D | H | —CH2CH2— | CONH2 | H | 0 | 4-cyanophenyl | 2-chloro-6-methyl-4-(1,2,2,2-tetrafluoro-1-trifluoromethyl-ethyl)-phenyl |
| 1-56 | —L—D | H | —CH2CH2— | CONH2 | H | 0 | 4-cyanophenyl | 2-bromo-6-methyl-4-(1,2,2,2-tetrafluoro-1-trifluoromethyl-ethyl)-phenyl |
| 1-57 | —L—D | H | —CH2CH2— | CONH2 | H | 0 | 4-cyanophenyl | 2-iodo-6-methyl-4-(1,2,2,2-tetrafluoro-1-trifluoromethyl-ethyl)-phenyl |
| 1-58 | —L—D | H | —CH2CH2— | CONH2 | H | 0 | 4-cyanophenyl | 2-bromo-6-ethyl-4-(1,2,2,2-tetrafluoro-1-trifluoromethyl-ethyl)-phenyl |
| 1-59 | —L—D | H | —CH2CH2— | CONH2 | H | 0 | 4-cyanophenyl | 2-iodo-6-ethyl-4-(1,2,2,2-tetrafluoro-1-trifluoromethyl-ethyl)-phenyl |
| 1-60 | —L—D | H | —CH2CH2— | CONH2 | H | 0 | 4-cyanophenyl | 2,6-dichloro-4-(1,2,2,2-tetrafluoro-1-trifluoromethyl-ethyl)-phenyl |
| 1-61 | —L—D | H | —CH2CH2— | CONH2 | H | 0 | 4-cyanophenyl | 2,6-dibromo-4-(1,2,2,2-tetrafluoro-1-trifluoromethyl-ethyl)-phenyl |
| 1-62 | —L—D | H | —CH2CH2— | CONH2 | H | 0 | 4-cyanophenyl | 2,6-diiodo-4-(1,2,2,2-tetrafluoro-1-trifluoromethyl-ethyl)-phenyl |
| 1-63 | —L—D | H | —CH2CH2— | CONH2 | H | 0 | 4-cyanophenyl | 2,6-ditrifluoromethyl-4-(1,2,2,2-tetrafluoro-1-trifluoromethyl-ethyl)-phenyl |
| 1-64 | —L—D | H | —CH2CH2— | CONH2 | H | 0 | 4-cyanophenyl | 2-bromo-6-trifluoromethyl-4-(1,2,2,2-tetrafluoro-1-trifluoromethyl-ethyl)-phenyl |
| 1-65 | —L—D | H | —CH2CH2— | CONH2 | H | 0 | 4-cyanophenyl | 2-iodo-6-trifluoromethyl-4-(1,2,2,2-tetrafluoro-1-trifluoromethyl-ethyl)-phenyl |
| 1-66 | —L—D | H | —CH2CH2— | CONH2 | H | 0 | 4-cyanophenyl | 2-bromo-6-trifluoromethoxy-4-(1,2,2,2-tetrafluoro-1-trifluoromethyl-ethyl)-phenyl |

TABLE 1-continued

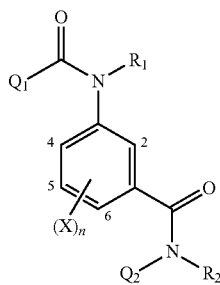

| compound number | $R_1$ | $R_2$ | L | D | X | n | $Q_1$ | $Q_2$ |
|---|---|---|---|---|---|---|---|---|
| 1-67 | —L—D | H | —CH2CH2— | CONH2 | H | 0 | 4-cyanophenyl | 2-bromo-6-iodo-4-(1,2,2,2-tetrafluoro-1-trifluoromethyl-ethyl)-phenyl |
| 1-68 | —L—D | H | —CH2CH2— | CONH2 | H | 0 | 4-cyanophenyl | 2-bromo-6-trifluoromethylthio-4-(1,2,2,2-tetrafluoro-1-trifluoromethyl-ethyl)-phenyl |
| 1-69 | —L—D | H | —CH2CH2— | CONH2 | H | 0 | 4-cyanophenyl | 2-bromo-6-trifluoromethylsulfinyl-4-(1,2,2,2-tetrafluoro-1-trifluoromethyl-ethyl)-phenyl |
| 1-70 | —L—D | H | —CH2CH2— | CONH2 | H | 0 | 4-cyanophenyl | 2-bromo-6-trifluoromethylsulfonyl-4-(1,2,2,2-tetrafluoro-1-trifluoromethyl-ethyl)-phenyl |
| 1-71 | —L—D | H | —CH2CH2— | CONH2 | H | 0 | 4-cyanophenyl | 2-bromo-6-pentafluoroethyl-4-(1,2,2,2-tetrafluoro-1-trifluoromethyl-ethyl)-phenyl |
| 1-72 | —L—D | H | —CH2CH2— | CONH2 | H | 0 | 4-cyanophenyl | 2-iodo-6-pentafluoroethyl-4-(1,2,2,2-tetrafluoro-1-trifluoromethyl-ethyl)-phenyl |
| 1-73 | —L—D | H | —CH2CH2— | CONH2 | H | 0 | 4-cyanophenyl | 2-chloro-6-methyl-4-(1,2,2,3,3,3-hexafluoro-1-trifluoromethyl-propyl)-phenyl |
| 1-74 | —L—D | H | —CH2CH2— | CONH2 | H | 0 | 4-cyanophenyl | 2-bromo-6-methyl-4-(1,2,2,3,3,3-hexafluoro-1-trifluoromethyl-propyl)-phenyl |
| 1-75 | —L—D | H | —CH2CH2— | CONH2 | H | 0 | 4-cyanophenyl | 2-iodo-6-methyl-4-(1,2,2,3,3,3-hexafluoro-1-trifluoromethyl-propyl)-phenyl |
| 1-76 | —L—D | H | —CH2CH2— | CONH2 | H | 0 | 4-cyanophenyl | 2-bromo-6-ethyl-4-(1,2,2,3,3,3-hexafluoro-1-trifluoromethyl-propyl)-phenyl |
| 1-77 | —L—D | H | —CH2CH2— | CONH2 | H | 0 | 4-cyanophenyl | 2-iodo-6-ethyl-4-(1,2,2,3,3,3-hexafluoro-1-trifluoromethyl-propyl)-phenyl |
| 1-78 | —L—D | H | —CH2CH2— | CONH2 | H | 0 | 4-cyanophenyl | 2,6-dichloro-4-(1,2,2,3,3,3-hexafluoro-1-trifluoromethyl-propyl)-phenyl |
| 1-79 | —L—D | H | —CH2CH2— | CONH2 | H | 0 | 4-cyanophenyl | 2,6-dibromo-4-(1,2,2,3,3,3-hexafluoro-1-trifluoromethyl-propyl)-phenyl |
| 1-80 | —L—D | H | —CH2CH2— | CONH2 | H | 0 | 4-cyanophenyl | 2,6-diiodo-4-(1,2,2,3,3,3-hexafluoro-1-trifluoromethyl-propyl)-phenyl |
| 1-81 | —L—D | H | —CH2CH2— | CONH2 | H | 0 | 4-cyanophenyl | 2,6-ditrifluoromethyl-4-(1,2,2,3,3,3-hexafluoro-1-trifluoromethyl-propyl)-phenyl |
| 1-82 | —L—D | H | —CH2CH2— | CONH2 | H | 0 | 4-cyanophenyl | 2-bromo-6-trifluoromethyl-4-(1,2,2,3,3,3-hexafluoro-1-trifluoromethyl-propyl)-phenyl |
| 1-83 | —L—D | H | —CH2CH2— | CONH2 | H | 0 | 4-cyanophenyl | 2-iodo-6-trifluoromethyl-4-(1,2,2,3,3,3-hexafluoro-1-trifluoromethyl-propyl)-phenyl |
| 1-84 | —L—D | H | —CH2CH2— | CONH2 | H | 0 | 4-cyanophenyl | 2-bromo-6-trifluoromethoxy-4-(1,2,2,3,3,3-hexafluoro-1-trifluoromethyl-propyl)-phenyl |
| 1-85 | —L—D | H | —CH2CH2— | CONH2 | H | 0 | 4-cyanophenyl | 2-bromo-6-iodo-4-(1,2,2,3,3,3-hexafluoro-1-trifluoromethyl-propyl)-phenyl |
| 1-86 | —L—D | H | —CH2CH2— | CONH2 | H | 0 | 4-cyanophenyl | 2-bromo-6-trifluoromethylthio-4-(1,2,2,3,3,3-hexafluoro-1-trifluoromethyl-propyl)-phenyl |
| 1-87 | —L—D | H | —CH2CH2— | CONH2 | H | 0 | 4-cyanophenyl | 2-bromo-6-trifluoromethylsulfinyl-4-(1,2,2,3,3,3-hexafluoro-1-trifluoromethyl-propyl)-phenyl |
| 1-88 | —L—D | H | —CH2CH2— | CONH2 | H | 0 | 4-cyanophenyl | 2-bromo-6-trifluoromethylsulfonyl-4-(1,2,2,3,3,3-hexafluoro-1-trifluoromethyl-propyl)-phenyl |
| 1-89 | —L—D | H | —CH2CH2— | CONH2 | H | 0 | 4-cyanophenyl | 2-bromo-6-pentafluoroethyl-4-(1,2,2,3,3,3-hexafluoro-1-trifluoromethyl-propyl)-phenyl |
| 1-90 | —L—D | H | —CH2CH2— | CONH2 | H | 0 | 4-cyanophenyl | 2-iodo-6-pentafluoroethyl-4-(1,2,2,3,3,3-hexafluoro-1-trifluoromethyl-propyl)-phenyl |
| 1-91 | —L—D | H | —CH2CH2— | CONH2 | H | 0 | phenyl | 2,6-dibromo-4-(1,2,2,2-tetrafluoro-1-trifluoromethyl-ethyl)-phenyl |
| 1-92 | —L—D | H | —CH2CH2— | CONH2 | H | 0 | 4-cyanophenyl | 2,6-dibromo-4-(1,2,2,2-tetrafluoro-1-trifluoromethyl-ethyl)-phenyl |
| 1-93 | —L—D | H | —CH2CH2— | CONH2 | H | 0 | 2-chloropyridin-3-yl | 2,6-dibromo-4-(1,2,2,2-tetrafluoro-1-trifluoromethyl-ethyl)-phenyl |
| 1-94 | —L—D | H | —CH2CH2— | CONH2 | H | 0 | 2-fluorophenyl | 2,6-dibromo-4-(1,2,2,2-tetrafluoro-1-trifluoromethyl-ethyl)-phenyl |
| 1-95 | —L—D | H | —CH2CH2— | CONH2 | H | 0 | phenyl | 2,6-diiodo-4-(1,2,2,2-tetrafluoro-1-trifluoromethyl-ethyl)-phenyl |
| 1-96 | —L—D | H | —CH2CH2— | CONH2 | H | 0 | 3-cyanophenyl | 2,6-diiodo-4-(1,2,2,2-tetrafluoro-1-trifluoromethyl-ethyl)-phenyl |
| 1-97 | —L—D | H | —CH2CH2— | CONH2 | H | 0 | 2-chloropyridin-3-yl | 2,6-diiodo-4-(1,2,2,2-tetrafluoro-1-trifluoromethyl-ethyl)-phenyl |

TABLE 1-continued

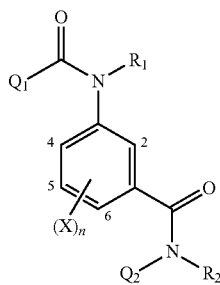

| compound number | $R_1$ | $R_2$ | L | D | X | n | $Q_1$ | $Q_2$ |
|---|---|---|---|---|---|---|---|---|
| 1-98 | —L—D | H | —CH2CH2— | CONH2 | H | 0 | 2-fluorophenyl | 2,6-diiodo-4-(1,2,2,2-tetrafluoro-1-trifluoromethyl-ethyl)-phenyl |
| 1-99 | —L—D | H | —CH2CH2— | CONH2 | H | 0 | phenyl | 2-bromo-6-trifluoromethyl-4-(1,2,2,2-tetrafluoro-1-trifluoromethyl-ethyl)-phenyl |
| 1-100 | —L—D | H | —CH2CH2— | CONH2 | H | 0 | 3-cyanophenyl | 2-bromo-6-trifluoromethyl-4-(1,2,2,2-tetrafluoro-1-trifluoromethyl-ethyl)-phenyl |
| 1-101 | —L—D | H | —CH2CH2— | CONH2 | H | 0 | 2-chloropyridin-3-yl | 2-bromo-6-trifluoromethyl-4-(1,2,2,2-tetrafluoro-1-trifluoromethyl-ethyl)-phenyl |
| 1-102 | —L—D | H | —CH2CH2— | CONH2 | H | 0 | 2-fluorophenyl | 2-bromo-6-trifluoromethyl-4-(1,2,2,2-tetrafluoro-1-trifluoromethyl-ethyl)-phenyl |
| 1-103 | —L—D | H | —CH2CH2— | CONH2 | H | 0 | phenyl | 2-iodo-6-trifluoromethyl-4-(1,2,2,2-tetrafluoro-1-trifluoromethyl-ethyl)-phenyl |
| 1-104 | —L—D | H | —CH2CH2— | CONH2 | H | 0 | 3-cyanophenyl | 2-iodo-6-trifluoromethyl-4-(1,2,2,2-tetrafluoro-1-trifluoromethyl-ethyl)-phenyl |
| 1-105 | —L—D | H | —CH2CH2— | CONH2 | H | 0 | 2-chloropyridin-3-yl | 2-iodo-6-trifluoromethyl-4-(1,2,2,2-tetrafluoro-1-trifluoromethyl-ethyl)-phenyl |
| 1-106 | —L—D | H | —CH2CH2— | CONH2 | H | 0 | 2-fluorophenyl | 2-iodo-6-trifluoromethyl-4-(1,2,2,2-tetrafluoro-1-trifluoromethyl-ethyl)-phenyl |
| 1-107 | —L—D | H | —CH2CH2— | CONH2 | H | 0 | phenyl | 2,6-dibromo-4-(1,2,2,3,3,3-hexafluoro-1-trifluoromethyl-propyl)-phenyl |
| 1-108 | —L—D | H | —CH2CH2— | CONH2 | H | 0 | 3-cyanophenyl | 2,6-dibromo-4-(1,2,2,3,3,3-hexafluoro-1-trifluoromethyl-propyl)-phenyl |
| 1-109 | —L—D | H | —CH2CH2— | CONH2 | H | 0 | 2-chloropyridin-3-yl | 2,6-dibromo-4-(1,2,2,3,3,3-hexafluoro-1-trifluoromethyl-propyl)-phenyl |
| 1-110 | —L—D | H | —CH2CH2— | CONH2 | H | 0 | 2-fluorophenyl | 2,6-dibromo-4-(1,2,2,3,3,3-hexafluoro-1-trifluoromethyl-propyl)-phenyl |
| 1-111 | —L—D | H | —CH2CH2— | CONH2 | H | 0 | phenyl | 2,6-diiodo-4-(1,2,2,3,3,3-hexafluoro-1-trifluoromethyl-propyl)-phenyl |
| 1-112 | —L—D | H | —CH2CH2— | CONH2 | H | 0 | 3-cyanophenyl | 2,6-diiodo-4-(1,2,2,3,3,3-hexafluoro-1-trifluoromethyl-propyl)-phenyl |
| 1-113 | —L—D | H | —CH2CH2— | CONH2 | H | 0 | 2-chloropyridin-3-yl | 2,6-diiodo-4-(1,2,2,3,3,3-hexafluoro-1-trifluoromethyl-propyl)-phenyl |
| 1-114 | —L—D | H | —CH2CH2— | CONH2 | H | 0 | 2-fluorophenyl | 2,6-diiodo-4-(1,2,2,3,3,3-hexafluoro-1-trifluoromethyl-propyl)-phenyl |
| 1-115 | —L—D | H | —CH2CH2— | CONH2 | H | 0 | phenyl | 2-bromo-6-trifluoromethyl-4-(1,2,2,3,3,3-hexafluoro-1-trifluoromethyl-propyl)-phenyl |
| 1-116 | —L—D | H | —CH2CH2— | CONH2 | H | 0 | 3-cyanophenyl | 2-bromo-6-trifluoromethyl-4-(1,2,2,3,3,3-hexafluoro-1-trifluoromethyl-propyl)-phenyl |
| 1-117 | —L—D | H | —CH2CH2— | CONH2 | H | 0 | 2-chloropyridin-3-yl | 2-bromo-6-trifluoromethyl-4-(1,2,2,3,3,3-hexafluoro-1-trifluoromethyl-propyl)-phenyl |
| 1-118 | —L—D | H | —CH2CH2— | CONH2 | H | 0 | 2-fluorophenyl | 2-bromo-6-trifluoromethyl-4-(1,2,2,3,3,3-hexafluoro-1-trifluoromethyl-propyl)-phenyl |
| 1-119 | —L—D | H | —CH2CH2— | CONH2 | H | 0 | phenyl | 2-iodo-6-trifluoromethyl-4-(1,2,2,3,3,3-hexafluoro-1-trifluoromethyl-propyl)-phenyl |
| 1-120 | —L—D | H | —CH2CH2— | CONH2 | H | 0 | 3-cyanophenyl | 2-iodo-6-trifluoromethyl-4-(1,2,2,3,3,3-hexafluoro-1-trifluoromethyl-propyl)-phenyl |
| 1-121 | —L—D | H | —CH2CH2— | CONH2 | H | 0 | 2-chloropyridin-3-yl | 2-iodo-6-trifluoromethyl-4-(1,2,2,3,3,3-hexafluoro-1-trifluoromethyl-propyl)-phenyl |
| 1-122 | —L—D | H | —CH2CH2— | CONH2 | H | 0 | 2-fluorophenyl | 2-iodo-6-trifluoromethyl-4-(1,2,2,3,3,3-hexafluoro-1-trifluoromethyl-propyl)-phenyl |
| 1-123 | —L—D | H | —CH2CH2— | CONH2 | 2-F | 1 | 4-cyanophenyl | 2,6-dibromo-4-pentafluoroethyl-phenyl |
| 1-124 | —L—D | H | —CH2CH2— | CONH2 | 2-F | 1 | 4-cyanophenyl | 2,6-diiodo-4-pentafluoroethyl-phenyl |
| 1-125 | —L—D | H | —CH2CH2— | CONH2 | 2-F | 1 | 4-cyanophenyl | 2-bromo-6-trifluoromethyl-4-pentafluoroethyl-phenyl |
| 1-126 | —L—D | H | —CH2CH2— | CONH2 | 2-F | 1 | 4-cyanophenyl | 2-iodo-6-trifluoromethyl-4-pentafluoroethyl-phenyl |
| 1-127 | —L—D | H | —CH2CH2— | CONH2 | 2-F | 1 | 4-cyanophenyl | 2-chloro-6-methyl-4-(1,2,2,2-tetrafluoro-1-trifluoromethyl-ethyl)-phenyl |
| 1-128 | —L—D | H | —CH2CH2— | CONH2 | 2-F | 1 | 4-cyanophenyl | 2-bromo-6-methyl-4-(1,2,2,2-tetrafluoro-1-trifluoromethyl-ethyl)-phenyl |
| 1-129 | —L—D | H | —CH2CH2— | CONH2 | 2-F | 1 | 4-cyanophenyl | 2-iodo-6-methyl-4-(1,2,2,2-tetrafluoro-1-trifluoromethyl-ethyl)-phenyl |

TABLE 1-continued

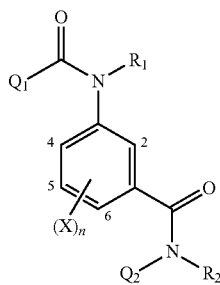

| compound number | R₁ | R₂ | L | D | X | n | Q₁ | Q₂ |
|---|---|---|---|---|---|---|---|---|
| 1-130 | —L—D | H | —CH2CH2— | CONH2 | 2-F | 1 | 4-cyanophenyl | 2-bromo-6-ethyl-4-(1,2,2,2-tetrafluoro-1-trifluoromethyl-ethyl)-phenyl |
| 1-131 | —L—D | H | —CH2CH2— | CONH2 | 2-F | 1 | 4-cyanophenyl | 2-iodo-6-ethyl-4-(1,2,2,2-tetrafluoro-1-trifluoromethyl-ethyl)-phenyl |
| 1-132 | —L—D | H | —CH2CH2— | CONH2 | 2-F | 1 | 4-cyanophenyl | 2,6-dichloro-4-(1,2,2,2-tetrafluoro-1-trifluoromethyl-ethyl)-phenyl |
| 1-133 | —L—D | H | —CH2CH2— | CONH2 | 2-F | 1 | 4-cyanophenyl | 2,6-dibromo-4-(1,2,2,2-tetrafluoro-1-trifluoromethyl-ethyl)-phenyl |
| 1-134 | —L—D | H | —CH2CH2— | CONH2 | 2-F | 1 | 4-cyanophenyl | 2,6-diiodo-4-(1,2,2,2-tetrafluoro-1-trifluoromethyl-ethyl)-phenyl |
| 1-135 | —L—D | H | —CH2CH2— | CONH2 | 2-F | 1 | 4-cyanophenyl | 2,6-ditrifluoromethyl-4-(1,2,2,2-tetrafluoro-1-trifluoromethyl-ethyl)-phenyl |
| 1-136 | —L—D | H | —CH2CH2— | CONH2 | 2-F | 1 | 4-cyanophenyl | 2-bromo-6-trifluoromethyl-4-(1,2,2,2-tetrafluoro-1-trifluoromethyl-ethyl)-phenyl |
| 1-137 | —L—D | H | —CH2CH2— | CONH2 | 2-F | 1 | 4-cyanophenyl | 2-iodo-6-trifluoromethyl-4-(1,2,2,2-tetrafluoro-1-trifluoromethyl-ethyl)-phenyl |
| 1-138 | —L—D | H | —CH2CH2— | CONH2 | 2-F | 1 | 4-cyanophenyl | 2-bromo-6-trifluoromethoxy-4-(1,2,2,2-tetrafluoro-1-trifluoromethyl-ethyl)-phenyl |
| 1-139 | —L—D | H | —CH2CH2— | CONH2 | 2-F | 1 | 4-cyanophenyl | 2-bromo-6-iodo-4-(1,2,2,2-tetrafluoro-1-trifluoromethyl-ethyl)-phenyl |
| 1-140 | —L—D | H | —CH2CH2— | CONH2 | 2-F | 1 | 4-cyanophenyl | 2-bromo-6-trifluoromethylthio-4-(1,2,2,2-tetrafluoro-1-trifluoromethyl-ethyl)-phenyl |
| 1-141 | —L—D | H | —CH2CH2— | CONH2 | 2-F | 1 | 4-cyanophenyl | 2-bromo-6-trifluoromethylsulfinyl-4-(1,2,2,2-tetrafluoro-1-trifluoromethyl-ethyl)-phenyl |
| 1-142 | —L—D | H | —CH2CH2— | CONH2 | 2-F | 1 | 4-cyanophenyl | 2-bromo-6-trifluoromethylsulfonyl-4-(1,2,2,2-tetrafluoro-1-trifluoromethyl-ethyl)-phenyl |
| 1-143 | —L—D | H | —CH2CH2— | CONH2 | 2-F | 1 | 4-cyanophenyl | 2-bromo-6-pentafluoroethyl-4-(1,2,2,2-tetrafluoro-1-trifluoromethyl-ethyl)-phenyl |
| 1-144 | —L—D | H | —CH2CH2— | CONH2 | 2-F | 1 | 4-cyanophenyl | 2-iodo-6-pentafluoroethyl-4-(1,2,2,2-tetrafluoro-1-trifluoromethyl-ethyl)-phenyl |
| 1-145 | —L—D | H | —CH2CH2— | CONH2 | 2-F | 1 | 4-cyanophenyl | 2-chloro-6-methyl-4-(1,2,2,3,3,3-hexafluoro-1-trifluoromethyl-propyl)-phenyl |
| 1-146 | —L—D | H | —CH2CH2— | CONH2 | 2-F | 1 | 4-cyanophenyl | 2-bromo-6-methyl-4-(1,2,2,3,3,3-hexafluoro-1-trifluoromethyl-propyl)-phenyl |
| 1-147 | —L—D | H | —CH2CH2— | CONH2 | 2-F | 1 | 4-cyanophenyl | 2-iodo-6-methyl-4-(1,2,2,3,3,3-hexafluoro-1-trifluoromethyl-propyl)-phenyl |
| 1-148 | —L—D | H | —CH2CH2— | CONH2 | 2-F | 1 | 4-cyanophenyl | 2-bromo-6-ethyl-4-(1,2,2,3,3,3-hexafluoro-1-trifluoromethyl-propyl)-phenyl |
| 1-149 | —L—D | H | —CH2CH2— | CONH2 | 2-F | 1 | 4-cyanophenyl | 2-iodo-6-ethyl-4-(1,2,2,3,3,3-hexafluoro-1-trifluoromethyl-propyl)-phenyl |
| 1-150 | —L—D | H | —CH2CH2— | CONH2 | 2-F | 1 | 4-cyanophenyl | 2,6-dichloro-4-(1,2,2,3,3,3-hexafluoro-1-trifluoromethyl-propyl)-phenyl |
| 1-151 | —L—D | H | —CH2CH2— | CONH2 | 2-F | 1 | 4-cyanophenyl | 2,6-dibromo-4-(1,2,2,3,3,3-hexafluoro-1-trifluoromethyl-propyl)-phenyl |
| 1-152 | —L—D | H | —CH2CH2— | CONH2 | 2-F | 1 | 4-cyanophenyl | 2,6-diiodo-4-(1,2,2,3,3,3-hexafluoro-1-trifluoromethyl-propyl)-phenyl |
| 1-153 | —L—D | H | —CH2CH2— | CONH2 | 2-F | 1 | 4-cyanophenyl | 2,6-ditrifluoromethyl-4-(1,2,2,3,3,3-hexafluoro-1-trifluoromethyl-propyl)-phenyl |
| 1-154 | —L—D | H | —CH2CH2— | CONH2 | 2-F | 1 | 4-cyanophenyl | 2-bromo-6-trifluoromethyl-4-(1,2,2,3,3,3-hexafluoro-1-trifluoromethyl-propyl)-phenyl |
| 1-155 | —L—D | H | —CH2CH2— | CONH2 | 2-F | 1 | 4-cyanophenyl | 2-iodo-6-trifluoromethyl-4-(1,2,2,3,3,3-hexafluoro-1-trifluoromethyl-propyl)-phenyl |
| 1-156 | —L—D | H | —CH2CH2— | CONH2 | 2-F | 1 | 4-cyanophenyl | 2-bromo-6-trifluoromethoxy-4-(1,2,2,3,3,3-hexafluoro-1-trifluoromethyl-propyl)-phenyl |
| 1-157 | —L—D | H | —CH2CH2— | CONH2 | 2-F | 1 | 4-cyanophenyl | 2-bromo-6-iodo-4-(1,2,2,3,3,3-hexafluoro-1-trifluoromethyl-propyl)-phenyl |
| 1-158 | —L—D | H | —CH2CH2— | CONH2 | 2-F | 1 | 4-cyanophenyl | 2-bromo-6-trifluoromethylthio-4-(1,2,2,3,3,3-hexafluoro-1-trifluoromethyl-propyl)-phenyl |
| 1-159 | —L—D | H | —CH2CH2— | CONH2 | 2-F | 1 | 4-cyanophenyl | 2-bromo-6-trifluoromethylsulfinyl-4-(1,2,2,3,3,3-hexafluoro-1-trifluoromethyl-propyl)-phenyl |
| 1-160 | —L—D | H | —CH2CH2— | CONH2 | 2-F | 1 | 4-cyanophenyl | 2-bromo-6-trifluoromethylsulfonyl-4-(1,2,2,3,3,3-hexafluoro-1-trifluoromethyl-propyl)-phenyl |

TABLE 1-continued

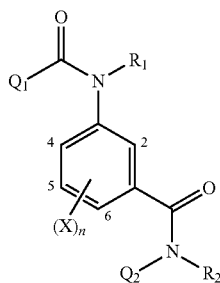

| compound number | R₁ | R₂ | L | D | X | n | Q₁ | Q₂ |
|---|---|---|---|---|---|---|---|---|
| 1-161 | —L—D | H | —CH2CH2— | CONH2 | 2-F | 1 | 4-cyanophenyl | 2-bromo-6-pentafluoroethyl-4-(1,2,2,3,3,3-hexafluoro-1-trifluoromethyl-propyl)-phenyl |
| 1-162 | —L—D | H | —CH2CH2— | CONH2 | 2-F | 1 | 4-cyanophenyl | 2-iodo-6-pentafluoroethyl-4-(1,2,2,3,3,3-hexafluoro-1-trifluoromethyl-propyl)-phenyl |
| 1-163 | —L—D | H | —CH2CH2— | CONH2 | 2-F | 1 | phenyl | 2,6-dibromo-4-(1,2,2,2-tetrafluoro-1-trifluoromethyl-ethyl)-phenyl |
| 1-164 | —L—D | H | —CH2CH2— | CONH2 | 2-F | 1 | 3-cyanophenyl | 2,6-dibromo-4-(1,2,2,2-tetrafluoro-1-trifluoromethyl-ethyl)-phenyl |
| 1-165 | —L—D | H | —CH2CH2— | CONH2 | 2-F | 1 | 2-chloropyridin-3-yl | 2,6-dibromo-4-(1,2,2,2-tetrafluoro-1-trifluoromethyl-ethyl)-phenyl |
| 1-166 | —L—D | H | —CH2CH2— | CONH2 | 2-F | 1 | 2-fluorophenyl | 2,6-dibromo-4-(1,2,2,2-tetrafluoro-1-trifluoromethyl-ethyl)-phenyl |
| 1-167 | —L—D | H | —CH2CH2— | CONH2 | 2-F | 1 | phenyl | 2,6-diiodo-4-(1,2,2,2-tetrafluoro-1-trifluoromethyl-ethyl)-phenyl |
| 1-168 | —L—D | H | —CH2CH2— | CONH2 | 2-F | 1 | 3-cyanophenyl | 2,6-diiodo-4-(1,2,2,2-tetrafluoro-1-trifluoromethyl-ethyl)-phenyl |
| 1-169 | —L—D | H | —CH2CH2— | CONH2 | 2-F | 1 | 2-chloropyridin-3-yl | 2,6-diiodo-4-(1,2,2,2-tetrafluoro-1-trifluoromethyl-ethyl)-phenyl |
| 1-170 | —L—D | H | —CH2CH2— | CONH2 | 2-F | 1 | 2-fluorophenyl | 2,6-diiodo-4-(1,2,2,2-tetrafluoro-1-trifluoromethyl-ethyl)-phenyl |
| 1-171 | —L—D | H | —CH2CH2— | CONH2 | 2-F | 1 | phenyl | 2-bromo-6-trifluoromethyl-4-(1,2,2,2-tetrafluoro-1-trifluoromethyl-ethyl)-phenyl |
| 1-172 | —L—D | H | —CH2CH2— | CONH2 | 2-F | 1 | 3-cyanophenyl | 2-bromo-6-trifluoromethyl-4-(1,2,2,2-tetrafluoro-1-trifluoromethyl-ethyl)-phenyl |
| 1-173 | —L—D | H | —CH2CH2— | CONH2 | 2-F | 1 | 2-chloropyridin-3-yl | 2-bromo-6-trifluoromethyl-4-(1,2,2,2-tetrafluoro-1-trifluoromethyl-ethyl)-phenyl |
| 1-174 | —L—D | H | —CH2CH2— | CONH2 | 2-F | 1 | 2-fluorophenyl | 2-bromo-6-trifluoromethyl-4-(1,2,2,2-tetrafluoro-1-trifluoromethyl-ethyl)-phenyl |
| 1-175 | —L—D | H | —CH2CH2— | CONH2 | 2-F | 1 | phenyl | 2-iodo-6-trifluoromethyl-4-(1,2,2,2-tetrafluoro-1-trifluoromethyl-ethyl)-phenyl |
| 1-176 | —L—D | H | —CH2CH2— | CONH2 | 2-F | 1 | 3-cyanophenyl | 2-iodo-6-trifluoromethyl-4-(1,2,2,2-tetrafluoro-1-trifluoromethyl-ethyl)-phenyl |
| 1-177 | —L—D | H | —CH2CH2— | CONH2 | 2-F | 1 | 2-chloropyridin-3-yl | 2-iodo-6-trifluoromethyl-4-(1,2,2,2-tetrafluoro-1-trifluoromethyl-ethyl)-phenyl |
| 1-178 | —L—D | H | —CH2CH2— | CONH2 | 2-F | 1 | 2-fluorophenyl | 2-iodo-6-trifluoromethyl-4-(1,2,2,2-tetrafluoro-1-trifluoromethyl-ethyl)-phenyl |
| 1-179 | —L—D | H | —CH2CH2— | CONH2 | 2-F | 1 | phenyl | 2,6-dibromo-4-(1,2,2,3,3,3-hexafluoro-1-trifluoromethyl-propyl)-phenyl |
| 1-180 | —L—D | H | —CH2CH2— | CONH2 | 2-F | 1 | 3-cyanophenyl | 2,6-dibromo-4-(1,2,2,3,3,3-hexafluoro-1-trifluoromethyl-propyl)-phenyl |
| 1-181 | —L—D | H | —CH2CH2— | CONH2 | 2-F | 1 | 2-chloropyridin-3-yl | 2,6-dibromo-4-(1,2,2,3,3,3-hexafluoro-1-trifluoromethyl-propyl)-phenyl |
| 1-182 | —L—D | H | —CH2CH2— | CONH2 | 2-F | 1 | 2-fluorophenyl | 2,6-dibromo-4-(1,2,2,3,3,3-hexafluoro-1-trifluoromethyl-propyl)-phenyl |
| 1-183 | —L—D | H | —CH2CH2— | CONH2 | 2-F | 1 | phenyl | 2,6-diiodo-4-(1,2,2,3,3,3-hexafluoro-1-trifluoromethyl-propyl)-phenyl |
| 1-184 | —L—D | H | —CH2CH2— | CONH2 | 2-F | 1 | 3-cyanophenyl | 2,6-diiodo-4-(1,2,2,3,3,3-hexafluoro-1-trifluoromethyl-propyl)-phenyl |
| 1-185 | —L—D | H | —CH2CH2— | CONH2 | 2-F | 1 | 2-chloropyridin-3-yl | 2,6-diiodo-4-(1,2,2,3,3,3-hexafluoro-1-trifluoromethyl-propyl)-phenyl |
| 1-186 | —L—D | H | —CH2CH2— | CONH2 | 2-F | 1 | 2-fluorophenyl | 2,6-diiodo-4-(1,2,2,3,3,3-hexafluoro-1-trifluoromethyl-propyl)-phenyl |
| 1-187 | —L—D | H | —CH2CH2— | CONH2 | 2-F | 1 | phenyl | 2-bromo-6-trifluoromethyl-4-(1,2,2,3,3,3-hexafluoro-1-trifluoromethyl-propyl)-phenyl |
| 1-188 | —L—D | H | —CH2CH2— | CONH2 | 2-F | 1 | 3-cyanophenyl | 2-bromo-6-trifluoromethyl-4-(1,2,2,3,3,3-hexafluoro-1-trifluoromethyl-propyl)-phenyl |
| 1-189 | —L—D | H | —CH2CH2— | CONH2 | 2-F | 1 | 2-chloropyridin-3-yl | 2-bromo-6-trifluoromethyl-4-(1,2,2,3,3,3-hexafluoro-1-trifluoromethyl-propyl)-phenyl |
| 1-190 | —L—D | H | —CH2CH2— | CONH2 | 2-F | 1 | 2-fluorophenyl | 2-bromo-6-trifluoromethyl-4-(1,2,2,3,3,3-hexafluoro-1-trifluoromethyl-propyl)-phenyl |
| 1-191 | —L—D | H | —CH2CH2— | CONH2 | 2-F | 1 | phenyl | 2-iodo-6-trifluoromethyl-4-(1,2,2,3,3,3-hexafluoro-1-trifluoromethyl-propyl)-phenyl |

TABLE 1-continued

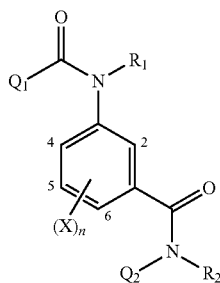

| compound number | $R_1$ | $R_2$ | L | D | X | n | $Q_1$ | $Q_2$ |
|---|---|---|---|---|---|---|---|---|
| 1-192 | —L—D | H | —CH2CH2— | CONH2 | 2-F | 1 | 3-cyanophenyl | 2-iodo-6-trifluoromethyl-4-(1,2,2,3,3,3-hexafluoro-1-trifluoromethyl-propyl)-phenyl |
| 1-193 | —L—D | H | —CH2CH2— | CONH2 | 2-F | 1 | 2-chloropyridin-3-yl | 2-iodo-6-trifluoromethyl-4-(1,2,2,3,3,3-hexafluoro-1-trifluoromethyl-propyl)-phenyl |
| 1-194 | —L—D | H | —CH2CH2— | CONH2 | 2-F | 1 | 2-fluorophenyl | 2-iodo-6-trifluoromethyl-4-(1,2,2,3,3,3-hexafluoro-1-trifluoromethyl-propyl)-phenyl |
| 1-195 | —L—D | H | —CH2CH2— | CONH2 | H | 0 | 6-chloropyridin-3-yl | 2-bromo-6-trifluoromethyl-4-(1,2,2,2-tetrafluoro-1-trifluoromethyl-ethyl)-phenyl |
| 1-196 | —L—D | H | —CH2CH2— | CONH2 | 2-F | 1 | 6-chloropyridin-3-yl | 2-bromo-6-trifluoromethyl-4-(1,2,2,2-tetrafluoro-1-trifluoromethyl-ethyl)-phenyl |
| 1-197 | —L—D | H | —CH2CH2— | CONH2 | 2-F | 1 | 6-chloropyridin-3-yl | 2,6-dibromo-4-(1,2,2,2-tetrafluoro-1-trifluoromethyl-ethyl)-phenyl |
| 1-198 | —L—D | H | —CH2CH2— | CONH2 | 2-F | 1 | 3,5-dicyanophenyl | 2-bromo-6-trifluoromethyl-4-(1,2,2,2-tetrafluoro-1-trifluoromethyl-ethyl)-phenyl |
| 1-199 | —L—D | H | —CH2CH2— | CONH2 | 2-F | 1 | 3,5-dicyanophenyl | 2,6-dibromo-4-(1,2,2,2-tetrafluoro-1-trifluoromethyl-ethyl)-phenyl |
| 1-200 | —L—D | H | —CH2CH2— | CONH2 | 2-F | 1 | pyridin-3-yl | 2,6-dibromo-4-(1,2,2,2-tetrafluoro-1-trifluoromethyl-ethyl)-phenyl |
| 1-201 | —L—D | H | —CH2CH2— | CONH2 | 2-F | 1 | pyridin-4-yl | 2,6-dibromo-4-(1,2,2,2-tetrafluoro-1-trifluoromethyl-ethyl)-phenyl |
| 1-202 | —L—D | H | —CH2CH2— | CONH2 | 2-F | 1 | 2-chloropyridin-4-yl | 2,6-dibromo-4-(1,2,2,2-tetrafluoro-1-trifluoromethyl-ethyl)-phenyl |
| 1-203 | —L—D | H | —CH2CH2— | CONH2 | 2-F | 1 | pyrazin-2-yl | 2,6-dibromo-4-(1,2,2,2-tetrafluoro-1-trifluoromethyl-ethyl)-phenyl |
| 1-204 | —L—D | H | —CH2CH2— | CONH2 | 2-F | 1 | pyrimidin-5-yl | 2,6-dibromo-4-(1,2,2,2-tetrafluoro-1-trifluoromethyl-ethyl)-phenyl |
| 1-205 | —L—D | H | —CH2CH2— | CONH2 | 2-F | 1 | 3-cyanophenyl | 2,6-dichloro-4-(1,2,2,2-tetrafluoro-1-trifluoromethyl-ethyl)-phenyl |
| 1-206 | —L—D | H | —CH2CH2— | CONH2 | 2-F | 1 | phenyl | 2,6-dichloro-4-(1,2,2,2-tetrafluoro-1-trifluoromethyl-ethyl)-phenyl |
| 1-207 | —L—D | H | —CH2CH2— | CONH2 | 2-F | 1 | 2-chloropyridin-3-yl | 2,6-dichloro-4-(1,2,2,2-tetrafluoro-1-trifluoromethyl-ethyl)-phenyl |
| 1-208 | —L—D | H | —CH2CH2— | CONH2 | 2-F | 1 | 6-cyanopyridin-3-yl | 2,6-dibromo-4-(1,2,2,2-tetrafluoro-1-trifluoromethyl-ethyl)-phenyl |
| 1-209 | —L—D | H | —CH2CH2— | CONH2 | 2-F | 1 | 4-fluorophenyl | 2,6-dibromo-4-(1,2,2,2-tetrafluoro-1-trifluoromethyl-ethyl)-phenyl |
| 1-210 | —L—D | H | —CH2CH2— | CONH2 | 2-F | 1 | 2,6-difluorophenyl | 2,6-dibromo-4-(1,2,2,2-tetrafluoro-1-trifluoromethyl-ethyl)-phenyl |
| 1-211 | —L—D | H | —CH2CH2— | CONH2 | 2-F | 1 | 2-chloropyridin-3-yl | 2-bromo-6-iodo-4-(1,2,2,2-tetrafluoro-1-trifluoromethyl-ethyl)-phenyl |
| 1-212 | —L—D | H | —CH2CH2— | CONH2 | 2-F | 1 | phenyl | 2-bromo-6-iodo-4-(1,2,2,2-tetrafluoro-1-trifluoromethyl-ethyl)-phenyl |
| 1-213 | —L—D | H | —CH2CH2— | CONH2 | 2-F | 1 | 6-chloropyridin-3-yl | 2,6-dibromo-4-(1,2,2,3,3,3-hexafluoro-1-trifluoromethyl-propyl)-phenyl |
| 1-214 | —L—D | H | —CH2CH2— | CONH2 | 2-F | 1 | phenyl | 2,6-dimethyl-4-(1,2,2,3,3,3-hexafluoro-1-trifluoromethyl-propyl)-phenyl |
| 1-215 | —L—D | H | —CH2CH2— | CONH2 | 2-F | 1 | 4-cyanophenyl | 2,6-dimethyl-4-(1,2,2,3,3,3-hexafluoro-1-trifluoromethyl-propyl)-phenyl |
| 1-216 | —L—D | H | —CH2CH2— | CONH2 | 2-F | 1 | 3-cyanophenyl | 2,6-dimethyl-4-(1,2,2,3,3,3-hexafluoro-1-trifluoromethyl-propyl)-phenyl |
| 1-217 | —L—D | H | —CH2CH2— | CONH2 | H | 0 | phenyl | 2,6-ditrifluoromethyl-4-(1,2,2,2-tetrafluoro-1-trifluoromethyl-ethyl)-phenyl |
| 1-218 | —L—D | H | —CH2CH2— | CONH2 | H | 0 | 2-chloropyridin-3-yl | 2,6-ditrifluoromethyl-4-(1,2,2,2-tetrafluoro-1-trifluoromethyl-ethyl)-phenyl |
| 1-219 | —L—D | H | —CH2CH2— | CONH2 | H | 0 | 3-cyanophenyl | 2,6-ditrifluoromethyl-4-(1,2,2,2-tetrafluoro-1-trifluoromethyl-ethyl)-phenyl |
| 1-220 | —L—D | H | —CH2CH2— | CONH2 | 2-F | 1 | 6-chloropyridin-3-yl | 2,6-dimethyl-4-(1,2,2,3,3,3-hexafluoro-1-trifluoromethyl-propyl)-phenyl |
| 1-221 | —L—D | H | —CH2CH2— | CONH2 | 2-F | 1 | 6-chloropyridin-3-yl | 2-iodo-6-trifluoromethyl-4-(1,2,2,2-tetrafluoro-1-trifluoromethyl-ethyl)-phenyl |
| 1-222 | —L—D | H | —CH2CH2— | CONH2 | 2-F | 1 | 6-chloropyridin-3-yl | 2,6-diiodo-4-(1,2,2,3,3,3-hexafluoro-1-trifluoromethyl-propyl)-phenyl |

TABLE 1-continued

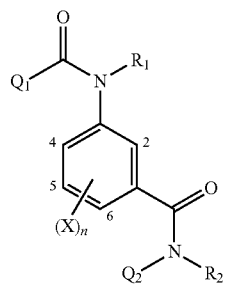

| compound number | R₁ | R₂ | L | D | X | n | Q₁ | Q₂ |
|---|---|---|---|---|---|---|---|---|
| 1-223 | —L—D | H | —CH2CH2— | CONH2 | 2-F | 1 | 4-fluorophenyl | 2-iodo-6-trifluoromethyl-4-(1,2,2,2-tetrafluoro-1-trifluoromethyl-ethyl)-phenyl |
| 1-224 | —L—D | H | —CH2CH2— | CONH2 | 2-F | 1 | 3,5-dicyanophenyl | 2,6-diiodo-4-(1,2,2,3,3,3-hexafluoro-1-trifluoromethyl-propyl)-phenyl |
| 1-225 | —L—D | H | —CH2CH2— | CONH2 | 2-F | 1 | 6-chloropyridin-3-yl | 2,6-diiodo-4-(1,2,2,2-tetrafluoro-1-trifluoromethyl-ethyl)-phenyl |
| 1-226 | —L—D | H | —CH2CH2— | CONH2 | H | 0 | 3-fluorophenyl | 2-iodo-6-trifluoromethyl-4-(1,2,2,2-tetrafluoro-1-trifluoromethyl-ethyl)-phenyl |
| 1-227 | —L—D | H | —CH2CH2— | CONH2 | 2-F | 1 | 2,6-difluorophenyl | 2-bromo-6-trifluoromethyl-4-(1,2,2,2-tetrafluoro-1-trifluoromethyl-ethyl)-phenyl |
| 1-228 | —L—D | H | —CH2CH2— | CONH2 | H | 0 | phenyl | 1,4-dimethyl-3-(2-trifluoromethyl)propyl-5-ピラゾール |
| 1-229 | —L—D | H | —CH2CH2— | CONH2 | H | 0 | 2-chloropyridin-3-yl | 1,4-dimethyl-3-(2-trifluoromethyl)propyl-5-ピラゾール |
| 1-230 | —L—D | H | —CH2CH2— | CONH2 | H | 0 | 2,6-difluorophenyl | 1,4-dimethyl-3-(2-trifluoromethyl)propyl-5-ピラゾール |
| 1-231 | —L—D | H | —CH2CH2— | CONH2 | H | 0 | 3-fluorophenyl | 2,6-diiodo-4-(1,2,2,2-tetrafluoro-1-trifluoromethyl-ethyl)-phenyl |
| 1-232 | —L—D | H | —CH2CH2— | CONH2 | H | 0 | 2,6-difluorophenyl | 2,6-diiodo-4-(1,2,2,2-tetrafluoro-1-trifluoromethyl-ethyl)-phenyl |
| 1-233 | —L—D | H | —CH2CH2— | CONH2 | H | 0 | 6-chloropyridin-3-yl | 2,6-diiodo-4-(1,2,2,2-tetrafluoro-1-trifluoromethyl-ethyl)-phenyl |
| 1-234 | —L—D | H | —CH2CH2— | CONH2 | H | 0 | 6-chloropyridin-3-yl | 2-bromo-6-trifluoromethyl-4-(1,2,2,3,3,3-hexafluoro-1-trifluoromethyl-propyl)-phenyl |
| 1-235 | —L—D | H | —CH2CH2— | CONH2 | 2-F | 1 | pyridin-3-yl | 2-iodo-6-trifluoromethyl-4-(1,2,2,2-tetrafluoro-1-trifluoromethyl-ethyl)-phenyl |
| 1-236 | —L—D | H | —CH2CH2— | CONH2 | H | 0 | 2-chloro-4-fluorophenyl | 2-iodo-6-trifluoromethyl-4-(1,2,2,2-tetrafluoro-1-trifluoromethyl-ethyl)-phenyl |
| 1-237 | —L—D | H | —CH2CH2— | CONH2 | H | 0 | phenyl | 2,6-difluoro-4-(1,2,2,2-tetrafluoro-1-trifluoromethyl-ethyl)-phenyl |
| 1-238 | —L—D | H | —CH2CH2— | CONH2 | H | 0 | 3-cyanophenyl | 2,6-difluoro-4-(1,2,2,2-tetrafluoro-1-trifluoromethyl-ethyl)-phenyl |
| 1-239 | —L—D | H | —CH2CH2— | CONH2 | H | 0 | 4-cyanophenyl | 2,6-difluoro-4-(1,2,2,2-tetrafluoro-1-trifluoromethyl-ethyl)-phenyl |
| 1-240 | —L—D | H | —CH2CH2— | CONH2 | H | 0 | 2-chloropyridin-3-yl | 2,6-difluoro-4-(1,2,2,2-tetrafluoro-1-trifluoromethyl-ethyl)-phenyl |
| 1-241 | —L—D | H | —CH2CH2— | CONH2 | H | 0 | phenyl | 2-bromo-6-trifluoromethylsulfinyl-4-(1,2,2,2-tetrafluoro-1-trifluoromethyl-ethyl)-phenyl |
| 1-242 | —L—D | H | —CH2CH2— | CONH2 | H | 0 | 2-chloropyridin-3-yl | 2-bromo-6-trifluoromethylsulfinyl-4-(1,2,2,2-tetrafluoro-1-trifluoromethyl-ethyl)-phenyl |
| 1-243 | —L—D | H | —CH2CH2— | CONH2 | 4-F | 1 | phenyl | 2,6-dibromo-4-(1,2,2,2-tetrafluoro-1-trifluoromethyl-ethyl)-phenyl |
| 1-244 | —L—D | H | —CH2CH2— | CONH2 | 4-F | 1 | 4-cyanophenyl | 2-bromo-6-trifluoromethyl-4-(1,2,2,2-tetrafluoro-1-trifluoromethyl-ethyl)-phenyl |
| 1-245 | —L—D | H | —CH2CH2— | CONH2 | 4-F | 1 | 3-cyanophenyl | 2-iodo-6-trifluoromethyl-4-(1,2,2,2-tetrafluoro-1-trifluoromethyl-ethyl)-phenyl |
| 1-246 | —L—D | H | —CH2CH2— | CONH2 | 4-F | 1 | 2-chloropyridin-3-yl | 2-bromo-6-trifluoromethyl-4-(1,2,2,3,3,3-hexafluoro-1-trifluoromethyl-propyl)-phenyl |
| 1-247 | —L—D | H | —CH2CH2— | CONH2 | 4-F | 1 | 2-fluorophenyl | 2-iodo-6-trifluoromethyl-4-(1,2,2,3,3,3-hexafluoro-1-trifluoromethyl-propyl)-phenyl |
| 1-248 | —L—D | H | —CH2CH2— | CONH2 | 4-CN | 1 | phenyl | 2,6-dibromo-4-(1,2,2,2-tetrafluoro-1-trifluoromethyl-ethyl)-phenyl |
| 1-249 | —L—D | H | —CH2CH2— | CONH2 | 4-CN | 1 | 4-cyanophenyl | 2-bromo-6-trifluoromethyl-4-(1,2,2,2-tetrafluoro-1-trifluoromethyl-ethyl)-phenyl |
| 1-250 | —L—D | H | —CH2CH2— | CONH2 | 4-CN | 1 | 3-cyanophenyl | 2-iodo-6-trifluoromethyl-4-(1,2,2,2-tetrafluoro-1-trifluoromethyl-ethyl)-phenyl |
| 1-251 | —L—D | H | —CH2CH2— | CONH2 | 4-CN | 1 | 2-chloropyridin-3-yl | 2-bromo-6-trifluoromethyl-4-(1,2,2,3,3,3-hexafluoro-1-trifluoromethyl-propyl)-phenyl |
| 1-252 | —L—D | H | —CH2CH2— | CONH2 | 4-CN | 1 | 2-fluorophenyl | 2-iodo-6-trifluoromethyl-4-(1,2,2,3,3,3-hexafluoro-1-trifluoromethyl-propyl)-phenyl |
| 1-253 | —L—D | H | —CH2CH2— | CONH2 | 2-NO2 | 1 | phenyl | 2,6-dibromo-4-(1,2,2,2-tetrafluoro-1-trifluoromethyl-ethyl)-phenyl |

TABLE 1-continued

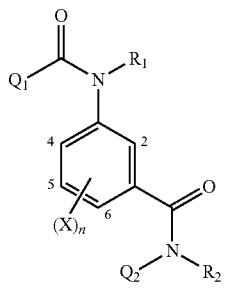

| compound number | R1 | R2 | L | D | X | n | Q1 | Q2 |
|---|---|---|---|---|---|---|---|---|
| 1-254 | —L—D | H | —CH2CH2— | CONH2 | 2-NO2 | 1 | 4-cyanophenyl | 2-bromo-6-trifluoromethyl-4-(1,2,2,2-tetrafluoro-1-trifluoromethyl-ethyl)-phenyl |
| 1-255 | —L—D | H | —CH2CH2— | CONH2 | 2-NO2 | 1 | 3-cyanophenyl | 2-iodo-6-trifluoromethyl-4-(1,2,2,2-tetrafluoro-1-trifluoromethyl-ethyl)-phenyl |
| 1-256 | —L—D | H | —CH2CH2— | CONH2 | 2-NO2 | 1 | 2-chloropyridin-3-yl | 2-bromo-6-trifluoromethyl-4-(1,2,2,3,3,3-hexafluoro-1-trifluoromethyl-propyl)-phenyl |
| 1-257 | —L—D | H | —CH2CH2— | CONH2 | 2-NO2 | 1 | 2-fluorophenyl | 2-iodo-6-trifluoromethyl-4-(1,2,2,3,3,3-hexafluoro-1-trifluoromethyl-propyl)-phenyl |

TABLE 2

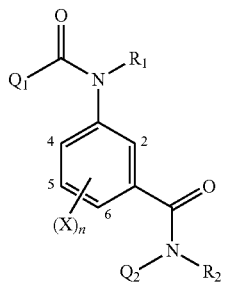

| compound number | R1 | R2 | L | D | X | n | Q1 | Q2 |
|---|---|---|---|---|---|---|---|---|
| 2-1 | —L—D | H | —CH2CH2— | SO2NH2 | H | 0 | phenyl | 2,6-dimethyl-4-(1,2,2,2-tetrafluoro-1-trifluoromethyl-ethyl)-phenyl |
| 2-2 | —L—D | H | —CH2CH2— | SO2NH2 | H | 0 | 4-cyanophenyl | 2,6-dimethyl-4-(1,2,2,2-tetrafluoro-1-trifluoromethyl-ethyl)-phenyl |
| 2-3 | —L—D | H | —CH2CH2— | SO2NH2 | H | 0 | 3-cyanophenyl | 2,6-dimethyl-4-(1,2,2,2-tetrafluoro-1-trifluoromethyl-ethyl)-phenyl |
| 2-4 | —L—D | H | —CH2CH2— | SO2NH2 | H | 0 | 3,5-dicyanophenyl | 2,6-dimethyl-4-(1,2,2,2-tetrafluoro-1-trifluoromethyl-ethyl)-phenyl |
| 2-5 | —L—D | H | —CH2CH2— | SO2NH2 | H | 0 | 2-fluorophenyl | 2,6-dimethyl-4-(1,2,2,2-tetrafluoro-1-trifluoromethyl-ethyl)-phenyl |
| 2-6 | —L—D | H | —CH2CH2— | SO2NH2 | H | 0 | 4-fluorophenyl | 2,6-dimethyl-4-(1,2,2,2-tetrafluoro-1-trifluoromethyl-ethyl)-phenyl |
| 2-7 | —L—D | H | —CH2CH2— | SO2NH2 | H | 0 | 2,6-difluorophenyl | 2,6-dimethyl-4-(1,2,2,2-tetrafluoro-1-trifluoromethyl-ethyl)-phenyl |
| 2-8 | —L—D | H | —CH2CH2— | SO2NH2 | H | 0 | 2-fluoro-4-cyanophenyl | 2,6-dimethyl-4-(1,2,2,2-tetrafluoro-1-trifluoromethyl-ethyl)-phenyl |
| 2-9 | —L—D | H | —CH2CH2— | SO2NH2 | H | 0 | 2-chlorophenyl | 2,6-dimethyl-4-(1,2,2,2-tetrafluoro-1-trifluoromethyl-ethyl)-phenyl |
| 2-10 | —L—D | H | —CH2CH2— | SO2NH2 | H | 0 | 4-chlorophenyl | 2,6-dimethyl-4-(1,2,2,2-tetrafluoro-1-trifluoromethyl-ethyl)-phenyl |
| 2-11 | —L—D | H | —CH2CH2— | SO2NH2 | H | 0 | 4-nitrophenyl | 2,6-dimethyl-4-(1,2,2,2-tetrafluoro-1-trifluoromethyl-ethyl)-phenyl |
| 2-12 | —L—D | H | —CH2CH2— | SO2NH2 | H | 0 | 2-methylphenyl | 2,6-dimethyl-4-(1,2,2,2-tetrafluoro-1-trifluoromethyl-ethyl)-phenyl |
| 2-13 | —L—D | H | —CH2CH2— | SO2NH2 | H | 0 | pyridin-2-yl | 2,6-dimethyl-4-(1,2,2,2-tetrafluoro-1-trifluoromethyl-ethyl)-phenyl |
| 2-14 | —L—D | H | —CH2CH2— | SO2NH2 | H | 0 | pyridin-3-yl | 2,6-dimethyl-4-(1,2,2,2-tetrafluoro-1-trifluoromethyl-ethyl)-phenyl |
| 2-15 | —L—D | H | —CH2CH2— | SO2NH2 | H | 0 | pyridin-4-yl | 2,6-dimethyl-4-(1,2,2,2-tetrafluoro-1-trifluoromethyl-ethyl)-phenyl |
| 2-16 | —L—D | H | —CH2CH2— | SO2NH2 | H | 0 | 2-chloropyridin-3-yl | 2,6-dimethyl-4-(1,2,2,2-tetrafluoro-1-trifluoromethyl-ethyl)-phenyl |

TABLE 2-continued

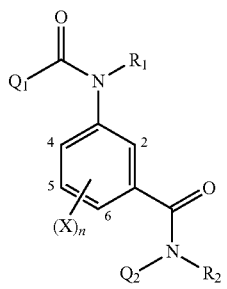

| compound number | R₁ | R₂ | L | D | X | n | Q₁ | Q₂ |
|---|---|---|---|---|---|---|---|---|
| 2-17 | —L—D | H | —CH2CH2— | SO2NH2 | H | 0 | 6-chloropyridin-3-yl | 2,6-dimethyl-4-(1,2,2,2-tetrafluoro-1-trifluoromethyl-ethyl)-phenyl |
| 2-18 | —L—D | H | —CH2CH2— | SO2NH2 | H | 0 | 2-chloropyridin-4-yl | 2,6-dimethyl-4-(1,2,2,2-tetrafluoro-1-trifluoromethyl-ethyl)-phenyl |
| 2-19 | —L—D | H | —CH2CH2— | SO2NH2 | H | 0 | pyrazin-2-yl | 2,6-dimethyl-4-(1,2,2,2-tetrafluoro-1-trifluoromethyl-ethyl)-phenyl |
| 2-20 | —L—D | H | —CH2CH2— | SO2NH2 | H | 0 | pyrimidin-5-yl | 2,6-dimethyl-4-(1,2,2,2-tetrafluoro-1-trifluoromethyl-ethyl)-phenyl |
| 2-21 | —L—D | H | —CH2CH2— | SO2NH2 | 2-F | 1 | phenyl | 2,6-dimethyl-4-(1,2,2,2-tetrafluoro-1-trifluoromethyl-ethyl)-phenyl |
| 2-22 | —L—D | H | —CH2CH2— | SO2NH2 | 2-F | 1 | 4-cyanophenyl | 2,6-dimethyl-4-(1,2,2,2-tetrafluoro-1-trifluoromethyl-ethyl)-phenyl |
| 2-23 | —L—D | H | —CH2CH2— | SO2NH2 | 2-F | 1 | 3-cyanophenyl | 2,6-dimethyl-4-(1,2,2,2-tetrafluoro-1-trifluoromethyl-ethyl)-phenyl |
| 2-24 | —L—D | H | —CH2CH2— | SO2NH2 | 2-F | 1 | 3,5-dicyanophenyl | 2,6-dimethyl-4-(1,2,2,2-tetrafluoro-1-trifluoromethyl-ethyl)-phenyl |
| 2-25 | —L—D | H | —CH2CH2— | SO2NH2 | 2-F | 1 | 2-fluorophenyl | 2,6-dimethyl-4-(1,2,2,2-tetrafluoro-1-trifluoromethyl-ethyl)-phenyl |
| 2-26 | —L—D | H | —CH2CH2— | SO2NH2 | 2-F | 1 | 4-fluorophenyl | 2,6-dimethyl-4-(1,2,2,2-tetrafluoro-1-trifluoromethyl-ethyl)-phenyl |
| 2-27 | —L—D | H | —CH2CH2— | SO2NH2 | 2-F | 1 | 2,6-difluorophenyl | 2,6-dimethyl-4-(1,2,2,2-tetrafluoro-1-trifluoromethyl-ethyl)-phenyl |
| 2-28 | —L—D | H | —CH2CH2— | SO2NH2 | 2-F | 1 | 2-fluoro-4-cyanophenyl | 2,6-dimethyl-4-(1,2,2,2-tetrafluoro-1-trifluoromethyl-ethyl)-phenyl |
| 2-29 | —L—D | H | —CH2CH2— | SO2NH2 | 2-F | 1 | 2-chlorophenyl | 2,6-dimethyl-4-(1,2,2,2-tetrafluoro-1-trifluoromethyl-ethyl)-phenyl |
| 2-30 | —L—D | H | —CH2CH2— | SO2NH2 | 2-F | 1 | 4-chlorophenyl | 2,6-dimethyl-4-(1,2,2,2-tetrafluoro-1-trifluoromethyl-ethyl)-phenyl |
| 2-31 | —L—D | H | —CH2CH2— | SO2NH2 | 2-F | 1 | 4-nitrophenyl | 2,6-dimethyl-4-(1,2,2,2-tetrafluoro-1-trifluoromethyl-ethyl)-phenyl |
| 2-32 | —L—D | H | —CH2CH2— | SO2NH2 | 2-F | 1 | 2-methylphenyl | 2,6-dimethyl-4-(1,2,2,2-tetrafluoro-1-trifluoromethyl-ethyl)-phenyl |
| 2-33 | —L—D | H | —CH2CH2— | SO2NH2 | 2-F | 1 | pyridin-2-yl | 2,6-dimethyl-4-(1,2,2,2-tetrafluoro-1-trifluoromethyl-ethyl)-phenyl |
| 2-34 | —L—D | H | —CH2CH2— | SO2NH2 | 2-F | 1 | pyridin-3-yl | 2,6-dimethyl-4-(1,2,2,2-tetrafluoro-1-trifluoromethyl-ethyl)-phenyl |
| 2-35 | —L—D | H | —CH2CH2— | SO2NH2 | 2-F | 1 | pyridin-4-yl | 2,6-dimethyl-4-(1,2,2,2-tetrafluoro-1-trifluoromethyl-ethyl)-phenyl |
| 2-36 | —L—D | H | —CH2CH2— | SO2NH2 | 2-F | 1 | 2-chloropyridin-3-yl | 2,6-dimethyl-4-(1,2,2,2-tetrafluoro-1-trifluoromethyl-ethyl)-phenyl |
| 2-37 | —L—D | H | —CH2CH2— | SO2NH2 | 2-F | 1 | 6-chloropyridin-3-yl | 2,6-dimethyl-4-(1,2,2,2-tetrafluoro-1-trifluoromethyl-ethyl)-phenyl |
| 2-38 | —L—D | H | —CH2CH2— | SO2NH2 | 2-F | 1 | 2-chloropyridin-4-yl | 2,6-dimethyl-4-(1,2,2,2-tetrafluoro-1-trifluoromethyl-ethyl)-phenyl |
| 2-39 | —L—D | H | —CH2CH2— | SO2NH2 | 2-F | 1 | pyrazin-2-yl | 2,6-dimethyl-4-(1,2,2,2-tetrafluoro-1-trifluoromethyl-ethyl)-phenyl |
| 2-40 | —L—D | H | —CH2CH2— | SO2NH2 | 2-F | 1 | pyrimidin-5-yl | 2,6-dimethyl-4-(1,2,2,2-tetrafluoro-1-trifluoromethyl-ethyl)-phenyl |
| 2-41 | —L—D | H | —CH2CH2— | SO2NH2 | 4-F | 1 | phenyl | 2,6-dimethyl-4-(1,2,2,2-tetrafluoro-1-trifluoromethyl-ethyl)-phenyl |
| 2-42 | —L—D | H | —CH2CH2— | SO2NH2 | 4-F | 1 | 4-cyanophenyl | 2,6-dimethyl-4-(1,2,2,2-tetrafluoro-1-trifluoromethyl-ethyl)-phenyl |
| 2-43 | —L—D | H | —CH2CH2— | SO2NH2 | 4-F | 1 | 3-cyanophenyl | 2,6-dimethyl-4-(1,2,2,2-tetrafluoro-1-trifluoromethyl-ethyl)-phenyl |
| 2-44 | —L—D | H | —CH2CH2— | SO2NH2 | 4-F | 1 | 2-chloropyridin-3-yl | 2,6-dimethyl-4-(1,2,2,2-tetrafluoro-1-trifluoromethyl-ethyl)-phenyl |
| 2-45 | —L—D | H | —CH2CH2— | SO2NH2 | 4-F | 1 | 2-fluorophenyl | 2,6-dimethyl-4-(1,2,2,2-tetrafluoro-1-trifluoromethyl-ethyl)-phenyl |
| 2-46 | —L—D | H | —CH2CH2— | SO2NH2 | 4-CN | 1 | phenyl | 2,6-dimethyl-4-(1,2,2,2-tetrafluoro-1-trifluoromethyl-ethyl)-phenyl |
| 2-47 | —L—D | H | —CH2CH2— | SO2NH2 | 4-CN | 1 | 4-cyanophenyl | 2,6-dimethyl-4-(1,2,2,2-tetrafluoro-1-trifluoromethyl-ethyl)-phenyl |

TABLE 2-continued

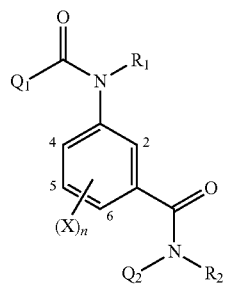

| compound number | R1 | R2 | L | D | X | n | Q1 | Q2 |
|---|---|---|---|---|---|---|---|---|
| 2-48 | —L—D | H | —CH2CH2— | SO2NH2 | 4-CN | 1 | 3-cyanophenyl | 2,6-dimethyl-4-(1,2,2,2-tetrafluoro-1-trifluoromethyl-ethyl)-phenyl |
| 2-49 | —L—D | H | —CH2CH2— | SO2NH2 | 4-CN | 1 | 2-chloropyridin-3-yl | 2,6-dimethyl-4-(1,2,2,2-tetrafluoro-1-trifluoromethyl-ethyl)-phenyl |
| 2-50 | —L—D | H | —CH2CH2— | SO2NH2 | 4-CN | 1 | 2-fluorophenyl | 2,6-dimethyl-4-(1,2,2,2-tetrafluoro-1-trifluoromethyl-ethyl)-phenyl |
| 2-51 | —L—D | H | —CH2CH2— | SO2NH2 | H | 0 | 4-cyanophenyl | 2,6-dibromo-4-pentafluoroethyl-phenyl |
| 2-52 | —L—D | H | —CH2CH2— | SO2NH2 | H | 0 | 4-cyanophenyl | 2,6-diiodo-4-pentafluoroethyl-phenyl |
| 2-53 | —L—D | H | —CH2CH2— | SO2NH2 | H | 0 | 4-cyanophenyl | 2-bromo-6-trifluoromethyl-4-pentafluoroethyl-phenyl |
| 2-54 | —L—D | H | —CH2CH2— | SO2NH2 | H | 0 | 4-cyanophenyl | 2-iodo-6-trifluoromethyl-4-pentafluoroethyl-phenyl |
| 2-55 | —L—D | H | —CH2CH2— | SO2NH2 | H | 0 | 4-cyanophenyl | 2-chloro-6-methyl-4-(1,2,2,2-tetrafluoro-1-trifluoromethyl-ethyl)-phenyl |
| 2-56 | —L—D | H | —CH2CH2— | SO2NH2 | H | 0 | 4-cyanophenyl | 2-bromo-6-methyl-4-(1,2,2,2-tetrafluoro-1-trifluoromethyl-ethyl)-phenyl |
| 2-57 | —L—D | H | —CH2CH2— | SO2NH2 | H | 0 | 4-cyanophenyl | 2-iodo-6-methyl-4-(1,2,2,2-tetrafluoro-1-trifluoromethyl-ethyl)-phenyl |
| 2-58 | —L—D | H | —CH2CH2— | SO2NH2 | H | 0 | 4-cyanophenyl | 2-bromo-6-ethyl-4-(1,2,2,2-tetrafluoro-1-trifluoromethyl-ethyl)-phenyl |
| 2-59 | —L—D | H | —CH2CH2— | SO2NH2 | H | 0 | 4-cyanophenyl | 2-iodo-6-ethyl-4-(1,2,2,2-tetrafluoro-1-trifluoromethyl-ethyl)-phenyl |
| 2-60 | —L—D | H | —CH2CH2— | SO2NH2 | H | 0 | 4-cyanophenyl | 2,6-dichloro-4-(1,2,2,2-tetrafluoro-1-trifluoromethyl-ethyl)-phenyl |
| 2-61 | —L—D | H | —CH2CH2— | SO2NH2 | H | 0 | 4-cyanophenyl | 2,6-dibromo-4-(1,2,2,2-tetrafluoro-1-trifluoromethyl-ethyl)-phenyl |
| 2-62 | —L—D | H | —CH2CH2— | SO2NH2 | H | 0 | 4-cyanophenyl | 2,6-diiodo-4-(1,2,2,2-tetrafluoro-1-trifluoromethyl-ethyl)-phenyl |
| 2-63 | —L—D | H | —CH2CH2— | SO2NH2 | H | 0 | 4-cyanophenyl | 2,6-ditrifluoromethyl-4-(1,2,2,2-tetrafluoro-1-trifluoromethyl-ethyl)-phenyl |
| 2-64 | —L—D | H | —CH2CH2— | SO2NH2 | H | 0 | 4-cyanophenyl | 2-bromo-6-trifluoromethyl-4-(1,2,2,2-tetrafluoro-1-trifluoromethyl-ethyl)-phenyl |
| 2-65 | —L—D | H | —CH2CH2— | SO2NH2 | H | 0 | 4-cyanophenyl | 2-iodo-6-trifluoromethyl-4-(1,2,2,2-tetrafluoro-1-trifluoromethyl-ethyl)-phenyl |
| 2-66 | —L—D | H | —CH2CH2— | SO2NH2 | H | 0 | 4-cyanophenyl | 2-bromo-6-trifluoromethoxy-4-(1,2,2,2-tetrafluoro-1-trifluoromethyl-ethyl)-phenyl |
| 2-67 | —L—D | H | —CH2CH2— | SO2NH2 | H | 0 | 4-cyanophenyl | 2-bromo-6-iodo-4-(1,2,2,2-tetrafluoro-1-trifluoromethyl-ethyl)-phenyl |
| 2-68 | —L—D | H | —CH2CH2— | SO2NH2 | H | 0 | 4-cyanophenyl | 2-bromo-6-trifluoromethylthio-4-(1,2,2,2-tetrafluoro-1-trifluoromethyl-ethyl)-phenyl |
| 2-69 | —L—D | H | —CH2CH2— | SO2NH2 | H | 0 | 4-cyanophenyl | 2-bromo-6-trifluoromethylsulfinyl-4-(1,2,2,2-tetrafluoro-1-trifluoromethyl-ethyl)-phenyl |
| 2-70 | —L—D | H | —CH2CH2— | SO2NH2 | H | 0 | 4-cyanophenyl | 2-bromo-6-trifluoromethylsulfonyl-4-(1,2,2,2-tetrafluoro-1-trifluoromethyl-ethyl)-phenyl |
| 2-71 | —L—D | H | —CH2CH2— | SO2NH2 | H | 0 | 4-cyanophenyl | 2-bromo-6-pentafluoroethyl-4-(1,2,2,2-tetrafluoro-1-trifluoromethyl-ethyl)-phenyl |
| 2-72 | —L—D | H | —CH2CH2— | SO2NH2 | H | 0 | 4-cyanophenyl | 2-iodo-6-pentafluoroethyl-4-(1,2,2,2-tetrafluoro-1-trifluoromethyl-ethyl)-phenyl |
| 2-73 | —L—D | H | —CH2CH2— | SO2NH2 | H | 0 | 4-cyanophenyl | 2-chloro-6-methyl-4-(1,2,2,3,3,3-hexafluoro-1-trifluoromethyl-propyl)-phenyl |
| 2-74 | —L—D | H | —CH2CH2— | SO2NH2 | H | 0 | 4-cyanophenyl | 2-bromo-6-methyl-4-(1,2,2,3,3,3-hexafluoro-1-trifluoromethyl-propyl)-phenyl |
| 2-75 | —L—D | H | —CH2CH2— | SO2NH2 | H | 0 | 4-cyanophenyl | 2-iodo-6-methyl-4-(1,2,2,3,3,3-hexafluoro-1-trifluoromethyl-propyl)-phenyl |
| 2-76 | —L—D | H | —CH2CH2— | SO2NH2 | H | 0 | 4-cyanophenyl | 2-bromo-6-ethyl-4-(1,2,2,3,3,3-hexafluoro-1-trifluoromethyl-propyl)-phenyl |
| 2-77 | —L—D | H | —CH2CH2— | SO2NH2 | H | 0 | 4-cyanophenyl | 2-iodo-6-ethyl-4-(1,2,2,3,3,3-hexafluoro-1-trifluoromethyl-propyl)-phenyl |
| 2-78 | —L—D | H | —CH2CH2— | SO2NH2 | H | 0 | 4-cyanophenyl | 2,6-dichloro-4-(1,2,2,3,3,3-hexafluoro-1-trifluoromethyl-propyl)-phenyl |
| 2-79 | —L—D | H | —CH2CH2— | SO2NH2 | H | 0 | 4-cyanophenyl | 2,6-dibromo-4-(1,2,2,3,3,3-hexafluoro-1-trifluoromethyl-propyl)-phenyl |
| 2-80 | —L—D | H | —CH2CH2— | SO2NH2 | H | 0 | 4-cyanophenyl | 2,6-diiodo-4-(1,2,2,3,3,3-hexafluoro-1-trifluoromethyl-propyl)-phenyl |

TABLE 2-continued

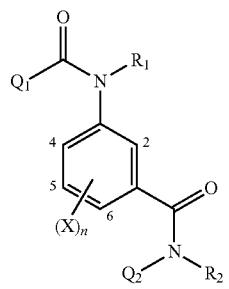

| compound number | R₁ | R₂ | L | D | X | n | Q₁ | Q₂ |
|---|---|---|---|---|---|---|---|---|
| 2-81 | —L—D | H | —CH2CH2— | SO2NH2 | H | 0 | 4-cyanophenyl | 2,6-ditrifluoromethyl-4-(1,2,2,3,3,3-hexafluoro-1-trifluoromethyl-propyl)-phenyl |
| 2-82 | —L—D | H | —CH2CH2— | SO2NH2 | H | 0 | 4-cyanophenyl | 2-bromo-6-trifluoromethyl-4-(1,2,2,3,3,3-hexafluoro-1-trifluoromethyl-propyl)-phenyl |
| 2-83 | —L—D | H | —CH2CH2— | SO2NH2 | H | 0 | 4-cyanophenyl | 2-iodo-6-trifluoromethyl-4-(1,2,2,3,3,3-hexafluoro-1-trifluoromethyl-propyl)-phenyl |
| 2-84 | —L—D | H | —CH2CH2— | SO2NH2 | H | 0 | 4-cyanophenyl | 2-bromo-6-trifluoromethoxy-4-(1,2,2,3,3,3-hexafluoro-1-trifluoromethyl-propyl)-phenyl |
| 2-85 | —L—D | H | —CH2CH2— | SO2NH2 | H | 0 | 4-cyanophenyl | 2-bromo-6-iodo-4-(1,2,2,3,3,3-hexafluoro-1-trifluoromethyl-propyl)-phenyl |
| 2-86 | —L—D | H | —CH2CH2— | SO2NH2 | H | 0 | 4-cyanophenyl | 2-bromo-6-trifluoromethylthio-4-(1,2,2,3,3,3-hexafluoro-1-trifluoromethyl-propyl)-phenyl |
| 2-87 | —L—D | H | —CH2CH2— | SO2NH2 | H | 0 | 4-cyanophenyl | 2-bromo-6-trifluoromethylsulfinyl-4-(1,2,2,3,3,3-hexafluoro-1-trifluoromethyl-propyl)-phenyl |
| 2-88 | —L—D | H | —CH2CH2— | SO2NH2 | H | 0 | 4-cyanophenyl | 2-bromo-6-trifluoromethylsulfonyl-4-(1,2,2,3,3,3-hexafluoro-1-trifluoromethyl-propyl)-phenyl |
| 2-89 | —L—D | H | —CH2CH2— | SO2NH2 | H | 0 | 4-cyanophenyl | 2-bromo-6-pentafluoroethyl-4-(1,2,2,3,3,3-hexafluoro-1-trifluoromethyl-propyl)-phenyl |
| 2-90 | —L—D | H | —CH2CH2— | SO2NH2 | H | 0 | 4-cyanophenyl | 2-iodo-6-pentafluoroethyl-4-(1,2,2,3,3,3-hexafluoro-1-trifluoromethyl-propyl)-phenyl |
| 2-91 | —L—D | H | —CH2CH2— | SO2NH2 | H | 0 | phenyl | 2,6-bromo-4-(1,2,2,2-tetrafluoro-1-trifluoromethyl-ethyl)-phenyl |
| 2-92 | —L—D | H | —CH2CH2— | SO2NH2 | H | 0 | 3-cyanophenyl | 2,6-dibromo-4-(1,2,2,2-tetrafluoro-1-trifluoromethyl-ethyl)-phenyl |
| 2-93 | —L—D | H | —CH2CH2— | SO2NH2 | H | 0 | 2-chloropyridin-3-yl | 2,6-dibromo-4-(1,2,2,2-tetrafluoro-1-trifluoromethyl-ethyl)-phenyl |
| 2-94 | —L—D | H | —CH2CH2— | SO2NH2 | H | 0 | 2-fluorophenyl | 2,6-dibromo-4-(1,2,2,2-tetrafluoro-1-trifluoromethyl-ethyl)-phenyl |
| 2-95 | —L—D | H | —CH2CH2— | SO2NH2 | H | 0 | phenyl | 2,6-diiodo-4-(1,2,2,2-tetrafluoro-1-trifluoromethyl-ethyl)-phenyl |
| 2-96 | —L—D | H | —CH2CH2— | SO2NH2 | H | 0 | 3-cyanophenyl | 2,6-diiodo-4-(1,2,2,2-tetrafluoro-1-trifluoromethyl-ethyl)-phenyl |
| 2-97 | —L—D | H | —CH2CH2— | SO2NH2 | H | 0 | 2-chloropyridin-3-yl | 2,6-diiodo-4-(1,2,2,2-tetrafluoro-1-trifluoromethyl-ethyl)-phenyl |
| 2-98 | —L—D | H | —CH2CH2— | SO2NH2 | H | 0 | 2-fluorophenyl | 2,6-diiodo-4-(1,2,2,2-tetrafluoro-1-trifluoromethyl-ethyl)-phenyl |
| 2-99 | —L—D | H | —CH2CH2— | SO2NH2 | H | 0 | phenyl | 2-bromo-6-trifluoromethyl-4-(1,2,2,2-tetrafluoro-1-trifluoromethyl-ethyl)-phenyl |
| 2-100 | —L—D | H | —CH2CH2— | SO2NH2 | H | 0 | 3-cyanophenyl | 2-bromo-6-trifluoromethyl-4-(1,2,2,2-tetrafluoro-1-trifluoromethyl-ethyl)-phenyl |
| 2-101 | —L—D | H | —CH2CH2— | SO2NH2 | H | 0 | 2-chloropyridin-3-yl | 2-bromo-6-trifluoromethyl-4-(1,2,2,2-tetrafluoro-1-trifluoromethyl-ethyl)-phenyl |
| 2-102 | —L—D | H | —CH2CH2— | SO2NH2 | H | 0 | 2-fluorophenyl | 2-bromo-6-trifluoromethyl-4-(1,2,2,2-tetrafluoro-1-trifluoromethyl-ethyl)-phenyl |
| 2-103 | —L—D | H | —CH2CH2— | SO2NH2 | H | 0 | phenyl | 2-iodo-6-trifluoromethyl-4-(1,2,2,2-tetrafluoro-1-trifluoromethyl-ethyl)-phenyl |
| 2-104 | —L—D | H | —CH2CH2— | SO2NH2 | H | 0 | 3-cyanophenyl | 2-iodo-6-trifluoromethyl-4-(1,2,2,2-tetrafluoro-1-trifluoromethyl-ethyl)-phenyl |
| 2-105 | —L—D | H | —CH2CH2— | SO2NH2 | H | 0 | 2-chloropyridin-3-yl | 2-iodo-6-trifluoromethyl-4-(1,2,2,2-tetrafluoro-1-trifluoromethyl-ethyl)-phenyl |
| 2-106 | —L—D | H | —CH2CH2— | SO2NH2 | H | 0 | 2-fluorophenyl | 2-iodo-6-trifluoromethyl-4-(1,2,2,2-tetrafluoro-1-trifluoromethyl-ethyl)-phenyl |
| 2-107 | —L—D | H | —CH2CH2— | SO2NH2 | H | 0 | phenyl | 2,6-dibromo-4-(1,2,2,3,3,3-hexafluoro-1-trifluoromethyl-propyl)-phenyl |
| 2-108 | —L—D | H | —CH2CH2— | SO2NH2 | H | 0 | 3-cyanophenyl | 2,6-dibromo-4-(1,2,2,3,3,3-hexafluoro-1-trifluoromethyl-propyl)-phenyl |
| 2-109 | —L—D | H | —CH2CH2— | SO2NH2 | H | 0 | 2-chloropyridin-3-yl | 2,6-dibromo-4-(1,2,2,3,3,3-hexafluoro-1-trifluoromethyl-propyl)-phenyl |
| 2-110 | —L—D | H | —CH2CH2— | SO2NH2 | H | 0 | 2-fluorophenyl | 2,6-dibromo-4-(1,2,2,3,3,3-hexafluoro-1-trifluoromethyl-propyl)-phenyl |
| 2-111 | —L—D | H | —CH2CH2— | SO2NH2 | H | 0 | phenyl | 2,6-diiodo-4-(1,2,2,3,3,3-hexafluoro-1-trifluoromethyl-propyl)-phenyl |

TABLE 2-continued

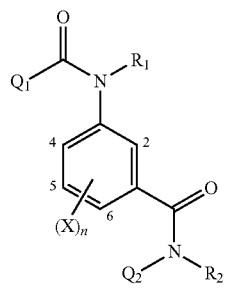

| compound number | R₁ | R₂ | L | D | X | n | Q₁ | Q₂ |
|---|---|---|---|---|---|---|---|---|
| 2-112 | —L—D | H | —CH2CH2— | SO2NH2 | H | 0 | 3-cyanophenyl | 2,6-diiodo-4-(1,2,2,3,3,3-hexafluoro-1-trifluoromethyl-propyl)-phenyl |
| 2-113 | —L—D | H | —CH2CH2— | SO2NH2 | H | 0 | 2-chloropyridin-3-yl | 2,6-diiodo-4-(1,2,2,3,3,3-hexafluoro-1-trifluoromethyl-propyl)-phenyl |
| 2-114 | —L—D | H | —CH2CH2— | SO2NH2 | H | 0 | 2-fluorophenyl | 2,6-diiodo-4-(1,2,2,3,3,3-hexafluoro-1-trifluoromethyl-propyl)-phenyl |
| 2-115 | —L—D | H | —CH2CH2— | SO2NH2 | H | 0 | phenyl | 2-bromo-6-trifluoromethyl-4-(1,2,2,3,3,3-hexafluoro-1-trifluoromethyl-propyl)-phenyl |
| 2-116 | —L—D | H | —CH2CH2— | SO2NH2 | H | 0 | 3-cyanophenyl | 2-bromo-6-trifluoromethyl-4-(1,2,2,3,3,3-hexafluoro-1-trifluoromethyl-propyl)-phenyl |
| 2-117 | —L—D | H | —CH2CH2— | SO2NH2 | H | 0 | 2-chloropyridin-3-yl | 2-bromo-6-trifluoromethyl-4-(1,2,2,3,3,3-hexafluoro-1-trifluoromethyl-propyl)-phenyl |
| 2-118 | —L—D | H | —CH2CH2— | SO2NH2 | H | 0 | 2-fluorophenyl | 2-bromo-6-trifluoromethyl-4-(1,2,2,3,3,3-hexafluoro-1-trifluoromethyl-propyl)-phenyl |
| 2-119 | —L—D | H | —CH2CH2— | SO2NH2 | H | 0 | phenyl | 2-iodo-6-trifluoromethyl-4-(1,2,2,3,3,3-hexafluoro-1-trifluoromethyl-propyl)-phenyl |
| 2-120 | —L—D | H | —CH2CH2— | SO2NH2 | H | 0 | 3-cyanophenyl | 2-iodo-6-trifluoromethyl-4-(1,2,2,3,3,3-hexafluoro-1-trifluoromethyl-propyl)-phenyl |
| 2-121 | —L—D | H | —CH2CH2— | SO2NH2 | H | 0 | 2-chloropyridin-3-yl | 2-iodo-6-trifluoromethyl-4-(1,2,2,3,3,3-hexafluoro-1-trifluoromethyl-propyl)-phenyl |
| 2-122 | —L—D | H | —CH2CH2— | SO2NH2 | H | 0 | 2-fluorophenyl | 2-iodo-6-trifluoromethyl-4-(1,2,2,3,3,3-hexafluoro-1-trifluoromethyl-propyl)-phenyl |
| 2-123 | —L—D | H | —CH2CH2— | SO2NH2 | 2-F | 1 | 4-cyanophenyl | 2,6-dibromo-4-pentafluoroethyl-phenyl |
| 2-124 | —L—D | H | —CH2CH2— | SO2NH2 | 2-F | 1 | 4-cyanophenyl | 2,6-diiodo-4-pentafluoroethyl-phenyl |
| 2-125 | —L—D | H | —CH2CH2— | SO2NH2 | 2-F | 1 | 4-cyanophenyl | 2-bromo-6-trifluoromethyl-4-pentafluoroethyl-phenyl |
| 2-126 | —L—D | H | —CH2CH2— | SO2NH2 | 2-F | 1 | 4-cyanophenyl | 2-iodo-6-trifluoromethyl-4-pentafluoroethyl-phenyl |
| 2-127 | —L—D | H | —CH2CH2— | SO2NH2 | 2-F | 1 | 4-cyanophenyl | 2-chloro-6-methyl-4-(1,2,2,2-tetrafluoro-1-trifluoromethyl-ethyl)-phenyl |
| 2-128 | —L—D | H | —CH2CH2— | SO2NH2 | 2-F | 1 | 4-cyanophenyl | 2-bromo-6-methyl-4-(1,2,2,2-tetrafluoro-1-trifluoromethyl-ethyl)-phenyl |
| 2-129 | —L—D | H | —CH2CH2— | SO2NH2 | 2-F | 1 | 4-cyanophenyl | 2-iodo-6-methyl-4-(1,2,2,2-tetrafluoro-1-trifluoromethyl-ethyl)-phenyl |
| 2-130 | —L—D | H | —CH2CH2— | SO2NH2 | 2-F | 1 | 4-cyanophenyl | 2-bromo-6-ethyl-4-(1,2,2,2-tetrafluoro-1-trifluoromethyl-ethyl)-phenyl |
| 2-131 | —L—D | H | —CH2CH2— | SO2NH2 | 2-F | 1 | 4-cyanophenyl | 2-iodo-6-ethyl-4-(1,2,2,2-tetrafluoro-1-trifluoromethyl-ethyl)-phenyl |
| 2-132 | —L—D | H | —CH2CH2— | SO2NH2 | 2-F | 1 | 4-cyanophenyl | 2,6-dichloro-4-(1,2,2,2-tetrafluoro-1-trifluoromethyl-ethyl)-phenyl |
| 2-133 | —L—D | H | —CH2CH2— | SO2NH2 | 2-F | 1 | 4-cyanophenyl | 2,6-dibromo-4-(1,2,2,2-tetrafluoro-1-trifluoromethyl-ethyl)-phenyl |
| 2-134 | —L—D | H | —CH2CH2— | SO2NH2 | 2-F | 1 | 4-cyanophenyl | 2,6-diiodo-4-(1,2,2,2-tetrafluoro-1-trifluoromethyl-ethyl)-phenyl |
| 2-135 | —L—D | H | —CH2CH2— | SO2NH2 | 2-F | 1 | 4-cyanophenyl | 2,6-ditrifluoromethyl-4-(1,2,2,2-tetrafluoro-1-trifluoromethyl-ethyl)-phenyl |
| 2-136 | —L—D | H | —CH2CH2— | SO2NH2 | 2-F | 1 | 4-cyanophenyl | 2-bromo-6-trifluoromethyl-4-(1,2,2,2-tetrafluoro-1-trifluoromethyl-ethyl)-phenyl |
| 2-137 | —L—D | H | —CH2CH2— | SO2NH2 | 2-F | 1 | 4-cyanophenyl | 2-iodo-6-trifluoromethyl-4-(1,2,2,2-tetrafluoro-1-trifluoromethyl-ethyl)-phenyl |
| 2-138 | —L—D | H | —CH2CH2— | SO2NH2 | 2-F | 1 | 4-cyanophenyl | 2-bromo-6-trifluoromethoxy-4-(1,2,2,2-tetrafluoro-1-trifluoromethyl-ethyl)-phenyl |
| 2-139 | —L—D | H | —CH2CH2— | SO2NH2 | 2-F | 1 | 4-cyanophenyl | 2-bromo-6-iodo-4-(1,2,2,2-tetrafluoro-1-trifluoromethyl-ethyl)-phenyl |
| 2-140 | —L—D | H | —CH2CH2— | SO2NH2 | 2-F | 1 | 4-cyanophenyl | 2-bromo-6-trifluoromethylthio-4-(1,2,2,2-tetrafluoro-1-trifluoromethyl-ethyl)-phenyl |
| 2-141 | —L—D | H | —CH2CH2— | SO2NH2 | 2-F | 1 | 4-cyanophenyl | 2-bromo-6-trifluoromethylsulfinyl-4-(1,2,2,2-tetrafluoro-1-trifluoromethyl-ethyl)-phenyl |
| 2-142 | —L—D | H | —CH2CH2— | SO2NH2 | 2-F | 1 | 4-cyanophenyl | 2-bromo-6-trifluoromethylsulfonyl-4-(1,2,2,2-tetrafluoro-1-trifluoromethyl-ethyl)-phenyl |
| 2-143 | —L—D | H | —CH2CH2— | SO2NH2 | 2-F | 1 | 4-cyanophenyl | 2-bromo-6-pentafluoroethyl-4-(1,2,2,2-tetrafluoro-1-trifluoromethyl-ethyl)-phenyl |
| 2-144 | —L—D | H | —CH2CH2— | SO2NH2 | 2-F | 1 | 4-cyanophenyl | 2-iodo-6-pentafluoroethyl-4-(1,2,2,2-tetrafluoro-1-trifluoromethyl-ethyl)-phenyl |

TABLE 2-continued

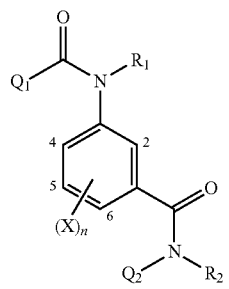

| compound number | R₁ | R₂ | L | D | X | n | Q₁ | Q₂ |
|---|---|---|---|---|---|---|---|---|
| 2-145 | —L—D | H | —CH2CH2— | SO2NH2 | 2-F | 1 | 4-cyanophenyl | 2-chloro-6-methyl-4-(1,2,2,3,3,3-hexafluoro-1-trifluoromethyl-propyl)-phenyl |
| 2-146 | —L—D | H | —CH2CH2— | SO2NH2 | 2-F | 1 | 4-cyanophenyl | 2-bromo-6-methyl-4-(1,2,2,3,3,3-hexafluoro-1-trifluoromethyl-propyl)-phenyl |
| 2-147 | —L—D | H | —CH2CH2— | SO2NH2 | 2-F | 1 | 4-cyanophenyl | 2-iodo-6-methyl-4-(1,2,2,3,3,3-hexafluoro-1-trifluoromethyl-propyl)-phenyl |
| 2-148 | —L—D | H | —CH2CH2— | SO2NH2 | 2-F | 1 | 4-cyanophenyl | 2-bromo-6-ethyl-4-(1,2,2,3,3,3-hexafluoro-1-trifluoromethyl-propyl)-phenyl |
| 2-149 | —L—D | H | —CH2CH2— | SO2NH2 | 2-F | 1 | 4-cyanophenyl | 2-iodo-6-ethyl-4-(1,2,2,3,3,3-hexafluoro-1-trifluoromethyl-propyl)-phenyl |
| 2-150 | —L—D | H | —CH2CH2— | SO2NH2 | 2-F | 1 | 4-cyanophenyl | 2,6-dichloro-4-(1,2,2,3,3,3-hexafluoro-1-trifluoromethyl-propyl)-phenyl |
| 2-151 | —L—D | H | —CH2CH2— | SO2NH2 | 2-F | 1 | 4-cyanophenyl | 2,6-dibromo-4-(1,2,2,3,3,3-hexafluoro-1-trifluoromethyl-propyl)-phenyl |
| 2-152 | —L—D | H | —CH2CH2— | SO2NH2 | 2-F | 1 | 4-cyanophenyl | 2,6-diiodo-4-(1,2,2,3,3,3-hexafluoro-1-trifluoromethyl-propyl)-phenyl |
| 2-153 | —L—D | H | —CH2CH2— | SO2NH2 | 2-F | 1 | 4-cyanophenyl | 2,6-ditrifluoromethyl-4-(1,2,2,3,3,3-hexafluoro-1-trifluoromethyl-propyl)-phenyl |
| 2-154 | —L—D | H | —CH2CH2— | SO2NH2 | 2-F | 1 | 4-cyanophenyl | 2-bromo-6-trifluoromethyl-4-(1,2,2,3,3,3-hexafluoro-1-trifluoromethyl-propyl)-phenyl |
| 2-155 | —L—D | H | —CH2CH2— | SO2NH2 | 2-F | 1 | 4-cyanophenyl | 2-iodo-6-trifluoromethyl-4-(1,2,2,3,3,3-hexafluoro-1-trifluoromethyl-propyl)-phenyl |
| 2-156 | —L—D | H | —CH2CH2— | SO2NH2 | 2-F | 1 | 4-cyanophenyl | 2-bromo-6-trifluoromethoxy-4-(1,2,2,3,3,3-hexafluoro-1-trifluoromethyl-propyl)-phenyl |
| 2-157 | —L—D | H | —CH2CH2— | SO2NH2 | 2-F | 1 | 4-cyanophenyl | 2-bromo-6-iodo-4-(1,2,2,3,3,3-hexafluoro-1-trifluoromethyl-propyl)-phenyl |
| 2-158 | —L—D | H | —CH2CH2— | SO2NH2 | 2-F | 1 | 4-cyanophenyl | 2-bromo-6-trifluoromethylthio-4-(1,2,2,3,3,3-hexafluoro-1-trifluoromethyl-propyl)-phenyl |
| 2-159 | —L—D | H | —CH2CH2— | SO2NH2 | 2-F | 1 | 4-cyanophenyl | 2-bromo-6-trifluoromethylsulfinyl-4-(1,2,2,3,3,3-hexafluoro-1-trifluoromethyl-propyl)-phenyl |
| 2-160 | —L—D | H | —CH2CH2— | SO2NH2 | 2-F | 1 | 4-cyanophenyl | 2-bromo-6-trifluoromethylsulfonyl-4-(1,2,2,3,3,3-hexafluoro-1-trifluoromethyl-propyl)-phenyl |
| 2-161 | —L—D | H | —CH2CH2— | SO2NH2 | 2-F | 1 | 4-cyanophenyl | 2-bromo-6-pentafluoroethyl-4-(1,2,2,3,3,3-hexafluoro-1-trifluoromethyl-propyl)-phenyl |
| 2-162 | —L—D | H | —CH2CH2— | SO2NH2 | 2-F | 1 | 4-cyanophenyl | 2-iodo-6-pentafluoroethyl-4-(1,2,2,3,3,3-hexafluoro-1-trifluoromethyl-propyl)-phenyl |
| 2-163 | —L—D | H | —CH2CH2— | SO2NH2 | 2-F | 1 | phenyl | 2,6-dibromo-4-(1,2,2,2-tetrafluoro-1-trifluoromethyl-ethyl)-phenyl |
| 2-164 | —L—D | H | —CH2CH2— | SO2NH2 | 2-F | 1 | 3-cyanophenyl | 2,6-dibromo-4-(1,2,2,2-tetrafluoro-1-trifluoromethyl-ethyl)-phenyl |
| 2-165 | —L—D | H | —CH2CH2— | SO2NH2 | 2-F | 1 | 2-chloropyridin-3-yl | 2,6-dibromo-4-(1,2,2,2-tetrafluoro-1-trifluoromethyl-ethyl)-phenyl |
| 2-166 | —L—D | H | —CH2CH2— | SO2NH2 | 2-F | 1 | 2-fluorophenyl | 2,6-dibromo-4-(1,2,2,2-tetrafluoro-1-trifluoromethyl-ethyl)-phenyl |
| 2-167 | —L—D | H | —CH2CH2— | SO2NH2 | 2-F | 1 | phenyl | 2,6-diiodo-4-(1,2,2,2-tetrafluoro-1-trifluoromethyl-ethyl)-phenyl |
| 2-168 | —L—D | H | —CH2CH2— | SO2NH2 | 2-F | 1 | 3-cyanophenyl | 2,6-diiodo-4-(1,2,2,2-tetrafluoro-1-trifluoromethyl-ethyl)-phenyl |
| 2-169 | —L—D | H | —CH2CH2— | SO2NH2 | 2-F | 1 | 2-chloropyridin-3-yl | 2,6-diiodo-4-(1,2,2,2-tetrafluoro-1-trifluoromethyl-ethyl)-phenyl |
| 2-170 | —L—D | H | —CH2CH2— | SO2NH2 | 2-F | 1 | 2-fluorophenyl | 2,6-diiodo-4-(1,2,2,2-tetrafluoro-1-trifluoromethyl-ethyl)-phenyl |
| 2-171 | —L—D | H | —CH2CH2— | SO2NH2 | 2-F | 1 | phenyl | 2-bromo-6-trifluoromethyl-4-(1,2,2,2-tetrafluoro-1-trifluoromethyl-ethyl)-phenyl |
| 2-172 | —L—D | H | —CH2CH2— | SO2NH2 | 2-F | 1 | 3-cyanophenyl | 2-bromo-6-trifluoromethyl-4-(1,2,2,2-tetrafluoro-1-trifluoromethyl-ethyl)-phenyl |
| 2-173 | —L—D | H | —CH2CH2— | SO2NH2 | 2-F | 1 | 2-chloropyridin-3-yl | 2-bromo-6-trifluoromethyl-4-(1,2,2,2-tetrafluoro-1-trifluoromethyl-ethyl)-phenyl |
| 2-174 | —L—D | H | —CH2CH2— | SO2NH2 | 2-F | 1 | 2-fluorophenyl | 2-bromo-6-trifluoromethyl-4-(1,2,2,2-tetrafluoro-1-trifluoromethyl-ethyl)-phenyl |
| 2-175 | —L—D | H | —CH2CH2— | SO2NH2 | 2-F | 1 | phenyl | 2-iodo-6-trifluoromethyl-4-(1,2,2,2-tetrafluoro-1-trifluoromethyl-ethyl)-phenyl |

TABLE 2-continued

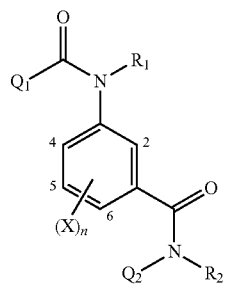

| compound number | R₁ | R₂ | L | D | X | n | Q₁ | Q₂ |
|---|---|---|---|---|---|---|---|---|
| 2-176 | —L—D | H | —CH2CH2— | SO2NH2 | 2-F | 1 | 3-cyanophenyl | 2-iodo-6-trifluoromethyl-4-(1,2,2,2-tetrafluoro-1-trifluoromethyl-ethyl)-phenyl |
| 2-177 | —L—D | H | —CH2CH2— | SO2NH2 | 2-F | 1 | 2-chloropyridin-3-yl | 2-iodo-6-trifluoromethyl-4-(1,2,2,2-tetrafluoro-1-trifluoromethyl-ethyl)-phenyl |
| 2-178 | —L—D | H | —CH2CH2— | SO2NH2 | 2-F | 1 | 2-fluorophenyl | 2-iodo-6-trifluoromethyl-4-(1,2,2,2-tetrafluoro-1-trifluoromethyl-ethyl)-phenyl |
| 2-179 | —L—D | H | —CH2CH2— | SO2NH2 | 2-F | 1 | phenyl | 2,6-dibromo-4-(1,2,2,3,3,3-hexafluoro-1-trifluoromethyl-propyl)-phenyl |
| 2-180 | —L—D | H | —CH2CH2— | SO2NH2 | 2-F | 1 | 3-cyanophenyl | 2,6-dibromo-4-(1,2,2,3,3,3-hexafluoro-1-trifluoromethyl-propyl)-phenyl |
| 2-181 | —L—D | H | —CH2CH2— | SO2NH2 | 2-F | 1 | 2-chloropyridin-3-yl | 2,6-dibromo-4-(1,2,2,3,3,3-hexafluoro-1-trifluoromethyl-propyl)-phenyl |
| 2-182 | —L—D | H | —CH2CH2— | SO2NH2 | 2-F | 1 | 2-fluorophenyl | 2,6-dibromo-4-(1,2,2,3,3,3-hexafluoro-1-trifluoromethyl-propyl)-phenyl |
| 2-183 | —L—D | H | —CH2CH2— | SO2NH2 | 2-F | 1 | phenyl | 2,6-diiodo-4-(1,2,2,3,3,3-hexafluoro-1-trifluoromethyl-propyl)-phenyl |
| 2-184 | —L—D | H | —CH2CH2— | SO2NH2 | 2-F | 1 | 3-cyanophenyl | 2,6-diiodo-4-(1,2,2,3,3,3-hexafluoro-1-trifluoromethyl-propyl)-phenyl |
| 2-185 | —L—D | H | —CH2CH2— | SO2NH2 | 2-F | 1 | 2-chloropyridin-3-yl | 2,6-diiodo-4-(1,2,2,3,3,3-hexafluoro-1-trifluoromethyl-propyl)-phenyl |
| 2-186 | —L—D | H | —CH2CH2— | SO2NH2 | 2-F | 1 | 2-fluorophenyl | 2,6-diiodo-4-(1,2,2,3,3,3-hexafluoro-1-trifluoromethyl-propyl)-phenyl |
| 2-187 | —L—D | H | —CH2CH2— | SO2NH2 | 2-F | 1 | phenyl | 2-bromo-6-trifluoromethyl-4-(1,2,2,3,3,3-hexafluoro-1-trifluoromethyl-propyl)-phenyl |
| 2-188 | —L—D | H | —CH2CH2— | SO2NH2 | 2-F | 1 | 3-cyanophenyl | 2-bromo-6-trifluoromethyl-4-(1,2,2,3,3,3-hexafluoro-1-trifluoromethyl-propyl)-phenyl |
| 2-189 | —L—D | H | —CH2CH2— | SO2NH2 | 2-F | 1 | 2-chloropyridin-3-yl | 2-bromo-6-trifluoromethyl-4-(1,2,2,3,3,3-hexafluoro-1-trifluoromethyl-propyl)-phenyl |
| 2-190 | —L—D | H | —CH2CH2— | SO2NH2 | 2-F | 1 | 2-fluorophenyl | 2-bromo-6-trifluoromethyl-4-(1,2,2,3,3,3-hexafluoro-1-trifluoromethyl-propyl)-phenyl |
| 2-191 | —L—D | H | —CH2CH2— | SO2NH2 | 2-F | 1 | phenyl | 2-iodo-6-trifluoromethyl-4-(1,2,2,3,3,3-hexafluoro-1-trifluoromethyl-propyl)-phenyl |
| 2-192 | —L—D | H | —CH2CH2— | SO2NH2 | 2-F | 1 | 3-cyanophenyl | 2-iodo-6-trifluoromethyl-4-(1,2,2,3,3,3-hexafluoro-1-trifluoromethyl-propyl)-phenyl |
| 2-193 | —L—D | H | —CH2CH2— | SO2NH2 | 2-F | 1 | 2-chloropyridin-3-yl | 2-iodo-6-trifluoromethyl-4-(1,2,2,3,3,3-hexafluoro-1-trifluoromethyl-propyl)-phenyl |
| 2-194 | —L—D | H | —CH2CH2— | SO2NH2 | 2-F | 1 | 2-fluorophenyl | 2-iodo-6-trifluoromethyl-4-(1,2,2,3,3,3-hexafluoro-1-trifluoromethyl-propyl)-phenyl |
| 2-195 | —L—D | H | —CH2CH2— | SO2NH2 | H | 0 | 6-chloropyridin-3-yl | 2-bromo-6-trifluoromethyl-4-(1,2,2,2-tetrafluoro-1-trifluoromethyl-ethyl)-phenyl |
| 2-196 | —L—D | H | —CH2CH2— | SO2NH2 | 2-F | 1 | 6-chloropyridin-3-yl | 2-bromo-6-trifluoromethyl-4-(1,2,2,2-tetrafluoro-1-trifluoromethyl-ethyl)-phenyl |
| 2-197 | —L—D | H | —CH2CH2— | SO2NH2 | 2-F | 1 | 6-chloropyridin-3-yl | 2,6-dibromo-4-(1,2,2,2-tetrafluoro-1-trifluoromethyl-ethyl)-phenyl |
| 2-198 | —L—D | H | —CH2CH2— | SO2NH2 | 2-F | 1 | 3,5-dicyanophenyl | 2-bromo-6-trifluoromethyl-4-(1,2,2,2-tetrafluoro-1-trifluoromethyl-ethyl)-phenyl |
| 2-199 | —L—D | H | —CH2CH2— | SO2NH2 | 2-F | 1 | 3,5-dicyanophenyl | 2,6-dibromo-4-(1,2,2,2-tetrafluoro-1-trifluoromethyl-ethyl)-phenyl |
| 2-200 | —L—D | H | —CH2CH2— | SO2NH2 | 2-F | 1 | pyridin-3-yl | 2,6-dibromo-4-(1,2,2,2-tetrafluoro-1-trifluoromethyl-ethyl)-phenyl |
| 2-201 | —L—D | H | —CH2CH2— | SO2NH2 | 2-F | 1 | pyridin-4-yl | 2,6-dibromo-4-(1,2,2,2-tetrafluoro-1-trifluoromethyl-ethyl)-phenyl |
| 2-202 | —L—D | H | —CH2CH2— | SO2NH2 | 2-F | 1 | 2-chloropyridin-4-yl | 2,6-dibromo-4-(1,2,2,2-tetrafluoro-1-trifluoromethyl-ethyl)-phenyl |
| 2-203 | —L—D | H | —CH2CH2— | SO2NH2 | 2-F | 1 | pyrazin-2-yl | 2,6-dibromo-4-(1,2,2,2-tetrafluoro-1-trifluoromethyl-ethyl)-phenyl |
| 2-204 | —L—D | H | —CH2CH2— | SO2NH2 | 2-F | 1 | pyrimidin-5-yl | 2,6-dibromo-4-(1,2,2,2-tetrafluoro-1-trifluoromethyl-ethyl)-phenyl |
| 2-205 | —L—D | H | —CH2CH2— | SO2NH2 | 2-F | 1 | 3-cyanophenyl | 2,6-dichloro-4-(1,2,2,2-tetrafluoro-1-trifluoromethyl-ethyl)-phenyl |
| 2-206 | —L—D | H | —CH2CH2— | SO2NH2 | 2-F | 1 | phenyl | 2,6-dichloro-4-(1,2,2,2-tetrafluoro-1-trifluoromethyl-ethyl)-phenyl |
| 2-207 | —L—D | H | —CH2CH2— | SO2NH2 | 2-F | 1 | 2-chloropyridin-3-yl | 2,6-dichloro-4-(1,2,2,2-tetrafluoro-1-trifluoromethyl-ethyl)-phenyl |

TABLE 2-continued

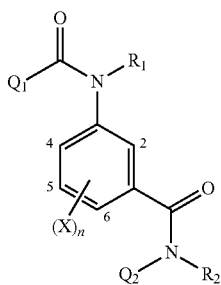

| compound number | R₁ | R₂ | L | D | X | n | Q₁ | Q₂ |
|---|---|---|---|---|---|---|---|---|
| 2-208 | —L—D | H | —CH2CH2— | SO2NH2 | 2-F | 1 | 6-cyanopyridin-3-yl | 2,6-dibromo-4-(1,2,2,2-tetrafluoro-1-trifluoromethyl-ethyl)-phenyl |
| 2-209 | —L—D | H | —CH2CH2— | SO2NH2 | 2-F | 1 | 4-fluorophenyl | 2,6-dibromo-4-(1,2,2,2-tetrafluoro-1-trifluoromethyl-ethyl)-phenyl |
| 2-210 | —L—D | H | —CH2CH2— | SO2NH2 | 2-F | 1 | 2,6-difluorophenyl | 2,6-dibromo-4-(1,2,2,2-tetrafluoro-1-trifluoromethyl-ethyl)-phenyl |
| 2-211 | —L—D | H | —CH2CH2— | SO2NH2 | 2-F | 1 | 2-chloropyridin-3-yl | 2-bromo-6-iodo-4-(1,2,2,2-tetrafluoro-1-trifluoromethyl-ethyl)-phenyl |
| 2-212 | —L—D | H | —CH2CH2— | SO2NH2 | 2-F | 1 | phenyl | 2-bromo-6-iodo-4-(1,2,2,2-tetrafluoro-1-trifluoromethyl-ethyl)-phenyl |
| 2-213 | —L—D | H | —CH2CH2— | SO2NH2 | 2-F | 1 | 6-chloropyridin-3-yl | 2,6-dibromo-4-(1,2,2,3,3,3-hexafluoro-1-trifluoromethyl-propyl)-phenyl |
| 2-214 | —L—D | H | —CH2CH2— | SO2NH2 | 2-F | 1 | phenyl | 2,6-dimethyl-4-(1,2,2,3,3,3-hexafluoro-1-trifluoromethyl-propyl)-phenyl |
| 2-215 | —L—D | H | —CH2CH2— | SO2NH2 | 2-F | 1 | 4-cyanophenyl | 2,6-dimethyl-4-(1,2,2,3,3,3-hexafluoro-1-trifluoromethyl-propyl)-phenyl |
| 2-216 | —L—D | H | —CH2CH2— | SO2NH2 | 2-F | 1 | 3-cyanophenyl | 2,6-dimethyl-4-(1,2,2,3,3,3-hexafluoro-1-trifluoromethyl-propyl)-phenyl |
| 2-217 | —L—D | H | —CH2CH2— | SO2NH2 | 4-F | 1 | phenyl | 2,6-dibromo-4-(1,2,2,2-tetrafluoro-1-trifluoromethyl-ethyl)-phenyl |
| 2-218 | —L—D | H | —CH2CH2— | SO2NH2 | 4-F | 1 | 4-cyanophenyl | 2-bromo-6-trifluoromethyl-4-(1,2,2,2-tetrafluoro-1-trifluoromethyl-ethyl)-phenyl |
| 2-219 | —L—D | H | —CH2CH2— | SO2NH2 | 4-F | 1 | 3-cyanophenyl | 2-iodo-6-trifluoromethyl-4-(1,2,2,2-tetrafluoro-1-trifluoromethyl-ethyl)-phenyl |
| 2-220 | —L—D | H | —CH2CH2— | SO2NH2 | 4-F | 1 | 2-chloropyridin-3-yl | 2-bromo-6-trifluoromethyl-4-(1,2,2,3,3,3-hexafluoro-1-trifluoromethyl-propyl)-phenyl |
| 2-221 | —L—D | H | —CH2CH2— | SO2NH2 | 4-F | 1 | 2-fluorophenyl | 2-iodo-6-trifluoromethyl-4-(1,2,2,3,3,3-hexafluoro-1-trifluoromethyl-propyl)-phenyl |
| 2-222 | —L—D | H | —CH2CH2— | SO2NH2 | 4-CN | 1 | phenyl | 2,6-dibromo-4-(1,2,2,2-tetrafluoro-1-trifluoromethyl-ethyl)-phenyl |
| 2-223 | —L—D | H | —CH2CH2— | SO2NH2 | 4-CN | 1 | 4-cyanophenyl | 2-bromo-6-trifluoromethyl-4-(1,2,2,2-tetrafluoro-1-trifluoromethyl-ethyl)-phenyl |
| 2-224 | —L—D | H | —CH2CH2— | SO2NH2 | 4-CN | 1 | 3-cyanophenyl | 2-iodo-6-trifluoromethyl-4-(1,2,2,2-tetrafluoro-1-trifluoromethyl-ethyl)-phenyl |
| 2-225 | —L—D | H | —CH2CH2— | SO2NH2 | 4-CN | 1 | 2-chloropyridin-3-yl | 2-bromo-6-trifluoromethyl-4-(1,2,2,3,3,3-hexafluoro-1-trifluoromethyl-propyl)-phenyl |
| 2-226 | —L—D | H | —CH2CH2— | SO2NH2 | 4-CN | 1 | 2-fluorophenyl | 2-iodo-6-trifluoromethyl-4-(1,2,2,3,3,3-hexafluoro-1-trifluoromethyl-propyl)-phenyl |
| 2-227 | —L—D | H | —CH2CH2— | SO2NH2 | 2-NO2 | 1 | phenyl | 2,6-dibromo-4-(1,2,2,2-tetrafluoro-1-trifluoromethyl-ethyl)-phenyl |
| 2-228 | —L—D | H | —CH2CH2— | SO2NH2 | 2-NO2 | 1 | 4-cyanophenyl | 2-bromo-6-trifluoromethyl-4-(1,2,2,2-tetrafluoro-1-trifluoromethyl-ethyl)-phenyl |
| 2-229 | —L—D | H | —CH2CH2— | SO2NH2 | 2-NO2 | 1 | 3-cyanophenyl | 2-iodo-6-trifluoromethyl-4-(1,2,2,2-tetrafluoro-1-trifluoromethyl-ethyl)-phenyl |
| 2-230 | —L—D | H | —CH2CH2— | SO2NH2 | 2-NO2 | 1 | 2-chloropyridin-3-yl | 2-bromo-6-trifluoromethyl-4-(1,2,2,3,3,3-hexafluoro-1-trifluoromethyl-propyl)-phenyl |
| 2-231 | —L—D | H | —CH2CH2— | SO2NH2 | 2-NO2 | 1 | 2-fluorophenyl | 2-iodo-6-trifluoromethyl-4-(1,2,2,3,3,3-hexafluoro-1-trifluoromethyl-propyl)-phenyl |

TABLE 3

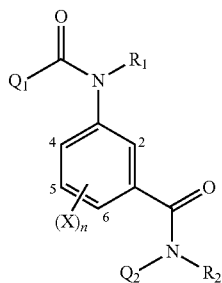

| compound number | R₁ | R₂ | L | D | X | n | Q₁ | Q₂ |
|---|---|---|---|---|---|---|---|---|
| 3-1 | -L-D | H | —CH2CH2— | SO2Me | H | 0 | phenyl | 2,6-dimethyl-4-(1,2,2,2-tetrafluoro-1-trifluoromethyl-ethyl)-phenyl |
| 3-2 | -L-D | H | —CH2CH2— | SO2Me | H | 0 | 4-cyanophenyl | 2,6-dimethyl-4-(1,2,2,2-tetrafluoro-1-trifluoromethyl-ethyl)-phenyl |
| 3-3 | -L-D | H | —CH2CH2— | SO2Me | H | 0 | 3-cyanophenyl | 2,6-dimethyl-4-(1,2,2,2-tetrafluoro-1-trifluoromethyl-ethyl)-phenyl |
| 3-4 | -L-D | H | —CH2CH2— | SO2Me | H | 0 | 3,5-dicyanophenyl | 2,6-dimethyl-4-(1,2,2,2-tetrafluoro-1-trifluoromethyl-ethyl)-phenyl |
| 3-5 | -L-D | H | —CH2CH2— | SO2Me | H | 0 | 2-fluorophenyl | 2,6-dimethyl-4-(1,2,2,2-tetrafluoro-1-trifluoromethyl-ethyl)-phenyl |
| 3-6 | -L-D | H | —CH2CH2— | SO2Me | H | 0 | 4-fluorophenyl | 2,6-dimethyl-4-(1,2,2,2-tetrafluoro-1-trifluoromethyl-ethyl)-phenyl |
| 3-7 | -L-D | H | —CH2CH2— | SO2Me | H | 0 | 2,6-difluorophenyl | 2,6-dimethyl-4-(1,2,2,2-tetrafluoro-1-trifluoromethyl-ethyl)-phenyl |
| 3-8 | -L-D | H | —CH2CH2— | SO2Me | H | 0 | 2-fluoro-4-cyanophenyl | 2,6-dimethyl-4-(1,2,2,2-tetrafluoro-1-trifluoromethyl-ethyl)-phenyl |
| 3-9 | -L-0 | H | —CH2CH2— | SO2Me | H | 0 | 2-chlorophenyl | 2,6-dimethyl-4-(1,2,2,2-tetrafluoro-1-trifluoromethyl-ethyl)-phenyl |
| 3-10 | -L-D | H | —CH2CH2— | SO2Me | H | 0 | 4-chlorophenyl | 2,6-dimethyl-4-(1,2,2,2-tetrafluoro-1-trifluoromethyl-ethyl)-phenyl |
| 3-11 | -L-D | H | —CH2CH2— | SO2Me | H | 0 | 4-nitrophenyl | 2,6-dimethyl-4-(1,2,2,2-tetrafluoro-1-trifluoromethyl-ethyl)-phenyl |
| 3-12 | -L-D | H | —CH2CH2— | SO2Me | H | 0 | 2-methylphenyl | 2,6-dimethyl-4-(1,2,2,2-tetrafluoro-1-trifluoromethyl-ethyl)-phenyl |
| 3-13 | -L-D | H | —CH2CH2— | SO2Me | H | 0 | pyridin-2-yl | 2,6-dimethyl-4-(1,2,2,2-tetrafluoro-1-trifluoromethyl-ethyl)-phenyl |
| 3-14 | -L-D | H | —CH2CH2— | SO2Me | H | 0 | pyridin-3-yl | 2,6-dimethyl-4-(1,2,2,2-tetrafluoro-1-trifluoromethyl-ethyl)-phenyl |
| 3-15 | -L-D | H | —CH2CH2— | SO2Me | H | 0 | pyridin-4-yl | 2,6-dimethyl-4-(1,2,2,2-tetrafluoro-1-trifluoromethyl-ethyl)-phenyl |
| 3-16 | -L-D | H | —CH2CH2— | SO2Me | H | 0 | 2-chloropyridin-3-yl | 2,6-dimethyl-4-(1,2,2,2-tetrafluoro-1-trifluoromethyl-ethyl)-phenyl |
| 3-17 | -L-D | H | —CH2CH2— | SO2Me | H | 0 | 6-chloropyridin-3-yl | 2,6-dimethyl-4-(1,2,2,2-tetrafluoro-1-trifluoromethyl-ethyl)-phenyl |
| 3-18 | -L-D | H | —CH2CH2— | SO2Me | H | 0 | 2-chloropyridin-4-yl | 2,6-dimethyl-4-(1,2,2,2-tetrafluoro-1-trifluoromethyl-ethyl)-phenyl |
| 3-19 | -L-D | H | —CH2CH2— | SO2Me | H | 0 | pyrazin-2-yl | 2,6-dimethyl-4-(1,2,2,2-tetrafluoro-1-trifluoromethyl-ethyl)-phenyl |
| 3-20 | -L-D | H | —CH2CH2— | SO2Me | H | 0 | pyrimidin-5-yl | 2,6-dimethyl-4-(1,2,2,2-tetrafluoro-1-trifluoromethyl-ethyl)-phenyl |
| 3-21 | -L-D | H | —CH2CH2— | SO2Me | 2-F | 1 | phenyl | 2,6-dimethyl-4-(1,2,2,2-tetrafluoro-1-trifluoromethyl-ethyl)-phenyl |
| 3-22 | -L-D | H | —CH2CH2— | SO2Me | 2-F | 1 | 4-cyanophenyl | 2,6-dimethyl-4-(1,2,2,2-tetrafluoro-1-trifluoromethyl-ethyl)-phenyl |
| 3-23 | -L-D | H | —CH2CH2— | SO2Mc | 2-F | 1 | 3-cyanophenyl | 2,6-dimethyl-4-(1,2,2,2-tetrafluoro-1-trifluoromethyl-ethyl)-phenyl |
| 3-24 | -L-D | H | —CH2CH2— | SO2Me | 2-F | 1 | 3,5-dicyanophenyl | 2,6-dimethyl-4-(1,2,2,2-tetrafluoro-1-trifluoromethyl-ethyl)-phenyl |
| 3-25 | -L-D | H | —CH2CH2— | SO2Me | 2-F | 1 | 2-fluorophenyl | 2,6-dimethyl-4-(1,2,2,2-tetrafluoro-1-trifluoromethyl-ethyl)-phenyl |
| 3-26 | -L-D | H | —CH2CH2— | SO2Me | 2-F | 1 | 4-fluorophenyl | 2,6-dimethyl-4-(1,2,2,2-tetrafluoro-1-trifluoromethyl-ethyl)-phenyl |
| 3-27 | -L-D | H | —CH2CH2— | SO2Me | 2-F | 1 | 2,6-difluorophenyl | 2,6-dimethyl-4-(1,2,2,2-tetrafluoro-1-trifluoromethyl-ethyl)-phenyl |
| 3-28 | -L-D | H | —CH2CH2— | SO2Me | 2-F | 1 | 2-fluoro-4-cyanophenyl | 2,6-dimethyl-4-(1,2,2,2-tetrafluoro-1-trifluoromethyl-ethyl)-phenyl |
| 3-29 | -L-D | H | —CH2CH2— | SO2Me | 2-F | 1 | 2-chlorophenyl | 2,6-dimethyl-4-(1,2,2,2-tetrafluoro-1-trifluoromethyl-ethyl)-phenyl |
| 3-30 | -L-D | H | —CH2CH2— | SO2Me | 2-F | 1 | 4-chlorophenyl | 2,6-dimethyl-4-(1,2,2,2-tetrafluoro-1-trifluoromethyl-ethyl)-phenyl |
| 3-31 | -L-D | H | —CH2CH2— | SO2Me | 2-F | 1 | 4-nitrophenyl | 2,6-dimethyl-4-(1,2,2,2-tetrafluoro-1-trifluoromethyl-ethyl)-phenyl |

TABLE 3-continued

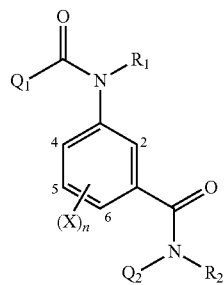

| compound number | R₁ | R₂ | L | D | X | n | Q₁ | Q₂ |
|---|---|---|---|---|---|---|---|---|
| 3-32 | -L-D | H | —CH2CH2— | SO2Me | 2-F | 1 | 2-methylphenyl | 2,6-dimethyl-4-(1,2,2,2-tetrafluoro-1-trifluoromethyl-ethyl)-phenyl |
| 3-33 | -L-D | H | —CH2CH2— | SO2Me | 2-F | 1 | pyridin-2-yl | 2,6-dimethyl-4-(1,2,2,2-tetrafluoro-1-trifluoromethyl-ethyl)-phenyl |
| 3-34 | -L-D | H | —CH2CH2— | SO2Me | 2-F | 1 | pyridin-3-yl | 2,6-dimethyl-4-(1,2,2,2-tetrafluoro-1-trifluoromethyl-ethyl)-phenyl |
| 3-35 | -L-D | H | —CH2CH2— | SO2Me | 2-F | 1 | pyridin-4-yl | 2,6-dimethyl-4-(1,2,2,2-tetrafluoro-1-trifluoromethyl-ethyl)-phenyl |
| 3-36 | -L-D | H | —CH2CH2— | SO2Me | 2-F | 1 | 2-chloropyridin-3-yl | 2,6-dimethyl-4-(1,2,2,2-tetrafluoro-1-trifluoromethyl-ethyl)-phenyl |
| 3-37 | -L-D | H | —CH2CH2— | SO2Me | 2-F | 1 | 6-chloropyridin-3-yl | 2,6-dimethyl-4-(1,2,2,2-tetrafluoro-1-trifluoromethyl-ethyl)-phenyl |
| 3-38 | -L-D | H | —CH2CH2— | SO2Me | 2-F | 1 | 2-chloropyridin-4-yl | 2,6-dimethyl-4-(1,2,2,2-tetrafluoro-1-trifluoromethyl-ethyl)-phenyl |
| 3-39 | -L-D | H | —CH2CH2— | SO2Me | 2-F | 1 | pyrazin-2-yl | 2,6-dimethyl-4-(1,2,2,2-tetrafluoro-1-trifluoromethyl-ethyl)-phenyl |
| 3-40 | -L-D | H | —CH2CH2— | SO2Me | 2-F | 1 | pyrimidin-5-yl | 2,6-dimethyl-4-(1,2,2,2-tetrafluoro-1-trifluoromethyl-ethyl)-phenyl |
| 3-41 | -L-D | H | —CH2CH2— | SO2Me | 4-F | 1 | phenyl | 2,6-dimethyl-4-(1,2,2,2-tetrafluoro-1-trifluoromethyl-ethyl)-phenyl |
| 3-42 | -L-D | H | —CH2CH2— | SO2Me | 4-F | 1 | 4-cyanophenyl | 2,6-dimethyl-4-(1,2,2,2-tetrafluoro-1-trifluoromethyl-ethyl)-phenyl |
| 3-43 | -L-D | H | —CH2CH2— | SO2Me | 4-F | 1 | 3-cyanophenyl | 2,6-dimethyl-4-(1,2,2,2-tetrafluoro-1-trifluoromethyl-ethyl)-phenyl |
| 3-44 | -L-D | H | —CH2CH2— | SO2Me | 4-F | 1 | 2-chloropyridin-3-yl | 2,6-dimethyl-4-(1,2,2,2-tetrafluoro-1-trifluoromethyl-ethyl)-phenyl |
| 3-45 | -L-D | H | —CH2CH2— | SO2Me | 4-F | 1 | 2-fluorophenyl | 2,6-dimethyl-4-(1,2,2,2-tetrafluoro-1-trifluoromethyl-ethyl)-phenyl |
| 3-46 | -L-D | H | —CH2CH2— | SO2Mc | 4-CN | 1 | phenyl | 2,6-dimethyl-4-(1,2,2,2-tetrafluoro-1-trifluoromethyl-ethyl)-phenyl |
| 3-47 | -L-D | H | —CH2CH2— | SO2Me | 4-CN | 1 | 4-cyanophenyl | 2,6-dimethyl-4-(1,2,2,2-tetrafluoro-1-trifluoromethyl-ethyl)-phenyl |
| 3-48 | -L-D | H | —CH2CH2— | SO2Me | 4-CN | 1 | 3-cyanophenyl | 2,6-dimethyl-4-(1,2,2,2-tetrafluoro-1-trifluoromethyl-ethyl)-phenyl |
| 3-49 | -L-D | H | —CH2CH2— | SO2Me | 4-CN | 1 | 2-chloropyridin-3-yl | 2,6-dimethyl-4-(1,2,2,2-tetrafluoro-1-trifluoromethyl-ethyl)-phenyl |
| 3-50 | -L-D | H | —CH2CH2— | SO2Me | 4-CN | 1 | 2-fluorophenyl | 2,6-dimethyl-4-(1,2,2,2-tetrafluoro-1-trifluoromethyl-ethyl)-phenyl |
| 3-51 | -L-D | H | —CH2CH2— | SO2Me | H | 0 | 4-cyanophenyl | 2,6-dibromo-4-pentafluoroethyl-phenyl |
| 3-52 | -L-D | H | —CH2CH2— | SO2Me | H | 0 | 4-cyanophenyl | 2,6-diiodo-4-pentafluoroethyl-phenyl |
| 3-53 | -L-D | H | —CH2CH2— | SO2Me | H | 0 | 4-cyanophenyl | 2-bromo-6-trifluoromethyl-4-pentafluoroethyl-phenyl |
| 3-54 | -L-D | H | —CH2CH2— | SO2Me | H | 0 | 4-cyanophenyl | 2-iodo-6-trifluoromethyl-4-pentafluoroethyl-phenyl |
| 3-55 | -L-D | 1-1 | —CH2CH2— | SO2Me | H | 0 | 4-cyanophenyl | 2-chloro-6-methyl-4-(1,2,2,2-tetrafluoro-1-trifluoromethyl-ethyl)-phenyl |
| 3-56 | -L-D | H | —CH2CH2— | SO2Me | H | 0 | 4-cyanophenyl | 2-bromo-6-methyl-4-(1,2,2,2-tetrafluoro-1-trifluoromethyl-ethyl)-phenyl |
| 3-57 | -L-D | H | —CH2CH2— | SO2Me | H | 0 | 4-cyanophenyl | 2-iodo-6-methyl-4-(1,2,2,2-tetrafluoro-1-trifluoromethyl-ethyl)-phenyl |
| 3-58 | -L-D | H | —CH2CH2— | SO2Me | H | 0 | 4-cyanophenyl | 2-bromo-6-ethyl-4-(1,2,2,2-tetrafluoro-1-trifluoromethyl-ethyl)-phenyl |
| 3-59 | -L-0 | H | —CH2CH2— | SO2Me | H | 0 | 4-cyanophenyl | 2-iodo-6-ethyl-4-(1,2,2,2-tetrafluoro-1-trifluoromethyl-ethyl)-phenyl |
| 3-60 | -L-D | H | —CH2CH2— | SO2Me | H | 0 | 4-cyanophenyl | 2,6-dichloro-4-(1,2,2,2-tetrafluoro-1-trifluoromethyl-ethyl)-phenyl |
| 3-61 | -L-D | H | —CH2CH2— | SO2Me | H | 0 | 4-cyanophenyl | 2,6-dibromo-4-(1,2,2,2-tetrafluoro-1-trifluoromethyl-ethyl)-phenyl |
| 3-62 | -L-D | H | —CH2CH2— | SO2Me | H | 0 | 4-cyanophenyl | 2,6-diiodo-4-(1,2,2,2-tetrafluoro-1-trifluoromethyl-ethyl)-phenyl |
| 3-63 | -L-D | H | —CH2CH2— | SO2Me | H | 0 | 4-cyanophenyl | 2,6-ditrifluoromethyl-4-(1,2,2,2-tetrafluoro-1-trifluoromethyl-ethyl)-phenyl |

TABLE 3-continued

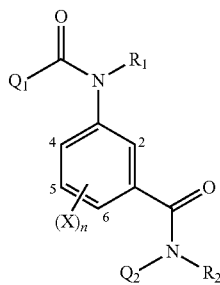

| compound number | R1 | R2 | L | D | X | n | Q1 | Q2 |
|---|---|---|---|---|---|---|---|---|
| 3-64 | -L-D | H | —CH2CH2— | SO2Me | H | 0 | 4-cyanophenyl | 2-bromo-6-trifluoromethyl-4-(1,2,2,2-tetrafluoro-1-trifluoromethyl-ethyl)-phenyl |
| 3-65 | -L-D | H | —CH2CH2— | SO2Me | H | 0 | 4-cyanophenyl | 2-iodo-6-trifluoromethyl-4-(1,2,2,2-tetrafluoro-1-trifluoromethyl-ethyl)-phenyl |
| 3-66 | -L-D | H | —CH2CH2— | SO2Me | H | 0 | 4-cyanophenyl | 2-bromo-6-trifluoromethoxy-4-(1,2,2,2-tetrafluoro-1-trifluoromethyl-ethyl)-phenyl |
| 3-67 | -L-D | H | —CH2CH2— | SO2Me | H | 0 | 4-cyanophenyl | 2-bromo-6-iodo-4-(1,2,2,2-tetrafluoro-1-trifluoromethyl-ethyl)-phenyl |
| 3-68 | -L-D | H | —CH2CH2— | SO2Me | H | 0 | 4-cyanophenyl | 2-bromo-6-trifluoromethylthio-4-(1,2,2,2-tetrafluoro-1-trifluoromethyl-ethyl)-phenyl |
| 3-69 | -L-D | H | —CH2CH2— | SO2Me | H | 0 | 4-cyanophenyl | 2-bromo-6-trifluoromethylsulfinyl-4-(1,2,2,2-tetrafluoro-1-trifluoromethyl-ethyl)-phenyl |
| 3-70 | -L-D | H | —CH2CH2— | SO2Me | H | 0 | 4-cyanophenyl | 2-bromo-6-trifluoromethylsulfonyl-4-(1,2,2,2-tetrafluoro-1-trifluoromethyl-ethyl)-phenyl |
| 3-71 | -L-D | H | —CH2CH2— | SO2Me | H | 0 | 4-cyanophenyl | 2-bromo-6-pentafluoroethyl-4-(1,2,2,2-tetrafluoro-1-trifluoromethyl-ethyl)-phenyl |
| 3-72 | -L-D | H | —CH2CH2— | SO2Me | H | 0 | 4-cyanophenyl | 2-iodo-6-pentafluoroethyl-4-(1,2,2,2-tetrafluoro-1-trifluoromethyl-ethyl)-phenyl |
| 3-73 | -L-D | H | —CH2CH2— | SO2Me | H | 0 | 4-cyanophenyl | 2-chloro-6-methyl-4-(1,2,2,3,3,3-hexafluoro-1-trifluoromethyl-propyl)-phenyl |
| 3-74 | -L-D | H | —CH2CH2— | SO2Me | H | 0 | 4-cyanophenyl | 2-bromo-6-methyl-4-(1,2,2,3,3,3-hexafluoro-1-trifluoromethyl-propyl)-phenyl |
| 3-75 | -L-D | H | —CH2CH2— | SO2Me | H | 0 | 4-cyanophenyl | 2-iodo-6-methyl-4-(1,2,2,3,3,3-hexafluoro-1-trifluoromethyl-propyl)-phenyl |
| 3-76 | -L-D | H | —CH2CH2— | SO2Me | H | 0 | 4-cyanophenyl | 2-bromo-6-ethyl-4-(1,2,2,3,3,3-hexafluoro-1-trifluoromethyl-propyl)-phenyl |
| 3-77 | -L-D | H | —CH2CH2— | SO2Me | H | 0 | 4-cyanophenyl | 2-iodo-6-ethyl-4-(1,2,2,3,3,3-hexafluoro-1-trifluoromethyl-propyl)-phenyl |
| 3-78 | -L-D | H | —CH2CH2— | SO2Me | H | 0 | 4-cyanophenyl | 2,6-dichloro-4-(1,2,2,3,3,3-hexafluoro-1-trifluoromethyl-propyl)-phenyl |
| 3-79 | -L-D | H | —CH2CH2— | SO2Me | H | 0 | 4-cyanophenyl | 2,6-dibromo-4-(1,2,2,3,3,3-hexafluoro-1-trifluoromethyl-propyl)-phenyl |
| 3-80 | -L-D | H | —CH2CH2— | SO2Me | H | 0 | 4-cyanophenyl | 2,6-diiodo-4-(1,2,2,3,3,3-hexafluoro-1-trifluoromethyl-propyl)-phenyl |
| 3-81 | -L-D | H | —CH2CH2— | SO2Me | H | 0 | 4-cyanophenyl | 2,6-ditrifluoromethyl-4-(1,2,2,3,3,3-hexafluoro-1-trifluoromethyl-propyl)-phenyl |
| 3-82 | -L-D | H | —CH2CH2— | SO2Me | H | 0 | 4-cyanophenyl | 2-bromo-6-trifluoromethyl-4-(1,2,2,3,3,3-hexafluoro-1-trifluoromethyl-propyl)-phenyl |
| 3-83 | -L-D | H | —CH2CH2— | SO2Me | H | 0 | 4-cyanophenyl | 2-iodo-6-trifluoromethyl-4-(1,2,2,3,3,3-hexafluoro-1-trifluoromethyl-propyl)-phenyl |
| 3-84 | -L-D | H | —CH2CH2— | SO2Me | H | 0 | 4-cyanophenyl | 2-bromo-6-trifluoromethoxy-4-(1,2,2,3,3,3-hexafluoro-1-trifluoromethyl-propyl)-phenyl |
| 3-85 | -L-D | H | —CH2CH2— | SO2Me | H | 0 | 4-cyanophenyl | 2-bromo-6-iodo-4-(1,2,2,3,3,3-hexafluoro-1-trifluoromethyl-propyl)-phenyl |
| 3-86 | -L-D | H | —CH2CH2— | SO2Me | H | 0 | 4-cyanophenyl | 2-bromo-6-trifluoromethylthio-4-(1,2,2,3,3,3-hexafluoro-1-trifluoromethyl-propyl)-phenyl |
| 3-87 | -L-D | H | —CH2CH2— | SO2Me | H | 0 | 4-cyanophenyl | 2-bromo-6-trifluoromethylsulfinyl-4-(1,2,2,3,3,3-hexafluoro-1-trifluoromethyl-propyl)-phenyl |
| 3-88 | -L-D | H | —CH2CH2— | SO2Me | H | 0 | 4-cyanophenyl | 2-bromo-6-trifluoromethylsulfonyl-4-(1,2,2,3,3,3-hexafluoro-1-trifluoromethyl-propyl)-phenyl |
| 3-89 | -L-D | H | —CH2CH2— | SO2Me | H | 0 | 4-cyanophenyl | 2-bromo-6-pentafluoroethyl-4-(1,2,2,3,3,3-hexafluoro-1-trifluoromethyl-propyl)-phenyl |
| 3-90 | -L-D | H | —CH2CH2— | SO2Me | H | 0 | 4-cyanophenyl | 2-iodo-6-pentafluoroethyl-4-(1,2,2,3,3,3-hexafluoro-1-trifluoromethyl-propyl)-phenyl |
| 3-91 | -L-D | H | —CH2CH2— | SO2Me | H | 0 | phenyl | 2,6-dibromo-4-(1,2,2,2-tetrafluoro-1-trifluoromethyl-ethyl)-phenyl |
| 3-92 | -L-D | H | —CH2CH2— | SO2Me | H | 0 | 3-cyanophenyl | 2,6-dibromo-4-(1,2,2,2-tetrafluoro-1-trifluoromethyl-ethyl)-phenyl |
| 3-93 | -L-D | H | —CH2CH2— | SO2Me | H | 0 | 2-chloropyridin-3-yl | 2,6-dibromo-4-(1,2,2,2-tetrafluoro-1-trifluoromethyl-ethyl)-phenyl |
| 3-94 | -L-D | H | —CH2CH2— | SO2Me | H | 0 | 2-fluorophenyl | 2,6-dibromo-4-(1,2,2,2-tetrafluoro-1-trifluoromethyl-ethyl)-phenyl |

TABLE 3-continued

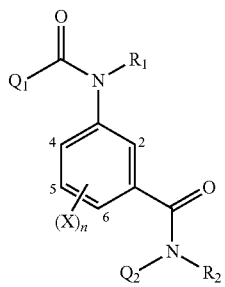

| compound number | R₁ | R₂ | L | D | X | n | Q₁ | Q₂ |
|---|---|---|---|---|---|---|---|---|
| 3-95 | -L-D | H | —CH2CH2— | SO2Me | H | 0 | phenyl | 2,6-diiodo-4-(1,2,2,2-tetrafluoro-1-trifluoromethyl-ethyl)-phenyl |
| 3-96 | -L-D | H | —CH2CH2— | SO2Me | H | 0 | 3-cyanophenyl | 2,6-diiodo-4-(1,2,2,2-tetrafluoro-1-trifluoromethyl-ethyl)-phenyl |
| 3-97 | -L-D | H | —CH2CH2— | SO2Me | H | 0 | 2-chloropyridin-3-yl | 2,6-diiodo-4-(1,2,2,2-tetrafluoro-1-trifluoromethyl-ethyl)-phenyl |
| 3-98 | -L-D | H | —CH2CH2— | SO2Me | H | 0 | 2-fluorophenyl | 2,6-diiodo-4-(1,2,2,2-tetrafluoro-1-trifluoromethyl-ethyl)-phenyl |
| 3-99 | -L-D | H | —CH2CH2— | SO2Me | H | 0 | phenyl | 2-bromo-6-trifluoromethyl-4-(1,2,2,2-tetrafluoro-1-trifluoromethyl-ethyl)-phenyl |
| 3-100 | -L-D | H | —CH2CH2— | SO2Me | H | 0 | 3-cyanophenyl | 2-bromo-6-trifluoromethyl-4-(1,2,2,2-tetrafluoro-1-trifluoromethyl-ethyl)-phenyl |
| 3-101 | -L-D | H | —CH2CH2— | SO2Me | H | 0 | 2-chloropyridin-3-yl | 2-bromo-6-trifluoromethyl-4-(1,2,2,2-tetrafluoro-1-trifluoromethyl-ethyl)-phenyl |
| 3-102 | -L-D | H | —CH2CH2— | SO2Me | H | 0 | 2-fluorophenyl | 2-bromo-6-trifluoromethyl-4-(1,2,2,2-tetrafluoro-1-trifluoromethyl-ethyl)-phenyl |
| 3-103 | -L-D | H | —CH2CH2— | SO2Me | H | 0 | phenyl | 2-iodo-6-trifluoromethyl-4-(1,2,2,2-tetrafluoro-1-trifluoromethyl-ethyl)-phenyl |
| 3-104 | -L-D | H | —CH2CH2— | SO2Me | H | 0 | 3-cyanophenyl | 2-iodo-6-trifluoromethyl-4-(1,2,2,2-tetrafluoro-1-trifluoromethyl-ethyl)-phenyl |
| 3-105 | -L-D | H | —CH2CH2— | SO2Me | H | 0 | 2-chloropyridin-3-yl | 2-iodo-6-trifluoromethyl-4-(1,2,2,2-tetrafluoro-1-trifluoromethyl-ethyl)-phenyl |
| 3-106 | -L-D | H | —CH2CH2— | SO2Me | H | 0 | 2-fluorophenyl | 2-iodo-6-trifluoromethyl-4-(1,2,2,2-tetrafluoro-1-trifluoromethyl-ethyl)-phenyl |
| 3-107 | -L-D | H | —CH2CH2— | SO2Me | H | 0 | phenyl | 2,6-dibromo-4-(1,2,2,3,3,3-hexafluoro-1-trifluoromethyl-propyl)-phenyl |
| 3-108 | -L-D | H | —CH2CH2— | SO2Me | H | 0 | 3-cyanophenyl | 2,6-dibromo-4-(1,2,2,3,3,3-hexafluoro-1-trifluoromethyl-propyl)-phenyl |
| 3-109 | -L-D | H | —CH2CH2— | SO2Me | H | 0 | 2-chloropyridin-3-yl | 2,6-dibromo-4-(1,2,2,3,3,3-hexafluoro-1-trifluoromethyl-propyl)-phenyl |
| 3-110 | -L-D | H | —CH2CH2— | SO2Me | H | 0 | 2-fluorophenyl | 2,6-dibromo-4-(1,2,2,3,3,3-hexafluoro-1-trifluoromethyl-propyl)-phenyl |
| 3-111 | -L-D | H | —CH2CH2— | SO2Me | H | 0 | phenyl | 2,6-diiodo-4-(1,2,2,3,3,3-hexafluoro-1-trifluoromethyl-propyl)-phenyl |
| 3-112 | -L-D | H | —CH2CH2— | SO2Me | H | 0 | 3-cyanophenyl | 2,6-diiodo-4-(1,2,2,3,3,3-hexafluoro-1-trifluoromethyl-propyl)-phenyl |
| 3-113 | -L-D | H | —CH2CH2— | SO2Me | H | 0 | 2-chloropyridin-3-yl | 2,6-diiodo-4-(1,2,2,3,3,3-hexafluoro-1-trifluoromethyl-propyl)-phenyl |
| 3-114 | -L-D | H | —CH2CH2— | SO2Me | H | 0 | 2-fluorophenyl | 2,6-diiodo-4-(1,2,2,3,3,3-hexafluoro-1-trifluoromethyl-propyl)-phenyl |
| 3-115 | -L-D | H | —CH2CH2— | SO2Me | H | 0 | phenyl | 2-bromo-6-trifluoromethyl-4-(1,2,2,3,3,3-hexafluoro-1-trifluoromethyl-propyl)-phenyl |
| 3-116 | -L-D | H | —CH2CH2— | SO2Me | H | 0 | 3-cyanophenyl | 2-bromo-6-trifluoromethyl-4-(1,2,2,3,3,3-hexafluoro-1-trifluoromethyl-propyl)-phenyl |
| 3-117 | -L-D | H | —CH2CH2— | SO2Me | H | 0 | 2-chloropyridin-3-yl | 2-bromo-6-trifluoromethyl-4-(1,2,2,3,3,3-hexafluoro-1-trifluoromethyl-propyl)-phenyl |
| 3-118 | -L-D | H | —CH2CH2— | SO2Me | H | 0 | 2-fluorophenyl | 2-bromo-6-trifluoromethyl-4-(1,2,2,3,3,3-hexafluoro-1-trifluoromethyl-propyl)-phenyl |
| 3-119 | -L-D | H | —CH2CH2— | SO2Me | H | 0 | phenyl | 2-iodo-6-trifluoromethyl-4-(1,2,2,3,3,3-hexafluoro-1-trifluoromethyl-propyl)-phenyl |
| 3-120 | -L-D | H | —CH2CH2— | SO2Me | H | 0 | 3-cyanophenyl | 2-iodo-6-trifluoromethyl-4-(1,2,2,3,3,3-hexafluoro-1-trifluoromethyl-propyl)-phenyl |
| 3-121 | -L-D | H | —CH2CH2— | SO2Me | H | 0 | 2-chloropyridin-3-yl | 2-iodo-6-trifluoromethyl-4-(1,2,2,3,3,3-hexafluoro-1-trifluoromethyl-propyl)-phenyl |
| 3-122 | -L-D | H | —CH2CH2— | SO2Me | H | 0 | 2-fluorophenyl | 2-iodo-6-trifluoromethyl-4-(1,2,2,3,3,3-hexafluoro-1-trifluoromethyl-propyl)-phenyl |
| 3-123 | -L-D | H | —CH2CH2— | SO2Me | 2-F | 1 | 4-cyanophenyl | 2,6-dibromo-4-pentafluoroethyl-phenyl |
| 3-124 | -L-D | H | —CH2CH2— | SO2Me | 2-F | 1 | 4-cyanophenyl | 2,6-diiodo-4-pentafluoroethyl-phenyl |
| 3-125 | -L-D | H | —CH2CH2— | SO2Me | 2-F | 1 | 4-cyanophenyl | 2-bromo-6-trifluoromethyl-4-pentafluoroethyl-phenyl |
| 3-126 | -L-D | H | —CH2CH2— | SO2Me | 2-F | 1 | 4-cyanophenyl | 2-iodo-6-trifluoromethyl-4-pentafluoroethyl-phenyl |

TABLE 3-continued

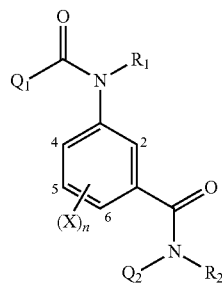

| compound number | $R_1$ | $R_2$ | L | D | X | n | $Q_1$ | $Q_2$ |
|---|---|---|---|---|---|---|---|---|
| 3-127 | -L-D | H | —CH2CH2— | SO2Me | 2-F | 1 | 4-cyanophenyl | 2-chloro-6-methyl-4-(1,2,2,2-tetrafluoro-1-trifluoromethyl-ethyl)-phenyl |
| 3-128 | -L-D | H | —CH2CH2— | SO2Me | 2-F | 1 | 4-cyanophenyl | 2-bromo-6-methyl-4-(1,2,2,2-tetrafluoro-1-trifluoromethyl-ethyl)-phenyl |
| 3-129 | -L-D | H | —CH2CH2— | SO2Me | 2-F | 1 | 4-cyanophenyl | 2-iodo-6-methyl-4-(1,2,2,2-tetrafluoro-1-trifluoromethyl-ethyl)-phenyl |
| 3-130 | -L-D | H | —CH2CH2— | SO2Me | 2-F | 1 | 4-cyanophenyl | 2-bromo-6-ethyl-4-(1,2,2,2-tetrafluoro-1-trifluoromethyl-ethyl)-phenyl |
| 3-131 | -L-D | H | —CH2CH2— | SO2Me | 2-F | 1 | 4-cyanophenyl | 2-iodo-6-ethyl-4-(1,2,2,2-tetrafluoro-1-trifluoromethyl-ethyl)-phenyl |
| 3-132 | -L-D | H | —CH2CH2— | SO2Me | 2-F | 1 | 4-cyanophenyl | 2,6-dichloro-4-(1,2,2,2-tetrafluoro-1-trifluoromethyl-ethyl)-phenyl |
| 3-133 | -L-D | H | —CH2CH2— | SO2Me | 2-F | 1 | 4-cyanophenyl | 2,6-dibromo-4-(1,2,2,2-tetrafluoro-1-trifluoromethyl-ethyl)-phenyl |
| 3-134 | -L-D | H | —CH2CH2— | SO2Me | 2-F | 1 | 4-cyanophenyl | 2,6-diiodo-4-(1,2,2,2-tetrafluoro-1-trifluoromethyl-ethyl)-phenyl |
| 3-135 | -L-D | H | —CH2CH2— | SO2Me | 2-F | 1 | 4-cyanophenyl | 2,6-ditrifluoromethyl-4-(1,2,2,2-tetrafluoro-1-trifluoromethyl-ethyl)-phenyl |
| 3-136 | -L-D | H | —CH2CH2— | SO2Me | 2-F | 1 | 4-cyanophenyl | 2-bromo-6-trifluoromethyl-4-(1,2,2,2-tetrafluoro-1-trifluoromethyl-ethyl)-phenyl |
| 3-137 | -L-D | H | —CH2CH2— | SO2Me | 2-F | 1 | 4-cyanophenyl | 2-iodo-6-trifluoromethyl-4-(1,2,2,2-tetrafluoro-1-trifluoromethyl-ethyl)-phenyl |
| 3-138 | -L-D | H | —CH2CH2— | SO2Me | 2-F | I | 4-cyanophenyl | 2-bromo-6-trifluoromethoxy-4-(1,2,2,2-tetrafluoro-1-trifluoromethyl-ethyl)-phenyl |
| 3-139 | -L-D | H | —CH2CH2— | SO2Me | 2-F | 1 | 4-cyanophenyl | 2-bromo-6-iodo-4-(1,2,2,2-tetrafluoro-1-trifluoromethyl-ethyl)-phenyl |
| 3-140 | -L-D | H | —CH2CH2— | SO2Me | 2-F | 1 | 4-cyanophenyl | 2-bromo-6-trifluoromethylthio-4-(1,2,2,2-tetrafluoro-1-trifluoromethyl-ethyl)-phenyl |
| 3-141 | -L-D | H | —CH2CH2— | SO2Me | 2-F | 1 | 4-cyanophenyl | 2-bromo-6-trifluoromethylsulfinyl-4-(1,2,2,2-tetrafluoro-1-trifluoromethyl-ethyl)-phenyl |
| 3-142 | -L-D | H | —CH2CH2— | SO2Me | 2-F | 1 | 4-cyanophenyl | 2-bromo-6-trifluoromethylsulfonyl-4-(1,2,2,2-tetrafluoro-1-trifluoromethyl-ethyl)-phenyl |
| 3-143 | -L-D | H | —CH2CH2— | SO2Me | 2-F | 1 | 4-cyanophenyl | 2-bromo-6-pentafluoroethyl-4-(1,2,2,2-tetrafluoro-1-trifluoromethyl-ethyl)-phenyl |
| 3-144 | -L-D | H | —CH2CH2— | SO2Me | 2-F | 1 | 4-cyanophenyl | 2-iodo-6-pentafluoroethyl-4-(1,2,2,2-tetrafluoro-1-trifluoromethyl-ethyl)-phenyl |
| 3-145 | -L-D | H | —CH2CH2— | SO2Me | 2-F | 1 | 4-cyanophenyl | 2-chloro-6-methyl-4-(1,2,2,3,3,3-hexafluoro-1-trifluoromethyl-propyl)-phenyl |
| 3-146 | -L-D | H | —CH2CH2— | SO2Me | 2-F | 1 | 4-cyanophenyl | 2-bromo-6-methyl-4-(1,2,2,3,3,3-hexafluoro-1-trifluoromethyl-propyl)-phenyl |
| 3-147 | -L-D | H | —CH2CH2— | SO2Me | 2-F | 1 | 4-cyanophenyl | 2-iodo-6-methyl-4-(1,2,2,3,3,3-hexafluoro-1-trifluoromethyl-propyl)-phenyl |
| 3-148 | -L-D | H | —CH2CH2— | SO2Me | 2-F | 1 | 4-cyanophenyl | 2-bromo-6-ethyl-4-(1,2,2,3,3,3-hexafluoro-1-trifluoromethyl-propyl)-phenyl |
| 3-149 | -L-D | H | —CH2CH2— | SO2Me | 2-F | 1 | 4-cyanophenyl | 2-iodo-6-ethyl-4-(1,2,2,3,3,3-hexafluoro-1-trifluoromethyl-propyl)-phenyl |
| 3-150 | -L-D | H | —CH2CH2— | SO2Me | 2-F | 1 | 4-cyanophenyl | 2,6-dichloro-4-(1,2,2,3,3,3-hexafluoro-1-trifluoromethyl-propyl)-phenyl |
| 3-151 | -L-D | H | —CH2CH2— | SO2Me | 2-F | 1 | 4-cyanophenyl | 2,6-dibromo-4-(1,2,2,3,3,3-hexafluoro-1-trifluoromethyl-propyl)-phenyl |
| 3-152 | -L-D | H | —CH2CH2— | SO2Me | 2-F | 1 | 4-cyanophenyl | 2,6-diiodo-4-(1,2,2,3,3,3-hexafluoro-1-trifluoromethyl-propyl)-phenyl |
| 3-153 | -L-D | H | —CH2CH2— | SO2Me | 2-F | 1 | 4-cyanophenyl | 2,6-ditrifluoromethyl-4-(1,2,2,3,3,3-hexafluoro-1-trifluoromethyl-propyl)-phenyl |
| 3-154 | -L-D | H | —CH2CH2— | SO2Me | 2-F | 1 | 4-cyanophenyl | 2-bromo-6-trifluoromethyl-4-(1,2,2,3,3,3-hexafluoro-1-trifluoromethyl-propyl)-phenyl |
| 3-155 | -L-D | H | —CH2CH2— | SO2Me | 2-F | 1 | 4-cyanophenyl | 2-iodo-6-trifluoromethyl-4-(1,2,2,3,3,3-hexafluoro-1-trifluoromethyl-propyl)-phenyl |
| 3-156 | -L-D | H | —CH2CH2— | SO2Me | 2-F | 1 | 4-cyanophenyl | 2-bromo-6-trifluoromethoxy-4-(1,2,2,3,3,3-hexafluoro-1-trifluoromethyl-propyl)-phenyl |
| 3-157 | -L-D | H | —CH2CH2— | SO2Me | 2-F | 1 | 4-cyanophenyl | 2-bromo-6-iodo-4-(1,2,2,3,3,3-hexafluoro-1-trifluoromethyl-propyl)-phenyl |

TABLE 3-continued

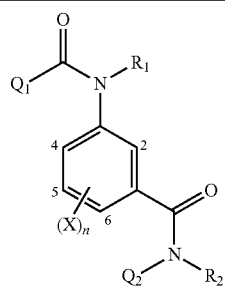

| compound number | $R_1$ | $R_2$ | L | D | X | n | $Q_1$ | $Q_2$ |
|---|---|---|---|---|---|---|---|---|
| 3-158 | -L-D | H | —CH2CH2— | SO2Me | 2-F | 1 | 4-cyanophenyl | 2-bromo-6-trifluoromethylthio-4-(1,2,2,3,3,3-hexafluoro-1-trifluoromethyl-propyl)-phenyl |
| 3-159 | -L-D | H | —CH2CH2— | SO2Me | 2-F | 1 | 4-cyanophenyl | 2-bromo-6-trifluoromethylsulfinyl-4-(1,2,2,3,3,3-hexafluoro-1-trifluoromethyl-propyl)-phenyl |
| 3-160 | -L-D | H | —CH2CH2— | SO2Me | 2-F | 1 | 4-cyanophenyl | 2-bromo-6-trifluoromethylsulfonyl-4-(1,2,2,3,3,3-hexafluoro-1-trifluoromethyl-propyl)-phenyl |
| 3-161 | -L-D | H | —CH2CH2— | SO2Me | 2-F | 1 | 4-cyanophenyl | 2-bromo-6-pentafluoroethyl-4-(1,2,2,3,3,3-hexafluoro-1-trifluoromethyl-propyl)-phenyl |
| 3-162 | -L-D | H | —CH2CH2— | SO2Me | 2-F | 1 | 4-cyanophenyl | 2-iodo-6-pentafluoroethyl-4-(1,2,2,3,3,3-hexafluoro-1-trifluoromethyl-propyl)-phenyl |
| 3-163 | -L-D | H | —CH2CH2— | SO2Me | 2-F | 1 | phenyl | 2,6-dibromo-4-(1,2,2,2-tetrafluoro-1-trifluoromethyl-ethyl)-phenyl |
| 3-164 | -L-D | H | —CH2CH2— | SO2Me | 2-F | 1 | 3-cyanophenyl | 2,6-dibromo-4-(1,2,2,2-tetrafluoro-1-trifluoromethyl-ethyl)-phenyl |
| 3-165 | -L-D | H | —CH2CH2— | SO2Me | 2-F | 1 | 2-chloropyridin-3-yl | 2,6-dibromo-4-(1,2,2,2-tetrafluoro-1-trifluoromethyl-ethyl)-phenyl |
| 3-166 | -L-D | H | —CH2CH2— | SO2Me | 2-F | 1 | 2-fluorophenyl | 2,6-dibromo-4-(1,2,2,2-tetrafluoro-1-trifluoromethyl-ethyl)-phenyl |
| 3-167 | -L-D | H | —CH2CH2— | SO2Me | 2-F | 1 | phenyl | 2,6-diiodo-4-(1,2,2,2-tetrafluoro-1-trifluoromethyl-ethyl)-phenyl |
| 3-168 | -L-D | H | —CH2CH2— | SO2Me | 2-F | 1 | 3-cyanophenyl | 2,6-diiodo-4-(1,2,2,2-tetrafluoro-1-trifluoromethyl-ethyl)-phenyl |
| 3-169 | -L-D | H | —CH2CH2— | SO2Me | 2-F | 1 | 2-chloropyridin-3-yl | 2,6-diiodo-4-(1,2,2,2-tetrafluoro-1-trifluoromethyl-ethyl)-phenyl |
| 3-170 | -L-D | H | —CH2CH2— | SO2Me | 2-F | 1 | 2-fluorophenyl | 2,6-diiodo-4-(1,2,2,2-tetrafluoro-1-trifluoromethyl-ethyl)-phenyl |
| 3-171 | -L-D | H | —CH2CH2— | SO2Me | 2-F | 1 | phenyl | 2-bromo-6-trifluoromethyl-4-(1,2,2,2-tetrafluoro-1-trifluoromethyl-ethyl)-phenyl |
| 3-172 | -L-D | H | —CH2CH2— | SO2Me | 2-F | 1 | 3-cyanophenyl | 2-bromo-6-trifluoromethyl-4-(1,2,2,2-tetrafluoro-1-trifluoromethyl-ethyl)-phenyl |
| 3-173 | -L-D | H | —CH2CH2— | SO2Me | 2-F | 1 | 2-chloropyridin-3-yl | 2-bromo-6-trifluoromethyl-4-(1,2,2,2-tetrafluoro-1-trifluoromethyl-ethyl)-phenyl |
| 3-174 | -L-D | H | —CH2CH2— | SO2Me | 2-F | 1 | 2-fluorophenyl | 2-bromo-6-trifluoromethyl-4-(1,2,2,2-tetrafluoro-1-trifluoromethyl-ethyl)-phenyl |
| 3-175 | -L-D | H | —CH2CH2— | SO2Me | 2-F | 1 | phenyl | 2-iodo-6-trifluoromethyl-4-(1,2,2,2-tetrafluoro-1-trifluoromethyl-ethyl)-phenyl |
| 3-176 | -L-D | H | —CH2CH2— | SO2Me | 2-F | 1 | 3-cyanophenyl | 2-iodo-6-trifluoromethyl-4-(1,2,2,2-tetrafluoro-1-trifluoromethyl-ethyl)-phenyl |
| 3-177 | -L-D | H | —CH2CH2— | SO2Me | 2-F | 1 | 2-chloropyridin-3-yl | 2-iodo-6-trifluoromethyl-4-(1,2,2,2-tetrafluoro-1-trifluoromethyl-ethyl)-phenyl |
| 3-178 | -L-D | H | —CH2CH2— | SO2Me | 2-F | 1 | 2-fluorophenyl | 2-iodo-6-trifluoromethyl-4-(1,2,2,2-tetrafluoro-1-trifluoromethyl-ethyl)-phenyl |
| 3-179 | -L-D | H | —CH2CH2— | SO2Me | 2-F | 1 | phenyl | 2,6-dibromo-4-(1,2,2,3,3,3-hexafluoro-1-trifluoromethyl-propyl)-phenyl |
| 3-180 | -L-D | H | —CH2CH2— | SO2Me | 2-F | 1 | 3-cyanophenyl | 2,6-dibromo-4-(1,2,2,3,3,3-hexafluoro-1-trifluoromethyl-propyl)-phenyl |
| 3-181 | -L-D | H | —CH2CH2— | SO2Me | 2-F | 1 | 2-chloropyridin-3-yl | 2,6-dibromo-4-(1,2,2,3,3,3-hexafluoro-1-trifluoromethyl-propyl)-phenyl |
| 3-182 | -L-D | H | —CH2CH2— | SO2Me | 2-F | 1 | 2-fluorophenyl | 2,6-dibromo-4-(1,2,2,3,3,3-hexafluoro-1-trifluoromethyl-propyl)-phenyl |
| 3-183 | -L-D | H | —CH2CH2— | SO2Me | 2-F | 1 | phenyl | 2,6-diiodo-4-(1,2,2,3,3,3-hexafluoro-1-trifluoromethyl-propyl)-phenyl |
| 3-164 | -L-D | H | —CH2CH2— | SO2Me | 2-F | 1 | 3-cyanophenyl | 2,6-diiodo-4-(1,2,2,3,3,3-hexafluoro-1-trifluoromethyl-propyl)-phenyl |
| 3-185 | -L-D | H | —CH2CH2— | SO2Me | 2-F | 1 | 2-chloropyridin-3-yl | 2,6-diiodo-4-(1,2,2,3,3,3-hexafluoro-1-trifluoromethyl-propyl)-phenyl |
| 3-186 | -L-D | H | —CH2CH2— | SO2Me | 2-F | 1 | 2-fluorophenyl | 2,6-diiodo-4-(1,2,2,3,3,3-hexafluoro-1-trifluoromethyl-propyl)-phenyl |
| 3-187 | -L-D | H | —CH2CH2— | SO2Me | 2-F | 1 | phenyl | 2-bromo-6-trifluoromethyl-4-(1,2,2,3,3,3-hexafluoro-1-trifluoromethyl-propyl)-phenyl |
| 3-188 | -L-D | H | —CH2CH2— | SO2Me | 2-F | 1 | 3-cyanophenyl | 2-bromo-6-trifluoromethyl-4-(1,2,2,3,3,3-hexafluoro-1-trifluoromethyl-propyl)-phenyl |

TABLE 3-continued

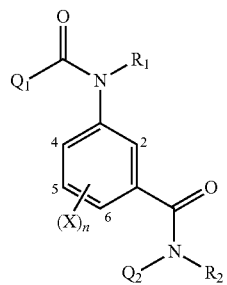

| compound number | R₁ | R₂ | L | D | X | n | Q₁ | Q₂ |
|---|---|---|---|---|---|---|---|---|
| 3-189 | -L-D | H | —CH2CH2— | SO2Me | 2-F | 1 | 2-chloropyridin-3-yl | 2-bromo-6-trifluoromethyl-4-(1,2,2,3,3,3-hexafluoro-1-trifluoromethyl-propyl)-phenyl |
| 3-190 | -L-D | H | —CH2CH2— | SO2Me | 2-F | 1 | 2-fluorophenyl | 2-bromo-6-trifluoromethyl-4-(1,2,2,3,3,3-hexafluoro-1-trifluoromethyl-propyl)-phenyl |
| 3-191 | -L-D | H | —CH2CH2— | SO2Me | 2-F | 1 | phenyl | 2-iodo-6-trifluoromethyl-4-(1,2,2,3,3,3-hexafluoro-1-trifluoromethyl-propyl)-phenyl |
| 3-192 | -L-D | H | —CH2CH2— | SO2Me | 2-F | 1 | 3-cyanophenyl | 2-iodo-6-trifluoromethyl-4-(1,2,2,3,3,3-hexafluoro-1-trifluoromethyl-propyl)-phenyl |
| 3-193 | -L-D | H | —CH2CH2— | SO2Me | 2-F | 1 | 2-chloropyridin-3-yl | 2-iodo-6-trifluoromethyl-4-(1,2,2,3,3,3-hexafluoro-1-trifluoromethyl-propyl)-phenyl |
| 3-194 | -L-D | H | —CH2CH2— | SO2Me | 2-F | 1 | 2-fluorophenyl | 2-iodo-6-trifluoromethyl-4-(1,2,2,3,3,3-hexafluoro-1-trifluoromethyl-propyl)-phenyl |
| 3-195 | -L-D | H | —CH2CH2— | SO2Me | H | 0 | 6-chloropyridin-3-yl | 2-bromo-6-trifluoromethyl-4-(1,2,2,2-tetrafluoro-1-trifluoromethyl-ethyl)-phenyl |
| 3-196 | -L-D | H | —CH2CH2— | SO2Me | 2-F | 1 | 6-chloropyridin-3-yl | 2-bromo-6-trifluoromethyl-4-(1,2,2,2-tetrafluoro-1-trifluoromethyl-ethyl)-phenyl |
| 3-197 | -L-D | H | —CH2CH2— | SO2Me | 2-F | 1 | 6-chloropyridin-3-yl | 2,6-dibromo-4-(1,2,2,2-tetrafluoro-1-trifluoromethyl-ethyl)-phenyl |
| 3-198 | -L-D | H | —CH2CH2— | SO2Me | 2-F | 1 | 3,5-dicyanophenyl | 2-bromo-6-trifluoromethyl-4-(1,2,2,2-tetrafluoro-1-trifluoromethyl-ethyl)-phenyl |
| 3-199 | -L-D | H | —CH2CH2— | SO2Me | 2-F | 1 | 3,5-dicyanophenyl | 2,6-dibromo-4-(1,2,2,2-tetrafluoro-1-trifluoromethyl-ethyl)-phenyl |
| 3-200 | -L-D | H | —CH2CH2— | SO2Me | 2-F | 1 | pyridin-3-yl | 2,6-dibromo-4-(1,2,2,2-tetrafluoro-1-trifluoromethyl-ethyl)-phenyl |
| 3-201 | -L-D | H | —CH2CH2— | SO2Me | 2-F | 1 | pyridin-4-yl | 2,6-dibromo-4-(1,2,2,2-tetrafluoro-1-trifluoromethyl-ethyl)-phenyl |
| 3-202 | -L-D | H | —CH2CH2— | SO2Me | 2-F | 1 | 2-chloropyridin-4-yl | 2,6-dibromo-4-(1,2,2,2-tetrafluoro-1-trifluoromethyl-ethyl)-phenyl |
| 3-203 | -L-D | H | —CH2CH2— | SO2Me | 2-F | 1 | pyrazin-2-yl | 2,6-dibromo-4-(1,2,2,2-tetrafluoro-1-trifluoromethyl-ethyl)-phenyl |
| 3-204 | -L-D | H | —CH2CH2— | SO2Me | 2-F | 1 | pyrimidin-5-yl | 2,6-dibromo-4-(1,2,2,2-tetrafluoro-1-trifluoromethyl-ethyl)-phenyl |
| 3-205 | -L-D | H | —CH2CH2— | SO2Me | 2-F | 1 | 3-cyanophenyl | 2,6-dichloro-4-(1,2,2,2-tetrafluoro-1-trifluoromethyl-ethyl)-phenyl |
| 3-206 | -L-D | H | —CH2CH2— | SO2Me | 2-F | 1 | phenyl | 2,6-dichloro-4-(1,2,2,2-tetrafluoro-1-trifluoromethyl-ethyl)-phenyl |
| 3-207 | -L-D | H | —CH2CH2— | SO2Me | 2-F | 1 | 2-chloropyridin-3-yl | 2,6-dichloro-4-(1,2,2,2-tetrafluoro-1-trifluoromethyl-ethyl)-phenyl |
| 3-208 | -L-D | H | —CH2CH2— | SO2Me | 2-F | 1 | 6-cyanopyridin-3-yl | 2,6-dibromo-4-(1,2,2,2-tetrafluoro-1-trifluoromethyl-ethyl)-phenyl |
| 3-209 | -L-D | H | —CH2CH2— | SO2Me | 2-F | 1 | 4-fluorophenyl | 2,6-dibromo-4-(1,2,2,2-tetrafluoro-1-trifluoromethyl-ethyl)-phenyl |
| 3-210 | -L-D | H | —CH2CH2— | SO2Me | 2-F | 1 | 2,6-difluorophenyl | 2,6-dibromo-4-(1,2,2,2-tetrafluoro-1-trifluoromethyl-ethyl)-phenyl |
| 3-211 | -L-D | H | —CH2CH2— | SO2Me | 2-F | 1 | 2-chloropyridin-3-yl | 2-bromo-6-iodo-4-(1,2,2,2-tetrafluoro-1-trifluoromethyl-ethyl)-phenyl |
| 3-212 | -L-D | H | —CH2CH2— | SO2Me | 2-F | 1 | phenyl | 2-bromo-6-iodo-4-(1,2,2,2-tetrafluoro-1-trifluoromethyl-ethyl)-phenyl |
| 3-213 | -L-D | H | —CH2CH2— | SO2Me | 2-F | 1 | 6-chloropyridin-3-yl | 2,6-dibromo-4-(1,2,2,3,3,3-hexafluoro-1-trifluoromethyl-propyl)-phenyl |
| 3-214 | -L-D | H | —CH2CH2— | SO2Me | 2-F | 1 | phenyl | 2,6-dimethyl-4-(1,2,2,3,3,3-hexafluoro-1-trifluoromethyl-propyl)-phenyl |
| 3-215 | -L-D | H | —CH2CH2— | SO2Me | 2-F | 1 | 4-cyanophenyl | 2,6-dimethyl-4-(1,2,2,3,3,3-hexafluoro-1-trifluoromethyl-propyl)-phenyl |
| 3-216 | -L-D | H | —CH2CH2— | SO2Me | 2-F | 1 | 3-cyanophenyl | 2,6-dimethyl-4-(1,2,2,3,3,3-hexafluoro-1-trifluoromethyl-propyl)-phenyl |
| 3-217 | -L-D | H | —CH2CH2— | SO2Me | 4-F | 1 | phenyl | 2,6-dibromo-4-(1,2,2,2-tetrafluoro-1-trifluoromethyl-ethyl) phenyl |
| 3-218 | -L-D | H | —CH2CH2— | SO2Me | 4-F | 1 | 4-cyanophenyl | 2-bromo-6-trifluoromethyl-4-(1,2,2,2-tetrafluoro-1-trifluoromethyl-ethyl)-phenyl |
| 3-219 | -L-D | H | —CH2CH2— | SO2Me | 4-F | 1 | 3-cyanophenyl | 2-iodo-6-trifluoromethyl-4-(1,2,2,2-tetrafluoro-1-trifluoromethyl-ethyl)-phenyl |

TABLE 3-continued

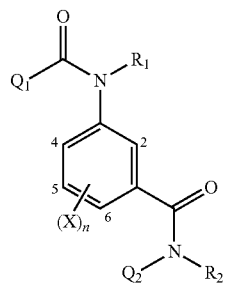

| compound number | R$_1$ | R$_2$ | L | D | X | n | Q$_1$ | Q$_2$ |
|---|---|---|---|---|---|---|---|---|
| 3-220 | -L-D | H | —CH2CH2— | SO2Me | 4-F | 1 | 2-chloropyridin-3-yl | 2-bromo-6-trifluoromethyl-4-(1,2,2,3,3,3-hexafluoro-1-trifluoromethyl-propyl)-phenyl |
| 3-221 | -L-D | H | —CH2CH2— | SO2Me | 4-F | 1 | 2-fluorophenyl | 2-iodo-6-trifluoromethyl-4-(1,2,2,3,3,3-hexafluoro-1-trifluoromethyl-propyl)-phenyl |
| 3-222 | -L-D | H | —CH2CH2— | SO2Me | 4-CN | 1 | phenyl | 2,6-dibromo-4-(1,2,2,2-tetrafluoro-1-trifluoromethyl-ethyl)-phenyl |
| 3-223 | -L-D | H | —CH2CH2— | SO2Me | 4-CN | 1 | 4-cyanophenyl | 2-bromo-6-trifluoromethyl-4-(1,2,2,2-tetrafluoro-1-trifluoromethyl-ethyl)-phenyl |
| 3-224 | -L-D | H | —CH2CH2— | SO2Me | 4-CN | 1 | 3-cyanophenyl | 2-iodo-6-trifluoromethyl-4-(1,2,2,2-tetrafluoro-1-trifluoromethyl-ethyl)-phenyl |
| 3-225 | -L-D | H | —CH2CH2— | SO2Me | 4-CN | 1 | 2-chloropyridin-3-yl | 2-bromo-6-trifluoromethyl-4-(1,2,2,3,3,3-hexafluoro-1-trifluoromethyl-propyl)-phenyl |
| 3-226 | -L-D | H | —CH2CH2— | SO2Me | 4-CN | 1 | 2-fluorophenyl | 2-iodo-6-trifluoromethyl-4-(1,2,2,3,3,3-hexafluoro-1-trifluoromethyl-propyl)-phenyl |
| 3-227 | -L-D | H | —CH2CH2— | SO2Me | 2-NO2 | 1 | phenyl | 2,6-dibromo-4-(1,2,2,2-tetrafluoro-1-trifluoromethyl-ethyl)-phenyl |
| 3-228 | -L-D | H | —CH2CH2— | SO2Me | 2-NO2 | 1 | 4-cyanophenyl | 2-bromo-6-trifluoromethyl-4-(1,2,2,2-tetrafluoro-1-trifluoromethyl-ethyl)-phenyl |
| 3-229 | -L-D | H | —CH2CH2— | SO2Me | 2-NO2 | 1 | 3-cyanophenyl | 2-iodo-6-trifluoromethyl-4-(1,2,2,2-tetrafluoro-1-trifluoromethyl-ethyl)-phenyl |
| 3-230 | -L-D | H | —CH2CH2— | SO2Me | 2-NO2 | 1 | 2-chloropyridin-3-yl | 2-bromo-6-trifluoromethyl-4-(1,2,2,3,3,3-hexafluoro-1-trifluoromethyl-propyl)-phenyl |
| 3-231 | -L-D | H | —CH2CH2— | SO2Me | 2-NO2 | 1 | 2-fluorophenyl | 2-iodo-6-trifluoromethyl-4-(1,2,2,3,3,3-hexafluoro-1-trifluoromethyl-propyl)-phenyl |

TABLE 4

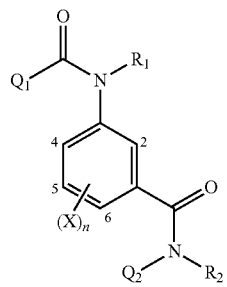

| compound number | R$_1$ | R$_2$ | L | D | X | n | Q$_1$ | Q$_2$ |
|---|---|---|---|---|---|---|---|---|
| 4-1 | -L-D | H | —CH2CH2— | SOMe | H | 0 | phenyl | 2,6-dimethyl-4-(1,2,2,2-tetrafluoro-1-trifluoromethyl-ethyl)-phenyl |
| 4-2 | -L-D | H | —CH2CH2— | SOMe | H | 0 | 4-cyanophenyl | 2,6-dimethyl-4-(1,2,2,2-tetrafluoro-1-trifluoromethyl-ethyl)-phenyl |
| 4-3 | -L-D | H | —CH2CH2— | SOMe | H | 0 | 3-cyanophenyl | 2,6-dimethyl-4-(1,2,2,2-tetrafluoro-1-trifluoromethyl-ethyl)-phenyl |
| 4-4 | -L-D | H | —CH2CH2— | SOMe | H | 0 | 3,5-dicyanophenyl | 2,6-dimethyl-4-(1,2,2,2-tetrafluoro-1-trifluoromethyl-ethyl)-phenyl |
| 4-5 | -L-D | H | —CH2CH2— | SOMe | H | 0 | 2-fluorophenyl | 2,6-dimethyl-4-(1,2,2,2-tetrafluoro-1-trifluoromethyl-ethyl)-phenyl |
| 4-6 | -L-D | H | —CH2CH2— | SOMe | H | 0 | 4-fluorophenyl | 2,6-dimethyl-4-(1,2,2,2-tetrafluoro-1-trifluoromethyl-ethyl)-phenyl |
| 4-7 | -L-D | H | —CH2CH2— | SOMe | H | 0 | 2,6-difluorophenyl | 2,6-dimethyl-4-(1,2,2,2-tetrafluoro-1-trifluoromethyl-ethyl)-phenyl |
| 4-8 | -L-D | H | —CH2CH2— | SOMe | H | 0 | 2-fluoro-4-cyanophenyl | 2,6-dimethyl-4-(1,2,2,2-tetrafluoro-1-trifluoromethyl-ethyl)-phenyl |

TABLE 4-continued

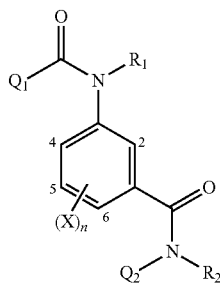

| compound number | R₁ | R₂ | L | D | X | n | Q₁ | Q₂ |
|---|---|---|---|---|---|---|---|---|
| 4-9 | -L-D | H | —CH2CH2— | SOMe | H | 0 | 2-chlorophenyl | 2,6-dimethyl-4-(1,2,2,2-tetrafluoro-1-trifluoromethyl-ethyl)-phenyl |
| 4-10 | -L-D | H | —CH2CH2— | SOMe | H | 0 | 4-chlorophenyl | 2,6-dimethyl-4-(1,2,2,2-tetrafluoro-1-trifluoromethyl-ethyl)-phenyl |
| 4-11 | -L-D | H | —CH2CH2— | SOMe | H | 0 | 4-nitrophenyl | 2,6-dimethyl-4-(1,2,2,2-tetrafluoro-1-trifluoromethyl-ethyl)-phenyl |
| 4-12 | -L-D | H | —CH2CH2— | SOMe | H | 0 | 2-methylphenyl | 2,6-dimethyl-4-(1,2,2,2-tetrafluoro-1-trifluoromethyl-ethyl)-phenyl |
| 4-13 | -L-D | H | —CH2CH2— | SOMe | H | 0 | pyridin-2-yl | 2,6-dimethyl-4-(1,2,2,2-tetrafluoro-1-trifluoromethyl-ethyl)-phenyl |
| 4-14 | -L-D | H | —CH2CH2— | SOMe | H | 0 | pyridin-3-yl | 2,6-dimethyl-4-(1,2,2,2-tetrafluoro-1-trifluoromethyl-ethyl)-phenyl |
| 4-15 | -L-D | H | —CH2CH2— | SOMe | H | 0 | pyridin-4-yl | 2,6-dimethyl-4-(1,2,2,2-tetrafluoro-1-trifluoromethyl-ethyl)-phenyl |
| 4-16 | -L-D | H | —CH2CH2— | SOMe | H | 0 | 2-chloropyridin-3-yl | 2,6-dimethyl-4-(1,2,2,2-tetrafluoro-1-trifluoromethyl-ethyl)-phenyl |
| 4-17 | -L-D | H | —CH2CH2— | SOMe | H | 0 | 6-chloropyridin-3-yl | 2,6-dimethyl-4-(1,2,2,2-tetrafluoro-1-trifluoromethyl-ethyl)-phenyl |
| 4-18 | -L-D | H | —CH2CH2— | SOMe | H | 0 | 2-chloropyridin-4-yl | 2,6-dimethyl-4-(1,2,2,2-tetrafluoro-1-trifluoromethyl-ethyl)-phenyl |
| 4-19 | -L-D | H | —CH2CH2— | SOMe | H | 0 | pyrazin-2-yl | 2,6-dimethyl-4-(1,2,2,2-tetrafluoro-1-trifluoromethyl-ethyl)-phenyl |
| 4-20 | -L-D | H | —CH2CH2— | SOMe | H | 0 | pyrimidin-5-yl | 2,6-dimethyl-4-(1,2,2,2-tetrafluoro-1-trifluoromethyl-ethyl)-phenyl |
| 4-21 | -L-D | H | —CH2CH2— | SOMe | 2-F | 1 | phenyl | 2,6-dimethyl-4-(1,2,2,2-tetrafluoro-1-trifluoromethyl-ethyl)-phenyl |
| 4-22 | -L-D | H | —CH2CH2— | SOMe | 2-F | 1 | 4-cyanophenyl | 2,6-dimethyl-4-(1,2,2,2-tetrafluoro-1-trifluoromethyl-ethyl)-phenyl |
| 4-23 | -L-D | H | —CH2CH2— | SOMe | 2-F | 1 | 3-cyanophenyl | 2,6-dimethyl-4-(1,2,2,2-tetrafluoro-1-trifluoromethyl-ethyl)-phenyl |
| 4-24 | -L-D | H | —CH2CH2— | SOMe | 2-F | 1 | 3,5-dicyanophenyl | 2,6-dimethyl-4-(1,2,2,2-tetrafluoro-1-trifluoromethyl-ethyl)-phenyl |
| 4-25 | -L-D | H | —CH2CH2— | SOMe | 2-F | 1 | 2-fluorophenyl | 2,6-dimethyl-4-(1,2,2,2-tetrafluoro-1-trifluoromethyl-ethyl)-phenyl |
| 4-26 | -L-D | H | —CH2CH2— | SOMe | 2-F | 1 | 4-fluorophenyl | 2,6-dimethyl-4-(1,2,2,2-tetrafluoro-1-trifluoromethyl-ethyl)-phenyl |
| 4-27 | -L-D | H | —CH2CH2— | SOMe | 2-F | 1 | 2,6-difluorophenyl | 2,6-dimethyl-4-(1,2,2,2-tetrafluoro-1-trifluoromethyl-ethyl)-phenyl |
| 4-28 | -L-D | H | —CH2CH2— | SOMe | 2-F | 1 | 2-fluoro-4-cyanophenyl | 2,6-dimethyl-4-(1,2,2,2-tetrafluoro-1-trifluoromethyl-ethyl)-phenyl |
| 4-29 | -L-D | H | —CH2CH2— | SOMe | 2-F | 1 | 2-chlorophenyl | 2,6-dimethyl-4-(1,2,2,2-tetrafluoro-1-trifluoromethyl-ethyl)-phenyl |
| 4-30 | -L-D | H | —CH2CH2— | SOMe | 2-F | 1 | 4-chlorophenyl | 2,6-dimethyl-4-(1,2,2,2-tetrafluoro-1-trifluoromethyl-ethyl)-phenyl |
| 4-31 | -L-D | H | —CH2CH2— | SOMe | 2-F | 1 | 4-nitrophenyl | 2,6-dimethyl-4-(1,2,2,2-tetrafluoro-1-trifluoromethyl-ethyl)-phenyl |
| 4-32 | -L-D | H | —CH2CH2— | SOMe | 2-F | 1 | 2-methylphenyl | 2,6-dimethyl-4-(1,2,2,2-tetrafluoro-1-trifluoromethyl-ethyl)-phenyl |
| 4-33 | -L-D | H | —CH2CH2— | SOMe | 2-F | 1 | pyridin-2-yl | 2,6-dimethyl-4-(1,2,2,2-tetrafluoro-1-trifluoromethyl-ethyl)-phenyl |
| 4-34 | -L-D | H | —CH2CH2— | SOMe | 2-F | 1 | pyridin-3-yl | 2,6-dimethyl-4-(1,2,2,2-tetrafluoro-1-trifluoromethyl-ethyl)-phenyl |
| 4-35 | -L-D | H | —CH2CH2— | SOMe | 2-F | 1 | pyridin-4-yl | 2,6-dimethyl-4-(1,2,2,2-tetrafluoro-1-trifluoromethyl-ethyl)-phenyl |
| 4-36 | -L-D | H | —CH2CH2— | SOMe | 2-F | 1 | 2-chloropyridin-3-yl | 2,6-dimethyl-4-(1,2,2,2-tetrafluoro-1-trifluoromethyl-ethyl)-phenyl |
| 4-37 | -L-D | H | —CH2CH2— | SOMe | 2-F | 1 | 6-chloropyridin-3-yl | 2,6-dimethyl-4-(1,2,2,2-tetrafluoro-1-trifluoromethyl-ethyl)-phenyl |
| 4-38 | -L-D | H | —CH2CH2— | SOMe | 2-F | 1 | 2-chloropyridin-4-yl | 2,6-dimethyl-4-(1,2,2,2-tetrafluoro-1-trifluoromethyl-ethyl)-phenyl |
| 4-39 | -L-D | H | —CH2CH2— | SOMe | 2-F | 1 | pyrazin-2-yl | 2,6-dimethyl-4-(1,2,2,2-tetrafluoro-1-trifluoromethyl-ethyl)-phenyl |

TABLE 4-continued

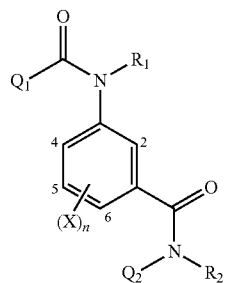

| compound number | R₁ | R₂ | L | D | X | n | Q₁ | Q₂ |
|---|---|---|---|---|---|---|---|---|
| 4-40 | -L-D | H | —CH2CH2— | SOMe | 2-F | 1 | pyrimidin-5-yl | 2,6-dimethyl-4-(1,2,2,2-tetrafluoro-1-trifluoromethyl-ethyl)-phenyl |
| 4-41 | -L-D | H | —CH2CH2— | SOMe | 4-F | 1 | phenyl | 2,6-dimethyl-4-(1,2,2,2-tetrafluoro-1-trifluoromethyl-ethyl)-phenyl |
| 4-42 | -L-D | H | —CH2CH2— | SOMe | 4-F | 1 | 4-cyanophenyl | 2,6-dimethyl-4-(1,2,2,2-tetrafluoro-1-trifluoromethyl-ethyl)-phenyl |
| 4-43 | -L-D | H | —CH2CH2— | SOMe | 4-F | 1 | 3-cyanophenyl | 2,6-dimethyl-4-(1,2,2,2-tetrafluoro-1-trifluoromethyl-ethyl)-phenyl |
| 4-44 | -L-D | H | —CH2CH2— | SOMe | 4-F | 1 | 2-chloropyridin-3-yl | 2,6-dimethyl-4-(1,2,2,2-tetrafluoro-1-trifluoromethyl-ethyl)-phenyl |
| 4-45 | -L-D | H | —CH2CH2— | SOMe | 4-F | 1 | 2-fluorophenyl | 2,6-dimethyl-4-(1,2,2,2-tetrafluoro-1-trifluoromethyl-ethyl)-phenyl |
| 4-46 | -L-D | H | —CH2CH2— | SOMe | 4-CN | 1 | phenyl | 2,6-dimethyl-4-(1,2,2,2-tetrafluoro-1-trifluoromethyl-ethyl)-phenyl |
| 4-47 | -L-D | H | —CH2CH2— | SOMe | 4-CN | 1 | 4-cyanophenyl | 2,6-dimethyl-4-(1,2,2,2-tetrafluoro-1-trifluoromethyl-ethyl)-phenyl |
| 4-48 | -L-D | H | —CH2CH2— | SOMe | 4-CN | 1 | 3-cyanophenyl | 2,6-dimethyl-4-(1,2,2,2-tetrafluoro-1-trifluoromethyl-ethyl)-phenyl |
| 4-49 | -L-D | H | —CH2CH2— | SOMe | 4-CN | 1 | 2-chloropyridin-3-yl | 2,6-dimethyl-4-(1,2,2,2-tetrafluoro-1-trifluoromethyl-ethyl)-phenyl |
| 4-50 | -L-D | H | —CH2CH2— | SOMe | 4-CN | 1 | 2-fluorophenyl | 2,6-dimethyl-4-(1,2,2,2-tetrafluoro-1-trifluoromethyl-ethyl)-phenyl |
| 4-51 | -L-D | H | —CH2CH2— | SOMe | H | 0 | 4-cyanophenyl | 2,6-dibromo-4-pentafluoroethyl-phenyl |
| 4-52 | -L-D | H | —CH2CH2— | SOMe | H | 0 | 4-cyanophenyl | 2,6-diiodo-4-pentafluoroethyl-phenyl |
| 4-53 | -L-D | H | —CH2CH2— | SOMe | H | 0 | 4-cyanophenyl | 2-bromo-6-trifluoromethyl-4-pentafluoroethyl-phenyl |
| 4-54 | -L-D | H | —CH2CH2— | SOMe | H | 0 | 4-cyanophenyl | 2-iodo-6-trifluoromethyl-4-pentafluoroethyl-phenyl |
| 4-55 | -L-D | H | —CH2CH2— | SOMe | H | 0 | 4-cyanophenyl | 2-chloro-6-methyl-4-(1,2,2,2-tetrafluoro-1-trifluoromethyl-ethyl)-phenyl |
| 4-56 | -L-D | H | —CH2CH2— | SOMe | H | 0 | 4-cyanophenyl | 2-bromo-6-methyl-4-(1,2,2,2-tetrafluoro-1-trifluoromethyl-ethyl)-phenyl |
| 4-57 | -L-D | H | —CH2CH2— | SOMe | H | 0 | 4-cyanophenyl | 2-iodo-6-methyl-4-(1,2,2,2-tetrafluoro-1-trifluoromethyl-ethyl)-phenyl |
| 4-58 | -L-D | H | —CH2CH2— | SOMe | H | 0 | 4-cyanophenyl | 2-bromo-6-ethyl-4-(1,2,2,2-tetrafluoro-1-trifluoromethyl-ethyl)-phenyl |
| 4-59 | -L-D | H | —CH2CH2— | SOMe | H | 0 | 4-cyanophenyl | 2-iodo-6-ethyl-4-(1,2,2,2-tetrafluoro-1-trifluoromethyl-ethyl)-phenyl |
| 4-60 | -L-D | H | —CH2CH2— | SOMe | H | 0 | 4-cyanophenyl | 2,6-dichloro-4-(1,2,2,2-tetrafluoro-1-trifluoromethyl-ethyl)-phenyl |
| 4-61 | -L-D | H | —CH2CH2— | SOMe | H | 0 | 4-cyanophenyl | 2,6-dibromo-4-(1,2,2,2-tetrafluoro-1-trifluoromethyl-ethyl)-phenyl |
| 4-62 | -L-D | H | —CH2CH2— | SOMe | H | 0 | 4-cyanophenyl | 2,6-diiodo-4-(1,2,2,2-tetrafluoro-1-trifluoromethyl-ethyl)-phenyl |
| 4-63 | -L-D | H | —CH2CH2— | SOMe | H | 0 | 4-cyanophenyl | 2,6-ditrifluoromethyl-4-(1,2,2,2-tetrafluoro-1-trifluoromethyl-ethyl)-phenyl |
| 4-64 | -L-D | H | —CH2CH2— | SOMe | H | 0 | 4-cyanophenyl | 2-bromo-6-trifluoromethyl-4-(1,2,2,2-tetrafluoro-1-trifluoromethyl-ethyl)-phenyl |
| 4-65 | -L-D | H | —CH2CH2— | SOMe | H | 0 | 4-cyanophenyl | 2-iodo-6-trifluoromethyl-4-(1,2,2,2-tetrafluoro-1-trifluoromethyl-ethyl)-phenyl |
| 4-66 | -L-D | H | —CH2CH2— | SOMe | H | 0 | 4-cyanophenyl | 2-bromo-6-trifluoromethoxy-4-(1,2,2,2-tetrafluoro-1-trifluoromethyl-ethyl)-phenyl |
| 4-67 | -L-D | H | —CH2CH2— | SOMe | H | 0 | 4-cyanophenyl | 2-bromo-6-iodo-4-(1,2,2,2-tetrafluoro-1-trifluoromethyl-ethyl)-phenyl |
| 4-68 | -L-D | H | —CH2CH2— | SOMe | H | 0 | 4-cyanophenyl | 2-bromo-6-trifluoromethylthio-4-(1,2,2,2-tetrafluoro-1-trifluoromethyl-ethyl)-phenyl |
| 4-69 | -L-D | H | —CH2CH2— | SOMe | H | 0 | 4-cyanophenyl | 2-bromo-6-trifluoromethylsulfinyl-4-(1,2,2,2-tetrafluoro-1-trifluoromethyl-ethyl)-phenyl |
| 4-70 | -L-D | H | —CH2CH2— | SOMe | H | 0 | 4-cyanophenyl | 2-bromo-6-trifluoromethylsulfonyl-4-(1,2,2,2-tetrafluoro-1-trifluoromethyl-ethyl)-phenyl |
| 4-71 | -L-D | H | —CH2CH2— | SOMe | H | 0 | 4-cyanophenyl | 2-bromo-6-pentefluoroethyl-4-(1,2,2,2-tetrafluoro-1-trifluoromethyl-ethyl)-phenyl |

TABLE 4-continued

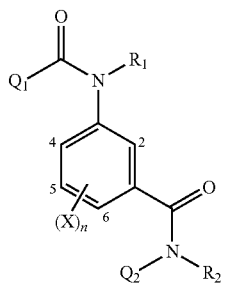

| compound number | R₁ | R₂ | L | D | X | n | Q₁ | Q₂ |
|---|---|---|---|---|---|---|---|---|
| 4-72 | -L-D | H | —CH2CH2— | SOMe | H | 0 | 4-cyanophenyl | 2-iodo-6-pentafluoroethyl-4-(1,2,2,2-tetrafluoro-1-trifluoromethyl-ethyl)-phenyl |
| 4-73 | -L-D | H | —CH2CH2— | SOMe | H | 0 | 4-cyanophenyl | 2-chloro-6-methyl-4-(1,2,2,3,3,3-hexafluoro-1-trifluoromethyl-propyl)-phenyl |
| 4-74 | -L-D | H | —CH2CH2— | SOMe | H | 0 | 4-cyanophenyl | 2-brome-6-methyl-4-(1,2,2,3,3,3-hexafluoro-1-trifluoromethyl-propyl)-phenyl |
| 4-75 | -L-D | H | —CH2CH2— | SOMe | H | 0 | 4-cyanophenyl | 2-iodo-6-methyl-4-(1,2,2,3,3,3-hexafluoro-1-trifluoromethyl-propyl)-phenyl |
| 4-76 | -L-D | H | —CH2CH2— | SOMe | H | 0 | 4-cyanophenyl | 2-bromo-6-ethyl-4-(1,2,2,3,3,3-hexafluoro-1-trifluoromethyl-propyl)-phenyl |
| 4-77 | -L-D | H | —CH2CH2— | SOMe | H | 0 | 4-cyanophenyl | 2-iodo-6-ethyl-4-(1,2,2,3,3,3-hexafluoro-1-trifluoromethyl-propyl)-phenyl |
| 4-78 | -L-D | H | —CH2CH2— | SOMe | H | 0 | 4-cyanophenyl | 2,6-dichloro-4-(1,2,2,3,3,3-hexafluoro-1-trifluoromethyl-propyl)-phenyl |
| 4-79 | -L-D | H | —CH2CH2— | SOMe | H | 0 | 4-cyanophenyl | 2,6-dibromo-4-(1,2,2,3,3,3-hexafluoro-1-trifluoromethyl-propyl)-phenyl |
| 4-80 | -L-D | H | —CH2CH2— | SOMe | H | 0 | 4-cyanophenyl | 2,6-diiodo-4-(1,2,2,3,3,3-hexafluoro-1-trifluoromethyl-propyl)-phenyl |
| 4-81 | -L-D | H | —CH2CH2— | SOMe | H | 0 | 4-cyanophenyl | 2,6-ditrifluoromethyl-4-(1,2,2,3,3,3-hexafluoro-1-trifluoromethyl-propyl)-phenyl |
| 4-82 | -L-D | H | —CH2CH2— | SOMe | H | 0 | 4-cyanophenyl | 2-bromo-6-trifluoromethyl-4-(1,2,2,3,3,3-hexafluoro-1-trifluoromethyl-propyl)-phenyl |
| 4-83 | -L-D | H | —CH2CH2— | SOMe | H | 0 | 4-cyanophenyl | 2-iodo-6-trifluoromethyl-4-(1,2,2,3,3,3-hexafluoro-1-trifluoromethyl-propyl)-phenyl |
| 4-84 | -L-D | H | —CH2CH2— | SOMe | H | 0 | 4-cyanophenyl | 2-bromo-6-trifluoromethoxy-4-(1,2,2,3,3,3-hexafluoro-1-trifluoromethyl-propyl)-phenyl |
| 4-85 | -L-D | H | —CH2CH2— | SOMe | H | 0 | 4-cyanophenyl | 2-bromo-6-iodo-4-(1,2,2,3,3,3-hexafluoro-1-trifluoromethyl-propyl) phenyl |
| 4-86 | -L-D | H | —CH2CH2— | SOMe | H | 0 | 4-cyanophenyl | 2-bromo-6-trifluoromethylthio-4-(1,2,2,3,3,3-hexafluoro-1-trifluoromethyl-propyl)-phenyl |
| 4-87 | -L-D | H | —CH2CH2— | SOMe | H | 0 | 4-cyanophenyl | 2-bromo-6-trifluoromethylsulfinyl-4-(1,2,2,3,3,3-hexafluoro-1-trifluoromethyl-propyl)-phenyl |
| 4-88 | -L-D | H | —CH2CH2— | SOMe | H | 0 | 4-cyanophenyl | 2-bromo-6-trifluoromethylsulfonyl-4-(1,2,2,3,3,3-hexafluoro-1-trifluoromethyl-propyl)-phenyl |
| 4-89 | -L-D | H | —CH2CH2— | SOMe | H | 0 | 4-cyanophenyl | 2-bromo-6-pentafluoroethyl-4-(1,2,2,3,3,3-hexafluoro-1-trifluoromethyl-propyl)-phenyl |
| 4-90 | -L-D | H | —CH2CH2— | SOMe | H | 0 | 4-cyanophenyl | 2-iodo-6-pentafluoroethyl-4-(1,2,2,3,3,3-hexafluoro-1-trifluoromethyl-propyl)-phenyl |
| 4-91 | -L-D | H | —CH2CH2— | SOMe | H | 0 | phenyl | 2,6-dibromo-4-(1,2,2,2-tetrafluoro-1-trifluoromethyl-ethyl)-phenyl |
| 4-92 | -L-D | H | —CH2CH2— | SOMe | H | 0 | 3-cyanophenyl | 2,6-dibromo-4-(1,2,2,2-tetrafluoro-1-trifluoromethyl-ethyl)-phenyl |
| 4-93 | -L-D | H | —CH2CH2— | SOMe | H | 0 | 2-chloropyridin-3-yl | 2,6-dibromo-4-(1,2,2,2-tetrafluoro-1-trifluoromethyl-ethyl)-phenyl |
| 4-94 | -L-D | H | —CH2CH2— | SOMe | H | 0 | 2-fluorophenyl | 2,6-dibromo-4-(1,2,2,2-tetrafluoro-1-trifluoromethyl-ethyl)-phenyl |
| 4-95 | -L-D | H | —CH2CH2— | SOMe | H | 0 | phenyl | 2,6-diiodo-4-(1,2,2,2-tetrafluoro-1-trifluoromethyl-ethyl)-phenyl |
| 4-96 | -L-D | H | —CH2CH2— | SOMe | H | 0 | 3-cyanophenyl | 2,6-diiodo-4-(1,2,2,2-tetrafluoro-1-trifluoromethyl-ethyl)-phenyl |
| 4-97 | -L-D | H | —CH2CH2— | SOMe | H | 0 | 2-chloropyridin-3-yl | 2,6-diiodo-4-(1,2,2,2-tetrafluoro-1-trifluoromethyl-ethyl)-phenyl |
| 4-98 | -L-D | H | —CH2CH2— | SOMe | H | 0 | 2-fluorophenyl | 2,6-diiodo-4-(1,2,2,2-tetrafluoro-1-trifluoromethyl-ethyl)-phenyl |
| 4-99 | -L-D | H | —CH2CH2— | SOMe | H | 0 | phenyl | 2-bromo-6-trifluoromethyl-4-(1,2,2,2-tetrafluoro-1-trifluoromethyl-ethyl)-phenyl |
| 4-100 | -L-D | H | —CH2CH2— | SOMe | H | 0 | 3-cyanophenyl | 2-bromo-6-trifluoromethyl-4-(1,2,2,2-tetrafluoro-1-trifluoromethyl-ethyl)-phenyl |
| 4-101 | -L-D | H | —CH2CH2— | SOMe | H | 0 | 2-chloropyridin-3-yl | 2-bromo-6-trifluoromethyl-4-(1,2,2,2-tetrafluoro-1-trifluoromethyl-ethyl)-phenyl |
| 4-102 | -L-D | H | —CH2CH2— | SOMe | H | 0 | 2-fluorophenyl | 2-bromo-6-trifluoromethyl-4-(1,2,2,2-tetrafluoro-1-trifluoromethyl-ethyl)-phenyl |

TABLE 4-continued

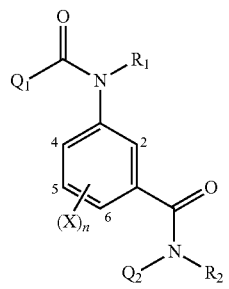

| compound number | R₁ | R₂ | L | D | X | n | Q₁ | Q₂ |
|---|---|---|---|---|---|---|---|---|
| 4-103 | -L-D | H | —CH2CH2— | SOMe | H | 0 | phenyl | 2-iodo-6-trifluoromethyl-4-(1,2,2,2-tetrafluoro-1-trifluoromethyl-ethyl-phenyl |
| 4-104 | -L-D | H | —CH2CH2— | SOMe | H | 0 | 3-cyanophenyl | 2-iodo-6-trifluoromethyl-4-(1,2,2,2-tetrafluoro-1-trifluoromethyl-ethyl-phenyl |
| 4-105 | -L-D | H | —CH2CH2— | SOMe | H | 0 | 2-chloropyridin-3-yl | 2-iodo-6-trifluoromethyl-4-(1,2,2,2-tetrafluoro-1-trifluoromethyl-ethyl-phenyl |
| 4-106 | -L-D | H | —CH2CH2— | SOMe | H | 0 | 2-fluorophenyl | 2-iodo-6-trifluoromethyl-4-(1,2,2,2-tetrafluoro-1-trifluoromethyl-ethyl-phenyl |
| 4-107 | -L-D | H | —CH2CH2— | SOMe | H | 0 | phenyl | 2,6-dibromo-4-(1,2,2,3,3,3-hexafluoro-1-trifluoromethyl-propyl)-phenyl |
| 4-108 | -L-D | H | —CH2CH2— | SOMe | H | 0 | 3-cyanophenyl | 2,6-dibromo-4-(1,2,2,3,3,3-hexafluoro-1-trifluoromethyl-propyl)-phenyl |
| 4-109 | -L-D | H | —CH2CH2— | SOMe | H | 0 | 2-chloropyridin-3-yl | 2,6-dibromo-4-(1,2,2,3,3,3-hexafluoro-1-trifluoromethyl-propyl)-phenyl |
| 4-110 | -L-D | H | —CH2CH2— | SOMe | H | 0 | 2-fluorophenyl | 2,6-dibromo-4-(1,2,2,3,3,3-hexafluoro-1-trifluoromethyl-propyl)-phenyl |
| 4-111 | -L-D | H | —CH2CH2— | SOMe | H | 0 | phenyl | 2,6-diiodo-4-(1,2,2,3,3,3-hexafluoro-1-trifluoromethyl-propyl)-phenyl |
| 4-112 | -L-D | H | —CH2CH2— | SOMe | H | 0 | 3-cyanophenyl | 2,6-diiodo-4-(1,2,2,3,3,3-hexafluoro-1-trifluoromethyl-propyl)-phenyl |
| 4-113 | -L-D | H | —CH2CH2— | SOMe | H | 0 | 2-chloropyridin-3-yl | 2,6-diiodo-4-(1,2,2,3,3,3-hexafluoro-1-trifluoromethyl-propyl)-phenyl |
| 4-114 | -L-D | H | —CH2CH2— | SOMe | H | 0 | 2-fluorophenyl | 2,6-diiodo-4-(1,2,2,3,3,3-hexafluoro-1-trifluoromethyl-propyl)-phenyl |
| 4-115 | -L-D | H | —CH2CH2— | SOMe | H | 0 | phenyl | 2-bromo-6-trifluoromethyl-4-(1,2,2,3,3,3-hexafluoro-1-trifluoromethyl-propyl)-phenyl |
| 4-116 | -L-D | H | —CH2CH2— | SOMe | H | 0 | 3-cyanophenyl | 2-bromo-6-trifluoromethyl-4-(1,2,2,3,3,3-hexafluoro-1-trifluoromethyl-propyl)-phenyl |
| 4-117 | -L-D | H | —CH2CH2— | SOMe | H | 0 | 2-chloropyridin-3-yl | 2-bromo-6-trifluoromethyl-4-(1,2,2,3,3,3-hexafluoro-1-trifluoromethyl-propyl)-phenyl |
| 4-118 | -L-D | H | —CH2CH2— | SOMe | H | 0 | 2-fluorophenyl | 2-bromo-6-trifluoromethyl-4-(1,2,2,3,3,3-hexafluoro-1-trifluoromethyl-propyl)-phenyl |
| 4-119 | -L-D | H | —CH2CH2— | SOMe | H | 0 | phenyl | 2-iodo-6-trifluoromethyl-4-(1,2,2,3,3,3-hexafluoro-1-trifluoromethyl-propyl)-phenyl |
| 4-120 | -L-D | H | —CH2CH2— | SOMe | H | 0 | 3-cyanophenyl | 2-iodo-6-trifluoromethyl-4-(1,2,2,3,3,3-hexafluoro-1-trifluoromethyl-propyl)-phenyl |
| 4-121 | -L-D | H | —CH2CH2— | SOMe | H | 0 | 2-chloropyridin-3-yl | 2-iodo-6-trifluoromethyl-4-(1,2,2,3,3,3-hexafluoro-1-trifluoromethyl-propyl)-phenyl |
| 4-122 | -L-D | H | —CH2CH2— | SOMe | H | 0 | 2-fluorophenyl | 2-iodo-6-trifluoromethyl-4-(1,2,2,3,3,3-hexafluoro-1-trifluoromethyl-propyl)-phenyl |
| 4-123 | -L-D | H | —CH2CH2— | SOMe | 2-F | 1 | 4-cyanophenyl | 2,6-dibromo-4-pentafluoroethyl-phenyl |
| 4-124 | -L-D | H | —CH2CH2— | SOMe | 2-F | 1 | 4-cyanophenyl | 2,6-diiodo-4-pentafluoroethyl-phenyl |
| 4-125 | -L-D | H | —CH2CH2— | SOMe | 2-F | 1 | 4-cyanophenyl | 2-bromo-6-trifluoromethyl-4-pentafluoroethyl-phenyl |
| 4-126 | -L-D | H | —CH2CH2— | SOMe | 2-F | 1 | 4-cyanophenyl | 2-iodo-6-trifluoromethyl-4-pentafluoroethyl-phenyl |
| 4-127 | -L-D | H | —CH2CH2— | SOMe | 2-F | 1 | 4-cyanophenyl | 2-chloro-6-methyl-4-(1,2,2,2-tetrafluoro-1-trifluoromethyl-ethyl)-phenyl |
| 4-128 | -L-D | H | —CH2CH2— | SOMe | 2-F | 1 | 4-cyanophenyl | 2-bromo-6-methyl-4-(1,2,2,2-tetrafluoro-1-trifluoromethyl-ethyl)-phenyl |
| 4-129 | -L-D | H | —CH2CH2— | SOMe | 2-F | 1 | 4-cyanophenyl | 2-iodo-6-methyl-4-(1,2,2,2-tetrafluoro-1-trifluoromethyl-ethyl)-phenyl |
| 4-130 | -L-D | H | —CH2CH2— | SOMe | 2-F | 1 | 4-cyanophenyl | 2-bromo-6-ethyl-4-(1,2,2,2-tetrafluoro-1-trifluoromethyl-ethyl)-phenyl |
| 4-131 | -L-D | H | —CH2CH2— | SOMe | 2-F | 1 | 4-cyanophenyl | 2-iodo-6-ethyl-4-(1,2,2,2-tetrafluoro-1-trifluoromethyl-ethyl)-phenyl |
| 4-132 | -L-D | H | —CH2CH2— | SOMe | 2-F | 1 | 4-cyanophenyl | 2,6-dichloro-4-(1,2,2,2-tetrafluoro-1-trifluoromethyl-ethyl)-phenyl |
| 4-133 | -L-D | H | —CH2CH2— | SOMe | 2-F | 1 | 4-cyanophenyl | 2,6-dibromo-4-(1,2,2,2-tetrafluoro-1-trifluoromethyl-ethyp-phenyl |
| 4-134 | -L-D | H | —CH2CH2— | SOMe | 2-F | 1 | 4-cyanophenyl | 2,6-diiodo-4-(1,2,2,2-tetrafluoro-1-trifluoromethyl-ethyl)-phenyl |

TABLE 4-continued

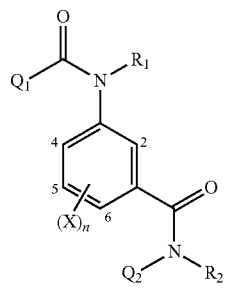

| compound number | R₁ | R₂ | L | D | X | n | Q₁ | Q₂ |
|---|---|---|---|---|---|---|---|---|
| 4-135 | -L-D | H | —CH2CH2— | SOMe | 2-F | 1 | 4-cyanophenyl | 2,6-ditrifluoromethyl-4-(1,2,2,2-tetrafluoro-1-trifluoromethyl-ethyl)-phenyl |
| 4-136 | -L-D | H | —CH2CH2— | SOMe | 2-F | 1 | 4-cyanophenyl | 2-bromo-6-trifluoromethyl-4-(1,2,2,2-tetrafluoro-1-trifluoromethyl-ethyl)-phenyl |
| 4-137 | -L-D | H | —CH2CH2— | SOMe | 2-F | 1 | 4-cyanophenyl | 2-iodo-6-trifluoromethyl-4-(1,2,2,2-tetrafluoro-1-trifluoromethyl-ethyl)-phenyl |
| 4-138 | -L-D | H | —CH2CH2— | SOMe | 2-F | 1 | 4-cyanophenyl | 2-bromo-6-trifluoromethoxy-4-(1,2,2,2-tetrafluoro-1-trifluoromethyl-ethyl)-phenyl |
| 4-139 | -L-D | H | —CH2CH2— | SOMe | 2-F | 1 | 4-cyanophenyl | 2-bromo-6-iodo-4-(1,2,2,2-tetrafluoro-1-trifluoromethyl-ethyl)-phenyl |
| 4-140 | -L-D | H | —CH2CH2— | SOMe | 2-F | 1 | 4-cyanophenyl | 2-bromo-6-trifluoromethylthio-4-(1,2,2,2-tetrafluoro-1-trifluoromethyl-ethyl)-phenyl |
| 4-141 | -L-D | H | —CH2CH2— | SOMe | 2-F | 1 | 4-cyanophenyl | 2-bromo-6-trifluoromethylsulfinyl-4-(1,2,2,2-tetrafluoro-1-trifluoromethyl-ethyl)-phenyl |
| 4-142 | -L-D | H | —CH2CH2— | SOMe | 2-F | 1 | 4-cyanophenyl | 2-bromo-6-trifluoromethylsulfonyl-4-(1,2,2,2-tetrafluoro-1-trifluoromethyl-ethyl)-phenyl |
| 4-143 | -L-D | H | —CH2CH2— | SOMe | 2-F | 1 | 4-cyanophenyl | 2-bromo-6-pentafluoroethyl-4-(1,2,2,2-tetrafluoro-1-trifluoromethyl-ethyl)-phenyl |
| 4-144 | -L-D | H | —CH2CH2— | SOMe | 2-F | 1 | 4-cyanophenyl | 2-iodo-6-pentafluoroethyl-4-(1,2,2,2-tetrafluoro-1-trifluoromethyl-ethyl)-phenyl |
| 4-145 | -L-D | H | —CH2CH2— | SOMe | 2-F | 1 | 4-cyanophenyl | 2-chloro-6-methyl-4-(1,2,2,3,3,3-hexafluoro-1-trifluoromethyl-propyl)-phenyl |
| 4-146 | -L-D | H | —CH2CH2— | SOMe | 2-F | 1 | 4-cyanophenyl | 2-bromo-6-methyl-4-(1,2,2,3,3,3-hexafluoro-1-trifluoromethyl-propyl)-phenyl |
| 4-147 | -L-D | H | —CH2CH2— | SOMe | 2-F | 1 | 4-cyanophenyl | 2-iodo-6-methyl-4-(1,2,2,3,3,3-hexafluoro-1-trifluoromethyl-propyl)-phenyl |
| 4-148 | -L-D | H | —CH2CH2— | SOMe | 2-F | 1 | 4-cyanophenyl | 2-bromo-6-ethyl-4-(1,2,2,3,3,3-hexafluoro-1-trifluoromethyl-propyl)-phenyl |
| 4-149 | -L-D | H | —CH2CH2— | SOMe | 2-F | 1 | 4-cyanophenyl | 2-iodo-6-ethyl-4-(1,2,2,3,3,3-hexafluoro-1-trifluoromethyl-propyl)-phenyl |
| 4-150 | -L-D | H | —CH2CH2— | SOMe | 2-F | 1 | 4-cyanophenyl | 2,6-dichloro-4-(1,2,2,3,3,3-hexafluoro-1-trifluoromethyl-propyl)-phenyl |
| 4-151 | -L-D | H | —CH2CH2— | SOMe | 2-F | 1 | 4-cyanophenyl | 2,6-dibromo-4-(1,2,2,3,3,3-hexafluoro-1-trifluoromethyl-propyl)-phenyl |
| 4-152 | -L-D | H | —CH2CH2— | SOMe | 2-F | 1 | 4-cyanophenyl | 2,6-diiodo-4-(1,2,2,3,3,3-hexafluoro-1-trifluoromethyl-propyl)-phenyl |
| 4-153 | -L-D | H | —CH2CH2— | SOMe | 2-F | 1 | 4-cyanophenyl | 2,6-ditrifluoromethyl-4-(1,2,2,3,3,3-hexafluoro-1-trifluoromethyl-propyl)-phenyl |
| 4-154 | -L-D | H | —CH2CH2— | SOMe | 2-F | 1 | 4-cyanophenyl | 2-bromo-trifluoromethyl-4-(1,2,2,3,3,3-hexafluoro-1-trifluoromethyl-propyl)-phenyl |
| 4-155 | -L-D | H | —CH2CH2— | SOMe | 2-F | 1 | 4-cyanophenyl | 2-iodo-trifluoromethyl-4-(1,2,2,3,3,3-hexafluoro-1-trifluoromethyl-propyl)-phenyl |
| 4-156 | -L-D | H | —CH2CH2— | SOMe | 2-F | 1 | 4-cyanophenyl | 2-bromo-trifluoromethoxy-4-(1,2,2,3,3,3-hexafluoro-1-trifluoromethyl-propyl)-phenyl |
| 4-157 | -L-D | H | —CH2CH2— | SOMe | 2-F | 1 | 4-cyanophenyl | 2-bromo-6-iodo-4-(1,2,2,3,3,3-hexafluoro-1-trifluoromethyl-propyl)-phenyl |
| 4-158 | -L-D | H | —CH2CH2— | SOMe | 2-F | 1 | 4-cyanophenyl | 2-bromo-trifluoromethylthio-4-(1,2,2,3,3,3-hexafluoro-1-trifluoromethyl-propyl)-phenyl |
| 4-159 | -L-D | H | —CH2CH2— | SOMe | 2-F | 1 | 4-cyanophenyl | 2-bromo-6-trifluoromethylsulfinyl-4-(1,2,2,3,3,3-hexafluoro-1-trifluoromethyl-propyl)-phenyl |
| 4-160 | -L-D | H | —CH2CH2— | SOMe | 2-F | 1 | 4-cyanophenyl | 2-bromo-6-trifluoromethylsulfonyl-4-(1,2,2,3,3,3-hexafluoro-1-trifluoromethyl-propyl)-phenyl |
| 4-161 | -L-D | H | —CH2CH2— | SOMe | 2-F | 1 | 4-cyanophenyl | 2-bromo-6-pentafluoroethyl-4-(1,2,2,3,3,3-hexafluoro-1-trifluoromethyl-propyl)-phenyl |
| 4-162 | -L-D | H | —CH2CH2— | SOMe | 2-F | 1 | 4-cyanophenyl | 2-iodo-6-pentafluoroethyl-4-(1,2,2,3,3,3-hexafluoro-1-trifluoromethyl-propyl)-phenyl |
| 4-163 | -L-D | H | —CH2CH2— | SOMe | 2-F | 1 | phenyl | 2,6-dibromo-4-(1,2,2,2-tetrafluoro-1-trifluoromethyl-ethyl)-phenyl |
| 4-164 | -L-D | H | —CH2CH2— | SOMe | 2-F | 1 | 3-cyanophenyl | 2,6-dibromo-4-(1,2,2,2-tetrafluoro-1-trifluoromethyl-ethyl)-phenyl |
| 4-165 | -L-D | H | —CH2CH2— | SOMe | 2-F | 1 | 2-chloropyridin-3-yl | 2,6-dibromo-4-(1,2,2,2-tetrafluoro-1-trifluoromethyl-ethyl)-phenyl |

TABLE 4-continued

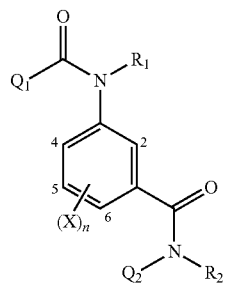

| compound number | R1 | R2 | L | D | X | n | Q1 | Q2 |
|---|---|---|---|---|---|---|---|---|
| 4-166 | -L-D | H | —CH2CH2— | SOMe | 2-F | 1 | 2-fluorophenyl | 2,6-dibromo-4-(1,2,2,2-tetrafluoro-1-trifluoromethyl-ethyl)-phenyl |
| 4-167 | -L-D | H | —CH2CH2— | SOMe | 2-F | 1 | phenyl | 2,6-diiodo-4-(1,2,2,2-tetrafluoro-1-trifluoromethyl-ethyl)-phenyl |
| 4-168 | -L-D | H | —CH2CH2— | SOMe | 2-F | 1 | 3-cyanophenyl | 2,6-diiodo-4-(1,2,2,2-tetrafluoro-1-trifluoromethyl-ethyl)-phenyl |
| 4-169 | -L-D | H | —CH2CH2— | SOMe | 2-F | 1 | 2-chloropyridin-3-yl | 2,6-diiodo-4-(1,2,2,2-tetrafluoro-1-trifluoromethyl-ethyl)-phenyl |
| 4-170 | -L-D | H | —CH2CH2— | SOMe | 2-F | 1 | 2-fluorophenyl | 2,6-diiodo-4-(1,2,2,2-tetrafluoro-1-trifluoromethyl-ethyl)-phenyl |
| 4-171 | -L-D | H | —CH2CH2— | SOMe | 2-F | 1 | phenyl | 2-bromo-6-trifluoromethyl-4-(1,2,2,2-tetrafluoro-1-trifluoromethyl-ethyl)-phenyl |
| 4-172 | -L-D | H | —CH2CH2— | SOMe | 2-F | 1 | 3-cyanophenyl | 2-bromo-6-trifluoromethyl-4-(1,2,2,2-tetrafluoro-1-trifluoromethyl-ethyl)-phenyl |
| 4-173 | -L-D | H | —CH2CH2— | SOMe | 2-F | 1 | 2-chloropyridin-3-yl | 2-bromo-6-trifluoromethyl-4-(1,2,2,2-tetrafluoro-1-trifluoromethyl-ethyl)-phenyl |
| 4-174 | -L-D | H | —CH2CH2— | SOMe | 2-F | 1 | 2-fluorophenyl | 2-bromo-6-trifluoromethyl-4-(1,2,2,2-tetrafluoro-1-trifluoromethyl-ethyl)-phenyl |
| 4-175 | -L-D | H | —CH2CH2— | SOMe | 2-F | 1 | phenyl | 2-iodo-6-trifluoromethyl-4-(1,2,2,2-tetrafluoro-1-trifluoromethyl-ethyl)-phenyl |
| 4-176 | -L-D | H | —CH2CH2— | SOMe | 2-F | 1 | 3-cyanophenyl | 2-iodo-6-trifluoromethyl-4-(1,2,2,2-tetrafluoro-1-trifluoromethyl-ethyl)-phenyl |
| 4-177 | -L-D | H | —CH2CH2— | SOMe | 2-F | 1 | 2-chloropyridin-3-yl | 2-iodo-6-trifluoromethyl-4-(1,2,2,2-tetrafluoro-1-trifluoromethyl-ethyl)-phenyl |
| 4-178 | -L-D | H | —CH2CH2— | SOMe | 2-F | 1 | 2-fluorophenyl | 2-iodo-6-trifluoromethyl-4-(1,2,2,2-tetrafluoro-1-trifluoromethyl-ethyl)-phenyl |
| 4-179 | -L-D | H | —CH2CH2— | SOMe | 2-F | 1 | phenyl | 2,6-dibromo-4-(1,2,2,3,3,3-hexafluoro-1-trifluoromethyl-propyl)-phenyl |
| 4-180 | -L-D | H | —CH2CH2— | SOMe | 2-F | 1 | 3-cyanophenyl | 2,6-dibromo-4-(1,2,2,3,3,3-hexafluoro-1-trifluoromethyl-propyl)-phenyl |
| 4-181 | -L-D | H | —CH2CH2— | SOMe | 2-F | 1 | 2-chloropyridin-3-yl | 2,6-dibromo-4-(1,2,2,3,3,3-hexafluoro-1-trifluoromethyl-propyl)-phenyl |
| 4-182 | -L-D | H | —CH2CH2— | SOMe | 2-F | 1 | 2-fluorophenyl | 2,6-dibromo-4-(1,2,2,3,3,3-hexafluoro-1-trifluoromethyl-propyl)-phenyl |
| 4-183 | -L-D | H | —CH2CH2— | SOMe | 2-F | 1 | phenyl | 2,6-diiodo-4-(1,2,2,3,3,3-hexafluoro-1-trifluoromethyl-propyl)-phenyl |
| 4-184 | -L-D | H | —CH2CH2— | SOMe | 2-F | 1 | 3-cyanophenyl | 2,6-diiodo-4-(1,2,2,3,3,3-hexafluoro-1-trifluoromethyl-propyl)-phenyl |
| 4-185 | -L-D | H | —CH2CH2— | SOMe | 2-F | 1 | 2-chloropyridin-3-yl | 2,6-diiodo-4-(1,2,2,3,3,3-hexafluoro-1-trifluoromethyl-propyl)-phenyl |
| 4-186 | -L-D | H | —CH2CH2— | SOMe | 2-F | 1 | 2-fluorophenyl | 2,6-diiodo-4-(1,2,2,3,3,3-hexafluoro-1-trifluoromethyl-propyl)-phenyl |
| 4-187 | -L-D | H | —CH2CH2— | SOMe | 2-F | 1 | phenyl | 2-bromo-6-trifluoromethyl-4-(1,2,2,3,3,3-hexafluoro-1-trifluoromethyl-propyl-phenyl |
| 4-188 | -L-D | H | —CH2CH2— | SOMe | 2-F | 1 | 3-cyanophenyl | 2-bromo-6-trifluoromethyl-4-(1,2,2,3,3,3-hexafluoro-1-trifluoromethyl-propyl-phenyl |
| 4-189 | -L-D | H | —CH2CH2— | SOMe | 2-F | 1 | 2-chloropyridin-3-yl | 2-bromo-6-trifluoromethyl-4-(1,2,2,3,3,3-hexafluoro-1-trifluoromethyl-propyl-phenyl |
| 4-190 | -L-D | H | —CH2CH2— | SOMe | 2-F | 1 | 2-fluorophenyl | 2-bromo-6-trifluoromethyl-4-(1,2,2,3,3,3-hexafluoro-1-trifluoromethyl-propyl-phenyl |
| 4-191 | -L-D | H | —CH2CH2— | SOMe | 2-F | 1 | phenyl | 2-iodo-6-trifluoromethyl-4-(1,2,2,3,3,3-hexafluoro-1-trifluoromethyl-propyl)-phenyl |
| 4-192 | -L-D | H | —CH2CH2— | SOMe | 2-F | 1 | 3-cyanophenyl | 2-iodo-6-trifluoromethyl-4-(1,2,2,3,3,3-hexafluoro-1-trifluoromethyl-propyl)-phenyl |
| 4-193 | -L-D | H | —CH2CH2— | SOMe | 2-F | 1 | 2-chloropyridin-3-yl | 2-iodo-6-trifluoromethyl-4-(1,2,2,3,3,3-hexafluoro-1-trifluoromethyl-propyl)-phenyl |
| 4-194 | -L-D | H | —CH2CH2— | SOMe | 2-F | 1 | 2-fluorophenyl | 2-iodo-6-trifluoromethyl-4-(1,2,2,3,3,3-hexafluoro-1-trifluoromethyl-propyl)-phenyl |
| 4-195 | -L-D | H | —CH2CH2— | SOMe | H | 0 | 6-chloropyridin-3-yl | 2-bromo-6-trifluoromethyl-4-(1,2,2,2-tetrafluoro-1-trifluoromethyl-ethyl)-phenyl |
| 4-196 | -L-D | H | —CH2CH2— | SOMe | 2-F | 1 | 6-chloropyridin-3-yl | 2-bromo-6-trifluoromethyl-4-(1,2,2,2-tetrafluoro-1-trifluoromethyl-ethyl)-phenyl |

TABLE 4-continued

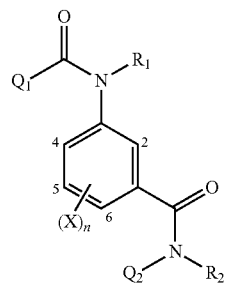

| compound number | R₁ | R₂ | L | D | X | n | Q₁ | Q₂ |
|---|---|---|---|---|---|---|---|---|
| 4-197 | -L-D | H | —CH2CH2— | SOMe | 2-F | 1 | 6-chloropyridin-3-yl | 2,6-dibromo-4-(1,2,2,2-tetrafluoro-1-trifluoromethyl-ethyl)-phenyl |
| 4-198 | -L-D | H | —CH2CH2— | SOMe | 2-F | 1 | 3,5-dicyanophenyl | 2-bromo-6-trifluoromethyl-4-(1,2,2,2-tetrafluoro-1-trifluoromethyl-ethyl)-phenyl |
| 4-199 | -L-D | H | —CH2CH2— | SOMe | 2-F | 1 | 3,5-dicyanophenyl | 2,6-dibromo-4-(1,2,2,2-tetrafluoro-1-trifluoromethyl-ethyl)-phenyl |
| 4-200 | -L-D | H | —CH2CH2— | SOMe | 2-F | 1 | pyridin-3-yl | 2,6-dibromo-4-(1,2,2,2-tetrafluoro-1-trifluoromethyl-ethyl)-phenyl |
| 4-201 | -L-D | H | —CH2CH2— | SOMe | 2-F | 1 | pyridin-4-yl | 2,6-dibromo-4-(1,2,2,2-tetrafluoro-1-trifluoromethyl-ethyl)-phenyl |
| 4-202 | -L-D | H | —CH2CH2— | SOMe | 2-F | 1 | 2-chloropyridin-4-yl | 2,6-dibromo-4-(1,2,2,2-tetrafluoro-1-trifluoromethyl-ethyl)-phenyl |
| 4-203 | -L-D | H | —CH2CH2— | SOMe | 2-F | 1 | pyrazin-2-yl | 2,6-dibromo-4-(1,2,2,2-tetrafluoro-1-trifluoromethyl-ethyl)-phenyl |
| 4-204 | -L-D | H | —CH2CH2— | SOMe | 2-F | 1 | pyrimidin-5-yl | 2,6-dibromo-4-(1,2,2,2-tetrafluoro-1-trifluoromethyl-ethyl)-phenyl |
| 4-205 | -L-D | H | —CH2CH2— | SOMe | 2-F | 1 | 3-cyanophenyl | 2,6-dichloro-4-(1,2,2,2-tetrafluoro-1-trifluoromethyl-ethyl)-phenyl |
| 4-206 | -L-D | H | —CH2CH2— | SOMe | 2-F | 1 | phenyl | 2,6-dichloro-4-(1,2,2,2-tetrafluoro-1-trifluoromethyl-ethyl)-phenyl |
| 4-207 | -L-D | H | —CH2CH2— | SOMe | 2-F | 1 | 2-chloropyridin-3-yl | 2,6-dichloro-4-(1,2,2,2-tetrafluoro-1-trifluoromethyl-ethyl)-phenyl |
| 4-208 | -L-D | H | —CH2CH2— | SOMe | 2-F | 1 | 6-cyanopyridin-3-yl | 2,6-dibromo-4-(1,2,2,2-tetrafluoro-1-trifluoromethyl-ethyl)-phenyl |
| 4-209 | -L-D | H | —CH2CH2— | SOMe | 2-F | 1 | 4-fluorophenyl | 2,6-dibromo-4-(1,2,2,2-tetrafluoro-1-trifluoromethyl-ethyl)-phenyl |
| 4-210 | -L-D | H | —CH2CH2— | SOMe | 2-F | 1 | 2,6-difluorophenyl | 2,6-dibromo-4-(1,2,2,2-tetrafluoro-1-trifluoromethyl-ethyl)-phenyl |
| 4-211 | -L-D | H | —CH2CH2— | SOMe | 2-F | 1 | 2-chloropyridin-3-yl | 2-bromo-6-iodo-4-(1,2,2,2-tetrafluoro-1-trifluoromethyl-ethyl)-phenyl |
| 4-212 | -L-D | H | —CH2CH2— | SOMe | 2-F | 1 | phenyl | 2-bromo-6-iodo-4-(1,2,2,2-tetrafluoro-1-trifluoromethyl-ethyl)-phenyl |
| 4-213 | -L-D | H | —CH2CH2— | SOMe | 2-F | 1 | 6-chloropyridin-3-yl | 2,6-dibromo-4-(1,2,2,3,3,3-hexafluoro-1-trifluoromethyl-propyl)-phenyl |
| 4-214 | -L-D | H | —CH2CH2— | SOMe | 2-F | 1 | phenyl | 2,6-dimethyl-4-(1,2,2,3,3,3-hexafluoro-1-trifluoromethyl-propyl)-phenyl |
| 4-215 | -L-D | H | —CH2CH2— | SOMe | 2-F | 1 | 4-cyanophenyl | 2,6-dimethyl-4-(1,2,2,3,3,3-hexafluoro-1-trifluoromethyl-propyl)-phenyl |
| 4-216 | -L-D | H | —CH2CH2— | SOMe | 2-F | 1 | 3-cyanophenyl | 2,6-dimethyl-4-(1,2,2,3,3,3-hexafluoro-1-trifluoromethyl-propyl)-phenyl |
| 4-217 | -L-D | H | —CH2CH2— | SOMe | 4-F | 1 | phenyl | 2,6-dibromo-4-(1,2,2,2-tetrafluoro-1-trifluoromethyl-ethyl)-phenyl |
| 4-218 | -L-D | H | —CH2CH2— | SOMe | 4-F | 1 | 4-cyanophenyl | 2-bromo-6-trifluoromethyl-4-(1,2,2,2-tetrafluoro-1-trifluoromethyl-ethyl)-phenyl |
| 4-219 | -L-D | H | —CH2CH2— | SOMe | 4-F | i | 3-cyanophenyl | 2-iodo-6-trifluoromethyl-4-(1,2,2,2-tetrafluoro-1-trifluoromethyl-ethyl)-phenyl |
| 4-220 | -L-D | H | —CH2CH2— | SOMe | 4-F | 1 | 2-chloropyridin-3-yl | 2-bromo-6-trifluoromethyl-4-(1,2,2,3,3,3-hexafluoro-1-trifluoromethyl-propyl)-phenyl |
| 4-221 | -L-D | H | —CH2CH2— | SOMe | 4-F | 1 | 2-fluorophenyl | 2-iodo-6-trifluoromethyl-4-(1,2,2,3,3,3-hexafluoro-1-trifluoromethyl-propyl)-phenyl |
| 4-222 | -L-D | H | —CH2CH2— | SOMe | 4-CN | 1 | phenyl | 2,6-dibromo-4-(1,2,2,2-tetrafluoro-1-trifluoromethyl-ethyl)-phenyl |
| 4-223 | -L-D | H | —CH2CH2— | SOMe | 4-CN | 1 | 4-cyanophenyl | 2-bromo-6-trifluoromethyl-4-(1,2,2,2-tetrafluoro-1-trifluoromethyl-ethyl)-phenyl |
| 4-224 | -L-D | H | —CH2CH2— | SOMe | 4-CN | 1 | 3-cyanophenyl | 2-iodo-6-trifluoromethyl-4-(1,2,2,2-tetrafluoro-1-trifluoromethyl-ethyl)-phenyl |
| 4-225 | -L-D | H | —CH2CH2— | SOMe | 4-CN | 1 | 2-chloropyridin-3-yl | 2-bromo-6-trifluoromethyl-4-(1,2,2,3,3,3-hexafluoro-1-trifluoromethyl-propyl)-phenyl |
| 4-226 | -L-D | H | —CH2CH2— | SOMe | 4-CN | 1 | 2-fluorophenyl | 2-iodo-6-trifluoromethyl-4-(1,2,2,3,3,3-hexafluoro-1-trifluoromethyl-propyl)-phenyl |
| 4-227 | -L-D | H | —CH2CH2— | SOMe | 2-NO2 | 1 | phenyl | 2,6-dibromo-4-(1,2,2,2-tetrafluoro-1-trifluoromethyl-ethyl)-phenyl |

TABLE 4-continued

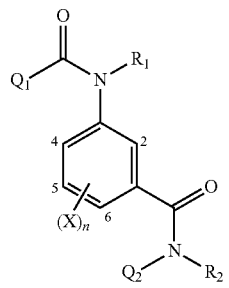

| compound number | R₁ | R₂ | L | D | X | n | Q₁ | Q₂ |
|---|---|---|---|---|---|---|---|---|
| 4-228 | -L-D | H | —CH2CH2— | SOMe | 2-NO2 | 1 | 4-cyanophenyl | 2-bromo-6-trifluoromethyl-4-(1,2,2,2-tetrafluoro-1-trifluoromethyl-ethyl)-phenyl |
| 4-229 | -L-D | H | —CH2CH2— | SOMe | 2-NO2 | 1 | 3-cyanophenyl | 2-iodo-6-trifluoromethyl-4-(1,2,2,2-tetrafluoro-1-trifluoromethyl-ethyl)-phenyl |
| 4-230 | -L-D | H | —CH2CH2— | SOMe | 2-NO2 | 1 | 2-chloropyridin-3-yl | 2-bromo-6-trifluoromethyl-4-(1,2,2,3,3,3-hexafluoro-1-trifluoromethyl-propyl)-phenyl |
| 4-231 | -L-D | H | —CH2CH2— | SOMe | 2-NO2 | 1 | 2-fluorophenyl | 2-iodo-6-trifluoromethyl-4-(1,2,2,3,3,3-hexafluoro-1-trifluoromethyl-propyl)-phenyl |

TABLE 5

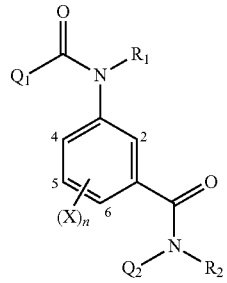

| compound number | R₁ | R₂ | L | D | X | n | Q₁ | Q₂ |
|---|---|---|---|---|---|---|---|---|
| 5-1 | -L-D | H | —CH2CH2— | CO2Me | H | 0 | phenyl | 2,6-dimethyl-4-(1,2,2,2-tetrafluoro-1-trifluoromethyl-ethyl)-phenyl |
| 5-2 | -L-D | H | —CH2CH2— | CO2Et | H | 0 | phenyl | 2,6-dimethyl-4-(1,2,2,2-tetrafluoro-1-trifluoromethyl-ethyl)-phenyl |
| 5-3 | -L-D | H | —CH2CH2— | CO2iPr | H | 0 | phenyl | 2,6-dimethyl-4-(1,2,2,2-tetrafluoro-1-trifluoromethyl-ethyl)-phenyl |
| 5-4 | -L-D | H | —CH2CH2— | CO2H | H | 0 | phenyl | 2,6-dimethyl-4-(1,2,2,2-tetrafluoro-1-trifluoromethyl-ethyl)-phenyl |
| 5-5 | -L-D | H | —CH2CH2— | OH | H | 0 | phenyl | 2,6-dimethyl-4-(1,2,2,2-tetrafluoro-1-trifluoromethyl-ethyl)-phenyl |
| 5-6 | -L-D | H | —CH2CH2— | NH2 | H | 0 | phenyl | 2,6-dimethyl-4-(1,2,2,2-tetrafluoro-1-trifluoromethyl-ethyl)-phenyl |
| 5-7 | -L-D | H | —CH2CH2— | NHAc | H | 0 | phenyl | 2,6-dimethyl-4-(1,2,2,2-tetrafluoro-1-trifluoromethyl-ethyl)-phenyl |
| 5-8 | -L-D | H | —CH2CH2— | CN | H | 0 | phenyl | 2,6-dimethyl-4-(1,2,2,2-tetrafluoro-1-trifluoromethyl-ethyl)-phenyl |
| 5-9 | -L-D | H | —CH2CH2— | CONHMe | H | 0 | phenyl | 2,6-dimethyl-4-(1,2,2,2-tetrafluoro-1-trifluoromethyl-ethyl)-phenyl |
| 5-10 | -L-D | H | —CH2CH2— | CONMe2 | H | 0 | phenyl | 2,6-dimethyl-4-(1,2,2,2-tetrafluoro-1-trifluoromethyl-ethyl)-phenyl |

TABLE 5-continued

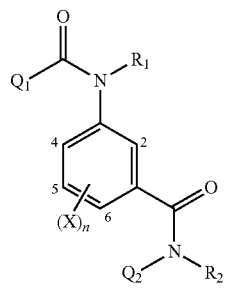

| compound number | R₁ | R₂ | L | D | X | n | Q₁ | Q₂ |
|---|---|---|---|---|---|---|---|---|
| 5-11 | -L-D | H | —CH2CH2— | CONHiPr | H | 0 | phenyl | 2,6-dimethyl-4-(1,2,2,2-tetrafluoro-1-trifluoromethyl-ethyl)-phenyl |
| 5-12 | -L-D | H | —CH2CH2— | CONHiPr | H | 0 | 4-cyanophenyl | 2,6-dimethyl-4-(1,2,2,2-tetrafluoro-1-trifluoromethyl-ethyl)-phenyl |
| 5-13 | -L-D | H | —CH2CH2— | CONHEt | H | 0 | phenyl | 2,6-dimethyl-4-(1,2,2,2-tetrafluoro-1-trifluoromethyl-ethyl)-phenyl |
| 5-14 | -L-D | H | —CH2CH2— | CO-morpholinyl | H | 0 | phenyl | 2,6-dimethyl-4-(1,2,2,2-tetrafluoro-1-trifluoromethyl-ethyl)-phenyl |
| 5-15 | -L-D | H | —CH2CH2— | CONH(CH2)3CH(CO2tBu)NHCO2tBu | H | 0 | phenyl | 2,6-dimethyl-4-(1,2,2,2-tetrafluoro-1-trifluoromethyl-ethyl)-phenyl |
| 5-16 | -L-D | H | —CH2CH2— | CONHCH(CO2tBu)CH2CH2CO2tBu | H | 0 | phenyl | 2,6-dimethyl-4-(1,2,2,2-tetrafluoro-1-trifluoromethyl-ethyl)-phenyl |
| 5-17 | -L-D | H | —CH2CH2— | CONHCH(CO2tBu)(CH2)3CH2NHCO2tBu | H | 0 | phenyl | 2,6-dimethyl-4-(1,2,2,2-tetrafluoro-1-trifluoromethyl-ethyl)-phenyl |
| 5-18 | -L-D | H | —CH2CH2— | CONHCH(CO2tBu)CH2OtBu | H | 0 | phenyl | 2,6-dimethyl-4-(1,2,2,2-tetrafluoro-1-trifluoromethyl-ethyl)-phenyl |
| 5-19 | -L-D | H | —CH2CH2— | CONHCH(CO2tBu)CH2CH2CONH2 | H | 0 | phenyl | 2,6-dimethyl-4-(1,2,2,2-tetrafluoro-1-trifluoromethyl-ethyl)-phenyl |
| 5-20 | -L-D | H | —CH2CH2— | CONHCH2CO2CH2Ph | H | 0 | phenyl | 2,6-dimethyl-4-(1,2,2,2-tetrafluoro-1-trifluoromethyl-ethyl)-phenyl |
| 5-21 | -L-D | H | —CH2CH2— | CONHCH2CONH2 | H | 0 | phenyl | 2,6-dimethyl-4-(1,2,2,2-tetrafluoro-1-trifluoromethyl-ethyl)-phenyl |
| 5-22 | -L-D | H | —CH2CH2— | CO2CH2CH(CO2tBu)NHCO2tBu | H | 0 | phenyl | 2,6-dimethyl-4-(1,2,2,2-tetrafluoro-1-trifluoromethyl-ethyl)-phenyl |
| 5-23 | -L-D | H | —CH2CH2— | CONHCH2CO2H | H | 0 | phenyl | 2,6-dimethyl-4-(1,2,2,2-tetrafluoro-1-trifluoromethyl-ethyl)-phenyl |
| 5-24 | -L-D | H | —CH2CH2— | CONH(CH2)3CH(NH2)CO2H | H | 0 | phenyl | 2,6-dimethyl-4-(1,2,2,2-tetrafluoro-1-trifluoromethyl-ethyl)-phenyl |
| 5-25 | -L-D | H | —CH2CH2— | CO2CH2CH(NH2)CO2H | H | 0 | phenyl | 2,6-dimethyl-4-(1,2,2,2-tetrafluoro-1-trifluoromethyl-ethyl)-phenyl |
| 5-26 | -L-D | H | —CH2CH2— | CONHCH(CO2H)(CH2)4NH2 | H | 0 | phenyl | 2,6-dimethyl-4-(1,2,2,2-tetrafluoro-1-trifluoromethyl-ethyl)-phenyl |
| 5-27 | -L-D | H | —CH2CH2— | CONHCH(CO2H)CH2OH | H | 0 | phenyl | 2,6-dimethyl-4-(1,2,2,2-tetrafluoro-1-trifluoromethyl-ethyl)-phenyl |
| 5-28 | -L-D | H | —CH2CH2— | CONHCH(CO2H)CH2CH2CO2H | H | 0 | phenyl | 2,6-dimethyl-4-(1,2,2,2-tetrafluoro-1-trifluoromethyl-ethyl)-phenyl |
| 5-29 | -L-D | H | —CH2CH2— | CONHCH(CO2H)CH2CH2CONH2 | H | 0 | phenyl | 2,6-dimethyl-4-(1,2,2,2-tetrafluoro-1-trifluoromethyl-ethyl)-phenyl |

TABLE 5-continued

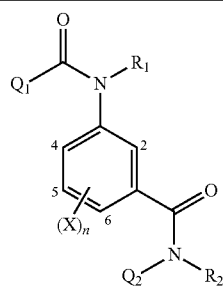

| compound number | R$_1$ | R$_2$ | L | D | X | n | Q$_1$ | Q$_2$ |
|---|---|---|---|---|---|---|---|---|
| 5-30 | -L-D | H | —CH2CH2— | CONHCH(CONH2)CH2CONH2 | H | 0 | phenyl | 2,6-dimethyl-4-(1,2,2,2-tetrafluoro-1-trifluoromethyl-ethyl)-phenyl |
| 5-31 | -L-D | H | —CH2CH2— | CONHCH2CONH2 | 2-F | 1 | 4-cyanophenyl | 2,6-dibromo-4-(1,2,2,2-tetrafluoro-1-trifluoromethyl-ethyl)-phenyl |
| 5-32 | -L-D | H | —CH2CH2— | CONHCH(CONH2)CH2CH2CONH2 | 2-F | 1 | 4-cyanophenyl | 2,6-dibromo-4-(1,2,2,2-tetrafluoro-1-trifluoromethyl-ethyl)-phenyl |
| 5-33 | -L-D | H | —CH2CH2— | CONHOH | 2-F | 1 | 3-cyanophenyl | 2,6-dibromo-4-(1,2,2,2-tetrafluoro-1-trifluoromethyl-ethyl)-phenyl |
| 5-34 | -L-D | H | —CH2CH2— | CONHOH | 2-F | 1 | 4-cyanophenyl | 2,6-dibromo-4-(1,2,2,2-tetrafluoro-1-trifluoromethyl-ethyl)-phenyl |
| 5-35 | -L-D | Me | —CH2CH2— | OH | H | 0 | phenyl | 2,6-dimethyl-4-(1,2,2,2-tetrafluoro-1-trifluoromethyl-ethyl)-phenyl |
| 5-36 | -L-D | H | —CH2CH2— | CONMe2 | H | 0 | 4-cyanophenyl | 2,6-dimethyl-4-(1,2,2,2-tetrafluoro-1-trifluoromethyl-ethyl)-phenyl |
| 5-37 | -L-D | H | —CH2CH2— | CONMe2 | H | 0 | 2-chloropyridin-3-yl | 2,6-dimethyl-4-(1,2,2,2-tetrafluoro-1-trifluoromethyl-ethyl)-phenyl |
| 5-38 | -L-D | H | —CH2CH2— | CO2Me | 2-F | 1 | phenyl | 2,6-dibromo-4-(1,2,2,2-tetrafluoro-1-trifluoromethyl-ethyl)-phenyl |
| 5-39 | -L-D | H | —CH2CH2— | CO2Et | 2-F | 1 | phenyl | 2,6-diiodo-4-(1,2,2,2-tetrafluoro-1-trifluoromethyl-ethyl)-phenyl |
| 5-40 | -L-D | H | —CH2CH2— | CO2iPr | 2-F | 1 | phenyl | 2-bromo-6-trifluoromethyl-4-(1,2,2,2-tetrafluoro-1-trifluoromethyl-ethyl)-phenyl |
| 5-41 | -L-D | H | —CH2CH2— | CO2H | 2-F | 1 | phenyl | 2-iodo-6-trifluoromethyl-4-(1,2,2,2-tetrafluoro-1-trifluoromethyl-ethyl)-phenyl |
| 5-42 | -L-D | H | —CH2CH2— | OH | 2-F | 1 | phenyl | 2,6-dibromo-4-(1,2,2,3,3,3-hexafluoro-1-trifluoromethyl-propyl)-phenyl |
| 5-43 | -L-D | H | —CH2CH2— | NH2 | 2-F | 1 | phenyl | 2,6-diiodo-4-(1,2,2,3,3,3-hexafluoro-1-trifluoromethyl-propyl)-phenyl |
| 5-44 | -L-D | H | —CH2CH2— | NHAc | 2-F | 1 | 4-nitrophenyl | 2-iodo-6-trifluoromethyl-4-(1,2,2,3,3,3-hexafluoro-1-trifluoromethyl-propyl)-phenyl |
| 5-45 | -L-D | H | —CH2CH2— | CN | 2-F | 1 | pyrazin-2-yl | 2,6-dimethyl-4-(1,2,2,2-tetrafluoro-1-trifluoromethyl-ethyl)-phenyl |
| 5-46 | -L-D | H | —CH2CH2— | CONHMe | 2-F | 1 | phenyl | 2,6-dimethyl-4-(1,2,2,2-tetrafluoro-1-trifluoromethyl-ethyl)-phenyl |
| 5-47 | -L-D | H | —CH2CH2— | CONMe2 | 2-F | 1 | phenyl | 2,6-dimethyl-4-(1,2,2,2-tetrafluoro-1-trifluoromethyl-ethyl)-phenyl |
| 5-48 | -L-D | H | —CH2CH2— | CONHiPr | 2-F | 1 | phenyl | 2,6-dimethyl-4-(1,2,2,2-tetrafluoro-1-trifluoromethyl-ethyl)-phenyl |
| 5-49 | -L-D | H | —CH2CH2— | CONHiPr | 2-F | 1 | 4-cyanophenyl | 2,6-dimethyl-4-(1,2,2,2-tetrafluoro-1-trifluoromethyl-ethyl)-phenyl |
| 5-50 | -L-D | H | —CH2CH2— | CONHEt | 2-F | 1 | 2-fluorophenyl | 2,6-dimethyl-4-(1,2,2,2-tetrafluoro-1-trifluoromethyl-ethyl)-phenyl |

TABLE 5-continued

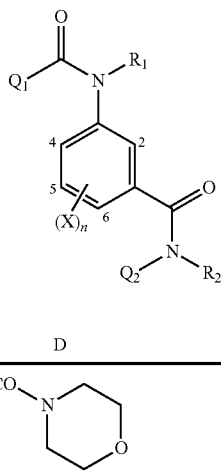

| compound number | R1 | R2 | L | D | X | n | Q1 | Q2 |
|---|---|---|---|---|---|---|---|---|
| 5-51 | -L-D | H | —CH2CH2— | CO-morpholino | 2-F | 1 | phenyl | 2,6-dimethyl-4-(1,2,2,2-tetrafluoro-1-trifluoromethyl-ethyl)-phenyl |
| 5-52 | -L-D | H | —CH2CH2— | CONH(CH2)3CH(CO2tBu)NHCO2tBu | 2-F | 1 | 3-pyrimidyl | 2,6-dimethyl-4-(1,2,2,2-tetrafluoro-1-trifluoromethyl-ethyl)-phenyl |
| 5-53 | -L-D | H | —CH2CH2— | CONHCH(CO2tBu)CH2CH2CO2tBu | 2-F | 1 | phenyl | 2,6-dimethyl-4-(1,2,2,2-tetrafluoro-1-trifluoromethyl-ethyl)-phenyl |
| 5-54 | -L-D | H | —CH2CH2— | CONH2CH(CO2tBu)CH2(CH2)3NHCO2tBu | 2-F | 1 | 2-chloropyridin-3-yl | 2,6-dimethyl-4-(1,2,2,2-tetrafluoro-1-trifluoromethyl-ethyl)-phenyl |
| 5-55 | -L-D | H | —CH2CH2— | CONHCH(CO2tBu)CH2OtBu | 2-F | 1 | phenyl | 2,6-dimethyl-4-(1,2,2,2-tetrafluoro-1-trifluoromethyl-ethyl)-phenyl |
| 5-56 | -L-D | H | —CH2CH2— | CONH2CH(CO2tBu)CH2CH2CONH2 | 2-F | 1 | phenyl | 2,6-dimethyl-4-(1,2,2,2-tetrafluoro-1-trifluoromethyl-ethyl)-phenyl |
| 5-57 | -L-D | H | —CH2CH2— | CONH2CH2CO2CH2Ph | 2-F | 1 | phenyl | 2,6-dimethyl-4-(1,2,2,2-tetrafluoro-1-trifluoromethyl-ethyl)-phenyl |
| 5-58 | -L-D | H | —CH2CH2— | CONH2CH2CONH2 | 2-F | 1 | 6-cyanopyridin-3-yl | 2,6-dimethyl-4-(1,2,2,2-tetrafluoro-1-trifluoromethyl-ethyl)-phenyl |
| 5-59 | -L-D | H | —CH2CH2— | CO2CH2CH(CO2tBu)NHCO2tBu | 2-F | 1 | phenyl | 2,6-dimethyl-4-(1,2,2,2-tetrafluoro-1-trifluoromethyl-ethyl)-phenyl |
| 5-60 | -L-D | H | —CH2CH2— | CONHCH2CO2H | 2-F | 1 | phenyl | 2,6-dimethyl-4-(1,2,2,2-tetrafluoro-1-trifluoromethyl-ethyl)-phenyl |
| 5-61 | -L-D | H | —CH2CH2— | CONH(CH2)3CH(NH2)CO2H | 2-F | 1 | phenyl | 2,6-dimethyl-4-(1,2,2,2-tetrafluoro-1-trifluoromethyl-ethyl)-phenyl |
| 5-62 | -L-D | H | —CH2CH2— | CO2CH2CH(NH2)CO2H | 2-F | 1 | phenyl | 2,6-dimethyl-4-(1,2,2,2-tetrafluoro-1-trifluoromethyl-ethyl)-phenyl |
| 5-63 | -L-D | H | —CH2CH2— | CO2CH2CH(CO2H)(CH2)4NH2 | 2-F | 1 | phenyl | 2,6-dimethyl-4-(1,2,2,2-tetrafluoro-1-trifluoromethyl-ethyl)-phenyl |
| 5-64 | -L-D | H | —CH2CH2— | CONHCH(CO2H)CH2OH | 2-F | 1 | phenyl | 2,6-dimethyl-4-(1,2,2,2-tetrafluoro-1-trifluoromethyl-ethyl)-phenyl |
| 5-65 | -L-D | H | —CH2CH2— | CONHCH(CO2H)CH2CH2CO2H | 2-F | 1 | phenyl | 2,6-dimethyl-4-(1,2,2,2-tetrafluoro-1-trifluoromethyl-ethyl)-phenyl |
| 5-66 | -L-D | H | —CH2CH2— | CONHCH(CO2H)CH2CH2CONH2 | 2-F | 1 | phenyl | 2,6-dimethyl-4-(1,2,2,2-tetrafluoro-1-trifluoromethyl-ethyl)-phenyl |
| 5-67 | -L-D | H | —CH2CH2— | CONHCH(CONH2)CH2CONH2 | 2-F | 1 | phenyl | 2,6-dimethyl-4-(1,2,2,2-tetrafluoro-1-trifluoromethyl-ethyl)-phenyl |
| 5-68 | -L-D | H | —CH2CH2— | OH | 2-F | 1 | phenyl | 2,6-dimethyl-4-(1,2,2,2-tetrafluoro-1-trifluoromethyl-ethyl)-phenyl |
| 5-69 | -L-D | H | —CH2CH2— | CONMe2 | 2-F | 1 | 4-cyanophenyl | 2,6-dimethyl-4-(1,2,2,2-tetrafluoro-1-trifluoromethyl-ethyl)-phenyl |
| 5-70 | -L-D | H | —CH2CH2— | CONMe2 | 2-F | 1 | 2-chloropyridin-3-yl | 2,6-dimethyl-4-(1,2,2,2-tetrafluoro-1-trifluoromethyl-ethyl)-phenyl |

TABLE 5-continued

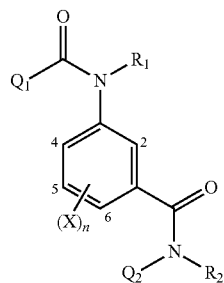

| compound number | $R_1$ | $R_2$ | L | D | X | n | $Q_1$ | $Q_2$ |
|---|---|---|---|---|---|---|---|---|
| 5-71 | -L-D | H | —CH2CH2— | SMe | H | 0 | phenyl | 2,6-dimethyl-4-(1,2,2,2-tetrafluoro-1-trifluoromethyl-ethyl)-phenyl |
| 5-72 | -L-D | H | —CH2CH2— | SOMe | H | 0 | phenyl | 2,6-dimethyl-4-(1,2,2,2-tetrafluoro-1-trifluoromethyl-ethyl)-phenyl |
| 5-73 | -L-D | H | —CH2CH2— | SO2Me | H | 0 | phenyl | 2,6-dimethyl-4-(1,2,2,2-tetrafluoro-1-trifluoromethyl-ethyl)-phenyl |
| 5-74 | -L-D | H | —CH2CH2— | OCH2Ph | H | 0 | phenyl | 2,6-dimethyl-4-(1,2,2,2-tetrafluoro-1-trifluoromethyl-ethyl)-phenyl |
| 5-75 | -L-D | H | —CH2CH2— | OCH2CH2OMe | H | 0 | phenyl | 2,6-dimethyl-4-(1,2,2,2-tetrafluoro-1-trifluoromethyl-ethyl)-phenyl |
| 5-76 | -L-D | H | —CH2CH2— | CONHCO2Et | 2-F | 1 | 4-cyanophenyl | 2-bromo-6-trifluoromethyl-4-(1,2,2,2-tetrafluoro-1-trifluoromethyl-ethyl)-phenyl |
| 5-77 | -L-D | H | —CH2CH2— | CONMe2 | H | 0 | phenyl | 2-iodo-6-trifluoromethyl-4-(1,2,2,2-tetrafluoro-1-trifluoromethyl-ethyl)-phenyl |
| 5-78 | -L-D | H | —CH2CH2— | CONMe2 | H | 0 | 4-cyanophenyl | 2-iodo-6-trifluoromethyl-4-(1,2,2,2-tetrafluoro-1-trifluoromethyl-ethyl)-phenyl |
| 5-79 | -L-D | H | —CH2CH2— | CONMe2 | H | 0 | 2-chloro-4-fluorophenyl | 2-iodo-6-trifluoromethyl-4-(1,2,2,2-tetrafluoro-1-trifluoromethyl-ethyl)-phenyl |
| 5-80 | -L-D | H | —CH2CH2— | CO2Me | H | 0 | phenyl | 2-iodo-6-trifluoromethyl-4-(1,2,2,2-tetrafluoro-1-trifluoromethyl-ethyl)-phenyl |
| 5-81 | -L-D | H | —CH2CH2— | CONHNH2 | H | 0 | phenyl | 2-iodo-6-trifluoromethyl-4-(1,2,2,2-tetrafluoro-1-trifluoromethyl-ethyl)-phenyl |
| 5-82 | -L-D | H | —CH2CH2— | CONMe2 | H | 0 | 3-cyanophenyl | 2-iodo-6-trifluoromethyl-4-(1,2,2,2-tetrafluoro-1-trifluoromethyl-ethyl)-phenyl |
| 5-83 | -L-D | H | —CH2CH2— | CONHNH2 | 2-F | 1 | 4-cyanophenyl | 2,6-dimethyl-4-(1,2,2,2-tetrafluoro-1-trifluoromethyl-ethyl)-phenyl |
| 5-84 | -L-D | H | —CH2CH2— | OCH2CH2OH | H | 0 | phenyl | 2,6-dimethyl-4-(1,2,2,2-tetrafluoro-1-trifluoromethyl-ethyl)-phenyl |
| 5-85 | -L-D | H | —CH2CH2— | OCH2CH2OH | H | 0 | phenyl | 2,6-dimethyl-4-(1,2,2,2-tetrafluoro-1-trifluoromethyl-ethyl)-phenyl |
| 5-86 | -L-D | H | —CH2CH2— | CONHMe | H | 0 | phenyl | 2-iodo-6-trifluoromethyl-4-(1,2,2,2-tetrafluoro-1-trifluoromethyl-ethyl)-phenyl |
| 5-87 | -L-D | H | —CH2CH2— | CONMe2 | 2-F | 1 | phenyl | 2-iodo-6-trifluoromethyl-4-(1,2,2,2-tetrafluoro-1-trifluoromethyl-ethyl)-phenyl |
| 5-88 | -L-D | H | —CH2CH2— | CO2H | H | 0 | phenyl | 2-iodo-6-trifluoromethyl-4-(1,2,2,2-tetrafluoro-1-trifluoromethyl-ethyl)-phenyl |
| 5-89 | -L-D | H | —CH2CH2— | OCH2CH2OCH2Ph | H | 0 | phenyl | 2,6-dimethyl-4-(1,2,2,2-tetrafluoro-1-trifluoromethyl-ethyl)-phenyl |
| 5-90 | -L-D | H | —CH2CH2— | OCH2CH2OCH2Ph | H | 0 | phenyl | 2,6-dimethyl-4-(1,2,2,2-tetrafluoro-1-trifluoromethyl-ethyl)-phenyl |

TABLE 5-continued

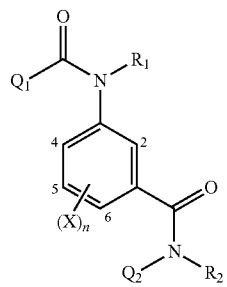

| compound number | R₁ | R₂ | L | D | X | n | Q₁ | Q₂ |
|---|---|---|---|---|---|---|---|---|
| 5-91 | -L-D | H | —CH2CH2— | C(=NOH)NH2 | H | 0 | phenyl | 2,6-dimethyl-4-(1,2,2,2-tetrafluoro-1-trifluoromethyl-ethyl)-phenyl |
| 5-92 | -L-D | H | —CH2CH2— | CONHCH2CN | 2-F | 1 | 4-cyanophenyl | 2,6-dimethyl-4-(1,2,2,2-tetrafluoro-1-trifluoromethyl-ethyl)-phenyl |
| 5-93 | -L-D | H | —CH2CH2— | CO2CH2CH2NMe2 | H | 0 | phenyl | 2-iodo-6-trifluoromethyl-4-(1,2,2,2-tetrafluoro-1-trifluoromethyl-ethyl)-phenyl |
| 5-94 | -L-D | H | —CH2CH2— | CO2CH2CH2NMe2 | H | 0 | 3-cyanophenyl | 2-iodo-6-trifluoromethyl-4-(1,2,2,2-tetrafluoro-1-trifluoromethyl-ethyl)-phenyl |
| 5-95 | -L-D | H | —CH2CH2— | CO2CH2CH2NMe2 | H | 0 | 4-cyanophenyl | 2-iodo-6-trifluoromethyl-4-(1,2,2,2-tetrafluoro-1-trifluoromethyl-ethyl)-phenyl |
| 5-96 | -L-D | H | —CH2CH2— | CONMe2 | H | 0 | pyridin-3-yl | 2-iodo-6-trifluoromethyl-4-(1,2,2,2-tetrafluoro-1-trifluoromethyl-ethyl)-phenyl |
| 5-97 | -L-D | H | —CH2CH2— | CONMe2 | H | 0 | pyridin-3-yl N-oxide | 2-iodo-6-trifluoromethyl-4-(1,2,2,2-tetrafluoro-1-trifluoromethyl-ethyl)-phenyl |
| 5-98 | -L-D | H | —CH2CH2— | CHO | H | 0 | phenyl | 2,6-dimethyl-4-(1,2,2,2-tetrafluoro-1-trifluoromethyl-ethyl)-phenyl |
| 5-99 | -L-D | H | —CH2CH2— | C(=NOH)NH2 | H | 0 | phenyl | 2,6-diiodo-4-(1,2,2,2-tetrafluoro-1-trifluoromethyl-ethyl)-phenyl |
| 5-100 | -L-D | H | —CH2CH2— | Ac | H | 0 | phenyl | 2,6-dimethyl-4-(1,2,2,2-tetrafluoro-1-trifluoromethyl-ethyl)-phenyl |
| 5-101 | -L-D | H | —CH2CH2— | CONMe2 | 2-F | 1 | pyridin-3-yl | 2-iodo-6-trifluoromethyl-4-(1,2,2,2-tetrafluoro-1-trifluoromethyl-ethyl)-phenyl |
| 5-102 | -L-D | H | —CH2CH2— | CONMe2 | 2-F | 1 | pyridin-3-yl N-oxide | 2-iodo-6-trifluoromethyl-4-(1,2,2,2-tetrafluoro-1-trifluoromethyl-ethyl)-phenyl |
| 5-103 | -L-D | H | —CH2CH2— | CONMe2 | H | 0 | phenyl | 2-bromo-6-trifluoromethylsulfinyl-4-(1,2,2,2-tetrafluoro-1-trifluoromethyl-ethyl)-phenyl |
| 5-104 | -L-D | H | —CH2CH2— | CONMe2 | H | 0 | 2-chloropyridin-3-yl | 2-bromo-6-trifluoromethylsulfinyl-4-(1,2,2,2-tetrafluoro-1-trifluoromethyl-ethyl)-phenyl |
| 5-105 | -L-D | H | —CH2CH2— | C(=NOH)Me | H | 0 | phenyl | 2,6-dimethyl-4-(1,2,2,2-tetrafluoro-1-trifluoromethyl-ethyl)-phenyl |
| 5-106 | -L-D | H | —CH2CH2— | CONHC(CH2OH)3 | H | 0 | phenyl | 2,6-dimethyl-4-(1,2,2,2-tetrafluoro-1-trifluoromethyl-ethyl)-phenyl |
| 5-107 | -L-D | H | —CH2CH2— | CONHCH2OCH2OMe | H | 0 | phenyl | 2,6-dimethyl-4-(1,2,2,2-tetrafluoro-1-trifluoromethyl-ethyl)-phenyl |
| 5-108 | -L-D | H | —CH2CH2— | CN | 2-F | 1 | pyrazin-5-yl | 2,6-dibromo-4-(1,2,2,2-tetrafluoro-1-trifluoromethyl-ethyl)-phenyl |
| 5-109 | -L-D | H | —CH2CH2— | NMe2 | H | 0 | phenyl | 2,6-dimethyl-4-(1,2,2,2-tetrafluoro-1-trifluoromethyl-ethyl)-phenyl |
| 5-110 | -L-D | H | —CH2CH2— | NMe3⁺ I⁻ | H | 0 | phenyl | 2,6-dimethyl-4-(1,2,2,2-tetrafluoro-1-trifluoromethyl-ethyl)-phenyl |

TABLE 5-continued

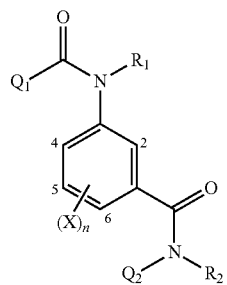

| compound number | $R_1$ | $R_2$ | L | D | X | n | $Q_1$ | $Q_2$ |
|---|---|---|---|---|---|---|---|---|
| 5-111 | -L-D | H | —CH2CH2— | CN | H | 0 | 3-fluorophenyl | 2,6-diiodo-4-(1,2,2,2-tetrafluoro-1-trifluoromethyl-ethyl)-phenyl |
| 5-112 | -L-D | H | —CH2CH2— | CN | H | 0 | phenyl | 2,6-diiodo-4-(1,2,2,2-tetrafluoro-1-trifluoromethyl-ethyl)-phenyl |
| 5-113 | -L-D | H | —CH2CH2— | CONMe2 | 4-F | 1 | phenyl | 2,6-diiodo-4-(1,2,2,2-tetrafluoro-1-trifluoromethyl-ethyl)-phenyl |
| 5-114 | -L-D | H | —CH2CH2— | CONMe2 | 4-F | 1 | 4-cyanophenyl | 2-bromo-6-trifluoromethyl-4-(1,2,2,2-tetrafluoro-1-trifluoromethyl-ethyl)-phenyl |
| 5-115 | -L-D | H | —CH2CH2— | CONMe2 | 4-F | 1 | 3-cyanophenyl | 2-iodo-6-trifluoromethyl-4-(1,2,2,2-tetrafluoro-1-trifluoromethyl-ethyl)-phenyl |
| 5-116 | -L-D | H | —CH2CH2— | CONMe2 | 4-F | 1 | 2-chloropyridin-3-yl | 2-bromo-6-trifluoromethyl-4-(1,2,2,3,3,3-hexafluoro-1-trifluoromethyl-propyl)-phenyl |
| 5-117 | -L-D | H | —CH2CH2— | CONMe2 | 4-F | 1 | 2-fluorophenyl | 2-iodo-6-trifluoromethyl-4-(1,2,2,3,3,3-hexafluoro-1-trifluoromethyl-propyl)-phenyl |
| 5-118 | -L-D | H | —CH2CH2— | CONMe2 | 4-CN | 1 | phenyl | 2,6-dibromo-4-(1,2,2,2-tetrafluoro-1-trifluoromethyl-ethyl)-phenyl |
| 5-119 | -L-D | H | —CH2CH2— | CONMe2 | 4-CN | 1 | 4-cyanophenyl | 2-bromo-6-trifluoromethyl-4-(1,2,2,2-tetrafluoro-1-trifluoromethyl-ethyl)-phenyl |
| 5-120 | -L-D | H | —CH2CH2— | CONMe2 | 4-CN | 1 | 3-cyanophenyl | 2-iodo-6-trifluoromethyl-4-(1,2,2,2-tetrafluoro-1-trifluoromethyl-ethyl)-phenyl |
| 5-121 | -L-D | H | —CH2CH2— | CONMe2 | 4-CN | 1 | 2-chloropyridin-3-yl | 2-bromo-6-trifluoromethyl-4-(1,2,2,3,3,3-hexafluoro-1-trifluoromethyl-propyl)-phenyl |
| 5-122 | -L-D | H | —CH2CH2— | CONMe2 | 4-CN | 1 | 2-fluorophenyl | 2-iodo-6-trifluoromethyl-4-(1,2,2,3,3,3-hexafluoro-1-trifluoromethyl-propyl)-phenyl |
| 5-123 | -L-D | H | —CH2CH2— | CONMe2 | 2-NO2 | 1 | phenyl | 2,6-dibromo-4-(1,2,2,2-tetrafluoro-1-trifluoromethyl-ethyl)-phenyl |
| 5-124 | -L-D | H | —CH2CH2— | CONMe2 | 2-NO2 | 1 | 4-cyanophenyl | 2-bromo-6-trifluoromethyl-4-(1,2,2,2-tetrafluoro-1-trifluoromethyl-ethyl)-phenyl |
| 5-125 | -L-D | H | —CH2CH2— | CONMe2 | 2-NO2 | 1 | 3-cyanophenyl | 2-iodo-6-trifluoromethyl-4-(1,2,2,2-tetrafluoro-1-trifluoromethyl-ethyl)-phenyl |
| 5-126 | -L-D | H | —CH2CH2— | CONMe2 | 2-NO2 | 1 | 2-chloropyridin-3-yl | 2-bromo-6-trifluoromethyl-4-(1,2,2,3,3,3-hexafluoro-1-trifluoromethyl-propyl)-phenyl |
| 5-127 | -L-D | H | —CH2CH2— | CONMe2 | 2-NO2 | 1 | 2-fluorophenyl | 2-iodo-6-trifluoromethyl-4-(1,2,2,3,3,3-hexafluoro-1-trifluoromethyl-propyl)-phenyl |
| 5-128 | -L-D | H | —CH2CH2— | CO2CH2CH2NMe2 | H | 0 | 2-chloropyridin-3-yl | 2-iodo-6-trifluoromethyl-4-(1,2,2,2-tetrafluoro-1-trifluoromethyl-ethyl)-phenyl |

TABLE 6

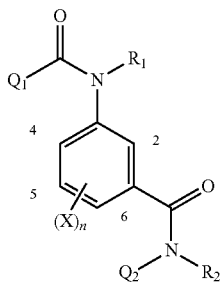

| compound number | R₁ | R₂ | L | D | X | n | Q₁ | Q₂ |
|---|---|---|---|---|---|---|---|---|
| 6-1 | —L—D | Me | —CH2— | CO2Me | H | 0 | phenyl | 2,6-dimethyl-4-(1,2,2,2-tetrafluoro-1-trifluoromethyl-ethyl)-phenyl |
| 6-2 | —L—D | H | —CH2— | CO2Me | H | 0 | phenyl | 2,6-dimethyl-4-(1,2,2,2-tetrafluoro-1-trifluoromethyl-ethyl)-phenyl |
| 6-3 | —L—D | Me | —CH2— | CO2H | H | 0 | phenyl | 2,6-dimethyl-4-(1,2,2,2-tetrafluoro-1-trifluoremethyl-ethyl)-phenyl |
| 6-4 | —L—D | H | —CH2— | CO2H | H | 0 | phenyl | 2,6-dimethyl-4-(1,2,2,2-tetrafluoro-1-trifluoromethyl-ethyl)-phenyl |
| 6-5 | —L—D | Me | —CH2— | CO2Et | H | 0 | phenyl | 2,6-dimethyl-4-(1,2,2,2-tetrafluoro-1-trifluoromethyl-ethyl)-phenyl |
| 6-6 | —L—D | Me | —CH2— | SMe | H | 0 | phenyl | 2,6-dimethyl-4-(1,2,2,2-tetrafluoro-1-trifluoromethyl-ethyl)-phenyl |
| 6-7 | —L—D | Me | —CH2— | SOMe | H | 0 | phenyl | 2,6-dimethyl-4-(1,2,2,2-tetrafluoro-1-trifluoromethyl-ethyl)-phenyl |
| 6-8 | —L—D | Me | —CH2— | SO2Me | H | 0 | phenyl | 2,6-dimethyl-4-(1,2,2,2-tetrafluoro-1-trifluoromethyl-ethyl)-phenyl |
| 6-9 | —L—D | H | —CH(CH3)CH2— | CONH2 | H | 0 | phenyl | 2,6-dimethyl-4-(1,2,2,2-tetrafluoro-1-trifluoromethyl-ethyl)-phenyl |
| 6-10 | —L—D | H | —CH2CH(CH3)— | CONH2 | H | 0 | phenyl | 2,6-dimethyl-4-(1,2,2,2-tetrafluoro-1-trifluoromethyl-ethyl)-phenyl |
| 6-11 | —L—D | Me | —CH2CH2CH2— | NH2 | H | 0 | phenyl | 2,6-dimethyl-4-(1,2,2,2-tetrafluoro-1-trifluoromethyl-ethyl)-phenyl |
| 6-12 | —L—D | Me | —CH2— | CONH2 | H | 0 | phenyl | 2,6-dimethyl-4-(1,2,2,2-tetrafluoro-1-trifluoromethyl-ethyl)-phenyl |
| 6-13 | —L—D | Me | —CH2CH2CH2— | CO2Me | H | 0 | phenyl | 2,6-dimethyl-4-(1,2,2,2-tetrafluoro-1-trifluoromethyl-ethyl)-phenyl |
| 6-14 | —L—D | Me | —CH2CH2CH2— | CO2H | H | 0 | phenyl | 2,6-dimethyl-4-(1,2,2,2-tetrafluoro-1-trifluoromethyl-ethyl)-phenyl |
| 6-15 | —L—D | Me | —CH2CH2CH2— | CONH2 | H | 0 | phenyl | 2,6-dimethyl-4-(1,2,2,2-tetrafluoro-1-trifluoromethyl-ethyl)-phenyl |
| 6-16 | —L—D | H | —CH2CH2CH2— | CONH2 | H | 0 | phenyl | 2,6-dimethyl-4-(1,2,2,2-tetrafluoro-1-trifluoremethyl-ethyl)-phenyl |
| 6-17 | —L—D | H | —CH2— | CONH2 | H | 0 | phenyl | 2,6-dimethyl-4-(1,2,2,2-tetrafluoro-1-trifluoromethyl-ethyl)-phenyl |
| 6-18 | —L—D | Me | —CH2— | CN | H | 0 | phenyl | 2,6-dimethyl-4-(1,2,2,2-tetrafluoro-1-trifluoromethyl-ethyl)-phenyl |
| 6-19 | —L—D | H | —CH2— | CN | H | 0 | pyrazin-2-yl | 2,6-dimethyl-4-(1,2,2,2-tetrafluoro-1-trifluoromethyl-ethyl)-phenyl |
| 6-20 | —L—D | H | —CH2CH2CH2— | NH2 | H | 0 | phenyl | 2,6-dimethyl-4-(1,2,2,2-tetrafluoro-1-trifluoromethyl-ethyl)-phenyl |
| 6-21 | —L—D | Me | —CH2— | CO2Me | 2-F | 1 | phenyl | 2,6-dimethyl-4-(1,2,2,2-tetrafluoro-1-trifluoromethyl-ethyl)-phenyl |
| 6-22 | —L—D | H | —CH2— | CO2Me | 2-F | 1 | 3-cyanophenyl | 2,6-dimethyl-4-(1,2,2,2-tetrafluoro-1-trifluoromethyl-ethyl)-phenyl |
| 6-23 | —L—D | Me | —CH2— | CO2H | 2-F | 1 | phenyl | 2,6-dimethyl-4-(1,2,2,2-tetrafluoro-1-trifluoromethyl-ethyl)-phenyl |
| 6-24 | —L—D | H | —CH2— | CO2H | 2-F | 1 | 4-cyanophenyl | 2,6-dimethyl-4-(1,2,2,2-tetrafluoro-1-trifluoromethyl-ethyl)-phenyl |
| 6-25 | —L—D | H | —CH2— | CO2Et | 2-F | 1 | phenyl | 2,6-dimethyl-4-(1,2,2,2-tetrafluoro-1-trifluoromethyl-ethyl)-phenyl |
| 6-26 | —L—D | Me | —CH2— | SMe | 2-F | 1 | phenyl | 2,6-dibromo-4-(1,2,2,2-tetrafluoro-1-trifluoromethyl-ethyl)-phenyl |
| 6-27 | —L—D | Me | —CH2— | SOMe | 2-F | 1 | phenyl | 2-iodo-6-trifluoromethyl-4-(1,2,2,2-tetrafluoro-1-trifluoromethyl-ethyl)-phenyl |
| 6-28 | —L—D | Me | —CH2— | SO2Me | 2-F | 1 | 2-fluorophenyl | 2,6-dimethyl-4-(1,2,2,2-tetrafluoro-1-trifluoromethyl-ethyl)-phenyl |
| 6-29 | —L—D | H | —CH(CH3)CH2— | CONH2 | 2-F | 1 | phenyl | 2-bromo-6-trifluoromethyl-4-(1,2,2,2-tetrafluoro-1-trifluoromethyl-ethyl)-phenyl |
| 6-30 | —L—D | H | —CH2CH(CH3)— | CONH2 | 2-F | 1 | phenyl | 2,6-diiodo-4-(1,2,2,2-tetrafluoro-1-trifluoromethyl-ethyl)-phenyl |

TABLE 6-continued

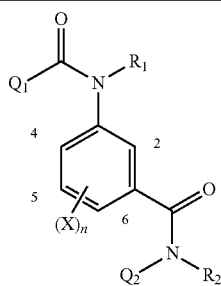

| compound number | R₁ | R₂ | L | D | X | n | Q₁ | Q₂ |
|---|---|---|---|---|---|---|---|---|
| 6-31 | —L—D | Me | —CH2CH2CH2— | NH2 | 2-F | 1 | 3-thienyl | 2,6-dimethyl-4-(1,2,2,2-tetrafluoro-1-trifluoromethyl-ethyl)-phenyl |
| 6-32 | —L—D | Me | —CH2— | CONH2 | 2-F | 1 | 6-cyanopyridin-3-yl | 2-iodo-6-trifluoromethyl-4-(1,2,2,3,3,3-hexafluoro-1-trifluoromethyl-propyl)-phenyl |
| 6-33 | —L—D | Me | —CH2CH2CH2— | CONH2 | 2-F | 1 | phenyl | 2,6-dimethyl-4-(1,2,2,2-tetrafluoro-1-trifluoromethyl-ethyl)-phenyl |
| 6-34 | —L—D | Me | —CH2CH2CH2— | CO2H | 2-F | 1 | 2-chloro-3-pyridyl | 2,6-dimethyl-4-(1,2,2,2-tetrafluoro-1-trifluoromethyl-ethyl)-phenyl |
| 6-35 | —L—D | Me | —CH2CH2CH2— | CONH2 | 2-F | 1 | phenyl | 2-bromo-6-trifluoromethyl-4-(1,2,2,3,3,3-hexafluoro-1-trifluoromethyl-propyl)-phenyl |
| 6-36 | —L—D | H | —CH2CH2CH2— | CONH2 | 2-F | 1 | phenyl | 2,6-dimethyl-4-(1,2,2,2-tetrafluoro-1-trifluoromethyl-ethyl)-phenyl |
| 6-37 | —L—D | H | —CH2— | CONH2 | 2-F | 1 | phenyl | 2,6-dibromo-4-(1,2,2,3,3,3-hexafluoro-1-trifluoromethyl-propyl)-phenyl |
| 6-38 | —L—D | Me | —CH2— | CN | 2-F | 1 | 2-furyl | 2,6-dimethyl-4-(1,2,2,2-tetrafluoro-1-trifluoromethyl-ethyl)-phenyl |
| 6-39 | —L—D | H | —CH2— | CN | 2-F | 1 | phenyl | 2,6-dimethyl-4-(1,2,2,2-tetrafluoro-1-trifluoromethyl-ethyl)-phenyl |
| 6-40 | —L—D | H | —CH2CH2CH2— | NH2 | 2-F | 1 | phenyl | 2,6-dimethyl-4-(1,2,2,2-tetrafluoro-1-trifluoromethyl-ethyl)-phenyl |
| 6-41 | —L—D | H | —CH2— | OEt | 2-F | 1 | phenyl | 2,6-dimethyl-4-(1,2,2,2-tetrafluoro-1-trifluoromethyl-ethyl)-phenyl |
| 6-42 | —L—D | Me | —CH2CH(OH)CH2— | OH | H | 0 | phenyl | 2,6-dimethyl-4-(1,2,2,2-tetrafluoro-1-trifluoromethyl-ethyl)-phenyl |
| 6-43 | —L—D | H | —CH2CH(CO2C(CH3)3)— | CO2C(CH3)3 | 2-F | 1 | phenyl | 2,6-dibromo-4-(1,2,2,2-tetrafluoro-1-trifluoromethyl-ethyl)-phenyl |
| 6-44 | —L—D | H | —CH2CH(CO2C(CH3)3)— | CO2C(CH3)3 | 2-F | 1 | 3-cyanophenyl | 2,6-dibromo-4-(1,2,2,2-tetrafluoro-1-trifluoromethyl-ethyl)-phenyl |
| 6-45 | —L—D | H | —CH2CH(CO2C(CH3)3)— | CO2C(CH3)3 | 2-F | 1 | 4-cyanophenyl | 2,6-dibromo-4-(1,2,2,2-tetrafluoro-1-trifluoromethyl-ethyl)-phenyl |
| 6-46 | —L—D | H | —CH2CH2CH2— | OH | H | 0 | phenyl | 2,6-dimethyl-4-(1,22,2-tetrafluoro-1-trifluoromethyl-ethyl)-phenyl |
| 6-47 | —L—D | H | —CH2CH2CH2— | OCH2Ph | H | 0 | phenyl | 2,6-dimethyl-4-(1,2,2,2-tetrefluoro-1-trifluoromethyl-ethy0-phenyl |
| 6-48 | —L—D | H | —CH2CH(OH)CH2— | OH | H | 0 | phenyl | 2,6-dimethyl-4-(1,2,2,2-tetrafluoro-1-trifluoromethyl-ethyl)-phenyl |
| 6-49 | —L—D | H | —CH2CH2CH2— | NHCONHMe | H | 0 | phenyl | 2,6-dimethyl-4-(1,2,2,2-tetrafluoro-1-trifluoromethyl-ethyl)-phenyl |
| 6-50 | —L—D | H | —CH2CH2CH2— | OCOMe | H | 0 | phenyl | 2,6-dimethyl-4-(1,2,2,2-tetrafluoro-1-trifluoromethyl-ethyl)-phenyl |
| 6-51 | —L—D | H | —CH2CH2CH2CH2— | OCH2Ph | H | 0 | phenyl | 2,6-dimethyl-4-(1,2,2,2-tetrafluoro-1-trifluoromethyl-ethyl)-phenyl |
| 6-52 | —L—D | H | —CH2CH2CH2CH2— | OH | H | 0 | phenyl | 2,6-dimethyl-4-(1,2,2,2-tetrafluoro-1-trifluoromethyl-ethyl)-phenyl |
| 6-53 | —L—D | H | —CH2CH2CH2CH2CH2— | OCH2Ph | H | 0 | phenyl | 2,6-dimethyl-4-(1,2,2,2-tetrafluoro-1-trifluoromethyl-ethyl)-phenyl |
| 6-54 | —L—D | H | —CH2CH2CH2CH2CH2— | OH | H | 0 | phenyl | 2,6-dimethyl-4-(1,2,2,2-tetrafluoro-1-trifluoromethyl-ethyl)-phenyl |
| 6-55 | —L—D | H | —CH2CH2CH2— | OH | H | 0 | phenyl | 2-iodo-6-trifluoromethyl-4-(1,2,2,2-tetrafluoro-1-trifluoromethyl-ethyl)-phenyl |
| 6-56 | —L—D | Me | —CH2CH2CH2CH2CH2— | OCOCH2Br | H | 0 | phenyl | 2,6-dimethyl-4-(1,2,2,2-tetrafluoro-1-trifluoromethyl-ethyl)-phenyl |
| 6-57 | —L—D | H | —CH2CH2CH2CH2— | CHO | H | 0 | phenyl | 2,6-dimethyl-4-(1,2,2,2-tetrafluoro-1-trifluoromethyl-ethyl)-phenyl |
| 6-58 | —L—D | H | —CH2CH2CH2— | CHO | H | 0 | phenyl | 2,6-dimethyl-4-(1,2,2,2-tetrafluoro-1-trifluoromethyl-ethyl)-phenyl |
| 6-59 | —L—D | H | —CH2— | CHO | H | 0 | phenyl | 2,6-dimethyl-4-(1,2,2,2-tetrafluoro-1-trifluoromethyl-ethyl)-phenyl |

TABLE 6-continued

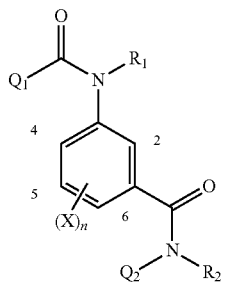

| compound number | R1 | R2 | L | D | X | n | Q1 | Q2 |
|---|---|---|---|---|---|---|---|---|
| 6-60 | —L—D | H | —CH2CH2CH2— | NHC(=NH)NH2 | H | 0 | phenyl | 2,6-dimethyl-4-(1,2,2,2-tetrafluoro-1-trifluoromethyl-ethyl)-phenyl |
| 6-61 | —L—D | H | —CH2CH2CH2— | NHC(=NNO2)NH2 | H | 0 | phenyl | 2,6-dimethyl-4-(1,2,2,2-tetrafluoro-1-trifluoromethylethyl)-phenyl |
| 6-62 | —L—D | Me | —CH2CH2CH2— | NMe2 | H | 0 | phenyl | 2,6-dimethyl-4-(1,2,2,2-tetrafluoro-1-trifluoromethyl-ethyl)-phenyl |
| 6-63 | —L—D | H | —CH2— |  | H | 0 | phenyl | 2,6-dimethyl-4-(1,2,2,2-tetrafluoro-1-trifluoromethyl-ethyl)-phenyl |
| 6-64 | —L—D | H | —CH2CH2CH2— | CN | H | 0 | phenyl | 2,6-dimethyl-4-(1,2,2,2-tetrafluoro-1-trifluoromethyl-ethyl)-phenyl |
| 6-65 | —L—D | H | —CH2CH2CH2— | CONMe2 | 4-F | 1 | phenyl | 2-bromo-6-trifluoromethyl-4-(1,2,2,2-tetrafluoro-1-trifluoromethyl-ethyl)-phenyl |
| 6-66 | —L—D | H | —CH2CH2CH2— | CONMe2 | 4-CN | 1 | phenyl | 2-iodo-6-trifluoromethyl-4-(1,2,2,2-tetrafluoro-1-trifluoromethyl-ethyl)-phenyl |
| 6-67 | —L—D | H | —CH2CH2CH2— | CONMe2 | 2-NO2 | 1 | phenyl | 2-bromo-6-trifluoromethyl-4-(1,2,2,3,3,3-hexafluoro-1-trifluoromethyl-propyl)-phenyl |
| 6-68 | —L—D | Me | —CH2CH2CH2CH2CH2— | OCH2Ph | H | 0 | phenyl | 2,6-dimethyl-4-(1,2,2,2-tetrafluoro-1-trifluoromethyl-ethyl)-phenyl |
| 6-69 | —L—D | Me | —CH2CH2CH2CH2CH2— | OH | H | 0 | phenyl | 2,6-dimethyl-4-(1,2,2,2-tetrafluoro-1-trifluoromethyl-ethyl)-phenyl |

TABLE 7

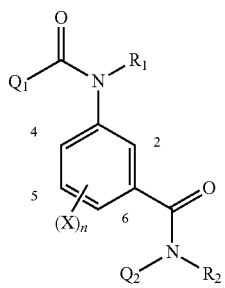

| compound number | R1 | R2 | L | D | X | n | Q1 | Q2 |
|---|---|---|---|---|---|---|---|---|
| 7-1 | H | —L—D | —CH2CH2— | CONH2 | H | 0 | phenyl | 2,6-dimethyl-4-(1,2,2,2-tetrafluoro-1-trifluoromethyl-ethyl)-phenyl |
| 7-2 | H | —L—D | —CH2CH2— | CONH2 | H | 0 | 4-cyanophenyl | 2,6-dimethyl-4-(1,2,2,2-tetrafluoro-1-trifluoromethyl-ethyl)-phenyl |
| 7-3 | H | —L—D | —CH2CH2— | SO2Me | H | 0 | 3-cyanophenyl | 2,6-dimethyl-4-(1,2,2,2-tetrafluoro-1-trifluoromethyl-ethyl)-phenyl |
| 7-4 | H | —L—D | —CH2CH2— | CONH2 | H | 0 | 3,5-dicyanophenyl | 2,6-dimethyl-4-(1,2,2,2-tetrafluoro-1-trifluoromethyl-ethyl)-phenyl |
| 7-5 | H | —L—D | —CH2CH2— | SOMe | H | 0 | 2-fluorophenyl | 2,6-dimethyl-4-(1,2,2,2-tetrafluoro-1-trifluoromethyl-ethyl)-phenyl |
| 7-6 | H | —L—D | —CH2CH2— | CO2Me | H | 0 | phenyl | 2,6-dimethyl-4-(1,2,2,2-tetrafluoro-1-trifluoromethyl-ethyl)-phenyl |
| 7-7 | H | —L—D | —CH2CH2— | CN | H | 0 | 2,6-difluorophenyl | 2,6-dimethyl-4-(1,2,2,2-tetrafluoro-1-trifluoromethyl-ethyl)-phenyl |

TABLE 7-continued

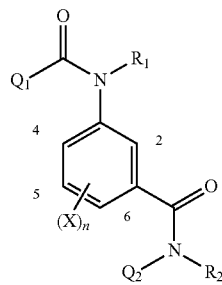

| compound number | R₁ | R₂ | L | D | X | n | Q₁ | Q₂ |
|---|---|---|---|---|---|---|---|---|
| 7-8 | H | —L—D | —CH2CH2— | CONH2 | H | 0 | 2-fluoro-4-cyanophenyl | 2,6-dimethyl-4-(1,2,2,2-tetrafluoro-1-trifluoromethyl-ethyl)-phenyl |
| 7-9 | H | —L—D | —CH2CH2— | CONH2 | H | 0 | 2-chlorophenyl | 2,6-dimethyl-4-(1,2,2,2-tetrafluoro-1-trifluoromethyl-ethyl)-phenyl |
| 7-10 | H | —L—D | —CH2CH2— | CONH2 | H | 0 | 4-chlorophenyl | 2,6-dimethyl-4-(1,2,2,2-tetrafluoro-1-trifluoromethyl-ethyl)-phenyl |
| 7-11 | H | —L—D | —CH2CH2— | CONH2 | H | 0 | 4-nitrophenyl | 2,6-dimethyl-4-(1,2,2,2-tetrafluoro-1-trifluoromethyl-ethyl)-phenyl |
| 7-12 | H | —L—D | —CH2CH2— | CONH2 | H | 0 | 2-methylphenyl | 2,6-dimethyl-4-(1,2,2,2-tetrafluoro-1-trifluoromethyl-ethyl)-phenyl |
| 7-13 | H | —L—D | —CH2CH2— | CONH2 | H | 0 | pyridin-2-yl | 2,6-dimethyl-4-(1,2,2,2-tetrafluoro-1-trifluoromethyl-ethyl)-phenyl |
| 7-14 | H | —L—D | —CH2CH2— | CONH2 | H | 0 | pyridin-3-yl | 2,6-dimethyl-4-(1,2,2,2-tetrafluoro-1-trifluoromethyl-ethyl)-phenyl |
| 7-15 | H | —L—D | —CH2CH2— | CONH2 | H | 0 | pyridin-4-yl | 2,6-dimethyl-4-(1,2,2,2-tetrafluoro-1-trifluoromethyl-ethyl)-phenyl |
| 7-16 | H | —L—D | —CH2CH2— | CONH2 | H | 0 | 2-chloropyridin-3-yl | 2,6-dimethyl-4-(1,2,2,2-tetrafluoro-1-trifluoromethyl-ethyl)-phenyl |
| 7-17 | H | —L—D | —CH2CH2— | CONH2 | H | 0 | 6-chloropyridin-3-yl | 2,6-dimethyl-4-(1,2,2,2-tetrafluoro-1-trifluoromethyl-ethyl)-phenyl |
| 7-18 | H | —L—D | —CH2CH2— | CONH2 | H | 0 | 2-chloropyridin-4-yl | 2,6-dimethyl-4-(1,2,2,2-tetrafluoro-1-trifluoromethyl-ethyl)-phenyl |
| 7-19 | H | —L—D | —CH2CH2— | CONH2 | pyrazin-2-yl | 0 | pyrazin-2-yl | 2,6-dimethyl-4-(1,2,2,2-tetrafluoro-1-trifluoromethyl-ethyl)-phenyl |
| 7-20 | H | —L—D | —CH2CH2— | CONH2 | H | 0 | pyrimidin-5-yl | 2,6-dimethyl-4-(1,2,2,2-tetrafluoro-1-trifluoromethyl-ethyl)-phenyl |
| 7-21 | H | —L—D | —CH2CH2— | CONH2 | 2-F | 1 | phenyl | 2,6-dimethyl-4-(1,2,2,2-tetrafluoro-1-trifluoromethyl-ethyl)-phenyl |
| 7-22 | H | —L—D | —CH2CH2— | SO2Me | 2-F | 1 | phenyl | 2,6-dimethyl-4-(1,2,2,2-tetrafluoro-1-trifluoromethyl-ethyl)-phenyl |
| 7-23 | Me | —L—D | —CH2CH2— | OH | 2-F | 1 | phenyl | 2,6-dimethyl-4-(1,2,2,2-tetrafluoro-1-trifluoromethyl-ethyl)-phenyl |
| 7-24 | H | —L—D | —CH2CH2— | CONH2 | 2-F | 1 | 4-cyanophenyl | 2,6-dimethyl-4-(1,2,2,2-tetrafluoro-1-trifluoromethyl-ethyl)-phenyl |
| 7-25 | H | —L—D | —CH2CH2— | SOMe | 2-F | 1 | 3-cyanophenyl | 2,6-dimethyl-4-(1,2,2,2-tetrafluoro-1-trifluoromethyl-ethyl)-phenyl |
| 7-26 | H | —L—D | —CH2CH2— | CONH2 | 2-F | 1 | 3,5-dicyanophenyl | 2,6-dimethyl-4-(1,2,2,2-tetrafluoro-1-trifluoromethyl-ethyl)-phenyl |
| 7-27 | Et | —L—D | —CH2CH2— | CONH2 | 2-F | 1 | 2-fluorophenyl | 2,6-dimethyl-4-(1,2,2,2-tetrafluoro-1-trifluoromethyl-ethyl)-phenyl |
| 7-28 | H | —L—D | —CH2CH2— | CN | 2-F | 1 | 4-fluorophenyl | 2,6-dimethyl-4-(1,2,2,2-tetrafluoro-1-trifluoromethyl-ethyl)-phenyl |
| 7-29 | H | —L—D | —CH2CH2— | CONH2 | 2-F | 1 | 2,6-difluorophenyl | 2,6-dimethyl-4-(1,2,2,2-tetrafluoro-1-trifluoromethyl-ethyl)-phenyl |
| 7-30 | H | —L—D | —CH2CH2— | CONH2 | 2-F | 1 | 2-fluoro-4-cyanophenyl | 2,6-dimethyl-4-(1,2,2,2-tetrafluoro-1-trifluoromethyl-ethyl)-phenyl |
| 7-31 | H | —L—D | —CH2CH2— | CONH2 | 2-F | 1 | 2-chlorophenyl | 2,6-dimethyl-4-(1,2,2,2-tetrafluoro-1-trifluoromethyl-ethyl)-phenyl |
| 7-32 | H | —L—D | —CH2CH2— | CONH2 | 2-F | 1 | 4-chlorophenyl | 2,6-dimethyl-4-(1,2,2,2-tetrafluoro-1-trifluoromethyl-ethyl)-phenyl |
| 7-33 | H | —L—D | —CH2CH2— | CONH2 | 2-F | 1 | 4-nitrophenyl | 2,6-dimethyl-4-(1,2,2,2-tetrafluoro-1-trifluoromethyl-ethyl)-phenyl |
| 7-34 | H | —L—D | —CH2CH2— | CONH2 | 2-F | 1 | 2-methylphenyl | 2,6-dimethyl-4-(1,2,2,2-tetrafluoro-1-trifluoromethyl-ethyl)-phenyl |
| 7-35 | H | —L—D | —CH2CH2— | CONH2 | 2-F | 1 | pyridin-2-yl | 2,6-dimethyl-4-(1,2,2,2-tetrafluoro-1-trifluoromethyl-ethyl)-phenyl |
| 7-36 | H | —L—D | —CH2CH2— | CONH2 | 2-F | 1 | pyridin-3-yl | 2,6-dimethyl-4-(1,2,2,2-tetrafluoro-1-trifluoromethyl-ethyl)-phenyl |
| 7-37 | H | —L—D | —CH2CH2— | CONH2 | 2-F | 1 | pyridin-4-yl | 2,6-dimethyl-4-(1,2,2,2-tetrafluoro-1-trifluoromethyl-ethyl)-phenyl |
| 7-38 | H | —L—D | —CH2CH2— | CONH2 | 2-F | 1 | 2-chloropyridin-3-yl | 2,6-dimethyl-4-(1,2,2,2-tetrafluoro-1-trifluoromethyl-ethyl)-phenyl |

TABLE 7-continued

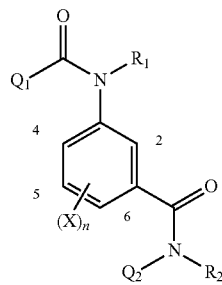

| compound number | $R_1$ | $R_2$ | L | D | X | n | $Q_1$ | $Q_2$ |
|---|---|---|---|---|---|---|---|---|
| 7-39 | H | —L—D | —CH2CH2— | CONH2 | 2-F | 1 | 6-chloropyridin-3-yl | 2,6-dimethyl-4-(1,2,2,2-tetrafluoro-1-trifluoromethyl-ethyl)-phenyl |
| 7-40 | n-Pr | —L—D | —CH2CH2— | CONH2 | 2-F | 1 | 2-chloropyridin-4-yl | 2,6-dimethyl-4-(1,2,2,2-tetrafluoro-1-trifluoromethyl-ethyl)-phenyl |
| 7-41 | H | —L—D | —CH2CH2— | CONH2 | 2-F | 1 | pyrazin-2-yl | 2,6-dimethyl-4-(1,2,2,2-tetrafluoro-1-trifluoromethyl-ethyl)-phenyl |
| 7-42 | H | —L—D | —CH2CH2— | CONH2 | 2-F | 1 | pyrimidin-5-yl | 2,6-dimethyl-4-(1,2,2,2-tetrafluoro-1-trifluoromethyl-ethyl)-phenyl |
| 7-43 | H | —L—D | —CH2CH2— | CONH2 | 4-F | 1 | phenyl | 2,6-dimethyl-4-(1,2,2,2-tetrafluoro-1-trifluoromethyl-ethyl)-phenyl |
| 7-44 | H | —L—D | —CH2CH2— | CONH2 | 4-F | 1 | 4-cyanophenyl | 2,6-dimethyl-4-(1,2,2,2-tetrafluoro-1-trifluoromethyl-ethyl)-phenyl |
| 7-45 | H | —L—D | —CH2CH2— | CONH2 | 4-F | 1 | 3-cyanophenyl | 2,6-dimethyl-4-(1,2,2,2-tetrafluoro-1-trifluoromethyl-ethyl)-phenyl |
| 7-46 | H | —L—D | —CH2CH2— | CONH2 | 4-F | 1 | 2-chloropyridin-3-yl | 2,6-dimethyl-4-(1,2,2,2-tetrafluoro-1-trifluoromethyl-ethyl)-phenyl |
| 7-47 | H | —L—D | —CH2CH2— | CONH2 | 4-F | 1 | 2-fluorophenyl | 2,6-dimethyl-4-(1,2,2,2-tetrafluoro-1-trifluoromethyl-ethyl)-phenyl |
| 7-48 | H | —L—D | —CH2CH2— | CONH2 | 4-CN | 1 | phenyl | 2,6-dimethyl-4-(1,2,2,2-tetrafluoro-1-trifluoromethyl-ethyl)-phenyl |
| 7-49 | H | —L—D | —CH2CH2— | CONH2 | 4-CN | 1 | 4-cyanophenyl | 2,6-dimethyl-4-(1,2,2,2-tetrafluoro-1-trifluoromethyl-ethyl)-phenyl |
| 7-50 | H | —L—D | —CH2CH2— | CONH2 | 4-CN | 1 | 3-cyanophenyl | 2,6-dimethyl-4-(1,2,2,2-tetrafluoro-1-trifluoromethyl-ethyl)-phenyl |
| 7-51 | H | —L—D | —CH2CH2— | CONH2 | 4-CN | 1 | 2-chloropyridin-3-yl | 2,6-dimethyl-4-(1,2,2,2-tetrafluoro-1-trifluoromethyl-ethyl)-phenyl |
| 7-52 | H | —L—D | —CH2CH2— | CONH2 | 4-CN | 1 | 2-fluorophenyl | 2,6-dimethyl-4-(1,2,2,2-tetrafluoro-1-trifluoromethyl-ethyl)-phenyl |
| 7-53 | H | —L—D | —CH2CH2— | CONH2 | H | 0 | 4-cyanophenyl | 2,6-dibromo-4-pentafluoroethyl-phenyl |
| 7-54 | H | —L—D | —CH2CH2— | CONH2 | H | 0 | 4-cyanophenyl | 2,6-diiodo-4-pentafluoroethyl-phenyl |
| 7-55 | H | —L—D | —CH2CH2— | CONH2 | H | 0 | 4-cyanophenyl | 2-bromo-6-trifluoromethyl-4-pentafluoroethyl-phenyl |
| 7-56 | H | —L—D | —CH2CH2— | CONH2 | H | 0 | 4-cyanophenyl | 2-iodo-6-trifluoromethyl-4-pentafluoroethyl-phenyl |
| 7-57 | H | —L—D | —CH2CH2— | CONH2 | H | 0 | 4-cyanophenyl | 2-chloro-6-methyl-4-(1,2,2,2-tetrafluoro-1-trifluoromethyl-ethyl)-phenyl |
| 7-58 | i-Pr | —L—D | —CH2CH2— | CONH2 | H | 0 | 4-cyanophenyl | 2-bromo-6-methyl-4-(1,2,2,2-tetrafluoro-1-trifluoromethyl-ethyl)-phenyl |
| 7-59 | H | —L—D | —CH2CH2— | CONH2 | H | 0 | 4-cyanophenyl | 2-iodo-6-methyl-4-(1,2,2,2-tetrafluoro-1-trifluoromethyl-ethyl)-phenyl |
| 7-60 | H | —L—D | —CH2CH2— | CONH2 | H | 0 | 4-cyanophenyl | 2-bromo-6-ethyl-4-(1,2,2,2-tetrafluoro-1-trifluoromethyl-ethyl)-phenyl |
| 7-61 | H | —L—D | —CH2CH2— | CONH2 | H | 0 | 4-cyanophenyl | 2-iodo-6-ethyl-4-(1,2,2,2-tetrafluoro-1-trifluoromethyl-ethyl)-phenyl |
| 7-62 | H | —L—D | —CH2CH2— | CONH2 | H | 0 | 4-cyanophenyl | 2,6-dichloro-4-(1,2,2,2-tetrafluoro-1-trifluoromethyl-ethyl)-phenyl |
| 7-63 | H | —L—D | —CH2CH2— | CONH2 | H | 0 | 4-cyanophenyl | 2,6-dibromo-4-(1,2,2,2-tetrafluoro-1-trifluoromethyl-ethyl)-phenyl |
| 7-64 | H | —L—D | —CH2CH2— | CONH2 | H | 0 | 4-cyanophenyl | 2,6-diiodo-4-(1,2,2,2-tetrafluoro-1-trifluoromethyl-ethyl)-phenyl |
| 7-65 | H | —L—D | —CH2CH2— | CONH2 | H | 0 | 4-cyanophenyl | 2,6-ditrifluoromethyl-4-(1,2,2,2-tetrafluoro-1-trifluoromethyl-ethyl)-phenyl |
| 7-66 | H | —L—D | —CH2CH2— | CONH2 | H | 0 | 4-cyanophenyl | 2-bromo-6-trifluoromethyl-4-(1,2,2,2-tetrafluoro-1-trifluoromethyl-ethyl)-phenyl |
| 7-67 | H | —L—D | —CH2CH2— | CONH2 | H | 0 | 4-cyanophenyl | 2-iodo-6-trifluoromethyl-4-(1,2,2,2-tetrafluoro-1-trifluoromethyl-ethyl)-phenyl |
| 7-68 | H | —L—D | —CH2CH2— | CONH2 | H | 0 | 4-cyanophenyl | 2-bromo-6-trifluoromethoxy-4-(1,2,2,2-tetrafluoro-1-trifluoromethyl-ethyl)-phenyl |
| 7-69 | H | —L—D | —CH2CH2— | CONH2 | H | 0 | 4-cyanophenyl | 2-bromo-6-iodo-4-(1,2,2,2-tetrafluoro-1-trifluoromethyl-ethyl)-phenyl |
| 7-70 | H | —L—D | —CH2CH2— | CONH2 | H | 0 | 4-cyanophenyl | 2-bromo-6-trifluoromethylthio-4-(1,2,2,2-tetrafluoro-1-trifluoromethyl-ethyl)-phenyl |

TABLE 7-continued

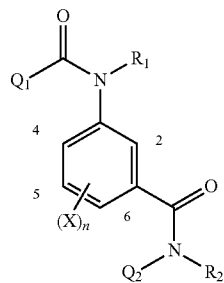

| compound number | R₁ | R₂ | L | D | X | n | Q₁ | Q₂ |
|---|---|---|---|---|---|---|---|---|
| 7-71 | H | —L—D | —CH2CH2— | CONH2 | H | 0 | 4-cyanophenyl | 2-bromo-6-trifluoromethylsulfinyl-4-(1,2,2,2-tetrafluoro-1-trifluoromethyl-ethyl)-phenyl |
| 7-72 | H | —L—D | —CH2CH2— | CONH2 | H | 0 | 4-cyanophenyl | 2-bromo-6-trifluoromethylsulfonyl-4-(1,2,2,2-tetrafluoro-1-trifluoromethyl-ethyl)-phenyl |
| 7-73 | H | —L—D | —CH2CH2— | CONH2 | H | 0 | 4-cyanophenyl | 2-bromo-6-pentafluoroethyl-4-(1,2,2,2-tetrafluoro-1-trifluoromethyl-ethyl)-phenyl |
| 7-74 | H | —L—D | —CH2CH2— | CONH2 | H | 0 | 4-cyanophenyl | 2-iodo-6-pentafluoroethyl-4-(1,2,2,2-tetrafluoro-1-trifluoromethyl-ethyl)-phenyl |
| 7-75 | H | —L—D | —CH2CH2— | CONH2 | H | 0 | 4-cyanophenyl | 2-chloro-6-methyl-4-(1,2,2,3,3,3-hexafluoro-1-trifluoromethyl-propyl)-phenyl |
| 7-76 | H | —L—D | —CH2CH2— | CONH2 | H | 0 | 4-cyanophenyl | 2-bromo-6-methyl-4-(1,2,2,3,3,3-hexafluoro-1-trifluoromethyl-propyl)-phenyl |
| 7-77 | H | —L—D | —CH2CH2— | CONH2 | H | 0 | 4-cyanophenyl | 2-iodo-6-methyl-4-(1,2,2,3,3,3-hexafluoro-1-trifluoromethyl-propyl)-phenyl |
| 7-78 | H | —L—D | —CH2CH2— | CONH2 | H | 0 | 4-cyanophenyl | 2-bromo-6-ethyl-4-(1,2,2,3,3,3-hexafluoro-1-trifluoromethyl-propyl)-phenyl |
| 7-79 | H | —L—D | —CH2CH2— | CONH2 | H | 0 | 4-cyanophenyl | 2-iodo-6-ethyl-4-(1,2,2,3,3,3-hexafluoro-1-trifluoromethyl-propyl)-phenyl |
| 7-80 | H | —L—D | —CH2CH2— | CONH2 | H | 0 | 4-cyanophenyl | 2,6-dichloro-4-(1,2,2,3,3,3-hexafluoro-1-trifluoromethyl-propyl)-phenyl |
| 7-81 | H | —L—D | —CH2CH2— | CONH2 | H | 0 | 4-cyanophenyl | 2,6-dibromo-4-(1,2,2,3,3,3-hexafluoro-1-trifluoromethyl-propyl)-phenyl |
| 7-82 | H | —L—D | —CH2CH2— | CONH2 | H | 0 | 4-cyanophenyl | 2,6-diiodo-4-(1,2,2,3,3,3-hexafluoro-1-trifluoromethyl-propyl)-phenyl |
| 7-83 | H | —L—D | —CH2CH2— | CONH2 | H | 0 | 4-cyanophenyl | 2,6-ditrifluoromethyl-4-(1,2,2,3,3,3-hexafluoro-1-trifluoromethyl-propyl)-phenyl |
| 7-84 | H | —L—D | —CH2CH2— | CONH2 | H | 0 | 4-cyanophenyl | 2-bromo-6-trifluoromethyl-4-(1,2,2,3,3,3-hexafluoro-1-trifluoromethyl-propyl)-phenyl |
| 7-85 | H | —L—D | —CH2CH2— | CONH2 | H | 0 | 4-cyanophenyl | 2-iodo-6-trifluoromethyl-4-(1,2,2,3,3,3-hexafluoro-1-trifluoromethyl-propyl)-phenyl |
| 7-86 | H | —L—D | —CH2CH2— | CONH2 | H | 0 | 4-cyanophenyl | 2-bromo-6-trifluoromethoxy-4-(1,2,2,3,3,3-hexafluoro-1-trifluoromethyl-propyl)-phenyl |
| 7-87 | H | —L—D | —CH2CH2— | CONH2 | H | 0 | 4-cyanophenyl | 2-bromo-6-iodo-4-(1,2,2,3,3,3-hexafluoro-1-trifluoromethyl-propyl)-phenyl |
| 7-88 | H | —L—D | —CH2CH2— | CONH2 | H | 0 | 4-cyanophenyl | 2-bromo-6-trifluoromethylthio-4-(1,2,2,3,3,3-hexafluoro-1-trifluoromethyl-propyl)-phenyl |
| 7-89 | H | —L—D | —CH2CH2— | CONH2 | H | 0 | 4-cyanophenyl | 2-bromo-6-trifluoromethylsulfinyl-4-(1,2,2,3,3,3-hexafluoro-1-trifluoromethyl-propyl)-phenyl |
| 7-90 | H | —L—D | —CH2CH2— | CONH2 | H | 0 | 4-cyanophenyl | 2-bromo-6-trifluoromethylsulfinyl-4-(1,2,2,3,3,3-hexafluoro-1-trifluoromethyl-propyl)-phenyl |
| 7-91 | H | —L—D | —CH2CH2— | CONH2 | H | 0 | 4-cyanophenyl | 2-bromo-6-pentafluoroethyl-4-(1,2,2,3,3,3-hexafluoro-1-trifluoromethyl-propyl)-phenyl |
| 7-92 | H | —L—D | —CH2CH2— | CONH2 | H | 0 | 4-cyanophenyl | 2-iodo-6-pentafluoroethyl-4-(1,2,2,3,3,3-hexafluoro-1-trifluoromethyl-propyl)-phenyl |
| 7-93 | H | —L—D | —CH2CH2— | CONH2 | H | 0 | phenyl | 2,6-dibromo-4-(1,2,2,2-tetrafluoro-1-trifluoromethyl-ethyl)-phenyl |
| 7-94 | H | —L—D | —CH2CH2— | CONH2 | H | 0 | 3-cyanophenyl | 2,6-dibromo-4-(1,2,2,2-tetrafluoro-1-trifluoromethyl-ethyl)-phenyl |
| 7-95 | H | —L—D | —CH2CH2— | CONH2 | H | 0 | 2-chloropyridin-3-yl | 2,6-dibromo-4-(1,2,2,2-tetrafluoro-1-trifluoromethyl-ethyl)-phenyl |
| 7-96 | H | —L—D | —CH2CH2— | CONH2 | H | 0 | 2-fluorophenyl | 2,6-dibromo-4-(1,2,2,2-tetrafluoro-1-trifluoromethyl-ethyl)-phenyl |
| 7-97 | H | —L—D | —CH2CH2— | CONH2 | H | 0 | phenyl | 2,6-diiodo-4-(1,2,2,2-tetrafluoro-1-trifluoromethyl-ethyl)-phenyl |
| 7-98 | H | —L—D | —CH2CH2— | CONH2 | H | 0 | 3-cyanophenyl | 2,6-diiodo-4-(1,2,2,2-tetrafluoro-1-trifluoromethyl-ethyl)-phenyl |
| 7-99 | H | —L—D | —CH2CH2— | CONH2 | H | 0 | 2-chloropyridin-3-yl | 2,6-diiodo-4-(1,2,2,2-tetrafluoro-1-trifluoromethyl-ethyl)-phenyl |
| 7-100 | H | —L—D | —CH2CH2— | CONH2 | H | 0 | 2-fluorophenyl | 2,6-diiodo-4-(1,2,2,2-tetrafluoro-1-trifluoromethyl-ethyl)-phenyl |
| 7-101 | H | —L—D | —CH2CH2— | CONH2 | H | 0 | phenyl | 2-bromo-6-trifluoromethyl-4-(1,2,2,2-tetrafluoro-1-trifluoromethyl-ethyl)-phenyl |

TABLE 7-continued

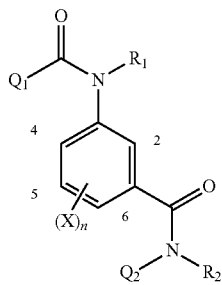

| compound number | R₁ | R₂ | L | D | X | n | Q₁ | Q₂ |
|---|---|---|---|---|---|---|---|---|
| 7-102 | H | —L—D | —CH2CH2— | CONH2 | H | 0 | 3-cyanophenyl | 2-bromo-6-trifluoromethyl-4-(1,2,2,2-tetrafluoro-1-trifluoromethyl-ethyl)-phenyl |
| 7-103 | H | —L—D | —CH2CH2— | CONH2 | H | 0 | 2-chloropyridin-3-yl | 2-bromo-6-trifluoromethyl-4-(1,2,2,2-tetrafluoro-1-trifluoromethyl-ethyl)-phenyl |
| 7-104 | H | —L—D | —CH2CH2— | CONH2 | H | 0 | 2-fluorophenyl | 2-bromo-6-trifluoromethyl-4-(1,2,2,2-tetrafluoro-1-trifluoromethyl-ethyl)-phenyl |
| 7-105 | H | —L—D | —CH2CH2— | CONH2 | H | 0 | phenyl | 2-iodo-6-trifluoromethyl-4-(1,2,2,2-tetrafluoro-1-trifluoromethyl-ethyl)-phenyl |
| 7-106 | H | —L—D | —CH2CH2— | CONH2 | H | 0 | 3-cyanophenyl | 2-iodo-6-trifluoromethyl-4-(1,2,2,2-tetrafluoro-1-trifluoromethyl-ethyl)-phenyl |
| 7-107 | H | —L—D | —CH2CH2— | CONH2 | H | 0 | 2-chloropyridin-3-yl | 2-iodo-6-trifluoromethyl-4-(1,2,2,2-tetrafluoro-1-trifluoromethyl-ethyl)-phenyl |
| 7-108 | H | —L—D | —CH2CH2— | CONH2 | H | 0 | 2-fluorophenyl | 2-iodo-6-trifluoromethyl-4-(1,2,2,2-tetrafluoro-1-trifluoromethyl-ethyl)-phenyl |
| 7-109 | H | —L—D | —CH2CH2— | CONH2 | H | 0 | phenyl | 2,6-dibromo-4-(1,2,2,3,3,3-hexafluoro-1-trifluoromethyl-propyl)-phenyl |
| 7-110 | H | —L—D | —CH2CH2— | CONH2 | H | 0 | 3-cyanophenyl | 2,6-dibromo-4-(1,2,2,3,3,3-hexafluoro-1-trifluoromethyl-propyl)-phenyl |
| 7-111 | H | —L—D | —CH2CH2— | CONH2 | H | 0 | 2-chloropyridin-3-yl | 2,6-dibromo-4-(1,2,2,3,3,3-hexfluoro-1-trifluoromethyl-propyl)-phenyl |
| 7-112 | H | —L—D | —CH2CH2— | CONH2 | H | 0 | 2-fluorophenyl | 2,6-dibromo-4-(1,2,2,3,3,3-hexafluoro-1-trifluoromethyl-propyl)-phenyl |
| 7-113 | H | —L—D | —CH2CH2— | CONH2 | H | 0 | phenyl | 2,6-diiodo-4-(1,2,2,3,3,3-hexafluoro-trifluoromethyl-propyl)-phenyl |
| 7-114 | H | —L—D | —CH2CH2— | CONH2 | H | 0 | 3-cyanophenyl | 2,6-diiodo-4-(1,2,2,3,3,3-hexafluoro-1-trifluoromethyl-propyl)-phenyl |
| 7-115 | H | —L—D | —CH2CH2— | CONH2 | H | 0 | 2-chloropyridin-3-yl | 2,6-iodo-4-(1,2,2,3,3,3-hexafluoro-1-trifluoromethyl-propyl)-phenyl |
| 7-116 | H | —L—D | —CH2CH2— | CONH2 | H | 0 | 2-fluorophenyl | 2,6-diiodo-4-(1,2,2,3,3,3-hexafluoro-1-trifluoromethyl-propyl)-phenyl |
| 7-117 | H | —L—D | —CH2CH2— | CONH2 | H | 0 | phenyl | 2-bromo-6-trifluoromethyl-4-(1,2,2,3,3,3-hexafluoro-1-trifluoromethyl-propyl)-phenyl |
| 7-118 | H | —L—D | —CH2CH2— | CONH2 | H | 0 | 3-cyanophenyl | 2-bromo-6-trifluoromethyl-4-(1,2,2,3,3,3-hexafluoro-1-trifluoromethyl-propyl)-phenyl |
| 7-119 | H | —L—D | —CH2CH2— | CONH2 | H | 0 | 2-chloropyridin-3-yl | 2-bromo-6-trifluoromethyl-4-(1,2,2,3,3,3-hexafluoro-1-trifluoromethyl-propyl)-phenyl |
| 7-120 | H | —L—D | —CH2CH2— | CONH2 | H | 0 | 2-fluorophenyl | 2-bromo-6-trifluoromethyl-4-(1,2,2,3,3,3-hexafluoro-1-trifluoromethyl-propyl)-phenyl |
| 7-121 | H | —L—D | —CH2CH2— | CONH2 | H | 0 | phenyl | 2-iodo-6-trifluoromethyl-4-(1,2,2,3,3,3-hexafluoro-1-trifluoromethyl-propyl)-phenyl |
| 7-122 | H | —L—D | —CH2CH2— | CONH2 | H | 0 | 3-cyanophenyl | 2-iodo-6-trifluoromethyl-4-(1,2,2,3,3,3-hexafluoro-1-trifluoromethyl-propyl)-phenyl |
| 7-123 | H | —L—D | —CH2CH2— | CONH2 | H | 0 | 2-chloropyridin-3-yl | 2-iodo-6-trifluoromethyl-4-(1,2,2,3,3,3-hexafluoro-1-trifluoromethyl-propyl)-phenyl |
| 7-124 | H | —L—D | —CH2CH2— | CONH2 | H | 0 | 2-fluorophenyl | 2-iodo-6-trifluoromethyl-4-(1,2,2,3,3,3-hexafluoro-1-trifluoromethyl-propyl)-phenyl |
| 7-125 | H | —L—D | —CH2CH2— | CONH2 | 2-F | 1 | 4-cyanophenyl | 2,6-dibromo-4-pentafluoroethyl-phenyl |
| 7-126 | H | —L—D | —CH2CH2— | CONH2 | 2-F | 1 | 4-cyanophenyl | 2,6-diiodo-4-pentafluoroethyl-phenyl |
| 7-127 | H | —L—D | —CH2CH2— | CONH2 | 2-F | 1 | 4-cyanophenyl | 2--bromo-6-trifluoromethyl-4-pentafluoroethyl-phenyl |
| 7-128 | H | —L—D | —CH2CH2— | CONH2 | 2-F | 1 | 4-cyanophenyl | 2-iodo-6-trifluoromethyl-4-pentafluoroethyl-phenyl |
| 7-129 | H | —L—D | —CH2CH2— | CONH2 | 2-F | 1 | 4-cyanophenyl | 2-chloro-6-methyl-4-(1,2,2,2-tetrafluoro-1-trifluoromethyl-ethyl)-phenyl |
| 7-130 | H | —L—D | —CH2CH2— | CONH2 | 2-F | 1 | 4-cyanophenyl | 2-bromo-6-methyl-4-(1,2,2,2-tetrafluoro-1-trifluoromethyl-ethyl)-phenyl |
| 7-131 | H | —L—D | —CH2CH2— | CONH2 | 2-F | 1 | 4-cyanophenyl | 2-iodo-6-methyl-4-(1,2,2,2-tetrafluoro-1-trifluoromethyl-ethyl)-phenyl |
| 7-132 | H | —L—D | —CH2CH2— | CONH2 | 2-F | 1 | 4-cyanophenyl | 2-bromo-6-ethyl-4-(1,2,2,2-tetrafluoro-1-trifluoromethyl-ethyl)-phenyl |
| 7-133 | H | —L—D | —CH2CH2— | CONH2 | 2-F | 1 | 4-oyanophenyl | 2-iodo-6-ethyl-4-(1,2,2,2-tetrafluoro-1-trifluoromethyl-ethyl)-phenyl |

TABLE 7-continued

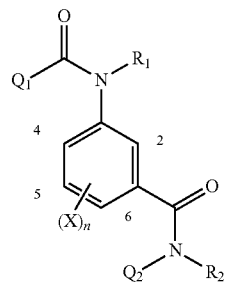

| compound number | $R_1$ | $R_2$ | L | D | X | n | $Q_1$ | $Q_2$ |
|---|---|---|---|---|---|---|---|---|
| 7-134 | H | —L—D | —CH2CH2— | CONH2 | 2-F | 1 | 4-cyanophenyl | 2,6-dichloro-4-(1,2,2,2-tetrafluoro-1-trifluoromethyl-ethyl)-phenyl |
| 7-135 | H | —L—D | —CH2CH2— | CONH2 | 2-F | 1 | 4-cyanophenyl | 2,6-dibromo-4-(1,2,2,2-tetrafluoro-1-trifluoromethyl-ethyl)-phenyl |
| 7-136 | H | —L—D | —CH2CH2— | CONH2 | 2-F | 1 | 4-cyanophenyl | 2,6-diiodo-4-(1,2,2,2-tetrafluoro-1-trifluoromethyl-ethyl)-phenyl |
| 7-137 | H | —L—D | —CH2CH2— | CONH2 | 2-F | 1 | 4-cyanophenyl | 2,6-ditrifluoromethyl-4-(1,2,2,2-tetrafluoro-1-trifluoromethyl-ethyl)-phenyl |
| 7-138 | H | —L—D | —CH2CH2— | CONH2 | 2-F | 1 | 4-cyanophenyl | 2-bromo-6-trifluoromethyl-4-(1,2,2,2-tetrafluoro-1-trifluoromethyl-ethyl)-phenyl |
| 7-139 | H | —L—D | —CH2CH2— | CONH2 | 2-F | 1 | 4-cyanophenyl | 2-iodo-6-trifluoromethyl-4-(1,2,2,2-tetrafluoro-1-trifluoromethyl-ethyl)-phenyl |
| 7-140 | H | —L—D | —CH2CH2— | CONH2 | 2-F | 1 | 4-cyanophenyl | 2-bromo-6-trifluoromethoxy-4-(1,2,2,2-tetrafluoro-1-trifluoromethyl-ethyl)-phenyl |
| 7-141 | H | —L—D | —CH2CH2— | CONH2 | 2-F | 1 | 4-cyanophenyl | 2-bromo-6-iodo-4-(1,2,2,2-tetrafluoro-1-trifluoromethyl-ethyl)-phenyl |
| 7-142 | H | —L—D | —CH2CH2— | CONH2 | 2-F | 1 | 4-cyanophenyl | 2-bromo-6-trifluoromethylthio-4-(1,2,2,2-tetrafluoro-1-trifluoromethyl-ethyl)-phenyl |
| 7-143 | H | —L—D | —CH2CH2— | CONH2 | 2-F | 1 | 4-cyanophenyl | 2-bromo-6-trifluoromethylsulfinyl-4-(1,2,2,2-tetrafluoro-1-trifluoromethyl-ethyl)-phenyl |
| 7-144 | H | —L—D | —CH2CH2— | CONH2 | 2-F | 1 | 4-cyanophenyl | 2-bromo-6-trifluoromethylsulfonyl-4-(1,2,2,2-tetrafluoro-1-trifluoromethyl-ethyl)-phenyl |
| 7-145 | H | —L—D | —CH2CH2— | CONH2 | 2-F | 1 | 4-cyanophenyl | 2-bromo-6-pentafluoroethyl-4-(1,2,2,2-tetrafluoro-1-trifluoromethyl-ethyl)-phenyl |
| 7-146 | H | —L—D | —CH2CH2— | CONH2 | 2-F | 1 | 4-cyanophenyl | 2-iodo-6-pentafluoroethyl-4-(1,2,2,2-tetrafluoro-1-trifluoromethyl-ethyl)-phenyl |
| 7-147 | H | —L—D | —CH2CH2— | CONH2 | 2-F | 1 | 4-cyanophenyl | 2-chloro-6-methyl-4-(1,2,2,3,3,3-hexafluoro-1-trifluoromethyl-propyl)-phenyl |
| 7-148 | H | —L—D | —CH2CH2— | CONH2 | 2-F | 1 | 4-cyanophenyl | 2-bromo-6-methyl-4-(1,2,2,3,3,3-hexafluoro-1-trifluoromethyl-propyl)-phenyl |
| 7-149 | H | —L—D | —CH2CH2— | CONH2 | 2-F | 1 | 4-cyanophenyl | 2-iodo-6-methyl-4-(1,2,2,3,3,3-hexafluoro-1-trifluoromethyl-propyl)-phenyl |
| 7-150 | H | —L—D | —CH2CH2— | CONH2 | 2-F | 1 | 4-cyanophenyl | 2-bromo-6-ethyl-4-(1,2,2,3,3,3-hexafluoro-1-trifluoromethyl-propyl)-phenyl |
| 7-151 | H | —L—D | —CH2CH2— | CONH2 | 2-F | 1 | 4-cyanophenyl | 2-iodo-6-ethyl-4-(1,2,2,3,3,3-hexafluoro-1-trifluoromethyl-propyl)-phenyl |
| 7-152 | H | —L—D | —CH2CH2— | CONH2 | 2-F | 1 | 4-cyanophenyl | 2,6-dichloro-4-(1,2,2,3,3,3-hexafluoro-1-trifluoromethyl-propyl)-phenyl |
| 7-153 | H | —L—D | —CH2CH2— | CONH2 | 2-F | 1 | 4-cyanophenyl | 2,6-dibromo-4-(1,2,2,3,3,3-hexafluoro-1-trifluoromethyl-propyl)-phenyl |
| 7-154 | H | —L—D | —CH2CH2— | CONH2 | 2-F | 1 | 4-cyanophenyl | 2,6-diiodo-4-(1,2,2,3,3,3-hexafluoro-1-trifluoromethyl-propyl)-phenyl |
| 7-155 | H | —L—D | —CH2CH2— | CONH2 | 2-F | 1 | 4-cyanophenyl | 2,6-ditrifluoromethyl-4-(1,2,2,3,3,3-hexafluoro-1-trifluoromethyl-propyl)-phenyl |
| 7-156 | H | —L—D | —CH2CH2— | CONH2 | 2-F | 1 | 4-cyanophenyl | 2-bromo-6-trifluoromethyl-4-(1,2,2,3,3,3-hexafluoro-1-trifluoromethyl-propyl)-phenyl |
| 7-157 | H | —L—D | —CH2CH2— | CONH2 | 2-F | 1 | 4-cyanophenyl | 2-iodo-6-trifluoromethyl-4-(1,2,2,3,3,3-hexafluoro-1-trifluoromethyl-propyl)-phenyl |
| 7-158 | H | —L—D | —CH2CH2— | CONH2 | 2-F | 1 | 4-cyanophenyl | 2-bromo-6-trifluoromethoxy-4-(1,2,2,3,3,3-hexafluoro-1-trifluoromethyl-propyl)-phenyl |
| 7-159 | H | —L—D | —CH2CH2— | CONH2 | 2-F | 1 | 4-cyanophenyl | 2-bromo-6-iodo-4-(1,2,2,3,3,3-hexafluoro-1-trifluoromethyl-propyl)-phenyl |
| 7-160 | H | —L—D | —CH2CH2— | CONH2 | 2-F | 1 | 4-cyanophenyl | 2-bromo-6-trifluoromethylthio-4-(1,2,2,3,3,3-hexafluoro-1-trifluoromethyl-propyl)-phenyl |
| 7-161 | H | —L—D | —CH2CH2— | CONH2 | 2-F | 1 | 4-cyanophenyl | 2-bromo-6-trifluoromethylsulfinyl-4-(1,2,2,3,3,3-hexafluoro-1-trifluoromethyl-propyl)-phenyl |
| 7-162 | H | —L—D | —CH2CH2— | CONH2 | 2-F | 1 | 4-cyanophenyl | 2-bromo-6-trifluoromethylsulfonyl-4-(1,2,2,3,3,3-hexafluoro-1-trifluoromethyl-propyl)-phenyl |
| 7-163 | H | —L—D | —CH2CH2— | CONH2 | 2-F | 1 | 4-cyanophenyl | 2-bromo-6-pentafluoroethyl-4-(1,2,2,3,3,3-hexafluoro-1-trifluoromethyl-propyl)-phenyl |
| 7-164 | H | —L—D | —CH2CH2— | CONH2 | 2-F | 1 | 4-cyanophenyl | 2-iodo-6-pentafluoroethyl-4-(1,2,2,3,3,3-hexafluoro-1-trifluoromethyl-propyl)-phenyl |

TABLE 7-continued

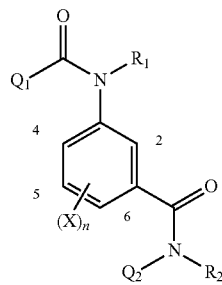

| compound number | R₁ | R₂ | L | D | X | n | Q₁ | Q₂ |
|---|---|---|---|---|---|---|---|---|
| 7-165 | H | —L—D | —CH2CH2— | CONH2 | 2-F | 1 | phenyl | 2,6-dibromo-4-(1,2,2,2-tetrafluoro-1-trifluoromethyl-ethyl)-phenyl |
| 7-166 | H | —L—D | —CH2CH2— | CONH2 | 2-F | 1 | 3-cyanophenyl | 2,6-dibromo-4-(1,2,2,2-tetrafluoro-1-trifluoromethyl-ethyl)-phenyl |
| 7-167 | H | —L—D | —CH2CH2— | CONH2 | 2-F | 1 | 2-chloropyridin-3-yl | 2,6-dibromo-4-(1,2,2,2-tetrafluoro-1-trifluoromethyl-ethyl)-phenyl |
| 7-168 | H | —L—D | —CH2CH2— | CONH2 | 2-F | 1 | 2-fluorophenyl | 2,6-dibromo-4-(1,2,2,2-tetrafluoro-1-trifluoromethyl-ethyl)-phenyl |
| 7-169 | H | —L—D | —CH2CH2— | SO2Me | 2-F | 1 | phenyl | 26-dibromo-4-(1,2,2,2-tetrafluoro-1-trifluoromethyl-ethyl)-phenyl |
| 7-170 | H | —L—D | —CH2CH2— | CONH2 | 2-F | 1 | phenyl | 2,6-diiodo-4-(1,2,2,2-tetrafluoro-1-trifluoromethyl-ethyl)-phenyl |
| 7-171 | H | —L—D | —CH2CH2— | CONH2 | 2-F | 1 | 3-cyanophenyl | 2,6-diiodo-4-(1,2,2,2-tetrafluoro-1-trifluoromethyl-ethyl)-phenyl |
| 7-172 | H | —L—D | —CH2CH2— | CONH2 | 2-F | 1 | 2-chloropyridin-3-yl | 2,6-diiodo-4-(1,2,2,2-tetrafluoro-1-trifluoromethyl-ethyl)-phenyl |
| 7-173 | H | —L—D | —CH2CH2— | CONH2 | 2-F | 1 | 2-fluorophenyl | 2,6-diiodo-4-(1,2,2,2-tetrafluoro-1-trifluoromethyl-ethyl)-phenyl |
| 7-174 | H | —L—D | —CH2CH2— | CONH2 | 2-F | 1 | phenyl | 2-bromo-6-trifluoromethyl-4-(1,2,2,2-tetrafluoro-1-trifluoromethyl-ethyl)-phenyl |
| 7-175 | H | —L—D | —CH2CH2— | CONH2 | 2-F | 1 | 3-cyanophenyl | 2-bromo-6-trifluoromethyl-4-(1,2,2,2-tetrafluoro-1-trifluoromethyl-ethyl)-phenyl |
| 7-176 | H | —L—D | —CH2CH2— | CONH2 | 2-F | 1 | 2-chloropyridin-3-yl | 2-bromo-6-trifluoromethyl-4-(1,2,2,2-tetrafluoro-1-trifluoromethyl-ethyl)-phenyl |
| 7-177 | H | —L—D | —CH2CH2— | CONH2 | 2-F | 1 | 2-fluorophenyl | 2-bromo-6-trifluoromethyl-4-(1,2,2,2-tetrafluoro-1-trifluoromethyl-ethyl)-phenyl |
| 7-178 | H | —L—D | —CH2CH2— | CONH2 | 2-F | 1 | phenyl | 2-iodo-6-trifluoromethyl-4-(1,2,2,2-tetrafluoro-1-trifluoromethyl-ethyl)-phenyl |
| 7-179 | H | —L—D | —CH2CH2— | CONH2 | 2-F | 1 | 3-cyanophenyl | 2-iodo-6-trifluoromethyl-4-(1,2,2,2-tetrafluoro-1-trifluoromethyl-ethyl)-phenyl |
| 7-180 | H | —L—D | —CH2CH2— | CONH2 | 2-F | 1 | 2-chloropyridin-3-yl | 2-iodo-6-trifluoromethyl-4-(1,2,2,2-tetrafluoro-1-trifluoromethyl-ethyl)-phenyl |
| 7-181 | H | —L—D | —CH2CH2— | CONH2 | 4-F | 1 | 2-fluorophenyl | 2-iodo-6-trifluoromethyl-4-(1,2,2,2-tetrafluoro-1-trifluoromethyl-ethyl)-phenyl |
| 7-182 | H | —L—D | —CH2CH2— | CONH2 | 2-F | 1 | phenyl | 2,6-dibromo-4-(1,2,2,3,3,3-hexafluoro-1-trifluoromethyl-propyl)-phenyl |
| 7-183 | H | —L—D | —CH2CH2— | CONH2 | 4-F | 1 | 3-cyanophenyl | 2,6-dibromo-4-(1,2,2,3,3,3-hexafluoro-1-trifluoromethyl-propyl)-phenyl |
| 7-184 | H | —L—D | —CH2CH2— | CONH2 | 2-F | 1 | 2-chloropyridin-3-yl | 2,6-dibromo-4-(1,2,2,3,3,3-hexafluoro-1-trifluoromethyl-propyl)-phenyl |
| 7-185 | H | —L—D | —CH2CH2— | CONH2 | 4-CN | 1 | 2-fluorophenyl | 2,6-dibromo-4-(1,2,2,3,3,3-hexafluoro-1-trifluoromethyl-propyl)-phenyl |
| 7-186 | H | —L—D | —CH2CH2— | CONH2 | 2-F | 1 | phenyl | 2,6-diiodo-4-(1,2,2,3,3,3-hexafluoro-1-trifluoromethyl-propyl)-phenyl |
| 7-187 | H | —L—D | —CH2CH2— | CONH2 | 2-F | 1 | 3-cyanophenyl | 2,6-diiodo-4-(1,2,2,3,3,3-hexafluoro-1-trifluoromethyl-propyl)-phenyl |
| 7-188 | H | —L—D | —CH2CH2— | CONH2 | 2-F | 1 | 2-chloropyridin-3-yl | 2,6-diiodo-4-(1,2,2,3,3,3-hexafluoro-1-trifluoromethyl-propyl)-phenyl |
| 7-189 | H | —L—D | —CH2CH2— | CONH2 | 2-F | 1 | 2-fluorophenyl | 2,6-diiodo-4-(1,2,2,3,3,3-hexafluoro-1-trifluoromethyl-propyl)-phenyl |
| 7-190 | H | —L—D | —CH2CH2— | CONH2 | 2-F | 1 | phenyl | 2-bromo-6-trifluoromethyl-4-(1,2,2,3,3,3-hexafluoro-1-trifluoromethyl-propyl)-phenyl |
| 7-191 | H | —L—D | —CH2CH2— | CONH2 | 4-CN | 1 | 3-cyanophenyl | 2-bromo-6-trifluoromethyl-4-(1,2,2,3,3,3-hexafluoro-1-trifluoromethyl-propyl)-phenyl |
| 7-192 | H | —L—D | —CH2CH2— | CONH2 | 2-F | 1 | 2-chloropyridin-3-yl | 2-bromo-6-trifluoromethyl-4-(1,2,2,3,3,3-hexafluoro-1-trifluoromethyl-propyl)-phenyl |
| 7-193 | H | —L—D | —CH2CH2— | CONH2 | 2-F | 1 | 2-fluorophenyl | 2-bromo-6-trifluoromethyl-4-(1,2,2,3,3,3-hexafluoro-1-trifluoromethyl-propyl)-phenyl |
| 7-194 | H | —L—D | —CH2CH2— | CONH2 | 2-F | 1 | phenyl | 2-iodo-6-trifluoromethyl-4-(1,2,2,3,3,3-hexafluoro-1-trifluoromethyl-propyl)-phenyl |
| 7-195 | H | —L—D | —CH2CH2— | CONH2 | 2-F | 1 | 3-cyanophenyl | 2-iodo-6-trifluoromethyl-4-(1,2,2,3,3,3-hexafluoro-1-trifluoromethyl-propyl)-phenyl |

TABLE 7-continued

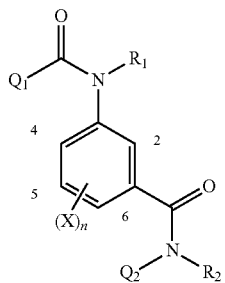

| compound number | R₁ | R₂ | L | D | X | n | Q₁ | Q₂ |
|---|---|---|---|---|---|---|---|---|
| 7-196 | H | —L—D | —CH2CH2— | CONH2 | 2-F | 1 | 2-chloropyridin-3-yl | 2-iodo-6-trifluoromethyl-4-(1,2,2,3,3,3-hexafluoro-1-trifluoromethyl-propyl)-phenyl |
| 7-197 | H | —L—D | —CH2CH2— | CONH2 | 2-F | 1 | 2-fluorophenyl | 2-iodo-6-trifluoromethyl-4-(1,2,2,3,3,3-hexafluoro-1-trifluoromethyl-propyl)-phenyl |
| 7-198 | H | —L—D | —CH2CH2— | CONH2 | H | 0 | 6-chloropyridin-3-yl | 2-bromo-6-trifluoromethyl-4-(1,2,2,2-tetrafluoro-1-trifluoromethyl-ethyl)-phenyl |
| 7-199 | H | —L—D | —CH2CH2— | CONH2 | 2-F | 1 | 6-chloropyridin-3-yl | 2-bromo-6-trifluoromethyl-4-(1,2,2,2-tetrafluoro-1-trifluoromethyl-ethyl)-phenyl |
| 7-200 | H | —L—D | —CH2CH2— | CONH2 | 2-F | 1 | 6-chloropyridin-3-yl | 2,6-dibromo-4-(1,2,2,2-tetrafluoro-1-trifluoromethyl-ethyl)-phenyl |
| 7-201 | H | —L—D | —CH2CH2— | CONH2 | 2-F | 1 | 3,5-dicyanophenyl | 2-bromo-6-trifluoromethyl-4-(1,2,2,2-tetrafluoro-1-trifluoromethyl-ethyl)-phenyl |
| 7-202 | H | —L—D | —CH2CH2— | CONH2 | 2-F | 1 | 3,5-dicyanophenyl | 2,6-dibromo-4-(1,2,2,2-tetrafluoro-1-trifluoromethyl-ethyl)-phenyl |
| 7-203 | H | —L—D | —CH2CH2— | CONH2 | 2-F | 1 | pyridin-3-yl | 2,6-dibromo-4-(1,22,2-tetrafluoro-1-trifluoromethyl-ethyl)-phenyl |
| 7-204 | H | —L—D | —CH2CH2— | CONH2 | 2-F | 1 | pyridin-4-yl | 2,6-dibromo-4-(1,2,2,2-tetrafluoro-1-trifluoromethyl-ethyl)-phenyl |
| 7-205 | H | —L—D | —CH2CH2— | CONH2 | 2-F | 1 | 2-chloropyridin-4-yl | 2,6-dibromo-4-(1,2,2,2-tetrafluoro-1-trifluoromethyl-ethyl)-phenyl |
| 7-206 | H | —L—D | —CH2CH2— | CONH2 | 2-F | 1 | pyrazin-2-yl | 2,6-dibromo-4-(1,2,2,2-tetrafluoro-1-trifluoromethyl-ethyl)-phenyl |
| 7-207 | H | —L—D | —CH2CH2— | CONH2 | 2-F | 1 | pyrimidin-5-yl | 2,6-dibromo-4-(1,2,2,2-tetrafluoro-1-trifluoromethyl-ethyl)-phenyl |
| 7-208 | H | —L—D | —CH2CH2— | CONH2 | 2-F | 1 | 3-cyanophenyl | 2,6-dichloro-4-(1,2,2,2-tetrafluoro-1-trifluoromethyl-ethyl)-phenyl |
| 7-209 | H | —L—D | —CH2CH2— | CONH2 | 2-F | 1 | phenyl | 2,6-dichloro-4-(1,2,2,2-tetrafluoro-1-trifluoromethyl-ethyl)-phenyl |
| 7-210 | H | —L—D | —CH2CH2— | CONH2 | 2-F | 1 | 2-chloropyridin-3-yl | 2,6-dichloro-4-(1,2,2,2-tetrafluoro-1-trifluoromethyl-ethyl)-phenyl |
| 7-211 | H | —L—D | —CH2CH2— | CONH2 | 2-F | 1 | 6-cyanopyridin-3-yl | 2,6-dibromo-4-(1,2,2,2-tetrafluoro-1-trifluoromethyl-ethyl)-phenyl |
| 7-212 | H | —L—D | —CH2CH2— | CONH2 | 2-F | 1 | 4-fluorophenyl | 2,6-dibromo-4-(1,2,2,2-tetrafluoro-1-trifluoromethyl-ethyl)-phenyl |
| 7-213 | H | —L—D | —CH2CH2— | CONH2 | 2-F | 1 | 2,6-difluorophenyl | 2,6-dibromo-4-(1,2,2,2-tetrafluoro-1-trifluoromethyl-ethyl)-phenyl |
| 7-214 | H | —L—D | —CH2CH2— | CONH2 | 2-F | 1 | 2-chloropyridin-3-yl | 2-bromo-6-iodo-4-(1,2,2,2-tetrafluoro-1-trifluoromethyl-ethyl)-phenyl |
| 7-215 | H | —L—D | —CH2CH2— | CONH2 | 2-F | 1 | phenyl | 2-bromo-6-iodo-4-(1,2,2,2-tetrafluoro-1-trifluoromethyl-ethyl)-phenyl |
| 7-216 | H | —L—D | —CH2CH2— | CONH2 | 2-F | 1 | 6-chloropyridin-3-yl | 2,6-dibromo-4-(1,2,2,3,3,3-hexafluoro-1-trifluoromethyl-propyl)-phenyl |
| 7-217 | H | —L—D | —CH2CH2— | CONH2 | 2-F | 1 | phenyl | 2,6-dimethyl-4-(1,2,2,3,3,3-hexafluoro-1-trifluoromethyl-propyl)-phenyl |
| 7-218 | H | —L—D | —CH2CH2— | CONH2 | 2-F | 1 | 4-cyanophenyl | 2,6-dimethyl-4-(1,2,2,3,3,3-hexafluoro-1-trifluoromethyl-propyl)-phenyl |
| 7-219 | H | —L—D | —CH2CH2— | CONH2 | 2-F | 1 | 3-cyanophenyl | 2,6-dimethyl-4-(1,2,2,3,3,3-hexafluoro-1-trifluoromethyl-propyl)-phenyl |
| 7-220 | Me | —L—D | —CH2— | CONH2 | 2-F | 1 | phenyl | 2,6-dimethyl-4-(1,2,2,2-tetrafluoro-1-trifluoromethyl-ethyl)-phenyl |
| 7-221 | Mc | —L—D | —CH2— | CO2Me | 2-F | 1 | phenyl | 2,6-dimethyl-4-(1,2,2,2-tetrafluoro-1-trifluoromethyl-ethyl)-phenyl |
| 7-222 | Me | —L—D | —CH2— | CO2H | 2-F | 1 | phenyl | 2,6-dimethyl-4-(1,2,2,2-tetrafluoro-1-trifluoromethyl-ethyl)-phenyl |
| 7-223 | Me | —L—D | —CH2CH2CH2— | CONH2 | 2-F | 1 | 3-cyanophenyl | 2,6-dimethyl-4-(1,2,2,2-tetrafluoro-1-trifluoromethyl-ethyl)-phenyl |
| 7-224 | H | —L—D | —CH2CH(CH3)— | CONH2 | 2-F | 1 | 4-cyanophenyl | 2,6-dimethyl-4-(1,2,2,2-tetrafluoro-1-trifluoromethyl-ethyl)-phenyl |
| 7-225 | H | —L—D | —CH(CH3)CH2— | CONH2 | 2-F | 1 | 4-cyanophenyl | 2,6-dimethyl-4-(1,2,2,2-tetrafluoro-1-trifluoromethyl-ethyl)-phenyl |
| 7-226 | H | —L—D | —CH2CH2CH2— | CO2Me | H | 0 | phenyl | 2,6-dimethyl-4-(1,2,2,2-tetrafluoro-1-trifluoromethyl-ethyl)-phenyl |

TABLE 7-continued

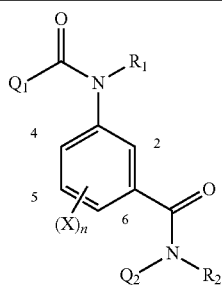

| compound number | R₁ | R₂ | L | D | X | n | Q₁ | Q₂ |
|---|---|---|---|---|---|---|---|---|
| 7-227 | —L—D | H | —CH2CH2— | CONMe2 | 2-F | 1 | phenyl | 2-bromo-6-trifluoromethyl-4-(1,2,2,2-tetrafluoro-1-trifluoromethyl-ethyl)-phenyl |
| 7-228 | —L—D | H | —CH2CH2— | CONH2 | 4-F | 1 | phenyl | 2-bromo-6-trifluoromethyl-4-(1,2,2,2-tetrafluoro-1-trifluoromethyl-ethyl)-phenyl |
| 7-229 | —L—D | H | —CH2CH2— | CONH2 | 4-CN | 1 | Phenyl | 2-iodo-6-trifluoromethyl-4-(1,2,2,2-tetrafluoro-1-trifluoromethyl-ethyl)-phenyl |
| 7-230 | —L—D | H | —CH2CH2— | CONH2 | 2-NO2 | 1 | phenyl | 2-bromo-6-trifluoromethyl-4-(1,2,2,3,3,3-hexafluoro-1-trifluoromethyl-propyl)-phenyl |

TABLE 8

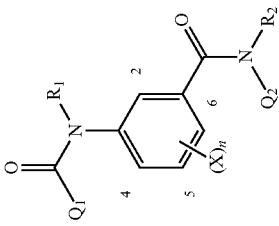

| compound number | R1 | R2 | L1 | D1 | L2 | D2 | X | n | Q1 | Q2 |
|---|---|---|---|---|---|---|---|---|---|---|
| 8-1 | —L1—D1 | —L2—D2 | —CH2CH2— | CONH2 | —CH2CH2— | CONH2 | H | 0 | phenyl | 2,6-dimethyl-4-(1,2,2,2-tetrafluoro-1-trifluoromethyl-ethyl)-phenyl |
| 8-2 | —L1—D1 | —L2—D2 | —CH2CH2— | CONH2 | —CH2CH2— | CONH2 | 2-F | 1 | phenyl | 2,6-dimethyl-4-O(1,2,2,2-tetrafluoro-1-trifluoromethyl-ethyl)-phenyl |
| 8-3 | —L1—D1 | —L2—D2 | —CH2CH2— | SO2Me | —CH2CH2— | CONH2 | 2-F | 1 | phenyl | 2,6-dimethyl-4-(1,2,2,2-tetrafluoro-1-trifluoromethyl-ethyl)-phenyl |
| 8-4 | —L1—D1 | —L2—D2 | —CH2CH2— | OH | —CH2CH2— | CONH2 | 2-F | 1 | phenyl | 2,6-dimethyl-4-(1,2,2,2-tetrafluoro-1-trifluoromethyl-ethyl)-phenyl |
| 8-5 | —L1—D1 | —L2—D2 | —CH2CH2— | CONH2 | —CH2CH2— | NH2 | 2-F | 1 | 4-cyanophenyl | 2,6-dimethyl-4-(1,2,2,2-tetrafluoro-1-trifluoromethyl-ethyl)-phenyl |
| 8-6 | —L1—D1 | —L2—D2 | —CH2CH2— | SOMe | —CH2CH2— | CONH2 | 2-F | 1 | 3-cyanophenyl | 2,6-dimethyl-4-(1,2,2,2-tetrafluoro-1-trifluoromethyl-ethyl)-phenyl |
| 8-7 | —L1—D1 | —L2—D2 | —CH2CH2— | CONH2 | —CH2CH2— | SOMe | 2-F | 1 | 3,5-dicyanophenyl | 2,6-dimethyl-4-(1,2,2,2-tetrafluoro-1-trifluoromethyl-ethyl)-phenyl |
| 8-8 | —L1—D1 | —L2—D2 | —CH2CH2— | CONH2 | —CH2— | CONH2 | 2-F | 1 | 2-fluorophenyl | 2,6-dimethyl-4-(1,2,2,2-tetrafluoro-1-trifluoromethyl-ethyl)-phenyl |
| 8-9 | —L1—D1 | —L2—D2 | —CH2— | CN | —CH2CH2— | CONH2 | 2-F | 1 | 4-fluorophenyl | 2,6-dimethyl-4-(1,2,2,2-tetrafluoro-1-trifluoromethyl-ethyl)-phenyl |
| 8-10 | —L1—D1 | —L2—D2 | —CH2CH2— | CONH2 | —CH2CH2— | SO2Me | 2-F | 1 | 2,6-difluorophenyl | 2,6-dimethyl-4-(1,2,2,2-tetrafluoro-1-trifluoromethyl-ethyl)-phenyl |
| 8-11 | —L1—D1 | —L2—D2 | —CH2CH2— | SOEt | —CH2CH2— | CONH2 | 2-F | 1 | 2-fluoro-4-cyanophenyl | 2,6-dimethyl-4-(1,2,2,2-tetrafluoro-1-trifluoromethyl-ethyl)-phenyl |

TABLE 8-continued

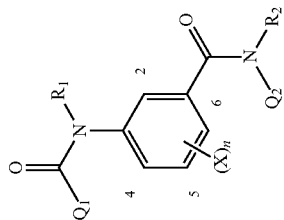

| compound number | R$_1$ | R$_2$ | L$_1$ | D$_1$ | L$_2$ | D$_2$ | X | n | Q$_1$ | Q$_2$ |
|---|---|---|---|---|---|---|---|---|---|---|
| 8-12 | —L$_1$—D$_1$ | —L$_2$—D$_2$ | —CH2— | CO2Me | —CH2— | CO2Me | 2-F | 1 | phenyl | 2,6-dimethyl-4-(1,2,2,2-tetrafluoro-1-trifluoromethyl-ethyl)-phenyl |
| 8-13 | —L$_1$—D$_1$ | —L$_2$—D$_2$ | —CH2— | CO2H | —CH2— | CO2H | 2-F | 1 | phenyl | 2,6-dimethyl-4-(1,2,2,2-tetrafluoro-1-trifluoromethyl-ethyl)-phenyl |
| 8-14 | —L$_1$—D$_1$ | —L$_2$—D$_2$ | —CH2CH2— | CONH2 | —CH2CH(CH3)— | CONH2 | 2-F | 1 | 4-nitrophenyl | 2,6-dimethyl-4-(1,2,2,2-tetrafluoro-1-trifluoromethyl-ethyl)-phenyl |
| 8-15 | —L$_1$—D$_1$ | —L$_2$—D$_2$ | —CH2CH2— | CONH2 | —CH2CH2— | CONH2 | 2-F | 1 | 2-methylphenyl | 2,6-dimethyl-4-(1,2,2,2-tetrafluoro-1-trifluoromethyl-ethyl)-phenyl |
| 8-16 | —L$_1$—D$_1$ | —L$_2$—D$_2$ | —CH2CH2— | CONH2 | —CH2CH2— | OH | 2-F | 1 | pyridin-2-yl | 2,6-dimethyl-4-(1,2,2,2-tetrafluoro-1-trifluoromethyl-ethyl)-phenyl |
| 8-17 | —L$_1$—D$_1$ | —L$_2$—D$_2$ | —CH2CH2— | CONH2 | —CH2CH2— | CONH2 | 2-F | 1 | pyridin-3-yl | 2,6-dimethyl-4-(1,2,2,2-tetrafluoro-1-trifluoromethyl-ethyl)-phenyl |
| 8-18 | —L$_1$—D$_1$ | —L$_2$—D$_2$ | —CH2CH2— | CONH2 | —CH2CH2— | CONH2 | 2-F | 1 | pyridin-4-yl | 2,6-dimethyl-4-(1,2,2,2-tetrafluoro-1-trifluoromethyl-ethyl)-phenyl |
| 8-19 | —L$_1$—D$_1$ | —L$_2$—D$_2$ | —CH2CH2— | pyrazin-2-yl | —CH(CH3)CH2— | CONH2 | 2-F | 1 | 2-chloropyridin-3-yl | 2,6-dimethyl-4-(1,2,2,2-tetrafluoro-1-trifluoromethyl-ethyl)-phenyl |
| 8-20 | —L$_1$—D$_1$ | —L$_2$—D$_2$ | —CH2CH2— | CONH2 | —CH2CH2— | CONH2 | 2-F | 1 | 6-chloropyridin-3-yl | 2,6-dimethyl-4-(1,2,2,2-tetrafluoro-1-trifluoromethyl-ethyl)-phenyl |
| 8-21 | —L$_1$—D$_1$ | —L$_2$—D$_2$ | —CH2CH2— | CONH2 | —CH2CH2— | SOMe | 2-F | 1 | 2-chloropyridin-4-yl | 2,6-dimethyl-4-(1,2,2,2-tetrafluoro-1-trifluoromethyl-ethyl)-phenyl |
| 8-22 | —L$_1$—D$_1$ | —L$_2$—D$_2$ | —CH2CH2— | CONH2 | —CH2CH2— | CONH2 | 2-F | 1 | pyrazin-2-yl | 2,6-dimethyl-4-(1,2,2,2-tetrafluoro-1-trifluoromethyl-ethyl)-phenyl |
| 8-23 | —L$_1$—D$_1$ | —L$_2$—D$_2$ | —CH2CH2— | CONH2 | —CH2CH2— | CONH2 | 2-F | 1 | pyrimidin-5-yl | 2,6-dimethyl-4-(1,2,2,2-tetrafluoro-1-trifluoromethyl-ethyl)-phenyl |

TABLE 8-continued

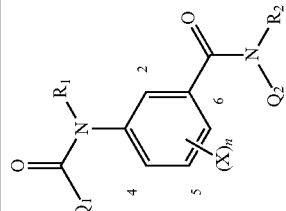

| compound number | R₁ | R₂ | L₁ | D₁ | L₂ | D₂ | X | n | Q₁ | Q₂ |
|---|---|---|---|---|---|---|---|---|---|---|
| 8-24 | —L₁—D₁ | —L₂—D₂ | —CH2CH2— | CONH2 | —CH2CH2— | CN | 4-F | 1 | phenyl | 2,6-dimethyl-4-(1,2,2,2-tetrafluoro-1-trifluoromethyl-ethyl)-phenyl |
| 8-25 | —L₁—D₁ | —L₂—D₂ | —CH2CH2— | CONH2 | —CH2CH2— | CONH2 | 4-F | 1 | 4-cyanophenyl | 2,6-dimethyl-4-(1,2,2,2-tetrafluoro-1-trifluoromethyl-ethyl)-phenyl |
| 8-26 | —L₁—D₁ | —L₂—D₂ | —CH2CH2— | CONH2 | —CH2CH2— | CONH2 | 4-F | 1 | 3-cyanophenyl | 2,6-dimethyl-4-(1,2,2,2-tetrafluoro-1-trifluoromethyl-ethyl)-phenyl |
| 8-27 | —L₁—D₁ | —L₂—D₂ | —CH2CH2— | CONH2 | —CH2CH2— | CONH2 | 4-F | 1 | 2-chloropyridin-3-yl | 2,6-dimethyl-4-(1,2,2,2-tetrafluoro-1-trifluoromethyl-ethyl)-phenyl |
| 8-28 | —L₁—D₁ | —L₂—D₂ | —CH2CH2— | CONH2 | —CH2CH2— | SO2Me | 4-F | 1 | 2-fluorophenyl | 2,6-dimethyl-4-(1,2,2,2-tetrafluoro-1-trifluoromethyl-ethyl)-phenyl |
| 8-29 | —L₁—D₁ | —L₂—D₂ | —CH2CH2— | CONH2 | —CH2CH2— | CONH2 | 4-CN | 1 | phenyl | 2,6-dimethyl-4-(1,2,2,2-tetrafluoro-1-trifluoromethyl-othyl)-phenyl |
| 8-30 | —L₁—D₁ | —L₂—D₂ | —CH2CH2— | CONH2 | —CH2CH2— | CONH2 | 4-CN | 1 | 4-cyanophenyl | 2,6-dimethyl-4-(1,2,2,2-tetrafluoro-1-trifluoromethyl-ethyl)-phenyl |
| 8-31 | —L₁—D₁ | —L₂—D₂ | —CH2CH2— | CONH2 | —CH2CH2— | CONH2 | 4-CN | 1 | 3-cyanophenyl | 2,6-dimethyl-4-(1,2,2,2-tetrafluoro-1-trifluoromethyl-ethyl)-phenyl |
| 8-32 | —L₁—D₁ | —L₂—D₂ | —CH2CH2— | CONH2 | —CH2CH2— | SO2Et | 4-CN | 1 | 2-chloropyridin-3-yl | 2,6-dimethyl-4-(1,2,2,2-tetrafluoro-1-trifluoromethyl-ethyl)-phenyl |
| 8-33 | —L₁—D₁ | —L₂—D₂ | —CH2CH2— | CONH2 | —CH2CH2— | CONH2 | 4-CN | 1 | 2-fluorophenyl | 2,6-dimethyl-4-(1,2,2,2-tetrafluoro-1-trifluoromethyl-ethyl)-phenyl |
| 8-34 | —L₁—D₁ | —L₂—D₂ | —CH2CH2— | CONH2 | —CH2CH2— | CONH2 | H | 0 | 4-cyanophenyl | 2,6-dibromo-4-pentafluoroethyl-phenyl |
| 8-35 | —L₁—D₁ | —L₂—D₂ | —CH2CH2— | CONH2 | —CH2CH2— | CONH2 | H | 0 | 4-cyanophenyl | 2,6-diiodo-4-pentafluoroethyl-phenyl |
| 8-36 | —L₁—D₁ | —L₂—D₂ | —CH2CH2— | CONH2 | —CH2CH2— | CONH2 | H | 0 | 4-cyanophenyl | 2-bromo-6-trifluoromethyl-4-pentafluoroethyl-phenyl |

TABLE 8-continued

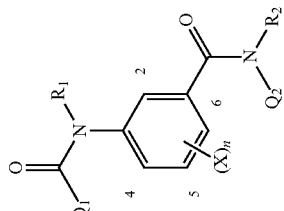

| compound number | R₁ | R₂ | L₁ | D₁ | L₂ | D₂ | X | n | Q₁ | Q₂ |
|---|---|---|---|---|---|---|---|---|---|---|
| 8-37 | —L₁—D₁ | —L₂—D₂ | —CH2CH2— | CONH2 | —CH2CH2— | CONH2 | H | 0 | 4-cyanophenyl | 2-iodo-6-trifluoromethyl-4-pentuafluoroethyl-phenyl |
| 8-38 | —L₁—D₁ | —L₂—D₂ | —CH2CH2— | CONH2 | —CH2CH2— | OH | H | 0 | 4-cyanophenyl | 2-chloro-6-methyl-4-(1,2,2,2-tetrafluoro-1-trifluoromethyl-ethyl)-phenyl |
| 8-39 | —L₁—D₁ | —L₂—D₂ | —CH2CH2— | CONH2 | —CH2CH2— | CONH2 | H | 0 | 4-cyanophenyl | 2-bromo-6-methyl-4-(1,2,2,2-tetrafluoro-1-trifluoromethyl-ethyl)-phenyl |
| 8-40 | —L₁—D₁ | —L₂—D₂ | —CH2CH2— | CONH2 | —CH2CH2— | CONH2 | H | 0 | 4-cyanophenyl | 2-iodo-6-methyl-4-(1,2,2,2-tetrafluoro-1-trifluoromethyl-ethyl)-phenyl |
| 8-41 | —L₁—D₁ | —L₂—D₂ | —CH2CH2— | CONH2 | —CH2CH2— | CONH2 | H | 0 | 4-cyanophenyl | 2-bromo-6-ethyl-4-(1,2,2,2-tetrafluoro-1-trifluoromethyl-ethyl)-phenyl |
| 8-42 | —L₁—D₁ | —L₂—D₂ | —CH2CH2— | CONH2 | —CH2CH2— | CONH2 | H | 0 | 4-cyanophenyl | 2-iodo-6-ethyl-4-(1,2,2,2-tetrafluoro-1-trifluoromethyl-ethyl)-phenyl |
| 8-43 | —L₁—D₁ | —L₂—D₂ | —CH2CH2— | CONH2 | —CH2CH2— | CONH2 | H | 0 | 4-cyanophenyl | 2,6-dichloro-4-(1,2,2,2-tetrafluoro-1-trifluoromethyl)-phenyl |
| 8-44 | —L₁—D₁ | —L₂—D₂ | —CH2CH2— | CONH2 | —CH2CH2— | CONH2 | H | 0 | 4-cyanophenyl | 2,6-dibromo-4-(1,2,2,2-tetrafluoro-1-trifluoromethyl-ethyl)-phenyl |
| 8-45 | —L₁—D₁ | —L₂—D₂ | —CH2CH2— | CONH2 | —CH2CH2— | CONH2 | H | 0 | 4-cyanophenyl | 2,6-diiodo-4-(1,2,2,2-tetrafluoro-1-trifluoromethyl-ethyl)-phenyl |
| 8-46 | —L₁—D₁ | —L₂—D₂ | —CH2CH2— | CONH2 | —CH2CH2— | CONH2 | H | 0 | 4-cyanophenyl | 2,6-ditrifluoromethyl-4-(1,2,2,2-tetrafluoro-1-trifluoromethyl-ethyl)-phenyl |
| 8-47 | —L₁—D₁ | —L₂—D₂ | —CH2CH2— | CONH2 | —CH2CH2— | CONH2 | H | 0 | 4-cyanophenyl | 2-bromo-6-trifluoromethyl-4-(1,2,2,2-tetrafluoro-1-trifluoromethyl-ethyl)-phenyl |
| 8-48 | —L₁—D₁ | —L₂—D₂ | —CH2CH2— | CONH2 | —CH2CH2— | CONH2 | 11 | 0 | 4-cyanophenyl | 2-iodo-6-trifluoromethyl-4-(1,2,2,2-tetrafluoro-1-trifluoromethyl-ethyl)-phenyl |

TABLE 8-continued

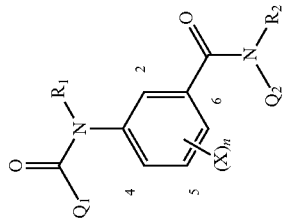

| compound number | R₁ | R₂ | L₁ | D₁ | L₂ | D₂ | X | n | Q₁ | Q₂ |
|---|---|---|---|---|---|---|---|---|---|---|
| 8-49 | —L₁—D₁ | —L₂—D₂ | —CH2CH2— | CONH2 | —CH2CH2— | CONH2 | H | 0 | 4-cyanophenyl | 2-bromo-6-trifluoromethoxy-4-(1,2,2,2-tetrafluoro-1-trifluoromethyl-ethyl)-phenyl |
| 8-50 | —L₁—D₁ | —L₂—D₂ | —CH2CH2— | CONH2 | —CH(CH3)CH(CH3)— | CONH2 | H | 0 | 4-cyanophenyl | 2-bromo-6-iodo-4-(1,2,2,2-tetrafluoro-1-trifluoromethyl-ethyl)-phenyl |
| 8-51 | —L₁—D₁ | —L₂—D₂ | —CH2CH2— | CONH2 | —CH2CH2— | CONH2 | H | 0 | 4-cyanophenyl | 2-bromo-6-trifluoromethylthio-4-(1,2,2,2-tetrafluoro-1-trifluoromethyl-ethyl)-phenyl |
| 8-52 | —L₁—D₁ | —L₂—D₂ | —CH2CH2— | CONH2 | —CH2CH2— | CONH2 | H | 0 | 4-cyanophenyl | 2-bromo-6-trifluoromethylsulfinyl-4-(1,2,2,2-tetrafluoro-1-trifluoromethyl-ethyl)-phenyl |
| 8-53 | —L₁—D₁ | —L₂—D₂ | —CH2CH2— | CONH2 | —CH2CH2— | CONH2 | H | 0 | 4-cyanophenyl | 2-bromo-6-trifluoromethylsulfonyl-4-(1,2,2,2-tetrafluoro-1-trifluoromethyl-ethyl)-phenyl |
| 8-54 | —L₁—D₁ | —L₂—D₂ | —CH2CH2— | CONH2 | —CH2CH2— | CONH2 | H | 0 | 4-cyanophenyl | 2-bromo-6-pentafluoroethyl-4-(1,2,2,2-tetrafluoro-1-trifluoromethyl-ethyl)-phenyl |
| 8-55 | —L₁—D₁ | —L₂—D₂ | —CH2CH2— | CONH2 | —CH2CH2— | CONH2 | H | 0 | 4-cyanophenyl | 2-iodo-6-pentafluoroethyl-4-(1,2,2,2-tetrafluoro-1-trifluoromethyl-ethyl)-phenyl |
| 8-56 | —L₁—D₁ | —L₂—D₂ | —CH2CH2— | CONH2 | —CH2CH2— | CONH2 | H | 0 | 4-cyanophenyl | 2-chloro-6-methyl-4-(1,2,2,3,3,3-hexafluoro-1-trifluoromethyl-propyl)-phenyl |
| 8-57 | —L₁—D₁ | —L₂—D₂ | —CH2CH2— | CONH2 | —CH2CH2— | CONH2 | H | 0 | 4-cyanophenyl | 2-bromo-6-methyl-4-(1,2,2,3,3,3-hexafluoro-1-trifluoromethyl-propyl)-phenyl |
| 8-58 | —L₁—D₁ | —L₂—D₂ | —CH2CH2— | CONH2 | —CH2CH2— | CONH2 | H | 0 | 4-cyanophenyl | 2-iodo-6-methyl-4-(1,2,2,3,3,3-hexafluoro-1-trifluoromethyl-propyl)-phenyl |
| 8-59 | —L₁—D₁ | —L₂—D₂ | —CH2CH2— | CONH2 | —CH2CH2— | CONH2 | H | 0 | 4-cyanophenyl | 2-bromo-6-ethyl-4-(1,2,2,3,3,3-hexafluoro-1-trifluoromethyl-propyl)-phenyl |

TABLE 8-continued

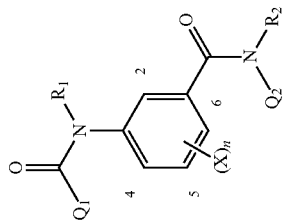

| compound number | R₁ | R₂ | L₁ | D₁ | L₂ | D₂ | X | n | Q₁ | Q₂ |
|---|---|---|---|---|---|---|---|---|---|---|
| 8-60 | —L₁—D₁ | —L₂—D₂ | —CH2CH2— | CONH2 | —CH2CH2— | CONH2 | H | 0 | 4-cyanophenyl | 2-iodo-6-ethyl-4-(1,2,2,3,3,3-hexafluoro-1-trifluoromethyl-propyl)-phenyl |
| 8-81 | —L₁—D₁ | —L₂—D₂ | —CH2CH2— | CONH2 | —CH2CH2— | CONH2 | H | 0 | 4-cyanophenyl | 2,6-dichloro-4-(1,2,2,3,3,3-hexafluoro-1-trifluoromethyl-propyl)-phenyl |
| 8-62 | —L₁—D₁ | —L₂—D₂ | —CH2CH2— | CONH2 | —CH2CH2— | CONH2 | H | 0 | 4-cyanophenyl | 2,6-dibromo-4-(1,2,2,3,3,3-hexafluoro-1-trifluoromethyl-propy)-phenyl |
| 8-63 | —L₁—D₁ | —L₂—D₂ | —CH2CH2— | CONH2 | —CH2CH2— | CONH2 | H | 0 | 4-cyanophenyl | 2,6-diiodo-4-(1,2,2,3,3,3-hexafluoro-1-trifluoromethyl-propyl)-phenyl |
| 8-64 | —L₁—D₁ | —L₂—D₂ | —CH2CH2— | CONH2 | —CH2CH2— | CONH2 | H | 0 | 4-cyanophenyl | 2,6-ditrifluoromethyl-4-(1,2,2,3,3,3-hexafluoro-1-trifluoromethyl-propyl)-phenyl |
| 8-65 | —L₁—D₁ | —L₂—D₂ | —CH2CH2— | CONH2 | —CH2CH2— | CONH2 | H | 0 | 4-cyanophenyl | 2-bromo-6-trifluoromethyl-4-(1,2,2,3,3,3-hexafluoro-1-trifluoromethyl-propyl)-phenyl |
| 8-66 | —L₁—D₁ | —L₂—D₂ | —CH2CH2— | SO2Me | —CH2CH2— | CONH2 | H | 0 | 4-cyanophenyl | 2-iodo-6-trifluoromethyl-4-(1,2,2,3,3,3-hexafluoro-1-trifluoromethyl-propyl)-phenyl |
| 8-67 | —L₁—D₁ | —L₂—D₂ | —CH2CH2— | CONH2 | —CH2CH2— | CONH2 | H | 0 | 4-cyanophenyl | 2-bromo-6-trifluoromethoxy-4-(1,2,2,3,3,3-hexafluoro-1-trifluoromethyl-propyl)-phenyl |
| 8-68 | —L₁—D₁ | —L₂—D₂ | —CH2CH2— | CONH2 | —CH2CH2— | CONH2 | H | 0 | 4-cyanophenyl | 2-bromo-6-iodo-4-(1,2,2,3,3,3-hexafluoro-1-trifluoromethyl-propyl)-phenyl |
| 8-69 | —L₁—D₁ | —L₂—D₂ | —CH2CH2— | CONH2 | —CH2CH2— | CONH2 | H | 0 | 4-cyanophenyl | 2-bromo-6-trifluoromethylthio-4-(1,2,2,3,3,3-hexafluoro-1-trifluoromethyl-propyl)-phenyl |
| 8-70 | —L₁—D₁ | —L₂—D₂ | —CH2CH2— | CONH2 | —CH2CH2— | CONH2 | H | 0 | 4-cyanophenyl | 2-bromo-6-trifluoromethylsulfinyl-4-(1,2,2,3,3,3-hexafluoro-1-trifluoromethyl-propyl)-phenyl |

TABLE 8-continued

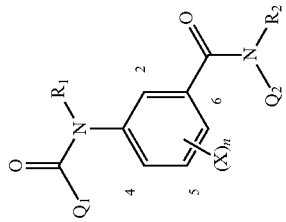

| compound number | R₁ | R₂ | L₁ | D₁ | L₂ | D₂ | X | n | Q₁ | Q₂ |
|---|---|---|---|---|---|---|---|---|---|---|
| 8-71 | —L₁—D₁ | —L₂—D₂ | —CH2CH2— | CONH2 | —CH2CH2— | CONH2 | H | 0 | 4-cyanophenyl | 2-bromo-6-trifluoromethylsulfonyl-4-(1,2,2,3,3,3-hexafluoro-1-trifluoromethyl-propyl)-phenyl |
| 8-72 | —L₁—D₁ | —L₂—D₂ | —CH2CH2— | CONH2 | —CH2CH2— | CONH2 | H | 0 | 4-cyanophenyl | 2-bromo-6-pentafluoroethyl-4-(1,2,2,3,3,3-hexafluoro-1-trifluoromethyl-propyl)-phenyl |
| 8-73 | —L₁—D₁ | —L₂—D₂ | —CH2CH2— | CONH2 | —CH2CH2— | CONH2 | H | 0 | 4-cyanophenyl | 2-iodo-6-pentafluoroethyl-4-(1,2,2,3,3,3-hexafluoro-1-trifluoromethyl-propyl)-phenyl |
| 8-74 | —L₁—D₁ | —L₂—D₂ | —CH2CH2— | CONH2 | —CH2CH2— | CONH2 | H | 0 | phenyl | 2,6-dibromo-4-(1,2,2,2-tetrafluoro-1-trifluoromethyl-ethyl)-phenyl |
| 8-75 | —L₁—D₁ | —L₂—D₂ | —CH2CH2— | CONH2 | —CH2CH2— | CONH2 | H | 0 | 3-cyanophenyl | 2,6-dibromo-4-(1,2,2,2-tetrafluoro-1-trifluoromethyl-ethyl)-phenyl |
| 8-76 | —L₁—D₁ | —L₂—D₂ | —CH2CH2— | CONH2 | —CH2CH2— | CONH2 | H | 0 | 2-chloropyridin-3-yl | 2,6-dibromo-4-(1,2,2,2-tetrafluoro-1-trifluoromethyl-ethyl)-phenyl |
| 8-77 | —L₁—D₁ | —L₂—D₂ | —CH2CH2— | CONH2 | —CH2CH2— | CONH2 | H | 0 | 2-fluorophenyl | 2,6-dibromo-4-(1,2,2,2-tetrafluoro-trifluoromethyl-ethyl)-phenyl |
| 8-78 | —L₁—D₁ | —L₂—D₂ | —CH2CH2— | CONH2 | —CH2CH2— | CONH2 | H | 0 | phenyl | 2,6-diiodo-4-(1,2,2,2-tetrafluoro-1-trifluoromethyl-ethyl)-phenyl |
| 8-78 | —L₁—D₁ | —L₂—D₂ | —CH2CH2— | CONH2 | —CH2CH2— | CONH2 | H | 0 | 3-cyanophenyl | 2,6-diiodo-4-(1,2,2,2-tetrafluoro-1-trifluoromethyl-ethyl)-phenyl |
| 8-80 | —L₁—D₁ | —L₂—D₂ | —CH2CH2— | CONH2 | —CH2CH2— | CONH2 | H | 0 | 2-chloropyridin-3-yl | 2,6-diiodo-4-(1,2,2,2-tetrafluoro-1-trifluoromethyl-ethyl)-phenyl |
| 8-81 | —L₁—D₁ | —L₂—D₂ | —CH2CH2— | CONH2 | —CH2CH2— | CONH2 | H | 0 | 2-fluorophenyl | 2,6-diiodo-4-(1,2,2,2-tetrafluoro-1-trifluoromethyl-ethyl)-phenyl |

TABLE 8-continued

| compound number | R₁ | R₂ | L₁ | D₁ | L₂ | D₂ | X | n | Q₁ | Q₂ |
|---|---|---|---|---|---|---|---|---|---|---|
| 8-82 | —L₁—D₁ | —L₂—D₂ | —CH2CH2— | CONH2 | —CH2CH2— | CONH2 | H | 0 | phenyl | 2-bromo-6-trifluoromethyl-4-(1,2,2,2-tetrafluoro-1-trifluoromethyl-ethyl)-phenyl |
| 8-83 | —L₁—D₁ | —L₂—D₂ | —CH2CH2— | CONH2 | —CH2CH2— | CONH2 | H | 0 | 3-cyanophenyl | 2-bromo-6-trifluoromethyl-4-(1,2,2,2-tetrafluoro-1-trifluoromethyl-ethyl)-phenyl |
| 8-84 | —L₁—D₁ | —L₂—D₂ | —CH2CH2— | CONH2 | —CH2CH2— | CONH2 | H | 0 | 2-chloropyridin-3-yl | 2-bromo-6-trifluoromethyl-4-(1,2,2,2-tetrafluoro-1-trifluoromethyl-ethyl)-phenyl |
| 8-85 | —L₁—D₁ | —L₂—D₂ | —CH2CH2— | CONH2 | —CH2CH2— | CONH2 | H | 0 | 2-fluorophenyl | 2-bromo-6-trifluoromethyl-4-(1,2,2,2-tetrafluoro-1-trifluoromethyl-ethyl)-phenyl |
| 8-86 | —L₁—D₁ | —L₂—D₂ | —CH2CH2— | CONH2 | —CH2CH2— | CONH2 | H | 0 | phenyl | 2-iodo-6-trifluoromethyl-4-(1,2,2,2-tetrafluoro-1-trifluoromethyl-ethyl)-phenyl |
| 8-87 | —L₁—D₁ | —L₂—D₂ | —CH2CH2— | CONH2 | —CH2CH2— | CONH2 | H | 0 | 3-cyanophenyl | 2-iodo-6-trifluoromethyl-4-(1,2,2,2-tetrafluoro-1-trifluoromethyl-ethyl)-phenyl |
| 8-88 | —L₁—D₁ | —L₂—D₂ | —CH2CH2— | CONH2 | —CH2CH2— | CONH2 | H | 0 | 2-chloropyridin-3-yl | 2-iodo-6-trifluoromethyl-4-(1,2,2,2-tetrafluoro-1-trifluoromethyl-ethyl)-phenyl |
| 8-89 | —L₁—D₁ | —L₂—D₂ | —CH2CH2— | CONH2 | —CH2CH2— | CONH2 | H | 0 | 2-fluorophenyl | 2-iodo-6-trifluoromethyl-4-(1,2,2,2-tetrafluoro-1-trifluoromethyl-ethyl)-phenyl |
| 8-90 | —L₁—D₁ | —L₂—D₂ | —CH2CH2— | CONH2 | —CH2CH2— | CONH2 | H | 0 | phenyl | 2,6-dibromo-4-(1,2,3,3,3-hexafluoro-1-trifluoromethyl-propyl)-phenyl |
| 8-91 | —L₁—D₁ | —L₂—D₂ | —CH2CH2— | CONH2 | —CH2CH2— | CONH2 | H | 0 | 3-cyanophenyl | 2,6-dibromo-4-(1,2,3,3,3-hexafluoro-1-trifluoromethyl-propyl)-phenyl |
| 8-92 | —L₁—D₁ | —L₂—D₂ | —CH2CH2— | CONH2 | —CH2CH2— | CONH2 | H | 0 | 2-chloropyridin-3-yl | 2,6-dibromo-4-(1,2,3,3,3-hexafluoro-1-trifluoromethyl-propyl)-phenyl |
| 8-93 | —L₁—D₁ | —L₂—D₂ | —CH2CH2— | CONH2 | —CH2CH2— | CONH2 | H | 0 | 2-fluorophenyl | 2,6-dibromo-4-(1,2,3,3,3-hexafluoro-1-trifluoromethyl-propyl)-phenyl |

TABLE 8-continued

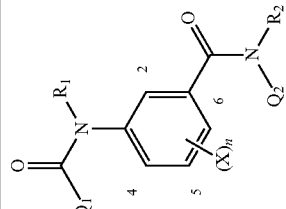

| compound number | R1 | R2 | L1 | D1 | L2 | D2 | X | n | Q1 | Q2 |
|---|---|---|---|---|---|---|---|---|---|---|
| 8-94 | —L1—D1 | —L2—D2 | —CH2CH2— | CONH2 | —CH2CH2— | CONH2 | H | 0 | phenyl | 2,6-diiodo-4-(1,2,2,3,3,3-hexafluoro-1-trifluoromethyl-propyl)-phenyl |
| 8-95 | —L1—D1 | —L2—D2 | —CH2CH2— | CONH2 | —CH2CH2— | CONH2 | H | 0 | 3-cyanophenyl | 2,6-diiodo-4-(1,2,2,3,3,3-hexafluoro-1-trifluoromethyl-propyl)-phenyl |
| 8-96 | —L1—D1 | —L2—D2 | —CH2CH2— | CONH2 | —CH2CH2— | CONH2 | H | 0 | 2-chloropyridin-3-yl | 2,6-diiodo-4-(1,2,2,3,3,3-hexafluoro-1-trifluoromethyl-propyl)-phenyl |
| 8-97 | —L1—D1 | —L2—D2 | —CH2CH2— | CONH2 | —CH2CH2— | CONH2 | H | 0 | 2-fluorophenyl | 2,6-diiodo-4-(1,2,2,3,3,3-hexafluoro-1-trifluoromethyl-propyl)-phenyl |
| 8-98 | —L1—D1 | —L2—D2 | —CH2CH2— | CONH2 | —CH2CH2— | CONH2 | H | 0 | phenyl | 2-bromo-6-trifluoromethyl-4-(1,2,2,3,3,3-hexafluoro-1-trifluoromethyl-propyl)-phenyl |
| 8-99 | —L1—D1 | —L2—D2 | —CH2CH2— | CONH2 | —CH2CH2— | CONH2 | H | 0 | 3-cyanophenyl | 2-bromo-6-trifluoromethyl-4-(1,2,2,3,3,3-hexafluoro-1-trifluoromethyl-propyl)-phenyl |
| 8-100 | —L1—D1 | —L2—D2 | —CH2CH2— | CONH2 | —CH2CH2— | CONH2 | H | 0 | 2-chloropyridin-3-yl | 2-bromo-6-trifluoromethyl-4-(1,2,2,3,3,3-hexafluoro-1-trifluoromethyl-propyl)-phenyl |
| 8-101 | —L1—D1 | —L2—D2 | —CH2CH2— | CONH2 | —CH2CH2— | CONH2 | H | 0 | 2-fluorophenyl | 2-bromo-6-trifluoromethyl-4-(1,2,2,3,3,3-hexafluoro-1-trifluoromethyl-propyl)-phenyl |
| 8-102 | —L1—D1 | —L2—D2 | —CH2CH2— | CONH2 | —CH2CH2— | CONH2 | H | 0 | phenyl | 2-iodo-6-trifluoromethyl-4-(1,2,2,3,3,3-hexafluoro-1-trifluoromethyl-propyl)-phenyl |
| 8-103 | —L1—D1 | —L2—D2 | —CH2CH2— | CONH2 | —CH2CH2— | CONH2 | H | 0 | 3-cyanophenyl | 2-iodo-6-trifluoromethyl-4-(1,2,2,3,3,3-hexafluoro-1-trifluoromethyl-propyl)-phenyl |
| 8-104 | —L1—D1 | —L2—D2 | —CH2CH2— | CONH2 | —CH2CH2— | CONH2 | H | 0 | 2-chloropyridin-3-yl | 2-iodo-6-trifluoromethyl-4-(1,2,2,3,3,3-hexafluoro-1-trifluoromethyl-propyl)-phenyl |
| 8-105 | —L1—D1 | —L2—D2 | —CH2CH2— | CONH2 | —CH2CH2— | CONH2 | H | 0 | 2-fluorophenyl | 2-iodo-6-trifluoromethyl-4-(1,2,2,3,3,3-hexafluoro-1-trifluoromethyl-propyl)-phenyl |

TABLE 8-continued

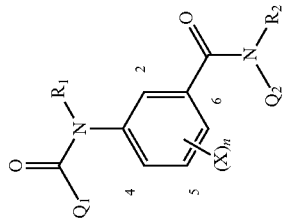

| compound number | R₁ | R₂ | L₁ | D₁ | L₂ | D₂ | X | n | Q₁ | Q₂ |
|---|---|---|---|---|---|---|---|---|---|---|
| 8-106 | —L₁—D₁ | —L₂—D₂ | —CH2CH2— | CONH2 | —CH2CH2— | CONH2 | 2-F | 1 | 4-cyanophenyl | 2,6-dibromo-4-pentafluoroethyl-phenyl |
| 8-107 | —L₁—D₁ | —L₂—D₂ | —CH2CH2— | CONH2 | —CH2CH2— | CONH2 | 2-F | 1 | 4-cyanophenyl | 2,6-diiodo-4-pentafluoroethyl-phenyl |
| 8-108 | —L₁—D₁ | —L₂—D₂ | —CH2CH2— | CONH2 | —CH2CH2— | CONH2 | 2-F | 1 | 4-cyanophenyl | 2-bromo-6-trifluoromethyl-4-pentafluoroethyl-phenyl |
| 8-109 | —L₁—D₁ | —L₂—D₂ | —CH2CH2— | CONH2 | —CH2CH2— | CONH2 | 2-F | 1 | 4-cyanophenyl | 2-iodo-6-trifluoromethyl-4-pentafluoroethyl-phenyl |
| 8-110 | —L₁—D₁ | —L₂—D₂ | —CH2CH2— | CONH2 | —CH2CH2— | CONH2 | 2-F | 1 | 4-cyanophenyl | 2-chloro-6-methyl-4-(1,2,2,2-tetrafluoro-1-trifluoromethyl-ethyl)-phenyl |
| 8-111 | —L₁—D₁ | —L₂—D₂ | —CH2CH2— | CONH2 | —CH2CH2— | CONH2 | 2-F | 1 | 4-cyanophenyl | 2-bromo-6-methyl-4-(1,2,2,2-tetrafluoro-1-trifluoromethyl-ethyl)-phenyl |
| 8-112 | —L₁—D₁ | —L₂—D₂ | —CH2CH2— | CONH2 | —CH2CH2— | CONH2 | 2-F | 1 | 4-cyanophenyl | 2-iodo-6-methyl-4-(1,2,2,2-tetrafluoro-1-trifluoromethyl-ethyl)-phenyl |
| 8-113 | —L₁—D₁ | —L₂—D₂ | —CH2CH2— | CONH2 | —CH2CH2— | CONH2 | 2-F | 1 | 4-cyanophenyl | 2-bromo-6-ethyl-4-(1,2,2,2-tetrafluoro-1-trifluoromethyl-ethyl)-phenyl |
| 8-114 | —L₁—D₁ | —L₂—D₂ | —CH2CH2— | CONH2 | —CH2CH2— | CONH2 | 2-F | 1 | 4-cyanophenyl | 2-iodo-6-ethyl-4-(1,2,2,2-tetrafluoro-1-trifluoromethyl-ethyl)-phenyl |
| 8-115 | —L₁—D₁ | —L₂—D₂ | —CH2CH2— | CONH2 | —CH2CH2— | CONH2 | 2-F | 1 | 4-cyanophenyl | 2,6-dichloro-4-(1,2,2,2-tetrafluoro-1-trifluoromethyl-ethyl)-phenyl |
| 8-116 | —L₁—D₁ | —L₂—D₂ | —CH2CH2— | CONH2 | —CH2CH2— | CONH2 | 2-F | 1 | 4-cyanophenyl | 2,6-dibromo-4-(1,2,2,2-tetrafluoro-1-trifluoromethyl-ethyl)-phenyl |
| 8-117 | —L₁—D₁ | —L₂—D₂ | —CH2CH2— | CONH2 | —CH2CH2— | CONH2 | 2-F | 1 | 4-cyanophenyl | 2,6-diiodo-4-(1,2,2,2-tetrafluoro-1-trifluoromethyl-ethyl)-phenyl |
| 8-118 | —L₁—D₁ | —L₂—D₂ | —CH2CH2— | CONH2 | —CH2CH2— | CONH2 | 2-F | 1 | 4-cyanophenyl | 2,6-ditrifluoromethyl-4-(1,2,2,2-tetrafluoro-1-trifluoromethyl-ethyl)-phenyl |

TABLE 8-continued

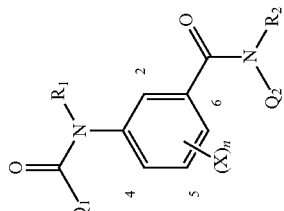

| compound number | R₁ | R₂ | L₁ | D₁ | L₂ | D₂ | X | n | Q₁ | Q₂ |
|---|---|---|---|---|---|---|---|---|---|---|
| 8-119 | —L₁—D₁ | —L₂—D₂ | —CH2CH2— | CONH2 | —CH2CH2— | CONH2 | 2-F | 1 | 4-cyanophenyl | 2-bromo-6-trifluoromethyl-4-(1,2,2,2-tetrafluoro-1-trifluoromethyl-ethyl)-phenyl |
| 8-120 | —L₁—D₁ | —L₂—D₂ | —CH2CH2— | CONH2 | —CH2CH2— | CONH2 | 2-F | 1 | 4-cyanophenyl | 2-iodo-6-trifluoromethyl-4-(1,2,2,2-tetrafluoro-1-trifluoromethyl-ethyl)-phenyl |
| 8-121 | —L₁—D₁ | —L₂—D₂ | —CH2CH2— | CONH2 | —CH2CH2— | CONH2 | 2-F | 1 | 4-cyanophenyl | 2-bromo-6-trifluoromethoxy-4-(1,2,2,2-tetrafluoro-1-trifluoromethyl-ethyl)-phenyl |
| 8-122 | —L₁—D₁ | —L₂—D₂ | —CH2CH2— | CONH2 | —CH2CH2— | CONH2 | 2-F | 1 | 4-cyanophenyl | 2-bromo-6-iodo-4-(1,2,2,2-tetrafluoro-1-trifluoromethyl-ethyl)-phenyl |
| 8-123 | —L₁—D₁ | —L₂—D₂ | —CH2CH2— | CONH2 | —CH2CH2— | CONH2 | 2-F | 1 | 4-cyanophenyl | 2-bromo-6-trifluoromethylthio-4-(1,2,2,2-tetrafluoro-1-trifluoromethyl-ethyl)-phenyl |
| 8-124 | —L₁—D₁ | —L₂—D₂ | —CH2CH2— | CONH2 | —CH2CH2— | CONH2 | 2-F | 1 | 4-cyanophenyl | 2-bromo-6-trifluoromethylsulfinyl-4-(1,2,2,2-tetrafluoro-1-trifluoromethyl-ethyl)-phenyl |
| 8-125 | —L₁—D₁ | —L₂—D₂ | —CH2CH2— | CONH2 | —CH2CH2— | CONH2 | 2-F | 1 | 4-cyanophenyl | 2-bromo-6-trifluoromethylsulfonyl-4-(1,2,2,2-tetrafluoro-1-trifluoromethyl-ethyl)-phenyl |
| 8-126 | —L₁—D₁ | —L₂—D₂ | —CH2CH2— | CONH2 | —CH2CH2— | CONH2 | 2-F | 1 | 4-cyanophenyl | 2-bromo-6-pentafluoroethyl-4-(1,2,2,2-tetrafluoro-1-trifluoromethyl-ethyl)-phenyl |
| 8-127 | —L₁—D₁ | —L₂—D₂ | —CH2CH2— | CONH2 | —CH2CH2— | CONH2 | 2-F | 1 | 4-cyanophenyl | 2-iodo-6-pentafluoroethyl-4-(1,2,2,2-tetrafluoro-1-trifluoromethyl-ethyl)-phenyl |
| 8-128 | —L₁—D₁ | —L₂—D₂ | —CH2CH2— | CONH2 | —CH2CH2— | CONH2 | 2-F | 1 | 4-cyanophenyl | 2-chloro-6-methyl-4-(1,2,2,3,3,3-hexafluoro-1-trifluoromethyl-propyl)-phenyl |
| 8-129 | —L₁—D₁ | —L₂—D₂ | —CH2CH2— | CONH2 | —CH2CH2— | CONH2 | 2-F | 1 | 4-cyanophenyl | 2-bromo-6-methyl-4-(1,2,2,3,3,3-hexafluoro-1-trifluoromethyl-propyl)-phenyl |

TABLE 8-continued

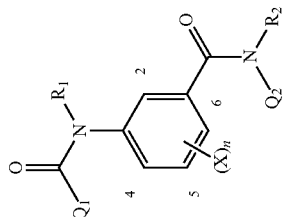

| compound number | R₁ | R₂ | L₁ | D₁ | L₂ | D₂ | X | n | Q₁ | Q₂ |
|---|---|---|---|---|---|---|---|---|---|---|
| 8-130 | —L₁—D₁ | —L₂—D₂ | —CH2CH2— | CONH2 | —CH2CH2— | CONH2 | 2-F | 1 | 4-cyanophenyl | 2-iodo-6-methyl-4-(1,2,2,3,3,3-hexafluoro-1-trifluoromethyl-propyl)-phenyl |
| 8-131 | —L₁—D₁ | —L₂—D₂ | —CH2CH2— | CONH2 | —CH2CH2— | CONH2 | 2-F | 1 | 4-cyanophenyl | 2-bromo-6-ethyl-4-(1,2,2,3,3,3-hexafluoro-1-trifluoromethyl-propyl)-phenyl |
| 8-132 | —L₁—D₁ | —L₂—D₂ | —CH2CH2— | CONH2 | —CH2CH2— | CONH2 | 2-F | 1 | 4-cyanophenyl | 2-iodo-6-ethyl-4-(1,2,2,3,3,3-hexafluoro-1-trifluoromethyl-propyl)-phenyl |
| 8-133 | —L₁—D₁ | —L₂—D₂ | —CH2CH2— | CONH2 | —CH2CH2— | CONH2 | 2-F | 1 | 4-cyanophenyl | 2-bromo-6-trifluoromethyl-4-(1,2,2,3,3,3-hexafluoro-1-trifluoromethyl-propyl)-phenyl |
| 8-134 | —L₁—D₁ | —L₂—D₂ | —CH2CH2— | CONH2 | —CH2CH2— | CONH2 | 2-F | 1 | 4-cyanophenyl | 2,6-dichloro-4-(1,2,2,3,3,3-hexafluoro-1-trifluoromethyl-propyl)-phenyl |
| 8-135 | —L₁—D₁ | —L₂—D₂ | —CH2CH2— | CONH2 | —CH2CH2— | CONH2 | 2-F | 1 | 4-cyanophenyl | 2,6-dibromo-4-(1,2,2,3,3,3-hexafluoro-1-trifluoromethyl-propyl)-phenyl |
| 8-136 | —L₁—D₁ | —L₂—D₂ | —CH2CH2— | CONH2 | —CH2CH2— | CONH2 | 2-F | 1 | 4-cyanophenyl | 2,6-diiodo-4-(1,2,2,3,3,3-hexafluoro-1-trifluoromethyl-propyl)-phenyl |
| 8-137 | —L₁—D₁ | —L₂—D₂ | —CH2CH2— | CONH2 | —CH2CH2— | CONH2 | 2-F | 1 | 4-cyanophenyl | 2,6-ditrifluoromethyl-4-(1,2,2,3,3,3-hexafluoro-1-trifluoromethyl-propyl)-phenyl |
| 8-138 | —L₁—D₁ | —L₂—D₂ | —CH2CH2— | CONH2 | —CH2CH2— | CONH2 | 2-F | 1 | 4-cyanophenyl | 2-bromo-6-trifluoromethyl-4-(1,2,2,3,3,3-hexafluoro-1-trifluoromethyl-propyl)-phenyl |
| 8-139 | —L₁—D₁ | —L₂—D₂ | —CH2CH2— | CONH2 | —CH2CH2— | CONH2 | 2-F | 1 | 4-cyanophenyl | 2-iodo-6-trifluoromethyl-4-(1,2,2,3,3,3-hexafluoro-1-trifluoromethyl-propyl)-phenyl |
| 8-140 | —L₁—D₁ | —L₂—D₂ | —CH2CH2— | CONH2 | —CH2CH2— | CONH2 | 2-F | 1 | 4-cyanophenyl | 2-bromo-6-trifluoromethoxy-4-(1,2,2,3,3,3-hexafluoro-1-trifluoromethyl-propyl)-phenyl |
| 8-140 | —L₁—D₁ | —L₂—D₂ | —CH2CH2— | CONH2 | —CH2CH2— | CONH2 | 2-F | 1 | 4-cyanophenyl | 2-bromo-6-iodo-4-(1,2,2,3,3,3-hexafluoro-1-trifluoromethyl-propyl)-phenyl |

TABLE 8-continued

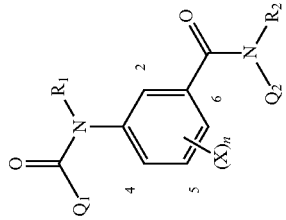

| compound number | R₁ | R₂ | L₁ | D₁ | L₂ | D₂ | X | n | Q₁ | Q₂ |
|---|---|---|---|---|---|---|---|---|---|---|
| 8-141 | —L₁—D₁ | —L₂—D₂ | —CH2CH2— | CONH2 | —CH2CH2— | CONH2 | 2-F | 1 | 4-cyanophenyl | 2-bromo-6-trifluoromethylthio-4-(1,2,2,3,3,3-hexafluoro-1-trifluoromethyl-propyl)-phenyl |
| 8-142 | —L₁—D₁ | —L₂—D₂ | —CH2CH2— | CONH2 | —CH2CH2— | CONH2 | 2-F | 1 | 4-cyanophenyl | 2-bromo-6-trifluoromethylsulfinyl-4-(1,2,2,3,3,3-hexafluoro-1-trifluoromethyl-propyl)-phenyl |
| 8-143 | —L₁—D₁ | —L₂—D₂ | —CH2CH2— | CONH2 | —CH2CH2— | CONH2 | 2-F | 1 | 4-cyanophenyl | 2-bromo-6-trifluoromethylsulfonyl-4-(1,2,2,3,3,3-hexafluoro-1-trifluoromethyl-propyl)-phenyl |
| 8-144 | —L₁—D₁ | —L₂—D₂ | —CH2CH2— | CONH2 | —CH2CH2— | CONH2 | 2-F | 1 | 4-cyanophenyl | 2-bromo-6-pentafluoroethyl-4-(1,2,2,3,3,3-hexafluoro-1-trifluoromethyl-propyl)-phenyl |
| 8-145 | —L₁—D₁ | —L₂—D₂ | —CH2CH2— | CONH2 | —CH2CH2— | CONH2 | 2-F | 1 | 4-cyanophenyl | 2-iodo-6-pentafluoroethyl-4-(1,2,2,3,3,3-hexafluoro-1-trifluoromethyl-propyl)-phenyl |
| 8-146 | —L₁—D₁ | —L₂—D₂ | —CH2CH2— | CONH2 | —CH2CH2— | CONH2 | 2-F | 1 | phenyl | 2,6-dibromo-4-(1,2,2,2-tetrafluoro-1-trifluoromethyl-ethyl)-phenyl |
| 8-147 | —L₁—D₁ | —L₂—D₂ | —CH2CH2— | CONH2 | —CH2CH2— | CONH2 | 2-F | 1 | 3-cyanophenyl | 2,6-dibromo-4-(1,2,2,2-tetrafluoro-1-trifluoromethyl-ethyl)-phenyl |
| 8-148 | —L₁—D₁ | —L₂—D₂ | —CH2CH2— | CONH2 | —CH2CH2— | CONH2 | 2-F | 1 | 2-chloropyridin-3-yl | 2,6-dibromo-4-(1,2,2,2-tetrafluoro-1-trifluoromethyl-ethyl)-phenyl |
| 8-149 | —L₁—D₁ | —L₂—D₂ | —CH2CH2— | CONH2 | —CH2CH2— | CONH2 | 2-F | 1 | 2-fluorophenyl | 2,6-dibromo-4-(1,2,2,2-tetrafluoro-1-trifluoromethyl-ethyl)-phenyl |

TABLE 8-continued

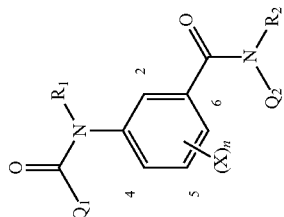

| compound number | R$_1$ | R$_2$ | L$_1$ | D$_1$ | L$_2$ | D$_2$ | X | n | Q$_1$ | Q$_2$ |
|---|---|---|---|---|---|---|---|---|---|---|
| 8-150 | —L$_1$—D$_1$ | —L$_2$—D$_2$ | —CH2CH2— | SO2Me | —CH2CH2— | CONH2 | 2-F | 1 | phenyl | 2,6-dibromo-4-(1,2,2,2-tetrafluoro-1-trifluoromethyl-ethyl)-phenyl |
| 8-151 | —L$_1$—D$_1$ | —L$_2$—D$_2$ | —CH2CH2— | CONH2 | —CH2CH2— | CONH2 | 2-F | 1 | phenyl | 2,6-diiodo-4-(1,2,2,2-tetrafluoro-1-trifluoromethyl-ethyl)-phenyl |
| 8-152 | —L$_1$—D$_1$ | —L$_2$—D$_2$ | —CH2CH2— | CONH2 | —CH2CH2— | CONH2 | 2-F | 1 | 3-cyanophenyl | 2,6-diiodo-4-(1,2,2,2-tetrafluoro-1-trifluoromethyl-ethyl)-phenyl |
| 8-153 | —L$_1$—D$_1$ | —L$_2$—D$_2$ | —CH2CH2— | CONH2 | —CH2CH2— | CONH2 | 2-F | 1 | 2-chloropyridin-3-yl | 2,6-diiodo-4-(1,2,2,2-tetrafluoro-1-trifluoromethyl-ethyl)-phenyl |
| 8-154 | —L$_1$—D$_1$ | —L$_2$—D$_2$ | —CH2CH2— | CONH2 | —CH2CH2— | CONH2 | 2-F | 1 | 2-fluorophenyl | 2,6-diiodo-4-(1,2,2,2-tetrafluoro-1-trifluoromethyl-ethyl)-phenyl |
| 8-155 | —L$_1$—D$_1$ | —L$_2$—D$_2$ | —CH2CH2— | CONH2 | —CH2CH2— | CONH2 | 2-F | 1 | phenyl | 2-bromo-6-trifluoromethyl-4-(1,2,2,2-tetrafluoro-1-trifluoromethyl-ethyl)-phenyl |
| 8-156 | —L$_1$—D$_1$ | —L$_2$—D$_2$ | —CH2CH2— | CONH2 | —CH2CH2— | CONH2 | 2-F | 1 | 3-cyanophenyl | 2-bromo-6-trifluoromethyl-4-(1,2,2,2-tetrafluoro-1-trifluoromethyl-ethyl)-phenyl |
| 8-157 | —L$_1$—D$_1$ | —L$_2$—D$_2$ | —CH2CH2— | CONH2 | —CH2CH2— | CONH2 | 2-F | 1 | 2-chloropyridin-3-yl | 2-bromo-6-trifluoromethyl-4-(1,2,2,2-tetrafluoro-1-trifluoromethyl-ethyl)-phenyl |
| 8-158 | —L$_1$—D$_1$ | —L$_2$—D$_2$ | —CH2CH2— | CONH2 | —CH2CH2— | CONH2 | 2-F | 1 | 2-fluorophenyl | 2-bromo-6-trifluoromethyl-4-(1,2,2,2-tetrafluoro-1-trifluoromethyl-ethyl)-phenyl |
| 8-159 | —L$_1$—D$_1$ | —L$_2$—D$_2$ | —CH2CH2— | CONH2 | —CH2CH2— | CONH2 | 2-F | 1 | phenyl | 2-iodo-6-trifluoromethyl-4-(1,2,2,2-tetrafluoro-1-trifluoromethyl-ethyl)-phenyl |
| 8-160 | —L$_1$—D$_1$ | —L$_2$—D$_2$ | —CH2CH2— | CONH2 | —CH2CH2— | CONH2 | 2-F | 1 | 3-cyanophenyl | 2-iodo-6-trifluoromethyl-4-(1,2,2,2-tetrafluoro-1-trifluoromethyl-ethyl)-phenyl |
| 8-161 | —L$_1$—D$_1$ | —L$_2$—D$_2$ | —CH2CH2— | CONH2 | —CH2CH2— | CONH2 | 2-F | 1 | 2-chloropyridin-3-yl | 2-iodo-6-trifluoromethyl-4-(1,2,2,2-tetrafluoro-1-trifluoromethyl-ethyl)-phenyl |

TABLE 8-continued

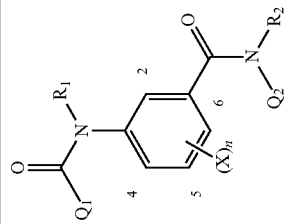

| compound number | R₁ | R₂ | L₁ | D₁ | L₂ | D₂ | X | n | Q₁ | Q₂ |
|---|---|---|---|---|---|---|---|---|---|---|
| 8-162 | —L₁—D₁ | —L₂—D₂ | —CH2CH2— | CONH2 | —CH2CH2— | CONH2 | 4-F | 1 | 2-fluorophenyl | 2-iodo-6-trifluoromethyl-4-(1,2,2,2-tetrafluoro-1-trifluoromethyl-ethyl)-phenyl |
| 8-163 | —L₁—D₁ | —L₂—D₂ | —CH2CH2— | CONH2 | —CH2CH2— | CONH2 | 2-F | 1 | phenyl | 2,6-dibromo-4-(1,2,2,3,3,3-hexafluoro-1-trifluoromethyl-propyl)-phenyl |
| 8-164 | —L₁—D₁ | —L₂—D₂ | —CH2CH2— | CONH2 | —CH2CH2— | CONH2 | 4-F | 1 | 3-cyanophenyl | 2,6-dibromo-4-(1,2,2,3,3,3-hexafluoro-1-trifluoromethyl-propyl)-phenyl |
| 8-165 | —L₁—D₁ | —L₂—D₂ | —CH2CH2— | CONH2 | —CH2CH2— | CONH2 | 2-F | 1 | 2-chloropyridin-3-yl | 2,6-dibromo-4-(1,2,2,3,3,3-hexafluoro-1-trifluoromethyl-propyl)-phenyl |
| 8-166 | —L₁—D₁ | —L₂—D₂ | —CH2CH2— | CONH2 | —CH2CH2— | CONH2 | 4-CN | 1 | 2-fluorophenyl | 2,5-dibromo-4-(1,2,2,3,3,3-hexafluoro-1-trifluoromethyl-propyl)-phenyl |
| 8-167 | —L₁—D₁ | —L₂—D₂ | —CH2CH2— | CONH2 | —CH2CH2— | CONH2 | 2-F | 1 | phenyl | 2,6-diiodo-4-(1,2,2,3,3,3-hexafluoro-1-trifluoromethyl-propyl)-phenyl |
| 8-168 | —L₁—D₁ | —L₂—D₂ | —CH2CH2— | CONH2 | —CH2CH2— | CONH2 | 2-F | 1 | 3-cyanophenyl | 2,6-diiodo-4-(1,2,2,3,3,3-hexafluoro-1-trifluoromethyl-propyl)-phenyl |
| 8-169 | —L₁—D₁ | —L₂—D₂ | —CH2CH2— | CONH2 | —CH2CH2— | CONH2 | 2-F | 1 | 2-chloropyridin-3-yl | 2,6-diiodo-4-(1,2,2,3,3,3-hexafluoro-1-trifluoromethyl-propyl)-phenyl |
| 8-170 | —L₁—D₁ | —L₂—D₂ | —CH2CH2— | CONH2 | —CH2CH2— | CONH2 | 2-F | 1 | 2-fluorophenyl | 2,6-diiodo-4-(1,2,2,3,3,3-hexafluoro-1-trifluoromethyl-propyl)-phenyl |
| 8-171 | —L₁—D₁ | —L₂—D₂ | —CH2CH2— | CONH2 | —CH2CH2— | CONH2 | 2-F | 1 | phenyl | 2-bromo-6-trifluoromethyl-4-(1,2,2,3,3,3-hexafluoro-1-trifluoromethyl-propyl)-phenyl |
| 8-172 | —L₁—D₁ | —L₂—D₂ | —CH2CH2— | CONH2 | —CH2CH2— | CONH2 | 4-CN | 1 | 3-cyanophenyl | 2-bromo-6-trifluoromethyl-4-(1,2,2,3,3,3-hexafluoro-1-trifluoromethyl-propyl)-phenyl |
| 8-173 | —L₁—D₁ | —L₂—D₂ | —CH2CH2— | CONH2 | —CH2CH2— | CONH2 | 2-F | 1 | 2-chloropyridin-3-yl | 2-bromo-6-trifluoromethyl-4-(1,2,2,3,3,3-hexafluoro-1-trifluoromethyl-propyl)-phenyl |

TABLE 8-continued

| compound number | R₁ | R₂ | L₁ | D₁ | L₂ | D₂ | X | n | Q₁ | Q₂ |
|---|---|---|---|---|---|---|---|---|---|---|
| 8-174 | —L₁—D₁ | —L₂—D₂ | —CH2CH2— | CONH2 | —CH2CH2— | CONH2 | 2-F | 1 | 2-fluorophenyl | 2-bromo-6-trifluoromethyl-4-(1,2,2,3,3,3-hexafluoro-1-trifluoromethyl-propyl)-phenyl |
| 8-175 | —L₁—D₁ | —L₂—D₂ | —CH2CH2— | CONH2 | —CH2CH2— | CONH2 | 2-F | 1 | phenyl | 2-iodo-6-trifluoromethyl-4-(1,2,2,3,3,3-hexafluoro-1-trifluoromethyl-propyl)-phenyl |
| 8-176 | —L₁—D₁ | —L₂—D₂ | —CH2CH2— | CONH2 | —CH2CH2— | CONH2 | 2-F | 1 | 3-cyanophenyl | 2-iodo-6-trifluoromethyl-4-(1,2,2,3,3,3-hexafluoro-1-trifluoromethyl-propyl)-phenyl |
| 8-177 | —L₁—D₁ | —L₂—D₂ | —CH2CH2— | CONH2 | —CH2CH2— | CONH2 | 2-F | 1 | 2-chloropyridin-3-yl | 2-iodo-6-trifluoromethyl-4-(1,2,2,3,3,3-hexafluoro-1-trifluoromethyl-propyl)-phenyl |
| 8-178 | —L₁—D₁ | —L₂—D₂ | —CH2CH2— | CONH2 | —CH2CH2— | CONH2 | 2-F | 1 | 2-fluorophenyl | 2-iodo-6-trifluoromethyl-4-(1,2,2,3,3,3-hexafluoro-1-trifluoromethyl-propyl)-phenyl |
| 8-179 | —L₁—D₁ | —L₂—D₂ | —CH2CH2— | CONH2 | —CH2CH2— | CONH2 | H | 0 | 6-chloropyridin-3-yl | 2-bromo-6-trifluoromethyl-4-(1,2,2,2-tetrafluoro-1-trifluoromethyl-ethyl)-phenyl |
| 8-180 | —L₁—D₁ | —L₂—D₂ | —CH2CH2— | CONH2 | —CH2CH2— | CONH2 | 2-F | 1 | 6-chloropyridin-3-yl | 2-bromo-6-trifluoromethyl-4-(1,2,2,2-tetrafluoro-1-trifluoromethyl-ethyl)-phenyl |
| 8-131 | —L₁—D₁ | —L₂—D₂ | —CH2CH2— | CONH2 | —CH2CH2— | CONH2 | 2-F | 1 | 6-chloropyridin-3-yl | 2-bromo-6-trifluoromethyl-4-(1,2,2,2-tetrafluoro-1-trifluoromethyl-ethyl)-phenyl |
| 8-182 | —L₁—D₁ | —L₂—D₂ | —CH2CH2— | CONH2 | —CH2CH2— | CONH2 | 2-F | 1 | 3,5-dicyanophenyl | 2-bromo-6-trifluoromethyl-4-(1,2,2,2-tetrafluoro-1-trifluoromethyl-ethyl)-phenyl |
| 8-183 | —L₁—D₁ | —L₂—D₂ | —CH2CH2— | CONH2 | —CH2CH2— | CONH2 | 2-F | 1 | 3,5-dicyanophenyl | 2,6-dibromo-4-(1,2,2,2-tetrafluoro-1-trifluoromethyl-ethyl)-phenyl |
| 8-184 | —L₁—D₁ | —L₂—D₂ | —CH2CH2— | CONH2 | —CH2CH2— | CONH2 | 2-F | 1 | pyridin-3-yl | 2,6-dibromo-4-(1,2,2,2-tetrafluoro-1-trifluoromethyl-ethyl)-phenyl |
| 8-185 | —L₁—D₁ | —L₂—D₂ | —CH2CH2— | CONH2 | —CH2CH2— | CONH2 | 2-F | 1 | pyridin-4-yl | 2,6-dibromo-4-(1,2,2,2-tetrafluoro-1-trifluoromethyl-ethyl)-phenyl |

TABLE 8-continued

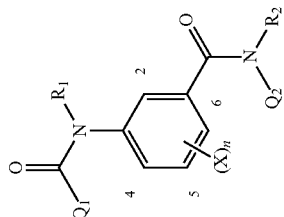

| compound number | R$_1$ | R$_2$ | L$_1$ | D$_1$ | L$_2$ | D$_2$ | X | n | Q$_1$ | Q$_2$ |
|---|---|---|---|---|---|---|---|---|---|---|
| 8-186 | —L$_1$—D$_1$ | —L$_2$—D$_2$ | —CH2CH2— | CONH2 | —CH2CH2— | CONH2 | 2-F | 1 | 2-chloropyridin-4-yl | 2,6-dibromo-4-(1,2,2,2-tetrafluoro-1-trifluoromethyl-ethyl)-phenyl |
| 8-187 | —L$_1$—D$_1$ | —L$_2$—D$_2$ | —CH2CH2— | CONH2 | —CH2CH2— | CONH2 | 2-F | 1 | pyrazin-2-yl | 2,6-dibromo-4-(1,2,2,2-tetrafluoro-1-trifluoromethyl-ethyl)-phenyl |
| 8-188 | —L$_1$—D$_1$ | —L$_2$—D$_2$ | —CH2CH2— | CONH2 | —CH2CH2— | CONH2 | 2-F | 1 | pyrimidin-5-yl | 2,6-dibromo-4-(1,2,2,2-tetrafluoro-1-trifluoromethyl-ethyl)-phenyl |
| 8-189 | —L$_1$—D$_1$ | —L$_2$—D$_2$ | —CH2CH2— | CONH2 | —CH2CH2— | CONH2 | 2-F | 1 | 3-cyanophenyl | 2,6-dichloro-4-(1,2,2,2-tetrafluoro-1-trifluoromethyl-ethyl)-phenyl |
| 8-190 | —L$_1$—D$_1$ | —L$_2$—D$_2$ | —CH2CH2— | CONH2 | —CH2CH2— | CONH2 | 2-F | 1 | phenyl | 2,6-dichloro-4-(1,2,2,2-tetrafluoro-1-trifluoromethyl-ethyl)-phenyl |
| 8-191 | —L$_1$—D$_1$ | —L$_2$—D$_2$ | —CH2CH2— | CONH2 | —CH2CH2— | CONH2 | 2-F | 1 | 2-chloropyridin-3-yl | 2,6-dibromo-4-(1,2,2,2-tetrafluoro-1-trifluoromethyl-ethyl)-phenyl |
| 8-192 | —L$_1$—D$_1$ | —L$_2$—D$_2$ | —CH2CH2— | CONH2 | —CH2CH2— | CONH2 | 2-F | 1 | 6-cyanopyridin-3-yl | 2,6-dibromo-4-(1,2,2,2-tetrafluoro-1-trifluoromethyl-ethyl)-phenyl |
| 8-193 | —L$_1$—D$_1$ | —L$_2$—D$_2$ | —CH2CH2— | CONH2 | —CH2CH2— | CONH2 | 2-F | 1 | 4-fluorophenyl | 2,6-dibromo-4-(1,2,2,2-tetrafluoro-1-trifluoromethyl-ethyl)-phenyl |
| 8-194 | —L$_1$—D$_1$ | —L$_2$—D$_2$ | —CH2CH2— | CONH2 | —CH2CH2— | CONH2 | 2-F | 1 | 2,6-difluorophenyl | 2,6-dibromo-4-(1,2,2,2-tetrafluoro-1-trifluoromethyl-ethyl)-phenyl |
| 8-195 | —L$_1$—D$_1$ | —L$_2$—D$_2$ | —CH2CH2— | CONH2 | —CH2CH2— | CONH2 | 2-F | 1 | 2-chloropyridin-3-yl | 2-bromo-6-iodo-4-(1,2,2,2-tetrafluoro-1-trifluoromethyl-ethyl)-phenyl |
| 8-196 | —L$_1$—D$_1$ | —L$_2$—D$_2$ | —CH2CH2— | CONH2 | —CH2CH2— | CONH2 | 2-F | 1 | phenyl | 2-bromo-6-iodo-4-(1,2,2,2-tetrafluoro-1-trifluoromethyl-ethyl)-phenyl |
| 8-197 | —L$_1$—D$_1$ | —L$_2$—D$_2$ | —CH2CH2— | CONH2 | —CH2CH2— | CONH2 | 2-F | 1 | 6-chloropyridin-3-yl | 2,6-dibromo-4-(1,2,2,3,3,3-hexafluoro-1-trifluoromethyl-propyl)-phenyl |

TABLE 8-continued

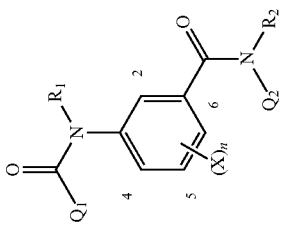

| compound number | R₁ | R₂ | L₁ | D₁ | L₂ | D₂ | X | n | Q₁ | Q₂ |
|---|---|---|---|---|---|---|---|---|---|---|
| 8-198 | —L₁—D₁ | —L₂—D₂ | —CH2CH2— | CONH2 | —CH2CH2— | CONH2 | 2-F | 1 | phenyl | 2,6-dimethyl-4-(1,2,2,3,3,3-hexafluoro-1-trifluoromethyl-propyl)-phenyl |
| 8-188 | —L₁—D₁ | —L₂—D₂ | —CH2CH2— | CONH2 | —CH2CH2— | CONH2 | 2-F | 1 | 4-cyanophenyl | 2,6-dimethyl-4-(1,2,2,3,3,3-hexafluoro-1-trifluoromethyl-propyl)-phenyl |
| 8-200 | —L₁—D₁ | —L₂—D₂ | —CH2CH2— | CONH2 | —CH2CH2— | CONH2 | 2-F | 1 | 3-cyanophenyl | 2,6-dimethyl-4-(1,2,2,3,3,3-hexafluoro-1-trifluoromethyl-propyl)-phenyl |
| 8-201 | —L₁—D₁ | —L₂—D₂ | —CH2— | CONH2 | —CH2CH2— | CONH2 | 2-F | 1 | phenyl | 2,6-dimethyl-4-(1,2,2,2-tetrafluoro-1-trifluoromethyl-ethyl)-phenyl |
| 8-202 | —L₁—D₁ | —L₂—D₂ | —CH2— | CO2Me | —CH2CH2— | CONH2 | 2-F | 1 | phenyl | 2,6-dimethyl-4-(1,2,2,2-tetrafluoro-1-trifluoromethyl-ethyl)-phenyl |
| 8-203 | —L₁—D₁ | —L₂—D₂ | —CH2— | CO2H | —CH2CH2— | CONH2 | 2-F | 1 | phenyl | 2,6-dimethyl-4-(1,2,2,2-tetrafluoro-1-trifluoromethyl-ethyl)-phenyl |
| 8-204 | —L₁—D₁ | —L₂—D₂ | —CH2CH2CH2— | CONH2 | —CH2CH2— | CONH2 | 2-F | 1 | 3-cyanophenyl | 2,6-dimethyl-4-(1,2,2,2-tetrafluoro-1-trifluoromethyl-ethyl)-phenyl |
| 8-205 | —L₁—D₁ | —L₂—D₂ | —CH2CH2(CH3)— | CONH2 | —CH2CH2— | CONH2 | 2-F | 1 | 4-cyanophenyl | 2,6-dimethyl-4-(1,2,2,2-tetrafluoro-1-trifluoromethyl-ethyl)-phenyl |
| 8-206 | —L₁—D₁ | —L₂—D₂ | —CH(CH3)CH2— | CONH2 | —CH2CH2— | CONH2 | 2-F | 1 | 4-cyanophenyl | 2,6-dimethyl-4-(1,2,2,2-tetrafluoro-1-trifluoromethyl-ethyl)-phenyl |
| 8-207 | —L₁—D₁ | —L₂—D₂ | —CH2CH2— | CONH2 | —CH2CH2— | CONH2 | 2-NO2 | 1 | phenyl | 2-bromo-6-trifluoromethyl-4-(1,2,2,3,3,3-hexafluoro-1-trifluoromethyl-propyl)-phenyl |
| 8-208 | —L₁—D₁ | —L₂—D₂ | —CH2CH2— | CONMe2 | —CH2CH2— | CONMe2 | 2-F | 1 | 4-cyanophenyl | 2-iodo-6-trifluoromethyl-4-(1,2,2,3,3,3-hexafluoro-1-trifluoromethyl-propyl)-phenyl |

TABLE 9

| compound number | R₁ | R₂ | L1 | D1 | L2 | D2 | X | n | Q₃ | Q₂ |
|---|---|---|---|---|---|---|---|---|---|---|
| 9-1 | —L₁—D₁ | H | —CH2CH2— | CONH2 | — | — | H | 0 | methyl | 2,6-dimethyl-4-(1,2,2,2-tetrafluoro-1-trifluoromethyl-ethyl)-phenyl |
| 9-2 | —L₁—D₁ | H | —CH2CH2— | CONH2 | — | — | H | 0 | ethyl | 2,6-dimethyl-4-(1,2,2,2-tetrafluoro-1-trifluoromethyl-ethyl)-phenyl |
| 9-3 | —L₁—D₁ | Me | —CH2CH2— | CONH2 | — | — | H | 0 | i-propyl | 2,6-dimethyl-4-(1,2,2,2-tetrafluoro-1-trifluoromethyl-ethyl)-phenyl |
| 9-4 | —L₁—D₁ | H | —CH2CH2— | CONH2 | — | — | H | 0 | n-butyl | 2,6-dimethyl-4-(1,2,2,2-tetrafluoro-1-trifluoromethyl-ethyl)-phenyl |
| 9-5 | —L₁—D₁ | H | —CH2CH2— | SO2Me | — | — | H | 0 | i-butyl | 2,6-dimethyl-4-(1,2,2,2-tetrafluoro-1-trifluoromethyl-ethyl)-phenyl |
| 9-6 | —L₁—D₁ | Me | —CH2CH2— | CONH2 | — | — | H | 0 | s-butyl | 2,6-dimethyl-4-(1,2,2,2-tetrafluoro-1-trifluoromethyl-ethyl)-phenyl |
| 9-7 | —L₁—D₁ | H | —CH2CH2— | CONH2 | — | — | H | 0 | t-butyl | 2,6-dimethyl-4-(1,2,2,2-tetrafluoro-1-trifluoromethyl-ethyl)-phenyl |
| 9-8 | —L₁—D₁ | H | —CH2CH2— | CONH2 | — | — | H | 0 | vinyl | 2,6-dimethyl-4-(1,2,2,2-tetrafluoro-1-trifluoromethyl-ethyl)-phenyl |
| 9-9 | —L₁—D₁ | H | —CH2CH2— | CONH2 | — | — | H | 0 | allyl | 2,6-dimethyl-4-(1,2,2,2-tetrafluoro-1-trifluoromethyl-ethyl)-phenyl |
| 9-10 | —L₁—D₁ | H | —CH2CH2— | SOMe | — | — | H | 0 | benzyl | 2,6-dimethyl-4-(1,2,2,2-tetrafluoro-1-trifluoromethyl-ethyl)-phenyl |
| 9-11 | —L₁—D₁ | H | —CH2CH2— | OH | — | — | H | 0 | chloromethyl | 2,6-dimethyl-4-(1,2,2,2-tetrafluoro-1-trifluoromethyl-ethyl)-phenyl |
| 9-12 | —L₁—D₁ | H | —CH2CH2— | CONH2 | — | — | H | 0 | 2,2,2-trichloroethyl | 2,6-dimethyl-4-(1,2,2,2-tetrafluoro-1-trifluoromethyl-ethyl)-phenyl |
| 9-13 | —L₁—D₁ | H | —CH2CH2— | CONH2 | — | — | H | 0 | 3,3,3-trifluoro-n-propyl | 2,6-dimethyl-4-(1,2,2,2-tetrafluoro-1-trifluoromethyl-ethyl)-phenyl |
| 9-14 | —L₁—D₁ | H | —CH2CH2— | CO2Me | — | — | H | 0 | 1,3-difluoro-2-propyl | 2,6-dimethyl-4-(1,2,2,2-tetrafluoro-1-trifluoromethyl-ethyl)-phenyl |
| 9-15 | —L₁—D₁ | H | —CH2CH2— | CN | — | — | H | 0 | cyclohexyl | 2,6-dimethyl-4-(1,2,2,2-tetrafluoro-1-trifluoromethyl-ethyl)-phenyl |
| 9-16 | —L₁—D₁ | H | —CH2CH2— | NH2 | — | — | 2-F | 1 | methyl | 2,6-dimethyl-4-(1,2,2,2-tetrafluoro-1-trifluoromethyl-ethyl)-phenyl |

TABLE 9-continued

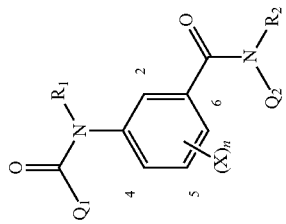

| compound number | R1 | R2 | L1 | D1 | L2 | D2 | X | n | Q3 | Q2 |
|---|---|---|---|---|---|---|---|---|---|---|
| 9-17 | —L1—D1 | H | —CH2CH2— | CONH2 | — | — | 2-F | 1 | ethyl | 2,6-dimethyl-4-(1,2,2,2-tetrafluoro-1-trifluoromethyl-ethyl)-phenyl |
| 9-18 | —L1—D1 | H | —CH2CH2— | CONH2 | — | — | 2-F | 1 | i-propyl | 2,6-dimethyl-4-(1,2,2,2-tetrafluoro-1-trifluoromethyl-ethyl)-phenyl |
| 9-19 | —L1—D1 | H | —CH2CH2— | CONH2 | — | — | 2-F | 1 | n-butyl | 2,6-dimethyl-4-(1,2,2,2-tetrafluoro-1-trifluoromethyl-ethyl)-phenyl |
| 9-20 | —L1—D1 | H | —CH2CH2— | CONH2 | — | — | 2-F | 1 | i-butyl | 2,6-dimethyl-4-(1,2,2,2-tetrafluoro-1-trifluoromethyl-ethyl)-phenyl |
| 9-21 | —L1—D1 | H | —CH2CH2— | CONH2 | — | — | 2-F | 1 | s-butyl | 2,6-dimethyl-4-(1,2,2,2-tetrafluoro-1-trifluoromethyl-ethyl)-phenyl |
| 9-22 | —L1—D1 | Me | —CH2CH2— | CONH2 | — | — | 2-F | 1 | t-butyl | 2,6-dimethyl-4-(1,2,2,2-tetrafluoro-1-trifluoromethyl-ethyl)-phenyl |
| 9-23 | —L1—D1 | H | —CH2CH2— | CONH2 | — | — | 2-F | 1 | vinyl | 2,6-dimethyl-4-(1,2,2,2-tetrafluoro-1-trifluoromethyl-ethyl)-phenyl |
| 9-24 | —L1—D1 | H | —CH2CH2— | CONH2 | — | — | 2-F | 1 | allyl | 2,6-dimethyl-4-(1,2,2,2-tetrafluoro-1-trifluoromethyl-ethyl)-phenyl |
| 9-25 | —L1—D1 | H | —CH2CH2— | CO2H | — | — | 2-F | 1 | benzyl | 2,6-dimethyl-4-(1,2,2,2-tetrafluoro-1-trifluoromethyl-ethyl)-phenyl |
| 9-26 | —L1—D1 | Me | —CH2CH2— | CONH2 | — | — | 2-F | 1 | chloromethyl | 2,6-dimethyl-4-(1,2,2,2-tetrafluoro-1-trifluoromethyl-ethyl)-phenyl |
| 9-27 | —L1—D1 | H | —CH2CH2— | CONH2 | — | — | 2-F | 1 | 2,2,2-trichloroethyl | 2,6-dimethyl-4-(1,2,2,2-tetrafluoro-1-trifluoromethyl-ethyl)-phenyl |
| 9-28 | —L1—D1 | H | —CH2CH2— | CONH2 | — | — | 2-F | 1 | 3,3,3-trifluoro-n-propyl | 2,6-dimethyl-4-(1,2,2,2-tetrafluoro-1-trifluoromethyl-ethyl)-phenyl |
| 9-29 | —L1—D1 | H | —CH2CH2— | CONH2 | — | — | 2-F | 1 | 1,3-difluoro-2-propyl | 2,6-dimethyl-4-(1,2,2,2-tetrafluoro-1-trifluoromethyl-ethyl)-phenyl |
| 9-30 | —L1—D1 | H | —CH2CH2— | CONMe2 | — | — | 2-F | 1 | cyclohexyl | 2,6-dimethyl-4-(1,2,2,2-tetrafluoro-1-trifluoromethyl-ethyl)-phenyl |
| 9-31 | —L1—D1 | H | —CH2CH2— | CONH2 | — | — | 4-F | 1 | i-propyl | 2,6-dimethyl-4-(1,2,2,2-tetrafluoro-1-trifluoromethyl-ethyl)-phenyl |
| 9-32 | —L1—D1 | H | —CH2CH2— | CONH2 | — | — | 4-F | 1 | 2,2,2-trichloroethyl | 2,6-dimethyl-4-(1,2,2,2-tetrafluoro-1-trifluoromethyl-ethyl)-phenyl |
| 9-33 | —L1—D1 | H | —CH2CH2— | CONH2 | — | — | 4-F | 1 | 3,3,3-trifluoro-n-propyl | 2,6-dimethyl-4-(1,2,2,2-tetrafluoro-1-trifluoromethyl-ethyl)-phenyl |

TABLE 9-continued

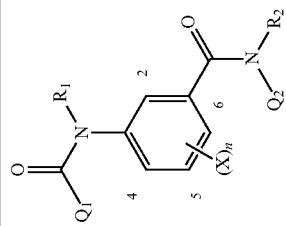

| compound number | R₁ | R₂ | L1 | D1 | L2 | D2 | X | n | Q₃ | Q₂ |
|---|---|---|---|---|---|---|---|---|---|---|
| 9-34 | —L₁—D₁ | H | —CH2CH2— | CONH2 | — | — | 4-CN | 1 | i-propyl | 2,6-dimethyl-4-(1,2,2,2-tetrafluoro-1-trifluoromethyl-ethyl)-phenyl |
| 9-35 | —L₁—D₁ | H | —CH2CH2— | CONH2 | — | — | 4-CN | 1 | 2,2,2-trichloroethyl | 2,6-dimethyl-4-(1,2,2,2-tetrafluoro-1-trifluoromethyl-ethyl)-phenyl |
| 9-36 | —L₁—D₁ | H | —CH2CH2— | CONH2 | — | — | 4-CN | 1 | 3,3,3-trifluoro-n-propyl | 2,6-dimethyl-4-(1,2,2,2-tetrafluoro-1-trifluoromethyl-ethyl)-phenyl |
| 9-37 | —L₁—D₁ | H | —CH2CH2— | CONH2 | — | — | H | 0 | 2,2,2-trichloroethyl | 2,6-dibromo-4-pentafluoroethyl-phenyl |
| 9-38 | —L₁—D₁ | H | —CH2CH2— | CONH2 | — | — | H | 0 | 3,3,3-trifluoro-n-propyl | 2,6-diiodo-4-pentafluoroethyl-phenyl |
| 9-39 | —L₁—D₁ | H | —CH2CH2— | CONH2 | — | — | H | 0 | 2,2,2-trichloroethyl | 2-bromo-6-trifluoromethyl-4-pentafluoroethyl-phenyl |
| 9-40 | —L₁—D₁ | H | —CH2CH2— | CONH2 | — | — | H | 0 | 3,3,3-trifluoro-n-propyl | 2-iodo-6-trifluoromethyl-4-pentafluoroethyl-phenyl |
| 9-41 | —L₁—D₁ | H | —CH2CH2— | CONH2 | — | — | H | 0 | 2,2,2-trichloroethyl | 2-chloro-6-methyl-4-(1,2,2,2-tetrafluoro-1-trifluoromethyl-ethyl)-phenyl |
| 9-42 | —L₁—D₁ | H | —CH2CH2— | CONH2 | — | — | H | 0 | 3,3,3-trifluoro-n-propyl | 2-bromo-6-methyl-4-(1,2,2,2-tetrafluoro-1-trifluoromethyl-ethyl)-phenyl |
| 9-43 | —L₁—D₁ | H | —CH2CH2— | CONH2 | — | — | H | 0 | 2,2,2-trichloroethyl | 2-iodo-6-methyl-4-(1,2,2,2-tetrafluoro-1-trifluoromethyl-ethyl)-phenyl |
| 9-44 | —L₁—D₁ | H | —CH2CH2— | SO2NH2 | — | — | H | 0 | 2,2,2-trichloroethyl | 2-bromo-6-ethyl-4-(1,2,2,2-tetrafluoro-1-trifluoromethyl-ethyl)-phenyl |
| 9-45 | —L₁—D₁ | H | —CH2CH2— | SO2Me | — | — | H | 0 | 2,2,2-trichloroethyl | 2-iodo-6-ethyl-4-(1,2,2,2-tetrafluoro-1-trifluoromethyl-ethyl)-phenyl |
| 9-46 | —L₁—D₁ | H | —CH2CH2— | CONH2 | — | — | H | 0 | 2,2,2-trichloroethyl | 2,6-dichloro-4-(1,2,2,2-tetrafluoro-1-trifluoromethyl-ethyl)-phenyl |
| 9-47 | —L₁—D₁ | H | —CH2CH2— | CONH2 | — | — | H | 0 | 2,2,2-trichloroethyl | 2,6-dibromo-4-(1,2,2,2-tetrafluoro-1-trifluoromethyl-ethyl)-phenyl |

TABLE 9-continued

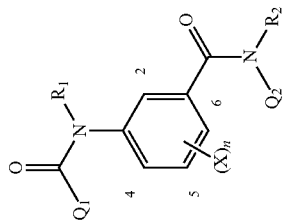

| compound number | R1 | R2 | L1 | D1 | L2 | D2 | X | n | Q3 | Q2 |
|---|---|---|---|---|---|---|---|---|---|---|
| 9-48 | —L1—D1 | H | —CH2CH2— | CONH2 | — | — | H | 0 | | 2,6-diiodo-4-(1,2,2,2-tetrafluoro-1-trifluoromethyl-ethyl)-phenyl |
| 9-49 | —L1—D1 | H | —CH2CH2— | CONH2 | — | — | H | 0 | 2,2,2-trichloroethyl | 2,6-ditrifluoromethyl-4-(1,2,2,2-tetrafluoro-1-trifluoromethyl-ethyl)-phenyl |
| 9-50 | —L1—D1 | H | —CH2CH2— | CONH2 | — | — | H | 0 | 2,2,2-trichloroethyl | 2-bromo-6-trifluoromethyl-4-(1,2,2,2-tetrafluoro-1-trifluoromethyl-ethyl)-phenyl |
| 9-51 | —L1—D1 | H | —CH2CH2— | CONH2 | — | — | H | 0 | 2,2,2-trichloroethyl | 2-iodo-6-trifluoromethyl-4-(1,2,2,2-tetrafluoro-1-trifluoromethyl-ethyl)-phenyl |
| 9-52 | —L1—D1 | H | —CH2CH2— | CONH2 | — | — | H | 0 | 2,2,2-trichloroethyl | 2-bromo-6-trifluoromethoxy-4-(1,2,2,2-tetrafluoro-1-trifluoromethyl-ethyl)-phenyl |
| 9-53 | —L1—D1 | H | —CH2CH2— | CONH2 | — | — | H | 0 | 2,2,2-trichloroethyl | 2-bromo-6-iodo-4-(1,2,2,2-tetrafluoro-1-trifluoromethyl-ethyl)-phenyl |
| 9-54 | —L1—D1 | H | —CH2CH2— | CONH2 | — | — | H | 0 | 2,2,2-trichloroethyl | 2-bromo-6-trifluoromethylthio-4-(1,2,2,2-tetrafluoro-1-trifluoromethyl-ethyl)-phenyl |
| 9-55 | —L1—D1 | H | —CH2CH2— | CONH2 | — | — | H | 0 | 2,2,2-trichloroethyl | 2-bromo-6-trifluoromethylsulfinyl-4-(1,2,2,2-tetrafluoro-1-trifluoromethyl-ethyl)-phenyl |
| 9-56 | —L1—D1 | H | —CH2CH2— | CONH2 | — | — | H | 0 | 2,2,2-trichloroethyl | 2bromo-6-trifluoromethylsulfonyl-4-(1,2,2,2-tetrafluoro-1-trifluoromethyl-ethyl)-phenyl |
| 9-57 | —L1—D1 | H | —CH2CH2— | CONH2 | — | — | H | 0 | 2,2,2-trichloroethyl | 2-bromo-6-pentafluoroethyl-4-(1,2,2,2-tetrafluoro-1-trifluoromethyl-ethyl)-phenyl |
| 9-58 | —L1—D1 | H | —CH2CH2— | CONH2 | — | — | H | 0 | 2,2,2-trichloroethyl | 2-iodo-6-pentafluoroethyl-4-(1,2,2,2-tetrafluoro-1-trifluoromethyl-ethyl)-phenyl |

TABLE 9-continued

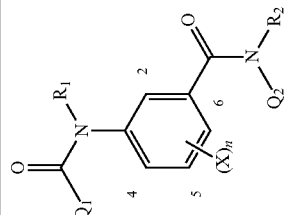

| compound number | R₁ | R₂ | L1 | D1 | L2 | D2 | X | n | Q₃ | Q₂ |
|---|---|---|---|---|---|---|---|---|---|---|
| 9-59 | —L₁—D₁ | H | —CH2CH2— | CONH2 | — | — | H | 0 | 2,2,2-trichloroethyl | 2-chloro-6-methyl-4-(1,2,2,3,3,3-hexafluoro-1-trifluoromethyl-propyl)-phenyl |
| 9-60 | —L₁—D₁ | H | —CH2CH2CH2— | CONH2 | — | — | H | 0 | 2,2,2-trichloroethyl | 2-bromo-6-methyl-4-(1,2,2,3,3,3-hexafluoro-1-trifluoromethyl-propyl)-phenyl |
| 9-61 | —L₁—D₁ | H | —CH2CH2— | CONH2 | — | — | H | 0 | 2,2,2-trichloroethyl | 2-iodo-6-methyl-4-(1,2,2,3,3,3-hexafluoro-1-trifluoromethyl-propyl)-phenyl |
| 9-62 | —L₁—D₁ | H | —CH2CH2— | CONH2 | — | — | H | 0 | 2,2,2-trichloroethyl | 2-bromo-6-ethyl-4-(1,2,2,3,3,3-hexafluoro-1-trifluoromethyl-propyl)-phenyl |
| 9-63 | —L₁—D₁ | Me | —CH2CH2— | CONH2 | — | — | H | 0 | 2,2,2-trichloroethyl | 2-iodo-6-ethyl-4-(1,2,2,3,3,3-hexafluoro-1-trifluoromethyl-propyl)-phenyl |
| 9-64 | —L₁—D₁ | H | —CH2CH2— | CONH2 | — | — | H | 0 | 2,2,2-trichloroethyl | 2,6-dichloro-4-(1,2,2,3,3,3-hexafluoro-1-trifluoromethyl-propyl)-phenyl |
| 9-65 | —L₁—D₁ | H | —CH2CH2— | CONH2 | — | — | H | 0 | 2,2,2-trichloroethyl | 2,6-dibromo-4-(1,2,2,3,3,3-hexafluoro-1-trifluoromethyl-propyl)-phenyl |
| 9-66 | —L₁—D₁ | Me | —CH2CH2— | CONH2 | — | — | H | 0 | 2,2,2-trichloroethyl | 2,6-diiodo-4-(1,2,2,3,3,3-hexafluoro-1-trifluoromethyl-propyl)-phenyl |
| 9-67 | —L₁—D₁ | H | —CH2— | CONH2 | — | — | H | 0 | 2,2,2-trichloroethyl | 2,6-ditrifluoromethyl-4-(1,2,2,3,3,3-hexafluoro-1-trifluoromethyl-propyl)-phenyl |
| 9-68 | —L₁—D₁ | H | —CH2CH2— | CONH2 | — | — | H | 0 | 2,2,2-trichloroethyl | 2-6-bromo-6-trifluoromethyl-4-(1,2,2,3,3,3-hexafluoro-1-trifluoromethyl-propyl)-phenyl |
| 9-69 | —L₁—D₁ | H | —CH2CH2— | CONH2 | — | — | H | 0 | 2,2,2-trichloroethyl | 2-iodo-6-trifluoromethyl-4-(1,2,2,3,3,3-hexafluoro-1-trifluoromethyl-propyl)-phenyl |

TABLE 9-continued

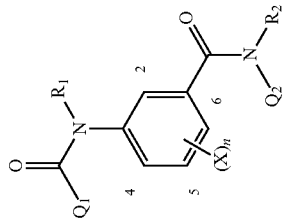

| compound number | R1 | R2 | L1 | D1 | L2 | D2 | X | n | Q3 | Q2 |
|---|---|---|---|---|---|---|---|---|---|---|
| 9-70 | —L1—D1 | H | —CH2CH2— | CONH2 | — | — | H | 0 | 2,2,2-trichloroethyl | 2-dibromo-6-trifluoromethoxy-4-(1,2,3,3,3-hexafluoro-1-trifluoromethyl-propyl)-phenyl |
| 9-71 | —L1—D1 | H | —CH2CH2— | CONH2 | — | — | H | 0 | 2,2,2-trichloroethyl | 2-bromo-6-iodo-4-(1,2,2,3,3,3-hexafluoro-1-trifluoromethyl-propyl)-phenyl |
| 9-72 | —L1—D1 | H | —CH2CH2— | CONH2 | — | — | H | 0 | 2,2,2-trichloroethyl | 2-bromo-6-trifluoromethylthio-4-(1,2,3,3,3-hexafluoro-1-trifluoromethyl-propyl)-phenyl |
| 9-73 | —L1—D1 | H | —CH2CH(CH3)— | CONH2 | — | — | H | 0 | 2,2,2-trichloroethyl | 2-bromo-6-trifluoromethylsulfinyl-4-(1,2,2,3,3,3-hexafluoro-1-trifluoromethyl-propyl)-phenyl |
| 9-74 | —L1—D1 | H | —CH2CH2— | CONH2 | — | — | H | 0 | 2,2,2-trichloroethyl | 2-bromo-6-trifluoromethylsulfonyl-4-(1,2,2,3,3,3-hexafluoro-1-trifluoromethyl-propyl)-phenyl |
| 9-75 | —L1—D1 | H | —CH2CH2— | CONH2 | — | — | H | 0 | 2,2,2-trichloroethyl | 2-bromo-6-pentafluoroethyl-4-(1,2,2,3,3,3-hexafluoro-1-trifluoromethyl-propyl)-phenyl |
| 9-76 | —L1—D1 | H | —CH2CH2— | CONH2 | — | — | H | 0 | 2,2,2-trichloroethyl | 2-iodo-6-pentafluoroethyl-4-(1,2,2,3,3,3-hexafluoro-1-trifluoromethyl-propyl)-phenyl |
| 9-77 | —L1—D1 | H | —CH2CH2— | CONH2 | — | — | H | 0 | i-propyl | 2,6-dibromo-4-(1,2,2,2-tetrafluoro-1-trifluoromethyl-ethyl)-phenyl |
| 9-78 | —L1—D1 | H | —CH2CH2— | CONH2 | — | — | H | 0 | 3,3,3-trifluoro-n-propyl | 2,6-dibromo-4-(1,2,2,2-tetrafluoro-1-trifluoromethyl-ethyl)-phenyl |
| 9-79 | —L1—D1 | H | —CH2CH2— | CONH2 | — | — | H | 0 | i-propyl | 2,6-diiodo-4-(1,2,2,2-tetrafluoro-1-trifluoromethyl-pentafluoroethyl-phenyl |
| 9-80 | —L1—D1 | H | —CH2CH2— | CONH2 | — | — | H | 0 | 3,3,3-trifluoro-n-propyl | 2,6-diiodo-4-(1,2,2,2-tetrafluoro-1-trifluoromethyl-ethyl)-phenyl |

TABLE 9-continued

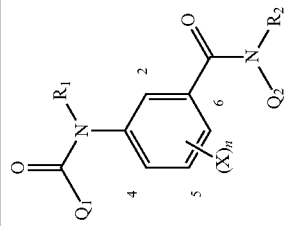

| compound number | R₁ | R₂ | L1 | D1 | L2 | D2 | X | n | Q₃ | Q₂ |
|---|---|---|---|---|---|---|---|---|---|---|
| 9-81 | —L₁—D₁ | H | —CH2CH2— | CONH2 | — | — | H | 0 | i-propyl | 2-bromo-6-trifluoromethyl-4-(1,2,2,2-tetrafluoro-1-trifluoromethyl-ethyl)-phenyl |
| 9-82 | —L₁—D₁ | H | —CH2CH2— | CONH2 | — | — | H | 0 | 3,3,3-trifluoro-n-propyl | 2-bromo-6-trifluoromethyl-4-(1,2,2,2-tetrafluoro-1-trifluoromethyl-ethyl)-phenyl |
| 9-83 | —L₁—D₁ | H | —CH2CH2— | CONH2 | — | — | H | 0 | i-propyl | 2-iodo-6-trifluoromethyl-4-(1,2,2,2-tetrafluoro-1-trifluoromethyl-ethyl)-phenyl |
| 9-84 | —L₁—D₁ | H | —CH2CH2— | CONH2 | — | — | H | 0 | 3,3,3-trifluoro-n-propyl | 2-iodo-6-trifluoromethyl-4-(1,2,2,2-tetrafluoro-1-trifluoromethyl-ethyl)-phenyl |
| 9-85 | —L₁—D₁ | H | —CH2CH2— | CONH2 | — | — | H | 0 | i-propyl | 2,6-dibromo-4-(1,2,2,3,3,3-hexafluoro-1-trifluoromethyl-propyl)-phenyl |
| 9-86 | —L₁—D₁ | H | —CH2CH2— | CONH2 | — | — | H | 0 | 3,3,3-trifluoro-n-propyl | 2,6-dibromo-4-(1,2,2,3,3,3-hexafluoro-1-trifluoromethyl-propyl)-phenyl |
| 9-87 | —L₁—D₁ | H | —CH2CH2— | CONH2 | — | — | H | 0 | i-propyl | 2,6-diiodo-4-(1,2,2,3,3,3-hexafluoro-1-trifluoromethyl-propyl)-phenyl |
| 9-88 | —L₁—D₁ | H | —CH2CH2— | CONH2 | — | — | H | 0 | 3,3,3-trifluoro-n-propyl | 2,6-diiodo-4-(1,2,2,3,3,3-hexafluoro-1-trifluoromethyl-propyl)-phenyl |
| 9-89 | —L₁—D₁ | H | —CH2CH2— | CONH2 | — | — | H | 0 | i-propyl | 2-bromo-6-trifluoromethyl-4-(1,2,2,3,3,3-hexafluoro-1-trifluoromethyl-propyl)-phenyl |
| 9-90 | —L₁—D₁ | H | —CH2CH2— | CONH2 | — | — | H | 0 | 3,3,3-trifluoro-n-propyl | 2-bromo-6-trifluoromethyl-4-(1,2,2,3,3,3-hexafluoro-1-trifluoromethyl-propyl)-phenyl |
| 9-91 | —L₁—D₁ | H | —CH2CH2— | CONH2 | — | — | H | 0 | i-propyl | 2-iodo-6-trifluoromethyl-4-(1,2,2,3,3,3-hexafluoro-1-trifluoromethyl-propyl)-phenyl |

TABLE 9-continued

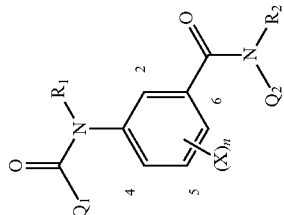

| compound number | R₁ | R₂ | L1 | D1 | L2 | D2 | X | n | Q₃ | Q₂ |
|---|---|---|---|---|---|---|---|---|---|---|
| 9-92 | —L₁—D₁ | H | —CH2CH2— | CONH2 | — | — | H | 0 | 3,3,3-trifluoro-n-propyl | 2-iodo-6-trifluoromethyl-4-(1,2,2,3,3,3-hexafluoro-1-trifluoromethyl-propyl)-phenyl |
| 9-93 | —L₁—D₁ | H | —CH2CH2— | CONH2 | — | — | 2-F | 1 | 2,2,2-trichloroethyl | 2,6-dibromo-4-pentafluoroethyl-phenyl |
| 9-94 | —L₁—D₁ | H | —CH2CH2— | CONH2 | — | — | 2-F | 1 | 3,3,3-trifluoro-n-propyl | 2,6-diiodo-4-pentafluoroethyl-phenyl |
| 9-95 | —L₁—D₁ | H | —CH2CH2— | CONH2 | — | — | 2-F | 1 | 2,2,2-trichloroethyl | 2-bromo-6-rifluoroethyl-4-pentafluoroethyl-phenyl |
| 9-96 | —L₁—D₁ | H | —CH2CH2— | CONH2 | — | — | 2-F | 1 | 3,3,3-trifluoro-n-propyl | 2-iodo-6-trifluoromethyl-4-pentafluoroethyl-phenyl |
| 9-97 | —L₁—D₁ | H | —CH2CH2— | CONH2 | — | — | 2-F | 1 | 2,2,2-trichloroethyl | 2-chloro-6-methyl-4-(1,2,2,2-tetrafluoro-1-trifluoromethyl-ethyl)-phenyl |
| 9-98 | —L₁—D₁ | H | —CH2CH2— | CONH2 | — | — | 2-F | 1 | 3,3,3-trifluoro-n-propyl | 2-bromo-6-methyl-4-(1,2,2,2-tetrafluoro-1-trifluoromethyl-ethyl)-phenyl |
| 9-99 | —L₁—D₁ | H | —CH2CH2— | CONH2 | — | — | 2-F | 1 | 2,2,2-trichloroethyl | 2-iodo-6-methyl-4-(1,2,2,2-tetrafluoro-1-trifluoromethyl-ethyl)-phenyl |
| 9-100 | —L₁—D₁ | H | —CH2CH2— | CONH2 | — | — | 2-F | 1 | 2,2,2-trichloroethyl | 2-bromo-6-ethyl-4-(1,2,2,2-tetrafluoro-1-trifluoromethyl-ethyl)-phenyl |
| 9-101 | —L₁—D₁ | H | —CH2CH2— | CONH2 | — | — | 2-F | 1 | 2,2,2-trichloroethyl | 2-iodo-6-ethyl-4-(1,2,2,2-tetrafluoro-1-trifluoromethyl-ethyl)-phenyl |
| 9-102 | —L₁—D₁ | H | —CH2CH2— | CONH2 | — | — | 2-F | 1 | 2,2,2-trichloroethyl | 2,6-dichloro-4-(1,2,2,2-tetrafluoro-1-trifluoromethyl-ethyl)-phenyl |
| 9-103 | —L₁—D₁ | Me | —CH2CH2— | CONH2 | — | — | 2-F | 1 | 2,2,2-trichloroethyl | 2,6-dibromo-4-(1,2,2,2-tetrafluoro-1-trifluoromethyl-ethyl)-phenyl |
| 9-104 | —L₁—D₁ | H | —CH2CH2— | CONH2 | — | — | 2-F | 1 | 2,2,2-trichloroethyl | 2,6-diiodo-4-(1,2,2,2-tetrafluoro-1-trifluoromethyl-ethyl)-phenyl |
| 9-105 | —L₁—D₁ | H | —CH2CH2— | CONH2 | — | — | 2-F | 1 | 2,2,2-trichloroethyl | 2,6-ditrifluoromethyl-4-(1,2,2,2-tetrafluoro-1-trifluoromethyl-ethyl)-phenyl |

TABLE 9-continued

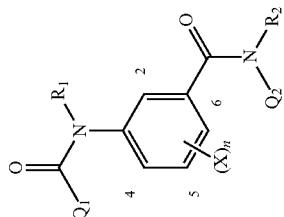

| compound number | R₁ | R₂ | L1 | D1 | L2 | D2 | X | n | Q₃ | Q₂ |
|---|---|---|---|---|---|---|---|---|---|---|
| 9-106 | —L₁—D₁ | Me | —CH2CH2— | CONH2 | — | — | 2-F | 1 | 2,2,2-trichloroethyl | 2-bromo-6-trifluoromethyl-4-(1,2,2,2-tetrafluoro-1-trifluoromethyl-ethyl)-phenyl |
| 9-107 | —L₁—D₁ | H | —CH2— | CONH2 | — | — | 2-F | 1 | 2,2,2-trichloroethyl | 2-iodo-6-trifluoromethyl-4-(1,2,2,2-tetrafluoro-1-trifluoromethyl-ethyl)-phenyl |
| 9-108 | —L₁—D₁ | H | —CH2CH2— | CONH2 | — | — | 2-F | 1 | 2,2,2-trichloroethyl | 2-bromo-6-trifluoromethoxy-4-(1,2,2,2-tetrafluoro-1-trifluoromethyl-ethyl)-phenyl |
| 9-109 | —L₁—D₁ | H | —CH2CH2— | CONH2 | — | — | 2-F | 1 | 2,2,2-trichloroethyl | 2-bromo-6-iodo-4-(1,2,2,2-tetrafluoro-1-trifluoromethyl-ethyl)-phenyl |
| 9-110 | —L₁—D₁ | H | —CH2CH2— | CONH2 | — | — | 2-F | 1 | 2,2,2-trichloroethyl | 2-bromo-6-trifluoromethylthio-4-(1,2,2,2-tetrafluoro-1-trifluoromethyl-ethyl)-phenyl |
| 9-111 | —L₁—D₁ | H | —CH2CH2— | CONH2 | — | — | 2-F | 1 | 2,2,2-trichloroethyl | 2-bromo-6-trifluoromethylsulfinyl-4-(1,2,2,2-tetrafluoro-1-trifluoromethyl-ethyl)-phenyl |
| 9-112 | —L₁—D₁ | H | —CH2CH2— | CONH2 | — | — | 2-F | 1 | 2,2,2-trichloroethyl | 2-bromo-6-trifluoromethylsulfonyl-4-(1,2,2,2-tetrafluoro-1-trifluoromethyl-ethyl)-phenyl |
| 9-113 | —L₁—D₁ | H | —CH2CH(CH3)— | CONH2 | — | — | 2-F | 1 | 2,2,2-trichloroethyl | 2-bromo-6-pentafluoroethyl-4-(1,2,2,2-tetrafluoromethyl-ethyl)-phenyl |
| 9-114 | —L₁—D₁ | H | —CH2CH2— | CONH2 | — | — | 2-F | 1 | 2,2,2-trichloroethyl | 2-iodo-6-pentafluoroethyl-4-(1,2,2,2-tetrafluoro-1-trifluoromethyl-ethyl)-phenyl |
| 9-115 | —L₁—D₁ | H | —CH2CH2— | CONH2 | — | — | 2-F | 1 | 2,2,2-trichloroethyl | 2-chloro-6-methyl-4-(1,2,2,3,3,3-hexfluoro-1-trifluoromethyl-propyl)-phenyl |
| 9-116 | —L₁—D₁ | H | —CH2CH2— | CONH2 | — | — | 2-F | 1 | 2,2,2-trichloroethyl | 2-bromo-6-methyl-4-(1,2,2,3,3,3-hexafluoro-1-trifluoromethyl-propyl)-phenyl |

TABLE 9-continued

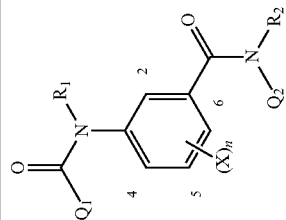

| compound number | R₁ | R₂ | L1 | D1 | L2 | D2 | X | n | Q₃ | Q₂ |
|---|---|---|---|---|---|---|---|---|---|---|
| 9-117 | —L₁—D₁ | H | —CH2CH2— | CONH2 | — | — | 2-F | 1 | 2,2,2-trichloroethyl | 2-iodo-6-methyl-4-(1,2,2,3,3,3-hexafluoro-1-trifluoromethyl-propyl)-phenyl |
| 9-118 | —L₁—D₁ | H | —CH2CH2— | CN | — | — | 2-F | 1 | 2,2,2-trichloroethyl | 2-bromo-6-ethyl-4-(1,2,2,3,3,3-hexafluoro-1-trifluoromethyl-propyl)-phenyl |
| 9-119 | —L₁—D₁ | H | —CH2CH2— | CONH2 | — | — | 2-F | 1 | 2,2,2-trichloroethyl | 2-iodo-6-ethyl-4-(1,2,2,3,3,3-hexafluoro-trifluoromethyl-1-propyl)-phenyl |
| 9-120 | —L₁—D₁ | H | —CH2CH2— | CONH2 | — | — | 2-F | 1 | 2,2,2-trichloroethyl | 2,6-dichloro-4-(1,2,2,3,3,3-hexafluoro-1-trifluoromethyl-propyl)-phenyl |
| 9-121 | —L₁—D₁ | H | —CH2CH2— | CONH2 | — | — | 2-F | 1 | 2,2,2-trichloroethyl | 2,6-dibromo-4-(1,2,2,3,3-hexafluoro-1-trifluoromethyl-propyl)-phenyl |
| 9-122 | —L₁—D₁ | H | —CH2CH2— | CONH2 | — | — | 2-F | 1 | 2,2,2-trichloroethyl | 2,6-diiodo-4-(1,2,2,3,3,3-hexafluoro-1-trifluoromethyl-propyl)-phenyl |
| 9-123 | —L₁—D₁ | H | —CH2CH2— | CONH2 | — | — | 2-F | 1 | 2,2,2-trichloroethyl | 2,6-ditrifluoromethyl-4-(1,2,2,3,3,3-hexafluoro-1-trifluoromethyl-propyl)-phenyl |
| 9-124 | —L₁—D₁ | H | —CH2CH2— | CONH2 | — | — | 2-F | 1 | 2,2,2-trichloroethyl | 2-bromo-6-trifluoromethyl-4-(1,2,2,3,3,3-hexafluoro-1-trifluoromethyl-propyl)-phenyl |
| 9-125 | —L₁—D₁ | H | —CH2CH2— | CONH2 | — | — | 2-F | 1 | 2,2,2-trichloroethyl | 2-iodo-6-trifluoromethyl-4-(1,2,2,3,3,3-hexafluoro-1-trifluoromethyl-propyl)-phenyl |
| 9-126 | —L₁—D₁ | H | —CH2CH2— | CONH2 | — | — | 2-F | 1 | 2,2,2-trichloroethyl | 2-bromo-6-trifluoromethoxy-4-(1,2,2,3,3,3-hexafluoro-1-trifluoromethyl-propyl)-phenyl |
| 9-127 | —L₁—D₁ | H | —CH2CH2— | CONH2 | — | — | 2-F | 1 | 2,2,2-trichloroethyl | 2-bromo-6-iodo-4-(1,2,2,3,3,3-hexafluoro-1-trifluoromethyl-propyl)-phenyl |

TABLE 9-continued

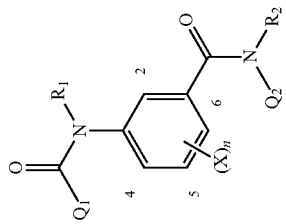

| compound number | R₁ | R₂ | L1 | D1 | L2 | D2 | X | n | Q₃ | Q₂ |
|---|---|---|---|---|---|---|---|---|---|---|
| 9-128 | —L₁—D₁ | H | —CH2CH2— | CONH2 | — | — | 2-F | 1 | 2,2,2-trichloroethyl | 2-bromo-6-trifluoromethylthio-4-(1,2,2,3,3,3-hexafluoro-1-trifluoromethyl-propyl)-phenyl |
| 9-129 | —L₁—D₁ | H | —CH2CH2— | CONH2 | — | — | 2-F | 1 | 2,2,2-trichloroethyl | 2-bromo-6-trifluoromethylsulfinyl-4-(1,2,2,3,3,3-hexafluoro-1-trifluoromethyl-propyl)-phenyl |
| 9-130 | —L₁—D₁ | H | —CH2CH2— | CONH2 | — | — | 2-F | 1 | 2,2,2-trichloroethyl | 2-bromo-6-trifluoromethylsulfonyl-4-(1,2,2,3,3,3-hexafluoro-1-trifluoromethyl-propyl)-phenyl |
| 9-131 | —L₁—D₁ | H | —CH2CH2— | CONH2 | — | — | 2-F | 1 | 2,2,2-trichloroethyl | 2-bromo-6-pentafluoroethyl-4-(1,2,2,3,3,3-hexafluoro-1-trifluoromethyl-propyl)-phenyl |
| 9-132 | —L₁—D₁ | H | —CH2CH2— | CONH2 | — | — | 2-F | 1 | 2,2,2-trichloroethyl | 2-iodo-pentafluoroethyl-4-(1,2,2,3,3,3-hexafluoro-1-trifluoromethyl-propyl)-phenyl |
| 9-133 | —L₁—D₁ | Me | —CH2CH2— | CONH2 | — | — | 2-F | 1 | i-propyl | 2,6-dibromo-4-(1,2,2,2-tetrafluoro-1-trifluoromethyl-ethyl)-phenyl |
| 9-134 | —L₁—D₁ | H | —CH2CH2— | CONH2 | — | — | 2-F | 1 | 3,3,3-trifluoro-n-propyl | 2,6-dibromo-4-(1,2,2,2-tetrafluoro-1-trifluoromethyl-ethyl)-phenyl |
| 9-135 | —L₁—D₁ | H | —CH2CH2— | CONH2 | — | — | 2-F | 1 | i-propyl | 2,6-diiodo-4-(1,2,2,2-tetrafluoro-1-trifluoromethyl-ethyl)-phenyl |
| 9-136 | —L₁—D₁ | Me | —CH2CH2— | CONH2 | — | — | 2-F | 1 | 3,3,3-trifluoro-n-propyl | 2,6-diiodo-4-(1,2,2,2-tetrafluoro-1-trifluoromethyl-ethyl)-phenyl |
| 9-137 | —L₁—D₁ | H | —CH2— | CONH2 | — | — | 2-F | 1 | i-propyl | 2-bromo-6-trifluoromethyl-4-(1,2,2,2-tetrafluoro-1-trifluoromethyl-ethyl)-phenyl |
| 9-138 | —L₁—D₁ | H | —CH2CH2— | CONH2 | — | — | 2-F | 1 | 3,3,3-trifluoro-n-propyl | 2-bromo-6-trifluoromethyl-4-(1,2,2,2-tetrafluoro-1-trifluoromethyl-ethyl)-phenyl |
| 9-139 | —L₁—D₁ | H | —CH2CH2— | CONH2 | — | — | 2-F | 1 | i-propyl | 2-iodo-6-trifluoromethyl-4-(1,2,2,2-tetrafluoro-1-trifluoromethyl-ethyl)-phenyl |
| 9-140 | —L₁—D₁ | H | —CH2CH2— | CONH2 | — | — | 2-F | 1 | 3,3,3-trifluoro-n-propyl | 2-iodo-6-trifluoromethyl-4-(1,2,2,2-tetrafluoro-1-trifluoromethyl-ethyl)-phenyl |

TABLE 9-continued

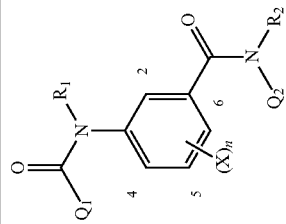

| compound number | R₁ | R₂ | L1 | D1 | L2 | D2 | X | n | Q₃ | Q₂ |
|---|---|---|---|---|---|---|---|---|---|---|
| 9-141 | —L₁—D₁ | H | —CH2CH2— | CONH2 | — | — | 2-F | 1 | i-propyl | 2,6-dibromo-4-(1,2,2,3,3,3-hexafluoro-1-trifluoromethyl-propyl)-phenyl |
| 9-142 | —L₁—D₁ | H | —CH2CH2— | CONH2 | — | — | 2-F | 1 | 3,3,3-trifluoro-n-propyl | 2,6-dibromo-4-(1,2,2,3,3,3-hexafluoro-1-trifluoromethyl-propyl)-phenyl |
| 9-143 | —L₁—D₁ | H | —CH2CH(CH3)— | CONH2 | — | — | 2-F | 1 | i-propyl | 2,6-diiodo-4-(1,2,2,3,3,3-hexafluoro-1-trifluoromethyl-propyl)-phenyl |
| 9-144 | —L₁—D₁ | H | —CH2CH2— | CONH2 | — | — | 2-F | 1 | 3,3,3-trifluoro-n-propyl | 2,6-diiodo-4-(1,2,2,3,3,3-hexafluoro-1-trifluoromethyl-propyl)-phenyl |
| 9-145 | —L₁—D₁ | H | —CH2CH2— | CONH2 | — | — | 2-F | 1 | i-propyl | 2-bromo-6-trifluoromethyl-4-(1,2,2,3,3,3-hexafluoro-1-trifluoromethyl-propyl)-phenyl |
| 9-146 | —L₁—D₁ | H | —CH2CH2— | CONH2 | — | — | 2-F | 1 | 3,3,3-trifluoro-n-propyl | 2-bromo-6-trifluoromethyl-4-(1,2,2,3,3,3-hexafluoro-1-trifluoromethyl-propyl)-phenyl |
| 9-147 | —L₁—D₁ | H | —CH2— | CONH2 | — | — | 2-F | 1 | i-propyl | 2-iodo-6-trifluoromethyl-4-(1,2,2,3,3,3-hexafluoro-1-trifluoromethyl-propyl)-phenyl |
| 9-148 | —L₁—D₁ | H | —CH2CH2— | CONH2 | — | — | 2-F | 1 | 3,3,3-trifluoro-n-propyl | 2-iodo-6-trifluoromethyl-4-(1,2,2,3,3,3-hexafluoro-1-trifluoromethyl-propyl)-phenyl |
| 9-149 | —L₁—D₁ | H | —CH2CH2— | CONH2 | — | — | 2-F | 1 | phenyl | 2,6-dimethyl-4-(1,2,2,3,3,3-hexafluoro-1-trifluoromethyl-propyl)-phenyl |
| 9-150 | —L₁—D₁ | H | —CH2CH2— | CONH2 | — | — | 2-F | 1 | 4-cyanophenyl | 2,6-dimethyl-4-(1,2,2,3,3,3-hexafluoro-1-trifluoromethyl-propyl)-phenyl |
| 9-151 | —L₁—D₁ | H | —CH2CH2— | CONH2 | — | — | 2-F | 1 | 3-cyanophenyl | 2,6-dimethyl-4-(1,2,2,3,3,3-hexafluoro-1-trifluoromethyl-propyl)-phenyl |
| 9-152 | —L₁—D₁ | H | —CH2CH2— | CONH2 | — | — | 4-F | 1 | 2,2,2-trichloroethyl | 2,6-dibromo-4-(1,2,2,2-tetrafluoro-1-trifluoromethyl-ethyl)-phenyl |

TABLE 9-continued

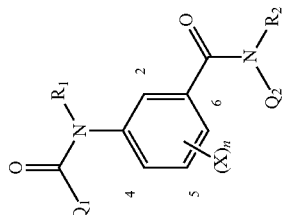

| compound number | R1 | R2 | L1 | D1 | L2 | D2 | X | n | Q3 | Q2 |
|---|---|---|---|---|---|---|---|---|---|---|
| 9-153 | —L1—D1 | H | —CH2CH(CH3)— | CONH2 | — | — | 4-F | 1 | 2,2,2-trichloroethyl | 2-bromo-6-trifluoromethyl-4-(1,2,2,2-tetrafluoro-1-trifluoromethyl-ethyl)-phenyl |
| 9-154 | —L1—D1 | H | —CH2CH2— | CONH2 | — | — | 4-F | 1 | 2,2,2-trichloroethyl | 2-iodo-6-trifluoro-1-trifluoromethyl-ethyl)-phenyl |
| 9-155 | —L1—D1 | H | —CH2CH2— | CONH2 | — | — | 4-F | 1 | 2,2,2-trichloroethyl | 2-bromo-6-trifluoromethyl-4-(1,2,2,3,3,3-hexafluoro-1-trifluoromethyl-propyl)-phenyl |
| 9-156 | —L1—D1 | H | —CH2CH2— | CONH2 | — | — | 4-F | 1 | 2,2,2-trichloroethyl | 2-iodo-trifluoromethyl-4-(1,2,2,3,3,3-hexafluoro-1-trifluoromethyl-propyl)-phenyl |
| 9-157 | —L1—D1 | H | —CH2CH2— | CONH2 | — | — | 4-CN | 1 | 2,2,2-trichloroethyl | 2,6-dibromo-4-(1,2,2,2-tetrafluoro-1-trifluoromethyl-ethyl)-phenyl |
| 9-158 | —L1—D1 | H | —CH2CH2— | CN | — | — | 4-CN | 1 | 2,2,2-trichloroethyl | 2-bromo-6-trifluoromethyl-4-(1,2,2,2-tetrafluoro-1-trifluoromethyl-ethyl)-phenyl |
| 9-159 | —L1—D1 | H | —CH2CH2— | CONH2 | — | — | 4-CN | 1 | 2,2,2-trichloroethyl | 2-iodo-6-trifluoromethyl-4-(1,2,2,2-tetrafluoro-1-trifluoromethyl-ethyl)-phenyl |
| 9-160 | —L1—D1 | H | —CH2CH2— | CONH2 | — | — | 4-CN | 1 | 2,2,2-trichloroethyl | 2-bromo-6-trifluoromethyl-4-(1,2,2,3,3,3-hexafluoro-1-trifluoromethyl-propyl)-phenyl |
| 9-161 | —L1—D1 | H | —CH2CH2— | CONH2 | — | — | 4-CN | 1 | 2,2,2-trichloroethyl | 2-iodo-6-trifluoromethyl-4-(1,2,2,3,3,3-hexafluoro-1-trifluoromethyl-propyl)-phenyl |
| 9-162 | —L1—D1 | H | —CH2CH2— | CONH2 | — | — | 2-NO2 | 1 | 2,2,2-trichloroethyl | 2,6-dibromo-4-(1,2,2,2-tetrafluoro-1-trifluoromethyl-ethyl)-phenyl |
| 9-163 | —L1—D1 | H | —CH2CH2— | CONH2 | — | — | 2-NO2 | 1 | 2,2,2-trichloroethyl | 2-bromo-6-trifluoromethyl-4-(1,2,2,2-tetrafluoro-1-trifluoromethyl-ethyl)-phenyl |

TABLE 9-continued

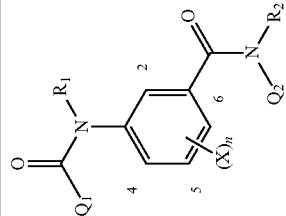

| compound number | R₁ | R₂ | L1 | D1 | L2 | D2 | X | n | Q₃ | Q₂ |
|---|---|---|---|---|---|---|---|---|---|---|
| 9-164 | —L₁—D₁ | H | —CH2CH2— | CONH2 | — | — | 2-NO2 | 1 | 2,2,2-trichloroethyl | 2-iodo-6-trifluoromethyl-4-(1,2,2,2-tetrafluoro-1-trifluoromethyl-ethyl)-phenyl |
| 9-165 | —L₁—D₁ | H | —CH2CH2— | CONH2 | — | — | 2-NO2 | 1 | 2,2,2-trichloroethyl | 2-bromo-6-trifluoromethyl-4-(1,2,2,3,3,3-hexafluoro-1-trifluoromethyl-propyl)-phenyl |
| 9-166 | —L₁—D₁ | H | —CH2CH2— | CONH2 | — | — | 2-NO2 | 1 | 2,2,2-trichloroethyl | 2-iodo-6-trifluoromethyl-4-(1,2,2,3,3,3-hexafluoro-1-trifluoromethyl-propyl)-phenyl |
| 9-167 | H | —L₂—D₂ | — | — | —CH2CH2— | CONH2 | H | 0 | methyl | 2,6-dimethyl-4-(1,2,2,2-tetrafluoro-1-trifluoromethyl-ethyl)-phenyl |
| 9-168 | H | —L₂—D₂ | — | — | —CH2CH2— | CONH2 | H | 0 | ethyl | 2,6-dimethyl-4-(1,2,2,2-tetrafluoro-1-trifluoromethyl-ethyl)-phenyl |
| 9-169 | Me | —L₂—D₂ | — | — | —CH2CH2— | CONH2 | H | 0 | i-propyl | 2,6-dimethyl-4-(1,2,2,2-tetrafluoro-1-trifluoromethyl-ethyl)-phenyl |
| 9-170 | H | —L₂—D₂ | — | — | —CH2CH2— | CONH2 | H | 0 | n-butyl | 2,6-dimethyl-4-(1,2,2,2-tetrafluoro-1-trifluoromethyl-ethyl)-phenyl |
| 9-171 | H | —L₂—D₂ | — | — | —CH2CH2— | SO2Me | H | 0 | i-butyl | 2,6-dimethyl-4-(1,2,2,2-tetrafluoro-1-trifluoromethyl-ethyl)-phenyl |
| 9-172 | Me | —L₂—D₂ | — | — | —CH2CH2— | CONH2 | H | 0 | s-butyl | 2,6-dimethyl-4-(1,2,2,2-tetrafluoro-1-trifluoromethyl-ethyl)-phenyl |
| 9-173 | H | —L₂—D₂ | — | — | —CH2CH2— | CONH2 | H | 0 | t-butyl | 2,6-dimethyl-4-(1,2,2,2-tetrafluoro-1-trifluoromethyl-ethyl)-phenyl |
| 9-174 | H | —L₂—D₂ | — | — | —CH2CH2— | CONH2 | H | 0 | vinyl | 2,6-dimethyl-4-(1,2,2,2-tetrafluoro-1-trifluoromethyl-ethyl)-phenyl |
| 9-175 | H | —L₂—D₂ | — | — | —CH2CH2— | CONH2 | H | 0 | allyl | 2,6-dimethyl-4-(1,2,2,2-tetrafluoro-1-trifluoromethyl-ethyl)-phenyl |
| 9-176 | H | —L₂—D₂ | — | — | —CH2CH2— | SOMe | H | 0 | benzyl | 2,6-dimethyl-4-(1,2,2,2-tetrafluoro-1-trifluoromethyl-ethyl)-phenyl |
| 9-177 | H | —L₂—D₂ | — | — | —CH2CH2— | OH | H | 0 | chloromethyl | 2,6-dimethyl-4-(1,2,2,2-tetrafluoro-1-trifluoromethyl-ethyl)-phenyl |
| 9-178 | H | —L₂—D₂ | — | — | —CH2CH2— | CONH2 | H | 0 | 2,2,2-trichloroethyl | 2,6-dimethyl-4-(1,2,2,2-tetrafluoro-1-trifluoromethyl-ethyl)-phenyl |
| 9-179 | H | —L₂—D₂ | — | — | —CH2CH2— | CONH2 | H | 0 | 3,3,3-trifluoro-n-propyl | 2,6-dimethyl-4-(1,2,2,2-tetrafluoro-1-trifluoromethyl-ethyl)-phenyl |

TABLE 9-continued

| compound number | R1 | R2 | L1 | D1 | L2 | D2 | X | n | Q3 | Q2 |
|---|---|---|---|---|---|---|---|---|---|---|
| 9-180 | H | —L2—D2 | — | — | —CH2CH2— | CO2Me | H | 0 | 1,3-difluoro-2-propyl | 2,6-dimethyl-4-(1,2,2,2-tetrafluoro-1-trifluoromethyl-ethyl)-phenyl |
| 9-181 | H | —L2—D2 | — | — | —CH2CH2— | CN | H | 0 | cyclohexyl | 2,6-dimethyl-4-(1,2,2,2-tetrafluoro-1-trifluoromethyl-ethyl)-phenyl |
| 9-182 | H | —L2—D2 | — | — | —CH2CH2— | NH2 | 2-F | 1 | methyl | 2,6-dimethyl-4-(1,2,2,2-tetrafluoro-1-trifluoromethyl-ethyl)-phenyl |
| 9-183 | H | —L2—D2 | — | — | —CH2CH2— | CONH2 | 2-F | 1 | ethyl | 2,6-dimethyl-4-(1,2,2,2-tetrafluoro-1-trifluoromethyl-ethyl)-phenyl |
| 9-184 | H | —L2—D2 | — | — | —CH2CH2— | CONH2 | 2-F | 1 | i-propyl | 2,6-dimethyl-4-(1,2,2,2-tetrafluoro-1-trifluoromethyl-ethyl)-phenyl |
| 9-185 | H | —L2—D2 | — | — | —CH2CH2— | CONH2 | 2-F | 1 | n-butyl | 2,6-dimethyl-4-(1,2,2,2-tetrafluoro-1-trifluoromethyl-ethyl)-phenyl |
| 9-186 | H | —L2—D2 | — | — | —CH2CH2— | CONH2 | 2-F | 1 | i-butyl | 2,6-dimethyl-4-(1,2,2,2-tetrafluoro-1-trifluoromethyl-ethyl)-phenyl |
| 9-187 | H | —L2—D2 | — | — | —CH2CH2— | CONH2 | 2-F | 1 | s-butyl | 2,6-dimethyl-4-(1,2,2,2-tetrafluoro-1-trifluoromethyl-ethyl)-phenyl |
| 9-188 | H | —L2—D2 | — | — | —CH2CH2— | CONH2 | 2-F | 1 | t-butyl | 2,6-dimethyl-4-(1,2,2,2-tetrafluoro-1-trifluoromethyl-ethyl)-phenyl |
| 9-189 | H | —L2—D2 | — | — | —CH2CH2— | CONH2 | 2-F | 1 | vinyl | 2,6-dimethyl-4-(1,2,2,2-tetrafluoro-1-trifluoromethyl-ethyl)-phenyl |
| 9-190 | H | —L2—D2 | — | — | —CH2CH2— | CONH2 | 2-F | 1 | allyl | 2,6-dimethyl-4-(1,2,2,2-tetrafluoro-1-trifluoromethyl-ethyl)-phenyl |
| 9-191 | H | —L2—D2 | — | — | —CH2CH2— | CONH2 | 2-F | 1 | benzyl | 2,6-dimethyl-4-(1,2,2,2-tetrafluoro-1-trifluoromethyl-ethyl)-phenyl |
| 9-192 | H | —L2—D2 | — | — | —CH2CH2— | CO2H | 2-F | 1 | chloromethyl | 2,6-dimethyl-4-(1,2,2,2-tetrafluoro-1-trifluoromethyl-ethyl)-phenyl |
| 9-193 | H | —L2—D2 | — | — | —CH2CH2— | CONH2 | 2-F | 1 | 2,2,2-trichloroethyl | 2,6-dimethyl-4-(1,2,2,2-tetrafluoro-1-trifluoromethyl-ethyl)-phenyl |
| 9-194 | H | —L2—D2 | — | — | —CH2CH2— | CONH2 | 2-F | 1 | 3,3,3-trifluoro-n-propyl | 2,6-dimethyl-4-(1,2,2,2-tetrafluoro-1-trifluoromethyl-ethyl)-phenyl |
| 9-195 | H | —L2—D2 | — | — | —CH2CH2— | CONH2 | 2-F | 1 | 1,3-difluoro-2-propyl | 2,6-dimethyl-4-(1,2,2,2-tetrafluoro-1-trifluoromethyl-ethyl)-phenyl |
| 9-196 | H | —L2—D2 | — | — | —CH2CH2— | CONMe2 | 2-F | 1 | cyclohexyl | 2,6-dimethyl-4-(1,2,2,2-tetrafluoro-1-trifluoromethyl-ethyl)-phenyl |

TABLE 9-continued

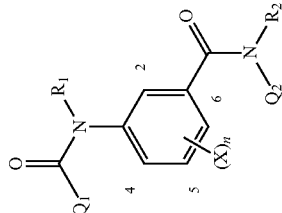

| compound number | R1 | R2 | L1 | D1 | L2 | D2 | X | n | Q3 | Q2 |
|---|---|---|---|---|---|---|---|---|---|---|
| 9-197 | H | —L2—D2 | — | — | —CH2CH2— | CONH2 | 4-F | 1 | i-propyl | 2,6-dimethyl-4-(1,2,2,2-tetrafluoro-1-trifluoromethyl-ethyl)-phenyl |
| 9-198 | H | —L2—D2 | — | — | —CH2CH2— | CONH2 | 4-F | 1 | 2,2,2-trichloroethyl | 2,6-dimethyl-4-(1,2,2,2-tetrafluoro-1-trifluoromethyl-ethyl)-phenyl |
| 9-199 | H | —L2—D2 | — | — | —CH2CH2— | CONH2 | 4-F | 1 | 3,3,3-trifluoro-n-propyl | 2,6-dimethyl-4-(1,2,2,2-tetrafluoro-1-trifluoromethyl-ethyl)-phenyl |
| 9-200 | H | —L2—D2 | — | — | —CH2CH2— | CONH2 | 4-CN | 1 | i-propyl | 2,6-dimethyl-4-(1,2,2,2-tetrafluoro-1-trifluoromethyl-ethyl)-phenyl |
| 9-201 | H | —L2—D2 | — | — | —CH2CH2— | CONH2 | 4-CN | 1 | 2,2,2-trichloroethyl | 2,6-dimethyl-4-(1,2,2,2-tetrafluoro-1-trifluoromethyl-ethyl)-phenyl |
| 9-202 | H | —L2—D2 | — | — | —CH2CH2— | CONH2 | 4-CN | 1 | 3,3,3-trifluoro-n-propyl | 2,6-dimethyl-4-(1,2,2,2-tetrafluoro-1-trifluoromethyl-ethyl)-phenyl |
| 9-203 | H | —L2—D2 | — | — | —CH2CH2— | CONH2 | H | 0 | 2,2,2-trichloroethyl | 2,6-dibromo-4-pentafluoroethyl-phenyl |
| 9-204 | H | —L2—D2 | — | — | —CH2CH2— | CONH2 | H | 0 | 3,3,3-trifluoro-n-propyl | 2,6-diiodo-4-pentafluoroethyl-phenyl |
| 9-205 | H | —L2—D2 | — | — | —CH2CH2— | CONH2 | H | 0 | 2,2,2-trichloroethyl | 2-bromo-6-trifluoromethyl-4-pentafluoroethyl-phenyl |
| 9-206 | H | —L2—D2 | — | — | —CH2CH2— | CONH2 | H | 0 | 3,3,3-trifluoro-n-propyl | 2-iodo-6-trifluoromethyl-4-pentafluoroethyl-phenyl |
| 9-207 | H | —L2—D2 | — | — | —CH2CH2— | CONH2 | H | 0 | 2,2,2-trichloroethyl | 2-chloro-6-methyl-4-(1,2,2,2-tetrafluoro-1-trifluoromethyl-ethyl)-phenyl |
| 9-208 | H | —L2—D2 | — | — | —CH2CH2— | CONH2 | H | 0 | 3,3,3-trifluoro-n-propyl | 2-bromo-6-methyl-4-(1,2,2,2-tetrafluoro-1-trifluoromethyl-ethyl)-phenyl |
| 9-209 | H | —L2—D2 | — | — | —CH2CH2— | CONH2 | H | 0 | 2,2,2-trichloroethyl | 2-iodo-6-methyl-4-(1,2,2,2-tetrafluoro-1-trifluoromethyl-ethyl)-phenyl |
| 9-210 | H | —L2—D2 | — | — | —CH2CH2— | CONH2 | H | 0 | 2,2,2-trichloroethyl | 2-bromo-6-ethyl-4-(1,2,2,2-tetrafluoro-1-trifluoromethyl-ethyl)-phenyl |
| 9-211 | H | —L2—D2 | — | — | —CH2CH2— | CONH2 | H | 0 | 2,2,2-trichloroethyl | 2-iodo-6-ethyl-4-(1,2,2,2-tetrafluoro-1-trifluoromethyl-ethyl)-phenyl |

TABLE 9-continued

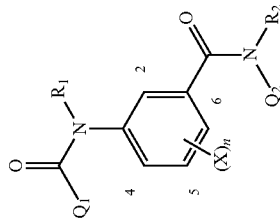

| compound number | $R_1$ | $R_2$ | L1 | D1 | L2 | D2 | X | n | $Q_3$ | $Q_2$ |
|---|---|---|---|---|---|---|---|---|---|---|
| 9-212 | H | —L$_2$—D$_2$ | — | — | —CH2CH2— | CONH2 | H | 0 | 2,2,2-trichloroethyl | 2,6-dichloro-4-(1,2,2,2-tetrafluoro-1-trifluoromethyl-ethyl)-phenyl |
| 9-213 | H | —L$_2$—D$_2$ | — | — | —CH2CH2— | CONH2 | H | 0 | 2,2,2-trichloroethyl | 2,6-dibromo-4-(1,2,2,2-tetrafluoro-1-trifluoromethyl-ethyl)-phenyl |
| 9-214 | H | —L$_2$—D$_2$ | — | — | —CH2CH2— | CONH2 | H | 0 | 2,2,2-trichloroethyl | 2,6-diiodo-4-(1,2,2,2-tetrafluoro-1-trifluoromethyl-ethyl)-phenyl |
| 9-215 | H | —L$_2$—D$_2$ | — | — | —CH2CH2— | CONH2 | H | 0 | 2,2,2-trichloroethyl | 2,6-ditrifluoromethyl-4-(1,2,2,2-tetrafluoro-1-trifluoromethyl-ethyl)-phenyl |
| 9-216 | H | —L$_2$—D$_2$ | — | — | —CH2CH2— | CONH2 | H | 0 | 2,2,2-trichloroethyl | 2-bromo-6-trifluoromethyl-4-(1,2,2,2-tetrafluoro-1-trifluoromethyl-ethyl)-phenyl |
| 9-217 | H | —L$_2$—D$_2$ | — | — | —CH2CH2— | CONH2 | H | 0 | 2,2,2-trichloroethyl | 2-iodo-6-trifluoromethyl-4-(1,2,2,2-tetrafluoro-1-trifluoromethyl-ethyl)-phenyl |
| 9-218 | H | —L$_2$—D$_2$ | — | — | —CH2CH2— | CONH2 | H | 0 | 2,2,2-trichloroethyl | 2-bromo-6-trifluoromethoxy-4-(1,2,2,2-tetrafluoro-1-trifluoromethyl-ethyl)-phenyl |
| 9-219 | H | —L$_2$—D$_2$ | — | — | —CH2CH2— | CONH2 | H | 0 | 2,2,2-trichloroethyl | 2-bromo-6-iodo-4-(1,2,2,2-tetrafluoro-1-trifluoromethyl-ethyl)-phenyl |
| 9-220 | H | —L$_2$—D$_2$ | — | — | —CH2CH2— | CONH2 | H | 0 | 2,2,2-trichloroethyl | 2-bromo-6-trifluoromethylthio-4-(1,2,2,2-tetrafluoro-1-trifluoromethyl-ethyl)-phenyl |
| 9-221 | H | —L$_2$—D$_2$ | — | — | —CH2CH2— | CONH2 | H | 0 | 2,2,2-trichloroethyl | 2-bromo-6-trifluoromethylsulfinyl-4-(1,2,2,2-tetrafluoro-1-trifluoromethyl-ethyl)-phenyl |
| 9-222 | H | —L$_2$—D$_2$ | — | — | —CH2CH2— | CONH2 | H | 0 | 2,2,2-trichloroethyl | 2-bromo-6-trifluoromethylsulfonyl-4-(1,2,2,2-tetrafluoro-1-trifluoromethyl-ethyl)-phenyl |
| 9-223 | H | —L$_2$—D$_2$ | — | — | —CH2CH2— | CONH2 | H | 0 | 2,2,2-trichloroethyl | 2-bromo-6-pentafluoroethl-4-(1,2,2,2-tetrafluoro-1-trifluoromethyl-ethyl)-phenyl |

TABLE 9-continued

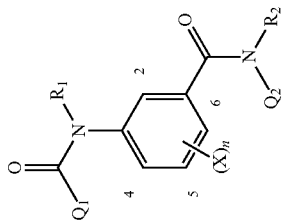

| compound number | R1 | R2 | L1 | D1 | L2 | D2 | X | n | Q3 | Q2 |
|---|---|---|---|---|---|---|---|---|---|---|
| 9-224 | H | —L2—D2 | — | — | —CH2CH2— | CONH2 | H | 0 | 2,2,2-trichloroethyl | 2-iodo-6-pentafluoroethyl-4-(1,2,2,2-tetrafluoro-1-trifluoromethyl-ethyl)-phenyl |
| 9-225 | H | —L2—D2 | — | — | —CH2CH2— | CONH2 | H | 0 | 2,2,2-trichloroethyl | 2-chloro-6-methyl-4-(1,2,2,3,3,3-hexafluoro-1-trifluoromethyl-propyl)-phenyl |
| 9-226 | H | —L2—D2 | — | — | —CH2CH2CH2— | CONH2 | H | 0 | 2,2,2-trichloroethyl | 2-bromo-6-methyl-4-(1,2,2,3,3,3-hexafluoro-1-trifluoromethyl-propyl)-phenyl |
| 9-227 | H | —L2—D2 | — | — | —CH2CH2— | CONH2 | H | 0 | 2,2,2-trichloroethyl | 2-iodo-6-methyl-4-(1,2,2,3,3,3-hexafluoro-1-trifluoromethyl-propyl)-phenyl |
| 9-228 | H | —L2—D2 | — | — | —CH2CH2— | CONH2 | H | 0 | 2,2,2-trichloroethyl | 2-bromo-6-ethyl-4-(1,2,2,3,3,3-hexafluoro-1-trifluoromethyl-propyl)-phenyl |
| 9-229 | H | —L2—D2 | — | — | —CH2CH2— | CONH2 | H | 0 | 2,2,2-trichloroethyl | 2-iodo-6-ethyl-4-(1,2,2,3,3,3-hexafluoro-1-trifluoromethyl-propyl)-phenyl |
| 9-230 | H | —L2—D2 | — | — | —CH2CH2— | CONH2 | H | 0 | 2,2,2-trichloroethyl | 2,6-dichloro-4-(1,2,2,3,3,3-hexafluoro-1-trifluoromethyl-propyl)-phenyl |
| 9-231 | H | —L2—D2 | — | — | —CH2CH2— | CONH2 | H | 0 | 2,2,2-trichloroethyl | 2,6-dibromo-4-(1,2,2,3,3,3-hexafluoro-1-trifluoromethyl-propyl)-phenyl |
| 9-232 | H | —L2—D2 | — | — | —CH2CH2— | CONH2 | H | 0 | 2,2,2-trichloroethyl | 2,6-diiodo-4-(1,2,2,3,3,3-hexafluoro-1-trifluoromethyl-propyl)-phenyl |
| 9-233 | H | —L2—D2 | — | — | —CH2— | CONH2 | H | 0 | 2,2,2-trichloroethyl | 2,6-ditrifluoromethyl-4-(1,2,2,3,3,3-hexafluoro-1-trifluoromethyl-propyl)-phenyl |
| 9-234 | H | —L2—D2 | — | — | —CH2CH2— | CONH2 | H | 0 | 2,2,2-trichloroethyl | 2-bromo-6-trifluoromethyl-4-(1,2,2,3,3,3-hexafluoro-1-trifluoromethyl-propyl)-phenyl |

TABLE 9-continued

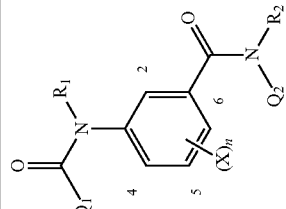

| compound number | R1 | R2 | L1 | D1 | L2 | D2 | X | n | Q3 | Q2 |
|---|---|---|---|---|---|---|---|---|---|---|
| 9-235 | H | —L2—D2 | — | — | —CH2CH2— | CONH2 | H | 0 | 2,2,2-trichloroethyl | 2-iodo-6-trifluoromethyl-4-(1,2,3,3,3-hexafluoro-1-trifluoromethyl-propyl)-phenyl |
| 9-236 | H | —L2—D2 | — | — | —CH2CH2— | CONH2 | H | 0 | 2,2,2-trichloroethyl | 2-bromo-6-trifluoromethoxy-4-(1,2,2,3,3,3-hexafluoro-1-trifluoromethyl-propyl)-phenyl |
| 9-237 | H | —L2—D2 | — | — | —CH2CH2— | CONH2 | H | 0 | 2,2,2-trichloroethyl | 2-bromo-6-iodo-4-(1,2,2,3,3,3-hexafluoro-1-trifluoromethyl-propyl)-phenyl |
| 9-238 | H | —L2—D2 | — | — | —CH2CH2— | CONH2 | H | 0 | 2,2,2-trichloroethyl | 2-bromo-6-trifluoromethylthio-4-(1,2,3,3,3-hexafluoro-1-trifluoromethyl-propyl)-phenyl |
| 9-239 | H | —L2—D2 | — | — | —CH2CH(CH3) | CONH2 | H | 0 | 2,2,2-trichloroethyl | 2-bromo-6-trifluoromethylsulfinyl-4-(1,2,2,3,3,3-hexafluoro-1-trifluoromethyl-propyl)-phenyl |
| 9-240 | H | —L2—D2 | — | — | —CH2CH2— | CONH2 | H | 0 | 2,2,2-trichloroethyl | 2-bromo-6-trifluoromethylsulfonyl-4-(1,2,2,3,3,3-hexafluoro-1-trifluoromethyl-propyl)-phenyl |
| 9-241 | H | —L2—D2 | — | — | —CH2CH2— | CONH2 | H | 0 | 2,2,2-trichloroethyl | 2-bromo-6-pentafluoroethyl-4-(1,2,2,3,3,3-hexafluoro-1-trifluoromethyl-propyl)-phenyl |
| 9-242 | H | —L2—D2 | — | — | —CH2CH2— | CONH2 | H | 0 | 2,2,2-trichloroethyl | 2-iodo-6-pentafluoroethyl-4-(1,2,2,3,3,3-hexafluoro-1-trifluoromethyl-propyl)-phenyl |
| 9-243 | H | —L2—D2 | — | — | —CH2CH2— | CONH2 | H | 0 | i-propyl | 2,6-dibromo-4-(1,2,2,2-tetrafluoro-1-trifluoromethyl-ethyl)-phenyl |
| 9-244 | H | —L2—D2 | — | — | —CH2CH2— | CONH2 | H | 0 | 3,3,3-trifluoro-n-propyl | 2,6-dibromo-4-(1,2,2,2-tetrafluoro-1-trifluoromethyl-ethyl)-phenyl |
| 9-245 | H | —L2—D2 | — | — | —CH2CH2— | CONH2 | H | 0 | i-propyl | 2,6-diiodo-4-(1,2,2,2-tetrafluoro-1-trifluoromethyl-ethyl)-phenyl |
| 9-246 | H | —L2—D2 | — | — | —CH2CH2— | CONH2 | H | 0 | 3,3,3-trifluoro-n-propyl | 2,6-diiodo-4-(1,2,2,2-tetrafluoro-1-trifluoromethyl-ethyl)-phenyl |
| 9-247 | H | —L2—D2 | — | — | —CH2CH2— | CONH2 | H | 0 | i-propyl | 2-bromo-6-trifluoromethyl-4-(1,2,2,2-tetrafluoro-1-trifluoromethyl-ethyl)-phenyl |

TABLE 9-continued

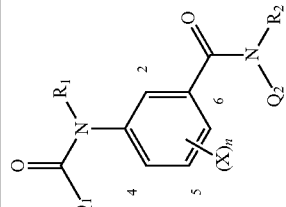

| compound number | R1 | R2 | L1 | D1 | L2 | D2 | X | n | Q3 | Q2 |
|---|---|---|---|---|---|---|---|---|---|---|
| 9-248 | H | —L2—D2 | — | — | —CH2CH2— | CONH2 | H | 0 | 3,3,3-trifluoro-n-propyl | 2-bromo-6-trifluoromethyl-4-(1,2,2,2-tetrafluoro-1-trifluoromethyl-ethyl)-phenyl |
| 9-249 | H | —L2—D2 | — | — | —CH2CH2— | CONH2 | H | 0 | i-propyl | 2-iodo-6-trifluoromethyl-4-(1,2,2,2-tetrafluoro-1-trifluoromethyl-ethyl)-phenyl |
| 9-250 | H | —L2—D2 | — | — | —CH2CH2— | CONH2 | H | 0 | 3,3,3-trifluoro-n-propyl | 2-iodo-6-trifluoromethyl-4-(1,2,2,2-tetrafluoro-1-trifluoromethyl-ethyl)-phenyl |
| 9-251 | H | —L2—D2 | — | — | —CH2CH2— | CONH2 | H | 0 | i-propyl | 2,6-dibromo-4-(1,2,3,3,3-hexafluoro-1-trifluoromethyl-propyl)-phenyl |
| 9-252 | H | —L2—D2 | — | — | —CH2CH2— | CONH2 | H | 0 | 3,3,3-trifluoro-n-propyl | 2,6-dibromo-4-(1,2,3,3,3-hexafluoro-1-trifluoromethyl-propyl)-phenyl |
| 9-253 | H | —L2—D2 | — | — | —CH2CH2— | CONH2 | H | 0 | i-propyl | 2,6-diiodo-4-(1,2,3,3,3-hexafluoro-1-trifluoromethyl-propyl)-phenyl |
| 9-254 | H | —L2—D2 | — | — | —CH2CH2— | CONH2 | H | 0 | 3,3,3-trifluoro-n-propyl | 2,6-diiodo-4-(1,2,3,3,3-hexafluoro-1-trifluoromethyl-propyl)-phenyl |
| 9-255 | H | —L2—D2 | — | — | —CH2CH2— | CONH2 | H | 0 | i-propyl | 2-bromo-6-trifluoromethyl-4-(1,2,3,3,3-hexafluoro-1-trifluoromethyl-propyl)-phenyl |
| 9-256 | H | —L2—D2 | — | — | —CH2CH2— | CONH2 | H | 0 | 3,3,3-trifluoro-n-propyl | 2-bromo-6-trifluoromethyl-4-(1,2,3,3,3-hexafluoro-1-trifluoromethyl-propyl)-phenyl |
| 9-257 | H | —L2—D2 | — | — | —CH2CH2— | CONH2 | H | 0 | i-propyl | 2-iodo-6-trifluoromethyl-4-(1,2,3,3,3-hexafluoro-1-trifluoromethyl-propyl)-phenyl |
| 9-258 | H | —L2—D2 | — | — | —CH2CH2— | CONH2 | H | 0 | 3,3,3-trifluoro-n-propyl | 2-iodo-6-trifluoromethyl-4-(1,2,3,3,3-hexafluoro-1-trifluoromethyl-propyl)-phenyl |
| 9-259 | H | —L2—D2 | — | — | —CH2CH2— | CONH2 | 2-F | 1 | 2,2,2-trichloroethyl | 2,6-dibromo-4-pentafluoroethyl-phenyl |
| 9-260 | H | —L2—D2 | — | — | —CH2CH2— | CONH2 | 2-F | 1 | 3,3,3-trifluoro-n-propyl | 2,6-diiodo-4-pentafluoroethyl-phenyl |

TABLE 9-continued

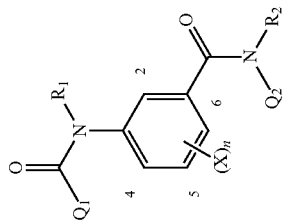

| compound number | R1 | R2 | L1 | D1 | L2 | D2 | X | n | Q3 | Q2 |
|---|---|---|---|---|---|---|---|---|---|---|
| 9-261 | H | —L2—D2 | — | — | —CH2CH2— | CONH2 | 2-F | 1 | 2,2,2-trichloroethyl | 2-bromo-6-trifluoromethyl-4-pentafluoroethyl-phenyl |
| 9-262 | H | —L2—D2 | — | — | —CH2CH2— | CONH2 | 2-F | 1 | 2,2,2-trichloroethyl | 2-iodo-6-trifluoromethyl-4-pentafluoroethyl-phenyl |
| 9-263 | H | —L2—D2 | — | — | —CH2CH2— | CONH2 | 2-F | 1 | 2,2,2-trichloroethyl | 2-chloro-6-methyl-4-(1,2,2,2-tetrafluoro-1-trifluoromethyl-ethyl)-phenyl |
| 9-264 | H | —L2—D2 | — | — | —CH2CH2— | CONH2 | 2-F | 1 | 2,2,2-trichloroethyl | 2-bromo-6-methyl-4-(1,2,2,2-tetrafluoro-1-trifluoromethyl-ethyl)-phenyl |
| 9-265 | H | —L2—D2 | — | — | —CH2CH2— | CONH2 | 2-F | 1 | 2,2,2-trichloroethyl | 2-iodo-6-methyl-4-(1,2,2,2-tetrafluoro-1-trifluoromethyl-ethyl)-phenyl |
| 9-266 | H | —L2—D2 | — | — | —CH2CH2— | CONH2 | 2-F | 1 | 2,2,2-trichloroethyl | 2-bromo-6-ethyl-4-(1,2,2,2-tetrafluoro-1-trifluoromethyl-ethyl)-phenyl |
| 9-267 | H | —L2—D2 | — | — | —CH2CH2— | CONH2 | 2-F | 1 | 2,2,2-trichloroethyl | 2-iodo-6-ethyl-4-(1,2,2,2-tetrafluoro-1-trifluoromethyl-ethyl)-phenyl |
| 9-268 | H | —L2—D2 | — | — | —CH2CH2— | CONH2 | 2-F | 1 | 2,2,2-trichloroethyl | 2,6-dichloro-4-(1,2,2,2-tetrafluoro-1-trifluoromethyl-ethyl)-phenyl |
| 9-269 | H | —L2—D2 | — | — | —CH2CH2— | CONH2 | 2-F | 1 | 2,2,2-trichloroethyl | 2,6-dibromo-4-(1,2,2,2-tetrafluoro-1-trifluoromethyl-ethyl)-phenyl |
| 9-270 | H | —L2—D2 | — | — | —CH2CH2— | CONH2 | 2-F | 1 | 2,2,2-trichloroethyl | 2,6-diiodo-4-(1,2,2,2-tetrafluoro-1-trifluoromethyl-ethyl)-phenyl |
| 9-271 | H | —L2—D2 | — | — | —CH2CH2— | CONH2 | 2-F | 1 | 2,2,2-trichloroethyl | 2,6-ditrifluoromethyl-4-(1,2,2,2-tetrafluoro-1-trifluoromethyl-ethyl)-phenyl |
| 9-272 | H | —L2—D2 | — | — | —CH2CH2— | CONH2 | 2-F | 1 | 2,2,2-trichloroethyl | 2-bromo-6-trifluoromethyl-4-(1,2,2,2-tetrafluoro-1-trifluoromethyl-ethyl)-phenyl |
| 9-273 | H | —L2—D2 | — | — | —CH2CH2— | CONH2 | 2-F | 1 | 2,2,2-trichloroethyl | 2-iodo-6-trifluoromethyl-4-(1,2,2,2-tetrafluoro-1-trifluoromethyl-ethyl)-phenyl |

TABLE 9-continued

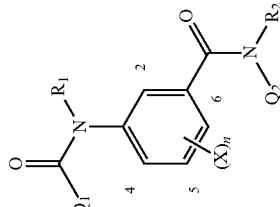

| compound number | R<sub>1</sub> | R<sub>2</sub> | L1 | D1 | L2 | D2 | X | n | Q<sub>3</sub> | Q<sub>2</sub> |
|---|---|---|---|---|---|---|---|---|---|---|
| 9-274 | H | —L$_2$—D$_2$ | — | — | —CH2CH2— | CONH2 | 2-F | 1 | 2,2,2-trichloroethyl | 2-bromo-6-trifluoromethoxy-4-(1,2,2,2-tetrafluoro-1-trifluoromethyl-ethyl)-phenyl |
| 9-275 | H | —L$_2$—D$_2$ | — | — | —CH2CH2— | CONH2 | 2-F | 1 | 2,2,2-trichloroethyl | 2-bromo-6-iodo-4-(1,2,2,2-tetrafluoro-1-trifluoromethyl-ethyl)-phenyl |
| 9-276 | H | —L$_2$—D$_2$ | — | — | —CH2CH2— | CONH2 | 2-F | 1 | 2,2,2-trichloroethyl | 2-bromo-6-trifluoromethylthio-4-(1,2,2,2-tetrafluoro-1-trifluoromethyl-ethyl)-phenyl |
| 9-277 | H | —L$_2$—D$_2$ | — | — | —CH2CH2— | CONH2 | 2-F | 1 | 2,2,2-trichloroethyl | 2-bromo-6-trifluoromethylsulfinyl-4-(1,2,2,2-tetrafluoro-1-trifluoromethyl-ethyl)-phenyl |
| 9-278 | H | —L$_2$—D$_2$ | — | — | —CH2CH2— | CONH2 | 2-F | 1 | 2,2,2-trichloroethyl | 2-bromo-6-trifluoromethylsulfonyl-4-(1,2,2,2-tetrafluoro-1-trifluoromethyl-ethyl)-phenyl |
| 9-279 | H | —L$_2$—D$_2$ | — | — | —CH2CH2— | CONH2 | 2-F | 1 | 2,2,2-trichloroethyl | 2-bromo-6-pentafluoroethyl-4-(1,2,2,2-tetrafluoro-1-trifluoromethyl-ethyl)-phenyl |
| 9-280 | H | —L$_2$—D$_2$ | — | — | —CH2CH2— | CONH2 | 2-F | 1 | 2,2,2-trichloroethyl | 2-iodo-6-pentafluoroethyl-4-(1,2,2,2-tetrafluoro-1-trifluoromethyl-ethyl)-phenyl |
| 9-281 | H | —L$_2$—D$_2$ | — | — | —CH2CH2— | CONMe2 | 2-F | 1 | 2,2,2-trichloroethyl | 2-chloro-6-methyl-4-(1,2,2,3,3,3-hexafluoro-1-trifluoromethyl-propyl)-phenyl |
| 9-282 | H | —L$_2$—D$_2$ | — | — | —CH2CH2— | CONH2 | 2-F | 1 | 2,2,2-trichloroethyl | 2-bromo-6-methyl-4-(1,2,2,3,3,3-hexafluoro-1-trifluoromethyl-propyl)-phenyl |
| 9-283 | H | —L$_2$—D$_2$ | — | — | —CH2CH2— | CONH2 | 2-F | 1 | 2,2,2-trichloroethyl | 2-iodo-6-methyl-4-(1,2,2,3,3,3-hexafluoro-1-trifluoromethyl-propyl)-phenyl |
| 9-284 | H | —L$_2$—D$_2$ | — | — | —CH2CH2— | CN | 2-F | 1 | 2,2,2-trichloroethyl | 2-bromo-6-ethyl-4-(1,2,2,3,3,3-hexafluoro-1-trifluoromethyl-propyl)-phenyl |

TABLE 9-continued

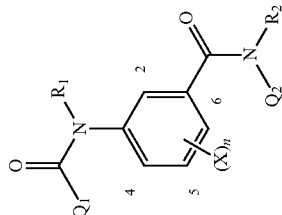

| compound number | R1 | R2 | L1 | D1 | L2 | D2 | X | n | Q3 | Q2 |
|---|---|---|---|---|---|---|---|---|---|---|
| 9-285 | H | —L2—D2 | — | — | —CH2CH2— | CONH2 | 2-F | 1 | 2,2,2-trichloroethyl | 2-iodo-6-ethyl-4-(1,2,2,3,3,3-hexafluoro-1-trifluoromethyl-propyl)-phenyl |
| 9-286 | H | —L2—D2 | — | — | —CH2CH2— | CONH2 | 2-F | 1 | 2,2,2-trichloroethyl | 2,6-dichloro-4-(1,2,2,3,3,3-hexafluoro-1-trifluoromethyl-propyl)-phenyl |
| 9-287 | H | —L2—D2 | — | — | —CH2CH2— | CONH2 | 2-F | 1 | 2,2,2-trichloroethyl | 2,6-dibromo-4-(1,2,2,3,3,3-hexafluoro-1-trifluoromethyl-propyl)-phenyl |
| 9-288 | H | —L2—D2 | — | — | —CH2CH2— | CONH2 | 2-F | 1 | 2,2,2-trichloroethyl | 2,6-diiodo-4-(1,2,2,3,3,3-hexafluoro-1-trifluoromethyl-propyl)-phenyl |
| 9-289 | H | —L2—D2 | — | — | —CH2CH2— | CONH2 | 2-F | 1 | 2,2,2-trichloroethyl | 2,6-ditrifluoromethyl-4-(1,2,2,3,3,3-hexafluoro-1-trifluoromethyl-propyl)-phenyl |
| 9-290 | H | —L2—D2 | — | — | —CH2CH2— | CONH2 | 2-F | 1 | 2,2,2-trichloroethyl | 2-bromo-6-trifluoromethyl-4-(1,2,2,3,3,3-hexafluoro-1-trifluoromethyl-propyl)-phenyl |
| 9-291 | H | —L2—D2 | — | — | —CH2CH2— | CONH2 | 2-F | 1 | 2,2,2-trichloroethyl | 2-iodo-6-trifluoromethyl-4-(1,2,2,3,3,3-hexafluoro-1-trifluoromethyl-propyl)-phenyl |
| 9-292 | H | —L2—D2 | — | — | —CH2CH2— | CONH2 | 2-F | 1 | 2,2,2-trichloroethyl | 2-bromo-6-trifluoromethoxy-4-(1,2,2,3,3,3-hexafluoro-1-trifluoromethyl-propyl)-phenyl |
| 9-293 | H | —L2—D2 | — | — | —CH2CH2— | CONH2 | 2-F | 1 | 2,2,2-trichloroethyl | 2-bromo-6-iodo-4-(1,2,2,3,3,3-hexafluoro-1-trifluoromethyl-propyl)-phenyl |
| 9-294 | H | —L2—D2 | — | — | —CH2CH2— | CONH2 | 2-F | 1 | 2,2,2-trichloroethyl | 2-bromo-6-trifluoromethylthio-4-(1,2,2,3,3,3-hexafluoro-1-trifluoromethyl-propyl)-phenyl |
| 9-295 | H | —L2—D2 | — | — | —CH2CH2— | CONH2 | 2-F | 1 | 2,2,2-trichloroethyl | 2-bromo-6-trifluoromethylsulfinyl-4-(1,2,2,3,3,3-hexafluoro-1-trifluoromethyl-propyl)-phenyl |

TABLE 9-continued

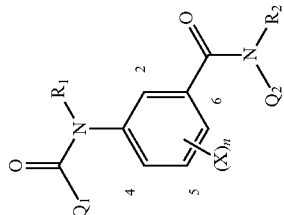

| compound number | $R_1$ | $R_2$ | L1 | D1 | L2 | D2 | X | n | $Q_3$ | $Q_2$ |
|---|---|---|---|---|---|---|---|---|---|---|
| 9-296 | H | —$L_2$—$D_2$ | — | — | —CH2CH2— | CONH2 | 2-F | 1 | 2,2,2-trichloroethyl | 2-bromo-6-trifluoromethylsulfonyl-4-(1,2,2,3,3,3-hexafluoro-1-trifluoromethyl-propyl)-phenyl |
| 9-297 | H | —$L_2$—$D_2$ | — | — | —CH2CH2— | CONH2 | 2-F | 1 | 2,2,2-trichloroethyl | 2-bromo-6-pentafluoroethyl-4-(1,2,2,3,3,3-hexafluoro-1-trifluoromethyl-propyl)-phenyl |
| 9-298 | H | —$L_2$—$D_2$ | — | — | —CH2CH2— | CONH2 | 2-F | 1 | 2,2,2-trichloroethyl | 2-iodo-6-pentafluoroethyl-4-(1,2,2,3,3,3-hexafluoro-1-trifluoromethyl-propyl)-phenyl |
| 9-299 | H | —$L_2$—$D_2$ | — | — | —CH2CH2— | CONH2 | 2-F | 1 | i-propyl | 2,6-dibromo-4-(1,2,2,2-tetrafluoro-1-trifluoromethyl-ethyl)-phenyl |
| 9-300 | H | —$L_2$—$D_2$ | — | — | —CH2CH2CH2— | CONH2 | 2-F | 1 | 3,3,3-trifluoro-n-propyl | 2,6-dibromo-4-(1,2,2,2-tetrafluoro-1-trifluoromethyl-ethyl)-phenyl |
| 9-301 | H | —$L_2$—$D_2$ | — | — | —CH2CH2— | CONH2 | 2-F | 1 | i-propyl | 2,6-diiodo-4-(1,2,2,2-tetrafluoro-1-trifluoromethyl-ethyl)-phenyl |
| 9-302 | H | —$L_2$—$D_2$ | — | — | —CH2CH2— | CONH2 | 2-F | 1 | 3,3,3-trifluoro-n-propyl | 2,6-diiodo-4-(1,2,2,2-tetrafluoro-1-trifluoromethyl-ethyl)-phenyl |
| 9-303 | H | —$L_2$—$D_2$ | — | — | —CH2CH2— | CONH2 | 2-F | 1 | 2,2,2-trichloroethyl | 2-bromo-6-trifluoromethyl-4-(1,2,2,2-tetrafluoro-1-trifluoromethyl-ethyl)-phenyl |
| 9-304 | H | —$L_2$—$D_2$ | — | — | —CH2CH2— | CONH2 | 2-F | 1 | 3,3,3-trifluoro-n-propyl | 2-bromo-6-trifluoromethyl-4-(1,2,2,2-tetrafluoro-1-trifluoromethyl-ethyl)-phenyl |
| 9-305 | H | —$L_2$—$D_2$ | — | — | —CH2CH2— | CONH2 | 2-F | 1 | i-propyl | 2-iodo-6-trifluoromethyl-4-(1,2,2,2-tetrafluoro-1-trifluoromethyl-ethyl)-phenyl |
| 9-306 | H | —$L_2$—$D_2$ | — | — | —CH2CH2— | CONH2 | 2-F | 1 | 3,3,3-trifluoro-n-propyl | 2-iodo-6-trifluoromethyl-4-(1,2,2,2-tetrafluoro-1-trifluoromethyl-ethyl)-phenyl |
| 9-307 | H | —$L_2$—$D_2$ | — | — | —CH2CH2— | CONH2 | 2-F | 1 | i-propyl | 2,6-dibromo-4-(1,2,2,3,3,3-hexafluoro-1-trifluoromethyl-propyl)-phenyl |

TABLE 9-continued

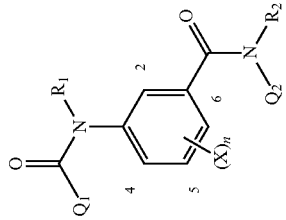

| compound number | R1 | R2 | L1 | D1 | L2 | D2 | X | n | Q3 | Q2 |
|---|---|---|---|---|---|---|---|---|---|---|
| 9-308 | H | —L2—D2 | — | — | —CH2CH2— | CONH2 | 2-F | 1 | 3,3,3-trifluoro-n-propyl | 2,6-dibromo-4-(1,2,2,3,3,3-hexafluoro-1-trifluoromethyl-propyl)-phenyl |
| 9-309 | H | —L2—D2 | — | — | —CH2CH2— | CONH2 | 2-F | 1 | i-propyl | 2,6-diiodo-4-(1,2,2,3,3,3-hexafluoro-1-trifluoromethyl-propyl)-phenyl |
| 9-310 | H | —L2—D2 | — | — | —CH2CH2— | CONH2 | 2-F | 1 | 3,3,3-trifluoro-n-propyl | 2,6-diiodo-4-(1,2,2,3,3,3-hexafluoro-1-trifluoromethyl-propyl)-phenyl |
| 9-311 | H | —L2—D2 | — | — | —CH2CH2— | CONH2 | 2-F | 1 | i-propyl | 2-bromo-6-trifluoromethyl-4-(1,2,2,3,3,3-hexafluoro-1-trifluoromethyl-propyl)-phenyl |
| 9-312 | H | —L2—D2 | — | — | —CH2CH2— | CONH2 | 2-F | 1 | 3,3,3-trifluoro-n-propyl | 2-bromo-6-trifluoromethyl-4-(1,2,2,3,3,3-hexafluoro-1-trifluoromethyl-propyl)-phenyl |
| 9-313 | H | —L2—D2 | — | — | —CH2CH2— | CONH2 | 2-F | 1 | i-propyl | 2-iodo-6-trifluoromethyl-4-(1,2,2,3,3,3-hexafluoro-1-trifluoromethyl-propyl)-phenyl |
| 9-314 | H | —L2—D2 | — | — | —CH2CH2— | CONH2 | 2-F | 1 | 3,3,3-trifluoro-n-propyl | 2-iodo-6-trifluoromethyl-4-(1,2,2,3,3,3-hexafluoro-1-trifluoromethyl-propyl)-phenyl |
| 9-315 | H | —L2—D2 | — | — | —CH2CH2— | CONH2 | 2-F | 1 | phenyl | 2,6-dimethyl-4-(1,2,2,3,3,3-hexafluoro-1-trifluoromethyl-propyl)-phenyl |
| 9-316 | H | —L2—D2 | — | — | —CH2CH2— | CONH2 | 2-F | 1 | 4-cyanophenyl | 2,6-dimethyl-4-(1,2,2,3,3,3-hexafluoro-1-trifluoromethyl-propyl)-phenyl |
| 9-317 | H | —L2—D2 | — | — | —CH2CH2— | CONH2 | 2-F | 1 | 3-cyanophenyl | 2,6-dimethyl-4-(1,2,2,3,3,3-hexafluoro-1-trifluoromethyl-propyl)-phenyl |
| 9-318 | H | —L2—D2 | — | — | —CH2CH2— | CONH2 | 4-F | 1 | 2,2,2-trichloroethyl | 2,6-dibromo-4-(1,2,2,2-tetrafluoro-1-trifluoromethyl-ethyl)-phenyl |
| 9-319 | H | —L2—D2 | — | — | —CH2CH2— | CONH2 | 4-F | 1 | 2,2,2-trichloroethyl | 2-bromo-6-trifluoromethyl-4-(1,2,2,2-tetrafluoro-1-trifluoromethyl-ethyl)-phenyl |

TABLE 9-continued

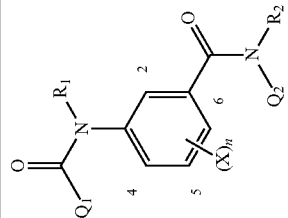

| compound number | R1 | R2 | L1 | D1 | L2 | D2 | X | n | Q3 | Q2 |
|---|---|---|---|---|---|---|---|---|---|---|
| 9-320 | H | —L2—D2 | — | — | —CH2CH2— | CONH2 | 4-F | 1 | 2,2,2-trichloroethyl | 2-iodo-6-trifluoromethyl-4-(1,2,2,2-tetrafluoro-1-trifluoromethyl-ethyl)-phenyl |
| 9-321 | H | —L2—D2 | — | — | —CH2CH2— | CONH2 | 4-F | 1 | 2,2,2-trichloroethyl | 2-bromo-6-trifluoromethyl-4-(1,2,2,3,3,3-hexafluoro-1-trifluoromethyl-ethyl)-phenyl |
| 9-322 | H | —L2—D2 | — | — | —CH2CH2— | CONH2 | 4-F | 1 | 2,2,2-trichloroethyl | 2-iodo-6-trifluoromethyl-4-(1,2,2,3,3,3-hexafluoro-1-trifluoromethyl-propyl)-phenyl |
| 9-323 | H | —L2—D2 | — | — | —CH2CH2— | CONH2 | 4-CN | 1 | 2,2,2-trichloroethyl | 2,6-dibromo-4-(1,2,2,2-tetrafluoro-1-trifluoromethyl-ethyl)-phenyl |
| 9-324 | H | —L2—D2 | — | — | —CH2CH2— | CONH2 | 4-CN | 1 | 2,2,2-trichloroethyl | 2-bromo-6-trifluoromethyl-4-(1,2,2,2-tetrafluoro-1-trifluoromethyl-ethyl)-phenyl |
| 9-325 | H | —L2—D2 | — | — | —CH2CH2— | CONH2 | 4-CN | 1 | 2,2,2-trichloroethyl | 2-iodo-6-trifluoromethyl-4-(1,2,2,2-tetrafluoro-1-trifluoromethyl-ethyl)-phenyl |
| 9-326 | H | —L2—D2 | — | — | —CH2CH2— | CONH2 | 4-CN | 1 | 2,2,2-trichloroethyl | 2-bromo-6-trifluoromethyl-4-(1,2,2,3,3,3-hexafluoro-1-trifluoromethyl-propyl)-phenyl |
| 9-327 | H | —L2—D2 | — | — | —CH2CH2— | CONH2 | 4-CN | 1 | 2,2,2-trichloroethyl | 2-iodo-6-trifluoromethyl-4-(1,2,2,3,3,3-hexafluoro-1-trifluoromethyl-propyl)-phenyl |
| 9-328 | H | —L2—D2 | — | — | —CH2CH2— | CONH2 | 2-NO2 | 1 | 2,2,2-trichloroethyl | 2,6-dibromo-4-(1,2,2,2-tetrafluoro-1-trifluoromethyl-ethyl)-phenyl |
| 9-329 | H | —L2—D2 | — | — | —CH2CH2— | CONH2 | 2-NO2 | 1 | 2,2,2-trichloroethyl | 2-bromo-6-trifluoromethyl-4-(1,2,2,2-tetrafluoro-1-trifluoromethyl-ethyl)-phenyl |
| 9-330 | H | —L2—D2 | — | — | —CH2CH2— | CONH2 | 2-NO2 | 1 | 2,2,2-trichloroethyl | 2-iodo-6-trifluoromethyl-4-(1,2,2,2-tetrafluoro-1-trifluoromethyl-ethyl)-phenyl |

TABLE 9-continued

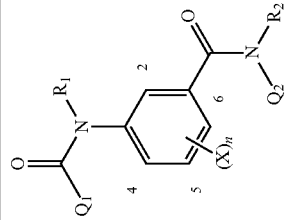

| compound number | R1 | R2 | L1 | D1 | L2 | D2 | X | n | Q3 | Q2 |
|---|---|---|---|---|---|---|---|---|---|---|
| 9-331 | H | —L2—D2 | — | — | —CH2CH2— | CONH2 | 2-NO2 | 1 | 2,2,2-trichloroethyl | 2-bromo-6-trifluoromethyl-4-(1,2,2,3,3,3-hexafluoro-1-trifluoromethyl-propyl)-phenyl |
| 9-332 | H | —L2—D2 | — | — | —CH2CH2— | CONH2 | 2-NO2 | 1 | 2,2,2-trichloroethyl | 2-iodo-6-trifluoromethyl-4-(1,2,2,3,3,3-hexafluoro-1-trifluoromethyl-propyl)-phenyl |
| 9-333 | —L1—D1 | —L2—D2 | —CH2CH2— | CONH2 | —CH2CH2— | CONH2 | H | 0 | methyl | 2,6-dimethyl-4-(1,2,2,2-tetrafluoro-1-trifluoromethyl-ethyl)-phenyl |
| 9-334 | —L1—D1 | —L2—D2 | —CH2CH2— | CONH2 | —CH2CH2— | CONH2 | H | 0 | ethyl | 2,6-dimethyl-4-(1,2,2,2-tetrafluoro-1-trifluoromethyl-ethyl)-phenyl |
| 9-335 | —L1—D1 | —L2—D2 | —CH2CH2— | CONH2 | —CH2CH2— | SO2Me | H | 0 | i-propyl | 2,6-dimethyl-4-(1,2,2,2-tetrafluoro-1-trifluoromethyl-ethyl)-phenyl |
| 9-336 | —L1—D1 | —L2—D2 | —CH2CH2— | CONH2 | —CH2CH2— | CONH2 | H | 0 | n-butyl | 2,6-dimethyl-4-(1,2,2,2-tetrafluoro-1-trifluoromethyl-ethyl)-phenyl |
| 9-337 | —L1—D1 | —L2—D2 | —CH2CH2— | SO2Me | —CH2CH2— | CONH2 | H | 0 | i-butyl | 2,6-dimethyl-4-(1,2,2,2-tetrafluoro-1-trifluoromethyl-ethyl)-phenyl |
| 9-338 | —L1—D1 | —L2—D2 | —CH2CH2— | CONH2 | —CH2CH2— | CONH2 | H | 0 | s-butyl | 2,6-dimethyl-4-(1,2,2,2-tetrafluoro-1-trifluoromethyl-ethyl)-phenyl |
| 9-339 | —L1—D1 | —L2—D2 | —CH2CH2— | CONH2 | —CH2CH2— | CONH2 | H | 0 | t-butyl | 2,6-dimethyl-4-(1,2,2,2-tetrafluoro-1-trifluoromethyl-ethyl)-phenyl |
| 9-340 | —L1—D1 | —L2—D2 | —CH2CH2— | CONH2 | —CH2CH2— | SOMe | H | 0 | vinyl | 2,6-dimethyl-4-(1,2,2,2-tetrafluoro-1-trifluoromethyl-ethyl)-phenyl |
| 9-341 | —L1—D1 | —L2—D2 | —CH2CH2— | CONH2 | —CH2CH2— | CONH2 | H | 0 | allyl | 2,6-dimethyl-4-(1,2,2,2-tetrafluoro-1-trifluoromethyl-ethyl)-phenyl |
| 9-342 | —L1—D1 | —L2—D2 | —CH2CH2— | SOMe | —CH2CH2— | CONH2 | H | 0 | benzyl | 2,6-dimethyl-4-(1,2,2,2-tetrafluoro-1-trifluoromethyl-ethyl)-phenyl |
| 9-343 | —L1—D1 | —L2—D2 | —CH2CH2— | OH | —CH2CH2— | OH | H | 0 | chloromethyl | 2,6-dimethyl-4-(1,2,2,2-tetrafluoro-1-trifluoromethyl-ethyl)-phenyl |
| 9-344 | —L1—D1 | —L2—D2 | —CH2CH2— | CONH2 | —CH2CH2— | CONH2 | H | 0 | 2,2,2-trichloroethyl | 2,6-dimethyl-4-(1,2,2,2-tetrafluoro-1-trifluoromethyl-ethyl)-phenyl |
| 9-345 | —L1—D1 | —L2—D2 | —CH2CH2— | CONH2 | —CH2CH2— | CONH2 | H | 0 | 3,3,3-trifluoro-n-propyl | 2,6-dimethyl-4-(1,2,2,2-tetrafluoro-1-trifluoromethyl-ethyl)-phenyl |
| 9-346 | —L1—D1 | —L2—D2 | —CH2CH2— | CO2Me | —CH2CH2— | CO2Me | H | 0 | 1,3-difluoro-2-propyl | 2,6-dimethyl-4-(1,2,2,2-tetrafluoro-1-trifluoromethyl-ethyl)-phenyl |

TABLE 9-continued

| compound number | R₁ | R₂ | L1 | D1 | L2 | D2 | X | n | Q₃ | Q₂ |
|---|---|---|---|---|---|---|---|---|---|---|
| 9-347 | —L₁—D₁ | —L₂—D₂ | —CH2CH2— | CN | —CH2CH2— | CN | H | 0 | cyclohexyl | 2,6-dimethyl-4-(1,2,2,2-tetrafluoro-1-trifluoromethyl-ethyl)-phenyl |
| 9-348 | —L₁—D₁ | —L₂—D₂ | —CH2CH2(CH3)— | CONH2 | —CH2CH(CH3)— | CONH2 | 2-F | 1 | methyl | 2,6-dimethyl-4-(1,2,2,2-tetrafluoro-1-trifluoromethyl-ethyl)-phenyl |
| 9-349 | —L₁—D₁ | —L₂—D₂ | —CH2CH2— | CONH2 | —CH2CH2— | CONH2 | 2-F | 1 | ethyl | 2,6-dimethyl-4-(1,2,2,2-tetrafluoro-1-trifluoromethyl-ethyl)-phenyl |
| 9-350 | —L₁—D₁ | —L₂—D₂ | —CH2CH2— | CONH2 | —CH2CH2— | CONH2 | 2-F | 1 | i-propyl | 2,6-dimethyl-4-(1,2,2,2-tetrafluoro-1-trifluoromethyl-ethyl)-phenyl |
| 9-351 | —L₁—D₁ | —L₂—D₂ | —CH2CH2— | NH2 | —CH2CH2— | CONH2 | 2-F | 1 | n-butyl | 2,6-dimethyl-4-(1,2,2,2-tetrafluoro-1-trifluoromethyl-ethyl)-phenyl |
| 9-352 | —L₁—D₁ | —L₂—D₂ | —CH2CH2— | CONH2 | —CH2CH2— | CONH2 | 2-F | 1 | i-butyl | 2,6-dimethyl-4-(1,2,2,2-tetrafluoro-1-trifluoromethyl-ethyl)-phenyl |
| 9-353 | —L₁—D₁ | —L₂—D₂ | —CH2CH2— | CONH2 | —CH2CH2— | CONH2 | 2-F | 1 | s-butyl | 2,6-dimethyl-4-(1,2,2,2-tetrafluoro-1-trifluoromethyl-ethyl)-phenyl |
| 9-354 | —L₁—D₁ | —L₂—D₂ | —CH2CH2— | CONH2 | —CH2CH2— | CONH2 | 2-F | 1 | t-butyl | 2,6-dimethyl-4-(1,2,2,2-tetrafluoro-1-trifluoromethyl-ethyl)-phenyl |
| 9-355 | —L₁—D₁ | —L₂—D₂ | —CH2— | CN | —CH2CH2— | CONH2 | 2-F | 1 | vinyl | 2,6-dimethyl-4-(1,2,2,2-tetrafluoro-1-trifluoromethyl-ethyl)-phenyl |
| 9-356 | —L₁—D₁ | —L₂—D₂ | —CH2CH2— | CONH2 | —CH2CH2— | CONH2 | 2-F | 1 | allyl | 2,6-dimethyl-4-(1,2,2,2-tetrafluoro-1-trifluoromethyl-ethyl)-phenyl |
| 9-357 | —L₁—D₁ | —L₂—D₂ | —CH2CH2— | CO2H | —CH2CH2— | CO2H | 2-F | 1 | benzyl | 2,6-dimethyl-4-(1,2,2,2-tetrafluoro-1-trifluoromethyl-ethyl)-phenyl |
| 9-358 | —L₁—D₁ | —L₂—D₂ | —CH2CH2— | CONH2 | —CH2CH2— | CONH2 | 2-F | 1 | chloromethyl | 2,6-dimethyl-4-(1,2,2,2-tetrafluoro-1-trifluoromethyl-ethyl)-phenyl |
| 9-359 | —L₁—D₁ | —L₂—D₂ | —CH2CH2— | CONH2 | —CH2CH2— | CONH2 | 2-F | 1 | 2,2,2-trichloroethyl | 2,6-dimethyl-4-(1,2,2,2-tetrafluoro-1-trifluoromethyl-ethyl)-phenyl |
| 9-360 | —L₁—D₁ | —L₂—D₂ | —CH2CH2— | CONH2 | —CH2CH2— | CONH2 | 2-F | 1 | 3,3,3-trifluoro-n-propyl | 2,6-dimethyl-4-(1,2,2,2-tetrafluoro-1-trifluoromethyl-ethyl)-phenyl |
| 9-361 | —L₁—D₁ | —L₂—D₂ | —CH2CH2— | CONH2 | —CH2CH2— | CONH2 | 2-F | 1 | 1,3-difluoro-2-propyl | 2,6-dimethyl-4-(1,2,2,2-tetrafluoro-1-trifluoromethyl-ethyl)-phenyl |
| 9-362 | —L₁—D₁ | —L₂—D₂ | —CH2CH2— | CONMe2 | —CH2CH2— | CONMe2 | 2-F | 1 | cyclohexyl | 2,6-dimethyl-4-(1,2,2,2-tetrafluoro-1-trifluoromethyl-ethyl)-phenyl |
| 9-363 | —L₁—D₁ | —L₂—D₂ | —CH2CH2— | CONH2 | —CH2CH2— | CONH2 | 4-F | 1 | i-propyl | 2,6-dimethyl-4-(1,2,2,2-tetrafluoro-1-trifluoromethyl-ethyl)-phenyl |
| 9-364 | —L₁—D₁ | —L₂—D₂ | —CH2CH2— | CONH2 | —CH2CH2— | CONH2 | 4-F | 1 | 2,2,2-trichloroethyl | 2,6-dimethyl-4-(1,2,2,2-tetrafluoro-1-trifluoromethyl-ethyl)-phenyl |

TABLE 9-continued

| compound number | R₁ | R₂ | L1 | D1 | L2 | D2 | X | n | Q₃ | Q₂ |
|---|---|---|---|---|---|---|---|---|---|---|
| 9-365 | —L₁—D₁ | —L₂—D₂ | —CH2CH2— | CONH2 | —CH2CH2— | CONH2 | 4-F | 1 | 3,3,3-trifluoro-n-propyl | 2,6-dimethyl-4-(1,2,2,2-tetrafluoro-1-trifluoromethyl-ethyl)-phenyl |
| 9-366 | —L₁—D₁ | —L₂—D₂ | —CH2CH2— | CONH2 | —CH2CH2— | CONH2 | 4-CN | 1 | i-propyl | 2,6-dimethyl-4-(1,2,2,2-tetrafluoro-1-trifluoromethyl-ethyl)-phenyl |
| 9-367 | —L₁—D₁ | —L₂—D₂ | —CH2CH2— | CONH2 | —CH2CH2— | CONH2 | 4-CN | 1 | 2,2,2-trichloroethyl | 2,6-dimethyl-4-(1,2,2,2-tetrafluoro-1-trifluoromethyl-ethyl)-phenyl |
| 9-368 | —L₁—D₁ | —L₂—D₂ | —CH2CH2— | CONH2 | —CH2CH2— | CONH2 | 4-CN | 1 | 3,3,3-trifluoro-n-propyl | 2,6-dimethyl-4-(1,2,2,2-tetrafluoro-1-trifluoromethyl-ethyl)-phenyl |
| 9-369 | —L₁—D₁ | —L₂—D₂ | —CH2CH2— | CONH2 | —CH2CH2— | CONH2 | H | 0 | 2,2,2-trichloroethyl | 2,6-dimethyl-4-(1,2,2,2-tetrafluoro-1-trifluoromethyl-ethyl)-phenyl |
| 9-370 | —L₁—D₁ | —L₂—D₂ | —CH2CH2— | CONH2 | —CH2CH2— | CONH2 | H | 0 | 3,3,3-trifluoro-n-propyl | 2,6-dibromo-4-pentafluoroethyl-phenyl |
| 9-371 | —L₁—D₁ | —L₂—D₂ | —CH2CH2— | CONH2 | —CH2CH2— | CONH2 | H | 0 | 2,2,2-trichloroethyl | 2,6-diiodo-4-pentafluoroethyl-phenyl |
| 9-372 | —L₁—D₁ | —L₂—D₂ | —CH2CH2— | CONH2 | —CH2CH2— | CONH2 | H | 0 | 2,2,2-trichloroethyl | 2-bromo-6-trifluoromethyl-4-pentafluoroethyl-phenyl |
| 9-373 | —L₁—D₁ | —L₂—D₂ | —CH2CH2— | CONH2 | —CH2CH2— | CONH2 | H | 0 | 2,2,2-trichloroethyl | 2-iodo-6-trifluoromethyl-4-pentafluoroethyl-phenyl |
| 9-374 | —L₁—D₁ | —L₂—D₂ | —CH2CH2— | CONH2 | —CH2CH2— | CONH2 | H | 0 | 2,2,2-trichloroethyl | 2-chloro-6-methyl-4-(1,2,2,2-tetrafluoro-1-trifluoromethyl-ethyl)-phenyl |
| 9-375 | —L₁—D₁ | —L₂—D₂ | —CH2CH2— | CONH2 | —CH2CH2— | CONH2 | H | 0 | 2,2,2-trichloroethyl | 2-bromo-6-methyl-4-(1,2,2,2-tetrafluoro-1-trifluoromethyl-ethyl)-phenyl |
| 9-376 | —L₁—D₁ | —L₂—D₂ | —CH2CH2— | SO2NH2 | —CH2CH2— | SO2NH2 | H | 0 | 2,2,2-trichloroethyl | 2-iodo-6-methyl-4-(1,2,2,2-tetrafluoro-1-trifluoromethyl-ethyl)-phenyl |
| 9-377 | —L₁—D₁ | —L₂—D₂ | —CH2CH2— | SO2Me | —CH2CH2— | SO2Me | H | 0 | 2,2,2-trichloroethyl | 2-bromo-6-ethyl-4-(1,2,2,2-tetrafluoro-1-trifluoromethyl-ethyl)-phenyl |
| 9-378 | —L₁—D₁ | —L₂—D₂ | —CH2CH2— | CONH2 | —CH2CH2— | CONH2 | H | 0 | 2,2,2-trichloroethyl | 2-iodo-6-ethyl-4-(1,2,2,2-tetrafluoro-1-trifluoromethyl-ethyl)-phenyl |

TABLE 9-continued

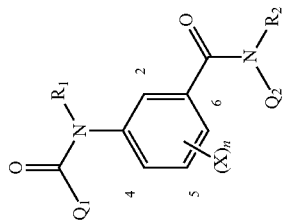

| compound number | R1 | R2 | L1 | D1 | L2 | D2 | X | n | Q3 | Q2 |
|---|---|---|---|---|---|---|---|---|---|---|
| 9-379 | —L1—D1 | —L2—D2 | —CH2CH2— | CONH2 | —CH2CH2— | CONH2 | H | 0 | 2,2,2-trichloroethyl | 2,6-dibromo-4-(1,2,2,2-tetrafluoro-1-trifluoromethyl-ethyl)-phenyl |
| 9-380 | —L1—D1 | —L2—D2 | —CH2CH2— | CONH2 | —CH2CH2— | CONH2 | H | 0 | 2,2,2-trichloroethyl | 2,6-diiodo-4-(1,2,2,2-tetrafluoro-1-trifluoromethyl-ethyl)-phenyl |
| 9-381 | —L1—D1 | —L2—D2 | —CH2CH2— | CONH2 | —CH2CH2— | CONH2 | H | 0 | 2,2,2-trichloroethyl | 2,6-ditrifluoromethyl-4-(1,2,2,2-tetrafluoro-1-trifluoromethyl-ethyl)-phenyl |
| 9-382 | —L1—D1 | —L2—D2 | —CH2CH2— | CONH2 | —CH2CH2— | CONH2 | H | 0 | 2,2,2-trichloroethyl | 2-bromo-6-trifluoromethyl-4-(1,2,2,2-tetrafluoro-1-trifluoromethyl-ethyl)-phenyl |
| 9-383 | —L1—D1 | —L2—D2 | —CH2CH2— | CONH2 | —CH2CH2— | CONH2 | H | 0 | 2,2,2-trichloroethyl | 2-iodo-6-trifluoromethyl-4-(1,2,2,2-tetrafluoro-1-trifluoromethyl-ethyl)-phenyl |
| 9-384 | —L1—D1 | —L2—D2 | —CH2CH2— | CONH2 | —CH2CH2— | CONH2 | H | 0 | 2,2,2-trichloroethyl | 2-bromo-6-trifluoromethoxy-4-(1,2,2,2-tetrafluoro-1-trifluoromethyl-ethyl)-phenyl |
| 9-385 | —L1—D1 | —L2—D2 | —CH2CH2— | CONH2 | —CH2CH2— | CONH2 | H | 0 | 2,2,2-trichloroethyl | 2-bromo-6-iodo-4-(1,2,2,2-tetrafluoro-1-trifluoromethyl-ethyl)-phenyl |
| 9-386 | —L1—D1 | —L2—D2 | —CH2CH2— | CONH2 | —CH2CH2— | CONH2 | H | 0 | 2,2,2-trichloroethyl | 2-bromo-6-trifluoromethylthio-4-(1,2,2,2-tetrafluoro-1-trifluoromethyl-ethyl)-phenyl |
| 9-387 | —L1—D1 | —L2—D2 | —CH2CH2— | CONH2 | —CH2CH2— | CONH2 | H | 0 | 2,2,2-trichloroethyl | 2-bromo-6-trifluoromethylsulfinyl-4-(1,2,2,2-tetrafluoro-1-trifluoromethyl-ethyl)-phenyl |
| 9-388 | —L1—D1 | —L2—D2 | —CH2CH2— | CONH2 | —CH2CH2— | CO2H | H | 0 | 2,2,2-trichloroethyl | 2-bromo-6-trifluoromethylsulfonyl-4-(1,2,2,2-tetrafluoro-1-trifluoromethyl-ethyl)-phenyl |
| 9-389 | —L1—D1 | —L2—D2 | —CH2CH2— | CONH2 | —CH2CH2— | CONH2 | H | 0 | 2,2,2-trichloroethyl | 2-bromo-6-pentafluoroethyl-4-(1,2,2,2-tetrafluoro-1-trifluoromethyl-ethyl)-phenyl |
| 9-390 | —L1—D1 | —L2—D2 | —CH2CH2— | CONH2 | —CH2CH2— | CONH2 | H | 0 | 2,2,2-trichloroethyl | 2-iodo-6-pentafluoroethyl-4-(1,2,2,2-tetrafluoro-1-trifluoromethyl-ethyl)-phenyl |

TABLE 9-continued

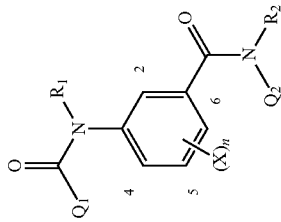

| compound number | R1 | R2 | L1 | D1 | L2 | D2 | X | n | Q3 | Q2 |
|---|---|---|---|---|---|---|---|---|---|---|
| 9-391 | —L1—D1 | —L2—D2 | —CH2CH2— | CONH2 | —CH2CH2— | CONH2 | H | 0 | 2,2,2-trichloroethyl | 2-chloro-6-methyl-4-(1,2,2,3,3,3-hexafluoro-1-trifluoromethyl-propyl)-phenyl |
| 9-392 | —L1—D1 | —L2—D2 | —CH2CH2CH2— | CONH2 | —CH2CH2CH2— | CONH2 | H | 0 | 2,2,2-trichloroethyl | 2-bromo-6-methyl-4-(1,2,2,3,3,3-hexafluoro-1-trifluoromethyl-propyl)-phenyl |
| 9-393 | —L1—D1 | —L2—D2 | —CH2CH2— | CONH2 | —CH2CH2— | CONH2 | H | 0 | 2,2,2-trichloroethyl | 2-iodo-6-methyl-4-(1,2,2,3,3,3-hexafluoro-1-trifluoromethyl-propyl)-phenyl |
| 9-394 | —L1—D1 | —L2—D2 | —CH2CH2— | CONH2 | —CH2CH2— | CONH2 | H | 0 | 2,2,2-trichloroethyl | 2-bromo-6-ethyl-4-(1,2,2,3,3,3-hexafluoro-1-trifluoromethyl-propyl)-phenyl |
| 9-395 | —L1—D1 | —L2—D2 | —CH2CH2— | CONH2 | —CH2CH2— | CONH2 | H | 0 | 2,2,2-trichloroethyl | 2-iodo-6-ethyl-4-(1,2,2,3,3,3-hexafluoro-1-trifluoromethyl-propyl)-phenyl |
| 9-396 | —L1—D1 | —L2—D2 | —CH2CH2— | CONH2 | —CH2CH2— | CONH2 | H | 0 | 2,2,2-trichloroethyl | 2,6-dichloro-4-(1,2,2,3,3,3-hexafluoro-1-trifluoromethyl-propyl)-phenyl |
| 9-397 | —L1—D1 | —L2—D2 | —CH2CH2— | CONH2 | —CH2CH2— | CONH2 | H | 0 | 2,2,2-trichloroethyl | 2,6-dibromo-4-(1,2,2,3,3,3-hexafluoro-1-trifluoromethyl-propyl)-phenyl |
| 9-398 | —L1—D1 | —L2—D2 | —CH2CH2— | CO2H | —CH2CH2— | CONH2 | H | 0 | 2,2,2-trichloroethyl | 2,6-diiodo-4-(1,2,2,3,3,3-hexafluoro-1-trifluoromethyl-propyl)-phenyl |
| 9-399 | —L1—D1 | —L2—D2 | —CH2— | CONH2 | —CH2— | CONH2 | H | 0 | 2,2,2-trichloroethyl | 2,6-ditrifluoromethyl-4-(1,2,2,3,3,3-hexafluoro-1-trifluoromethyl-propyl)-phenyl |
| 9-400 | —L1—D1 | —L2—D2 | —CH2CH2— | CONH2 | —CH2CH2— | CONH2 | H | 0 | 2,2,2-trichloroethyl | 2-bromo-6-trifluoromethyl-4-(1,2,2,3,3,3-hexafluoro-1-trifluoromethyl-propyl)-phenyl |
| 9-401 | —L1—D1 | —L2—D2 | —CH2CH2— | CONH2 | —CH2CH2— | CONH2 | H | 0 | 2,2,2-trichloroethyl | 2-iodo-6-trifluoromethyl-4-(1,2,2,3,3,3-hexafluoro-1-trifluoromethyl-propyl)-phenyl |

TABLE 9-continued

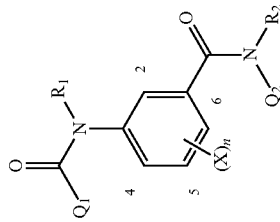

| compound number | R₁ | R₂ | L1 | D1 | L2 | D2 | X | n | Q₃ | Q₂ |
|---|---|---|---|---|---|---|---|---|---|---|
| 9-402 | —L₁—D₁ | —L₂—D₂ | —CH2CH2— | CONH2 | —CH2CH2— | CONH2 | H | 0 | 2,2,2-trichloroethyl | 2-bromo-6-trifluoromethoxy-4-(1,2,2,3,3,3-hexafluoro-1-trifluoromethyl-propyl)-phenyl |
| 9-403 | —L₁—D₁ | —L₂—D₂ | —CH2CH2— | CONH2 | —CH2CH2— | CONH2 | H | 0 | 2,2,2-trichloroethyl | 2-bromo-6-iodo-4-(1,2,2,3,3,3-hexafluoro-1-trifluoromethyl-propyl)-phenyl |
| 9-404 | —L₁—D₁ | —L₂—D₂ | —CH2CH2— | CONH2 | —CH2CH2— | CONH2 | H | 0 | 2,2,2-trichloroethyl | 2-bromo-6-trifluoromethylthio-4-(1,2,2,3,3,3-hexafluoro-1-trifluoromethyl-propyl)-phenyl |
| 9-405 | —L₁—D₁ | —L₂—D₂ | —CH2CH2— | CONH2 | —CH2CH2— | CONH2 | H | 0 | 2,2,2-trichloroethyl | 2-bromo-6-trifluoromethylsulfinyl-4-(1,2,2,3,3,3-hexafluoro-1-trifluoromethyl-propyl)-phenyl |
| 9-406 | —L₁—D₁ | —L₂—D₂ | —CH2CH(CH3)— | CONH2 | —CH2CH2(CH3)— | CONH2 | H | 0 | 2,2,2-trichloroethyl | 2-bromo-6-trifluoromethylsulfonyl-4-(1,2,2,3,3,3-hexafluoro-1-trifluoromethyl-propyl)-phenyl |
| 9-407 | —L₁—D₁ | —L₂—D₂ | —CH2CH2— | CONH2 | —CH2CH2— | CONH2 | H | 0 | 2,2,2-trichloroethyl | 2-bromo-6-pentafluoroethyl-4-(1,2,2,3,3,3-hexafluoro-1-trifluoromethyl-propyl)-phenyl |
| 9-408 | —L₁—D₁ | —L₂—D₂ | —CH2CH2— | CONH2 | —CH2CH2— | CONH2 | H | 0 | 2,2,2-trichloroethyl | 2-iodo-pentafluoroethyl-4-(1,2,2,3,3,3-hexafluoro-1-trifluoromethyl-propyl)-phenyl |
| 9-409 | —L₁—D₁ | —L₂—D₂ | —CH2CH2— | CONH2 | —CH2CH2— | CONH2 | H | 0 | i-propyl | 2,6-dibromo-4-(1,2,2,2-tetrafluoro-1-trifluoromethyl-ethyl)-phenyl |
| 9-410 | —L₁—D₁ | —L₂—D₂ | —CH2CH2— | CONH2 | —CH2CH2— | CONH2 | H | 0 | 3,3,3-trifluoro-n-propyl | 2,6-dibromo-4-(1,2,2,2-tetrafluoro-1-trifluoromethyl-ethyl)-phenyl |
| 9-411 | —L₁—D₁ | —L₂—D₂ | —CH2CH2— | CONH2 | —CH2CH2— | CONH2 | H | 0 | i-propyl | 2,6-diiodo-4-(1,2,2,2-tetrafluoro-1-trifluoromethyl-ethyl)-phenyl |
| 9-412 | —L₁—D₁ | —L₂—D₂ | —CH2CH2— | CONH2 | —CH2CH2— | CONH2 | H | 0 | 3,3,3-trifluoro-n-propyl | 2,6-diiodo-4-(1,2,2,2-tetrafluoro-1-trifluoromethyl-ethyl)-phenyl |
| 9-413 | —L₁—D₁ | —L₂—D₂ | —CH2CH2— | CONH2 | —CH2CH2— | CONH2 | H | 0 | i-propyl | 2-bromo-6-trifluoromethyl-4-(1,2,2,2-tetrafluoro-1-trifluoromethyl-ethyl)-phenyl |
| 9-414 | —L₁—D₁ | —L₂—D₂ | —CH2CH2— | CONH2 | —CH2CH2— | CONH2 | H | 0 | 3,3,3-trifluoro-n-propyl | 2-bromo-6-trifluoromethyl-4-(1,2,2,2-tetrafluoro-1-trifluoromethyl-ethyl)-phenyl |

TABLE 9-continued

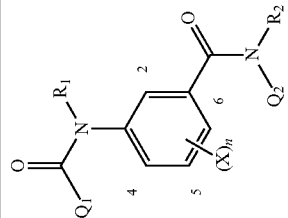

| compound number | R1 | R2 | L1 | D1 | L2 | D2 | X | n | Q3 | Q2 |
|---|---|---|---|---|---|---|---|---|---|---|
| 9-415 | —L1—D1 | —L2—D2 | —CH2CH2— | CONH2 | —CH2CH2— | CONH2 | H | 0 | i-propyl | 2-iodo-6-trifluoromethyl-4-(1,2,2,2-tetrafluoro-1-trifluoromethyl-ethyl)-phenyl |
| 9-416 | —L1—D1 | —L2—D2 | —CH2CH2— | CONH2 | —CH2CH2— | CONH2 | H | 0 | 3,3,3-trifluoro-n-propyl | 2-iodo-6-trifluoromethyl-4-(1,2,2,2-tetrafluoro-1-trifluoromethyl-ethyl)-phenyl |
| 9-417 | —L1—D1 | —L2—D2 | —CH2CH2— | CONH2 | —CH2CH2— | CONH2 | H | 0 | i-propyl | 2,6-dibromo-4-(1,2,2,3,3,3-hexafluoro-1-trifluoromethyl-propyl)-phenyl |
| 9-418 | —L1—D1 | —L2—D2 | —CH2CH2— | CONH2 | —CH2CH2— | CONH2 | H | 0 | 3,3,3-trifluoro-n-propyl | 2,6-dibromo-4-(1,2,2,3,3,3-hexafluoro-1-trifluoromethyl-propyl)-phenyl |
| 9-419 | —L1—D1 | —L2—D2 | —CH2CH2— | CONH2 | —CH2CH2— | CONH2 | H | 0 | i-propyl | 2,6-diiodo-4-(1,2,2,3,3,3-hexafluoro-1-trifluoromethyl-propyl)-phenyl |
| 9-420 | —L1—D1 | —L2—D2 | —CH2CH2— | CONH2 | —CH2CH2— | CONH2 | H | 0 | 3,3,3-trifluoro-n-propyl | 2,6-diiodo-4-(1,2,2,3,3,3-hexafluoro-1-trifluoromethyl-propyl)-phenyl |
| 9-421 | —L1—D1 | —L2—D2 | —CH2CH2— | CONH2 | —CH2CH2— | CONH2 | H | 0 | i-propyl | 2-bromo-6-trifluoromethyl-4-(1,2,2,3,3,3-hexafluoro-1-trifluoromethyl-propyl)-phenyl |
| 9-422 | —L1—D1 | —L2—D2 | —CH2CH2— | CONH2 | —CH2CH2— | CONH2 | H | 0 | 3,3,3-trifluoro-n-propyl | 2-bromo-6-trifluoromethyl-4-(1,2,2,3,3,3-hexafluoro-1-trifluoromethyl-propyl)-phenyl |
| 9-423 | —L1—D1 | —L2—D2 | —CH2CH2— | CONH2 | —CH2CH2— | CONH2 | H | 0 | i-propyl | 2-iodo-6-trifluoromethyl-4-(1,2,2,3,3,3-hexafluoro-1-trifluoromethyl-propyl)-phenyl |
| 9-424 | —L1—D1 | —L2—D2 | —CH2CH2— | CONH2 | —CH2CH2— | CONH2 | H | 0 | 3,3,3-trifluoro-n-propyl | 2-iodo-6-trifluoromethyl-4-(1,2,2,3,3,3-hexafluoro-1-trifluoromethyl-propyl)-phenyl |
| 9-425 | —L1—D1 | —L2—D2 | —CH2CH2— | CONH2 | —CH2CH2— | CONH2 | 2-F | 1 | 2,2,2-trichloroethyl | 2,6-dibromo-4-pentafluoroethyl-phenyl |
| 9-426 | —L1—D1 | —L2—D2 | —CH2CH2— | CONH2 | —CH2CH2— | CONH2 | 2-F | 1 | 3,3,3-trifluoro-n-propyl | 2,6-diiodo-4-pentafluoroethyl-phenyl |

TABLE 9-continued

| compound number | R₁ | R₂ | L1 | D1 | L2 | D2 | X | n | Q₃ | Q₂ |
|---|---|---|---|---|---|---|---|---|---|---|
| 9-427 | —L₁—D₁ | —L₂—D₂ | —CH2CH2— | CONH2 | —CH2CH2— | CONH2 | 2-F | 1 | 2,2,2-trichloroethyl | 2-bromo-6-trifluoromethyl-4-pentafluoroethyl-phenyl |
| 9-428 | —L₁—D₁ | —L₂—D₂ | —CH2CH2— | CONH2 | —CH2CH2— | CONH2 | 2-F | 1 | 3,3,3-trifluoro-n-propyl | 2-iodo-6-trifluoromethyl-4-pentafluoroethyl-phenyl |
| 9-429 | —L₁—D₁ | —L₂—D₂ | —CH2CH2— | CONH2 | —CH2CH2— | CONH2 | 2-F | 1 | 2,2,2-trichloroethyl | 2-chloro-6-methyl-4-(1,2,2,2-tetrafluoro-1-trifluoromethyl-ethyl)-phenyl |
| 9-430 | —L₁—D₁ | —L₂—D₂ | —CH2CH2— | CONH2 | —CH2CH2— | CONH2 | 2-F | 1 | 3,3,3-trifluoro-n-propyl | 2-bromo-6-methyl-4-(1,2,2,2-tetrafluoro-1-trifluoromethyl-ethyl)-phenyl |
| 9-431 | —L₁—D₁ | —L₂—D₂ | —CH2CH2— | CONH2 | —CH2CH2— | CONH2 | 2-F | 1 | 2,2,2-trichloroethyl | 2-iodo-6-methyl-4-(1,2,2,2-tetrafluoro-1-trifluoromethyl-ethyl)-phenyl |
| 9-432 | —L₁—D₁ | —L₂—D₂ | —CH2CH2— | CONH2 | —CH2CH2— | CONH2 | 2-F | 1 | 2,2,2-trichloroethyl | 2-bromo-6-ethyl-4-(1,2,2,2-tetrafluoro-1-trifluoromethyl-ethyl)-phenyl |
| 9-433 | —L₁—D₁ | —L₂—D₂ | —CH2CH2— | CONH2 | —CH2CH2— | CONH2 | 2-F | 1 | 2,2,2-trichloroethyl | 2-iodo-6-ethyl-4-(1,2,2,2-tetrafluoro-1-trifluoromethyl-ethyl)-phenyl |
| 9-434 | —L₁—D₁ | —L₂—D₂ | —CH2CH2— | CONH2 | —CH2CH2— | CONH2 | 2-F | 1 | 2,2,2-trichloroethyl | 2,6-dichloro-4-(1,2,2,2-tetrafluoro-1-trifluoromethyl-ethyl)-phenyl |
| 9-435 | —L₁—D₁ | —L₂—D₂ | —CH2CH2— | CONH2 | —CH2CH2— | CONH2 | 2-F | 1 | 2,2,2-trichloroethyl | 2,6-dibromo-4-(1,2,2,2-tetrafluoro-1-trifluoromethyl-ethyl)-phenyl |
| 9-436 | —L₁—D₁ | —L₂—D₂ | —CH2CH2— | CONH2 | —CH2CH2— | CONH2 | 2-F | 1 | 2,2,2-trichloroethyl | 2,6-diiodo-4-(1,2,2,2-tetrafluoro-1-trifluoromethyl-ethyl)-phenyl |
| 9-437 | —L₁—D₁ | —L₂—D₂ | —CH2CH2— | CONH2 | —CH2CH2— | CONH2 | 2-F | 1 | 2,2,2-trichloroethyl | 2,6-ditrifluoromethyl-4-(1,2,2,2-tetrafluoro-1-trifluoromethyl-ethyl)-phenyl |
| 9-438 | —L₁—D₁ | —L₂—D₂ | —CH2CH2— | CONH2 | —CH2CH2— | CONH2 | 2-F | 1 | 2,2,2-trichloroethyl | 2-bromo-6-trifluoromethyl-4-(1,2,2,2-tetrafluoro-1-trifluoromethyl-ethyl)-phenyl |

TABLE 9-continued

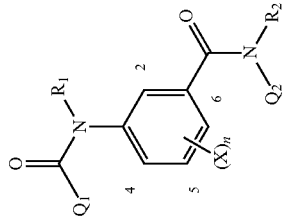

| compound number | $R_1$ | $R_2$ | L1 | D1 | L2 | D2 | X | n | $Q_3$ | $Q_2$ |
|---|---|---|---|---|---|---|---|---|---|---|
| 9-439 | —L₁—D₁ | —L₂—D₂ | —CH2CH2— | CONH2 | —CH2CH2— | CONH2 | 2-F | 1 | 2,2,2-trichloroethyl | 2-iodo-6-trifluoromethyl-4-(1,2,2,2-tetrafluoro-1-trifluoromethyl-ethyl)-phenyl |
| 9-440 | —L₁—D₁ | —L₂—D₂ | —CH2CH2— | CONH2 | —CH2CH2— | CONH2 | 2-F | 1 | 2,2,2-trichloroethyl | 2-bromo-6-trifluoromethoxy-4-(1,2,2,2-tetrafluoro-1-trifluoromethyl-ethyl)-phenyl |
| 9-441 | —L₁—D₁ | —L₂—D₂ | —CH2CH2— | CONH2 | —CH2CH2— | CONH2 | 2-F | 1 | 2,2,2-trichloroethyl | 2-bromo-6-iodo-4-(1,2,2,2-tetrafluoro-1-trifluoromethyl-ethyl)-phenyl |
| 9-442 | —L₁—D₁ | —L₂—D₂ | —CH2CH2— | CONH2 | —CH2CH2— | CONH2 | 2-F | 1 | 2,2,2-trichloroethyl | 2-bromo-6-trifluoromethylthio-4-(1,2,2,2-tetrafluoro-1-trifluoromethyl-ethyl)-phenyl |
| 9-443 | —L₁—D₁ | —L₂—D₂ | —CH2CH2— | CONH2 | —CH2CH2— | CONH2 | 2-F | 1 | 2,2,2-trichloroethyl | 2-bromo-6-trimethylsulfinyl-4-(1,2,2,2-tetrafluoro-1-trifluoromethyl-ethyl)-phenyl |
| 9-444 | —L₁—D₁ | —L₂—D₂ | —CH2CH2— | CONH2 | —CH2CH2— | CONH2 | 2-F | 1 | 2,2,2-trichloroethyl | 2-bromo-6-trifluoromethylsulfonyl-4-(1,2,2,2-tetrafluoro-1-trifluoromethyl-ethyl)-phenyl |
| 9-445 | —L₁—D₁ | —L₂—D₂ | —CH2CH2— | CONH2 | —CH2CH2— | CONH2 | 2-F | 1 | 2,2,2-trichloroethyl | 2-bromo-6-pentafluoroethyl-4-(1,2,2,2-tetrafluoro-1-trifluoromethyl-ethyl)-phenyl |
| 9-446 | —L₁—D₁ | —L₂—D₂ | —CH2CH2— | CONH2 | —CH2CH2— | CONH2 | 2-F | 1 | 2,2,2-trichloroethyl | 2-iodo-6-pentafluoroethyl-4-(1,2,2,2-tetrafluoro-1-trifluoromethyl-ethyl)-phenyl |
| 9-447 | —L₁—D₁ | —L₂—D₂ | —CH2CH2— | CONMe2 | —CH2CH2— | CONMe2 | 2-F | 1 | 2,2,2-trichloroethyl | 2-chloro-6-methyl-4-(1,2,2,3,3,3-hexafluoro-1-trifluoromethyl-propyl)-phenyl |
| 9-448 | —L₁—D₁ | —L₂—D₂ | —CH2CH2— | CONH2 | —CH2CH2— | CONH2 | 2-F | 1 | 2,2,2-trichloroethyl | 2-bromo-6-methyl-4-(1,2,2,3,3,3-hexafluoro-1-trifluoromethyl-propyl)-phenyl |
| 9-449 | —L₁—D₁ | —L₂—D₂ | —CH2CH2— | CONH2 | —CH2CH2— | CONH2 | 2-F | 1 | 2,2,2-trichloroethyl | 2-iodo-6-methyl-4-(1,2,2,3,3,3-hexafluoro-1-trifluoromethyl-propyl)-phenyl |

TABLE 9-continued

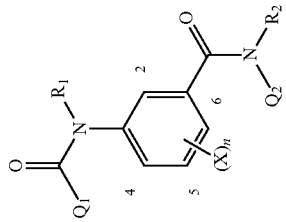

| compound number | R1 | R2 | L1 | D1 | L2 | D2 | X | n | Q3 | Q2 |
|---|---|---|---|---|---|---|---|---|---|---|
| 9-450 | —L1—D1 | —L2—D2 | —CH2CH2— | CN | —CH2CH2— | CN | 2-F | 1 | 2,2,2-trichloroethyl | 2-bromo-6-ethyl-4-(1,2,2,3,3,3-hexafluoro-1-trifluoromethyl-propyl)-phenyl |
| 9-451 | —L1—D1 | —L2—D2 | —CH2CH2— | CONH2 | —CH2CH2— | CONH2 | 2-F | 1 | 2,2,2-trichloroethyl | 2-iodo-6-ethyl-4-(1,2,2,3,3,3-hexafluoro-1-trifluoromethyl-propyl)-phenyl |
| 9-452 | —L1—D1 | —L2—D2 | —CH2CH2— | CONH2 | —CH2CH2— | CONH2 | 2-F | 1 | 2,2,2-trichloroethyl | 2,6-dichloro-4-(1,2,2,3,3,3-hexafluoro-1-trifluoromethyl-propyl)-phenyl |
| 9-453 | —L1—D1 | —L2—D2 | —CH2CH2— | CONH2 | —CH2CH2— | CONH2 | 2-F | 1 | 2,2,2-trichloroethyl | 2,6-dibromo-4-(1,2,2,3,3,3-hexafluoro-1-trifluoromethyl-propyl)-phenyl |
| 9-454 | —L1—D1 | —L2—D2 | —CH2CH2— | CONH2 | —CH2CH2— | CONH2 | 2-F | 1 | 2,2,2-trichloroethyl | 2,6-diiodo-4-(1,2,2,3,3,3-hexafluoro-1-trifluoromethyl-propyl)-phenyl |
| 9-455 | —L1—D1 | —L2—D2 | —CH2CH2— | CONH2 | —CH2CH2— | CONH2 | 2-F | 1 | 2,2,2-trichloroethyl | 2,6-ditrifluoromethyl-4-(1,2,2,3,3,3-hexafluoro-1-trifluoromethyl-propyl)-phenyl |
| 9-456 | —L1—D1 | —L2—D2 | —CH2CH2— | CONH2 | —CH2CH2— | CONH2 | 2-F | 1 | 2,2,2-trichloroethyl | 2-bromo-6-trifluoromethyl-4-(1,2,2,3,3,3-hexafluoro-1-trifluoromethyl-propyl)-phenyl |
| 9-457 | —L1—D1 | —L2—D2 | —CH2CH2— | CONH2 | —CH2CH2— | CONH2 | 2-F | 1 | 2,2,2-trichloroethyl | 2-iodo-6-trifluoromethyl-4-(1,2,2,3,3,3-hexafluoro-1-trifluoromethyl-propyl)-phenyl |
| 9-458 | —L1—D1 | —L2—D2 | —CH2CH2— | CONH2 | —CH2CH2— | CONH2 | 2-F | 1 | 2,2,2-trichloroethyl | 2-bromo-6-trifluoromethoxy-4-(1,2,2,3,3,3-hexafluoro-1-trifluoromethyl-propyl)-phenyl |
| 9-459 | —L1—D1 | —L2—D2 | —CH2CH2— | CONH2 | —CH2CH2— | CONH2 | 2-F | 1 | 2,2,2-trichloroethyl | 2-bromo-6-iodo-4-(1,2,2,3,3,3-hexafluoro-1-trifluoromethyl-propyl)-phenyl |
| 9-460 | —L1—D1 | —L2—D2 | —CH2CH2— | CONH2 | —CH2CH2— | CONH2 | 2-F | 1 | 2,2,2-trichloroethyl | 2-bromo-6-trifluoromethylthio-4-(1,2,2,3,3,3-hexafluoro-1-trifluoromethyl-propyl)-phenyl |

TABLE 9-continued

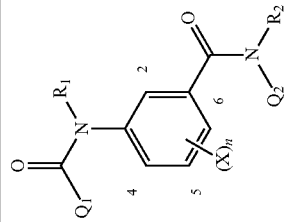

| compound number | R₁ | R₂ | L1 | D1 | L2 | D2 | X | n | Q₃ | Q₂ |
|---|---|---|---|---|---|---|---|---|---|---|
| 9-461 | —L₁—D₁ | —L₂—D₂ | —CH2CH2— | CONH2 | —CH2CH2— | CONH2 | 2-F | 1 | 2,2,2-trichloroethyl | 2-bromo-6-trifluoromethylsulfinyl-4-(1,2,3,3,3-hexafluoro-1-trifluoromethyl-propyl)-phenyl |
| 9-462 | —L₁—D₁ | —L₂—D₂ | —CH2CH2— | CONH2 | —CH2CH2— | CONH2 | 2-F | 1 | 2,2,2-trichloroethyl | 2-bromo-6-trifluoromethylsulfonyl-4-(1,2,3,3,3-hexafluoro-1-trifluoromethyl-propyl)-phenyl |
| 9-463 | —L₁—D₁ | —L₂—D₂ | —CH2CH2— | CONH2 | —CH2CH2— | CONH2 | 2-F | 1 | 2,2,2-trichloroethyl | 2-bromo-6-pentafluoroethyl-4-(1,2,3,3,3-hexafluoro-1-trifluoromethyl-propyl)-phenyl |
| 9-464 | —L₁—D₁ | —L₂—D₂ | —CH2CH2— | CONH2 | —CH2CH2— | CONH2 | 2-F | 1 | 2,2,2-trichloroethyl | 2-iodo-6-pentafluoroethyl-4-(1,2,3,3,3-hexafluoro-1-trifluoromethyl-propyl)-phenyl |
| 9-465 | —L₁—D₁ | —L₂—D₂ | —CH2CH2— | CONH2 | —CH2CH2— | CONH2 | 2-F | 1 | i-propyl | 2,6-dibromo-4-(1,2,2,2-tetrafluoro-1-trifluoromethyl-ethyl)-phenyl |
| 9-466 | —L₁—D₁ | —L₂—D₂ | —CH2CH2CH2— | CONH2 | —CH2CH2CH2— | CONH2 | 2-F | 1 | 3,3,3-trifluoro-n-propyl | 2,6-dibromo-4-(1,2,2,2-tetrafluoro-1-trifluoromethyl-ethyl)-phenyl |
| 9-467 | —L₁—D₁ | —L₂—D₂ | —CH2CH2— | CONH2 | —CH2CH2— | CONH2 | 2-F | 1 | i-propyl | 2,6-diiodo-4-(1,2,2,2-tetrafluoro-1-trifluoromethyl-ethyl)-phenyl |
| 9-468 | —L₁—D₁ | —L₂—D₂ | —CH2CH2— | CONH2 | —CH2CH2— | CONH2 | 2-F | 1 | 3,3,3-trifluoro-n-propyl | 2,6-diiodo-4-(1,2,2,2-tetrafluoro-1-trifluoromethyl-ethyl)-phenyl |
| 9-469 | —L₁—D₁ | —L₂—D₂ | —CH2CH2— | CONH2 | —CH2CH2— | CONH2 | 2-F | 1 | i-propyl | 2-bromo-6-trifluoromethyl-4-(1,2,2,2-tetrafluoro-1-trifluoromethyl-ethyl)-phenyl |
| 9-470 | —L₁—D₁ | —L₂—D₂ | —CH2CH2— | CONH2 | —CH2CH2— | CONH2 | 2-F | 1 | 3,3,3-trifluoro-n-propyl | 2-bromo-6-trifluoromethyl-4-(1,2,2,2-tetrafluoro-1-trifluoromethyl-ethyl)-phenyl |
| 9-471 | —L₁—D₁ | —L₂—D₂ | —CH2CH2— | CONH2 | —CH2CH2— | CONH2 | 2-F | 1 | i-propyl | 2-iodo-6-trifluoromethyl-4-(1,2,2,2-tetrafluoro-1-trifluoromethyl-ethyl)-phenyl |
| 9-472 | —L₁—D₁ | —L₂—D₂ | —CH2CH2— | CONH2 | —CH2CH2— | CONH2 | 2-F | 1 | 3,3,3-trifluoro-n-propyl | 2-iodo-6-trifluoromethyl-4-(1,2,2,2-tetrafluoro-1-trifluoromethyl-ethyl)-phenyl |
| 9-473 | —L₁—D₁ | —L₂—D₂ | —CH2CH2— | CONH2 | —CH2CH2— | CONH2 | 2-F | 1 | i-propyl | 2,6-dibromo-4-(1,2,3,3,3-hexafluoro-1-trifluoromethyl-propyl)-phenyl |

TABLE 9-continued

| compound number | R1 | R2 | L1 | D1 | L2 | D2 | X | n | Q3 | Q2 |
|---|---|---|---|---|---|---|---|---|---|---|
| 9-474 | —L1—D1 | —L2—D2 | —CH2CH2— | CONH2 | —CH2CH2— | CONH2 | 2-F | 1 | 3,3,3-trifluoro-n-propyl | 2,6-dibromo-4-(1,2,2,3,3,3-hexafluoro-1-trifluoromethyl-propyl)-phenyl |
| 9-475 | —L1—D1 | —L2—D2 | —CH2CH2— | CONH2 | —CH2CH2— | CONH2 | 2-F | 1 | i-propyl | 2,6-diiodo-4-(1,2,2,3,3,3-hexafluoro-1-trifluoromethyl-propyl)-phenyl |
| 9-476 | —L1—D1 | —L2—D2 | —CH2CH2— | CONH2 | —CH2CH2— | CONH2 | 2-F | 1 | 3,3,3-trifluoro-n-propyl | 2,6-diiodo-4-(1,2,2,3,3,3-hexafluoro-1-trifluoromethyl-propyl)-phenyl |
| 9-477 | —L1—D1 | —L2—D2 | —CH2CH2— | CONH2 | —CH2CH2— | CONH2 | 2-F | 1 | i-propyl | 2-bromo-6-trifluoromethyl-4-(1,2,2,3,3,3-hexafluoro-1-trifluoromethyl-propyl)-phenyl |
| 9-478 | —L1—D1 | —L2—D2 | —CH2CH2— | CONH2 | —CH2CH2— | CONH2 | 2-F | 1 | 3,3,3-trifluoro-n-propyl | 2-bromo-6-trifluoromethyl-4-(1,2,2,3,3,3-hexafluoro-1-trifluoromethyl-propyl)-phenyl |
| 9-479 | —L1—D1 | —L2—D2 | —CH2CH2— | CONH2 | —CH2CH2— | CONH2 | 2-F | 1 | i-propyl | 2-iodo-6-trifluoromethyl-4-(1,2,2,3,3,3-hexafluoro-1-trifluoromethyl-propyl)-phenyl |
| 9-480 | —L1—D1 | —L2—D2 | —CH2CH2— | CONH2 | —CH2CH2— | CONH2 | 2-F | 1 | 3,3,3-trifluoro-n-propyl | 2-iodo-6-trifluoromethyl-4-(1,2,2,3,3,3-hexafluoro-1-trifluoromethyl-propyl)-phenyl |
| 9-481 | —L1—D1 | —L2—D2 | —CH2CH2— | CONH2 | —CH2CH2— | CONH2 | 2-F | 1 | phenyl | 2,6-dimethyl-4-(1,2,2,3,3,3-hexafluoro-1-trifluoromethyl-propyl)-phenyl |
| 9-482 | —L1—D1 | —L2—D2 | —CH2CH2— | CONH2 | —CH2CH2— | CONH2 | 2-F | 1 | 4-cyanophenyl | 2,6-dimethyl-4-(1,2,2,3,3,3-hexafluoro-1-trifluoromethyl-propyl)-phenyl |
| 9-483 | —L1—D1 | —L2—D2 | —CH2CH2— | CONH2 | —CH2CH2— | CONH2 | 2-F | 1 | 3-cyanophenyl | 2,6-dimethyl-4-(1,2,2,3,3,3-hexafluoro-1-trifluoromethyl-propyl)-phenyl |
| 9-484 | —L1—D1 | —L2—D2 | —CH2CH2— | CONH2 | —CH2CH2— | CONH2 | 4-F | 1 | 2,2,2-trichloroethyl | 2,6-dibromo-4-(1,2,2,2-tetrafluoro-1-trifluoromethyl-ethyl)-phenyl |
| 9-485 | —L1—D1 | —L2—D2 | —CH2CH2— | CONH2 | —CH2CH2— | CONH2 | 4-F | 1 | 2,2,2-trichloroethyl | 2-bromo-6-trifluoromethyl-4-(1,2,2,2-tetrafluoro-1-trifluoromethyl-ethyl)-phenyl |

TABLE 9-continued

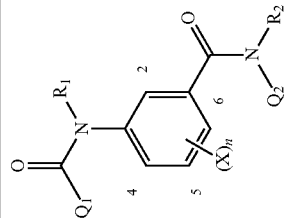

| compound number | R1 | R2 | L1 | D1 | L2 | D2 | X | n | Q3 | Q2 |
|---|---|---|---|---|---|---|---|---|---|---|
| 9-486 | —L1—D1 | —L2—D2 | —CH2CH2— | CONH2 | —CH2CH2— | CONH2 | 4-F | 1 | 2,2,2-trichloroethyl | 2-iodo-6-trifluoromethyl-4-(1,2,2,2-tetrafluoro-1-trifluoromethyl-ethyl)-phenyl |
| 9-487 | —L1—D1 | —L2—D2 | —CH2CH2— | CONH2 | —CH2CH2— | CONH2 | 4-F | 1 | 2,2,2-trichloroethyl | 2-bromo-6-trifluoromethyl-4-(1,2,2,3,3,3-hexafluoro-1-trifluoromethyl-propyl)-phenyl |
| 9-488 | —L1—D1 | —L2—D2 | —CH2CH2— | CONH2 | —CH2CH2— | CONH2 | 4-F | 1 | 2,2,2-trichloroethyl | 2-iodo-6-trifluoromethyl-4-(1,2,2,3,3,3-hexafluoro-1-trifluoromethyl-propyl)-phenyl |
| 9-489 | —L1—D1 | —L2—D2 | —CH2CH2— | CONH2 | —CH2CH2— | CONH2 | 4-CN | 1 | 2,2,2-trichloroethyl | 2,6-dibromo-4-(1,2,2,2-tetrafluoro-1-trifluoromethyl-ethyl)-phenyl |
| 9-490 | —L1—D1 | —L2—D2 | —CH2CH2— | CONH2 | —CH2CH2— | CONH2 | 4-CN | 1 | 2,2,2-trichloroethyl | 2-bromo-6-trifluoromethyl-4-(1,2,2,2-tetrafluoro-1-trifluoromethyl-ethyl)-phenyl |
| 9-491 | —L1—D1 | —L2—D2 | —CH2CH2— | CONH2 | —CH2CH2— | CONH2 | 4-CN | 1 | 2,2,2-trichloroethyl | 2-iodo-6-trifluoromethyl-4-(1,2,2,2-tetrafluoro-1-trifluoromethyl-ethyl)-phenyl |
| 9-492 | —L1—D1 | —L2—D2 | —CH2CH2— | CONH2 | —CH2CH2— | CONH2 | 4-CN | 1 | 2,2,2-trichloroethyl | 2-bromo-6-trifluoromethyl-4-(1,2,2,3,3,3-hexafluoro-1-trifluoromethyl-propyl)-phenyl |
| 9-493 | —L1—D1 | —L2—D2 | —CH2CH2— | CONH2 | —CH2CH2— | CONH2 | 4-CN | 1 | 2,2,2-trichloroethyl | 2-iodo-6-trifluoromethyl-4-(1,2,2,3,3,3-hexafluoro-1-trifluoromethyl-propyl)-phenyl |
| 9-494 | —L1—D1 | —L2—D2 | —CH2CH2— | CONH2 | —CH2CH2— | CONH2 | 2-NO2 | 1 | 2,2,2-trichloroethyl | 2,6-dibromo-4-(1,2,2,2-tetrafluoro-1-trifluoromethyl-ethyl)-phenyl |
| 9-495 | —L1—D1 | —L2—D2 | —CH2CH2— | CONH2 | —CH2CH2— | CONH2 | 2-NO2 | 1 | 2,2,2-trichloroethyl | 2-bromo-6-trifluoromethyl-4-(1,2,2,2-tetrafluoro-1-trifluoromethyl-ethyl)-phenyl |
| 9-496 | —L1—D1 | —L2—D2 | —CH2CH2— | CONH2 | —CH2CH2— | CONH2 | 2-NO2 | 1 | 2,2,2-trichloroethyl | 2-iodo-6-trifluoromethyl-4-(1,2,2,2-tetrafluoro-1-trifluoromethyl-ethyl)-phenyl |

TABLE 9-continued
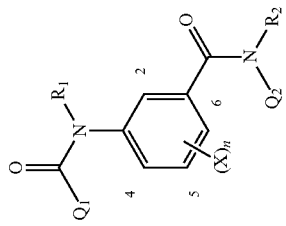
| compound number | R₁ | R₂ | L1 | D1 | L2 | D2 | X | n | Q₃ | Q₂ |
|---|---|---|---|---|---|---|---|---|---|---|
| 9-497 | —L₁—D₁ | —L₂—D₂ | —CH2CH2— | CONH2 | —CH2CH2— | CONH2 | 2-NO2 | 1 | 2,2,2-trichloroethyl | 2-bromo-6-trifluoromethyl-4-(1,2,2,3,3,3-tetrafluoro-1-trifluoromethyl-propyl)-phenyl |
| 9-498 | —L₁—D₁ | —L₂—D₂ | —CH2CH2— | CONH2 | —CH2CH2— | CONH2 | 2-NO2 | 1 | 2,2,2-trichloroethyl | 2-iodo-trifluoromethyl-4-(1,2,2,3,3,3-hexafluoro-1-trifluoromethyl-propyl)-phenyl |

TABLE 11

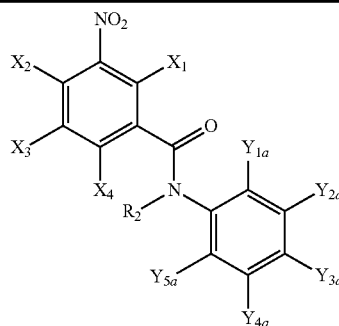

| compound number | R$_2$ | X$_1$ | X$_2$ | X$_3$ | X$_4$ | Y$_{1a}$ | Y$_{2a}$ | Y$_{3a}$ | Y$_{4a}$ | Y$_{5a}$ |
|---|---|---|---|---|---|---|---|---|---|---|
| 11-1 | H | H | H | H | H | F | H | nonafluoro-2-butyl | H | F |
| 11-2 | H | H | H | H | H | Cl | H | nonafluoro-2-butyl | H | Cl |
| 11-3 | H | H | H | H | H | Br | H | nonafluoro-2-butyl | H | Br |
| 11-4 | H | H | H | H | H | I | H | nonafluoro-2-butyl | H | I |
| 11-5 | H | H | H | H | H | Br | H | nonafluoro-2-butyl | H | Cl |
| 11-6 | H | H | H | H | H | Br | H | nonafluoro-2-butyl | H | I |
| 11-7 | H | H | H | H | H | Br | H | nonafluoro-2-butyl | H | OCF3 |
| 11-8 | H | H | H | H | H | Br | H | pentafluoroethyl | H | CF3 |
| 11-9 | H | H | H | H | H | F | H | heptafluoroisopropyl | H | CF3 |
| 11-10 | H | H | H | H | H | Cl | H | heptafluoroisopropyl | H | CF3 |
| 11-11 | H | H | H | H | H | Br | H | heptafluoroisopropyl | H | CF3 |
| 11-12 | H | H | H | H | H | I | H | heptafluoroisopropyl | H | CF3 |
| 11-13 | H | H | H | H | H | F | H | nonafluoro-2-butyl | H | CF3 |
| 11-14 | H | H | H | H | H | Cl | H | nonafluoro-2-butyl | H | CF3 |
| 11-15 | H | H | H | H | H | Br | H | nonafluoro-2-butyl | H | CF3 |
| 11-16 | H | H | H | H | H | I | H | nonafluoro-2-butyl | H | CF3 |
| 11-17 | H | H | H | H | H | OCF3 | H | heptafluoroisopropyl | H | CF3 |
| 11-18 | H | H | H | H | H | OCF3 | H | nonafluoro-2-butyl | H | CF3 |
| 11-19 | H | H | H | H | H | CF3 | H | heptafluoroisopropyl | H | CF3 |
| 11-20 | H | H | H | H | H | CF3 | H | nonafluoro-2-butyl | H | CF3 |
| 11-21 | H | H | H | H | H | Br | H | heptafluoroisopropyl | H | C2F5 |
| 11-22 | H | Cl | H | H | H | F | H | heptafluoroisopropyl | H | F |
| 11-23 | H | Cl | H | H | H | Cl | H | heptafluoroisopropyl | H | Cl |
| 11-24 | H | Cl | H | H | H | Br | H | heptafluoroisopropyl | H | Br |
| 11-25 | H | Cl | H | H | H | I | H | heptafluoroisopropyl | H | I |
| 11-26 | H | Cl | H | H | H | Br | H | heptafluoroisopropyl | H | Cl |
| 11-27 | H | Cl | H | H | H | Br | H | heptafluoroisopropyl | H | I |
| 11-28 | H | Cl | H | H | H | Cl | H | nonafluoro-2-butyl | H | Cl |
| 11-29 | H | Cl | H | H | H | Br | H | nonafluoro-2-butyl | H | Br |
| 11-30 | H | Cl | H | H | H | I | H | nonafluoro-2-butyl | H | I |
| 11-31 | H | Cl | H | H | H | Br | H | nonafluoro-2-butyl | H | Cl |
| 11-32 | H | Cl | H | H | H | Br | H | nonafluoro-2-butyl | H | I |
| 11-33 | H | Cl | H | H | H | Br | H | heptafluoroisopropyl | H | OCF3 |
| 11-34 | H | Cl | H | H | H | I | H | nonafluoro-2-butyl | H | OCF3 |
| 11-35 | H | Cl | H | H | H | Br | H | pentafluoroethyl | H | CF3 |
| 11-36 | H | Cl | H | H | H | F | H | heptafluoroisopropyl | H | CF3 |
| 11-37 | H | Cl | H | H | H | Cl | H | heptafluoroisopropyl | H | CF3 |
| 11-38 | H | Cl | H | H | H | Br | H | heptafluoroisopropyl | H | CF3 |
| 11-39 | H | Cl | H | H | H | I | H | heptafluoroisopropyl | H | CF3 |
| 11-40 | H | Cl | H | H | H | F | H | nonafluoro-2-butyl | H | CF3 |
| 11-41 | H | Cl | H | H | H | Cl | H | nonafluoro-2-butyl | H | CF3 |
| 11-42 | H | Cl | H | H | H | Br | H | nonafluoro-2-butyl | H | CF3 |
| 11-43 | H | Cl | H | H | H | I | H | nonafluoro-2-butyl | H | CF3 |
| 11-44 | H | Cl | H | H | H | OCF3 | H | heptafluoroisopropyl | H | CF3 |
| 11-45 | H | Cl | H | H | H | OCF3 | H | nonafluoro-2-butyl | H | CF3 |
| 11-46 | H | Cl | H | H | H | CF3 | H | heptafluoroisopropyl | H | CF3 |
| 11-47 | H | Cl | H | H | H | CF3 | H | nonafluoro-2-butyl | H | CF3 |
| 11-48 | H | Cl | H | H | H | Br | H | heptafluoroisopropyl | H | C2F5 |
| 11-49 | H | F | H | H | H | F | H | heptafluoroisopropyl | H | F |
| 11-50 | H | F | H | H | H | Cl | H | heptafluoroisopropyl | H | Cl |
| 11-51 | H | F | H | H | H | Br | H | heptafluoroisopropyl | H | Br |
| 11-52 | H | F | H | H | H | I | H | heptafluoroisopropyl | H | I |
| 11-53 | H | F | H | H | H | Br | H | heptafluoroisopropyl | H | Cl |
| 11-54 | H | F | H | H | H | Br | H | heptafluoroisopropyl | H | I |
| 11-55 | H | F | H | H | H | Cl | H | nonafluoro-2-butyl | H | Cl |
| 11-56 | H | F | H | H | H | Br | H | nonafluoro-2-butyl | H | Br |
| 11-57 | H | F | H | H | H | I | H | nonafluoro-2-butyl | H | I |
| 11-58 | H | F | H | H | H | Br | H | nonafluoro-2-butyl | H | Cl |
| 11-59 | H | F | H | H | H | Br | H | nonafluoro-2-butyl | H | I |
| 11-60 | H | F | H | H | H | Br | H | heptafluoroisopropyl | H | OCF3 |
| 11-61 | H | F | H | H | H | I | H | nonafluoro-2-butyl | H | OCF3 |

TABLE 11-continued

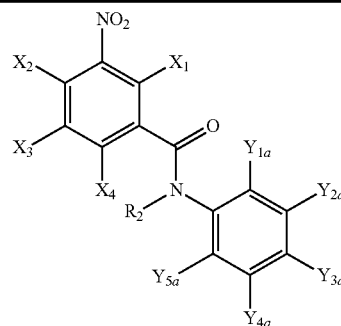

| compound number | R$_2$ | X$_1$ | X$_2$ | X$_3$ | X$_4$ | Y$_{1a}$ | Y$_{2a}$ | Y$_{3a}$ | Y$_{4a}$ | Y$_{5a}$ |
|---|---|---|---|---|---|---|---|---|---|---|
| 11-62 | H | F | H | H | H | Br | H | pentafluoroethyl | H | CF3 |
| 11-63 | H | F | H | H | H | F | H | heptafluoroisopropyl | H | CF3 |
| 11-64 | H | F | H | H | H | Cl | H | heptafluoroisopropyl | H | CF3 |
| 11-65 | H | F | H | H | H | Br | H | heptafluoroisopropyl | H | CF3 |
| 11-66 | H | F | H | H | H | I | H | heptafluoroisopropyl | H | CF3 |
| 11-67 | H | F | H | H | H | F | H | nonafluoro-2-butyl | H | CF3 |
| 11-68 | H | F | H | H | H | Cl | H | nonafluoro-2-butyl | H | CF3 |
| 11-69 | H | F | H | H | H | Br | H | nonafluoro-2-butyl | H | CF3 |
| 11-70 | H | F | H | H | H | I | H | nonafluoro-2-butyl | H | CF3 |
| 11-71 | H | F | H | H | H | OCF3 | H | heptafluoroisopropyl | H | CF3 |
| 11-72 | H | F | H | H | H | OCF3 | H | nonafluoro-2-butyl | H | CF3 |
| 11-73 | H | F | H | H | H | CF3 | H | heptafluoroisopropyl | H | CF3 |
| 11-74 | H | F | H | H | H | CF3 | H | nonafluoro-2-butyl | H | CF3 |
| 11-75 | H | F | H | H | H | Br | H | heptafluoroisopropyl | H | C2F5 |
| 11-76 | H | H | F | H | H | Br | H | heptafluoroisopropyl | H | Br |
| 11-77 | H | H | F | H | H | Br | H | heptafluoroisopropyl | H | Cl |
| 11-78 | H | H | F | H | H | I | H | nonafluoro-2-butyl | H | I |
| 11-79 | H | H | F | H | H | Br | H | nonafluoro-2-butyl | H | I |
| 11-80 | H | H | F | H | H | Br | H | heptafluoroisopropyl | H | OCF3 |
| 11-81 | H | H | F | H | H | I | H | nonafluoro-2-butyl | H | OCF3 |
| 11-82 | H | H | F | H | H | Br | H | pentafluoroethyl | H | CF3 |
| 11-83 | H | H | F | H | H | Cl | H | heptafluoroisopropyl | H | CF3 |
| 11-84 | H | H | F | H | H | Br | H | heptafluoroisopropyl | H | CF3 |
| 11-85 | H | H | F | H | H | I | H | heptafluoroisopropyl | H | CF3 |
| 11-86 | H | H | F | H | H | Cl | H | nonafluoro-2-butyl | H | CF3 |
| 11-87 | H | H | F | H | H | Br | H | nonafluoro-2-butyl | H | CF3 |
| 11-88 | H | H | F | H | H | I | H | nonafluoro-2-butyl | H | CF3 |
| 11-89 | H | H | F | H | H | OCF3 | H | heptafluoroisopropyl | H | CF3 |
| 11-90 | H | H | F | H | H | OCF3 | H | nonafluoro-2-butyl | H | CF3 |
| 11-91 | H | H | F | H | H | CF3 | H | heptafluoroisopropyl | H | CF3 |
| 11-92 | H | H | F | H | H | CF3 | H | nonafluoro-2-butyl | H | CF3 |
| 11-93 | H | H | F | H | H | Br | H | heptafluoroisopropyl | H | C2F5 |
| 11-94 | H | H | I | H | H | Br | H | heptafluoroisopropyl | H | Br |
| 11-95 | H | H | I | H | H | Br | H | heptafluoroisopropyl | H | I |
| 11-96 | H | H | I | H | H | I | H | nonafluoro-2-butyl | H | I |
| 11-97 | H | H | I | H | H | Br | H | nonafluoro-2-butyl | H | Cl |
| 11-98 | H | H | I | H | H | I | H | heptafluoroisopropyl | H | OCF3 |
| 11-99 | H | H | I | H | H | Br | H | nonafluoro-2-butyl | H | OCF3 |
| 11-100 | H | H | I | H | H | Cl | H | heptafluoroisopropyl | H | CF3 |
| 11-101 | H | H | I | H | H | Br | H | heptafluoroisopropyl | H | CF3 |
| 11-102 | H | H | I | H | H | I | H | heptafluoroisopropyl | H | CF3 |
| 11-103 | H | H | I | H | H | Br | H | nonafluoro-2-butyl | H | CF3 |
| 11-104 | H | H | I | H | H | I | H | nonafluoro-2-butyl | H | CF3 |
| 11-105 | H | H | I | H | H | OCF3 | H | heptafluoroisopropyl | H | CF3 |
| 11-106 | H | H | I | H | H | OCF3 | H | nonafluoro-2-butyl | H | CF3 |
| 11-107 | H | H | I | H | H | CF3 | H | heptafluoroisopropyl | H | CF3 |
| 11-108 | H | H | I | H | H | CF3 | H | nonafluoro-2-butyl | H | CF3 |
| 11-109 | H | H | I | H | H | Br | H | heptafluoroisopropyl | H | C2F5 |
| 11-110 | H | H | CN | H | H | Cl | H | heptafluoroisopropyl | H | Cl |
| 11-112 | H | H | CN | H | H | I | H | heptafluoroisopropyl | H | I |
| 11-113 | H | H | CN | H | H | Br | H | heptafluoroisopropyl | H | Cl |
| 11-114 | H | H | CN | H | H | Cl | H | nonafluoro-2-butyl | H | Cl |
| 11-115 | H | H | CN | H | H | Br | H | nonafluoro-2-butyl | H | Br |
| 11-116 | H | H | CN | H | H | I | H | nonafluoro-2-butyl | H | I |
| 11-117 | H | H | CN | H | H | Br | H | nonafluoro-2-butyl | H | I |
| 11-118 | H | H | CN | H | H | Br | H | heptafluoroisopropyl | H | OCF3 |
| 11-119 | H | H | CN | H | H | I | H | nonafluoro-2-butyl | H | OCF3 |
| 11-120 | H | H | CN | H | H | Br | H | pentafluoroethyl | H | CF3 |
| 11-121 | H | H | CN | H | H | Cl | H | heptafluoroisopropyl | H | CF3 |
| 11-122 | H | H | CN | H | H | Br | H | heptafluoroisopropyl | H | CF3 |
| 11-123 | H | H | CN | H | H | I | H | heptafluoroisopropyl | H | CF3 |

TABLE 11-continued

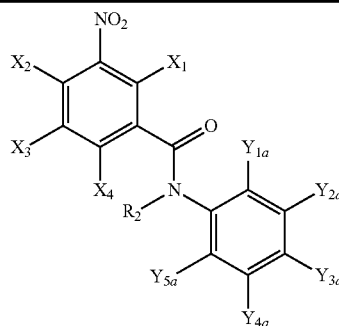

| compound number | R$_2$ | X$_1$ | X$_2$ | X$_3$ | X$_4$ | Y$_{1a}$ | Y$_{2a}$ | Y$_{3a}$ | Y$_{4a}$ | Y$_{5a}$ |
|---|---|---|---|---|---|---|---|---|---|---|
| 11-124 | H | H | CN | H | H | Cl | H | nonafluoro-2-butyl | H | CF3 |
| 11-125 | H | H | CN | H | H | Br | H | nonafluoro-2-butyl | H | CF3 |
| 11-126 | H | H | CN | H | H | I | H | nonafluoro-2-butyl | H | CF3 |
| 11-127 | H | H | CN | H | H | OCF3 | H | heptafluoroisopropyl | H | CF3 |
| 11-128 | H | H | CN | H | H | OCF3 | H | nonafluoro-2-butyl | H | CF3 |
| 11-129 | H | H | CN | H | H | CF3 | H | heptafluoroisopropyl | H | CF3 |
| 11-130 | H | H | CN | H | H | CF3 | H | nonafluoro-2-butyl | H | CF3 |
| 11-131 | H | H | CN | H | H | Br | H | heptafluoroisopropyl | H | C2F5 |
| 11-132 | Me | H | H | H | H | Br | H | heptafluoroisopropyl | H | Br |
| 11-133 | Me | H | H | H | H | I | H | nonafluoro-2-butyl | H | I |
| 11-134 | Me | H | H | H | H | Br | H | heptafluoroisopropyl | H | OCF3 |
| 11-135 | Me | H | H | H | H | Br | H | nonafluoro-2-butyl | H | OCF3 |
| 11-136 | Me | H | H | H | H | Br | H | heptafluoroisopropyl | H | CF3 |
| 11-137 | Me | H | H | H | H | I | H | heptafluoroisopropyl | H | CF3 |
| 11-138 | Me | H | H | H | H | Br | H | nonafluoro-2-butyl | H | CF3 |
| 11-139 | Me | H | H | H | H | I | H | nonafluoro-2-butyl | H | CF3 |
| 11-140 | Me | H | H | H | H | OCF3 | H | heptafluoroisopropyl | H | CF3 |
| 11-141 | Me | H | H | H | H | OCF3 | H | nonafluoro-2-butyl | H | CF3 |
| 11-142 | Me | H | H | H | H | CF3 | H | heptafluoroisopropyl | H | CF3 |
| 11-143 | Me | H | H | H | H | CF3 | H | nonafluoro-2-butyl | H | CF3 |
| 11-144 | Me | Cl | H | H | H | Br | H | heptafluoroisopropyl | H | Br |
| 11-145 | Me | Cl | H | H | H | I | H | nonafluoro-2-butyl | H | I |
| 11-146 | Me | Cl | H | H | H | Br | H | heptafluoroisopropyl | H | OCF3 |
| 11-147 | Me | Cl | H | H | H | Br | H | nonafluoro-2-butyl | H | OCF3 |
| 11-148 | Me | Cl | H | H | H | Br | H | heptafluoroisopropyl | H | CF3 |
| 11-149 | Me | Cl | H | H | H | I | H | heptafluoroisopropyl | H | CF3 |
| 11-150 | Me | Cl | H | H | H | Br | H | nonafluoro-2-butyl | H | CF3 |
| 11-151 | Me | Cl | H | H | H | I | H | nonafluoro-2-butyl | H | CF3 |
| 11-152 | Me | Cl | H | H | H | OCF3 | H | heptafluoroisopropyl | H | CF3 |
| 11-153 | Me | Cl | H | H | H | OCF3 | H | nonafluoro-2-butyl | H | CF3 |
| 11-154 | Me | Cl | H | H | H | CF3 | H | heptafluoroisopropyl | H | CF3 |
| 11-155 | Me | Cl | H | H | H | CF3 | H | nonafluoro-2-butyl | H | CF3 |
| 11-156 | Me | F | H | H | H | Br | H | heptafluoroisopropyl | H | Br |
| 11-157 | Me | F | H | H | H | I | H | nonafluoro-2-butyl | H | I |
| 11-158 | Me | F | H | H | H | Br | H | heptafluoroisopropyl | H | OCF3 |
| 11-159 | Me | F | H | H | H | Br | H | nonafluoro-2-butyl | H | OCF3 |
| 11-160 | Me | F | H | H | H | Br | H | heptafluoroisopropyl | H | CF3 |
| 11-161 | Me | F | H | H | H | I | H | heptafluoroisopropyl | H | CF3 |
| 11-162 | Me | F | H | H | H | Cl | H | nonafluoro-2-butyl | H | CF3 |
| 11-163 | Me | F | H | H | H | Br | H | nonafluoro-2-butyl | H | CF3 |
| 11-164 | Me | F | H | H | H | I | H | nonafluoro-2-butyl | H | CF3 |
| 11-165 | Et | F | H | H | H | OCF3 | H | heptafluoroisopropyl | H | CF3 |
| 11-166 | Me | F | H | H | H | OCF3 | H | nonafluoro-2-butyl | H | CF3 |
| 11-167 | Me | F | H | H | H | CF3 | H | heptafluoroisopropyl | H | CF3 |
| 11-168 | Me | F | H | H | H | CF3 | H | nonafluoro-2-butyl | H | CF3 |
| 11-169 | Me | H | F | H | H | Br | H | heptafluoroisopropyl | H | Br |
| 11-170 | Me | H | F | H | H | I | H | nonafluoro-2-butyl | H | I |
| 11-171 | Me | H | F | H | H | Br | H | heptafluoroisopropyl | H | OCF3 |
| 11-172 | Me | H | F | H | H | Br | H | nonafluoro-2-butyl | H | OCF3 |
| 11-173 | Me | H | F | H | H | Br | H | heptafluoroisopropyl | H | CF3 |
| 11-174 | Me | H | F | H | H | I | H | nonafluoro-2-butyl | H | CF3 |
| 11-175 | Me | H | F | H | H | OCF3 | H | heptafluoroisopropyl | H | CF3 |
| 11-176 | nPr | H | F | H | H | OCF3 | H | nonafluoro-2-butyl | H | CF3 |
| 11-177 | Me | H | F | H | H | CF3 | H | heptafluoroisopropyl | H | CF3 |
| 11-178 | Me | H | F | H | H | CF3 | H | nonafluoro-2-butyl | H | CF3 |
| 11-179 | Me | H | I | H | H | Br | H | heptafluoroisopropyl | H | Br |
| 11-180 | Me | H | I | H | H | I | H | nonafluoro-2-butyl | H | I |
| 11-181 | Me | H | I | H | H | Br | H | heptafluoroisopropyl | H | OCF3 |
| 11-182 | Me | H | I | H | H | Br | H | nonafluoro-2-butyl | H | OCF3 |
| 11-183 | Me | H | I | H | H | Br | H | heptafluoroisopropyl | H | CF3 |
| 11-184 | Me | H | I | H | H | I | H | nonafluoro-2-butyl | H | CF3 |

TABLE 11-continued

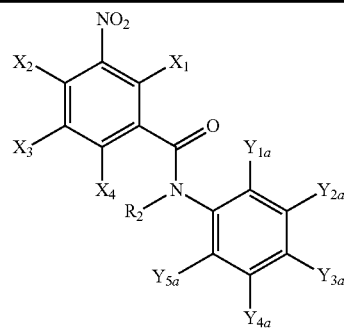

| compound number | R₂ | X₁ | X₂ | X₃ | X₄ | Y₁ₐ | Y₂ₐ | Y₃ₐ | Y₄ₐ | Y₅ₐ |
|---|---|---|---|---|---|---|---|---|---|---|
| 11-185 | Me | H | I | H | H | OCF3 | H | heptafluoroisopropyl | H | CF3 |
| 11-186 | iPr | H | I | H | H | OCF3 | H | nonafluoro-2-butyl | H | CF3 |
| 11-187 | Me | H | I | H | H | CF3 | H | heptafluoroisopropyl | H | CF3 |
| 11-188 | Me | H | I | H | H | CF3 | H | nonafluoro-2-butyl | H | CF3 |
| 11-189 | Me | H | CN | H | H | Br | H | heptafluoroisopropyl | H | Br |
| 11-190 | Me | H | CN | H | H | I | H | nonafluoro-2-butyl | H | I |
| 11-191 | Me | H | CN | H | H | Br | H | heptafluoroisopropyl | H | OCF3 |
| 11-192 | Me | H | CN | H | H | Br | H | nonafluoro-2-butyl | H | OCF3 |
| 11-193 | Me | H | CN | H | H | I | H | heptafluoroisopropyl | H | CF3 |
| 11-194 | Me | H | CN | H | H | Br | H | nonafluoro-2-butyl | H | CF3 |
| 11-195 | Me | H | CN | H | H | OCF3 | H | heptafluoroisopropyl | H | CF3 |
| 11-196 | Me | H | CN | H | H | OCF3 | H | nonafluoro-2-butyl | H | CF3 |
| 11-197 | Me | H | CN | H | H | CF3 | H | heptafluoroisopropyl | H | CF3 |
| 11-198 | Me | H | CN | H | H | CF3 | H | nonafluoro-2-butyl | H | CF3 |
| 11-199 | H | F | H | H | H | Br | H | heptafluoroisopropyl | F | CF3 |
| 11-200 | H | F | H | H | H | Br | Me | nonafluoro-2-butyl | H | CF3 |
| 11-201 | H | F | H | H | H | Br | F | heptafluoroisopropyl | Cl | CF3 |
| 11-202 | H | F | H | H | H | Br | Me | nonafluoro-2-butyl | F | CF3 |
| 11-203 | H | F | H | H | H | Br | Et | heptafluoroisopropyl | Me | CF3 |
| 11-204 | Me | F | H | H | H | I | H | heptafluoroisopropyl | F | CF3 |
| 11-205 | Me | F | H | H | H | I | Me | nonafluoro-2-butyl | H | CF3 |
| 11-206 | Me | F | H | H | H | I | F | heptafluoroisopropyl | Cl | CF3 |
| 11-207 | Me | F | H | H | H | I | Me | nonafluoro-2-butyl | F | CF3 |
| 11-208 | Me | F | H | H | H | I | Et | heptafluoroisopropyl | Me | CF3 |

TABLE 12

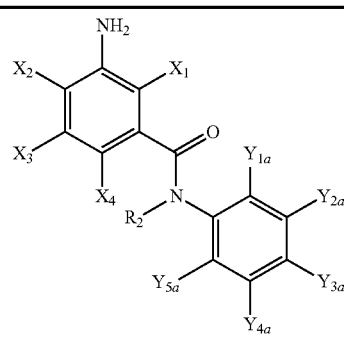

| compound number | R₂ | X₁ | X₂ | X₃ | X₄ | Y₁ₐ | Y₂ₐ | Y₃ₐ | Y₄ₐ | Y₅ₐ |
|---|---|---|---|---|---|---|---|---|---|---|
| 12-1 | H | H | H | H | H | Cl | H | nonafluoro-2-butyl | H | Cl |
| 12-2 | H | H | H | H | H | Br | H | nonafluoro-2-butyl | H | Br |
| 12-3 | H | H | H | H | H | I | H | nonafluoro-2-butyl | H | I |
| 12-4 | H | H | H | H | H | Br | H | nonafluoro-2-butyl | H | OCF3 |
| 12-5 | H | H | H | H | H | Br | H | pentafluoroethyl | H | CF3 |
| 12-6 | H | H | H | H | H | Cl | H | heptafluoroisopropyl | H | CF3 |
| 12-7 | H | H | H | H | H | Br | H | heptafluoroisopropyl | H | CF3 |
| 12-8 | H | H | H | H | H | I | H | heptafluoroisopropyl | H | CF3 |
| 12-9 | H | H | H | H | H | Cl | H | nonafluoro-2-butyl | H | CF3 |
| 12-10 | H | H | H | H | H | Br | H | nonafluoro-2-butyl | H | CF3 |
| 12-11 | H | H | H | H | H | I | H | nonafluoro-2-butyl | H | CF3 |
| 12-12 | H | H | H | H | H | OCF3 | H | heptafluoroisopropyl | H | CF3 |

TABLE 12-continued

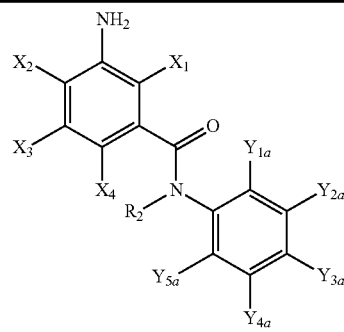

| compound number | R2 | X1 | X2 | X3 | X4 | Y1a | Y2a | Y3a | Y4a | Y5a |
|---|---|---|---|---|---|---|---|---|---|---|
| 12-13 | H | H | H | H | H | OCF3 | H | nonafluoro-2-butyl | H | CF3 |
| 12-14 | H | H | H | H | H | CF3 | H | heptafluoroisopropyl | H | CF3 |
| 12-15 | H | H | H | H | H | CF3 | H | nonafluoro-2-butyl | H | CF3 |
| 12-16 | H | H | H | H | H | Br | H | heptafluoroisopropyl | H | C2F5 |
| 12-17 | H | Cl | H | H | H | Br | H | heptafluoroisopropyl | H | Br |
| 12-18 | H | Cl | H | H | H | I | H | nonafluoro-2-butyl | H | I |
| 12-19 | H | Cl | H | H | H | Br | H | heptafluoroisopropyl | H | OCF3 |
| 12-20 | H | Cl | H | H | H | I | H | nonafluoro-2-butyl | H | OCF3 |
| 12-21 | H | Cl | H | H | H | Br | H | heptafluoroisopropyl | H | CF3 |
| 12-22 | H | Cl | H | H | H | I | H | nonafluoro-2-butyl | H | CF3 |
| 12-23 | H | Cl | H | H | H | OCF3 | H | heptafluoroisopropyl | H | CF3 |
| 12-24 | H | Cl | H | H | H | CF3 | H | heptafluoroisopropyl | H | CF3 |
| 12-25 | H | F | H | H | H | Cl | H | heptafluoroisopropyl | H | Cl |
| 12-26 | H | F | H | H | H | Br | H | heptafluoroisopropyl | H | Br |
| 12-27 | H | F | H | H | H | I | H | heptafluoroisopropyl | H | I |
| 12-28 | H | F | H | H | H | Br | H | heptafluoroisopropyl | H | Cl |
| 12-29 | H | F | H | H | H | Br | H | heptafluoroisopropyl | H | I |
| 12-30 | H | F | H | H | H | Br | H | nonafluoro-2-butyl | H | Br |
| 12-31 | H | F | H | H | H | I | H | nonafluoro-2-butyl | H | I |
| 12-32 | H | F | H | H | H | Br | H | nonafluoro-2-butyl | H | I |
| 12-33 | H | F | H | H | H | Br | H | heptafluoroisopropyl | H | OCF3 |
| 12-34 | H | F | H | H | H | I | H | nonafluoro-2-butyl | H | OCF3 |
| 12-35 | H | F | H | H | H | Br | H | pentafluoroethyl | H | CF3 |
| 12-36 | H | F | H | H | H | Cl | H | heptafluoroisopropyl | H | CF3 |
| 12-37 | H | F | H | H | H | Br | H | heptafluoroisopropyl | H | CF3 |
| 12-38 | H | F | H | H | H | I | H | heptafluoroisopropyl | H | CF3 |
| 12-39 | H | F | H | H | H | Cl | H | nonafluoro-2-butyl | H | CF3 |
| 12-40 | H | F | H | H | H | Br | H | nonafluoro-2-butyl | H | CF3 |
| 12-41 | H | F | H | H | H | I | H | nonafluoro-2-butyl | H | CF3 |
| 12-42 | H | F | H | H | H | OCF3 | H | heptafluoroisopropyl | H | CF3 |
| 12-43 | H | F | H | H | H | OCF3 | H | nonafluoro-2-butyl | H | CF3 |
| 12-44 | H | F | H | H | H | CF3 | H | heptafluoroisopropyl | H | CF3 |
| 12-45 | H | F | H | H | H | CF3 | H | nonafluoro-2-butyl | H | CF3 |
| 12-46 | H | F | H | H | H | Br | H | heptafluoroisopropyl | H | C2F5 |
| 12-47 | H | H | F | H | H | Br | H | heptafluoroisopropyl | H | Br |
| 12-48 | H | H | F | H | H | Br | H | heptafluoroisopropyl | H | Cl |
| 12-49 | H | H | F | H | H | I | H | nonafluoro-2-butyl | H | I |
| 12-50 | H | H | F | H | H | Br | H | nonafluoro-2-butyl | H | I |
| 12-51 | H | H | F | H | H | Br | H | heptafluoroisopropyl | H | OCF3 |
| 12-52 | H | H | F | H | H | I | H | nonafluoro-2-butyl | H | OCF3 |
| 12-53 | H | H | F | H | H | Br | H | heptafluoroisopropyl | H | CF3 |
| 12-54 | H | H | F | H | H | I | H | nonafluoro-2-butyl | H | CF3 |
| 12-55 | H | H | F | H | H | OCF3 | H | heptafluoroisopropyl | H | CF3 |
| 12-56 | H | H | F | H | H | OCF3 | H | nonafluoro-2-butyl | H | CF3 |
| 12-57 | H | H | F | H | H | CF3 | H | heptafluoroisopropyl | H | CF3 |
| 12-58 | H | H | F | H | H | CF3 | H | nonafluoro-2-butyl | H | CF3 |
| 12-59 | H | H | I | H | H | I | H | heptafluoroisopropyl | H | I |
| 12-60 | H | H | I | H | H | Br | H | nonafluoro-2-butyl | H | Br |
| 12-61 | H | H | I | H | H | Br | H | heptafluoroisopropyl | H | OCF3 |
| 12-62 | H | H | I | H | H | I | H | nonafluoro-2-butyl | H | OCF3 |
| 12-63 | H | H | I | H | H | Cl | H | heptafluoroisopropyl | H | CF3 |
| 12-64 | H | H | I | H | H | Br | H | heptafluoroisopropyl | H | CF3 |
| 12-65 | H | H | I | H | H | I | H | heptafluoroisopropyl | H | CF3 |
| 12-66 | H | H | I | H | H | Br | H | nonafluoro-2-butyl | H | CF3 |
| 12-67 | H | H | I | H | H | I | H | nonafluoro-2-butyl | H | CF3 |
| 12-68 | H | H | I | H | H | OCF3 | H | heptafluoroisopropyl | H | CF3 |
| 12-69 | H | H | I | H | H | OCF3 | H | nonafluoro-2-butyl | H | CF3 |
| 12-70 | H | H | I | H | H | CF3 | H | heptafluoroisopropyl | H | CF3 |
| 12-71 | H | H | I | H | H | CF3 | H | nonafluoro-2-butyl | H | CF3 |
| 12-73 | H | H | CN | H | H | Br | H | heptafluoroisopropyl | H | Cl |
| 12-74 | H | H | CN | H | H | I | H | nonafluoro-2-butyl | H | I |

TABLE 12-continued

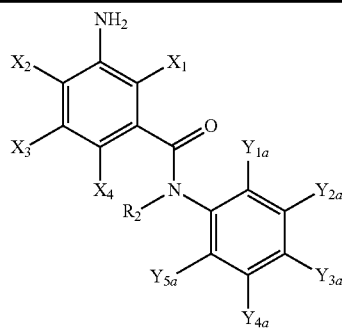

| compound number | $R_2$ | $X_1$ | $X_2$ | $X_3$ | $X_4$ | $Y_{1a}$ | $Y_{2a}$ | $Y_{3a}$ | $Y_{4a}$ | $Y_{5a}$ |
|---|---|---|---|---|---|---|---|---|---|---|
| 12-75 | H | H | CN | H | H | Br | H | nonafluoro-2-butyl | H | I |
| 12-76 | H | H | CN | H | H | Br | H | heptafluoroisopropyl | H | OCF3 |
| 12-77 | H | H | CN | H | H | I | H | nonafluoro-2-butyl | H | OCF3 |
| 12-78 | H | H | CN | H | H | Cl | H | heptafluoroisopropyl | H | CF3 |
| 12-79 | H | H | CN | H | H | Br | H | heptafluoroisopropyl | H | CF3 |
| 12-80 | H | H | CN | H | H | I | H | heptafluoroisopropyl | H | CF3 |
| 12-81 | H | H | CN | H | H | Cl | H | nonafluoro-2-butyl | H | CF3 |
| 12-82 | H | H | CN | H | H | Br | H | nonafluoro-2-butyl | H | CF3 |
| 12-83 | H | H | CN | H | H | I | H | nonafluoro-2-butyl | H | CF3 |
| 12-84 | H | H | CN | H | H | OCF3 | H | heptafluoroisopropyl | H | CF3 |
| 12-85 | H | H | CN | H | H | OCF3 | H | nonafluoro-2-butyl | H | CF3 |
| 12-86 | H | H | CN | H | H | CF3 | H | heptafluoroisopropyl | H | CF3 |
| 12-87 | H | H | CN | H | H | CF3 | H | nonafluoro-2-butyl | H | CF3 |
| 12-88 | H | H | CN | H | H | Br | H | heptafluoroisopropyl | H | C2F5 |
| 12-89 | H | F | CN | H | H | Br | H | heptafluoroisopropyl | H | Br |
| 12-90 | H | F | CN | H | H | I | H | nonafluoro-2-butyl | H | I |
| 12-91 | H | F | CN | H | H | Br | H | heptafluoroisopropyl | H | OCF3 |
| 12-92 | H | F | CN | H | H | I | H | nonafluoro-2-butyl | H | OCF3 |
| 12-93 | H | F | CN | H | H | Cl | H | heptafluoroisopropyl | H | CF3 |
| 12-94 | H | F | CN | H | H | Br | H | heptafluoroisopropyl | H | CF3 |
| 12-95 | H | F | CN | H | H | I | H | heptafluoroisopropyl | H | CF3 |
| 12-96 | H | F | CN | H | H | Cl | H | nonafluoro-2-butyl | H | CF3 |
| 12-97 | H | F | CN | H | H | Br | H | nonafluoro-2-butyl | H | CF3 |
| 12-98 | H | F | CN | H | H | I | H | nonafluoro-2-butyl | H | CF3 |
| 12-99 | H | F | CN | H | H | OCF3 | H | heptafluoroisopropyl | H | CF3 |
| 12-100 | H | F | CN | H | H | OCF3 | H | nonafluoro-2-butyl | H | CF3 |
| 12-101 | H | F | CN | H | H | CF3 | H | heptafluoroisopropyl | H | CF3 |
| 12-102 | H | F | CN | H | H | CF3 | H | nonafluoro-2-butyl | H | CF3 |
| 12-103 | Me | H | H | H | H | Br | H | heptafluoroisopropyl | H | Br |
| 12-104 | Me | H | H | H | H | I | H | nonafluoro-2-butyl | H | I |
| 12-105 | Me | H | H | H | H | Br | H | heptafluoroisopropyl | H | OCF3 |
| 12-106 | Me | H | H | H | H | Br | H | nonafluoro-2-butyl | H | OCF3 |
| 12-107 | Me | H | H | H | H | Br | H | heptafluoroisopropyl | H | CF3 |
| 12-108 | Me | H | H | H | H | I | H | nonafluoro-2-butyl | H | CF3 |
| 12-109 | Me | H | H | H | H | OCF3 | H | heptafluoroisopropyl | H | CF3 |
| 12-110 | Me | H | H | H | H | OCF3 | H | nonafluoro-2-butyl | H | CF3 |
| 12-111 | Me | H | H | H | H | CF3 | H | heptafluoroisopropyl | H | CF3 |
| 12-112 | Me | H | H | H | H | CF3 | H | nonafluoro-2-butyl | H | CF3 |
| 12-113 | Me | Cl | H | H | H | Br | H | heptafluoroisopropyl | H | Br |
| 12-114 | Me | Cl | H | H | H | I | H | nonafluoro-2-butyl | H | I |
| 12-115 | Me | Cl | H | H | H | Br | H | heptafluoroisopropyl | H | OCF3 |
| 12-116 | Me | Cl | H | H | H | Br | H | nonafluoro-2-butyl | H | OCF3 |
| 12-117 | Me | Cl | H | H | H | I | H | heptafluoroisopropyl | H | CF3 |
| 12-118 | Me | Cl | H | H | H | Br | H | nonafluoro-2-butyl | H | CF3 |
| 12-119 | Me | Cl | H | H | H | OCF3 | H | heptafluoroisopropyl | H | CF3 |
| 12-120 | Me | Cl | H | H | H | OCF3 | H | nonafluoro-2-butyl | H | CF3 |
| 12-121 | Me | Cl | H | H | H | CF3 | H | heptafluoroisopropyl | H | CF3 |
| 12-122 | Me | Cl | H | H | H | CF3 | H | nonafluoro-2-butyl | H | CF3 |
| 12-123 | Me | F | H | H | H | Br | H | heptafluoroisopropyl | H | Br |
| 12-124 | Me | F | H | H | H | I | H | nonafluoro-2-butyl | H | I |
| 12-125 | Me | F | H | H | H | Br | H | heptafluoroisopropyl | H | OCF3 |
| 12-126 | Me | F | H | H | H | Br | H | nonafluoro-2-butyl | H | OCF3 |
| 12-127 | Me | F | H | H | H | Br | H | heptafluoroisopropyl | H | CF3 |
| 12-128 | Me | F | H | H | H | I | H | heptafluoroisopropyl | H | CF3 |
| 12-129 | Me | F | H | H | H | Br | H | nonafluoro-2-butyl | H | CF3 |
| 12-130 | Me | F | H | H | H | I | H | nonafluoro-2-butyl | H | CF3 |
| 12-131 | Me | F | H | H | H | OCF3 | H | heptafluoroisopropyl | H | CF3 |
| 12-132 | Me | F | H | H | H | OCF3 | H | nonafluoro-2-butyl | H | CF3 |
| 12-133 | Me | F | H | H | H | CF3 | H | heptafluoroisopropyl | H | CF3 |
| 12-134 | Me | F | H | H | H | CF3 | H | nonafluoro-2-butyl | H | CF3 |
| 12-135 | Me | H | F | H | H | Br | H | heptafluoroisopropyl | H | Br |

TABLE 12-continued

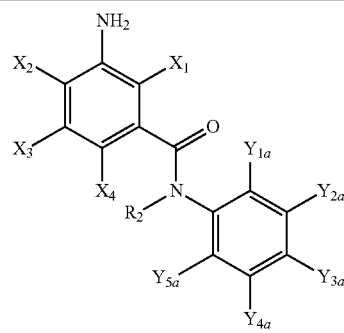

| compound number | $R_2$ | $X_1$ | $X_2$ | $X_3$ | $X_4$ | $Y_{1a}$ | $Y_{2a}$ | $Y_{3a}$ | $Y_{4a}$ | $Y_{5a}$ |
|---|---|---|---|---|---|---|---|---|---|---|
| 12-136 | Me | H | F | H | H | I | H | nonafluoro-2-butyl | H | I |
| 12-137 | Me | H | F | H | H | Br | H | heptafluoroisopropyl | H | OCF3 |
| 12-138 | Me | H | F | H | H | Br | H | nonafluoro-2-butyl | H | OCF3 |
| 12-139 | Me | H | F | H | H | Br | H | heptafluoroisopropyl | H | CF3 |
| 12-140 | Me | H | F | H | H | I | H | nonafluoro-2-butyl | H | CF3 |
| 12-141 | Et | H | F | H | H | OCF3 | H | heptafluoroisopropyl | H | CF3 |
| 12-142 | Me | H | F | H | H | OCF3 | H | nonafluoro-2-butyl | H | CF3 |
| 12-143 | Me | H | F | H | H | CF3 | H | heptafluoroisopropyl | H | CF3 |
| 12-144 | Me | H | F | H | H | CF3 | H | nonafluoro-2-butyl | H | CF3 |
| 12-145 | Me | H | I | H | H | Br | H | heptafluoroisopropyl | H | Br |
| 12-146 | Me | H | I | H | H | I | H | nonafluoro-2-butyl | H | I |
| 12-147 | Me | H | I | H | H | Br | H | heptafluoroisopropyl | H | OCF3 |
| 12-148 | Me | H | I | H | H | Br | H | nonafluoro-2-butyl | H | OCF3 |
| 12-149 | Me | H | I | H | H | I | H | heptafluoroisopropyl | H | CF3 |
| 12-150 | Me | H | I | H | H | Br | H | nonafluoro-2-butyl | H | CF3 |
| 12-151 | Me | H | I | H | H | OCF3 | H | heptafluoroisopropyl | H | CF3 |
| 12-152 | iPr | H | I | H | H | OCF3 | H | nonafluoro-2-butyl | H | CF3 |
| 12-153 | Me | H | I | H | H | CF3 | H | heptafluoroisopropyl | H | CF3 |
| 12-154 | Me | H | I | H | H | CF3 | H | nonafluoro-2-butyl | H | CF3 |
| 12-155 | Me | H | CN | H | H | Br | H | heptafluoroisopropyl | H | Br |
| 12-156 | Me | H | CN | H | H | I | H | nonafluoro-2-butyl | H | I |
| 12-157 | Me | H | CN | H | H | Br | H | heptafluoroisopropyl | H | OCF3 |
| 12-158 | Me | H | CN | H | H | Br | H | nonafluoro-2-butyl | H | OCF3 |
| 12-159 | Me | H | CN | H | H | Br | H | heptafluoroisopropyl | H | CF3 |
| 12-160 | Me | H | CN | H | H | I | H | nonafluoro-2-butyl | H | CF3 |
| 12-161 | Me | H | CN | H | H | OCF3 | H | heptafluoroisopropyl | H | CF3 |
| 12-162 | Me | H | CN | H | H | OCF3 | H | nonafluoro-2-butyl | H | CF3 |
| 12-163 | Me | H | CN | H | H | CF3 | H | heptafluoroisopropyl | H | CF3 |
| 12-164 | Me | H | CN | H | H | CF3 | H | nonafluoro-2-butyl | H | CF3 |
| 12-165 | Me | F | CN | H | H | Br | H | heptafluoroisopropyl | H | Br |
| 12-166 | Me | F | CN | H | H | I | H | nonafluoro-2-butyl | H | I |
| 12-167 | Me | F | CN | H | H | Br | H | heptafluoroisopropyl | H | OCF3 |
| 12-168 | Me | F | CN | H | H | Br | H | nonafluoro-2-butyl | H | OCF3 |
| 12-169 | Me | F | CN | H | H | Br | H | heptafluoroisopropyl | H | CF3 |
| 12-170 | Me | F | CN | H | H | I | H | nonafluoro-2-butyl | H | CF3 |
| 12-171 | nPr | F | CN | H | H | OCF3 | H | heptafluoroisopropyl | H | CF3 |
| 12-172 | Me | F | CN | H | H | OCF3 | H | nonafluoro-2-butyl | H | CF3 |
| 12-173 | Me | F | CN | H | H | CF3 | H | heptafluoroisopropyl | H | CF3 |
| 12-174 | Me | F | CN | H | H | CF3 | H | nonafluoro-2-butyl | H | CF3 |
| 12-175 | H | F | H | H | H | Br | H | heptafluoroisopropyl | F | CF3 |
| 12-176 | H | F | H | H | H | Br | Me | nonafluoro-2-butyl | H | CF3 |
| 12-177 | H | F | H | H | H | Br | F | heptafluoroisopropyl | Cl | CF3 |
| 12-178 | H | F | H | H | H | Br | Me | nonafluoro-2-butyl | F | CF3 |
| 12-179 | H | F | H | H | H | Br | Et | heptafluoroisopropyl | Me | CF3 |
| 12-180 | Me | F | H | H | H | I | H | heptafluoroisopropyl | F | CF3 |
| 12-181 | Me | F | H | H | H | I | Me | nonafluoro-2-butyl | H | CF3 |
| 12-182 | Me | F | H | H | H | I | F | heptafluoroisopropyl | Cl | CF3 |
| 12-183 | Me | F | H | H | H | I | Me | nonafluoro-2-butyl | F | CF3 |
| 12-184 | Me | F | H | H | H | I | Et | heptafluoroisopropyl | Me | CF3 |

TABLE 13

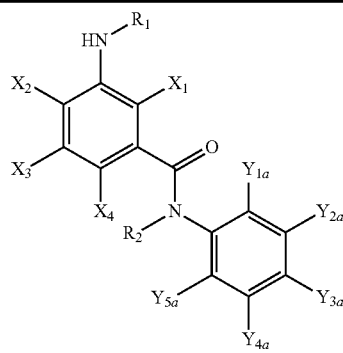

| compound number | $R_1$ | $R_2$ | $X_1$ | $X_2$ | $X_3$ | $X_4$ | $Y_{1a}$ | $Y_{2a}$ | $Y_{3a}$ | $Y_{4a}$ | $Y_{5a}$ |
|---|---|---|---|---|---|---|---|---|---|---|---|
| 13-1 | Me | H | H | H | H | H | Br | H | nonafluoro-2-butyl | H | Br |
| 13-2 | Me | H | H | H | H | H | I | H | nonafluoro-2-butyl | H | I |
| 13-3 | Me | H | H | H | H | H | Br | H | nonafluoro-2-butyl | H | OCF3 |
| 13-4 | Me | H | H | H | H | H | Br | H | pentafluoroethyl | H | CF3 |
| 13-5 | Me | H | H | H | H | H | Cl | H | heptafluoroisopropyl | H | CF3 |
| 13-6 | Me | H | H | H | H | H | Br | H | heptafluoroisopropyl | H | CF3 |
| 13-7 | Me | H | H | H | H | H | I | H | heptafluoroisopropyl | H | CF3 |
| 13-8 | Me | H | H | H | H | H | Br | H | nonafluoro-2-butyl | H | CF3 |
| 13-9 | Me | H | H | H | H | H | I | H | nonafluoro-2-butyl | H | CF3 |
| 13-10 | Me | H | H | H | H | H | OCF3 | H | heptafluoroisopropyl | H | CF3 |
| 13-11 | Me | H | H | H | H | H | OCF3 | H | nonafluoro-2-butyl | H | CF3 |
| 13-12 | Me | H | H | H | H | H | CF3 | H | heptafluoroisopropyl | H | CF3 |
| 13-13 | Me | H | H | H | H | H | CF3 | H | nonafluoro-2-butyl | H | CF3 |
| 13-14 | Me | H | H | H | H | H | Br | H | heptafluoroisopropyl | H | C2F5 |
| 13-15 | Me | H | Cl | H | H | H | Br | H | heptafluoroisopropyl | H | Br |
| 13-16 | Me | H | Cl | H | H | H | I | H | nonafluoro-2-butyl | H | I |
| 13-17 | Me | H | Cl | H | H | H | Br | H | heptafluoroisopropyl | H | OCF3 |
| 13-18 | Me | H | Cl | H | H | H | I | H | nonafluoro-2-butyl | H | OCF3 |
| 13-19 | Me | H | Cl | H | H | H | Br | H | pentafluoroethyl | H | CF3 |
| 13-20 | Me | H | Cl | H | H | H | Br | H | heptafluoroisopropyl | H | CF3 |
| 13-21 | Me | H | Cl | H | H | H | I | H | nonafluoro-2-butyl | H | CF3 |
| 13-22 | Me | H | Cl | H | H | H | OCF3 | H | heptafluoroisopropyl | H | CF3 |
| 13-23 | Me | H | Cl | H | H | H | OCF3 | H | nonafluoro-2-butyl | H | CF3 |
| 13-24 | Me | H | Cl | H | H | H | CF3 | H | heptafluoroisopropyl | H | CF3 |
| 13-25 | Me | H | Cl | H | H | H | CF3 | H | nonafluoro-2-butyl | H | CF3 |
| 13-26 | Me | H | F | H | H | H | Cl | H | heptafluoroisopropyl | H | Cl |
| 13-27 | Me | H | F | H | H | H | Br | H | heptafluoroisopropyl | H | Br |
| 13-28 | Me | H | F | H | H | H | I | H | heptafluoroisopropyl | H | I |
| 13-29 | Me | H | F | H | H | H | Br | H | heptafluoroisopropyl | H | Cl |
| 13-30 | Me | H | F | H | H | H | Br | H | heptafluoroisopropyl | H | I |
| 13-31 | Me | H | F | H | H | H | Cl | H | nonafluoro-2-butyl | H | Cl |
| 13-32 | Me | H | F | H | H | H | Br | H | nonafluoro-2-butyl | H | Br |
| 13-33 | Me | H | F | H | H | H | I | H | nonafluoro-2-butyl | H | I |
| 13-34 | Me | H | F | H | H | H | Br | H | nonafluoro-2-butyl | H | Cl |
| 13-35 | Me | H | F | H | H | H | Br | H | nonafluoro-2-butyl | H | I |
| 13-36 | Me | H | F | H | H | H | Br | H | heptafluoroisopropyl | H | OCF3 |
| 13-37 | Me | H | F | H | H | H | I | H | nonafluoro-2-butyl | H | OCF3 |
| 13-38 | Me | H | F | H | H | H | Br | H | pentafluoroethyl | H | CF3 |
| 13-39 | Me | H | F | H | H | H | Cl | H | heptafluoroisopropyl | H | CF3 |
| 13-40 | Me | H | F | H | H | H | Br | H | heptafluoroisopropyl | H | CF3 |
| 13-41 | Me | H | F | H | H | H | I | H | heptafluoroisopropyl | H | CF3 |
| 13-42 | Me | H | F | H | H | H | Cl | H | nonafluoro-2-butyl | H | CF3 |
| 13-43 | Me | H | F | H | H | H | Br | H | nonafluoro-2-butyl | H | CF3 |
| 13-44 | Me | H | F | H | H | H | I | H | nonafluoro-2-butyl | H | CF3 |
| 13-45 | Me | H | F | H | H | H | OCF3 | H | heptafluoroisopropyl | H | CF3 |
| 13-46 | Me | H | F | H | H | H | OCF3 | H | nonafluoro-2-butyl | H | CF3 |
| 13-47 | Me | H | F | H | H | H | CF3 | H | heptafluoroisopropyl | H | CF3 |
| 13-48 | Me | H | F | H | H | H | CF3 | H | nonafluoro-2-butyl | H | CF3 |
| 13-49 | Me | H | F | H | H | H | Br | H | heptafluoroisopropyl | H | C2F5 |
| 13-50 | Me | H | H | F | H | H | Br | H | heptafluoroisopropyl | H | Br |
| 13-51 | Me | H | H | F | H | H | Br | H | heptafluoroisopropyl | H | Cl |
| 13-52 | Me | H | H | F | H | H | I | H | nonafluoro-2-butyl | H | I |
| 13-53 | Me | H | H | F | H | H | Br | H | nonafluoro-2-butyl | H | I |
| 13-54 | Me | H | H | F | H | H | Br | H | heptafluoroisopropyl | H | OCF3 |
| 13-55 | Me | H | H | F | H | H | I | H | nonafluoro-2-butyl | H | OCF3 |
| 13-56 | Me | H | H | F | H | H | Br | H | heptafluoroisopropyl | H | CF3 |
| 13-57 | Me | H | H | F | H | H | I | H | nonafluoro-2-butyl | H | CF3 |
| 13-58 | Me | H | H | F | H | H | OCF3 | H | heptafluoroisopropyl | H | CF3 |
| 13-59 | Me | H | H | F | H | H | OCF3 | H | nonafluoro-2-butyl | H | CF3 |
| 13-60 | Me | H | H | F | H | H | CF3 | H | heptafluoroisopropyl | H | CF3 |

TABLE 13-continued

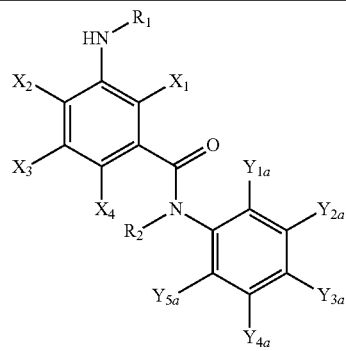

| compound number | $R_1$ | $R_2$ | $X_1$ | $X_2$ | $X_3$ | $X_4$ | $Y_{1a}$ | $Y_{2a}$ | $Y_{3a}$ | $Y_{4a}$ | $Y_{5a}$ |
|---|---|---|---|---|---|---|---|---|---|---|---|
| 13-61 | Me | H | H | F | H | H | CF3 | H | nonafluoro-2-butyl | H | CF3 |
| 13-62 | Me | H | H | I | H | H | I | H | heptafluoroisopropyl | H | I |
| 13-63 | Me | H | H | I | H | H | Br | H | heptafluoroisopropyl | H | Cl |
| 13-64 | Me | H | H | I | H | H | I | H | nonafluoro-2-butyl | H | I |
| 13-65 | Me | H | H | I | H | H | Br | H | nonafluoro-2-butyl | H | Cl |
| 13-66 | Me | H | H | I | H | H | I | H | heptafluoroisopropyl | H | OCF3 |
| 13-67 | Me | H | H | I | H | H | Br | H | nonafluoro-2-butyl | H | OCF3 |
| 13-68 | Me | H | H | I | H | H | Cl | H | heptafluoroisopropyl | H | CF3 |
| 13-69 | Me | H | H | I | H | H | Br | H | heptafluoroisopropyl | H | CF3 |
| 13-70 | Me | H | H | I | H | H | Br | H | nonafluoro-2-butyl | H | CF3 |
| 13-71 | Me | H | H | I | H | H | I | H | nonafluoro-2-butyl | H | CF3 |
| 13-72 | Me | H | H | I | H | H | OCF3 | H | heptafluoroisopropyl | H | CF3 |
| 13-73 | Me | H | H | I | H | H | OCF3 | H | nonafluoro-2-butyl | H | CF3 |
| 13-74 | Me | H | H | I | H | H | CF3 | H | heptafluoroisopropyl | H | CF3 |
| 13-75 | Me | H | H | I | H | H | CF3 | H | nonafluoro-2-butyl | H | CF3 |
| 13-76 | Me | H | H | CN | H | H | Cl | H | heptafluoroisopropyl | H | Cl |
| 13-77 | Me | H | H | CN | H | H | Br | H | heptafluoroisopropyl | H | Br |
| 13-78 | Me | H | H | CN | H | H | I | H | heptafluoroisopropyl | H | I |
| 13-79 | Me | H | H | CN | H | H | Br | H | heptafluoroisopropyl | H | Cl |
| 13-80 | Me | H | H | CN | H | H | Br | H | nonafluoro-2-butyl | H | Br |
| 13-81 | Me | H | H | CN | H | H | I | H | nonafluoro-2-butyl | H | I |
| 13-82 | Me | H | H | CN | H | H | Br | H | nonafluoro-2-butyl | H | I |
| 13-83 | Me | H | H | CN | H | H | Br | H | heptafluoroisopropyl | H | OCF3 |
| 13-84 | Me | H | H | CN | H | H | I | H | nonafluoro-2-butyl | H | OCF3 |
| 13-85 | Me | H | H | CN | H | H | Cl | H | heptafluoroisopropyl | H | CF3 |
| 13-86 | Me | H | H | CN | H | H | Br | H | heptafluoroisopropyl | H | CF3 |
| 13-87 | Me | H | H | CN | H | H | I | H | heptafluoroisopropyl | H | CF3 |
| 13-88 | Me | H | H | CN | H | H | Br | H | nonafluoro-2-butyl | H | CF3 |
| 13-89 | Me | H | H | CN | H | H | I | H | nonafluoro-2-butyl | H | CF3 |
| 13-90 | Me | H | H | CN | H | H | OCF3 | H | heptafluoroisopropyl | H | CF3 |
| 13-91 | Me | H | H | CN | H | H | OCF3 | H | nonafluoro-2-butyl | H | CF3 |
| 13-92 | Me | H | H | CN | H | H | CF3 | H | heptafluoroisopropyl | H | CF3 |
| 13-93 | Me | H | H | CN | H | H | CF3 | H | nonafluoro-2-butyl | H | CF3 |
| 13-94 | Me | H | F | CN | H | H | Br | H | heptafluoroisopropyl | H | Br |
| 13-95 | Me | H | F | CN | H | H | Br | H | heptafluoroisopropyl | H | Cl |
| 13-96 | Me | H | F | CN | H | H | I | H | nonafluoro-2-butyl | H | I |
| 13-97 | Me | H | F | CN | H | H | Br | H | nonafluoro-2-butyl | H | I |
| 13-98 | Me | H | F | CN | H | H | Br | H | heptafluoroisopropyl | H | OCF3 |
| 13-99 | Me | H | F | CN | H | H | I | H | nonafluoro-2-butyl | H | OCF3 |
| 13-100 | Me | H | F | CN | H | H | Br | H | heptafluoroisopropyl | H | CF3 |
| 13-101 | Me | H | F | CN | H | H | I | H | nonafluoro-2-butyl | H | CF3 |
| 13-102 | Me | H | F | CN | H | H | OCF3 | H | heptafluoroisopropyl | H | CF3 |
| 13-103 | Me | H | F | CN | H | H | OCF3 | H | nonafluoro-2-butyl | H | CF3 |
| 13-104 | Me | H | F | CN | H | H | CF3 | H | heptafluoroisopropyl | H | CF3 |
| 13-105 | Me | H | F | CN | H | H | CF3 | H | nonafluoro-2-butyl | H | CF3 |
| 13-106 | Me | Me | H | H | H | H | Br | H | heptafluoroisopropyl | H | Br |
| 13-107 | Me | Me | H | H | H | H | I | H | nonafluoro-2-butyl | H | I |
| 13-108 | Me | Me | H | H | H | H | Br | H | heptafluoroisopropyl | H | OCF3 |
| 13-109 | Me | Me | H | H | H | H | Br | H | nonafluoro-2-butyl | H | OCF3 |
| 13-110 | Me | Me | H | H | H | H | Br | H | heptafluoroisopropyl | H | CF3 |
| 13-111 | Me | Me | H | H | H | H | I | H | nonafluoro-2-butyl | H | CF3 |
| 13-112 | Me | Me | H | H | H | H | OCF3 | H | heptafluoroisopropyl | H | CF3 |
| 13-113 | Me | Me | H | H | H | H | OCF3 | H | nonafluoro-2-butyl | H | CF3 |
| 13-114 | Me | Me | H | H | H | H | CF3 | H | heptafluoroisopropyl | H | CF3 |
| 13-115 | Me | Me | H | H | H | H | CF3 | H | nonafluoro-2-butyl | H | CF3 |
| 13-116 | Me | Me | Cl | H | H | H | Br | H | heptafluoroisopropyl | H | Br |
| 13-117 | Me | Me | Cl | H | H | H | I | H | nonafluoro-2-butyl | H | I |
| 13-118 | Me | Me | Cl | H | H | H | Br | H | heptafluoroisopropyl | H | OCF3 |
| 13-119 | Me | Me | Cl | H | H | H | Br | H | nonafluoro-2-butyl | H | OCF3 |
| 13-120 | Me | Me | Cl | H | H | H | Br | H | heptafluoroisopropyl | H | CF3 |

TABLE 13-continued

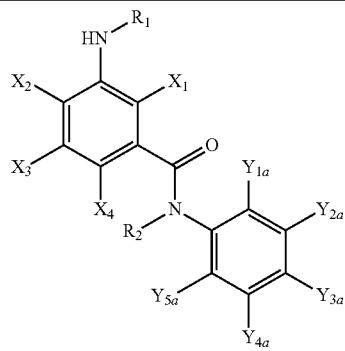

| compound number | $R_1$ | $R_2$ | $X_1$ | $X_2$ | $X_3$ | $X_4$ | $Y_{1a}$ | $Y_{2a}$ | $Y_{3a}$ | $Y_{4a}$ | $Y_{5a}$ |
|---|---|---|---|---|---|---|---|---|---|---|---|
| 13-121 | Me | Me | Cl | H | H | H | I | H | nonafluoro-2-butyl | H | CF3 |
| 13-122 | Me | Me | Cl | H | H | H | OCF3 | H | heptafluoroisopropyl | H | CF3 |
| 13-123 | Me | Me | Cl | H | H | H | OCF3 | H | nonafluoro-2-butyl | H | CF3 |
| 13-124 | Me | Me | Cl | H | H | H | CF3 | H | heptafluoroisopropyl | H | CF3 |
| 13-125 | Me | Me | Cl | H | H | H | CF3 | H | nonafluoro-2-butyl | H | CF3 |
| 13-126 | Me | Me | F | H | H | H | Br | H | heptafluoroisopropyl | H | Br |
| 13-127 | Me | Me | F | H | H | H | I | H | nonafluoro-2-butyl | H | I |
| 13-128 | Me | Me | F | H | H | H | Br | H | heptafluoroisopropyl | H | OCF3 |
| 13-129 | Me | Me | F | H | H | H | Br | H | nonafluoro-2-butyl | H | OCF3 |
| 13-130 | Me | Me | F | H | H | H | Br | H | heptafluoroisopropyl | H | CF3 |
| 13-131 | Me | Me | F | H | H | H | I | H | nonafluoro-2-butyl | H | CF3 |
| 13-132 | Me | Me | F | H | H | H | OCF3 | H | heptafluoroisopropyl | H | CF3 |
| 13-133 | Me | Me | F | H | H | H | OCF3 | H | nonafluoro-2-butyl | H | CF3 |
| 13-134 | Me | Me | F | H | H | H | CF3 | H | heptafluoroisopropyl | H | CF3 |
| 13-135 | Me | Me | F | H | H | H | CF3 | H | nonafluoro-2-butyl | H | CF3 |
| 13-136 | Me | Me | H | F | H | H | Br | H | heptafluoroisopropyl | H | Br |
| 13-137 | Me | Me | H | F | H | H | I | H | nonafluoro-2-butyl | H | I |
| 13-138 | Me | Me | H | F | H | H | Br | H | heptafluoroisopropyl | H | OCF3 |
| 13-139 | Me | Me | H | F | H | H | Br | H | nonafluoro-2-butyl | H | OCF3 |
| 13-140 | Me | Me | H | F | H | H | Br | H | heptafluoroisopropyl | H | CF3 |
| 13-141 | Me | Me | H | F | H | H | I | H | nonafluoro-2-butyl | H | CF3 |
| 13-142 | Me | Me | H | F | H | H | OCF3 | H | heptafluoroisopropyl | H | CF3 |
| 13-143 | Me | Me | H | F | H | H | OCF3 | H | nonafluoro-2-butyl | H | CF3 |
| 13-144 | Me | Me | H | F | H | H | CF3 | H | heptafluoroisopropyl | H | CF3 |
| 13-145 | Me | Me | H | F | H | H | CF3 | H | nonafluoro-2-butyl | H | CF3 |
| 13-146 | Me | Me | H | I | H | H | Br | H | heptafluoroisopropyl | H | Br |
| 13-147 | Me | Me | H | I | H | H | I | H | nonafluoro-2-butyl | H | I |
| 13-148 | Me | Me | H | I | H | H | Br | H | heptafluoroisopropyl | H | OCF3 |
| 13-149 | Me | Me | H | I | H | H | Br | H | nonafluoro-2-butyl | H | OCF3 |
| 13-150 | Me | Me | H | I | H | H | Br | H | heptafluoroisopropyl | H | CF3 |
| 13-151 | Me | Me | H | I | H | H | I | H | nonafluoro-2-butyl | H | CF3 |
| 13-152 | Me | Me | H | I | H | H | OCF3 | H | heptafluoroisopropyl | H | CF3 |
| 13-153 | Me | Me | H | I | H | H | OCF3 | H | nonafluoro-2-butyl | H | CF3 |
| 13-154 | Me | Me | H | I | H | H | CF3 | H | heptafluoroisopropyl | H | CF3 |
| 13-155 | Me | Me | H | I | H | H | CF3 | H | nonafluoro-2-butyl | H | CF3 |
| 13-156 | Me | Me | H | CN | H | H | Br | H | heptafluoroisopropyl | H | Br |
| 13-157 | Me | Me | H | CN | H | H | I | H | nonafluoro-2-butyl | H | I |
| 13-158 | Me | Me | H | CN | H | H | Br | H | heptafluoroisopropyl | H | OCF3 |
| 13-159 | Me | Me | H | CN | H | H | Br | H | nonafluoro-2-butyl | H | OCF3 |
| 13-160 | Me | Me | H | CN | H | H | Br | H | heptafluoroisopropyl | H | CF3 |
| 13-161 | Me | Me | H | CN | H | H | I | H | nonafluoro-2-butyl | H | CF3 |
| 13-162 | Me | Me | H | CN | H | H | OCF3 | H | heptafluoroisopropyl | H | CF3 |
| 13-163 | Me | Me | H | CN | H | H | OCF3 | H | nonafluoro-2-butyl | H | CF3 |
| 13-164 | Me | Me | H | CN | H | H | CF3 | H | heptafluoroisopropyl | H | CF3 |
| 13-165 | Me | Me | H | CN | H | H | CF3 | H | nonafluoro-2-butyl | H | CF3 |
| 13-166 | Me | Me | F | CN | H | H | Br | H | heptafluoroisopropyl | H | Br |
| 13-167 | Me | Me | F | CN | H | H | I | H | nonafluoro-2-butyl | H | I |
| 13-168 | Me | Me | F | CN | H | H | Br | H | heptafluoroisopropyl | H | OCF3 |
| 13-169 | Me | Me | F | CN | H | H | Br | H | nonafluoro-2-butyl | H | OCF3 |
| 13-170 | Me | Me | F | CN | H | H | Br | H | heptafluoroisopropyl | H | CF3 |
| 13-171 | Me | Me | F | CN | H | H | I | H | nonafluoro-2-butyl | H | CF3 |
| 13-172 | Me | Me | F | CN | H | H | OCF3 | H | heptafluoroisopropyl | H | CF3 |
| 13-173 | Me | Me | F | CN | H | H | OCF3 | H | nonafluoro-2-butyl | H | CF3 |
| 13-174 | Me | Me | F | CN | H | H | CF3 | H | heptafluoroisopropyl | H | CF3 |
| 13-175 | Me | Me | F | CN | H | H | CF3 | H | nonafluoro-2-butyl | H | CF3 |
| 13-176 | Me | H | F | H | H | H | Br | H | heptafluoroisopropyl | F | CF3 |
| 13-177 | Me | H | F | H | H | H | Br | Me | nonafluoro-2-butyl | H | CF3 |
| 13-178 | Me | H | F | H | H | H | Br | F | heptafluoroisopropyl | Cl | CF3 |
| 13-179 | Me | H | F | H | H | H | Br | Me | nonafluoro-2-butyl | F | CF3 |
| 13-180 | Me | H | F | H | H | H | Br | Et | heptafluoroisopropyl | Me | CF3 |

TABLE 13-continued

| compound number | R₁ | R₂ | X₁ | X₂ | X₃ | X₄ | Y₁ₐ | Y₂ₐ | Y₃ₐ | Y₄ₐ | Y₅ₐ |
|---|---|---|---|---|---|---|---|---|---|---|---|
| 13-181 | Me | Me | F | H | H | H | I | H | heptafluoroisopropyl | F | CF3 |
| 13-182 | Me | Me | F | H | H | H | I | Me | nonafluoro-2-butyl | H | CF3 |
| 13-183 | Me | Me | F | H | H | H | I | F | heptafluoroisopropyl | Cl | CF3 |
| 13-184 | Me | Me | F | H | H | H | I | Me | nonafluoro-2-butyl | F | CF3 |
| 13-185 | Me | Me | F | H | H | H | I | Et | heptafluoroisopropyl | Me | CF3 |

TABLE 14

| compound number | R₂ | A | Xa | X₂ | X₃ | X₄ | Y₁ₐ | Y₂ₐ | Y₃ₐ | Y₄ₐ | Y₅ₐ |
|---|---|---|---|---|---|---|---|---|---|---|---|
| 14-1 | H | N | Cl | H | H | H | Br | H | heptafluoroisopropyl | H | Br |
| 14-2 | H | N | Cl | H | H | H | I | H | nonafluoro-2-butyl | H | I |
| 14-3 | H | N | Cl | H | H | H | Br | H | heptafluoroisopropyl | H | OCF3 |
| 14-4 | H | N | Cl | H | H | H | I | H | nonafluoro-2-butyl | H | OCF3 |
| 14-5 | H | N | Cl | H | H | H | Br | H | pentafluoroethyl | H | CF3 |
| 14-6 | H | N | Cl | H | H | H | Br | H | heptafluoroisopropyl | H | CF3 |
| 14-7 | H | N | Cl | H | H | H | I | H | nonafluoro-2-butyl | H | CF3 |
| 14-8 | H | N | Cl | H | H | H | OCF3 | H | heptafluoroisopropyl | H | CF3 |
| 14-9 | H | N | Cl | H | H | H | OCF3 | H | nonafluoro-2-butyl | H | CF3 |
| 14-10 | H | N | Cl | H | H | H | CF3 | H | heptafluoroisopropyl | H | CF3 |
| 14-11 | H | N | Cl | H | H | H | CF3 | H | nonafluoro-2-butyl | H | CF3 |
| 14-12 | H | N | Cl | H | H | H | Br | H | heptafluoroisopropyl | H | C2F5 |
| 14-13 | H | N | Cl | H | H | H | Br | H | nonafluoro-2-butyl | H | C2F5 |
| 14-14 | Me | N | Cl | H | H | H | Cl | H | heptafluoroisopropyl | H | Cl |
| 14-15 | Me | N | Cl | H | H | H | Br | H | nonafluoro-2-butyl | H | Cl |
| 14-16 | Me | N | Cl | H | H | H | Br | H | heptafluoroisopropyl | H | OCF3 |
| 14-17 | Et | N | Cl | H | H | H | Cl | H | nonafluoro-2-butyl | H | OCF3 |
| 14-18 | Me | N | Cl | H | H | H | Br | H | pentafluoroethyl | H | CF3 |
| 14-19 | Me | N | Cl | H | H | H | Br | H | heptafluoroisopropyl | H | CF3 |
| 14-20 | Me | N | Cl | H | H | H | I | H | nonafluoro-2-butyl | H | CF3 |
| 14-21 | Me | N | Cl | H | H | H | OCF3 | H | heptafluoroisopropyl | H | CF3 |
| 14-22 | Me | N | Cl | H | H | H | OCF3 | H | nonafluoro-2-butyl | H | CF3 |
| 14-23 | Me | N | Cl | H | H | H | CF3 | H | heptafluoroisopropyl | H | CF3 |
| 14-24 | Me | N | I | H | H | H | CF3 | H | nonafluoro-2-butyl | H | CF3 |
| 14-25 | Et | N | Cl | H | H | H | Br | H | heptafluoroisopropyl | H | C2F5 |
| 14-26 | Me | N | Cl | H | H | H | Br | H | nonafluoro-2-butyl | H | C2F5 |
| 14-27 | H | N | Cl | H | H | H | Br | H | heptafluoroisopropyl | F | CF3 |
| 14-28 | H | N | Cl | H | H | H | Br | Me | nonafluoro-2-butyl | H | CF3 |
| 14-29 | H | N | Cl | H | H | H | Br | F | heptafluoroisopropyl | Cl | CF3 |
| 14-30 | H | N | Cl | H | H | H | Br | Me | nonafluoro-2-butyl | F | CF3 |

TABLE 14-continued

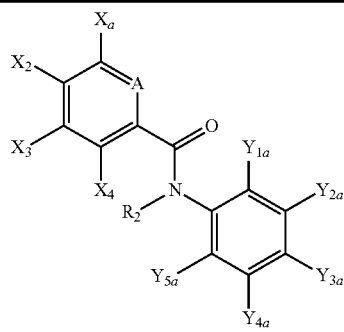

| compound number | R₂ | A | Xa | X₂ | X₃ | X₄ | Y₁ₐ | Y₂ₐ | Y₃ₐ | Y₄ₐ | Y₅ₐ |
|---|---|---|---|---|---|---|---|---|---|---|---|
| 14-31 | H | N | Cl | H | H | H | Br | Et | heptafluoroisopropyl | Me | CF3 |
| 14-32 | Me | N | Cl | H | H | H | I | H | heptafluoroisopropyl | F | CF3 |
| 14-33 | Me | N | Cl | H | H | H | I | Me | nonafluoro-2-butyl | H | CF3 |
| 14-34 | Me | N | Cl | H | H | H | I | F | heptafluoroisopropyl | Cl | CF3 |
| 14-35 | Me | N | Cl | H | H | H | I | Me | nonafluoro-2-butyl | F | CF3 |
| 14-36 | Me | N | Cl | H | H | H | I | Et | heptafluoroisopropyl | Me | CF3 |
| 14-37 | H | N-oxide | Cl | H | H | H | Br | H | heptafluoroisopropyl | H | Br |
| 14-38 | H | N-oxide | Cl | H | H | H | I | H | nonafluoro-2-butyl | H | I |
| 14-39 | H | N-oxide | Cl | H | H | H | Br | H | heptafluoroisopropyl | H | OCF3 |
| 14-40 | H | N-oxide | Cl | H | H | H | I | H | nonafluoro-2-butyl | H | OCF3 |
| 14-41 | H | N-oxide | Cl | H | H | H | Br | H | pentafluoroethyl | H | CF3 |
| 14-42 | H | N-oxide | Cl | H | H | H | Br | H | heptafluoroisopropyl | H | CF3 |
| 14-43 | H | N-oxide | Cl | H | H | H | I | H | nonafluoro-2-butyl | H | CF3 |
| 14-44 | H | N-oxide | Cl | H | H | H | OCF3 | H | heptafluoroisopropyl | H | CF3 |
| 14-45 | H | N-oxide | Cl | H | H | H | OCF3 | H | nonafluoro-2-butyl | H | CF3 |
| 14-46 | H | N-oxide | Cl | H | H | H | CF3 | H | heptafluoroisopropyl | H | CF3 |
| 14-47 | H | N-oxide | Cl | H | H | H | CF3 | H | nonafluoro-2-butyl | H | CF3 |
| 14-48 | H | N-oxide | Cl | H | H | H | Br | H | heptafluoroisopropyl | H | C2F5 |
| 14-49 | H | N-oxide | Cl | H | H | H | Br | H | nonafluoro-2-butyl | H | C2F5 |
| 14-50 | Me | N-oxide | Cl | H | H | H | Br | H | heptafluoroisopropyl | H | Br |
| 14-51 | Me | N-oxide | Cl | H | H | H | I | H | nonafluoro-2-butyl | H | I |
| 14-52 | Me | N-oxide | Cl | H | H | H | Br | H | heptafluoroisopropyl | H | OCF3 |
| 14-53 | Me | N-oxide | Cl | H | H | H | I | H | nonafluoro-2-butyl | H | OCF3 |
| 14-54 | Me | N-oxide | Cl | H | H | H | Br | H | pentafluoroethyl | H | CF3 |
| 14-55 | Me | N-oxide | Cl | H | H | H | Br | H | heptafluoroisopropyl | H | CF3 |
| 14-56 | Me | N-oxide | Cl | H | H | H | I | H | nonafluoro-2-butyl | H | CF3 |
| 14-57 | Et | N-oxide | Cl | H | H | H | OCF3 | H | heptafluoroisopropyl | H | CF3 |
| 14-58 | Me | N-oxide | Cl | H | H | H | OCF3 | H | nonafluoro-2-butyl | H | CF3 |
| 14-59 | Me | N-oxide | Cl | H | H | H | CF3 | H | heptafluoroisopropyl | H | CF3 |
| 14-60 | Me | N-oxide | Cl | H | H | H | CF3 | H | nonafluoro-2-butyl | H | CF3 |
| 14-61 | Me | N-oxide | Cl | H | H | H | Br | H | heptafluoroisopropyl | H | C2F5 |
| 14-62 | Me | N-oxide | Cl | H | H | H | Br | H | nonafluoro-2-butyl | H | C2F5 |

TABLE 15

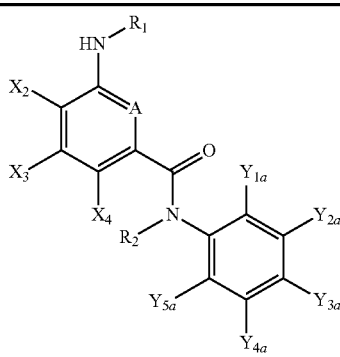

| compound number | R₁ | R₂ | A | X₂ | X₃ | X₄ | Y₁ₐ | Y₂ₐ | Y₃ₐ | Y₄ₐ | Y₅ₐ |
|---|---|---|---|---|---|---|---|---|---|---|---|
| 15-1 | H | H | N | H | H | H | Br | H | heptafluoroisopropyl | H | Br |
| 15-2 | H | H | N | H | H | H | I | H | nonafluoro-2-butyl | H | I |
| 15-3 | H | H | N | H | H | H | Br | H | heptafluoroisopropyl | H | OCF3 |

TABLE 15-continued

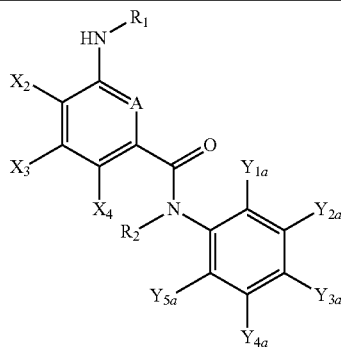

| compound number | R₁ | R₂ | A | X₂ | X₃ | X₄ | Y₁ₐ | Y₂ₐ | Y₃ₐ | Y₄ₐ | Y₅ₐ |
|---|---|---|---|---|---|---|---|---|---|---|---|
| 15-4 | H | H | N | H | H | H | I | H | nonafluoro-2-butyl | H | OCF3 |
| 15-5 | H | H | N | H | H | H | Br | H | pentafluoroethyl | H | CF3 |
| 15-6 | H | H | N | H | H | H | Br | H | heptafluoroisopropyl | H | CF3 |
| 15-7 | H | H | N | H | H | H | I | H | nonafluoro-2-butyl | H | CF3 |
| 15-8 | H | H | N | H | H | H | OCF3 | H | heptafluoroisopropyl | H | CF3 |
| 15-9 | H | H | N | H | H | H | OCF3 | H | nonafluoro-2-butyl | H | CF3 |
| 15-10 | H | H | N | H | H | H | CF3 | H | heptafluoroisopropyl | H | CF3 |
| 15-11 | H | H | N | H | H | H | CF3 | H | nonafluoro-2-butyl | H | CF3 |
| 15-12 | H | H | N | H | H | H | Br | H | heptafluoroisopropyl | H | C2F5 |
| 15-13 | H | H | N | H | H | H | Br | H | nonafluoro-2-butyl | H | C2F5 |
| 15-14 | H | Me | N | H | H | H | Cl | H | heptafluoroisopropyl | H | Cl |
| 15-15 | H | Me | N | H | H | H | Br | H | nonafluoro-2-butyl | H | Cl |
| 15-16 | H | Me | N | H | H | H | Br | H | heptafluoroisopropyl | H | OCF3 |
| 15-17 | H | Et | N | H | H | H | Cl | H | nonafluoro-2-butyl | H | OCF3 |
| 15-18 | H | Me | N | H | H | H | Br | H | pentafluoroethyl | H | CF3 |
| 15-19 | H | Me | N | H | H | H | Br | H | heptafluoroisopropyl | H | CF3 |
| 15-20 | H | Me | N | H | H | H | I | H | nonafluoro-2-butyl | H | CF3 |
| 15-21 | H | Me | N | H | H | H | OCF3 | H | heptafluoroisopropyl | H | CF3 |
| 15-22 | H | Me | N | H | H | H | OCF3 | H | nonafluoro-2-butyl | H | CF3 |
| 15-23 | H | Me | N | H | H | H | CF3 | H | heptafluoroisopropyl | H | CF3 |
| 15-24 | H | Me | N | H | H | H | CF3 | H | nonafluoro-2-butyl | H | CF3 |
| 15-25 | H | Et | N | H | H | H | Br | H | heptafluoroisopropyl | H | C2F5 |
| 15-26 | H | Me | N | H | H | H | Br | H | nonafluoro-2-butyl | H | C2F5 |
| 15-27 | H | H | N | H | H | H | Br | H | heptafluoroisopropyl | F | CF3 |
| 15-28 | H | H | N | H | H | H | Br | Me | nonafluoro-2-butyl | H | CF3 |
| 15-29 | H | H | N | H | H | H | Br | F | heptafluoroisopropyl | Cl | CF3 |
| 15-30 | H | H | N | H | H | H | Br | Me | nonafluoro-2-butyl | F | CF3 |
| 15-31 | H | H | N | H | H | H | Br | Et | heptafluoroisopropyl | Me | CF3 |
| 15-32 | H | Me | N | H | H | H | I | H | heptafluoroisopropyl | F | CF3 |
| 15-33 | H | Me | N | H | H | H | I | Me | nonafluoro-2-butyl | H | CF3 |
| 15-34 | H | Me | N | H | H | H | I | F | heptafluoroisopropyl | Cl | CF3 |
| 15-35 | H | Me | N | H | H | H | I | Me | nonafluoro-2-butyl | F | CF3 |
| 15-36 | H | Me | N | H | H | H | I | Et | heptafluoroisopropyl | Me | CF3 |
| 15-37 | H | H | N-oxide | H | H | H | Br | H | heptafluoroisopropyl | H | Br |
| 15-38 | H | H | N-oxide | H | H | H | I | H | nonafluoro-2-butyl | H | I |
| 15-39 | H | H | N-oxide | H | H | H | Br | H | heptafluoroisopropyl | H | OCF3 |
| 15-40 | H | H | N-oxide | H | H | H | I | H | nonafluoro-2-butyl | H | OCF3 |
| 15-41 | H | H | N-oxide | H | H | H | Br | H | pentafluoroethyl | H | CF3 |
| 15-42 | H | H | N-oxide | H | H | H | Br | H | heptafluoroisopropyl | H | CF3 |
| 15-43 | H | H | N-oxide | H | H | H | I | H | nonafluoro-2-butyl | H | CF3 |
| 15-44 | H | H | N-oxide | H | H | H | OCF3 | H | heptafluoroisopropyl | H | CF3 |
| 15-45 | H | H | N-oxide | H | H | H | OCF3 | H | nonafluoro-2-butyl | H | CF3 |
| 15-46 | H | H | N-oxide | H | H | H | CF3 | H | heptafluoroisopropyl | H | CF3 |
| 15-47 | H | H | N-oxide | H | H | H | CF3 | H | nonafluoro-2-butyl | H | CF3 |
| 15-48 | H | H | N-oxide | H | H | H | Br | H | heptafluoroisopropyl | H | C2F5 |
| 15-49 | H | H | N-oxide | H | H | H | Br | H | nonafluoro-2-butyl | Fl | C2F5 |
| 15-50 | H | Me | N-oxide | H | H | H | Br | H | heptafluoroisopropyl | H | Br |
| 15-51 | H | Me | N-oxide | H | H | H | I | H | nonafluoro-2-butyl | H | I |
| 15-52 | H | Me | N-oxide | H | H | H | Br | H | heptafluoroisopropyl | H | OCF3 |
| 15-53 | H | Me | N-oxide | H | H | H | I | H | nonafluoro-2-butyl | H | OCF3 |
| 15-54 | H | Me | N-oxide | H | H | H | Br | H | pentafluoroethyl | H | CF3 |
| 15-55 | H | Me | N-oxide | H | H | H | Br | H | heptafluoroisopropyl | H | CF3 |
| 15-56 | H | Me | N-oxide | H | H | H | I | H | nonafluoro-2-butyl | H | CF3 |
| 15-57 | H | Et | N-oxide | H | H | H | OCF3 | H | heptafluoroisopropyl | H | CF3 |
| 15-58 | H | Me | N-oxide | H | H | H | OCF3 | H | nonafluoro-2-butyl | H | CF3 |
| 15-59 | H | Me | N-oxide | H | H | H | CF3 | H | heptafluoroisopropyl | H | CF3 |
| 15-60 | H | Me | N-oxide | H | H | H | CF3 | H | nonafluoro-2-butyl | H | CF3 |
| 15-61 | H | Me | N-oxide | H | H | H | Br | H | heptafluoroisopropyl | H | C2F5 |
| 15-62 | H | Me | N-oxide | H | H | H | Br | H | nonafluoro-2-butyl | H | C2F5 |
| 15-63 | Me | H | N | H | H | H | Br | H | heptafluoroisopropyl | H | Br |

TABLE 15-continued

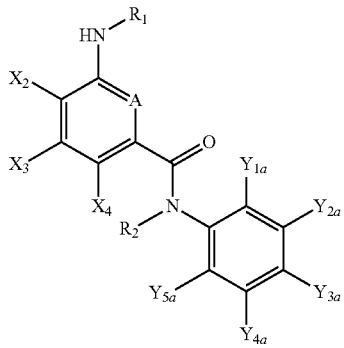

| compound number | $R_1$ | $R_2$ | A | $X_2$ | $X_3$ | $X_4$ | $Y_{1a}$ | $Y_{2a}$ | $Y_{3a}$ | $Y_{4a}$ | $Y_{5a}$ |
|---|---|---|---|---|---|---|---|---|---|---|---|
| 15-64 | Me | H | N | H | H | H | I | H | nonafluoro-2-butyl | H | I |
| 15-65 | Me | H | N | H | H | H | Br | H | heptafluoroisopropyl | H | OCF3 |
| 15-66 | Me | H | N | H | H | H | I | H | nonafluoro-2-butyl | H | OCF3 |
| 15-67 | Me | H | N | H | H | H | Br | H | pentafluoroethyl | H | CF3 |
| 15-68 | Me | H | N | H | H | H | Br | H | heptafluoroisopropyl | H | CF3 |
| 15-69 | Me | H | N | H | H | H | I | H | nonafluoro-2-butyl | H | CF3 |
| 15-70 | Me | H | N | H | H | H | OCF3 | H | heptafluoroisopropyl | H | CF3 |
| 15-71 | Me | H | N | H | H | H | OCF3 | H | nonafluoro-2-butyl | H | CF3 |
| 15-72 | Me | H | N | H | H | H | CF3 | H | heptafluoroisopropyl | H | CF3 |
| 15-73 | Me | H | N | H | H | H | CF3 | H | nonafluoro-2-butyl | H | CF3 |
| 15-74 | Me | H | N | H | H | H | Br | H | heptafluoroisopropyl | H | C2F5 |
| 15-75 | Me | H | N | H | H | H | Br | H | nonafluoro-2-butyl | H | C2F5 |
| 15-76 | Me | Me | N | H | H | H | Cl | H | heptafluoroisopropyl | H | Cl |
| 15-77 | Me | Me | N | H | H | H | Br | H | nonafluoro-2-butyl | H | Cl |
| 15-78 | Me | Me | N | H | H | H | Br | H | heptafluoroisopropyl | H | OCF3 |
| 15-79 | Me | Et | N | H | H | H | Cl | H | nonafluoro-2-butyl | H | OCF3 |
| 15-80 | Me | Me | N | H | H | Id | Br | H | pentafluoroethyl | H | CF3 |
| 15-81 | Me | Me | N | H | H | H | Br | H | heptafluoroisopropyl | H | CF3 |
| 15-82 | Me | Me | N | H | H | H | I | H | nonafluoro-2-butyl | H | CF3 |
| 15-83 | Me | Me | N | H | H | H | OCF3 | H | heptafluoroisopropyl | H | CF3 |
| 15-84 | Et | Me | N | H | H | H | OCF3 | H | nonafluoro-2-butyl | H | CF3 |
| 15-85 | Me | Me | N | H | H | H | CF3 | H | heptafluoroisopropyl | H | CF3 |
| 15-86 | Me | Me | N | H | H | H | CF3 | H | nonafluoro-2-butyl | H | CF3 |
| 15-87 | Me | Et | N | H | H | H | Br | H | heptafluoroisopropyl | H | C2F5 |
| 15-88 | Me | Me | N | H | H | H | Br | H | nonafluoro-2-butyl | H | C2F5 |
| 15-89 | Me | H | N | H | H | H | Br | H | heptafluoroisopropyl | F | CF3 |
| 15-90 | Me | H | N | H | H | H | Br | Me | nonafluoro-2-butyl | H | CF3 |
| 15-91 | Me | H | N | H | H | H | Br | F | heptafluoroisopropyl | Cl | CF3 |
| 15-92 | Me | H | N | H | H | H | Br | Me | nonafluoro-2-butyl | F | CF3 |
| 15-93 | Me | H | N | H | H | H | Br | Et | heptafluoroisopropyl | Me | CF3 |
| 15-94 | Et | Me | N | H | H | H | I | H | heptafluoroisopropyl | F | CF3 |
| 15-95 | Me | Me | N | H | H | H | I | Me | nonafluoro-2-butyl | H | CF3 |
| 15-96 | Me | Me | N | H | H | H | I | F | heptafluoroisopropyl | Cl | CF3 |
| 15-97 | Me | Me | N | H | H | H | I | Me | nonafluoro-2-butyl | F | CF3 |
| 15-98 | Me | Me | N | H | H | H | I | Et | heptafluoroisopropyl | Me | CF3 |
| 15-99 | Me | H | N-oxide | H | H | H | Br | H | heptafluoroisopropyl | H | Br |
| 15-100 | Me | H | N-oxide | H | H | H | I | H | nonafluoro-2-butyl | H | I |
| 15-101 | Me | H | N-oxide | H | H | H | Br | H | heptafluoroisopropyl | H | OCF3 |
| 15-102 | Me | H | N-oxide | H | H | H | I | H | nonafluoro-2-butyl | H | OCF3 |
| 15-103 | Me | H | N-oxide | H | H | H | Br | H | pentafluoroethyl | H | CF3 |
| 15-104 | Me | H | N-oxide | H | H | H | Br | H | heptafluoroisopropyl | H | CF3 |
| 15-105 | Me | H | N-oxide | H | H | H | I | H | nonafluoro-2-butyl | H | CF3 |
| 15-106 | Me | H | N-oxide | H | H | H | OCF3 | H | heptafluoroisopropyl | H | CF3 |
| 15-107 | Me | H | N-oxide | H | H | H | OCF3 | H | nonafluoro-2-butyl | H | CF3 |
| 15-108 | Me | H | N-oxide | H | H | H | CF3 | H | heptafluoroisopropyl | H | CF3 |
| 15-109 | Me | H | N-oxide | H | H | H | CF3 | H | nonafluoro-2-butyl | H | CF3 |
| 15-110 | Me | H | N-oxide | H | H | H | Br | H | heptafluoroisopropyl | H | C2F5 |
| 15-111 | Me | H | N-oxide | H | H | H | Br | H | nonafluoro-2-butyl | H | C2F5 |
| 15-112 | Me | Me | N-oxide | H | H | H | Br | H | heptafluoroisopropyl | H | Br |
| 15-113 | Me | Me | N-oxide | H | H | H | I | H | nonafluoro-2-butyl | H | I |
| 15-114 | Me | Me | N-oxide | H | H | H | Br | H | heptafluoroisopropyl | H | OCF3 |
| 15-115 | Me | Me | N-oxide | H | H | H | I | H | nonafluoro-2-butyl | H | OCF3 |
| 15-116 | Me | Me | N-oxide | H | H | H | Br | H | pentafluoroethyl | H | CF3 |
| 15-117 | Me | Me | N-oxide | H | H | H | Br | H | heptafluoroisopropyl | H | CF3 |
| 15-118 | Me | Me | N-oxide | H | H | H | I | H | nonafluoro-2-butyl | H | CF3 |
| 15-119 | Me | Et | N-oxide | H | H | H | OCF3 | H | heptafluoroisopropyl | H | CF3 |
| 15-120 | Me | Me | N-oxide | H | H | H | OCF3 | H | nonafluoro-2-butyl | H | CF3 |
| 15-121 | Me | Me | N-oxide | H | H | H | CF3 | H | heptafluoroisopropyl | H | CF3 |
| 15-122 | Et | Me | N-oxide | H | H | H | CF3 | H | nonafluoro-2-butyl | H | CF3 |
| 15-123 | Me | Me | N-oxide | H | H | H | Br | H | heptafluoroisopropyl | H | C2F5 |

TABLE 15-continued

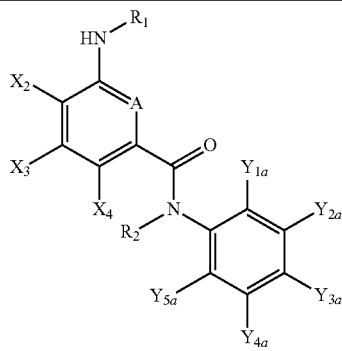

| compound number | R₁ | R₂ | A | X₂ | X₃ | X₄ | Y₁ₐ | Y₂ₐ | Y₃ₐ | Y₄ₐ | Y₅ₐ |
|---|---|---|---|---|---|---|---|---|---|---|---|
| 15-124 | Me | Me | N-oxide | H | H | H | Br | H | nonafluoro-2-butyl | H | C2F5 |

TABLE 16

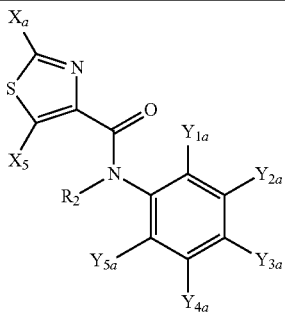

TABLE 16-continued

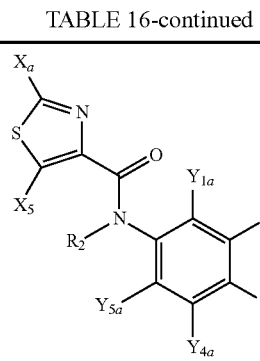

| compound number | R₂ | Xa | X₅ | Y₁ₐ | Y₂ₐ | Y₃ₐ | Y₄ₐ | Y₅ₐ |
|---|---|---|---|---|---|---|---|---|
| 16-1 | H | Cl | H | Br | H | heptafluoroisopropyl | H | Br |
| 16-2 | H | Cl | H | I | H | nonafluoro-2-butyl | H | I |
| 16-3 | H | Cl | H | Br | H | heptafluoroisopropyl | H | OCF3 |
| 16-4 | H | Cl | H | I | H | nonafluoro-2-butyl | H | OCF3 |
| 16-5 | H | Cl | H | Br | H | pentafluoroethyl | H | CF3 |
| 16-6 | H | Cl | H | Br | H | heptafluoroisopropyl | H | CF3 |
| 16-7 | H | Cl | H | I | H | nonafluoro-2-butyl | H | CF3 |
| 16-8 | H | Cl | H | OCF3 | H | heptafluoroisopropyl | H | CF3 |
| 16-9 | H | Cl | H | OCF3 | H | nonafluoro-2-butyl | H | CF3 |
| 16-10 | H | Cl | Cl | CF3 | H | heptafluoroisopropyl | H | CF3 |
| 16-11 | H | Cl | H | CF3 | H | nonafluoro-2-butyl | H | CF3 |
| 16-12 | H | Cl | H | Br | H | heptafluoroisopropyl | H | C2F5 |
| 16-13 | H | Cl | H | Br | H | nonafluoro-2-butyl | H | C2F5 |
| 16-14 | Me | Cl | H | Cl | H | heptafluoroisopropyl | H | Cl |
| 16-15 | Me | Cl | H | Br | H | nonafluoro-2-butyl | H | Cl |
| 16-16 | Me | Cl | H | Br | H | heptafluoroisopropyl | H | OCF3 |
| 16-17 | Et | Cl | H | Cl | H | nonafluoro-2-butyl | H | OCF3 |
| 16-18 | Me | Cl | H | Br | H | pentafluoroethyl | H | CF3 |
| 16-19 | Me | Cl | H | Br | H | heptafluoroisopropyl | H | CF3 |
| 16-20 | Me | Cl | H | I | H | nonafluoro-2-butyl | H | CF3 |
| 16-21 | Me | Cl | H | OCF3 | H | heptafluoroisopropyl | H | CF3 |
| 16-22 | Me | Cl | H | OCF3 | H | nonafluoro-2-butyl | H | CF3 |
| 16-23 | Me | Cl | Cl | CF3 | H | heptafluoroisopropyl | H | CF3 |
| 16-24 | Me | I | H | CF3 | H | nonafluoro-2-butyl | H | CF3 |
| 16-25 | Et | Cl | H | Br | H | heptafluoroisopropyl | H | C2F5 |
| 16-26 | Me | Cl | H | Br | H | nonafluoro-2-butyl | H | C2F5 |
| 16-27 | H | Cl | H | Br | H | heptafluoroisopropyl | F | CF3 |
| 16-28 | H | Cl | H | Br | Me | nonafluoro-2-butyl | H | CF3 |
| 16-29 | H | Cl | H | Br | F | heptafluoroisopropyl | Cl | CF3 |
| 16-30 | H | Cl | H | Br | Me | nonafluoro-2-butyl | F | CF3 |
| 16-31 | H | Cl | H | Br | Et | heptafluoroisopropyl | Me | CF3 |
| 16-32 | Me | Cl | H | I | H | nonafluoro-2-butyl | F | CF3 |
| 16-33 | Me | Cl | H | I | Me | nonafluoro-2-butyl | H | CF3 |
| 16-34 | Me | Cl | H | I | F | heptafluoroisopropyl | Cl | CF3 |
| 16-35 | Me | Cl | H | I | Me | nonafluoro-2-butyl | F | CF3 |
| 16-36 | Me | Cl | H | I | Et | heptafluoroisopropyl | Me | CF3 |

TABLE 17

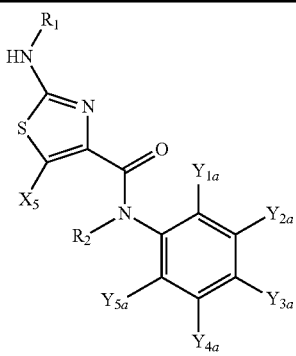

| compound number | R₁ | R₂ | X₅ | Y₁ₐ | Y₂ₐ | Y₃ₐ | Y₄ₐ | Y₅ₐ |
|---|---|---|---|---|---|---|---|---|
| 17-1 | H | H | H | Br | H | heptafluoroisopropyl | H | Br |
| 17-2 | H | H | H | I | H | nonafluoro-2-butyl | H | I |
| 17-3 | H | H | H | Br | H | heptafluoroisopropyl | H | OCF3 |
| 17-4 | H | H | H | I | H | nonafluoro-2-butyl | H | OCF3 |
| 17-5 | H | H | H | Br | H | pentafluoroethyl | H | CF3 |
| 17-6 | H | H | H | Br | H | heptafluoroisopropyl | H | CF3 |
| 17-7 | H | H | H | I | H | nonafluoro-2-butyl | H | CF3 |

TABLE 17-continued

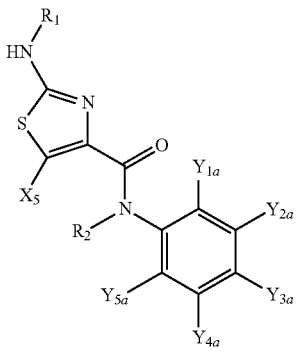

| compound number | R₁ | R₂ | X₅ | Y₁ₐ | Y₂ₐ | Y₃ₐ | Y₄ₐ | Y₅ₐ |
|---|---|---|---|---|---|---|---|---|
| 17-8 | H | H | H | OCF3 | H | heptafluoroisopropyl | H | CF3 |
| 17-9 | H | H | Cl | OCF3 | H | nonafluoro-2-butyl | H | CF3 |
| 17-10 | H | H | H | CF3 | H | heptafluoroisopropyl | H | CF3 |
| 17-11 | H | H | H | CF3 | H | nonafluoro-2-butyl | H | CF3 |
| 17-12 | H | H | H | Br | H | heptafluoroisopropyl | H | C2F5 |
| 17-13 | H | H | H | Br | H | nonafluoro-2-butyl | H | C2F5 |
| 17-14 | H | Me | H | Cl | H | heptafluoroisopropyl | H | Cl |
| 17-15 | H | Me | H | Br | H | nonafluoro-2-butyl | H | Cl |
| 17-16 | H | Me | H | Br | H | heptafluoroisopropyl | H | OCF3 |
| 17-17 | H | Et | H | Cl | H | nonafluoro-2-butyl | H | OCF3 |
| 17-18 | H | Me | H | Br | H | pentafluoroethyl | H | CF3 |
| 17-19 | H | Me | H | Br | H | heptafluoroisopropyl | H | CF3 |
| 17-20 | H | Me | H | I | H | nonafluoro-2-butyl | H | CF3 |
| 17-21 | H | Me | H | OCF3 | H | heptafluoroisopropyl | H | CF3 |
| 17-22 | H | Me | H | OCF3 | H | nonafluoro-2-butyl | H | CF3 |
| 17-23 | H | Me | H | CF3 | H | heptafluoroisopropyl | H | CF3 |
| 17-24 | H | Me | H | CF3 | H | nonafluoro-2-butyl | H | CF3 |
| 17-25 | H | Et | H | Br | H | heptafluoroisopropyl | H | C2F5 |
| 17-26 | H | Me | H | Br | H | nonafluoro-2-butyl | H | C2F5 |
| 17-27 | H | H | H | Br | H | heptafluoroisopropyl | F | CF3 |
| 17-28 | H | H | H | Br | Me | nonafluoro-2-butyl | H | CF3 |
| 17-29 | H | H | H | Br | F | heptafluoroisopropyl | Cl | CF3 |
| 17-30 | H | H | H | Br | Me | nonafluoro-2-butyl | F | CF3 |
| 17-31 | H | H | H | Br | Et | heptafluoroisopropyl | Me | CF3 |
| 17-32 | H | Me | H | I | H | heptafluoroisopropyl | F | CF3 |
| 17-33 | H | Me | H | I | Me | nonafluoro-2-butyl | H | CF3 |
| 17-34 | H | Me | H | I | F | heptafluoroisopropyl | Cl | CF3 |
| 17-35 | H | Me | H | I | Me | nonafluoro-2-butyl | F | CF3 |
| 17-36 | H | Me | H | I | Et | heptafluoroisopropyl | Me | CF3 |
| 17-37 | Me | H | H | Br | H | heptafluoroisopropyl | H | Br |
| 17-38 | Me | H | H | I | H | nonafluoro-2-butyl | H | I |
| 17-39 | Me | H | H | Br | H | heptafluoroisopropyl | H | OCF3 |
| 17-40 | Me | H | H | I | H | nonafluoro-2-butyl | H | OCF3 |

TABLE 17-continued

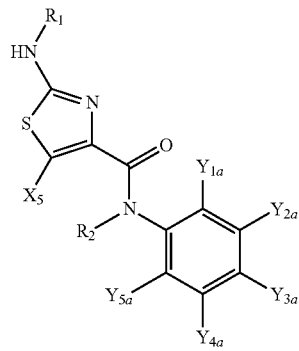

| compound number | R₁ | R₂ | X₅ | Y₁ₐ | Y₂ₐ | Y₃ₐ | Y₄ₐ | Y₅ₐ |
|---|---|---|---|---|---|---|---|---|
| 17-41 | Me | H | H | Br | H | pentafluoroethyl | H | CF3 |
| 17-42 | Me | H | H | Br | H | heptafluoroisopropyl | H | CF3 |
| 17-43 | Me | H | H | I | H | nonafluoro-2-butyl | H | CF3 |
| 17-44 | Me | H | H | OCF3 | H | heptafluoroisopropyl | H | CF3 |
| 17-45 | Me | H | H | OCF3 | H | nonafluoro-2-butyl | H | CF3 |
| 17-46 | Me | H | H | CF3 | H | heptafluoroisopropyl | H | CF3 |
| 17-47 | Me | H | H | CF3 | H | nonafluoro-2-butyl | H | CF3 |
| 17-48 | Me | H | H | Br | H | heptafluoroisopropyl | H | C2F5 |
| 17-49 | Me | H | H | Br | H | nonafluoro-2-butyl | H | C2F5 |
| 17-50 | Me | Me | H | Cl | H | heptafluoroisopropyl | H | Cl |
| 17-51 | Me | Me | H | Br | H | nonafluoro-2-butyl | H | Cl |
| 17-52 | Me | Me | H | Br | H | heptafluoroisopropyl | H | OCF3 |
| 17-53 | Me | Et | H | Cl | H | nonafluoro-2-butyl | H | OCF3 |
| 17-54 | Me | Me | Cl | Br | H | pentafluoroethyl | H | CF3 |
| 17-55 | Me | Me | H | Br | H | heptafluoroisopropyl | H | CF3 |
| 17-56 | Me | Me | H | I | H | nonafluoro-2-butyl | H | CF3 |
| 17-57 | Me | Me | H | OCF3 | H | heptafluoroisopropyl | H | CF3 |
| 17-58 | Et | Me | H | OCF3 | H | nonafluoro-2-butyl | H | CF3 |
| 17-59 | Me | Me | H | CF3 | H | heptafluoroisopropyl | H | CF3 |
| 17-60 | Me | Me | H | CF3 | H | nonafluoro-2-butyl | H | CF3 |
| 17-61 | Me | Et | H | Br | H | heptafluoroisopropyl | H | C2F5 |
| 17-62 | Me | Me | H | Br | H | nonafluoro-2-butyl | H | C2F5 |
| 17-63 | Me | H | H | Br | H | heptafluoroisopropyl | F | CF3 |
| 17-64 | Me | H | H | Br | Me | nonafluoro-2-butyl | H | CF3 |
| 17-65 | Me | H | H | Br | F | heptafluoroisopropyl | Cl | CF3 |
| 17-66 | Me | H | H | Br | Me | nonafluoro-2-butyl | F | CF3 |
| 17-67 | Me | H | H | Br | Et | heptafluoroisopropyl | Me | CF3 |
| 17-68 | Et | Me | H | I | H | heptafluoroisopropyl | F | CF3 |
| 17-69 | Me | Me | H | I | Me | nonafluoro-2-butyl | H | CF3 |
| 17-70 | Me | Me | H | I | F | heptafluoroisopropyl | Cl | CF3 |
| 17-71 | Me | Me | H | I | Me | nonafluoro-2-butyl | F | CF3 |
| 17-72 | Me | Me | H | I | Et | heptafluoroisopropyl | Me | CF3 |

TABLE 18

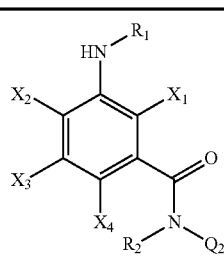

| compound number | R₁ | R₂ | L | D | X₁ | X₂ | X₃ | X₄ | Q₂ |
|---|---|---|---|---|---|---|---|---|---|
| 18-1 | —L—D | H | —CH2CH2— | CONH2 | H | H | H | H | 2,6-dimethyl-4-(1,2,2,2-tetrafluoro-1-trifluoromethyl-ethyl)-phenyl |
| 18-2 | —L—D | H | —CH2CH2— | CONH2 | H | H | H | H | 2,6-dibromo-4-pentafluoroethyl-phenyl |
| 18-3 | —L—D | H | —CH2CH2— | CONH2 | H | H | H | H | 2,6-diiodo-4-pentafluoroethyl-phenyl |
| 18-4 | —L—D | H | —CH2CH2— | CONH2 | H | H | H | H | 2-bromo-6-trifluoromethyl-4-pentafluoroethyl-phenyl |

TABLE 18-continued

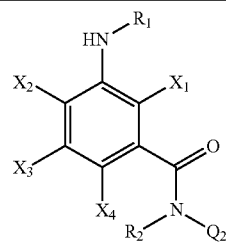

| compound number | R₁ | R₂ | L | D | X₁ | X₂ | X₃ | X₄ | Q₂ |
|---|---|---|---|---|---|---|---|---|---|
| 18-5 | —L—D | H | —CH2CH2— | CONH2 | H | H | H | H | 2-iodo-6-trifluoromethyl-4-pentafluoroethyl-phenyl |
| 18-6 | —L—D | H | —CH2CH2— | CONH2 | H | H | H | H | 2-chloro-6-methyl-4-(1,2,2,2-tetrafluoro-1-trifluoromethyl-ethyl)-phenyl |
| 18-7 | —L—D | H | —CH2CH2— | CONH2 | H | H | H | H | 2-bromo-6-methyl-4-(1,2,2,2-tetrafluoro-1-trifluoromethyl-ethyl)-phenyl |
| 18-8 | —L—D | H | —CH2CH2— | CONH2 | H | H | H | H | 2-iodo-6-methyl-4-(1,2,2,2-tetrafluoro-1-trifluoromethyl-ethyl)-phenyl |
| 18-9 | —L—D | H | —CH2CH2— | CONH2 | H | H | H | H | 2-bromo-6-ethyl-4-(1,2,2,2-tetrafluoro-1-trifluoromethyl-ethyl)-phenyl |
| 18-10 | —L—D | H | —CH2CH2— | CONH2 | H | H | H | H | 2-iodo-6-ethyl-4-(1,2,2,2-tetrafluoro-1-trifluoromethyl-ethyl)-phenyl |
| 18-11 | —L—D | H | —CH2CH2— | CONH2 | H | H | H | H | 2,6-dichloro-4-(1,2,2,2-tetrafluoro-1-trifluoromethyl-ethyl)-phenyl |
| 18-12 | —L—D | H | —CH2CH2— | CONH2 | H | H | H | H | 2,6-dibromo-4-(1,2,2,2-tetrafluoro-1-trifluoromethyl-ethyl)-phenyl |
| 18-13 | —L—D | H | —CH2CH2— | CONH2 | H | H | H | H | 2,6-diiodo-4-(1,2,2,2-tetrafluoro-1-trifluoromethyl-ethyl)-phenyl |
| 18-14 | —L—D | H | —CH2CH2— | CONH2 | H | H | H | H | 2,6-ditrifluoromethyl-4-(1,2,2,2-tetrafluoro-1-trifluoromethyl-ethyl)-phenyl |
| 18-15 | —L—D | H | —CH2CH2— | CONH2 | H | H | H | H | 2-bromo-6-trifluoromethyl-4-(1,2,2,2-tetrafluoro-1-trifluoromethyl-ethyl)-phenyl |
| 18-16 | —L—D | H | —CH2CH2— | CONH2 | H | H | H | H | 2-iodo-6-trifluoromethyl-4-(1,2,2,2-tetrafluoro-1-trifluoromethyl-ethyl)-phenyl |
| 18-17 | —L—D | H | —CH2CH2— | CONH2 | H | H | H | H | 2-bromo-6-trifluoromethoxy-4-(1,2,2,2-tetrafluoro-1-trifluoromethyl-ethyl)-phenyl |
| 18-18 | —L—D | H | —CH2CH2— | CONH2 | H | H | H | H | 2-bromo-6-iodo-4-(1,2,2,2-tetrafluoro-1-trifluoromethyl-ethyl)-phenyl |
| 18-19 | —L—D | H | —CH2CH2— | CONH2 | H | H | H | H | 2-bromo-6-trifluoromethylthio-4-(1,2,2,2-tetrafluoro-1-trifluoromethyl-ethyl)-phenyl |
| 18-20 | —L—D | H | —CH2CH2— | CONH2 | H | H | H | H | 2-bromo-6-trifluoromethylsulfinyl-4-(1,2,2,2-tetrafluoro-1-trifluoromethyl-ethyl)-phenyl |
| 18-21 | —L—D | H | —CH2CH2— | CONH2 | H | H | H | H | 2-bromo-6-trifluoromethylsulfonyl-4-(1,2,2,2-tetrafluoro-1-trifluoromethyl-ethyl)-phenyl |
| 18-22 | —L—D | H | —CH2CH2— | CONH2 | H | H | H | H | 2-bromo-6-pentafluoroethyl-4-(1,2,2,2-tetrafluoro-1-trifluoromethyl-ethyl)-phenyl |
| 18-23 | —L—D | H | —CH2CH2— | CONH2 | H | H | H | H | 2-iodo-6-pentafluoroethyl-4-(1,2,2,2-tetrafluoro-1-trifluoromethyl-ethyl)-phenyl |
| 18-24 | —L—D | H | —CH2CH2— | CONH2 | H | H | H | H | 2-chloro-6-methyl-4-(1,2,2,3,3,3-hexafluoro-1-trifluoromethyl-propyl)-phenyl |
| 18-25 | —L—D | H | —CH2CH2— | CONH2 | H | H | H | H | 2-bromo-6-methyl-4-(1,2,2,3,3,3-hexafluoro-1-trifluoromethyl-propyl)-phenyl |
| 18-26 | —L—D | H | —CH2CH2— | CONH2 | H | H | H | H | 2-iodo-6-methyl-4-(1,2,2,3,3,3-hexafluoro-1-trifluoromethyl-propyl)-phenyl |
| 18-27 | —L—D | H | —CH2CH2— | CONH2 | H | H | H | H | 2-bromo-6-ethyl-4-(1,2,2,3,3,3-hexafluoro-1-trifluoromethyl-propyl)-phenyl |
| 18-28 | —L—D | H | —CH2CH2— | CONH2 | H | H | H | H | 2-iodo-6-ethyl-4-(1,2,2,3,3,3-hexafluoro-1-trifluoromethyl-propyl)-phenyl |
| 18-29 | —L—D | H | —CH2CH2— | CONH2 | H | H | H | H | 2,6-dichloro-4-(1,2,2,3,3,3-hexafluoro-1-trifluoromethyl-propyl)-phenyl |
| 18-30 | —L—D | H | —CH2CH2— | CONH2 | H | H | H | H | 2,6-dibromo-4-(1,2,2,3,3,3-hexafluoro-1-trifluoromethyl-propyl)-phenyl |
| 18-31 | —L—D | H | —CH2CH2— | CONH2 | H | H | H | H | 2,6-diiodo-4-(1,2,2,3,3,3-hexafluoro-1-trifluoromethyl-propyl)-phenyl |
| 18-32 | —L—D | H | —CH2CH2— | CONH2 | H | H | H | H | 2,6-ditrifluoromethyl-4-(1,2,2,3,3,3-hexafluoro-1-trifluoromethyl-propyl)-phenyl |
| 18-33 | —L—D | H | —CH2CH2— | CONH2 | H | H | H | H | 2-bromo-6-trifluoromethyl-4-(1,2,2,3,3,3-hexafluoro-1-trifluoromethyl-propyl)-phenyl |
| 18-34 | —L—D | H | —CH2CH2— | CONH2 | H | H | H | H | 2-iodo-6-trifluoromethyl-4-(1,2,2,3,3,3-hexafluoro-1-trifluoromethyl-propyl)-phenyl |
| 18-35 | —L—D | H | —CH2CH2— | CONH2 | H | H | H | H | 2-bromo-6-trifluoromethoxy-4-(1,2,2,3,3,3-hexafluoro-1-trifluoromethyl-propyl)-phenyl |
| 18-36 | —L—D | H | —CH2CH2— | CONH2 | H | H | H | H | 2-bromo-6-iodo-4-(1,2,2,3,3,3-hexafluoro-1-trifluoromethyl-propyl)-phenyl |

TABLE 18-continued

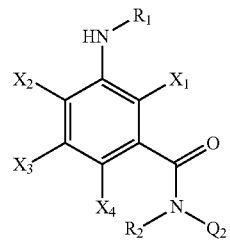

| compound number | $R_1$ | $R_2$ | L | D | $X_1$ | $X_2$ | $X_3$ | $X_4$ | $Q_2$ |
|---|---|---|---|---|---|---|---|---|---|
| 18-37 | —L—D | H | —CH2CH2— | CONH2 | H | H | H | H | 2-bromo-6-trifluoromethylthio-4-(1,2,2,3,3,3-hexafluoro-1-trifluoromethyl-ethyl)-phenyl |
| 18-38 | —L—D | H | —CH2CH2— | CONH2 | H | H | H | H | 2-bromo-6-trifluoromethylsulfinyl-4-(1,2,2,3,3,3-hexafluoro-1-trifluoromethyl-propyl)-phenyl |
| 18-39 | —L—D | H | —CH2CH2— | CONH2 | H | H | H | H | 2-bromo-6-trifluoromethylsulfonyl-4-(1,2,2,3,3,3-hexafluoro-1-trifluoromethyl-propyl)-phenyl |
| 18-40 | —L—D | H | —CH2CH2— | CONH2 | H | H | H | H | 2-bromo-6-pentafluoroethyl-4-(1,2,2,3,3,3-hexafluoro-1-trifluoromethyl-propyl)-phenyl |
| 18-41 | —L—D | H | —CH2CH2— | CONH2 | H | H | H | H | 2-iodo-6-pentafluoroethyl-4-(1,2,2,3,3,3-hexafluoro-1-trifluoromethyl-propyl)-phenyl |
| 18-42 | —L—D | H | —CH2CH2— | CONH2 | F | H | H | H | 2,6-dimethyl-4-(1,2,2,2-tetrafluoro-1-trifluoromethyl-ethyl)-phenyl |
| 18-43 | —L—D | H | —CH2CH2— | CONH2 | F | H | H | H | 2,6-dichloro-4-(1,2,2,2-tetrafluoro-1-trifluoromethyl-ethyl)-phenyl |
| 18-44 | —L—D | H | —CH2CH2— | CONH2 | F | H | H | H | 2,6-dibromo-4-(1,2,2,2-tetrafluoro-1-trifluoromethyl-ethyl)-phenyl |
| 18-45 | —L—D | H | —CH2CH2— | CONH2 | F | H | H | H | 2,6-diiodo-4-(1,2,2,2-tetrafluoro-1-trifluoromethyl-ethyl)-phenyl |
| 18-46 | —L—D | H | —CH2CH2— | CONH2 | F | H | H | H | 2-bromo-6-iodo-4-(1,2,2,2-tetrafluoro-1-trifluoromethyl-ethyl)-phenyl |
| 18-47 | —L—D | H | —CH2CH2— | CONH2 | F | H | H | H | 2-bromo-6-trifluoromethoxy-4-(1,2,2,2-tetrafluoro-1-trifluoromethyl-ethyl)-phenyl |
| 18-48 | —L—D | H | —CH2CH2— | CONH2 | F | H | H | H | 2-bromo-6-trifluoromethyl-4-(1,2,2,2-tetrafluoro-1-trifluoromethyl-ethyl)-phenyl |
| 18-49 | —L—D | H | —CH2CH2— | CONH2 | F | H | H | H | 2-iodo-6-trifluoromethyl-4-(1,2,2,2-tetrafluoro-1-trifluoromethyl-ethyl)-phenyl |
| 18-50 | —L—D | H | —CH2CH2— | CONH2 | F | H | H | H | 2-bromo-6-trifluoromethyl-4-(1,2,2,3,3,3-hexafluoro-1-trifluoromethyl-propyl)-phenyl |
| 18-51 | —L—D | H | —CH2CH2— | CONH2 | F | H | H | H | 2-iodo-6-trifluoromethyl-4-(1,2,2,3,3,3-hexafluoro-1-trifluoromethyl-propyl)-phenyl |
| 18-52 | —L—D | H | —CH2CH2— | CONH2 | F | H | H | H | 2,6-ditrifluoromethyl-4-(1,2,2,2-tetrafluoro-1-trifluoromethyl-ethyl)-phenyl |
| 18-53 | —L—D | H | —CH2CH2— | CONH2 | F | H | H | H | 2-bromo-6-trifluoromethylsulfinyl-4-(1,2,2,2-tetrafluoro-1-trifluoromethyl-ethyl)-phenyl |
| 18-54 | —L—D | H | —CH2CH2— | CONH2 | H | F | H | H | 2,6-dimethyl-4-(1,2,2,2-tetrafluoro-1-trifluoromethyl-ethyl)-phenyl |
| 18-55 | —L—D | H | —CH2CH2— | CONH2 | H | F | H | H | 2,6-dibromo-4-(1,2,2,2-tetrafluoro-1-trifluoromethyl-ethyl)-phenyl |
| 18-56 | —L—D | H | —CH2CH2— | CONH2 | H | F | H | H | 2-bromo-6-trifluoromethyl-4-(1,2,2,2-tetrafluoro-1-trifluoromethyl-ethyl)-phenyl |
| 18-57 | —L—D | H | —CH2CH2— | CONH2 | H | F | H | H | 2-iodo-6-trifluoromethyl-4-(1,2,2,2-tetrafluoro-1-trifluoromethyl-ethyl)-phenyl |
| 18-58 | —L—D | H | —CH2CH2— | CONH2 | H | F | H | H | 2-bromo-6-trifluoromethyl-4-(1,2,2,3,3,3-hexafluoro-1-trifluoromethyl-propyl)-phenyl |
| 18-59 | —L—D | H | —CH2CH2— | CONH2 | H | F | H | H | 2-iodo-6-trifluoromethyl-4-(1,2,2,3,3,3-hexafluoro-1-trifluoromethyl-propyl)-phenyl |
| 18-60 | —L—D | H | —CH2CH2— | CONH2 | H | CN | H | H | 2,6-dimethyl-4-(1,2,2,2-tetrafluoro-1-trifluoromethyl-ethyl)-phenyl |
| 18-61 | —L—D | H | —CH2CH2— | CONH2 | H | CN | H | H | 2,6-dibromo-4-(1,2,2,2-tetrafluoro-1-trifluoromethyl-ethyl)-phenyl |
| 18-62 | —L—D | H | —CH2CH2— | CONH2 | H | CN | H | H | 2-bromo-6-trifluoromethyl-4-(1,2,2,2-tetrafluoro-1-trifluoromethyl-ethyl)-phenyl |
| 18-63 | —L—D | H | —CH2CH2— | CONH2 | H | CN | H | H | 2-iodo-6-trifluoromethyl-4-(1,2,2,2-tetrafluoro-1-trifluoromethyl-ethyl)-phenyl |
| 18-64 | —L—D | H | —CH2CH2— | CONH2 | H | CN | H | H | 2-bromo-6-trifluoromethyl-4-(1,2,2,3,3,3-hexafluoro-1-trifluoromethyl-propyl)-phenyl |
| 18-65 | —L—D | H | —CH2CH2— | CONH2 | H | CN | H | H | 2-iodo-6-trifluoromethyl-4-(1,2,2,3,3,3-hexafluoro-1-trifluoromethyl-propyl)-phenyl |
| 18-66 | —L—D | H | —CH2CH2— | CONH2 | NO2 | H | H | H | 2,6-dimethyl-4-(1,2,2,2-tetrafluoro-1-trifluoromethyl-ethyl)-phenyl |
| 18-67 | —L—D | H | —CH2CH2— | CONH2 | NO2 | H | H | H | 2,6-dibromo-4-(1,2,2,2-tetrafluoro-1-trifluoromethyl-ethyl)-phenyl |
| 18-68 | —L—D | H | —CH2CH2— | CONH2 | NO2 | H | H | H | 2-bromo-6-trifluoromethyl-4-(1,2,2,2-tetrafluoro-1-trifluoromethyl-ethyl)-phenyl |

TABLE 18-continued

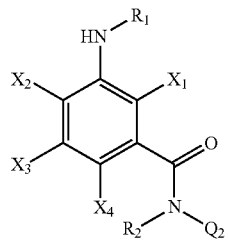

| compound number | R₁ | R₂ | L | D | X₁ | X₂ | X₃ | X₄ | Q₂ |
|---|---|---|---|---|---|---|---|---|---|
| 18-69 | —L—D | H | —CH2CH2— | CONH2 | NO2 | H | H | H | 2-iodo-6-trifluoromethyl-4-(1,2,2,2-tetrafluoro-1-trifluoromethyl-ethyl)-phenyl |
| 18-70 | —L—D | H | —CH2CH2— | CONH2 | NO2 | H | H | H | 2-bromo-6-trifluoromethyl-4-(1,2,2,3,3,3-hexafluoro-1-trifluoromethyl-propyl)-phenyl |
| 18-71 | —L—D | H | —CH2CH2— | CONH2 | NO2 | H | H | H | 2-iodo-6-trifluoromethyl-4-(1,2,2,3,3,3-hexafluoro-1-trifluoromethyl-propyl)-phenyl |
| 18-72 | H | —L—D | —CH2CH2— | CONH2 | H | H | H | H | 2,6-dimethyl-4-(1,2,2,2-tetrafluoro-1-trifluoromethyl-ethyl)-phenyl |
| 18-73 | H | —L—D | —CH2CH2— | CONH2 | H | H | H | H | 2,6-dibromo-4-(1,2,2,2-tetrafluoro-1-trifluoromethyl-ethyl)-phenyl |
| 18-74 | H | —L—D | —CH2CH2— | CONH2 | H | H | H | H | 2-bromo-6-trifluoromethyl-4-(1,2,2,2-tetrafluoro-1-trifluoromethyl-ethyl)-phenyl |
| 18-75 | H | —L—D | —CH2CH2— | CONH2 | H | H | H | H | 2-iodo-6-trifluoromethyl-4-(1,2,2,2-tetrafluoro-1-trifluoromethyl-ethyl)-phenyl |
| 18-76 | H | —L—D | —CH2CH2— | CONH2 | H | H | H | H | 2-bromo-6-trifluoromethyl-4-(1,2,2,3,3,3-hexafluoro-1-trifluoromethyl-propyl)-phenyl |
| 18-77 | H | —L—D | —CH2CH2— | CONH2 | H | H | H | H | 2-iodo-6-trifluoromethyl-4-(1,2,2,3,3,3-hexafluoro-1-trifluoromethyl-propyl)-phenyl |
| 18-78 | H | —L—D | —CH2CH2— | CONH2 | F | H | H | H | 2,6-dimethyl-4-(1,2,2,2-tetrafluoro-1-trifluoromethyl-ethyl)-phenyl |
| 18-79 | H | —L—D | —CH2CH2— | CONH2 | F | H | H | H | 2,6-dibromo-4-(1,2,2,2-tetrafluoro-1-trifluoromethyl-ethyl)-phenyl |
| 18-80 | H | —L—D | —CH2CH2— | CONH2 | F | H | H | H | 2-bromo-6-trifluoromethyl-4-(1,2,2,2-tetrafluoro-1-trifluoromethyl-ethyl)-phenyl |
| 18-81 | H | —L—D | —CH2CH2— | CONH2 | F | H | H | H | 2-iodo-6-trifluoromethyl-4-(1,2,2,2-tetrafluoro-1-trifluoromethyl-ethyl)-phenyl |
| 18-82 | H | —L—D | —CH2CH2— | CONH2 | F | H | H | H | 2-bromo-6-trifluoromethyl-4-(1,2,2,3,3,3-hexafluoro-1-trifluoromethyl-propyl)-phenyl |
| 18-83 | H | —L—D | —CH2CH2— | CONH2 | F | H | H | H | 2-iodo-6-trifluoromethyl-4-(1,2,2,3,3,3-hexafluoro-1-trifluoromethyl-propyl)-phenyl |
| 18-84 | H | —L—D | —CH2CH2— | CONH2 | H | F | H | H | 2,6-dimethyl-4-(1,2,2,2-tetrafluoro-1-trifluoromethyl-ethyl)-phenyl |
| 18-85 | H | —L—D | —CH2CH2— | CONH2 | H | CN | H | H | 2,6-dimethyl-4-(1,2,2,2-tetrafluoro-1-trifluoromethyl-ethyl)-phenyl |
| 18-86 | H | —L—D | —CH2CH2— | CONH2 | NO2 | H | H | H | 2,6-dimethyl-4-(1,2,2,2-tetrafluoro-1-trifluoromethyl-ethyl)-phenyl |
| 18-87 | —L—D | —L—D | —CH2CH2— | CONH2 | H | H | H | H | 2,6-dimethyl-4-(1,2,2,2-tetrafluoro-1-trifluoromethyl-ethyl-phenyl |
| 18-88 | —L—D | —L—D | —CH2CH2— | CONH2 | H | H | H | H | 2,6-dibromo-4-(1,2,2,2-tetrafluoro-1-trifluoromethyl-ethyl)-phenyl |
| 18-89 | —L—D | —L—D | —CH2CH2— | CONH2 | H | H | H | H | 2-bromo-6-trifluoromethyl-4-(1,2,2,2-tetrafluoro-1-trifluoromethyl-ethyl)-phenyl |
| 18-90 | —L—D | —L—D | —CH2CH2— | CONH2 | H | H | H | H | 2-iodo-6-trifluoromethyl-4-(1,2,2,2-tetrafluoro-1-trifluoromethyl-ethyl)-phenyl |
| 18-91 | —L—D | —L—D | —CH2CH2— | CONH2 | H | H | H | H | 2-bromo-6-trifluoromethyl-4-(1,2,2,3,3,3-hexafluoro-1-trifluoromethyl-propyl)-phenyl |
| 18-92 | —L—D | —L—D | —CH2CH2— | CONH2 | H | H | H | H | 2-iodo-6-trifluoromethyl-4-(1,2,2,3,3,3-hexafluoro-1-trifluoromethyl-propyl)-phenyl |
| 18-93 | —L—D | —L—D | —CH2CH2— | CONH2 | F | H | H | H | 2,6-dimethyl-4-(1,2,2,2-tetrafluoro-1-trifluoromethyl-ethyl)-phenyl |
| 18-94 | —L—D | —L—D | —CH2CH2— | CONH2 | F | H | H | H | 2,6-dibromo-4-(1,2,2,2-tetrafluoro-1-trifluoromethyl-ethyl)-phenyl |
| 18-95 | —L—D | —L—D | —CH2CH2— | CONH2 | F | H | H | H | 2-bromo-6-trifluoromethyl-4-(1,2,2,2-tetrafluoro-1-trifluoromethyl-ethyl)-phenyl |
| 18-96 | —L—D | —L—D | —CH2CH2— | CONH2 | F | H | H | H | 2-iodo-6-trifluoromethyl-4-(1,2,2,2-tetrafluoro-1-trifluoromethyl-ethyl)-phenyl |
| 18-97 | —L—D | —L—D | —CH2CH2— | CONH2 | F | H | H | H | 2-bromo-6-trifluoromethyl-4-(1,2,2,3,3,3-hexafluoro-1-trifluoromethyl-propyl)-phenyl |
| 18-98 | —L—D | —L—D | —CH2CH2— | CONH2 | F | H | H | H | 2-iodo-6-trifluoromethyl-4-(1,2,2,3,3,3-hexafluoro-1-trifluoromethyl-propyl)-phenyl |
| 18-99 | —L—D | —L—D | —CH2CH2— | CONH2 | H | F | H | H | 2,6-dimethyl-4-(1,2,2,2-tetrafluoro-1-trifluoromethyl-ethyl)-phenyl |
| 18-100 | —L—D | —L—D | —CH2CH2— | CONH2 | H | CN | H | H | 2,6-dimethyl-4-(1,2,2,2-tetrafluoro-1-trifluoromethyl-ethyl)-phenyl |

TABLE 18-continued

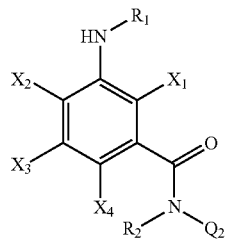

| compound number | R₁ | R₂ | L | D | X₁ | X₂ | X₃ | X₄ | Q₂ |
|---|---|---|---|---|---|---|---|---|---|
| 18-101 | —L—D | —L—D | —CH2CH2— | CONH2 | NO2 | H | H | H | 2,6-dimethyl-4-(1,2,2,2-tetrafluoro-1-trifluoromethyl-ethyl)-phenyl |
| 18-102 | —L—D | H | —CH2CH2— | CONHMe | H | H | H | H | 2,6-dimethyl-4-(1,2,2,2-tetrafluoro-1-trifluoromethyl-ethyl)-phenyl |
| 18-103 | —L—D | H | —CH2CH2— | CONHMe | H | H | H | H | 2,6-dibromo-4-(1,2,2,2-tetrafluoro-1-trifluoromethyl-ethyl)-phenyl |
| 18-104 | —L—D | H | —CH2CH2— | CONHMe | H | H | H | H | 2-bromo-6-trifluoromethyl-4-(1,2,2,2-tetrafluoro-1-trifluoromethyl-ethyl)-phenyl |
| 18-105 | —L—D | H | —CH2CH2— | CONMe2 | H | H | H | H | 2,6-dimethyl-4-(1,2,2,2-tetrafluoro-1-trifluoromethyl-ethyl)-phenyl |
| 18-106 | —L—D | H | —CH2CH2— | CONMe2 | H | H | H | H | 2,6-dibromo-4-(1,2,2,2-tetrafluoro-1-trifluoromethyl-ethyl)-phenyl |
| 18-107 | —L—D | H | —CH2CH2— | CONMe2 | H | H | H | H | 2-iodo-6-trifluoromethyl-4-(1,2,2,2-tetrafluoro-1-trifluoromethyl-ethyl)-phenyl |
| 18-108 | —L—D | H | —CH2CH2— | CONMe2 | F | H | H | H | 2,6-dimethyl-4-(1,2,2,2-tetrafluoro-1 trifluoromethyl-ethyl)-phenyl |
| 18-109 | —L—D | H | —CH2CH2— | CONMe2 | F | H | H | H | 2,6-dibromo-4-(1,2,2,2-tetrafluoro-1-trifluoromethyl-ethyl)-phenyl |
| 18-110 | —L—D | H | —CH2CH2— | CONMe2 | F | H | H | H | 2-iodo-6-trifluoromethyl-4-(1,2,2,2-tetrafluoro-1-trifluoromethyl-ethyl)-phenyl |
| 18-111 | —L—D | H | —CH2CH2— | CONMe2 | H | H | H | H | 2-bromo-6-trifluoromethylsulfinyl-4-(1,2,2,2-tetrafluoro-1-trifluoromethyl-ethyl)-phenyl |

TABLE 19

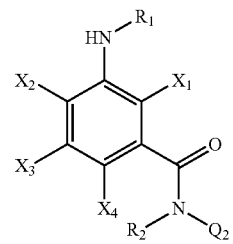

| compound number | R₁ | R₂ | L | D | X₁ | X₂ | X₃ | X₄ | Q₂ |
|---|---|---|---|---|---|---|---|---|---|
| 19-1 | —L—D | H | —CH2CH2— | SO2NH2 | H | H | H | H | 2,6-dimethyl-4-(1,2,2,2-tetrafluoro-1-trifluoromethyl-ethyl)-phenyl |
| 19-2 | —L—D | H | —CH2CH2— | SO2NH2 | H | H | H | H | 2,6-dibromo-4-pentafluoroethyl-phenyl |
| 19-3 | —L—D | H | —CH2CH2— | SO2NH2 | H | H | H | H | 2,6-diiodo-4-pentafluoroethyl-phenyl |
| 19-4 | —L—D | H | —CH2CH2— | SO2NH2 | H | H | H | H | 2-bromo-6-trifluoromethyl-4-pentafluoroethyl-phenyl |
| 19-5 | —L—D | H | —CH2CH2— | SO2NH2 | H | H | H | H | 2-iodo-6-trifluoromethyl-4-pentafluoroethyl-phenyl |
| 19-6 | —L—D | H | —CH2CH2— | SO2NH2 | H | H | H | H | 2-chloro-6-methyl-4-(1,2,2,2-tetrafluoro-1-trifluoromethyl-ethyl)-phenyl |
| 19-7 | —L—D | H | —CH2CH2— | SO2NH2 | H | H | H | H | 2-bromo-6-methyl-4-(1,2,2,2-tetrafluoro-1-trifluoromethyl-ethyl)-phenyl |
| 19-8 | —L—D | H | —CH2CH2— | S02NH2 | H | H | H | H | 2-iodo-6-methyl-4-(1,2,2,2-tetrafluoro-1-trifluoromethyl-ethyl)-phenyl |
| 19-9 | —L—D | H | —CH2CH2— | SO2NH2 | H | H | H | H | 2-bromo-6-ethyl-4-(1,2,2,2-tetrafluoro-1-trifluoromethyl-ethyl)-phenyl |
| 19-10 | —L—D | H | —CH2CH2— | SO2NH2 | H | H | H | H | 2-iodo-6-ethyl-4-(1,2,2,2-tetrafluoro-1-trifluoromethyl-ethyl)-phenyl |
| 19-11 | —L—D | H | —CH2CH2— | SO2NH2 | H | H | H | H | 2,6-dichloro-4-(1,2,2,2-tetrafluoro-1-trifluoromethyl-ethyl)-phenyl |
| 19-12 | —L—D | H | —CH2CH2— | SO2NH2 | H | H | H | H | 2,6-dibromo-4-(1,2,2,2-tetrafluoro-1-trifluoromethyl-ethyl)-phenyl |

TABLE 19-continued

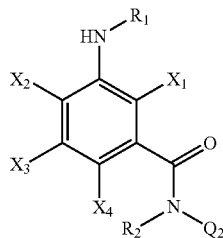

| compound number | $R_1$ | $R_2$ | L | D | $X_1$ | $X_2$ | $X_3$ | $X_4$ | $Q_2$ |
|---|---|---|---|---|---|---|---|---|---|
| 19-13 | —L—D | H | —CH2CH2— | SO2NH2 | H | H | H | H | 2,6-diiodo-4-(1,2,2,2-tetrafluoro-1-trifluoromethyl-ethyl)-phenyl |
| 19-14 | —L—D | H | —CH2CH2— | SO2NH2 | H | H | H | H | 2,6-ditrifluoromethyl-4-(1,2,2,2-tetrafluoro-1-trifluoromethyl-ethyl)-phenyl |
| 19-15 | —L—D | H | —CH2CH2— | SO2NH2 | H | H | H | H | 2-bromo-6-trifluoromethyl-4-(1,2,2,2-tetrafluoro-1-trifluoromethyl-ethyl)-phenyl |
| 19-16 | —L—D | H | —CH2CH2— | SO2NH2 | H | H | H | H | 2-iodo-6-trifluoromethyl-4-(1,2,2,2-tetrafluoro-1-trifluoromethyl-ethyl)-phenyl |
| 19-17 | —L—D | H | —CH2CH2— | SO2NH2 | H | H | H | H | 2-bromo-6-trifluoromethoxy-4-(1,2,2,2-tetrafluoro-1-trifluoromethyl-ethyl)-phenyl |
| 19-18 | —L—D | H | —CH2CH2— | SO2NH2 | H | H | H | H | 2-bromo-6-iodo-4-(1,2,2,2-tetrafluoro-1-trifluoromethyl-ethyl)-phenyl |
| 19-19 | —L—D | H | —CH2CH2— | SO2NH2 | H | H | H | H | 2-bromo-6-trifluoromethylthio-4-(1,2,2,2-tetrafluoro-1-trifluoromethyl-ethyl)-phenyl |
| 19-20 | —L—D | H | —CH2CH2— | SO2NH2 | H | H | H | H | 2-bromo-6-trifluoromethylsulfinyl-4-(1,2,2,2-tetrafluoro-1-trifluoromethyl-ethyl)-phenyl |
| 19-21 | —L—D | H | —CH2CH2— | SO2NH2 | H | H | H | H | 2-bromo-6-trifluoromethylsulfonyl-4-(1,2,2,2-tetrafluoro-1-trifluoromethyl-ethyl)-phenyl |
| 19-22 | —L—D | H | —CH2CH2— | SO2NH2 | H | H | H | H | 2-bromo-6-pentafluoroethyl-4-(1,2,2,2-tetrafluoro-1-trifluoromethyl-ethyl)-phenyl |
| 19-23 | —L—D | H | —CH2CH2— | SO2NH2 | H | H | H | H | 2-iodo-6-pentafluoroethyl-4-(1,2,2,2-tetrafluoro-1-trifluoromethyl-ethyl)-phenyl |
| 19-24 | —L—D | H | —CH2CH2— | SO2NH2 | H | H | H | H | 2-chloro-6-methyl-4-(1,2,2,3,3,3-hexafluoro-1-trifluoromethyl-propyl)-phenyl |
| 19-25 | —L—D | H | —CH2CH2— | SO2NH2 | H | H | H | H | 2-bromo-6-methyl-4-(1,2,2,3,3,3-hexafluoro-1-trifluoromethyl-propyl)-phenyl |
| 19-26 | —L—D | H | —CH2CH2— | SO2NH2 | H | H | H | H | 2-iodo-6-methyl-4-(1,2,2,3,3,3-hexafluoro-1-trifluoromethyl-propyl)-phenyl |
| 19-27 | —L—D | H | —CH2CH2— | SO2NH2 | H | H | H | H | 2-bromo-6-ethyl-4-(1,2,2,3,3,3-hexafluoro-1-trifluoromethyl-propyl)-phenyl |
| 19-28 | —L—D | H | —CH2CH2— | SO2NH2 | H | H | H | H | 2-iodo-6-ethyl-4-(1,2,2,3,3,3-hexafluoro-1-trifluoromethyl-propyl)-phenyl |
| 19-29 | —L—D | H | —CH2CH2— | SO2NH2 | H | H | H | H | 2,6-dichloro-4-(1,2,2,3,3,3-hexafluoro-1-trifluoromethyl-propyl)-phenyl |
| 19-30 | —L—D | H | —CH2CH2— | SO2NH2 | H | H | H | H | 2,6-dibromo-4-(1,2,2,3,3,3-hexafluoro-1-trifluoromethyl-propyl)-phenyl |
| 19-31 | —L—D | H | —CH2CH2— | SO2NH2 | H | H | H | H | 2,6-diiodo-4-(1,2,2,3,3,3-hexafluoro-1-trifluoromethyl-propyl)-phenyl |
| 19-32 | —L—D | H | —CH2CH2— | SO2NH2 | H | H | H | H | 2,6-ditrifluoromethyl-4-(1,2,2,3,3,3-hexafluoro-1-trifluoromethyl-propyl)-phenyl |
| 19-33 | —L—D | H | —CH2CH2— | SO2NH2 | H | H | H | H | 2-bromo-6-trifluoromethyl-4-(1,2,2,3,3,3-hexafluoro-1-trifluoromethyl-propyl)-phenyl |
| 19-34 | —L—D | H | —CH2CH2— | SO2NH2 | H | H | H | H | 2-iodo-6-trifluoromethyl-4-(1,2,2,3,3,3-hexafluoro-1-trifluoromethyl-propyl)-phenyl |
| 19-35 | —L—D | H | —CH2CH2— | SO2NH2 | H | H | H | H | 2-bromo-6-trifluoromethoxy-4-(1,2,2,3,3,3-hexafluoro-1-trifluoromethyl-propyl)-phenyl |
| 19-36 | —L—D | H | —CH2CH2— | SO2NH2 | H | H | H | H | 2-bromo-6-iodo-4-(1,2,2,3,3,3-hexafluoro-1-trifluoromethyl-propyl)-phenyl |
| 19-37 | —L—D | H | —CH2CH2— | SO2NH2 | H | H | H | H | 2-bromo-6-trifluoromethylthio-4-(1,2,2,3,3,3-hexafluoro-1-trifluoromethyl-propyl)-phenyl |
| 19-38 | —L—D | H | —CH2CH2— | SO2NH2 | H | H | H | H | 2-bromo-6-trifluoromethylsulfinyl-4-(1,2,2,3,3,3-hexafluoro-1-trifluoromethyl-propyl)-phenyl |
| 19-39 | —L—D | H | —CH2CH2— | SO2NH2 | H | H | H | H | 2-bromo-6-trifluoromethylsulfonyl-4-(1,2,2,3,3,3-hexafluoro-1-trifluoromethyl-propyl)-phenyl |
| 19-40 | —L—D | H | —CH2CH2— | SO2NH2 | H | H | H | H | 2-bromo-6-pentafluoroethyl-4-(1,2,2,3,3,3-hexafluoro-1-trifluoromethyl-propyl)-phenyl |
| 19-41 | —L—D | H | —CH2CH2— | SO2NH2 | H | H | H | H | 2-iodo-6-pentafluoroethyl-4-(1,2,2,3,3,3-hexafluoro-1-trifluoromethyl-propyl)-phenyl |
| 19-42 | —L—D | H | —CH2CH2— | SO2NH2 | F | H | H | H | 2,6-dimethyl-4-(1,2,2,2-tetrafluoro-1-trifluoromethyl-ethyl)-phenyl |
| 19-43 | —L—D | H | —CH2CH2— | SO2NH2 | F | H | H | H | 2,6-dichloro-4-(1,2,2,2-tetrafluoro-1-trifluoromethyl-ethyl)-phenyl |
| 19-44 | —L—D | H | —CH2CH2— | SO2NH2 | F | H | H | H | 2,6-dibromo-4-(1,2,2,2-tetrafluoro-1-trifluoromethyl-ethyl)-phenyl |

TABLE 19-continued

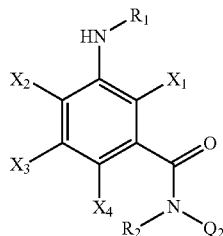

| compound number | R₁ | R₂ | L | D | X₁ | X₂ | X₃ | X₄ | Q₂ |
|---|---|---|---|---|---|---|---|---|---|
| 19-45 | —L—D | H | —CH2CH2— | SO2NH2 | F | H | H | H | 2,6-diiodo-4-(1,2,2,2-tetrafluoro-1-trifluoromethyl-ethyl)-phenyl |
| 19-46 | —L—D | H | —CH2CH2— | SO2NH2 | F | H | H | H | 2-bromo-6-iodo-4-(1,2,2,2-tetrafluoro-1-trifluoromethyl-ethyl)-phenyl |
| 19-47 | —L—D | H | —CH2CH2— | SO2NH2 | F | H | H | H | 2-bromo-6-trifluoromethoxy-4-(1,2,2,2-tetrafluoro-1-trifluoromethyl-ethyl)-phenyl |
| 19-48 | —L—D | H | —CH2CH2— | SO2NH2 | F | H | H | H | 2-bromo-6-trifluoromethyl-4-(1,2,2,2-tetrafluoro-1-trifluoromethyl-ethyl)-phenyl |
| 19-49 | —L—D | H | —CH2CH2— | SO2NH2 | F | H | H | H | 2-iodo-6-trifluoromethyl-4-(1,2,2,2-tetrafluoro-1-trifluoromethyl-ethyl)-phenyl |
| 19-50 | —L—D | H | —CH2CH2— | SO2NH2 | F | H | H | H | 2-bromo-6-trifluoromethyl-4-(1,2,2,3,3,3-hexafluoro-1-trifluoromethyl-propyl)-phenyl |
| 19-51 | —L—D | H | —CH2CH2— | SO2NH2 | F | H | H | H | 2-iodo-6-trifluoromethyl-4-(1,2,2,3,3,3-hexafluoro-1-trifluoromethyl-propyl)-phenyl |
| 19-52 | —L—D | H | —CH2CH2— | SO2NH2 | F | H | H | H | 2,6-ditrifluoromethyl-4-(1,2,2,2-tetrafluoro-1-trifluoromethyl-ethyl)-phenyl |
| 19-53 | —L—D | H | —CH2CH2— | SO2NH2 | F | H | H | H | 2-bromo-6-trifluoromethylsulfinyl-4-(1,2,2,2-tetrafluoro-1-trifluoromethyl-ethyl)-phenyl |
| 19-54 | —L—D | H | —CH2CH2— | SO2NH2 | H | F | H | H | 2,6-dimethyl-4-(1,2,2,2-tetrafluoro-1-trifluoromethyl-ethyl)-phenyl |
| 19-55 | —L—D | H | —CH2CH2— | SO2NH2 | H | F | H | H | 2,6-dibromo-4-(1,2,2,2-tetrafluoro-1-trifluoromethyl-ethyl)-phenyl |
| 19-56 | —L—D | H | —CH2CH2— | SO2NH2 | H | F | H | H | 2-bromo-6-trifluoromethyl-4-(1,2,2,2-tetrafluoro-1-trifluoromethyl-ethyl)-phenyl |
| 19-57 | —L—D | H | —CH2CH2— | SO2NH2 | H | F | H | H | 2-iodo-6-trifluoromethyl-4-(1,2,2,2-tetrafluoro-1-trifluoromethyl-ethyl)-phenyl |
| 19-58 | —L—D | H | —CH2CH2— | SO2NH2 | H | F | H | H | 2-bromo-6-trifluoromethyl-4-(1,2,2,3,3,3-hexafluoro-1-trifluoromethyl-propyl)-phenyl |
| 19-59 | —L—D | H | —CH2CH2— | SO2NH2 | H | F | H | H | 2-iodo-6-trifluoromethyl-4-(1,2,2,3,3,3-hexafluoro-1-trifluoromethyl-propyl)-phenyl |
| 19-60 | —L—D | H | —CH2CH2— | SO2NH2 | H | CN | H | H | 2,6-dimethyl-4-(1,2,2,2-tetrafluoro-1-trifluoromethyl-ethyl)-phenyl |
| 19-61 | —L—D | H | —CH2CH2— | SO2NH2 | H | CN | H | H | 2,6-dibromo-4-(1,2,2,2-tetrafluoro-1-trifluoromethyl-ethyl)-phenyl |
| 19-62 | —L—D | H | —CH2CH2— | SO2NH2 | H | CN | H | H | 2-bromo-6-trifluoromethyl-4-(1,2,2,2-tetrafluoro-1-trifluoromethyl-ethyl)-phenyl |
| 19-63 | —L—D | H | —CH2CH2— | SO2NH2 | H | CN | H | H | 2-iodo-6-trifluoromethyl-4-(1,2,2,2-tetrafluoro-1-trifluoromethyl-ethyl)-phenyl |
| 19-64 | —L—D | H | —CH2CH2— | SO2NH2 | H | CN | H | H | 2-bromo-6-trifluoromethyl-4-(1,2,2,3,3,3-hexafluoro-1-trifluoromethyl-propyl)-phenyl |
| 19-65 | —L—D | H | —CH2CH2— | SO2NH2 | H | CN | H | H | 2-iodo-6-trifluoromethyl-4-(1,2,2,3,3,3-hexafluoro-1-trifluoromethyl-propyl)-phenyl |
| 19-66 | —L—D | H | —CH2CH2— | SO2NH2 | NO2 | H | H | H | 2,6-dimethyl-4-(1,2,2,2-tetrafluoro-1-trifluoromethyl-ethyl)-phenyl |
| 19-67 | —L—D | H | —CH2CH2— | SO2NH2 | NO2 | H | H | H | 2,6-dibromo-4-(1,2,2,2-tetrafluoro-1-trifluoromethyl-ethyl)-phenyl |
| 19-68 | —L—D | H | —CH2CH2— | SO2NH2 | NO2 | H | H | H | 2-bromo-6-trifluoromethyl-4-(1,2,2,2-tetrafluoro-1-trifluoromethyl-ethyl)-phenyl |
| 19-69 | —L—D | H | —CH2CH2— | SO2NH2 | NO2 | H | H | H | 2-iodo-6-trifluoromethyl-4-(1,2,2,2-tetrafluoro-1-trifluoromethyl-ethyl)-phenyl |
| 19-70 | —L—D | H | —CH2CH2— | SO2NH2 | NO2 | H | H | H | 2-bromo-6-trifluoromethyl-4-(1,2,2,3,3,3-hexafluoro-1-trifluoromethyl-propyl)-phenyl |
| 19-71 | —L—D | H | —CH2CH2— | SO2NH2 | NO2 | H | H | H | 2-iodo-6-trifluoromethyl-4-(1,2,2,3,3,3-hexafluoro-1-trifluoromethyl-propyl)-phenyl |
| 19-72 | H | —L—D | —CH2CH2— | SO2NH2 | H | H | H | H | 2,6-dimethyl-4-(1,2,2,2-tetrafluoro-1-trifluoromethyl-ethyl)-phenyl |
| 19-73 | H | —L—D | —CH2CH2— | SO2NH2 | H | H | H | H | 2,6-dibromo-4-(1,2,2,2-tetrafluoro-1-trifluoromethyl-ethyl)-phenyl |
| 19-74 | H | —L—D | —CH2CH2— | SO2NH2 | H | H | H | H | 2-bromo-6-trifluoromethyl-4-(1,2,2,2-tetrafluoro-1-trifluoromethyl-ethyl)-phenyl |
| 19-75 | H | —L—D | —CH2CH2— | SO2NH2 | H | H | H | H | 2-iodo-6-trifluoromethyl-4-(1,2,2,3,3,3-hexafluoro-1-trifluoromethyl-propyl)-phenyl |
| 19-76 | H | —L—D | —CH2CH2— | SO2NH2 | F | H | H | H | 2,6-dimethyl-4-(1,2,2,2-tetrafluoro-1-trifluoromethyl-ethyl)-phenyl |

TABLE 19-continued

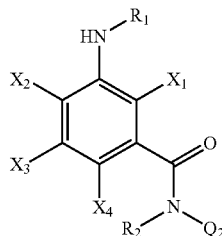

| compound number | R₁ | R₂ | L | D | X₁ | X₂ | X₃ | X₄ | Q₂ |
|---|---|---|---|---|---|---|---|---|---|
| 19-77 | H | —L—D | —CH2CH2— | SO2NH2 | F | H | H | H | 2,6-dibromo-4-(1,2,2,2-tetrafluoro-1-trifluoromethyl-ethyl)-phenyl |
| 19-78 | H | —L—D | —CH2CH2— | SO2NH2 | F | H | H | H | 2-bromo-6-trifluoromethyl-4-(1,2,2,2-tetrafluoro-1-trifluoromethyl-ethyl)-phenyl |
| 19-79 | H | —L—D | —CH2CH2— | SO2NH2 | F | H | H | H | 2-iodo-6-trifluoromethyl-4-(1,2,2,3,3,3-hexafluoro-1-trifluoromethyl-propyl)-phenyl |
| 19-80 | H | —L—D | —CH2CH2— | SO2NH2 | H | F | H | H | 2,6-dimethyl-4-(1,2,2,2-tetrafluoro-1-trifluoromethyl-ethyl)-phenyl |
| 19-81 | H | —L—D | —CH2CH2— | SO2NH2 | H | CN | H | H | 2,6-dimethyl-4-(1,2,2,2-tetrafluoro-1-trifluoromethyl-ethyl)-phenyl |
| 19-82 | H | —L—D | —CH2CH2— | SO2NH2 | NO2 | H | H | H | 2,6-dimethyl-4-(1,2,2,2-tetrafluoro-1-trifluoromethyl-ethyl)-phenyl |
| 19-83 | —L—D | —L—D | —CH2CH2— | SO2NH2 | H | H | H | H | 2,6-dimethyl-4-(1,2,2,2-tetrafluoro-1-trifluoromethyl-ethyl)-phenyl |
| 19-84 | —L—D | —L—D | —CH2CH2— | SO2NH2 | H | H | H | H | 2,6-dibromo-4-(1,2,2,2-tetrafluoro-1-trifluoromethyl-ethyl)-phenyl |
| 19-85 | —L—D | —L—D | —CH2CH2— | SO2NH2 | H | H | H | H | 2-bromo-6-trifluoromethyl-4-(1,2,2,2-tetrafluoro-1-trifluoromethyl-ethyl)-phenyl |
| 19-86 | —L—D | —L—D | —CH2CH2— | SO2NH2 | H | H | H | H | 2-iodo-6-trifluoromethyl-4-(1,2,2,3,3,3-hexafluoro-1-trifluoromethyl-propyl)-phenyl |
| 19-87 | —L—D | —L—D | —CH2CH2— | SO2NH2 | F | H | H | H | 2,6-dimethyl-4-(1,2,2,2-tetrafluoro-1-trifluoromethyl-ethyl)-phenyl |
| 19-88 | —L—D | —L—D | —CH2CH2— | SO2NH2 | F | H | H | H | 2,6-dibromo-4-(1,2,2,2-tetrafluoro-1-trifluoromethyl-ethyl)-phenyl |
| 19-89 | —L—D | —L—D | —CH2CH2— | SO2NH2 | F | H | H | H | 2-bromo-6-trifluoromethyl-4-(1,2,2,2-tetrafluoro-1-trifluoromethyl-ethyl)-phenyl |
| 19-90 | —L—D | —L—D | —CH2CH2— | SO2NH2 | F | H | H | H | 2-iodo-6-trifluoromethyl-4-(1,2,2,3,3,3-hexafluoro-1-trifluoromethyl-propyl)-phenyl |
| 19-91 | —L—D | —L—D | —CH2CH2— | SO2NH2 | H | F | H | H | 2,6-dimethyl-4-(1,2,2,2-tetrafluoro-1-trifluoromethyl-ethyl)-phenyl |
| 19-92 | —L—D | —L—D | —CH2CH2— | SO2NH2 | H | CN | H | H | 2,6-dimethyl-4-(1,2,2,2-tetrafluoro-1-trifluoromethyl-ethyl)-phenyl |
| 19-93 | —L—D | —L—D | —CH2CH2— | SO2NH2 | NO2 | H | H | H | 2,6-dimethyl-4-(1,2,2,2-tetrafluoro-1-trifluoromethyl-ethyl)-phenyl |

TABLE 20

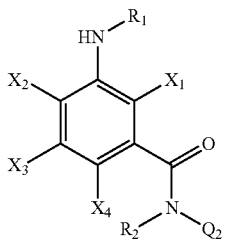

| compound number | R₁ | R₂ | L | D | X₁ | X₂ | X₃ | X₄ | Q₂ |
|---|---|---|---|---|---|---|---|---|---|
| 20-1 | —L—D | H | —CH2CH2— | SO2Me | H | H | H | H | 2,6-dimethyl-4-(1,2,2,2-tetrafluoro-1-trifluoromethyl-ethyl)-phenyl |
| 20-2 | —L—D | H | —CH2CH2— | SO2Me | H | H | H | H | 2,6-dibromo-4-(1,2,2,2-tetrafluoro-1-trifluoromethyl-ethyl)-phenyl |
| 20-3 | —L—D | H | —CH2CH2— | SO2Me | H | H | H | H | 2-bromo-6-trifluoromethyl-4-(1,2,2,2-tetrafluoro-1-trifluoromethyl-ethyl)-phenyl |
| 20-4 | —L—D | H | —CH2CH2— | SO2Me | H | H | H | H | 2-iodo-6-trifluoromethyl-4-(1,2,2,2-tetrafluoro-1-trifluoromethyl-ethyl)-phenyl |
| 20-5 | —L—D | H | —CH2CH2— | SO2Me | H | H | H | H | 2-bromo-6-trifluoromethyl-4-(1,2,2,3,3,3-hexafluoro-1-trifluoromethyl-propyl)-phenyl |

TABLE 20-continued

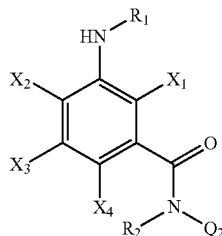

| compound number | $R_1$ | $R_2$ | L | D | $X_1$ | $X_2$ | $X_3$ | $X_4$ | $Q_2$ |
|---|---|---|---|---|---|---|---|---|---|
| 20-6 | —L—D | H | —CH2CH2— | SO2Me | H | H | H | H | 2-iodo-6-trifluoromethyl-4-(1,2,2,3,3,3-hexafluoro-1-trifluoromethyl-propyl)-phenyl |
| 20-7 | —L—D | H | —CH2CH2— | SO2Me | F | H | H | H | 2,6-dimethyl-4-(1,2,2,2-tetrafluoro-1-trifluoromethyl-ethyl)-phenyl |
| 20-8 | —L—D | H | —CH2CH2— | SO2Me | F | H | H | H | 2,6-dichloro-4-(1,2,2,2-tetrafluoro-1-trifluoromethyl-ethyl)-phenyl |
| 20-9 | —L—D | H | —CH2CH2— | SO2Me | F | H | H | H | 2,6-dibromo-4-(1,2,2,2-tetrafluoro-1-trifluoromethyl-ethyl)-phenyl |
| 20-10 | —L—D | H | —CH2CH2— | SO2Me | F | H | H | H | 2,6-diiodo-4-(1,2,2,2-tetrafluoro-1-trifluoromethyl-ethyl)-phenyl |
| 20-11 | —L—D | H | —CH2CH2— | SO2Me | F | H | H | H | 2-bromo-6-iodo-4-(1,2,2,2-tetrafluoro-1-trifluoromethyl-ethyl)-phenyl |
| 20-12 | —L—D | H | —CH2CH2— | SO2Me | F | H | H | H | 2-bromo-6-trifluoromethoxy-4-(1,2,2,2-tetrafluoro-1-trifluoromethyl-ethyl)-phenyl |
| 20-13 | —L—D | H | —CH2CH2— | SO2Me | F | H | H | H | 2-bromo-6-trifluoromethyl-4-(1,2,2,2-tetrafluoro-1-trifluoromethyl-ethyl)-phenyl |
| 20-14 | —L—D | H | —CH2CH2— | SO2Me | F | H | H | H | 2-iodo-6-trifluoromethyl-4-(1,2,2,2-tetrafluoro-1-trifluoromethyl-ethyl)-phenyl |
| 20-15 | —L—D | H | —CH2CH2— | SO2Me | F | H | H | H | 2-bromo-6-trifluoromethyl-4-(1,2,2,3,3,3-hexafluoro-1-trifluoromethyl-propyl)-phenyl |
| 20-16 | —L—D | H | —CH2CH2— | SO2Me | F | H | H | H | 2-iodo-6-trifluoromethyl-4-(1,2,2,3,3,3-hexafluoro-1-trifluoromethyl-propyl)-phenyl |
| 20-17 | —L—D | H | —CH2CH2— | SO2Me | F | H | H | H | 2,6-ditrifluoromethyl-4-(1,2,2,2-tetrafluoro-1-trifluoromethyl-ethyl)-phenyl |
| 20-18 | —L—D | H | —CH2CH2— | SO2Me | F | H | H | H | 2-bromo-6-trifluoromethylsulfinyl-4-(1,2,2,2-tetrafluoro-1-trifluoromethyl-ethyl)-phenyl |
| 20-19 | —L—D | H | —CH2CH2— | SO2Me | H | F | H | H | 2,6-dimethyl-4-(1,2,2,2-tetrafluoro-1-trifluoromethyl-ethyl)-phenyl |
| 20-20 | —L—D | H | —CH2CH2— | SO2Me | H | F | H | H | 2,6-dibromo-4-(1,2,2,2-tetrafluoro-1-trifluoromethyl-ethyl)-phenyl |
| 20-21 | —L—D | H | —CH2CH2— | SO2Me | H | F | H | H | 2-bromo-6-trifluoromethyl-4-(1,2,2,2-tetrafluoro-1-trifluoromethyl-ethyl)-phenyl |
| 20-22 | —L—D | H | —CH2CH2— | SO2Me | H | F | H | H | 2-iodo-6-trifluoromethyl-4-(1,2,3,3,3-hexafluoro-1-trifluoromethyl-propyl)-phenyl |
| 20-23 | —L—D | H | —CH2CH2— | SO2Me | H | CN | H | H | 2,6-dimethyl-4-(1,2,2,2-tetrafluoro-1-trifluoromethyl-ethyl)-phenyl |
| 20-24 | —L—D | H | —CH2CH2— | SO2Me | H | CN | H | H | 2,6-dibromo-4-(1,2,2,2-tetrafluoro-1-trifluoromethyl-ethyl)-phenyl |
| 20-25 | —L—D | H | —CH2CH2— | SO2Me | H | CN | H | H | 2-bromo-6-trifluoromethyl-4-(1,2,2,2-tetrafluoro-1-trifluoromethyl-ethyl)-phenyl |
| 20-26 | —L—D | H | —CH2CH2— | SO2Me | H | CN | H | H | 2-iodo-6-trifluoromethyl-4-(1,2,2,3,3,3-hexafluoro-1-trifluoromethyl-propyl)-phenyl |
| 20-27 | —L—D | H | —CH2CH2— | SO2Me | NO2 | H | H | H | 2,6-dimethyl-4-(1,2,2,2-tetrafluoro-1-trifluoromethyl-ethyl)-phenyl |
| 20-28 | —L—D | H | —CH2CH2— | SO2Me | NO2 | H | H | H | 2,6-dibromo-4-(1,2,2,2-tetrafluoro-1-trifluoromethyl-ethyl)-phenyl |
| 20-29 | —L—D | H | —CH2CH2— | SO2Me | NO2 | H | H | H | 2-bromo-6-trifluoromethyl-4-(1,2,2,2-tetrafluoro-1-trifluoromethyl-ethyl)-phenyl |
| 20-30 | —L—D | H | —CH2CH2— | SO2Me | NO2 | H | H | H | 2-iodo-6-trifluoromethyl-4-(1,2,2,3,3,3-hexafluoro-1-trifluoromethyl-propyl)-phenyl |
| 20-31 | H | —L—D | —CH2CH2— | SO2Me | H | H | H | H | 2,6-dimethyl-4-(1,2,2,2-tetrafluoro-1-trifluoromethyl-ethyl)-phenyl |
| 20-32 | H | —L—D | —CH2CH2— | SO2Me | H | H | H | H | 2,6-dibromo-4-(1,2,2,2-tetrafluoro-1-trifluoromethyl-ethyl)-phenyl |
| 20-33 | H | —L—D | —CH2CH2— | SO2Me | H | H | H | H | 2-bromo-6-trifluoromethyl-4-(1,2,2,2-tetrafluoro-1-trifluoromethyl-ethyl)-phenyl |
| 20-34 | H | —L—D | —CH2CH2— | SO2Me | H | H | H | H | 2-iodo-6-trifluoromethyl-4-(1,2,2,3,3,3-hexafluoro-1-trifluoromethyl-propyl)-phenyl |
| 20-35 | H | —L—D | —CH2CH2— | SO2Me | F | H | H | H | 2,6-dimethyl-4-(1,2,2,2-tetrafluoro-1-trifluoromethyl-ethyl)-phenyl |
| 20-36 | H | —L—D | —CH2CH2— | SO2Me | F | H | H | H | 2,6-dibromo-4-(1,2,2,2-tetrafluoro-1-trifluoromethyl-ethyl)-phenyl |
| 20-37 | H | —L—D | —CH2CH2— | SO2Me | F | H | H | H | 2-bromo-6-trifluoromethylthio-4-(1,2,2,3,3,3-hexafluoro-1-trifluoromethyl-ethyl)-phenyl |

TABLE 20-continued

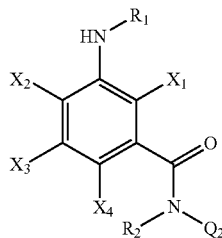

| compound number | $R_1$ | $R_2$ | L | D | $X_1$ | $X_2$ | $X_3$ | $X_4$ | $Q_2$ |
|---|---|---|---|---|---|---|---|---|---|
| 20-38 | H | —L—D | —CH2CH2— | SO2Me | F | H | H | H | 2-iodo-6-trifluoromethyl-4-(1,2,2,3,3,3-hexafluoro-1-trifluoromethyl-propyl)-phenyl |
| 20-39 | H | —L—D | —CH2CH2— | SO2Me | H | F | H | H | 2,6-dimethyl-4-(1,2,2,2-tetrafluoro-1-trifluoromethyl-ethyl)-phenyl |
| 20-40 | H | —L—D | —CH2CH2— | SO2Me | H | CN | H | H | 2,6-dimethyl-4-(1,2,2,2-tetrafluoro-1-trifluoromethyl-ethyl)-phenyl |
| 20-41 | H | —L—D | —CH2CH2— | SO2Me | NO2 | H | H | H | 2,6-dimethyl-4-(1,2,2,2-tetrafluoro-1-trifluoromethyl-ethyl)-phenyl |
| 20-42 | —L—D | —L—D | —CH2CH2— | SO2Me | H | H | H | H | 2,6-dimethyl-4-(1,2,2,2-tetrafluoro-1-trifluoromethyl-ethyl)-phenyl |
| 20-43 | —L—D | —L—D | —CH2CH2— | SO2Me | H | H | H | H | 2,6-dibromo-4-(1,2,2,2-tetrafluoro-1-trifluoromethyl-ethyl)-phenyl |
| 20-44 | —L—D | —L—D | —CH2CH2— | SO2Me | H | H | H | H | 2-bromo-6-trifluoromethyl-4-(1,2,2,2-tetrafluoro-1-trifluoromethyl-ethyl)-phenyl |
| 20-45 | —L—D | —L—D | —CH2CH2— | SO2Me | H | H | H | H | 2-iodo-6-trifluoromethyl-4-(1,2,2,3,3,3-hexafluoro-1-trifluoromethyl-propyl)-phenyl |
| 20-46 | —L—D | —L—D | —CH2CH2— | SO2Me | F | H | H | H | 2,6-dimethyl-4-(1,2,2,2-tetrafluoro-1-trifluoromethyl-ethyl)-phenyl |
| 20-47 | —L—D | —L—D | —CH2CH2— | SO2Me | F | H | H | H | 2,6-dibromo-4-(1,2,2,2-tetrafluoro-1-trifluoromethyl-ethyl)-phenyl |
| 20-48 | —L—D | —L—D | —CH2CH2— | SO2Me | F | H | H | H | 2-bromo-6-trifluoromethyl-4-(1,2,2,2-tetrafluoro-1-trifluoromethyl-ethyl)-phenyl |
| 20-49 | —L—D | —L—D | —CH2CH2— | SO2Me | F | H | H | H | 2-iodo-6-trifluoromethyl-4-(1,2,2,3,3,3-hexafluoro-1-trifluoromethyl-propyl)-phenyl |
| 20-50 | —L—D | —L—D | —CH2CH2— | SO2Me | H | F | H | H | 2,6-dimethyl-4-(1,2,2,2-tetrafluoro-1-trifluoromethyl-ethyl)-phenyl |
| 20-51 | —L—D | —L—D | —CH2CH2— | SO2Me | H | CN | H | H | 2,6-dimethyl-4-(1,2,2,2-tetrafluoro-1-trifluoromethyl-ethyl)-phenyl |
| 20-52 | —L—D | —L—D | —CH2CH2— | SO2Me | NO2 | H | H | H | 2,6-dimethyl-4-(1,2,2,2-tetrafluoro-1-trifluoromethyl-ethyl)-phenyl |
| 20-53 | —L—D | H | —CH2CH2— | SOMe | H | H | H | H | 2,6-dimethyl-4-(1,2,2,2-tetrafluoro-1-trifluoromethyl-ethyl)-phenyl |
| 20-54 | —L—D | H | —CH2CH2— | SOMe | H | H | H | H | 2,6-dibromo-4-(1,2,2,2-tetrafluoro-1-trifluoromethyl-ethyl)-phenyl |
| 20-55 | —L—D | H | —CH2CH2— | SOMe | H | H | H | H | 2-bromo-6-trifluoromethyl-4-(1,2,2,2-tetrafluoro-1-trifluoromethyl-ethyl)-phenyl |
| 20-56 | —L—D | H | —CH2CH2— | SOMe | H | H | H | H | 2-iodo-6-trifluoromethyl-4-(1,2,2,3,3,3-hexafluoro-1-trifluoromethyl-propyl)-phenyl |
| 20-57 | —L—D | H | —CH2CH2— | SOMe | F | H | H | H | 2,6-dimethyl-4-(1,2,2,2-tetrafluoro-1-trifluoromethyl-ethyl)-phenyl |
| 20-58 | —L—D | H | —CH2CH2— | SOMe | F | H | H | H | 2,6-dichloro-4-(1,2,2,2-tetrafluoro-1-trifluoromethyl-ethyl)-phenyl |
| 20-59 | —L—D | H | —CH2CH2— | SOMe | F | H | H | H | 2,6-dibromo-4-(1,2,2,2-tetrafluoro-1-trifluoromethyl-ethyl)-phenyl |
| 20-60 | —L—D | H | —CH2CH2— | SOMe | F | H | H | H | 2,6-diiodo-4-(1,2,2,2-tetrafluoro-1-trifluoromethyl-ethyl)-phenyl |
| 20-61 | —L—D | H | —CH2CH2— | SOMe | F | H | H | H | 2-bromo-6-iodo-4-(1,2,2,2-tetrafluoro-1-trifluoromethyl-ethyl)-phenyl |
| 20-62 | —L—D | H | —CH2CH2— | SOMe | F | H | H | H | 2-bromo-6-trifluoromethoxy-4-(1,2,2,2-tetrafluoro-1-trifluoromethyl-ethyl)-phenyl |
| 20-63 | —L—D | H | —CH2CH2— | SOMe | F | H | H | H | 2-bromo-6-trifluoromethyl-4-(1,2,2,2-tetrafluoro-1-trifluoromethyl-ethyl)-phenyl |
| 20-64 | —L—D | H | —CH2CH2— | SOMe | F | H | H | H | 2-iodo-6-trifluoromethyl-4-(1,2,2,2-tetrafluoro-1-trifluoromethyl-ethyl)-phenyl |
| 20-65 | —L—D | H | —CH2CH2— | SOMe | F | H | H | H | 2-bromo-6-trifluoromethyl-4-(1,2,2,3,3,3-hexafluoro-1-trifluoromethyl-propyl)-phenyl |
| 20-66 | —L—D | H | —CH2CH2— | SOMe | F | H | H | H | 2-iodo-6-trifluoromethyl-4-(1,2,2,3,3,3-hexafluoro-1-trifluoromethyl-propyl)-phenyl |
| 20-67 | —L—D | H | —CH2CH2— | SOMe | F | H | H | H | 2,6-ditrifluoromethyl-4-(1,2,2,2-tetrafluoro-1-trifluoromethyl-ethyl)-phenyl |
| 20-68 | —L—D | H | —CH2CH2— | SOMe | F | H | H | H | 2-bromo-6-trifluoromethylsulfinyl-4-(1,2,2,2-tetrafluoro-1-trifluoromethyl-ethyl)-phenyl |
| 20-69 | —L—D | H | —CH2CH2— | SOMe | H | F | H | H | 2,6-dimethyl-4-(1,2,2,2-tetrafluoro-1-trifluoromethyl-ethyl)-phenyl |

TABLE 20-continued

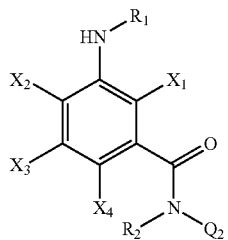

| compound number | R₁ | R₂ | L | D | X₁ | X₂ | X₃ | X₄ | Q₂ |
|---|---|---|---|---|---|---|---|---|---|
| 20-70 | —L—D | H | —CH2CH2— | SOMe | H | F | H | H | 2,6-dibromo-4-(1,2,2,2-tetrafluoro-1-trifluoromethyl-ethyl)-phenyl |
| 20-71 | —L—D | H | —CH2CH2— | SOMe | H | F | H | H | 2-bromo-6-trifluoromethyl-4-(1,2,2,2-tetrafluoro-1-trifluoromethyl-ethyl)-phenyl |
| 20-72 | —L—D | H | —CH2CH2— | SOMe | H | F | H | H | 2-iodo-6-trifluoromethyl-4-(1,2,2,3,3,3-hexafluoro-1-trifluoromethyl-propyl)-phenyl |
| 20-73 | —L—D | H | —CH2CH2— | SOMe | H | CN | H | H | 2,6-dimethyl-4-(1,2,2,2-tetrafluoro-1-trifluoromethyl-ethyl)-phenyl |
| 20-74 | —L—D | H | —CH2CH2— | SOMe | H | CN | H | H | 2,6-dibromo-4-(1,2,2,2-tetrafluoro-1-trifluoromethyl-ethyl)-phenyl |
| 20-75 | —L—D | H | —CH2CH2— | SOMe | H | CN | H | H | 2-bromo-6-trifluoromethyl-4-(1,2,2,2-tetrafluoro-1-trifluoromethyl-ethyl)-phenyl |
| 20-76 | —L—D | H | —CH2CH2— | SOMe | H | CN | H | H | 2-iodo-6-trifluoromethyl-4-(1,2,2,3,3,3-hexafluoro-1-trifluoromethyl-propyl)-phenyl |
| 20-77 | —L—D | H | —CH2CH2— | SOMe | NO2 | H | H | H | 2,6-dimethyl-4-(1,2,2,2-tetrafluoro-1-trifluoromethyl-ethyl)-phenyl |
| 20-78 | —L—D | H | —CH2CH2— | SOMe | NO2 | H | H | H | 2,6-dibromo-4-(1,2,2,2-tetrafluoro-1-trifluoromethyl-ethyl)-phenyl |
| 20-79 | —L—D | H | —CH2CH2— | SOMe | NO2 | H | H | H | 2-bromo-6-trifluoromethyl-4-(1,2,2,2-tetrafluoro-1-trifluoromethyl-ethyl)-phenyl |
| 20-80 | —L—D | H | —CH2CH2— | SOMe | NO2 | H | H | H | 2-iodo-6-trifluoromethyl-4-(1,2,2,3,3,3-hexafluoro-1-trifluoromethyl-propyl)-phenyl |
| 20-81 | H | —L—D | —CH2CH2— | SOMe | H | H | H | H | 2,6-dimethyl-4-(1,2,2,2-tetrafluoro-1-trifluoromethyl-ethyl)-phenyl |
| 20-82 | H | —L—D | —CH2CH2— | SOMe | H | H | H | H | 2,6-dibromo-4-(1,2,2,2-tetrafluoro-1-trifluoromethyl-ethyl)-phenyl |
| 20-83 | H | —L—D | —CH2CH2— | SOMe | H | H | H | H | 2-bromo-6-trifluoromethyl-4-(1,2,2,2-tetrafluoro-1-trifluoromethyl-ethyl)-phenyl |
| 20-84 | H | —L—D | —CH2CH2— | SOMe | H | H | H | H | 2-iodo-6-trifluoromethyl-4-(1,2,2,3,3,3-hexafluoro-1-trifluoromethyl-propyl)-phenyl |
| 20-85 | H | —L—D | —CH2CH2— | SOMe | F | H | H | H | 2,6-dimethyl-4-(1,2,2,2-tetrafluoro-1-trifluoromethyl-ethyl)-phenyl |
| 20-86 | H | —L—D | —CH2CH2— | SOMe | F | H | H | H | 2,6-dibromo-4-(1,2,2,2-tetrafluoro-1-trifluoromethyl-ethyl)-phenyl |
| 20-87 | H | —L—D | —CH2CH2— | SOMe | F | H | H | H | 2-bromo-6-trifluoromethyl-4-(1,2,2,2-tetrafluoro-1-trifluoromethyl-ethyl)-phenyl |
| 20-88 | H | —L—D | —CH2CH2— | SOMe | F | H | H | H | 2-iodo-6-trifluoromethyl-4-(1,2,2,3,3,3-hexafluoro-1-trifluoromethyl-propyl)-phenyl |
| 20-89 | H | —L—D | —CH2CH2— | SOMe | H | F | H | H | 2,6-dimethyl-4-(1,2,2,2-tetrafluoro-1-trifluoromethyl-ethyl)-phenyl |
| 20-90 | H | —L—D | —CH2CH2— | SOMe | H | CN | H | H | 2,6-dimethyl-4-(1,2,2,2-tetrafluoro-1-trifluoromethyl-ethyl)-phenyl |
| 20-91 | H | —L—D | —CH2CH2— | SOMe | NO2 | H | H | H | 2,6-dimethyl-4-(1,2,2,2-tetrafluoro-1 trifluoromethyl-ethyl)-phenyl |
| 20-92 | —L—D | —L—D | —CH2CH2— | SOMe | H | H | H | H | 2,6-dimethyl-4-(1,2,2,2-tetrafluoro-1-trifluoromethyl-ethyl)-phenyl |
| 20-93 | —L—D | —L—D | —CH2CH2— | SOMe | H | H | H | H | 2,6-dibromo-4-(1,2,2,2-tetrafluoro-1-trifluoromethyl-ethyl)-phenyl |
| 20-94 | —L—D | —L—D | —CH2CH2— | SOMe | H | H | H | H | 2-bromo-6-trifluoromethyl-4-(1,2,2,2-tetrafluoro-1-trifluoromethyl-ethyl)-phenyl |
| 20-95 | —L—D | —L—D | —CH2CH2— | SOMe | H | H | H | H | 2-iodo-6-trifluoromethyl-4-(1,2,2,3,3,3-hexafluoro-1-trifluoromethyl-propyl)-phenyl |
| 20-96 | —L—D | —L—D | —CH2CH2— | SOMe | F | H | H | H | 2,6-dimethyl-4-(1,2,2,2-tetrafluoro-1-trifluoromethyl-ethyl)-phenyl |
| 20-97 | —L—D | —L—D | —CH2CH2— | SOMe | F | H | H | H | 2,6-dibromo-4-(1,2,2,2-tetrafluoro-1-trifluoromethyl-ethyl)-phenyl |
| 20-98 | —L—D | —L—D | —CH2CH2— | SOMe | F | H | H | H | 2-bromo-6-trifluoromethyl-4-(1,2,2,2-tetrafluoro-1-trifluoromethyl-ethyl)-phenyl |

TABLE 20-continued

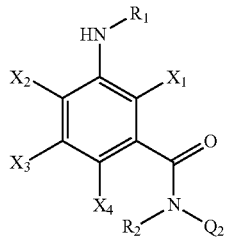

| compound number | R₁ | R₂ | L | D | X₁ | X₂ | X₃ | X₄ | Q₂ |
|---|---|---|---|---|---|---|---|---|---|
| 20-99 | —L—D | —L—D | —CH2CH2— | SOMe | F | H | H | H | 2-iodo-6-trifluoromethyl-4-(1,2,2,3,3,3-hexafluoro-1-trifluoromethyl-propyl)-phenyl |
| 20-100 | —L—D | —L—D | —CH2CH2— | SOMe | H | F | H | H | 2,6-dimethyl-4-(1,2,2,2-tetrafluoro-1-trifluoromethyl-ethyl)-phenyl |
| 20-101 | —L—D | —L—D | —CH2CH2— | SOMe | H | CN | H | H | 2,6-dimethyl-4-(1,2,2,2-tetrafluoro-1-trifluoromethyl-ethyl)-phenyl |
| 20-102 | —L—D | —L—D | —CH2CH2— | SOMe | NO2 | H | H | H | 2,6-dimethyl-4-(1,2,2,2-tetrafluoro-1-trifluoromethyl-ethyl)-phenyl |

TABLE 21

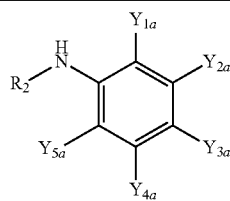

| compound number | R₂ | Y₁ₐ | Y₂ₐ | Y₃ₐ | Y₄ₐ | Y₅ₐ |
|---|---|---|---|---|---|---|
| 21-1 | H | H | H | pentafluoroethyl | H | CF3 |
| 21-2 | H | H | H | heptafluoroisopropyl | H | CF3 |
| 21-3 | H | H | H | nonafluoro-2-butyl | H | CF3 |
| 21-4 | H | H | H | heptafluoroisopropyl | H | C2F5 |
| 21-5 | H | H | H | nonafluoro-2-butyl | H | C2F5 |
| 21-6 | H | Br | H | pentafluoroethyl | H | CF3 |
| 21-7 | H | F | H | heptafluoroisopropyl | H | CF3 |
| 21-8 | H | Cl | H | heptafluoroisopropyl | H | CF3 |
| 21-9 | H | Br | H | heptafluoroisopropyl | H | CF3 |
| 21-10 | H | I | H | heptafluoroisopropyl | H | CF3 |
| 21-11 | H | F | H | nonafluoro-2-butyl | H | CF3 |
| 21-12 | H | Cl | H | nonafluoro-2-butyl | H | CF3 |
| 21-13 | H | Br | H | nonafluoro-2-butyl | H | CF3 |
| 21-14 | H | I | H | nonafluoro-2-butyl | H | CF3 |
| 21-15 | H | OCF3 | H | heptafluoroisopropyl | H | CF3 |
| 21-16 | H | OCF3 | H | nonafluoro-2-butyl | H | CF3 |
| 21-17 | H | CF3 | H | heptafluoroisopropyl | H | CF3 |
| 21-18 | H | CF3 | H | nonafluoro-2-butyl | H | CF3 |
| 21-19 | H | Br | H | heptafluoroisopropyl | H | C2F5 |
| 21-20 | H | Br | H | nonafluoro-2-butyl | H | C2F5 |
| 21-21 | Me | H | H | pentafluoroethyl | H | CF3 |
| 21-22 | Me | H | H | heptafluoroisopropyl | H | CF3 |
| 21-23 | Me | H | H | nonafluoro-2-butyl | H | CF3 |
| 21-24 | Me | H | H | heptafluoroisopropyl | H | C2F5 |
| 21-25 | Me | H | H | nonafluoro-2-butyl | H | C2F5 |
| 21-26 | Me | Br | H | pentafluoroethyl | H | CF3 |
| 21-27 | Me | F | H | heptafluoroisopropyl | H | CF3 |
| 21-28 | Me | Cl | H | heptafluoroisopropyl | H | CF3 |
| 21-29 | Me | Br | H | heptafluoroisopropyl | H | CF3 |
| 21-30 | Me | I | H | heptafluoroisopropyl | H | CF3 |
| 21-31 | Me | Br | H | nonafluoro-2-butyl | H | CF3 |
| 21-32 | Me | I | H | nonafluoro-2-butyl | H | CF3 |
| 21-33 | Me | OCF3 | H | heptafluoroisopropyl | H | CF3 |
| 21-34 | Et | OCF3 | H | nonafluoro-2-butyl | H | CF3 |
| 21-35 | Me | CF3 | H | heptafluoroisopropyl | H | CF3 |
| 21-36 | nPr | CF3 | H | nonafluoro-2-butyl | H | CF3 |
| 21-37 | Me | Br | H | heptafluoroisopropyl | H | C2F5 |
| 21-38 | Me | Br | H | nonafluoro-2-butyl | H | C2F5 |
| 21-39 | Me | H | H | heptafluoroisopropyl | Cl | CF3 |
| 21-40 | H | H | Et | nonafluoro-2-butyl | H | CF3 |
| 21-41 | H | H | Br | heptafluoroisopropyl | I | CF3 |
| 21-42 | H | H | Et | nonafluoro-2-butyl | Cl | CF3 |
| 21-43 | H | H | Me | heptafluoroisopropyl | Me | CF3 |
| 21-44 | H | Br | H | heptafluoroisopropyl | F | CF3 |
| 21-45 | H | Br | Me | nonafluoro-2-butyl | H | CF3 |
| 21-46 | H | Br | F | heptafluoroisopropyl | Cl | CF3 |
| 21-47 | H | Br | Me | nonafluoro-2-butyl | F | CF3 |
| 21-48 | H | Br | Et | heptafluoroisopropyl | Me | CF3 |
| 21-49 | Me | I | H | heptafluoroisopropyl | F | CF3 |
| 21-50 | Me | I | Me | nonafluoro-2-butyl | H | CF3 |
| 21-51 | Me | I | F | heptafluoroisopropyl | Cl | CF3 |
| 21-52 | iPr | I | Me | nonafluoro-2-butyl | F | CF3 |
| 21-53 | Me | I | Et | heptafluoroisopropyl | Me | CF3 |

Hereinbelow, Table 10 shows the physical properties of the compound represented by the Formula (1) according to the present invention. Also, Table 22 shows the physical properties of the compounds represented by the Formula (6a), the Formula (6b), the Formula (6c), and the Formula (6d), which are intermediates of the compounds according to the present invention. The ¹H-NMR shift values shown therein are based on tetramethylsilane as an internal standard substance unless specified otherwise.

TABLE 10

| compound number | ¹H-NMR(CDCl₃, ppm) |
|---|---|
| 1-1 | δ 2.28(6H, s), 2.71(2H, t, J = 6.8 Hz), 4.30(2H, t, J = 6.8 Hz), 5.43(1H, broad-s), 6.17(1H, broad-s), 7.17-7.37(9H, m), 7.66(1H, broad-s), 7.70-7.73(2H, m). |
| 1-16 | δ 2.30(6H, s), 2.74(2H, t, J = 6.8 Hz), 4.29(2H, t, J = 6.8 Hz), 5.52(1H, broad-s), 6.12(1H, broad-s), 7.08-7.11(1H, m), 7.34-7.37(4H, m), 7.52-7.54(1H, m), 7.74-7.75(1H, m), 7.80(1H, broad-s), 7.84(1H, broad-s), 8.23-8.25(1H, m). |
| 1-21 | δ 2.26(6H, s), 2.60(1H, broad-s), 2.75(1H, broad-s), 4.22-4.23(2H, m), 5.45(1H, broad-s), 6.03(1H, broad-s), 7.19-7.34(8H, m), 7.49-7.52(2H, m), 7.90-7.96(1H, m). |
| 1-36 | δ 2.33(6H, s), 2.64-2.80(2H, m), 4.11-4.13(1H, m), 4.30-4.40(1H, m), 5.40(1H, broad-s), 5.95(1H, broad-s), 7.11-7.14(1H, m), 7.21(1H, t, J = 8.3 Hz), 7.37(2H, s), 7.50-7.62(2H, m), 7.79(1H, d, J = 10.2 Hz), 7.93-7.95(1H, m), 8.29(1H, dd, J = 2.0, 4.8 Hz). |
| 1-62 | (DMSO-d6) δ 2.46-2.51(2H, m), 4.08(2H, broad-s), 6.90(1H, s), 7.45-7.50(5H, m), 7.74-7.82(4H, m), 8.14(2H, s), 10.56(1H, s). |
| 1-63 | δ2.70 (2H, m), 4.31 (2H, t, J = 6.8 Hz), 5.78 (1H, broad-s.), 6.86 (1H, broad-s), 7.34-7.51 (6H, m), 7.68 (1H, s), 7.81-7.82 (1H, broad-s), 8.12 (2H, s), 10.04 (1H, s). |
| 1-64 | δ 2.72 (2H, t, J = 6.8 Hz), 4.33 (2H, t, J = 6.8 Hz), 5.35 (1H, broad-s), 5.85 (1H, broad-s), 7.23-7.26 (1H, m), 7.39-7.43 (3H, m), 7.51-7.53 (2H, m), 7.69-7.74 (2H, m), 7.90 (2H, d, J = 7.8 Hz), 8.14 (1H, s). |
| 1-65 | (DMSO-d₆) δ 2.47-2.48(2H, m), 4.08-4.09(2H, m), 6.90(1H, s), 7.45-7.58(6H, m), 7.65-7.79(3H, m), 7.95(1H, s), 8.51(1H, s), 10.57(1H, s). |
| 1-82 | (CDCl3 + DMSO-d6) δ 2.68 (2H, t, J = 6.8 Hz), 4.30 (2H, t, J = 6.8 Hz), 5.69 (1H, broad-s), 6.73 (1H, broad-s), 7.27-7.29 (1H, m), 7.35-7.42 (3H, m), 7.48-7.50 (2H, m), 7.75 (1H, s), 7.84-7.86 (1H, m), 7.86 (1H, s), 8.12 (1H, s), 9.75 (1H, s). |
| 1-95 | (DMSO-d₆) δ 2.44-2.51(2H, m), 4.02-4.09(2H, m), 6.89(1H, s), 7.22-7.28(5H, m), 7.41-7.48(3H, m), 7.78(2H, s), 8.13(2H, s), 10.57(1H, s). |
| 1-96 | (DMSO-d₆) δ 2.46-2.51(2H, m), 4.04-4.08(2H, m), 6.91(1H, s), 7.46-7.54(5H, m), 7.56-7.83(4H, m), 8.14(2H, s), 10.55(1H, s). |
| 1-97 | (DMSO-d₆) δ 2.49-2.51(2H, m), 4.09-4.13(2H, m), 6.93(1H, s), 7.31-7.34(1H, m), 7.46-7.50(2H, m), 7.55-7.57(1H, m), 7.79-7.90(3H, m), 8.15(2H, s), 8.26(1H, s), 10.57(1H, s). |
| 1-99 | δ 2.72 (2H, t, J = 6.8 Hz), 4.33 (2H, t, J = 6.8 Hz), 5.38 (1H, broad-s), 6.07 (1H, broad-s), 7.18-7.31 (6H, m), 7.38 (1H, t, J = 7.8 Hz), 7.64 (1H, d, J = 2.0 Hz), 7.70 (1H, d, J = 7.8 Hz), 7.90 (1H, s), 7.98 (1H, s), 8.12 (1H, s). |
| 1-100 | δ 2.71 (2H, t, J = 6.8 Hz), 4.32 (2H, t, J = 6.8 Hz), 5.44 (1H, broad-s), 5.80 (1H, broad-s), 7.23-7.34 (2H, m), 7.42-7.48 (2H, m), 7.57 (1H, broad-d, J = 7.8 Hz), 7.67-7.69 (2H, m), 7.75 (1H, d, J = 7.8 Hz), 7.91 (1H, s), 8.04 (1H, s), 8.13 (1H, s). |
| 1-101 | δ 2.77 (2H, t, J = 6.8 Hz), 4.32 (2H, t, J = 6.8 Hz), 5.44 (1H, broad-s), 6.00 (1H, broad-s), 7.12 (1H, dd, J = 4.9, 7.8 Hz), 7.40-7.42 (2H, m), 7.52-7.55 (1H, m), 7.73 (1H, d, J = 6.8 Hz), 7.77 (1H, s), 7.91 (1H, s), 8.07 (1H, s), 8.14 (1H, s), 8.26 (1H, dd, J = 2.0, 4.9 Hz). |
| 1-103 | (DMSO-d₆) δ 2.44-2.54(2H, m), 4.05-4.09(2H, m), 6.89(1H, s), 7.23-7.29(5H, m), 7.44-7.48(3H, m), 7.70-7.75(2H, m), 7.95(1H, s), 8.51(1H, s), 10.59(1H, s). |
| 1-104 | (DMSO-d₆) δ 2.35-2.38 (2H, m), 4.04-4.08 (2H, m), 6.80-6.91 (1H, m), 7.14-7.25 (2H, m), 7.46-7.58 (4H, m), 7.70-7.78 (3H, m), 7.95 (1H, s), 8.51 (1H, s), 10.58 (1H, s). |
| 1-105 | δ 2.76 (2H, t, J = 6.8 Hz), 4.31 (2H, t, J = 6.8 Hz), 5.48 (1H, broad-s), 6.06 (1H, broad-s), 7.11 (1H, dd, J = 4.9,7.8 Hz), 7.40-7.42 (2H, m), 7.53 (1H, dd, J = 2.0, 7.8 Hz), 7.74 (1H, d, J = 6.3 Hz), 7.78 (1H, s), 7.93 (1H, s), 8.19 (1H, broad-s), 8.24 (1H, dd, J = 2.0, 4.9 Hz), 8.34 (1H, s). |
| 1-115 | δ 2.73 (2H, t, J = 6.3 Hz), 4.34 (2H, t, J = 6.3 Hz), 5.62 (1H, broad-s), 6.14 (1H, broad-s), 7.18-7.36 (4H, m), 7.36-7.40 (1H, m), 7.43-7.47 (1H, m), 7.64 (1H, s), 7.69-7.71 (1H, m), 7.88 (1H, s), 7.92 (1H, s), 8.05-8.07 (1H, m), 8.10-8.11 (1H, m). |
| 1-116 | δ 2.68 (2H, t, J = 6.8 Hz), 4.28 (2H, t, J = 6.8 Hz), 5.63 (1H, broad-s), 6.14 (1H, broad-s), 7.27-7.31 (2H, m). 7.40-7.45 (2H, m), 7.55 (1H, d, J = 7.8 Hz), 7.65 (1H, s), 7.69 (1H, s), 7.76 (1H, d, J = 7.8 Hz), 7.88 (1H, s), 8.11 (1H, s), 8.41 (1H, s). |
| 1-117 | δ 2.74 (2H, t, J = 6.8 Hz), 4.29 (2H, t, J = 6.8 Hz), 5.51 (1H, broad-s), 6.08 (1H, broad-s), 7.11 (1H, dd, J = 4.9, 7.8 Hz), 7.36-7.43 (2H, m), 7.53 (1H, dd, J = 2.0, 7.8 Hz), 7.73 (1H, d, J = 7.8 Hz), 7.78 (1H, s), 7.89 (1H, s), 8.09-8.11 (2H, m), 8.24 (1H, dd, J = 2.0, 4.9 Hz). |
| 1-118 | δ 2.70-2.71 (2H, m), 4.28-4.29 (2H, m), 5.48 (1H, broad-s), 6.20 (1H, broad-s), 6.82-6.83 (1H, m), 7.00-7.04 (1H, m), 7.23-7.24 (1H, m), 7.29-7.37 (3H, m), 7.67 (1H, s), 7.72-7.73 (1H, m), 7.88 (1H, s), 8.06 (1H, s), 8.10 (1H, s). |
| 1-132 | δ 2.69-2.70 (1H, m), 2.81-2.82 (1H, m), 4.22-4.24 (2H, m), 5.38 (1H, broad-s), 5.78 (1H, broad-s), 7.30-7.32 (1H, m), 7.42-7.44 (2H, m), 7.51-7.55 (3H, m), 7.66 (2H, s), 7.90-7.93 (1H, m), 8.00-8.01 (1H, m). |
| 1-133 | δ 2.68-2.71 (1H, m), 2.81-2.84 (1H, m), 4.23-4.26 (2H, m), 5.37 (1H, broad-s), 5.77 (1H, broad-s), 7.32 (1H, t, J = 7.8 Hz), 7.43-7.58 (5H, m), 7.87 (2H, s), 7.87-7.90 (1H, m), 8.00-8.03 (1H, m). |
| 1-134 | δ 2.63-2.89 (2H, m), 4.21-4.25 (2H, m), 5.50 (1H, broad-s.), 5.91 (1H, broad-s.), 7.26-7.61 (6H, m), 8.02-8.09 (4H, m). |
| 1-136 | δ 2.71 (1H, broad-s), 2.85 (1H, broad-s), 4.24 (2H, broad-t, J = 6.3 Hz), 5.39 (1H, broad-s), 5.80 (1H, broad-s), 7.32 (1H, t, J = 7.8 Hz), 7.42 (2H, d, J = 7.8 Hz), 7.52 (2H, broad-d, J = 7.8 Hz), 7.58-7.59 (1H, m), 7.91 (1H, s), 7.98-8.08 (2H, m), 8.13 (1H, s). |
| 1-137 | δ 2.65-2.71 (1H, m), 2.83-2.89 (1H, m), 4.25 (2H, broad-t, J = 6.3 Hz), 5.38 (1H, broad-s), 5.76 (1H, broad-s), 7.34 (1H, t, J = 7.8 Hz), 7.43 (2H, broad-d, J = 7.8 Hz), 7.51-7.53 (2H, m), 7.60-7.63 (2H, m), 7.93 (1H, s), 8.02 (2H, broad-t, J = 7.8 Hz), 8.34 (1H, s). |
| 1-138 | δ 2.66-2.70 (1H, m), 2.83-2.86 (1H, m), 4.23 (2H, broad-s), 5.38 (1H, broad-s), 5.79 (1H, broad-s), 7.31 (1H, t, J = 7.8 Hz), 7.42-7.44 (2H, m), 7.50-7.59 (4H, m), 7.87-7.91 (2H, m), 7.98 (1H, t, J = 6.8 Hz). |
| 1-139 | δ 2.69-2.84 (2H, m), 4.22-4.26 (2H, m), 5.45 (1H, broad-s), 5.90 (1H, broad-s), 7.32 (1H, t, J = 7.8 Hz), 7.43-7.45 (2H, m), 7.51-7.52 (2H, m), 7.58-7.59 (1H, m), 7.86-8.04 (2H, m), 7.89 (1H, broad-s), 8.06 (1H, d, J = 1.5 Hz). |
| 1-151 | δ 2.65-2.69 (1H, m), 2.80-2.83 (1H, m), 4.20-4.25 (2H, m), 5.42 (1H, s), 5.80 (1H, s), 7.31-7.32 (1H, m), 7.43-7.58 (5H, m), 7.85-7.92 (3H, m), 8.01-8.03 (1H, m). |
| 1-152 | δ 2.60-2.75 (1H, m), 2.75-2.90 (1H, m), 4.24-4.25 (2H, m), 5.46 (1H, broad-s), 5.90 (1H, broad-s), 7.33-7.34 (1H, m), 7.44 (2H, d, J = 7.8 Hz), 7.52 (2H, d, J = 7.8 Hz), 7.58-7.59 (1H, m), 7.97-8.08 (4H, m). |

TABLE 10-continued

| compound number | $^1$H-NMR(CDCl$_3$, ppm) |
|---|---|
| 1-154 | δ 2.67-2.68 (1H, m), 2.83-2.84 (1H, m), 4.23 (2H, t, J = 6.3 Hz), 5.44 (1H, broad-s), 5.83 (1H, broad-s), 7.32 (1H, t, J = 7.8 Hz), 7.41 (2H, d, J = 7.8 Hz), 7.52 (2H, d, J = 7.8 Hz), 7.57-7.61 (1H, m), 7.89 (1H, s), 7.98-8.04 (2H, m), 8.12 (1H, s). |
| 1-163 | δ 2.68 (1H, broad-s), 2.83 (1H, broad-s), 4.24 (2H, t, J = 6.8 Hz), 5.42 (1H, broad-s), 6.02 (1H, broad-s), 7.18-7.22 (1H, m), 7.26-7.34 (4H, m), 7.55-7.56 (1H, m), 7.85 (2H, s), 7.94-8.00 (2H, m). |
| 1-164 | δ 2.70 (1H, broad-s), 2.80 (1H, broad-s), 4.23 (2H, t, J = 6.8 Hz), 5.45 (1H, broad-s), 5.80 (1H, broad-s), 7.29-7.36 (2H, m), 7.47 (1H, m), 7.58-7.62 (2H, m), 7.72 (1H, broad-s), 7.86 (2H, s), 7.95-8.05 (2H, m). |
| 1-167 | δ 2.64-2.68 (2H, m), 4.22-4.25 (2H, m), 5.44 (1H, broad-s.), 6.06 (1H, broad-s.), 7.17-7.35 (6H, m), 7.56-7.60 (1H, m), 7.96-8.07 (4H, m). |
| 1-168 | δ 2.70-2.71 (1H, m), 2.83-2.84 (1H, m), 4.23 (2H, t, J = 6.8 Hz), 5.43 (1H, broad-s), 5.89 (1H, broad-s), 7.29-7.36 (2H, m), 7.50 (1H, d, J = 7.8 Hz), 7.56-7.60 (2H, m), 7.70 (1H, s), 8.03-8.08 (4H, m). |
| 1-169 | δ 2.77-2.78 (1H, m), 2.83-2.84 (1H, m), 4.20-4.21 (1H, m), 4.31-4.32 (1H, m), 5.40 (1H, broad-s), 5.90 (1H, broad-s), 7.10-7.13 (1H, m), 7.61-7.63 (2H, m), 8.00-8.01 (1H, m), 8.10-8.17 (4H, m), 8.27 (1H, dd, J = 2.0, 4.8 Hz). |
| 1-171 | δ 2.55-2.80 (2H, m), 4.22-4.26 (2H, m), 5.45 (1H, broad-s), 6.00 (1H, broad-s), 7.21-7.30 (6H, m), 7.52-7.57 (1H, m), 7.89-8.12 (4H, m). |
| 1-172 | δ 2.66-2.70 (1H, m), 2.81-2.85 (1H, m), 4.21-4.25 (2H, m), 5.46 (1H, broad-s), 5.83 (1H, broad-s), 7.30-7.37 (2H, m), 7.47 (1H, broad-d, J = 7.3 Hz), 7.58-7.65 (2H, m), 7.70 (1H, s), 7.90 (1H, s), 7.99-8.06 (2H, m), 8.13 (1H, s). |
| 1-173 | δ 2.74-2.78 (1H, m), 2.81-2.84 (1H, m), 4.13-4.18 (1H, m), 4.31-4.33 (1H, m), 5.44 (1H, broad-s), 5.90 (1H, broad-s), 7.14 (1H, dd, J = 4.9, 7.3 Hz), 7.24 (1H, t, J = 7.8 Hz), 7.63-7.65 (2H, m), 7.92 (1H, s), 7.95-7.99 (1H, m), 8.14-8.17 (2H, m), 8.29 (1H, dd, J = 2.0,4.9 Hz). |
| 1-175 | δ 2.67-2.68 (1H, m), 2.81-2.82 (1H, m), 4.21-4.23 (2H, m), 5.75-5.76 (1H, m), 6.21-6.22 (1H, m), 7.19-7.21 (2H, m), 7.27-7.31 (4H, m), 7.54 (1H, t, J = 6.8 Hz), 7.91-7.96 (2H, m), 8.17-8.18 (1H, m), 8.31-8.32 (1H, m). |
| 1-176 | δ 2.63-2.64 (1H, m), 2.86-2.87 (1H, m), 4.24-4.25 (2H, m), 5.40 (1H, broad-s), 5.81 (1H, broad-s), 7.30-7.37 (2H, m), 7.58-7.69 (4H, m), 7.93 (1H, s), 8.00-8.09 (2H, m), 8.33 (1H, s). |
| 1-177 | δ 2.75-2.86 (2H, m), 4.14-4.21 (1H, m), 4.28-4.35 (1H, m), 5.49 (1H, broad-s), 5.95 (1H, broad-s), 7.13 (1H, dd, J = 4.9, 7.8 Hz), 7.22-7.24 (1H, m), 7.63-7.65 (2H, m), 7.49-7.99 (2H, m), 8.27-8.29 (2H, m), 8.35 (1H, s). |
| 1-179 | δ 2.60-2.74 (1H, m), 2.74-2.90 (1H, m), 4.22-4.25 (2H, m), 5.42 (1H, broad-s), 6.03 (1H, broad-s), 7.15-7.34 (6H, m), 7.53-7.57 (1H, m), 7.83 (2H, s), 7.94-8.01 (2H, m). |
| 1-180 | δ 2.34-2.70 (1H, m), 2.78-2.89 (1H, m), 4.21-4.25 (2H, m), 5.60 (1H, s), 5.88 (1H, s), 7.27-7.35 (2H, m), 7.48-7.61 (3H, m), 7.72 (1H, s), 7.85 (2H, s), 7.91-8.10 (2H, m). |
| 1-183 | δ 2.60-2.75 (1H, m), 2.75-2.90 (1H, m), 4.20-4.24 (2H, m), 5.43 (1H, broad-s), 5.86 (1H, broad-s), 7.26-7.36 (3H, m), 7.50-7.62 (3H, m), 7.71 (1H, s), 8.01-8.08 (4H, m). |
| 1-184 | δ 2.60-2.75 (1H, m), 2.75-2.90 (1H, m), 4.24 (2H, t, J = 6.8 Hz), 5.44 (1H, broad-s), 5.86 (1H, broad-s), 7.30-7.36 (2H, m), 7.51 (1H, d, J = 7.8 Hz), 7.56-7.62 (2H, m), 7.71 (1H, s), 8.01-8.08 (4H, m). |
| 1-185 | δ 2.77-2.78 (1H, m), 2.84-2.85 (1H, m), 4.20-4.21 (1H, m), 4.31-4.32 (1H, m), 5.40 (1H, broad-s), 5.90 (1H, broad-s), 7.10-7.13 (1H, m), 7.23-7.25 (1H, m), 7.61-7.63 (2H, m), 8.01-8.02 (1H, m), 8.09 (2H, s). 8.11-8.14 (1H, m), 8.27 (1H, dd, J = 2.0,4.9 Hz). |
| 1-187 | δ 2.63-2.64 (1H, m), 2.68-2.69 (1H, m), 4.23 (2H, t, J = 6.8 Hz), 5.39 (1H, broad-s), 6.99 (1H, broad-s), 7.18-7.23 (2H, m), 7.28-7.32 (4H, m), 7.52-7.57 (1H, m), 7.83 (1H, s), 7.94-8.02 (2H, m), 8.10 (1H, s). |
| 1-188 | δ 2.66-2.68 (1H, m), 2.83-2.84 (1H, m), 4.22-4.23 (2H, m), 5.46 (1H, broad-s), 5.84 (1H, broad-s), 7.29-7.36 (2H, m), 7.47 (1H, d, J = 7.3 Hz), 7.58-7.65 (2H, m), 7.70 (1H, s), 7.88 (1H, s), 7.99-8.06 (2H, m), 8.11 (1H, s). |
| 1-195 | δ 2.64 (2H, t, J = 6.8 Hz), 4.30 (2H, t, J = 6.8 Hz), 5.44 (1H, broad-s), 5.91 (1H, broad-s), 7.20 (1H, d, J = 8.3 Hz), 7.29-7.30 (1H, m), 7.45 (1H, t, J = 7.8 Hz), 7.60 (1H, dd, J = 2.4, 8.3 Hz), 7.73-7.78 (2H, m), 7.91 (1H s), 8.08 (1H, s), 8.13 (1H, s), 8.27 (1H, d, J = 2.4 Hz). |
| 1-196 | δ 2.65-2.68 (1H, m), 2.83-2.84 (1H, m), 4.20-4.27 (2H, m), 5.38 (1H, s), 5.78 (1H, s), 7.21 (1H, d, J = 8.8 Hz), 7.37 (1H, t, J = 7.8 Hz), 7.61-7.65 (2H, m), 7.90 (1H, s), 8.01-8.04 (2H, m), 8.13 (1H, s), 8.32 (1H, broad-s). |
| 1-197 | δ 2.65-2.68 (1H, m), 2.80-2.84 (1H, m), 4.21-4.24 (2H, m), 5.42 (1H, broad-s), 5.79 (1H, broad-s), 7.20 (1H, d, J = 8.3 Hz), 7.36 (1H, t, J = 7.8 Hz), 7.60-7.64 (2H, m), 7.86 (2H, s), 7.88-7.93 (1H, m), 8.06 (1H, t, J = 6.8 Hz), 8.35 (1H, s). |
| 1-198 | δ 2.67-2.69 (1H, m), 2.84-2.85 (1H, m), 4.22-4.23 (2H, m), 5.45 (1H, broad-s), 5.69 (1H, broad-s), 7.42 (1H, t, J = 7.8 Hz), 7.71-7.74 (1H, m), 7.81-7.85 (3H, m), 7.90 (1H, s), 8.00-8.08 (2H, m), 8.13 (1H, s). |
| 1-199 | δ 2.64-2.65 (1H, m), 2.80-2.81 (1H, m), 4.20-4.24 (2H, m), 5.47 (1H, broad-s), 5.70 (1H, broad-s), 7.39 (1H, t, J = 7.8 Hz), 7.67 (1H, t, J = 7.8 Hz), 7.83-7.87 (5H, m), 7.96-7.99 (1H, m), 8.06-8.10 (1H, m). |
| 1-200 | δ 2.69-2.70 (1H, m), 2.83-2.84 (1H, m), 4.23-4.24 (2H, m), 5.41 (1H, broad-s), 5.89 (1H, broad-s), 7.17-7.22 (1H, m), 7.32 (1H, t, J = 7.8 Hz), 7.58 (1H, t, J = 7.3 Hz), 7.63-7.65 (1H, m), 7.85 (2H, s), 7.99-8.03 (2H, m), 8.51-8.58 (2H, m). |
| 1-201 | δ 2.69-2.70 (1H, m), 2.83-2.84 (1H, m), 4.24-4.25 (2H, m), 5.39 (1H, broad-s), 5.81 (1H, broad-s), 7.19-7.20 (2H, m), 7.31 (1H, t, J = 7.8 Hz), 7.56 (1H, t, J = 7.3 Hz), 7.85 (2H, s), 7.93-7.96 (1H, m), 8.03-8.04 (1H, m), 8.52-8.53 (2H, m). |
| 1-202 | δ 2.63-2.69 (1H, m), 2.84 (1H, t, J = 8.3 Hz), 4.20-4.25 (2H, m), 5.40-5.41 (1H, broad-s), 5.75-5.76 (1H, broad-s), 7.00-7.01 (1H, m), 7.31-7.36 (2H, m), 7.56-7.61 (1H, m), 7.86 (2H, s), 7.96-7.99 (1H, m), 8.07 (1H, t, J = 7.3 Hz), 8.24-8.25 (1H, m). |
| 1-203 | δ 2.74-2.83 (2H, m), 4.24-4.31 (2H, m), 5.45 (1H, broad-s), 5.90 (1H, broad-s), 7.24-7.26 (1H, m), 7.44-7.45 (1H, m), 7.86 (2H, s), 8.04-8.10 (2H, m), 8.18 (1H, s), 8.49 (1H, d, J = 2.4 Hz), 9.01 (1H, d, J = 1.0 Hz). |
| 1-204 | δ 2.66-2.70 (1H, m), 2.83-2.87 (1H, m), 4.24 (2H, broad-s), 5.46 (1H, broad-s), 5.76 (1H, broad-s), 7.38 (1H, t, J = 7.8 Hz), 7.64-7.65 (1H, m), 7.86 (2H, s), 7.94 (1H, d, J = 11.7 Hz), 8.07 (1H, broad-t, J = 7.8 Hz), 8.69 (2H, broad-s), 9.11 (1H, s). |
| 1-205 | δ 2.69-2.70 (1H, m), 2.82-2.83 (1H, m), 4.22 (2H, t, J = 6.3 Hz), 5.41 (1H, broad-s), 5.80 (1H, broad-s), 7.29-7.35 (2H, m), 7.47-7.48 (1H, m), 7.57-7.60 (2H, m), 7.66 (2H, s), 7.72 (1H, s), 7.94-7.97 (1H, m), 8.02 (1H, t. J = 6.8 Hz). |

TABLE 10-continued

| compound number | $^1$H-NMR(CDCl$_3$, ppm) |
|---|---|
| 1-206 | δ 2.69 (1H, broad-s), 2.75 (1H, broad-s), 4.23 (2H, t, J = 6.8 Hz), 5.43 (1H, broad-s), 6.05 (1H, broad-s), 7.18-7.33 (6H, m), 7.49-7.54 (1H, m), 7.65 (2H, s), 7.95-7.98 (2H, m). |
| 1-207 | δ 2.74-2.83 (2H, m), 4.10-4.15 (1H, m), 4.30-4.35 (1H, m), 5.47 (1H, broad-s), 5.91 (1H, broad-s), 7.12-7.15 (1H, m), 7.21-7.25 (1H, m), 7.59-7.63 (2H, m), 7.68 (2H, s), 7.95-7.99 (1H, m), 8.07 (1H, d, J = 11.8 Hz), 8.28 (1H, dd, J = 2.0, 4.8 Hz). |
| 1-208 | δ 2.66-2.70 (1H, m), 2.84-2.85 (1H, m), 4.25-4.26 (2H, m), 5.38 (1H, broad-s), 5.69 (1H, broad-s), 7.36 (1H, t, J = 7.8 Hz), 7.54-7.64 (2H, m), 7.64 (1H, d, J = 6.3 Hz), 7.86-7.87 (3H, m), 8.05-8.06 (1H, m), 8.66 (1H, s). |
| 1-209 | δ 2.65-2.85 (2H, m), 4.22 (2H, t, J = 6.8 Hz), 5.42 (1H, broad-s), 5.95 (1H, broad-s), 6.87-6.92 (2H, m), 7.29-7.37 (3H, m), 7.54-7.58 (1H, m), 7.85 (2H, s), 7.92 (1H, d, J = 12.7 Hz), 8.01 (1H, t, J = 7.8 Hz). |
| 1-210 | δ 2.75-3.03 (2H, m), 4.11-4.30 (2H, m), 5.40 (1H, broad-s), 5.90 (1H, broad-s), 6.70-6.80 (2H, m), 7.19-7.24 (2H, m), 7.50-7.52 (1H, m), 7.87 (2H, s), 8.00-8.05 (1H, m), 8.11 (1H, d, J = 13.7 Hz). |
| 1-211 | δ 2.76-2.94 (2H, m), 4.10-4.15 (1H, m), 4.31-4.35 (1H, m), 5.43 (1H, broad-s), 5.88 (1H, broad-s), 7.12 (1H, dd, J = 4.9, 7.8 Hz), 7.22-7.26 (1H, m), 7.62 (2H, broad-d, J = 7.3 Hz), 7.90 (1H, s), 8.01-8.06 (2H, m), 8.08 (1H, s), 8.28 (1H, dd, J = 2.0, 4.9 Hz). |
| 1-212 | δ 2.70 (1H, broad-s), 2.80 (1H, broad-s), 4.22-4.25 (2H, m), 5.43 (1H, broad-s), 6.05 (1H, broad-s), 7.17-7.23 (2H, m), 7.28-7.34 (4H, m), 7.55-7.59 (1H, m), 7.85-8.02 (2H, m), 7.87 (1H, s), 8.04 (1H, s). |
| 1-213 | δ 2.60-2.90 (2H, m), 4.20-4.25 (2H, m), 5.62 (1H, s), 5.90 (1H, broad-s), 7.20 (1H, d, J = 8.3 Hz), 7.36-7.37 (1H, m), 7.59-7.63 (2H, m), 7.85 (2H, s), 8.00-8.05 (2H, m), 8.36 (1H, s). |
| 1-214 | δ 2.52 (6H, s), 2.70-2.90 (2H, m), 4.22-4.24 (2H, m), 5.45 (1H, broad-s), 6.10 (1H, broad-s), 7.18-7.32 8H, m), 7.49-7.50 (1H, m), 7.60-7.70 (1H, m), 7.92-7.96 (1H, m). |
| 1-215 | δ 2.28 (6H, s), 2.64-2.79 (2H, m), 4.23-4.24 (2H, m), 5.43 (1H, broad-s), 5.85 (1H, broad-s), 7.27-7.31 4H, m), 7.34-7.53 (4H, m), 7.65 (1H, d, J = 10.2 Hz), 7.97-7.98 (1H, m). |
| 1-216 | δ 2.27 (6H, s), 2.60-2.80 (2H, m), 4.21-4.24 (2H, m), 5.43 (1H, broad-s), 5.85 (1H, broad-s), 7.29-7.34 4H, m), 7.47-7.55 (2H, m), 7.59 (1H, d, J = 7.8 Hz), 7.70-7.72 (2H, m), 7.90-8.00 (1H, m). |
| 1-217 | δ 2.69 (2H, t, J = 7.3 Hz), 4.29 (2H, t, J = 7.3 Hz), 5.85 (1H, broad-s.), 7.00 (1H, broad-s.), 7.17-7.38 (8H, m), 7.71-7.76 (2H, m), 8.16 (1H, s), 10.08 (1H, s). |
| 1-218 | δ 2.74 (2H, t, J = 6.8 Hz), 4.30 (2H, t, J = 6.8 Hz), 5.47 (1H, broad-s.), 6.06 (1H, broad-s.), 7.10-7.13 (1H, m), 7.38-7.43 (2H, m), 7.53-7.55 (1H, m), 7.69-7.73 (2H, m), 8.18-8.20 (3H, m), 8.24-8.26(1H, m). |
| 1-219 | δ 2.70 (2H, t, J = 6.8 Hz), 4.33 (2H, t, J = 6.8 Hz), 5.37 (1H, broad-s.), 5.79 (1H, broad-s.), 7.22-7.33 (2H, m), 7.42-7.46 (2H, m), 7.52-7.71 (4H, m), 7.92 (1H, s), 8.18 (2H, s). |
| 1-220 | δ 2.28 (6H, s), 2.60-2.75 (1H, m), 2.75-2.90 (1H, m), 4.21-4.24 (2H, m), 5.43 (1H, broad-s), 5.86 (1H, broad-s), 7.20-7.23 (1H, m), 7.30-7.34 (3H, m), 7.51-7.52 (1H, m), 7.61-7.63 (1H, m), 7.68-7.71 (1H, m), 7.98-8.01 (1H, m), 8.35 (1H, s). |
| 1-221 | δ 2.66-2.68 (1H, m), 2.83-2.84 (1H, m), 4.19-4.20 (1H, m), 4.26-4.28 (1H, m), 5.49 (1H, broad-s), 5.88 (1H, broad-s), 7.20 (1H, d, J = 7.8 Hz), 7.37 (1H, t, J = 7.8 Hz), 7.60-7.66 (2H, m), 7.92 (1H, s), 8.03 (1H, t, J = 6.8 Hz), 8.12-8.13 (1H, m), 8.32-8.33 (2H, m). |
| 1-222 | δ 2.66-2.68 (1H, m), 2.84-2.86 (1H, m), 4.18-4.21 (1H, m), 4.28-4.30 (1H, m), 5.52 (1H, broad-s), 5.91 (1H, broad-s), 7.18 (1H, d, J = 8.3 Hz), 7.38 (1H, t, J = 8.3 Hz), 7.58-7.60 (1H, m), 7.64-7.68 (1H, m), 8.00-8.09 (4H, m), 8.37 (1H, s). |
| 1-223 | δ 2.67-2.68 (1H, m), 2.82-2.83 (1H, m), 4.21-4.22 (2H, m), 5.44 (1H, broad-s), 5.99 (1H, broad-s), 6.87-6.91 (2H, m), 7.29-7.35 (3H, m), 7.58 (1H, t, J = 7.3 Hz), 7.29 (1H, s), 7.97-8.01 (1H, m), 8.12-8.13 (1H, m), 8.32 (1H, s). |
| 1-224 | δ 2.70-2.71 (1H, m), 2.84-2.85 (1H, m), 4.20-4.21 (1H, m), 4.26-4.27 (1H, m), 5.49 (1H, broad-s), 5.72 (1H, broad-s), 7.39 (1H, t, J = 7.8 Hz), 7.65 (1H, t, J = 7.8 Hz), 7.83-7.84 (3H, m), 7.98-8.01 (1H, m), 8.08-8.13 (3H, m). |
| 1-225 | δ 2.68-2.67 (1H, m), 2.85-2.86 (1H, m), 4.19-4.20 (1H, m), 4.28-4.29 (1H, m), 5.42 (1H, broad-s), 5.85 (1H, broad-s), 7.18 (1H, d, J = 8.3 Hz), 7.38 (1H, t, J = 7.8 Hz), 7.59 (1H, d, J = 7.8 Hz), 7.66 (1H, t, J = 7.8 Hz), 7.69-7.99 (1H, m), 8.07-8.10 (3H, m), 8.37 (1H, s). |
| 1-226 | δ 2.70 (2H, t, J = 6.8 Hz), 4.31 (2H, t, J = 6.8 Hz), 5.40 (1H, broad-s), 6.05 (1H, broad-s), 6.97-7.07 (3H, m), 7.14-7.16 (1H, m), 7.30-7.32 (1H, m), 7.41 (1H, t, J = 7.8 Hz), 7.66 (1H, d, J = 2.0 Hz), 7.74 (1H, d, J = 7.8 Hz), 7.92 (1H, s), 8.12 (1H, s), 8.33 (1H, s). |
| 1-227 | δ 2.75 (1H, t, J = 6.8 Hz), 2.82 (1H, t, J = 6.8 Hz), 4.22-4.27 (2H, m), 5.54 (1H, broad-s), 6.07 (1H, broad-s), 6.69-6.70 (1H, m), 6.78-6.79 (1H, m), 7.18-7.24 (2H, m), 7.51 (1H, t, J = 7.8 Hz), 7.91 (1H, s), 7.99 (1H, t, J = 6.8 Hz), 8.13 (1H, s), 8.28 (1H, d, J = 13.1 Hz). |
| 1-228 | δ 1.07 (3H, d, J = 6.3 Hz), 1.85 (3H, s), 2.45 (1H, m), 2.52-2.55 (1H, m), 2.64 (2H, t, J = 6.8 Hz), 2.92 (1H, dd, J = 2.9, 14.1 Hz), 3.59 (3H, s), 4.22 (2H, t, J = 6.8 Hz), 5.79 (1H, broad-s), 6.46 (1H, broad-s), 7.12-7.19 (3H, m), 7.27-7.32 (4H, m), 7.76 (1H, d, J = 7.8 Hz), 7.80 (1H, s), 8.85 (1H, s). |
| 1-229 | δ 1.08 (3H, d, J = 6.3 Hz), 1.87 (3H, s), 2.46-2.47 (1H, m), 2.49-2.50 (1H, m), 2.69 (2H, t, J = 6.8 Hz), 2.89-2.90 (1H, m), 3.61 (3H, s), 4.21 (2H, t, J = 6.8 Hz), 5.38 (1H, broad-s), 6.34 (1H, broad-s), 7.08 (1H, dd, J = 4.9, 7.3 Hz), 7.32-7.34 (2H, m), 7.50 (1H, dd, J = 2.0, 7.8 Hz), 7.77 (1H, d, J = 6.3 Hz), 7.87 (1H, s), 8.23 (1H, dd, J = 2.0, 4.9 Hz), 8.71 (1H, s). |
| 1-230 | δ 1.08 (3H, d, J = 6.3 Hz), 1.88 (3H, s), 2.44-2.47 (1H, m), 2.50-2.51 (1H, m), 2.71 (2H, t, J = 6.8 Hz), 2.92 1H, dd, J = 2.9, 13.7 Hz), 3.63 (3H, s), 4.20 (2H, t, J = 6.8 Hz), 5.72 (1H, broad-s), 6.26 (1H, broad-s), 6.71 2H, t, J = 7.8 Hz), 7.15-7.19 (1H, m), 7.32-7.38 (2H, m), 7.80-7.83 (2H, m), 8.70 (1H, s). |
| 1-231 | DMSO-d$_6$) δ 2.44-2.51 (2H, m), 4.00-4.09(2H, m), 6.90(1H, s), 7.07-7.15(3H, m), 7.25-7.29(1H, m), 7.45-7.52(3H, m), 7.78-7.82(2H, m), 8.14(2H, s), 10.57(1H, s). |
| 1-232 | DMSO-d$_6$) δ 2.47-2.51 (2H, m), 4.07-4.12(2H, m), 6.92-6.99(3H, m), 7.29-7.36(1H, m), 7.48-7.53(3H, m), 7.76(1H, s), 7.84 (1H, d, J = 7.3 Hz), 8.14(2H, s), 10.60(1H, s). |
| 1-233 | DMSO-d6) δ 2.44-2.51(2H, m), 4.04-4.10(2H, m), 6.91(1H, s), 7.45-7.54(4H, m), 7.74-7.85(3H, m), 8.14(2H, s), 8.27(1H, broad-s), 10.60(1H, s). |
| 1-234 | δ 2.69 (2H, t, J = 6.8 Hz), 4.29 (2H, t, J = 6.8 Hz), 5.46 (1H, broad-s), 5.91 (1H, broad-s), 7.18-7.21 (1H, m), 7.30-7.32 (1H, m), 7.44 (1H, t, J = 7.8 Hz), 7.60 (1H, dd, J = 2.4, 8.3 Hz), 7.72-7.73 (1H, m), 7.76 (1H, d, J = 8.3 Hz), 7.89 (1H, s), 8.02 (1H, s), 8.12 (1H, s), 8.26 (1H, d, J = 2.0 Hz). |
| 1-235 | δ 2.69-2.70 (1H, m), 2.84-2.85 (1H, m), 4.22-4.26 (2H, m), 5.38 (1H, broad-s), 5.85 (1H, broad-s), 7.17-7.18 (1H, m), 7.34 (1H, t, J = 7.8 Hz), 7.61-7.65 (2H, m), 7.91 (1H, s), 7.98-8.01 (2H, m), 8.32 (1H, s), 8.52 (1H, s), 8.56 (1H, s). |

TABLE 10-continued

| compound number | ¹H-NMR(CDCl₃, ppm) |
|---|---|
| 1-236 | δ 2.75 (2H, m), 4.32 (2H, m), 5.40 (1H, m), 6.00 (1H, m), 6.83 (1H, m), 6.95-6.97 (1H, d, J = 8.4 Hz), 7.18-7.26 (1H, m), 7.38-7.40 (2H, d, J = 8.8 Hz), 7.94 (2H, m), 7.97 (2H, m), 8.35 (1H, m). |
| 1-237 | δ 2.69 (2H, t, J = 6.3 Hz), 4.29 (2H, t, J = 6.3 Hz), 5.05 (1H, broad-s), 6.21 (1H, broad-s), 7.16-7.21 (3H, m), 7.28-7.33 (6H, m), 7.73 (1H, d, J = 7.8 Hz), 7.79 (1H, s), 8.19 (1H, s). |
| 1-238 | δ 2.69 (2H, t, J = 6.8 Hz), 4.28 (2H, t, J = 6.8 Hz), 5.55 (1H, s), 5.99 (1H, s), 7.19-7.21 (1H, m), 7.28-7.39 (4H, m), 7.45 (1H, d, J = 7.8 Hz), 7.56 (1H, d, J = 7.8 Hz), 7.68 (1H, s), 7.78 (1H, d, J = 7.8 Hz), 7.82 (1H, s), 8.23 (1H, s). |
| 1-239 | (CDCl3 + DMSO-d6) δ 2.64-2.65 (2H, m), 4.27-4.28 (2H, m), 5.96 (1H, broad-s), 7.03 (1H, broad-s), 7.20-7.21 (1H, m), 7.27-7.36 (3H, m), 7.43-7.44 (2H, m), 7.50-7.52 (2H, m), 7.90-7.91 (2H, m), 10.06 (1H, s). |
| 1-240 | δ 2.72-2.76 (2H, m), 4.29 (2H, t, J = 6.8 Hz), 5.54 (1H, broad-s), 6.09 (1H, broad-s), 7.09-7.13 (1H, m), 7.28-7.33 (2H, m), 7.36-7.38 (2H, m), 7.53 (1H, dd, J = 2.0, 7.8 Hz), 7.73-7.75 (1H, m), 7.84 (1H, s), 8.07 (1H, s), 8.25 (1H, dd, J = 2.0, 4.9 Hz). |
| 1-241 | δ 2.72 (2H, t, J = 6.8 Hz), 4.31 (2H, t, J = 6.8 Hz), 5.47 (1H, broad-s), 6.09 (1H, broad-s), 7.18-7.21 (2H, m), 7.28-7.30 (3H, m), 7.33-7.35 (1H, m), 7.41 (1H, t, J = 7.8 Hz), 7.70 (1H, s), 7.73-7.75 (1H, m), 8.11-8.12 (1H, m), 8.25 (1H, s), 8.47 (1H, s). |
| 1-242 | δ 2.77 (2H, t, J = 6.3 Hz), 4.29 (2H, t, J = 6.3 Hz), 5.56 (1H, broad-s), 6.02 (1H, broad-s), 7.11-7.14 (1H, m), 7.39-7.44 (2H, m), 7.56 (1H, d, J = 6.3 Hz), 7.77 (1H, d, J = 7.3 Hz), 7.85 (1H, s), 8.13 (1H, s), 8.25-8.26 (2H, m), 8.57 (1H, s). |
| 2-133 | δ 3.33-3.41 (2H, m), 3.97-3.99 (1H, m), 5.10-5.15 (1H, m), 5.32 (2H, broad-s), 7.22-7.24 (1H, m), 7.43 (2H, d, J = 7.8 Hz), 7.53 (2H, d, J = 7.8 Hz), 7.59 (1H, t, J = 7.8 Hz), 7.89 (2H, s), 7.97 (1H, d, J = 12.2 Hz), 8.06-8.08 (1H, m). |
| 3-133 | δ 3.10 (3H, s), 3.34-3.38 (1H, m), 3.70-3.74 (1H, m), 4.24 (1H, t, J = 6.8 Hz), 4.51 (1H, t, J = 6.8 Hz), 7.33 (1H, t, J = 7.8 Hz), 7.45 (2H, d, J = 8.3 Hz), 7.52 (2H, d, J = 8.3 Hz), 7.62-7.66 (1H, m), 7.83-7.85 (1H, m), 7.87 (2H, s), 8.05 (1H, t, J = 7.3 Hz). |
| 3-163 | δ 3.09 (3H, s), 3.40-3.41 (1H, m), 3.70-3.71 (1H, m), 4.34-4.37 (2H, m), 7.19-7.23 (2H, m), 7.28-7.34 (4H, m), 7.55-7.59 (1H, m), 7.85 (2H, s), 7.90-7.93 (1H, m), 8.02-8.03 (1H, m). |
| 3-164 | δ 3.10 (3H, s), 3.38-3.39 (1H, m), 3.79-3.80 (1H, m), 4.27-4.28 (1H, m), 4.47-4.48 (1H, m), 7.28-7.37 (2H, m), 7.51 (1H, d, J = 7.8 Hz), 7.60 (1H, d, J = 7.8 Hz), 7.65-7.70 (1H, m), 7.72 (1H, s), 7.86 (2H, s), 7.91-7.94 (1H, m), 8.06 (1H, t, J = 6.8 Hz). |
| 3-197 | δ 3.08 (3H, s), 3.37-3.38 (1H, m), 3.71-3.72 (1H, m), 4.29-4.30 (1H, m), 4.42 (1H, t, J = 7.3 Hz), 7.22 (1H, d, J = 8.3 Hz), 7.36-7.41 (1H, m), 7.63-7.70 (2H, m), 7.86 (2H, s), 7.89 (1H, s), 8.09 (1H, t, J = 6.8 Hz), 8.36-8.37 (1H, m). |
| 5-1 | δ 2.27 (6H, s), 2.77 (2H, t, J = 6.8 Hz), 3.61 (3H, s), 4.30 (2H, t, J = 6.8 Hz), 7.18-7.34 (9H, m), 7.39-7.40 (1H, m), 7.58 (1H, d, J = 7.3 Hz), 7.70 (1H, d, J = 7.3 Hz). |
| 5-4 | (DMSO-d6) δ 2.19 (6H, s), 2.57 (2H, t, J = 7.3 Hz), 4.08 (2H, t, J = 7.3 Hz), 7.21-7.26 (5H, m), 7.41-7.42 (4H, m), 7.73 (2H, s), 9.89 (1H, s). A proton assigned for carboxylic acid is not detected. |
| 5-5 | δ 2.37 (6H, s), 3.88-4.01 (5H, m), 6.95 (1H, d, J = 7.8 Hz), 7.13 (1H, t, J = 7.8 Hz), 7.26 (2H, s), 7.49 (2H, t, J = 7.8 Hz), 7.52-7.58 (2H, m), 7.68 (1H, broad-s), 7.72 (1H, t, J = 1.9 Hz), 7.77-7.79 (2H, m). |
| 5-8 | δ 2.26 (6H, s), 2.93 (2H, t, J = 6.3 Hz), 4.23 (2H, t, J = 6.3 Hz), 7.20-7.37 (9H, m), 7.44-7.45 (1H, m), 7.68 (1H, s), 7.42 (1H, d, J = 7.8 Hz). |
| 5-10 | δ 2.30(6H, s), 2.84(2H, t, J = 7.3 Hz), 2.90(3H, s), 3.05(3H, s), 4.31 (2H, t J = 7.3 Hz), 7.18-7.26(3H, m), 7.27-7.35(6H, m), 7.68-7.71 (2H, m), 7.75(1H, s). |
| 5-11 | δ 1.10(6H, d, J = 6.8 Hz), 2.30(6H, s), 2.64(2H, t, J = 6.8 Hz), 3.96-4.04(1H, m), 4.31 (2H, t, J = 6.8 Hz), 5.85(1H, d, J = 7.8 Hz), 7.18-7.22(3H, m), 7.28-7.34(6H, m), 7.70-7.72(3H, m). |
| 5-12 | δ 1.10(6H, d, J = 6.8 Hz), 2.32(6H, s), 2.62(2H, t, J = 6.3 Hz), 3.97-4.01 (1H, m), 4.30(2H, t, J = 6.3 Hz), 5.68(1H, d, J = 6.8 Hz), 7.1 5(1H, d, J = 8.3 Hz), 7.32-7.41 (5H, m), 7.50(2H, d, J = 8.3 Hz), 7.73(1H, d, J = 7.8 Hz), 7.81 (2H, broad-s). |
| 5-14 | δ 2.28(6H, s), 2.84(2H, t, J = 7.3 Hz), 3.55-3.58(4H, m), 3.63-3.70(4H, m), 4.29(2H, t, J = 7.3 Hz), 7.18-7.24(2H, m), 7.28-7.38(7H, m), 7.49(1H, broad-s), 7.69-7.71(2H, m). A proton assigned for NH is not detected. |
| 5-15 | δ 1.41-1.45 (18H, m), 1.56-1.59 (2H, m), 1.68-1.69 (1H, m), 2.04 (6H, s), 2.66-2.69 (2H, m), 3.35-3.36 (2H, m), 4.20-4.24 (1H, m), 4.25-4.29 (1H, m), 5.10-5.11 (1H, m), 6.40-6.41 (1H, m), 7.19-7.21 (3H, m), 7.24-7.29 (5H, m), 7.38-7.39 (2H, m), 7.77 (1H, s), 7.94-7.95 (1H, m). A proton assigned for NH is not detected. |
| 5-16 | δ 1.25 (9H, s), 1.41 (9H, s), 1.85-2.00 (1H, m), 2.05-2.16 (1H, m), 2.17 (6H, s), 2.33 (2H, dd, J = 2.0, 7.8 Hz), 2.62 (2H, t, J = 6.3 Hz), 4.15-4.35 (2H, m), 4.55-4.65 (1H, m), 7.15-7.24 (2H, m), 7.27-7.30 (6H, m), 7.42-7.44 (2H, m), 7.69 (1H, s), 7.83 (1H, d, J = 7.8 Hz), 8.04 (1H, s). |
| 5-17 | δ 1.20 (9H, s), 1.40 (9H, s), 1.28-1.80 (6H, m), 2.20 (6H, s), 2.60-2.64 (2H, m), 3.12-3.13 (2H, m), 4.11 (1H, m), 4.30 (1H, m), 4.50 (2H, m), 7.16-7.19 (3H, m), 7.24-7.30 (4H, m), 7.43-7.46 (2H, m), 7.71 (1H, s), 7.84 (1H, d, J = 7.8 Hz), 8.02 (1H, s). A proton assigned for NH is not detected. |
| 5-18 | δ 1.16 (9H, s), 1.25 (9H, s), 2.22 (6H, s), 2.64 (2H, t, J = 6.3 Hz), 3.50 (1H, dd, J = 2.9, 8.8 Hz), 3.79 (1H, dd, J = 2.9, 8.8 Hz), 4.25-4.35 (1H, m), 4.40-4.60 (2H, m), 6.60-6.70 (1H, m), 7.23-7.31 (7H, m), 7.37-7.42 (2H, m), 7.74 (1H, s), 7.82 (1H, d, J = 7.3 Hz), 7.93 (1H, s). |
| 5-19 | δ 1.29 (9H, s), 1.90-2.10 (1H, m), 2.21 (6H, s), 2.20-2.40 (3H, m), 2.55-2.65 (2H, m), 4.25-4.55 (3H, m), 5.30-5.40 (1H, broad-s), 6.35-6.45 (1H, broad-s), 7.16-7.20 (3H, m), 7.24-7.31 (5H, m), 7.39-7.45 (2H, m), 7.70 (1H, s), 7.81 (1H, d, J = 7.3 Hz), 8.05 (1H, s). |
| 5-20 | δ 2.21 (6H, s), 2.66 (2H, t, J = 6.3 Hz), 4.06 (2H, d, J = 5.9 Hz), 4.41 (2H, t, J = 6.3 Hz), 4.86 (2H, s), 7.11-7.24 (4H, m), 7.26-7.43 (11H, m), 7.78-7.81 (2H, m), 7.89 (1H, s). |
| 5-21 | DMSO-d6) δ 2.21 (6H, s), 2.53 (2H, t, J = 7.3 Hz), 3.58 (2H, d, J = 5.9 Hz), 4.10 (2H, t, J = 7.3 Hz), 7.02 (1H, s), 7.21-7.30 (6H, m), 7.43-7.45 (4H, m), 7.74-7.78 (2H, m), 8.19-8.20 (1H, m), 9.89 (1H, s). |
| 5-22 | δ 1.38 (9H, s), 1.42 (9H, s), 2.26 (6H, s), 2.77-2.78 (2H, m), 4.23-4.33 (5H, m), 5.40 (1H, m), 7.25-7.33 8H, m), 7.39 (1H, m), 7.59 (1H, s), 7.73-7.75 (2H, m, J = 3.9 Hz). |
| 5-23 | DMSO-d6) δ 2.21 (6H, s), 2.48-2.56 (2H, m), 3.67 (2H, d, J = 5.9 Hz), 4.08 (2H, t, J = 7.3 Hz), 7.21-7.29 (5H, m), 7.42-7.45 (4H, m), 7.73-7.77 (2H, m), 8.28 (1H, s), 9.93 (1H, s). A proton assigned for carboxylic acid is not detected. |

TABLE 10-continued

| compound number | $^1$H-NMR(CDCl$_3$, ppm) |
|---|---|
| 5-24 | (DMSO-d6) δ 1.45-1.50 (2H, m), 1.50-1.52 (2H, m), 2.20 (6H, s), 2.46-2.47 (2H, m), 2.99 (2H, t, J = 6.3 Hz), 4.10 (2H, t, J = 7.3 Hz), 7.23-7.28 (5H, m), 7.41-7.42 (4H, m), 7.78 (2H, s), 8.15-8.16 (1H, m), 8.33-8.34 (3H, m), 10.05 (1H, s). A proton assigned for carboxylic acid is not detected. |
| 5-25 | (DMSO-d6) δ 2.22 (6H, s), 2.71-2.76 (2H, m), 4.13-4.19 (2H, m), 4.27-4.33 (2H, m), 4.48-4.51 (1H, m), 7.21-7.29 (5H, m), 7.40-7.43 (4H, m), 7.78-7.80 (2H, m), 8.50 (3H, broad-s), 10.07 (1H, s). |
| 5-26 | (DMSO-d6) δ 1.33-1.35 (2H, m), 1.52-1.75 (4H, m), 2.22 (6H, s), 2.56 (2H, t, J = 7.6 Hz), 3.36-3.74 (2H, m), 4.07-4.15 (3H, m), 7.23-7.27 (5H, m), 7.43-7.44 (4H, m), 7.76-7.81 (5H, m), 8.32 (1H, d, J = 7.8 Hz), 9.98 (1H, s). |
| 5-27 | (DMSO-d6) δ 2.21 (6H, s), 2.58 (2H, t, J = 7.8 Hz), 4.07-4.28 (5H, m), 4.53-4.54 (1H, m), 7.23-7.29 (5H, m), 7.43-7.44 (4H, m), 7.73-7.77 (2H, m), 8.49 (1H, d, J = 7.8 Hz), 9.89 (1H, s). A proton assigned for carboxylic acid is not detected. |
| 5-28 | (DMSO-d6) δ1.70-1.75 (1H, m), 1.90-1.92 (1H, m), 2.21 (6H, s), 2.24-2.34 (2H, m), 2.53-2.57 (2H, m), 4.07-4.09 (2H, m), 4.18-4.19 (1H, m), 7.21-7.29 (5H, m), 7.43-7.44 (4H, m), 7.72 (1H, m), 7.76 (1H, s), 8.30 (1H, d, J = 7.8 Hz), 9.88 (1H, s). A proton assigned for carboxylic acid is not detected. |
| 5-29 | (DMSO-d6) δ 1.68-1.70 (1H, m), 1.90-1.92 (1H, m), 2.09-2.13 (2H, m), 2.21 (6H, s), 2.53-2.56 (2H, m), 4.06-4.14 (3H, m), 6.78 (1H, m), 7.23-7.29 (6H, m), 7.43-7.45 (4H, s), 7.70-7.73 (2H, s), 8.32 (1H, d, J = 7.3 Hz), 9.92 (1H, s). A proton assigned for carboxylic acid is not detected. |
| 5-30 | (DMSO-d6) δ 2.21 (6H, s), 2.33 (1H, dt, J = 7.8 Hz), 2.46-2.58 (3H, m), 4.09 (1H, t, J = 7.1 Hz), 4.48 (1H, dt, J = 7.8 Hz), 4.45-4.50 (1H, m), 6.86 (1H, s), 7.03 (1H, s), 7.23-7.28 (7H, m), 7.43-7.44 (4H, m), 7.73-7.78 (2H, m), 8.13 (1H, d, J = 8.3 Hz), 9.90 (1H, s). |
| 5-31 | (DMSO-d6) δ 2.40-2.70 (2H, m), 3.56-3.58 (2H, m), 3.97 (1H, broad-s), 4.10 (1H, broad-s), 7.02 (1H, s), 7.31 (2H, broad-s), 7.45-7.47 (2H, m), 7.61 (1H, broad-s), 7.73-7.75 (3H, m), 7.95 (1H, s), 8.03 (2H, s). 8.25 (1H, broad-s). |
| 5-32 | (DMSO-d6) δ 1.60-1.75 (1H, m), 1.75-1.90 (1H, m), 2.06 (2H), 1.95-2.20 (2H, m), 4.00 (1H), 4.12 (2H), 6.76 (1H), 7.00-7.05 (1H, m), 7.25-7.35 (3H, m), 7.44-7.46 (2H, m), 7.61-7.75 (5H, m), 7.95 (1H), 8.02-8.20 (2H, m). |
| 5-33 | δ 2.63-2.64 (2H, m), 4.20-4.21 (2H, m), 7.12-7.24 (2H, m), 7.39-7.40 (1H, m), 7.51-7.52 (3H, m), 7.69-7.70 (1H, m), 7.81 (2H, s), 7.85-7.86 (1H, m), 7.91-7.92 (1H, m), 8.31-8.32 (1H, m). |
| 5-34 | δ 2.63-2.64 (2H, m), 4.18-4.19 (2H, m), 7.23-7.24 (1H, m), 7.29-7.52 (6H, m), 7.83 (2H, s), 7.86-7.87 (1H, m), 7.91-7.92 (1H, m), 8.14-8.15 (1H, m). |
| 5-35 | δ 2.17 (6H, s), 2.90 (1H, broad-s), 3.28 (3H, s), 3.70-3.72 (2H, m), 3.85-3.92 (2H, m), 6.91-7.07 (3H, m), 7.11-7.39 (8H, m). |
| 5-36 | δ 2.36(6H, s), 2.82(2H, t, J = 6.8 Hz), 2.90(3H, s), 3.05(3H, s), 4.30(2H, t, J = 6.8 Hz), 7.19(1H, d, J = 7.8 Hz), 7.34-7.38(3H, m), 7.42(2H, d, J = 8.3 Hz), 7.50(2H, d, J = 8.3 Hz), 7.72(1H, d, J = 7.8 Hz), 7.77(1H, broad-s), 7.84(1H, broad-s). |
| 5-37 | δ 2.31(6H, s), 2.87(2H, t, J = 6.8 Hz), 2.90(3H, s), 3.10(3H, s), 4.30(2H, t), 7.10-7.13(1H, m), 7.34-7.41(4H, m), 7.57-7.59(1H, m), 7.72(1H, broad-s), 7.74(1H, broad-s), 7.87(1H, broad-s), 8.24-8.25(1H, m). |
| 5-71 | δ 2.13 (6H, s), 2.18 (3H, s), 2.66 (2H, t, J = 7.3 Hz), 3.27 (3H, s), 3.92 (2H, t, J = 7.3 Hz), 6.90-6.96 (3H, m), 7.11-7.16 (4H, m), 7.21-7.26 (3H, m), 7.33-7.34 (1H, m). |
| 5-72 | δ 2.17 (6H, s), 2.66 (3H, s), 2.90-2.94 (1H, m), 3.17-3.19 (1H, m), 3.26 (3H, s), 4.00-4.02 (1H, m), 4.11-4.13 (1H, m), 6.85-6.87 (1H, m), 6.97 (1H, t, J = 7.8 Hz), 7.08-7.29 (9H, m). |
| 5-73 | δ 2.09 (6H, s), 3.03 (3H, s), 3.26 (3H, s), 3.35 (2H, t, J = 7.3 Hz), 4.19 (2H, t, J = 7.3 Hz), 6.85-6.87 (1H, m), 6.96 (1H, t, J = 7.8 Hz), 7.06-7.07 (1H, m), 7.14-7.29 (8H, m). |
| 5-74 | δ 2.29 (6H, s), 3.84 (2H, t, J = 5.4 Hz), 4.03 (2H, t, J = 5.4 Hz), 4.46 (2H, s), 6.80-7.79 (17H, m). |
| 5-75 | δ 2.35 (6H, s), 3.39 (3H, s), 3.38-3.85 (8H, m), 7.20-8.05 (12H, m). |
| 5-76 | δ 1.24-1.30 (3H, m), 3.25 (2H, m), 3.37 (2H, m), 4.20 (1H, m), 4.35 (2H, m), 7.29 (3H, m), 7.41 (2H, m), 7.52 (2H, m), 7.91 (1H, m), 8.05 (1H, m), 8.14 (1H, m). |
| 5-77 | (DMSO-d$_6$) δ 2.68-2.72(2H, m), 2.78(3H, m), 2.95(3H, s), 4.04-4.09(2H, m), 7.22-7.29(5H, m), 7.45-7.49(2H, m), 7.74-7.76(2H, m), 7.95(1H, s), 8.51 (1H, s), 10.60(1H, s). |
| 5-78 | (DMSO-d$_6$) δ 2.71-2.72(2H, m), 2.78(3H, m), 2.94(3H, s), 4.08-4.09(2H, m), 7.45-7.54(4H, m), 7.73-7.78(4H, m), 7.96(1H, s), 8.52(1H, s), 10.58(1H, s). |
| 5-79 | (DMSO-d$_6$) δ 2.72-2.76(2H, m), 2.79(3H, m), 2.97(3H, s), 4.09-4.10(2H, m), 7.10-7.11(1H, m), 7.29-7.32(1H, m), 7.43-7.48(2H, m), 7.52-7.54(1H, m), 7.74-7.76(2H, m), 7.95(1H, s), 8.52(1H, s), 10.60(1H, s). |
| 5-80 | (DMSO-d$_6$) δ 2.66-2.70(2H, m), 3.54(3H, s), 4.12-4.15(2H, m), 7.21-7.29(5H, m), 7.45-7.47(2H, m), 7.72(1H, s), 7.76(1H, d, J = 7.3 Hz), 7.95(1H, s), 8.51 (1H, s), 10.59(1H, s). |
| 5-81 | (DMSO-d$_6$) δ 2.41-2.47(2H, m), 4.05-4.09(2H, m), 7.23-7.29(5H, m), 7.43-7.48(2H, m), 7.68-7.75(2H, m), 7.95(1H, s), 8.50(1H, s), 9.14-9.15(2H, m), 10.59(1H, s). |
| 5-82 | (DMSO-d$_6$) δ 2.71-2.72(2H, m), 2.78(3H, m), 2.95(3H, s), 4.04-4.07(2H, m), 7.44-7.58(4H, m), 7.74-7.81(4H, m), 7.95(1H, s), 8.52(1H, s), 10.58(1H, s). |
| 5-83 | δ 2.24 (6H, s), 2.65 (2H, m), 3.65 (2H, m), 4.23 (2H, m), 5.35 (1H, m), 7.26-7.53 (6H, m), 7.86-7.93 (4H, m). |
| 5-84 | δ 2.26(6H, s), 2.38 (1H, t, J = 6.3 Hz), 3.58-3.62 (2H, m), 3.73-3.77 (2H, m), 3.84 (2H, t, J = 4.9 Hz), 4.19 (2H, t, J = 4.9 Hz), 7.18-7.36 (9H, m), 7.71 (1H, d, J = 7.8 Hz), 7.77 (1H, s), 7.96 (1H, s). |
| 5-85 | δ 2.08 (6H, s), 3.00 (1H, t, J = 6.3 Hz), 3.27 (3H, s), 3.53 (2H, t, J = 4.4 Hz), 3.67-3.72 (4H, m), 3.96 (2H, t, J = 4.4 Hz), 6.73 (1H, d, J = 7.8 Hz), 6.88 (1H, t, J = 7.8 Hz), 6.98 (1H, d, J = 7.8 Hz), 7.10-7.46 (8H, m). |
| 5-86 | DMSO-d6) δ 2.44-2.46(2H, m), 3.33(3H, m), 4.02-4.09(2H, m), 7.23-7.28(5H, m), 7.46-7.47(2H, m), 7.68(1H, broad-s), 7.74-7.76(1H, m), 7.91-7.92(1H, m), 7.95(1H, s), 8.50(1H, s), 10.57(1H, s). |
| 5-87 | (DMSO-d6) δ 2.63-2.68(2H, m), 2.81 (3H, s), 2.95(3H, s), 4.17-4.20(2H, m), 7.30-7.31 (6H, m), 7.57-7.62(2H, m), 7.94(1H, s), 8.50(1H, s), 10.68(1H, broad-s). |
| 5-88 | (DMSO-d6) δ 2.58-2.62(2H, m), 4.02-4.11(2H, m), 7.21-7.30(5H, m), 7.46-7.49(2H, m), 7.74-7.76(2H, m), 7.95(1H, s), 8.51(1H, s), 10.6(1H, broad-s), 12.5(1H, broad-s). |
| 5-89 | δ 2.17(6H, s), 3.65 (4H, s), 3.80 (2H, broad-s), 4.18 (2H, broad-s), 4.43 (2H, s), 7.06-7.84 (17H, m). |
| 5-90 | δ 2.10 (6H, s), 3.26 (3H, s), 3.61-3.69 (6H, m), 3.84 (2H, t, J = 4.9 Hz), 4.54 (2H, s), 6.88-7.34 (16H, m). |

TABLE 10-continued

| compound number | ¹H-NMR(CDCl₃, ppm) |
|---|---|
| 5-91 | δ 2.19 (1/2*6H, s), 2.24 (1/2*6H, s), 2.42 (1/2*2H, t, J = 6.8 Hz), 2.67 (1/2*2H, t, J = 6.8 Hz), 4.11 (1/2*2H, t, J = 6.8 Hz), 4.26 (1/2*2H, t, J = 6.8 Hz), 4.75 (1H, s), 5.69 (1/2*1H, broad-s), 6.30 (1/2*1H, broad-s), 7.12-7.95 (13H, m). |
| 5-92 | δ 2.23 (6H, m), 2.75 (2H, m), 4.08 (2H, m), 4.21 (2H, m), 7.03 (1H, m), 7.27-7.53 (7H, m), 7.71-7.74 (2H, m), 7.92-7.96 (1H, m). |
| 5-93 | δ 2.17-2.18 (6H, m), 2.49 (2H, t, J = 5.3 Hz), 2.81 (2H, t, J = 6.3 Hz), 4.04 (2H, t, J = 5.3 Hz), 4.33 (2H, t, J = 6.3 Hz), 7.16-7.20 (2H, m), 7.24-7.25 (1H, m), 7.27-7.29 (2H, m), 7.39-7.48 (3H, m), 7.72 (1H, d, J = 7.8 Hz), 7.91 (1H, s), 8.22 (1H, s), 8.31 (1H, s). |
| 5-94 | δ 2.22 (6H, s), 2.51-2.52 (2H, m), 2.80 (2H, t, J = 6.3 Hz), 4.07 (2H, t, J = 5.3 Hz), 4.32 (2H, t, J = 6.3 Hz), 7.29-7.33 (2H, m), 7.37-7.39 (2H, m), 7.45-7.56 (2H, m), 7.76 (1H, s), 7.77 (1H, d, J = 7.8 Hz), 7.92 (1H, s), 8.30-8.31 (1H, m), 8.33 (1H, s). |
| 5-95 | δ 2.21 (6H, s), 2.49 (2H, t, J = 5.8 Hz), 2.79 (2H, t, J = 6.3 Hz), 4.07 (2H, t, J = 5.8 Hz), 4.32 (2H, t, J = 6.3 Hz), 7.34-7.40 (3H, m), 7.44-7.54 (4H, m), 7.75 (1H, d, J = 7.3 Hz), 7.93 (1H, s), 8.16 (1H, s), 8.33 (1H, s). |
| 5-96 | δ 2.83 (2H, t, J = 6.8 Hz), 2.89 (3H, s), 3.04 (3H, s), 4.32 (2H, t, J = 6.8 Hz), 7.19-7.20 (1H, m), 7.32-7.34 (1H, m), 7.41 (1H, t, J = 7.8 Hz), 7.65 (1H, d, J = 7.8 Hz), 7.70-7.73 (2H, m), 7.92 (1H, s), 8.09 (1H, s), 8.32 (1H, s), 8.52-8.53 (2H, m). |
| 5-97 | δ 2.78-2.79 (2H, m), 2.88 (3H, s), 3.02 (3H, s), 4.25 (2H, t, J = 6.3 Hz), 7.08-7.10 (2H, m), 7.38-7.46 (2H, m), 7.80-7.83 (2H, m), 7.91 (1H, s), 7.97-7.98 (1H, m), 8.19 (1H, s), 8.31 (1H, s), 9.03 (1H, s). |
| 5-98 | δ 2.25 (6H, s), 2.88 (2H, t, J = 6.8 Hz), 4.30 (2H, t, J = 6.8 Hz), 7.16-7.72 (12H, m), 9.81 (1H, s). |
| 5-99 | δ 2.55 (2/3*2H, t, J = 6.8 Hz), 2.70 (1/3*2H, t, J = 6.8 Hz), 3.50 (2H, broad-s), 4.17 (2/3*2H, t, J = 6.8 Hz), 4.30 (1/3*2H, t, J = 6.8 Hz), 4.88 (1H, broad-s), 7.14-7.78 (10H, m), 8.04 (2/3*2H, s), 8.06 (1/3*2H, s). |
| 5-100 | δ 2.17 (3H, s), 2.28 (6H, s), 2.92 (2H, t, J = 6.8 Hz), 4.25 (2H, t, J = 6.8 Hz), 7.18-7.39 (10H, m), 7.58 (1H, s), 7.69 (1H, d, J = 7.8 Hz). |
| 5-101 | δ 2.77-2.78 (1H, m), 2.92 (3H, s), 2.97-2.98 (1H, m), 3.07 (3H, s), 4.21-4.26 (2H, m), 7.17-7.18 (1H, m), 7.33 (1H, t, J = 7.8 Hz), 7.64-7.66 (2H, m), 7.91 (1H, s), 7.96-8.00 (2H, m), 8.32 (1H, s), 8.51-8.52 (1H, m), 8.57-8.58 (1H, m). |
| 5-102 | δ 2.74-2.75 (1H, m), 2.91 (3H, s), 2.95-2.96 (1H, m), 3.06 (3H, s), 4.21-4.22 (2H, m), 7.12-7.13 (2H, m), 7.35 (1H, t, J = 7.8 Hz), 7.69-7.70 (1H, m), 7.92 (1H, s), 7.99-8.00 (1H, m), 8.06-8.07 (1H, m), 8.25-8.26 (1H, m), 8.30-8.33 (2H, m). |
| 5-103 | δ 2.84 (2H, t), 2.90 (3H, s), 3.05 (3H, s), 4.40 (2H, t), 7.18-7.22 (2H, m), 7.28-7.39 (5H, m), 7.71 (1H, d), 7.76 (1H, s), 8.11-8.12 (1H, m), 8.27 (1H, s), 8.49 (1H, s). |
| 5-104 | δ 2.87-2.91 (5H, m), 3.11 (3H, s), 4.39 (2H, t, J = 6.8 Hz), 7.11-7.14 (1H, m), 7.39 (1H, t, J = 7.8 Hz), 7.46 (1H, d, J = 7.8 Hz), 7.59-7.60 (1H, m), 7.75-7.77 (1H, m), 7.90-7.92 (1H, m), 8.13-8.15 (1H, m), 8.24-8.26 (2H, m), 8.69 (1H, s). |
| 5-105 | δ 1.82 (3/4*3H, s), 1.92 (1/4*3H, s), 2.24 (3/4*6H, s), 2.26 (1/4*6H, s), 2.58 (3/4*2H, t, J = 6.8 Hz), 2.78 (1/4*2H, t, J = 6.8 Hz), 4.21 (2H, t, J = 6.8 Hz), 7.18-7.71 (13H, m). |
| 5-106 | δ 2.23 (6H, s), 2.59 (2H, t, J = 5.4 Hz), 3.71 (6H, s), 4.35-4.47 (5H, m), 6.90 (1H, s), 7.18-7.49 (10H, m), 7.61 (1H, s), 7.74 (1H, d, J = 6.8 Hz). |
| 5-107 | δ 2.29 (6H, s), 2.75 (2H, t, J = 6.4 Hz), 3.26 (3H, s), 4.32 (2H, t, J = 6.4 Hz), 4.61 (2H, s), 4.79 (2H, d, J = 6.4 Hz), 6.75-7.42 (10H, m), 7.52 (1H, s), 7.63 (1H, s), 7.73 (1H, d, J = 7.8 Hz). |
| 5-108 | δ 2.88-3.04 (2H, m), 4.17-4.21 (2H, m), 7.43 (1H, t, J = 7.8 Hz), 7.69-7.70 (1H, m), 7.86 (2H, s), 7.90 (1H, d, J = 10.7 Hz), 8.09-8.12 (1H, m), 8.73 (2H, s), 9.15 (1H, s). |
| 5-109 | δ 2.11 (6H, s), 2.25 (6H, s), 2.48 (2H, t, J = 6.8 Hz), 3.27 (3H, s), 3.89 (2H, t, J = 6.8 Hz), 6.81-7.34 (11H, m). |
| 5-110 | δ 1.84-1.87 (2H, m), 2.35 (6H, s), 3.57 (9H, s), 3.75 (2H, t, J = 6.8 Hz), 7.02-8.09 (12H, m). |
| 5-111 | (DMSO-d6) δ 2.90-2.93(2H, m), 4.15-4.19(2H, m), 7.10-7.15(3H, m), 7.30-7.32(1H, m), 7.50-7.52(2H, m), 7.84-7.85(2H, m), 8.14(2H, s), 10.58(1H, s). |
| 5-112 | δ 2.75 (2H, t, J = 6.8 Hz), 4.07 (2H, broad-s), 7.12-7.89 (10H, m), 8.01 (2H, s). |
| 5-128 | δ 2.24 (6H, s), 2.50 (2H, t, J = 5.8 Hz), 2.83 (2H, t, J = 6.3 Hz), 4.09 (2H, t, J = 5.8 Hz), 4.32 (2H, t, J = 6.3 Hz), 7.09-7.12 (1H, m), 7.43-7.47 (2H, m), 7.54-7.56 (1H, m), 7.68 (1H, s), 7.72 (1H, d, J = 7.3 Hz), 7.93 (1H, s), 8.01 (1H, s), 8.23 (1H, dd, J = 1.5, 4.4 Hz), 8.34 (1H, s). |
| 6-1 | δ 2.18 (6H, s), 3.29 (3H, s), 3.79 (3H, s), 4.27 (2H, s), 6.92-6.94 (2H, m), 7.02-7.05 (1H, m), 7.10-7.14 (2H, m), 7.18-7.41 (6H, m). |
| 6-3 | δ 2.15 (6H, s), 3.29 (3H, s), 4.34 (2H, s), 4.70 (1H, broad-s), 6.92-6.94 (2H, m), 6.99-7.03 (1H, m), 7.10-7.28 (8H, m). |
| 6-5 | δ 1.31 (3H, t, J = 7.3 Hz), 2.17 (6H, s), 3.29 (3H, s), 4.23 (2H, q, J = 7.3 Hz), 4.26 (2H, s), 6.92-6.93 (2H, m), 7.00-7.02 (1H, m), 7.11-7.26 (7H, m), 7.40-7.50 (1H, m). |
| 6-6 | δ 2.12 (3H, s), 2.18 (6H, s), 3.29 (3H, s), 4.82 (2H, s), 6.93-6.97 (2H, m), 7.03-7.05 (1H, m), 7.10-7.15 (4H, m), 7.22-7.26 (4H, m). |
| 6-7 | δ 2.18 (6H, s), 2.65 (3H, s), 3.26 (3H, s), 4.43 (1H, d, J = 13.1 Hz), 5.09 (1H, d, J = 13.1 Hz), 6.99-7.01 (2H, m), 7.16-7.32 (9H, m). |
| 6-8 | δ 2.18 (6H, s), 3.05 (3H, s), 3.28 (3H, s), 4.92 (2H, s), 6.99-7.01 (1H, m), 7.08-7.11 (2H, m), 7.16-7.24 (3H, m), 7.29-7.41 (5H, m). |
| 6-9 | δ 1.45(3H, d, J = 6.8 Hz), 2.29(6H, s), 2.57-2.63(1H, m), 2.98-3.00(1H, m), 4.95(1H, broad-s), 5.53(1H, broad-s), 6.19(1H, broad-s), 7.14-7.18(5H, m), 7.30-7.39(4H, m), 7.70(1H, broad-s), 7.77(2H, d, J = 7.3 Hz). |
| 6-10 | δ 1.25(3H, t, J = 7.3 Hz), 2.30(6H, s), 3.00-3.08(1H, m), 4.09-4.12(2H, m), 5.67(1H, broad-s), 6.69(1H, broad-s), 7.17-7.32(9H, m), 7.75-7.78(2H, m), 8.73(1H, broad-s). |
| 6-12 | δ 2.16 (6H, s), 3.28 (3H, s), 4.20 (2H, s), 5.50 (1H, broad-s), 6.10 (1H, broad-s), 6.94-6.95 (2H, m), 7.04-7.06 (1H, m), 7.12-7.33 (8H, m). |
| 6-13 | δ 1.86-1.89(2H, m), 2.15(6H, s), 2.35(2H, t, J = 7.3 Hz), 3.28(3H, s), 3.66(3H, s), 3.78(2H, t, J = 7.3 Hz), 6.89-6.94(3H, m), 7.11-7.12(4H, m), 7.21-7.25(3H, m), 7.34(1H, broad-s). |
| 6-14 | δ 1.85-1.87(2H, m), 2.26(6H, s), 2.42-2.43(2H, m), 3.28(3H, s), 3.83(2H, t, J = 7.3 Hz), 6.88-6.94(3H, m), 7.09-7.14(4H, m), 7.19-7.26(3H, m), 7.35(1H, broad-s).<br>A proton assigned for carboxylic acid is not detected. |
| 6-15 | δ 1.86(2H, t, J = 6.8 Hz), 2.13(6H, s), 2.25-2.30(2H, m), 3.27(3H, s), 3.84(2H, t, J = 6.8 Hz), 5.35(1H, broad-s), 6.50(1H, broad-s), 6.90-6.95(3H, m), 7.11-7.13(4H, m), 7.25-7.30(3H, m), 7.34(1H, broad-s). |
| 6-16 | δ 2.08 (2H, quintet, J = 6.8 Hz), 2.31 (6H, s), 2.40 (2H, t, J = 6.8 Hz), 4.08 (2H, t, J = 6.8 Hz), 5.32 (1H, broad-s), 6.02 (1H, broad-s), 7.14-7.34 (9H, m), 7.74 (1H, d, J = 7.8 Hz), 7.80 (1H, s), 8.10 (1H, s). |

TABLE 10-continued

| compound number | ¹H-NMR(CDCl₃, ppm) |
|---|---|
| 6-18 | δ 2.20 (6H, s), 3.31 (3H, s), 4.45 (2H, s), 6.92-6.94 (1H, m), 7.04-7.05 (1H, m), 7.13-7.34 (9H, m). |
| 6-20 | δ 1.83 (6H, s), 1.89 (2H, broad-s), 3.31 (2H, t, J = 7.3 Hz), 4.09 (2H, t, J = 7.3 Hz), 7.18-7.36 (9H, m), 7.69-7.71 (2H, m), 7.89 (1H, s).<br>A proton assigned for NH2 is not detected. |
| 6-42 | δ 2.12 (6H, s), 2.98 (1H, t, J = 6.8 Hz), 3.27 (3H, s), 3.29 (1H, d, J = 6.8 Hz), 3.61-3.96 (5H, m), 6.86-6.96 3H, m), 7.13-7.16 (3H, m), 7.22 (2H, s), 7.22-7.29 (3H, m). |
| 6-43 | δ 1.44-1.47 (18H, m), 3.85-3.86 (1H, m), 4.25-4.26 (1H, m), 4.50-4.51 (1H, m), 7.18-7.19 (2H, m), 7.26-7.28 (2H, m), 7.58-7.61 (2H, m), 7.84 (2H, s), 7.96-7.99 (2H, m), 8.08-8.10 (1H, m). |
| 6-44 | δ 1.40-1.46 (18H, m), 3.78-3.79 (1H, m), 4.14-4.15 (1H, m), 4.24-4.25 (1H, m), 7.29-7.33 (2H, m), 7.44-7.45 (1H, m), 7.55-7.66 (3H, m), 7.86 (2H, s), 7.94-8.03 (2H, m). |
| 6-45 | δ 1.40 (9H, s), 1.45 (9H, s), 3.78-3.79 (1H, m), 4.24-4.26 (1H, m), 4.54-4.55 (1H, m), 7.38-7.40 (1H, m), 7.49-7.51 (1H, m), 7.58 (1H, t, J = 7.8 Hz), 7.78 (2H, d, J = 8.3 Hz), 7.86-8.01 (3H, m), 8.19 (2H, d, J = 7.8 Hz) |
| 6-46 | δ 1.80 (2H, broad-t, J = 5.4 Hz), 2.27 (6H, s), 3.59 (1H, broad-s), 3.72 (2H, broad-s), 4.23 (2H, t, J = 5.4 Hz), 7.16-7.42 (10H, m), 7.57 (1H, s), 7.68 (1H, d, J = 7.3 Hz). |
| 6-47 | δ 1.98-2.07 (2H, m), 2.22 (6H, s), 3.63 (2H, t, J = 6.8 Hz), 4.09-4.15 (2H, m), 4.47 (2H, s), 7.05-7.70 (17H, m). |
| 6-48 | δ 2.31 (2/5*6H, s), 2.35 (1/5*6H, s), 2.42 (2/5*6H, s), 3.59-4.49 (7H, m), 6.94-7.79 (12H, m). |
| 6-49 | δ 1.78-1.79 (2H, m), 2.28 (6H, s), 2.44 (3H, d, J = 4.9 Hz), 3.36-3.42 (1H, m), 4.09-4.10 (2H, m), 4.20 (1H, broad-s), 4.93 (1H, broad-s), 7.14-7.18 (2H, m), 7.21-7.23 (2H, m), 7.27-7.31 (3H, m), 7.39-7.43 (2H, m), 7.81-7.83 (1H, m), 7.87 (1H, s), 8.95 (1H, s). |
| 6-50 | δ 1.97 (3H, s), 1.97-2.03 (2H, m), 2.24 (6H, s), 4.12 (2H, t, J = 6.8 Hz), 4.23 (2H, t, J = 6.8 Hz), 7.16-7.74 (12H, m). |
| 6-51 | δ 1.65-1.75 (4H, m), 2.24 (6H, s), 3.50 (2H, t, J = 6.3 Hz), 4.02 (2H, t, J = 6.3 Hz), 4.47 (2H, s), 7.07 (1H, broad-s), 7.20-7.34 (14H, m), 7.50 (1H, s), 7.66 (1H, d, J = 7.3 Hz). |
| 6-52 | δ 1.62-1.67 (2H, m), 1.78-1.82 (2H, m), 2.16 (1H, broad-s), 2.23 (6H, s), 3.68 (2H, broad-s), 4.04 (2H, t, J = 7.3 Hz), 7.16-7.29 (6H, m), 7.32 (2H, s), 7.39 (1H, t, J = 7.8 Hz), 7.57 (1H, s), 7.59 (1H, s), 7.70 (1H, d, J = 7.8 Hz). |
| 6-53 | δ 1.51-1.67 (6H, m), 2.19 (6H, s), 3.47 (2H, t, J = 5.9 Hz), 4.01 (2H, t, J = 7.3 Hz), 4.43 (2H, s), 7.18-7.71 (17H, m). |
| 6-54 | δ 1.50-1.69 (7H, m), 2.24 (6H, s), 3.61 (2H, q, J = 5.3 Hz), 4.03 (2H, t, J = 7.3 Hz), 7.17-7.33 (8H, m), 7.42 (1H, t, J = 7.8 Hz), 7.52 (2H, s), 7.70 (1H, d, J = 7.8 Hz). |
| 6-55 | δ 1.72-1.74 (2H, m), 3.46-3.47 (2H, m), 3.92-3.96 (2H, m), 4.49-4.52 (1H, m), 7.23-7.29 (7H, m), 7.41-7.45 (2H, m), 7.75 (1H, s), 7.94 (1H, s), 10.30 (1H, s). |
| 6-56 | δ 1.36-1.70 (5H, m), 2.14 (6H, s), 3.28 (3H, s), 3.76 (2H, t, J = 7.3 Hz), 3.83 (3H, s), 4.15 (2H, t, J = 6.3 Hz), 6.87-7.34 (11H, m). |
| 6-57 | δ 1.62-1.78 (4H, m), 2.50 (6H, s), 2.56 (2H, t, J = 6.8 Hz), 4.04 (2H, t, J = 6.8 Hz), 7.16-7.33 (8H, m), 7.40 1H, t, J = 7.8 Hz), 7.58 (1H, s), 7.72 (1H, d, J = 7.8 Hz), 7.82 (1H, broad-s), 9.75 (1H, s). |
| 6-58 | δ 2.04 (2H, t, J = 6.8 Hz), 2.29 (6H, s), 2.64 (2H, t, J = 6.8 Hz), 4.02 (2H, t, J = 6.8 Hz), 7.16-7.72 (12H, m), 9.80 (1H, s). |
| 6-59 | δ 2.36 (6H, s), 4.27 (2H, s), 6.97 (1H, d, J = 7.8 Hz), 7.14 (1H, t, J = 7.8 Hz), 7.28 (2H, s), 7.47 (2H, t, J = 7, 8 Hz), 7.55 (1H, t, J = 7.8 Hz), 7.61 (1H, dd, J = 1.5, 7.8 Hz), 7.73-7.82 (4H, m), 9.85 (1H, s). |
| 6-60 | δ 1.80-1.90 (2H, m), 2.35 (6H, s), 3.20-3.30 (2H, m), 3.95-4.02 (2H, m), 7.23-7.45 (8H, m), 7.73 (1H, s), 7.79 (1H, d, J = 7.3 Hz), 8.31 (2H, s), 9.89 (1H, broad-s). |
| 6-61 | δ 1.90 (2H, broad-s), 2.02-2.07 (2H, m), 2.26 (6H, s), 3.41 (2H, q, J = 6.4 Hz), 4.13 (2H, t, J = 6.4 Hz), 7.16-7.82 (12H, m), 8.56 (1H, s). |
| 6-62 | δ 1.71 (2H, quintet, J = 7.3 Hz), 2.13 (6H, s), 2.18 (6H, s), 2.29 (2H, t, J = 7.3 Hz), 3.27 (3H, s), 3.80 (2H, t, J = 7.3 Hz), 6.84-7.34 (11H, m). |
| 6-63 | δ 1.60-1.75 (1H, m), 2.00-2.10 (1H, m), 2.36 (6H, s), 2.52-2.62 (1H, m), 3.49-4.00 (6H, m), 2.80-8.00 (12H, m). |
| 6-64 | δ 2.05 (2H, q, J = 6.8 Hz), 2.25 (6H, s), 2.54 (2H, t, J = 6.8 Hz), 7.21 (2H, t, J = 6.8 Hz), 7.19-7.33 (9H, m), 7.42 (1H, t, J = 7.8 Hz), 7.62 (1H, s), 7.71 (1H, d, J = 7.8 Hz). |
| 6-68 | δ 1.35-1.65 (6H, m), 2.13 (6H, s), 3.27 (3H, s), 3.72-3.73 (2H, m), 4.49 (2H, s), 6.90-7.34 (16H, m), 7.45 (2H, t, J = 6.8 Hz). |
| 6-69 | δ 1.25-1.65 (7H, m), 2.11 (6H, s), 3.27 (3H, s), 3.60-3.65 (2H, m), 3.78 (2H, t, J = 7.8 Hz), 6.85-7.34 (11H, m). |
| 7-1 | δ 2.33(6H, s), 2.72-2.74(2H, m), 4.02(2H, m), 6.10(1H, broad-s), 6.78-6.80(1H, m), 7.04(1H, t, J = 7.8 Hz), 7.21(3H, broad-s), 7.35-7.61(5H, m), 7.87-7.89(2H, m), 9.80(1H, s). |
| 7-6 | δ 2.31(6H, s), 2.84(2H, t, J = 7.8 Hz), 3.63(3H, s), 4.07(2H, t, J = 7.8 Hz), 6.87-6.89(1H, m), 7.10(1H, t, J = 7.8 Hz), 7.24-7.26(2H, m), 7.46-7.58(4H, m), 7.65-7.69(2H, m), 7.77-7.79(2H, m). |
| 7-22 | δ 2.32 (6H, s), 3.11 (3H, s), 3.58-3.63 (2H, m), 4.13-4.17 (2H, m), 6.70-6.72 (1H, m), 6.94-6.96 (1H, m), 7.25 (2H, s), 7.50-7.60 (3H, m), 7.80-7.82 (2H, m), 7.91 (1H, d, J = 3.9 Hz), 8.42-8.43 (1H, m). |
| 7-23 | δ 2.34(6H, broad-s), 3.08(3H, s), 3.20-3.22(1H, broad-s), 3.47(1H, broad-s), 3.89(2H, broad-s), 6.79-6.83(1H, m), 6.88-6.89(1H, m), 7.06-7.35(9H, m). |
| 7-169 | δ 3.10 (3H, s), 3.74-3.78 (2H, m), 4.20-4.24 (2H, m), 6.85-7.26 (2H, m), 7.51-7.60 (3H, m), 7.78 (2H, s), 7.85-7.87 (2H, m), 8.06 (1H, d, J = 3.9 Hz), 8.48-8.50 (1H, m). |
| 7-220 | δ 2.44(6H, broad-s), 3.13(3H, s), 4.45(1H, broad-s), 5.77(1H, broad-s), 6.79-7.04(6H, m), 7.15-7.34(6H, m). |
| 7-221 | δ 2.37(6H, broad-s), 3.05(3H, s), 3.81(3H, s), 4.25(1H, broad-s), 4.40(1H, broad-s), 6.80-6.89(2H, m), 7.15-7.37(8H, m). |
| 7-222 | δ 2.47(6H, broad-s), 3.06(3H, s), 4.38(2H, broad-s), 6.81-6.89(2H, m), 7.14-7.52(8H, m).<br>A proton assigned for carboxylic acid is not detected. |
| 7-226 | δ 2.04-2.08 (2H, m), 2.30 (6H, s), 2.46 (2H, t, J = 7.3 Hz), 3.63 (3H, s), 4.05 (2H, t, J = 7.3 Hz), 7.19-7.23 (3H, m), 7.28-7.37 (5H, m), 7.58-7.61 (2H, m), 7.70-7.72 (2H, m). |
| 8-1 | δ 2.11(6H, s), 2.58(2H, t, J = 6.8 Hz), 2.70(2H, t, J = 6.8 Hz), 3.96-4.05(4H, m), 5.45(1H, broad-s), 5.55(1H, broad-s), 6.20(1H, broad-s), 6.25(1H, broad-s), 6.80-6.82(1H, m), 6.91-6.99(2H, m), 7.11-7.17(5H, m), 7.22(2H, s), 7.30-7.40(1H, m). |
| 8-12 | δ 2.50(6H, broad-s), 3.51 (1H, s), 3.73(3H, s), 3.81(3H, s), 4.30(1H, broad-s), 4.35(1H, broad-s), 4.75(1H, broad-s), 6.79(1H, t, J = 7.8 Hz), 7.08-7.24(6H, m), 7.28-7.34(3H, m). |

TABLE 10-continued

| compound number | $^1$H-NMR(CDCl$_3$, ppm) |
|---|---|
| 8-13 | δ 2.18-2.38(6H, broad-s), 4.10(1H, broad-s), 4.32(2H, s), 4.52(1H, broad-s), 6.02(2H, broad-s), 6.77(1H, t, J = 7.8 Hz), 7.03-7.41 (9H, m). |
| 9-12 | δ 2.36 (6H, s), 2.63-2.66 (2H, broad-s), 4.13 (2H, t, J = 7.3 Hz), 4.78 (2H, broad-s), 5.31 (2H, broad-s), 7.36 (2H, s), 7.52-7.59 (3H, m), 7.84-7.88 (2H, m). |

TABLE 22

| compound number | $^1$H-NMR (CDCl$_3$, ppm) or APCI-MS |
|---|---|
| 11-3 | APCI-MS m/z (M + 1): 617 |
| 11-4 | δ7.74(1H, t, J = 8.0 Hz), 8.11(2H, s), 8.42(1H, d, J = 7.6 Hz), 8.46(1H, d, J = 8.4 Hz), 8.90(1H, d, J = 12.4 Hz), 8.92(1H, s). |
| 11-8 | δ7.75(1H, s), 7.78(1H, t, J = 7.8 Hz), 7.94(1H, s), 8.17(1H, s), 8.29-8.30(1H, m), 8.50-8.52(1H, m), 8.78(1H, t, J = 2.0 Hz). |
| 11-10 | δ7.77(1H, t, J = 8.3 Hz), 7.82(1H, s), 7.90(1H, s), 8.00(1H, s), 8.28-8.29(1H, m), 8.49-8.50(1H, m), 8.77(1H, broad-s). |
| 11-11 | δ7.75-7.79(2H, m), 7.94(1H, s), 8.17(1H, d, J = 1.0 Hz), 8.28(1H, dd, J = 1.5, 7.8 Hz), 8.48-8.51(1H, m). 8.76-8.77(1H, m). |
| 11-12 | δ7.76-7.80(2H, m), 7.97(1H, s), 8.28-8.30(1H, m), 8.37(1H, s), 8.49-8.52(1H, m), 8.78(1H, s). |
| 11-15 | APCI-MS m/z (M + 1): 607 |
| 11-16 | APCI-MS m/z (M + 1): 655 |
| 11-19 | δ7.75-7.78(2H, m), 8.21(2H, s), 8.23-8.26(1H, m), 8.48-8.50(1H, m), 8.72(1H, t, J = 1.9 Hz). |
| 11-23 | δ7.55-7.58(1H, m), 7.67(1H, broad-s), 7.70(2H, s), 7.92-7.95(2H, m). |
| 11-24 | δ7.58(1H, t, J = 7.8 Hz), 7.66(1H, broad-s), 7.90(2H, s), 7.93(1H, dd, J = 1.5, 7.8 Hz), 7.98(1H, d, J = 7.8 Hz). |
| 11-25 | δ7.58(1H, t, J = 8.3 Hz), 7.70(1H, d, J = 3.4 Hz), 7.93(1H, dd, J = 1.5, 6.3 Hz), 8.08-8.10(1H, m). 8.13(2H, s). |
| 11-26 | (DMSO-d$_6$) δ7.78(1H, t, J = 7.8 Hz), 7.94(1H, dd, J = 2.0, 7.8 Hz), 7.97(1H, s), 8.03(1H, s), 8.21(1H, dd, J = 2.0, 7.8 Hz), 11.10(1H, s). |
| 11-27 | δ7.58-7.62(2H, m), 7.93-7.95(2H, m), 8.04(1H, dd, J = 1.5, 7.8 Hz), 8.10(1H, d, J = 1.5 Hz). |
| 11-29 | δ7.52-7.61(2H, m), 7.89(2H, s), 7.94(1H, dd, J = 1.5, 8.3 Hz), 7.99(1H, d, J = 7.8 Hz). |
| 11-30 | δ7.56-7.60(1H, m), 7.90-7.93(1H, m), 8.08-8.10(1H, m), 8.12(2H, s), 8.19(1H, s). |
| 11-33 | δ7.49-7.61(3H, m), 7.80-7.96(3H, m). |
| 11-38 | δ7.61(1H, t, J = 7.8 Hz), 7.67(1H, broad-s), 7.93-7.97(3H, m), 8.18(1H, broad-s). |
| 11-39 | δ7.60(1H, t, J = 7.8 Hz), 7.76(1H, s), 7.94(1H, dd, J = 1.5, 7.8 Hz), 7.97(1H, s), 8.03(1H, dd, J = 1.5, 7.8 Hz), 8.39(1H, s). |
| 11-42 | δ7.59(1H, t, J = 7.8 Hz), 7.66(1H, broad-s), 7.93-7.97(3H, m), 8.17(1H, s). |
| 11-43 | δ7.60-7.61(1H, m), 7.77(1H, s), 7.89-7.96(2H, m), 8.03-8.04(1H, m), 8.38(1H, s). |
| 11-48 | δ7.56-7.61(1H, m), 7.73(1H, s), 7.88(1H, d, J = 1.5 Hz), 7.92-7.98(2H, m), 8.21(1H, s). |
| 11-50 | APCI-MS m/z (M + 1): 497 |
| 11-51 | δ7.51-7.55(1H, m), 7.90(2H, s), 8.16(1H, d, J = 11.7 Hz), 8.27-8.31(1H, m), 8.48(1H, t, J = 6.3 Hz). |
| 11-52 | δ7.52-7.55(1H, m), 8.12-8.18(3H, m), 8.29-8.32(1H, m), 8.48-8.51(1H, m). |
| 11-53 | APCI-MS m/z (M + 1): 541 |
| 11-54 | δ7.53(1H, t, J = 8.3 Hz), 7.92(1H, d, J = 1.5 Hz), 8.10(1H, d, J = 1.5 Hz), 8.16(1H, d, J = 12.2 Hz), 8.29-8.30(1H, m), 8.47-8.51(1H, m). |
| 11-56 | δ7.53-7.54(1H, m), 7.89(2H, s), 8.17(1H, d, J = 12.2 Hz), 8.29-8.30(1H, m), 8.48-8.49 (1H, m). |
| 11-57 | δ7.51-7.55(1H, m), 8.12(2H, s), 8.18(1H, d, J = 12.2 Hz), 8.28-8.32(1H, m), 8.47-8.51 (1H, m). |
| 11-60 | δ7.53(1H, t, J = 7.8 Hz), 7.60(1H, broad-s), 7.89(1H, d, J = 1.5 Hz), 8.07(1H, broad-d, J = 12.7 Hz), 8.29-8.30(1H, m), 8.43-8.47(1H, m). |
| 11-65 | δ7.53(1H, t, J = 7.3 Hz), 7.93(1H, broad-s), 8.17-8.18(2H, m), 8.28-8.32(1H, m), 8.44-8.48(1H, m). |
| 11-66 | δ7.51-7.55(1H, m), 7.97(1H, s), 8.23(1H, d, J = 12.2 Hz), 8.28-8.32(1H, m), 8.37(1H, s), 8.44-8.48(1H, m). |
| 11-69 | δ7.53(1H, t, J = 7.8 Hz), 7.93(1H, s), 8.16(1H, s), 8.20(1H, d, J = 12.7 Hz), 8.30-8.31(1H, m), 8.43-8.47(1H, m). |
| 11-70 | δ7.53-7.54(1H, m), 7.95(1H, s), 8.24-8.32(2H, m), 8.36(1H, s), 8.44-8.48(1H, m). |
| 11-75 | APCI-MS m/z (M + 1): 626 |
| 11-84 | δ7.47-7.50(1H, m), 7.92(2H, d, J = 5.9 Hz), 8.16(1H, s), 8.23-8.28(1H, m), 8.65-8.67(1H, m). |
| 11-100 | δ7.52-7.81(2H, m), 7.89(1H, s), 8.00(1H, s), 8.25(1H, d, J = 8.3 Hz), 8.38(1H, d, J = 1.9 Hz). |
| 11-101 | APCI-MS m/z (M + 1): 683 |
| 11-121 | δ7.52-7.81(2H, m), 7.89(1H, s), 8.00(1H, s), 8.25(1H, d, J = 8.3 Hz), 8.38(1H, d, J = 1.9 Hz). |
| 11-122 | δ7.80(1H, s), 7.96(1H, s), 8.12-8.14(1H, m), 8.18(1H, s), 8.36(1H, dd, J = 2.0, 8.3 Hz), 8.84(1H, d, J = 1.5 Hz). |
| 11-136 | δ3.28(1/2*3H, s), 3.44(1/2*3H, s), 7.41(1/2*1H, t, J = 7.8 Hz), 7.71-7.76(2/2*1H, m), 7.84(1/2*1H, s), 7.93-7.95(1/2*1H, m), 7.98(1/2*1H, s), 8.07-8.09(2/2*1H, m), 8.14-8.16 (1/2*1H, m), 8.19(1/2*1H, s), 8.39-8.41(1/2*1H, m), 8.45-8.46(1/2*1H, m). |
| 11-142 | APCI-MS m/z (M + 1): 561 |
| 12-2 | APCI-MS m/z (M + 1): 587 |
| 12-3 | δ5.39(2H, broad-s), 6.89-6.93(1H, m), 7.29-7.31(3H, m), 7.68(1H, s), 8.08(2H, s). |
| 12-5 | δ3.89(2H, broad-s), 6.90-6.92(1H, m), 7.23-7.32(3H, m), 7.64(1H, s), 7.90(1H, s), 8.13(1H, s). |
| 12-6 | δ3.89(2H, broad-s), 6.91-6.92(1H, m), 7.21-7.32(3H, m), 7.61(1H, s), 7.86(1H, s), 7.97(1H, s). |
| 12-7 | δ3.89(2H, broad-s), 6.88-6.92(1H, m), 7.21-7.32(3H, m), 7.65(1H, s), 7.90(1H, s), 8.13(1H, d, J = 2.4 Hz). |

TABLE 22-continued

| compound number | ¹H-NMR (CDCl₃, ppm) or APCI-MS |
|---|---|
| 12-8 | δ3.89(2H, broad-s), 6.89-6.92(1H, m), 7.23-7.32(3H, m), 7.68(1H, s), 7.93(1H, s), 8.34-8.36(1H, m). |
| 12-10 | APCI-MS m/z (M + 1): 577 |
| 12-11 | APCI-MS m/z (M + 1): 625 |
| 12-14 | δ3.89(2H, broad-s.), 6.89-6.91(1H, m), 7.17-7.31(3H, m), 7.53(1H, s), 8.18(2H, s). |
| 12-25 | δ3.91(2H, broad-s), 6.98-7.02(1H, m), 7.06-7.12(1H, m), 7.47-7.52(1H, m), 7.66(2H, s), 8.20(1H, d, J = 14.1 Hz). |
| 12-26 | δ3.93(2H, broad-s), 6.99-7.04(1H, m), 7.11(1H, t, J = 1.8 Hz), 7.47-7.49(1H, m), 7.91(1H, s), 8.14(1H, s), 8.28(1H, d, J = 14.6 Hz). |
| 12-27 | δ3.93(2H, broad-s), 6.99-7.04(1H, m), 7.08(1H, t, J = 7.8 Hz), 7.39-7.43(1H, m), 8.10(2H, s), 8.72(1H, d, J = 11.2 Hz). |
| 12-29 | δ3.92(2H, broad-s), 7.01-7.02(1H, m), 7.11(1H, t, J = 7.8 Hz), 7.49-7.53(1H, m), 7.89(1H, d, J = 1.5 Hz), 8.08(1H, d, J = 1.5 Hz), 8.21(1H, d, J = 14.1 Hz). |
| 12-30 | δ3.92(2H, broad-s), 6.99-7.04(1H, m), 7.11-7.12(1H, m), 7.48-7.52(1H, m), 7.86(2H, s), 8.22(1H, d, J = 14.1 Hz). |
| 12-31 | δ3.93(2H, broad-s), 7.02-7.03(1H, m), 7.11-7.12(1H, m), 7.50-7.54(1H, m), 8.10(2H, s), 8.22(1H, d, J = 13.7 Hz). |
| 12-33 | δ3.92(2H, broad-s), 6.99-7.04(1H, m), 7.11(1H, t, J = 7.8 Hz), 7.45-7.49(1H, m), 7.57(1H, broad-s), 7.87(1H, d, J = 2.0 Hz), 8.14(1H, d, J = 14.2 Hz). |
| 12-37 | δ3.93(2H, broad-s), 6.99-7.04(1H, m), 7.11(1H, t, J = 7.8 Hz), 7.47-7.49(1H, m), 7.91(1H, s), 8.14(1H, s), 8.28(1H, d, J = 14.6 Hz). |
| 12-38 | δ3.92(2H, broad-s), 7.02-7.04(1H, m), 7.11(1H, t, J = 7.8 Hz), 7.47-7.52(1H, m), 7.94(1H, s), 8.30-8.35(2H, m). |
| 12-40 | δ3.92(2H, broad-s), 7.02-7.03(1H, m), 7.11(1H, t, J = 7.8 Hz), 7.49-7.50(1H, m), 7.90(1H, s), 8.13(1H, s), 8.29(1H, d, J = 14, 6 Hz). |
| 12-41 | δ3.93(2H, broad-s), 7.02-7.03(1H, m), 7.11-7.13(1H, m), 7.47-7.51(1H, m), 7.92(1H, s), 8.31-8.34(2H, m). |
| 12-46 | δ3.92(2H, broad-s), 6.99-7.04(1H, m), 7.05-7.18(1H, m), 7.46-7.51(1H, m), 7.85(1H, broad-s), 8.17(1H, broad-s), 8.34(1H, d, J = 15.1 Hz). |
| 12-53 | APCI-MS m/z (M + 1): 546 |
| 12-63 | δ4.35(2H, s), 6.92(1H, dd, J = 1.9, 8.3 Hz), 7.29(1H, d, J = 1.9 Hz), 7.60(1H, s), 7.79(1H, d, J = 8.3 Hz), 7.86(1H, s), 7.97(1H, s). |
| 12-64 | APCI-MS m/z (M + 1): 653 |
| 12-78 | δ4.68(2H, broad-s), 7.17(1H, d, J = 9.3 Hz), 7.30(1H, s), 7.57(1H, d, J = 9.3 Hz), 7.64(1H, s), 7.87(1H, s), 7.98(1H, s). |
| 12-79 | δ4.68(2H, broad-s), 7.18(1H, dd, J = 1.9, 8.3 Hz), 7.29(1H, s), 7.52-7.55(1H, m), 7.68(1H, s), 7.92(1H, s), 8.14(1H, d, J = 1.5 Hz). |
| 12-94 | δ4.71(2H, broad-s), 7.35-7.39(1H, m), 7.40-7.44(1H, m), 7.92(1H, s), 8.12-8.15(2H, m). |
| 12-107 | δ3.24(3/4*3H, s), 3.37(1/4*3H, s), 3.80(2H, broad-s), 6.47(1/4*1H, d, J = 7.8 Hz), 6.54-6.57(1/4*1H, m), 6.78-6.84(5/4*1H, m), 6.86(3/4*1H, t, J = 2.0 Hz), 6.96(3/4*1H, d, J = 7.8 Hz), 7.23-7.27(3/4*1H, m), 7.79(1/4*1H, s), 7.94(3/4*1H, s), 8.00(1/4*1H, s), 8.15(3/4*1H, s). |
| 13-1 | APCI-MS m/z (M + 1): 601 |
| 13-2 | APCI-MS m/z (M + 1): 697 |
| 13-4 | δ2.91(3H, s), 3.95(1H, broad-s), 6.82-6.84(1H, m), 7.16-7.18(2H, m), 7.30-7.34(1H, m), 7.66(1H, s), 7.90(1H, s), 8.13(1H, s). |
| 13-5 | δ2.90(3H, s), 4.00(1H, broad-s), 6.82-6.83(1H, m), 7.15-7.17(2H, m), 7.32-7.33(1H, m), 7.65(1H, s), 7.86(1H, s), 7.97(1H, s). |
| 13-6 | δ2.91(3H, s), 3.97(1H, broad-s), 6.82(1H, dd, J = 2.4, 8.3 Hz), 7.15-7.17(2H, m), 7.29-7.34(1H, m), 7.66(1H, s), 7.91(1H, s), 8.14(1H, s). |
| 13-7 | δ2.91(3H, s), 3.98(1H, broad-s), 6.81-6.84(1H, m), 7.16-7.19(2H, m), 7.30-7.34(1H, m), 7.72(1H, broad-s), 7.93(1H, s), 8.34(1H, s). |
| 13-8 | APCI-MS m/z (M + 1): 591 |
| 13-9 | APCI-MS m/z (M + 1) 639 |
| 13-12 | APCI-MS m/z (M + 1): 531 |
| 13-26 | δ2.93-2.95(3H, m), 4.13(1H, broad-s), 6.82-6.92(1H, m), 7.18(1H, t, J = 7.8 Hz), 7.37-7.41(1H, m), 7.69(2H, s), 8.19(1H, d, J = 14.1 Hz). |
| 13-27 | δ2.94-2.30(3H, m), 4.87-4.91(1H, m), 6.91(1H, t, J = 7.9 Hz), 7.18(1H, t, J = 7.9 Hz), 7.41(1H, t, J = 7.1 Hz), 7.87(2H, s), 8.20(1H, d, J = 13.5 Hz). |
| 13-28 | δ2.95(3H, s), 4.13-4.15(1H, m), 6.89-6.94(1H, m), 7.18-7.22(1H, m), 7.41-7.45(1H, m), 8.10(2H, s), 8.20(1H, d, J = 14.1 Hz). |
| 13-30 | δ2.95-2.96(3H, m), 4.15(1H, broad-s), 6.89-6.93(1H, m), 7.19(1H, t, J = 7.8 Hz), 7.40-7.44(1H, m), 7.89(1H, s), 8.08(1H, s), 8.20(1H, d, J = 14.1 Hz). |
| 13-32 | δ2.95(3H, s), 4.14(1H, broad-s), 6.91-6.92(1H, m), 7.17-7.21(1H, m), 7.39-7.43(1H, m), 7.85(2H, s), 8.21(1H, d, J = 14.1 Hz). |
| 13-33 | δ2.95(3H, s), 4.16(1H, broad-s), 6.91-6.92(1H, m), 7.20-7.21(1H, m), 7.41-7.45(1H, m), 8.09(2H, s), 8.21(1H, d, J = 14.1 Hz). |
| 13-40 | δ2.94(3H, s), 4.14(1H, broad-s), 6.88-6.93(1H, m), 7.18(1H, t, J = 7.8 Hz), 7.37-7.41 (1H, m), 7.90(1H, s), 8.13(1H, s), 8.27(1H, d, J = 14.6 Hz). |
| 13-41 | δ2.95(3H, s), 4.15(1H, broad-s), 6.90(1H, t, J = 8.2 Hz), 7.19(1H, t, J = 7.8 Hz), 7.40(1H, t, J = 7.8 Hz), 7.92(1H, s), 8.30(1H, s), 8.34(1H, s). |
| 13-43 | δ2.95(3H, s), 4.14(1H, broad-s), 6.88-6.99(1H, m), 7.18(1H, t, J = 7.3 Hz), 7.36-7.41 (1H, m), 7.89(1H, s), 8.12(1H, s), 8.28(1H, d, J = 14.6 Hz). |
| 13-44 | δ2.95-2.96(3H, m), 4.15(1H, broad-s), 6.91-6.93(1H, m), 7.19-7.20(1H, m), 7.38-7.42(1H, m), 7.92(1H, s), 8.32(1H, d, J = 14.1 Hz), 8.34(1H, s). |
| 13-56 | APCI-MS m/z (M + 1): 545 |
| 13-68 | δ2.97(3H, s), 4.46(1H, broad-s), 6.89(1H, dd, J = 1.9, 8.3 Hz), 7.07(1H, d, J = 1.9 Hz), 7.65(1H, s), 7.80(1H, d, J = 8.3 Hz), 7.86(1H, s), 7.97(1H, s). |

TABLE 22-continued

| compound number | ¹H-NMR (CDCl₃, ppm) or APCI-MS |
|---|---|
| 13-85 | δ3.01(1/2*3H, s), 3.03(1/2*3H, s), 4.89(1/2*1H, s), 4.90(1/2*1H, s), 7.80(1H, dd, J = 1.5,8.3 Hz), 7.21-7.22(1H, m), 7.54(1H, d, J = 8.3 Hz), 7.67(1H, s), 7.88(1H, s), 7.99(1H, s). |
| 14-6 | δ7.59(1H, d, J = 7.3 Hz), 7.90-7.93(2H, m), 8.14(1H, s), 8.20-8.24(1H, m), 9.60(1H, s). |
| 15-68 | δ2.64(3H, s), 3.79(1H, broad-s), 7.56-7.60(1H, m), 7.87-7.93(2H, m), 8.14-8.15(1H, m), 8.20-8.23(1H, m), 9.60(1H, s). |
| 16-6 | δ7.91(1H, s), 8.13(1H, s), 8.19(1H, s), 8.82(1H, s). |
| 17-42 | δ3.03(3H, s), 5.11-5.12(1H, m), 7.50(1H, s), 7.88(1H, s), 8.11(1H, s), 8.99(1H, s). |
| 18-1 | δ2.33(6H, s), 2.52(2H, t, J = 5.8 Hz), 3.51(2H, t, J = 5.8 Hz), 4.45(1H, broad-s), 5.54(1H, broad-s), 5.73(1H, broad-s), 6.81(1H, d, J = 8.3 Hz), 7.17-7.21(2H, m), 7.28-7.30(1H, m), 7.34(2H, s), 7.54-7.59(1H, m). |
| 18-13 | δ2.54-2.57(2H, m), 3.52-3.56(2H, m), 4.49(1H, broad-s), 5.54(1H, broad-s), 6.83-6.86(1H, m), 7.26-7.33(4H, m), 7.85(1H, s), 8.09(2H, s). |
| 18-14 | δ2.55-2.60(2H, m), 3.52(2H, t, J = 6.3 Hz), 4.62(1H, broad-s), 5.62(1H, broad-s), 6.46(1H, broad-s), 6.82-6.83(1H, m), 7.26-7.36(3H, m), 8.16(2H, s), 9.25(1H, s). |
| 18-15 | δ2.54-2.57 (2H, m), 3.53-3.56 (2H, m), 4.47(1H, broad-s), 5.38 (1H, broad-s), 5.59 (1H, broad-s), 6.84-6.85 (1H, m), 7.18-7.24 (2H, m), 7.31 (1H, t, J = 7.8 Hz), 7.73 (1H, s), 7.90 (1H, s), 8.13 (1H, s). |
| 18-16 | δ2.54-2.58(2H, m), 3.54-3.57(2H, m), 5.43(1H, broad-s), 5.59(1H, broad-s), 6.84-6.86(1H, m), 7.19-7.21(2H, m), 7.32(1H, t, J = 7.8 Hz), 7.78(1H, s), 7.93(1H, s), 8.34(1H, s), A proton asigned for NH is not detected. |
| 18-20 | δ2.56(2H, t, J = 6.3 Hz), 3.54(2H, t, J = 6.3 Hz), 4.60(1H, broad-s), 5.49(1H, broad-s), 5.60(1H, broad-s), 6.86-6.88(1H, m), 7.19-7.21(2H, m), 7.30-7.34(1H, m), 8.11(1H, d, J = 1.5 Hz), 8.28-8.29(2H, m). |
| 18-33 | δ2.55(2H, t, J = 5.8 Hz), 3.55(2H, t, J = 5.8 Hz), 4.50(1H, broad-s), 5.37(1H, broad-s), 5.58(1H, broad-s), 6.84(1H, dd, J = 2.4, 7.8 Hz), 7.17-7.20(2H, m), 7.28-7.32(1H, m), 7.72(1H, s), 7.89(1H, s), 8.12(1H, s). |
| 18-42 | δ2.36(6H, s), 2.57-2.60(2H, m), 3.54-3.57(2H, m), 4.64(1H, broad-s), 5.48(1H, broad-s), 5.61(1H, broad-s), 6.89-6.94(1H, m), 7.15(1H, t, J = 7.8 Hz), 7.35-7.39(3H, m), 7.84(1H, broad-d, J = 12.7 Hz). |
| 18-43 | δ2.55-2.60(2H, m), 3.54-3.56(2H, m), 4.60(1H, broad-s), 5.71-5.74(2H, m), 6.94-6.95(1H, m), 7.15(1H, t, J = 7.8 Hz), 7.40-7.41(1H, m), 7.66(2H, s), 8.23(1H, d, J = 13.6 Hz). |
| 18-44 | δ2.55-2.61(2H, m), 3.54-3.57(2H, m), 4.60(1H, broad-s), 5.69-5.74(2H, m), 6.90-6.98(1H, m), 7.16(1H, t, J = 7.8 Hz), 7.35-7.45(1H, m), 7.87(2H, s), 8.24(1H, d, J = 14.1 Hz). |
| 18-45 | δ2.59-2.62(2H, m), 3.55-3.59(2H, m), 4.64(1H, broad-s), 5.40(1H, broad-s), 5.55(1H, broad-s), 6.94(1H t, J = 8.3 Hz), 7.18(1H, t, J = 8.3 Hz), 7.43-7.44(1H, m), 8.10(2H, s), 8.18-8.22(1H, m). |
| 18-46 | δ2.60(2H, t, J = 6.3 Hz), 3.57(2H, t, J = 6.3 Hz), 4.70(1H, broad-s), 5.42(1H, broad-s), 5.55(1H, broad-s), 6.95-6.97(1H, m), 7.17(1H, t, J = 7.8 Hz), 7.40-7.46(1H, m), 7.89(1H, d, J = 1.5 Hz), 8.07(1H, d, J = 1.5 Hz), 8.20(1H, d, J = 14.1 Hz). |
| 18-47 | δ2.58-2.62(2H, m), 3.56-3.58(2H, m), 4.65(1H, broad-s), 5.40(1H, broad-s), 5.55(1H, broad-s), 6.95-6.96(1H, m), 7.18(1H, t, J = 7.3 Hz), 7.38-7.42(1H, m), 7.57(1H, s), 7.86(1H, d, J = 2.0 Hz), 8.13(1H, d, J = 14.1 Hz). |
| 18-48 | δ2.58-2.61(2H, m), 3.55-3.59(2H, m), 4.60(1H, broad-s), 5.40(1H, broad-s), 5.60(1H, broad-s), 6.96-6.98(1H, m), 7.15-7.19(1H, m), 7.39-7.43(1H, m), 7.91(1H, s), 8.13(1H, s), 8.26(1H, d, J = 14.6 Hz). |
| 18-49 | δ2.59-2.62(2H, m), 3.57(2H, q, J = 5.9 Hz), 4.62(1H, broad-s), 5.42(1H, broad-s), 5.56(1H, broad-s), 6.94-6.98(1H, m), 7.17(1H, t, J = 7.8 Hz), 7.40-7.44(1H, m), 7.93(1H, broad-s), 8.30(1H, d, J = 14.6 Hz), 8.35(1H, d, J = 1.5 Hz). |
| 18-50 | δ2.58-2.63(2H, m), 3.57(2H, t, J = 6.3 Hz), 5.43(1H, broad-s), 5.55(1H, broad-s), 6.93-6.98(1H, m), 7.16(1H, t, J = 7.8 Hz), 7.38-7.42(1H, m), 7.89(1H, s), 8.12(1H, s), 8.27(1H, d, J = 14.6 Hz), A proton asigned for NH is not detected. |
| 18-72 | δ2.27(6H, s), 2.72(2H, t, J = 7.8 Hz), 3.57(2H, broad-s), 4.03(2H, t, J = 7.8 Hz), 5.40(1H, broad-s), 6.37(1H, broad-s), 6.38-6.41(1H, m), 6.56-6.59(1H, m), 6.64-6.65(1H, m), 6.83(1H, t, J = 7.8 Hz), 7.37(2H, s). |
| 18-87 | δ2.39-2.42(2H, m), 2.62(6H, s), 2.72-2.74(2H, m), 3.19-3.20(2H, m), 3.99-4.02(2H, m), 4.41(1H, broad-s), 5.80(1H, broad-s), 5.84(1H, broad-s), 6.41(1H, d, J = 7.8 Hz), 6.51-6.54(2H, m), 6.84-6.88(3H, m), 7.40(2H, s). |
| 18-105 | δ2.34(6H, s), 2.61-2.66(2H, m), 2.96(3H, s), 3.01(3H, s), 3.53-3.56(2H, m), 6.83(1H, dd, J = 2.4, 8.3 Hz), 7.16(1H, d, J = 1.8 Hz), 7.22(1H, s), 7.27-7.29(1H, m), 7.34(2H, s), 7.49(1H, s), A proton asigned for NH is not detected. |
| 18-107 | APCI-MS m/z (M + 1): 674 |
| 18-110 | δ2.63-2.68(2H, m), 3.01(6H, s), 3.56(2H, t, J = 5.8 Hz), 3.90-3.91(1H, m), 6.97-6.99 (1H, m), 7.16(1H, t, J = 7.8 Hz), 7.37-7.41(1H, m), 7.93(1H, s), 8.32-8.36(2H, m). |
| 18-111 | δ2.66 (2H, t, J = 5.8 Hz), 2.99-3.01(6H, s), 3.54(2H, t, J = 5.8 Hz), 3.70(1H, broad-s), 6.87(1H, dd, J = 1.5, 7.8 Hz), 7.18-7.21(2H, m), 7.28-7.32(1H, m), 8.12(1H, d, J = 2.0 Hz), 8.30-8.31 (2H, m). |
| 19-44 | δ3.46(2H, t, J = 6.3 Hz), 3.77-3.81(2H, m), 4.74(1H, broad-s), 4.80-4.82(2H, m), 6.92-6.96(1H, m), 7.19(1H, t, J = 7.8 Hz), 7.44-7.49(2H, m), 7.86(2H, s), 8.17(1H, d, J = 13.6 Hz). |
| 20-7 | δ2.05(6H, s), 3.01(3H, s), 3.36-3.37(2H, m), 3.82-3.86(2H, m), 4.70(1H, broad-s), 6.90-6.91 (1H, m), 7.20-7.21 (1H, m), 7.32 (1H, s), 7.36 (2H, s), 7.80-7.82(1H, m). |
| 20-9 | δ3.01(3H, s), 3.36(2H, t, J = 6.3 Hz), 3.82-3.86(2H, m), 4.71(1H, broad-s), 6.95(1H, t, J = 7.8 Hz), 7.20(1H, t, J = 7.8 Hz), 7.47-7.53(1H, m), 7.86(2H, s), 8.16-8.19(1H, m). |
| 20-35 | δ2.30(6H, s), 3.10(3H, s), 3.58-3.62(2H, m), 3.67(2H, broad-s), 4.10-4.14(2H, m), 6.32-6.36(1H, m), 6.65-6.69(2H, m), 7.21(2H, s), A proton asigned for CONH is not detected. |
| 20-36 | δ3.10(3H, s), 3.74-3.78(4H, m), 4.18-4.22(2H, m), 6.44-6.48(1H, m), 6.62-6.73(2H, m), 7.74 (2H, s). |
| 21-1 | δ4.53(2H, broad-s), 6.81(1H, d, J = 8.3 Hz), 7.48(1H, d, J = 8.3 Hz), 7.63(1H, broad-s). |
| 21-2 | δ4.49(2H, broad-s), 6.81(1H, d, J = 8.3 Hz), 7.48(1H, d, J = 8.3 Hz), 7.64(1H, s). |
| 21-3 | δ4.49(2H, broad-s), 6.81(1H, d, J = 8.8 Hz), 7.47(1H, d, J = 8.8 Hz), 7.61(1H, s). |

TABLE 22-continued

| compound number | ¹H-NMR (CDCl₃, ppm) or APCI-MS |
|---|---|
| 21-4 | δ4.56(2H, broad-s), 6.79(1H, d, J = 8.8 Hz), 7.47(1H, d, J = 8.8 Hz), 7.53(1H, s). |
| 21-6 | δ5.08(2H, broad-s), 7.62(1H, s), 7.80(1H, s). |
| 21-8 | δ4.97(2H, broad-s), 7.57(1H, s), 7.64(1H, s). |
| 21-9 | δ5.03(2H, broad-s), 7.61(1H, s), 7.79(1H, s). |
| 21-10 | δ5.04(2H, broad-s), 7.64(1H, s), 7.99(1H, s). |
| 21-13 | δ5.03(2H, broad-s), 7.52(1H, s), 7.78(1H, s). |
| 21-14 | δ5.04(2H, broad-s), 7.62(1H, s), 7.97(1H, s). |
| 21-19 | δ5.14(2H, broad-s), 7.58(1H, s), 7.81(1H, s). |
| 21-29 | δ3.09-3.11(3H, m), 4.56(1H, broad-s), 7.79(1H, s), 7.82(1H, s). |

The compound according to the present invention can effectively control, at a low concentration thereof, any pests such as insects including various so-called agricultural pests damaging agricultural/horticultural crops, trees, and the like, so-called domestic animal pests parasitic on birds grown in the houses for domestic animals, so-called insanitary pests adversely affecting the living environment of humans such as houses and the like in various manners, so-called wood-eating pests damaging wood such as buildings and the like, so-called stored grain pests damaging grain and the like stored in a warehouse, and mites, crustaceans, molluscs, and nematodes which are propagated and cause damage in a manner similar to that in the case of the insects.

Specific examples of the insects, the mites, the crustaceans, the molluscs and the nematodes which can be controlled using the compound according to the present invention include lepidopteran insects such as *Adoxophyes honmai, Adoxophyes orana faciata, Archips breviplicanus, Archips fuscocupreanus, Grapholita molesta, Homona magnanima, Leguminivora glycinivorella, Matsumuraeses phaseoli, Pandemis heparana, Bucculatrix pyrivorella, Lyonetia clerkella, Lyonetia prunifoliella malinella, Caloptilia theivora, Phyllonorycter ringoniella, Phyllocnistis citrella, Acrolepiopsis sapporensis, Acrolepiopsis suzukiella, Plutella xylostella, Stathmopoda masinissa, Helcystogramma triannulella, Pectinophora gossypiella, Carposina sasakii, Cydla pomonella, Chilo suppressalis, Cnaphalocrocis medinalis, Conogethes punctiferalis, Diaphania indica, Etiella zinckenella, Glyphodes pyloalis, Hellula undalis, Ostrinia furnacalis, Ostrinia scapulalis, Ostrinia nubilalis, Parapediasia teterrella, Parnara guttata, Pieris brassicae, Pieris rapae crucivora, Ascotis selenaria, Pseudoplusia includens, Euproctis pseudoconspersa, Lymantria dispar, Orgyia thyellina, Hyphantria cunea, Lemyra imparilis, Adris tyrannus, Aedia leucomelas, Agrotis ipsilon, Agrotis segetum, Autographa nigrisigna, Ctenoplusia agnata, Helicoverpa armigera, Helicoverpa assulta, Helicoverpa zea, Heliothis virescens, Mamestra brassicae, Mythimna separata, Naranga aenescens, Spodoptera eridania, Spodoptera exigua, Spodoptera frugiperda, Spodoptera littoralis, Spodoptera litura, Spodoptera depravata, Trichoplusia ni, Endopiza viteana, Manduca quinquemaculata, Manduca sexta*, and the like, Thysanopteran insects such as *Frankliniella intonsa, Frankliniella occidentalis, Heliothrips haemorrhoidalis, Scirtothrips dorsalis, Thrips palmi, Thrips tabaci, Ponticulothrips diospyrosi*, and the like, Hemipteran insects such as *Dolycoris baccarum, Eurydema rugosum, Eysarcoris aeneus, Eysarcoris lewisi, Eysarcoris ventralis, Glaucias subpunctatus, Halyomorpha halys, Nezara antennata, Nezara viridula, Piezodorus hybneri, Plautia crossota, Scotinophora lurida, Cletus punctiger, Leptocorisa chinensis, Riptortus clavatus, Rhopalus msculatus, Cavelerius saccharivorus, Togo hemipterus, Dysdercus cingulatus, Stephanitis pyrioides, Halticus insularis, Lygus lineolaris, Stenodema sibiricum, Stenotus rubrovittatus, Trigonotylus caelestialium, Arboridia apicalis, Balclutha saltuella, Epiacanthus stramineus, Empoasca fabae, Empoasca nipponica, Empoasca onukii, Empoasca sakaii, Macrosteles striifrons, Nephotettix cinctinceps, Psuedatomoscelis seriatus, Laodelphax striatella, Nilaparvata lugens, Sogatella furcifera, Diaphorina citri, Psylla pyrisuga, Aleurocanthus spiniferus, Bemisia argentifolii, Bemisia tabaci, Dialeurodes citri, Trialeurodes vaporariorum, Viteus vitifolii, Aphis gossypii, Aphis spiraecola, Myzus persicae, Toxoptera aurantii, Drosicha corpulenta, Icerya purchasi, Phenacoccus solani, Planococcus citri, Planococcus kuraunhiae, Pseudococcus comstocki, Ceroplastes ceriferus, Ceroplastes rubens, Aonidiella aurantii, Comstockaspis perniciosa, Fiorinia theae, Pseudaonidia paeoniae, Pseudaulacaspis pentagona, Pseudaulacaspis prunicola, Unaspis euonymi, Unaspis yanonensis, Cimex lectularius*, and the like, Coleopteran insects such as *Anomala cuprea, Anomala rufocuprea, Gametis jucunda, Heptophylla picea, Popillia japonica, Lepinotarsa decemlineata, Melanotus fortnumi, Melanotus tamsuyensis, Lasioderma serricorne, Epuraea domina, Lyctus brunneus, Rhizopertha dominica, Epilachna varivestis, Epilachna vigintioctopunctata, Tenebrio molitor, Tribolium castaneum, Anoplophora malasiaca, Monochamus alternatus, Psacothea hilaris, Xylotrechus pyrrhoderus, Callosobruchus chinensis, Aulacophora femoralis, Chaetocnema concinna, Diabrotica undecimpunctata, Diabrotica virgifera, Diabrotica barberi, Oulema oryzae, Phyllotreta striolata, Psylliodes angusticollis, Rhynchites heros, Cylas formicarius, Anthonomus grandis, Echinocnemus squameus, Euscepes postfasciatus, Hypera postica, Lissohoptrus oryzophilus, Otiorhynchus sulcatus, Sitophilus granarius, Sitophilus zeamais, Sphenophorus venatus vestitus, Paederus fuscipes*, and the like, Dipterous insects such as *Asphondylia yushimai, Sitodiplosis mosellana, Bactrocera cucurbitae, Bactrocera dorsalis, Ceratitis capitata, Hydrellia griseola, Drosophila suzukii, Agromyza oryzae, Chromatomyia horticola, Liriomyza bryoniae, Liriomyza chinensis, Liriomyza sativae, Liriomyza trifolii, Delia plalura, Pegomya cunicularia, Rhagoletis pomonella, Mayetiola destructor, Musca domestica, Stomoxys calcitrans, Melophagus ovinus, Hypoderma bovis, Hypoderma lineatum, Oestrus ovis, Glossina palpalis, Glossina morsilans, Prosimulium yezoensis, Tabanus trigonus, Telmatoscopus albipunctatus, Leptoconops nipponensis, Culex pipiens pallens, Aedes aegypti, Aedes albopicutus, Anopheles hyracanus sinesis*, and the like, Hymenopteran insects such as *Apethymus kuri, Athalia rosae, Arge pagana, Neodiprion sertifer, Dryocosmus kuriphilus, Eciton burchelli, Eciton schmitti, Camponotus japonicus, Vespa mandarina, Myrmecia* spp., *Solenopsis* spp., *Monomorium pharaonis*, and the like;

Orthopteran insects such as *Teleogryllus emma, Gryllotalpa orientalis, Locusta migratoria, Oxya yezoensis, Schistocerca gregaria*, and the like;

Collembolan insects such as *Onychiurus folsomi, Onychiurus sibiricus, Bourletiella hortensis*, and the like;

Dictyopteran insects such as *Periplaneta fuliginosa, Periplaneta japonica, Blattella germanica*, and the like;

Isopterous insects such as *Coptotermes formosanus, Reticulitermes speratus, Odontotermes formosanus*, and the like;

Isopterous insects such as *Ctenocephalidae felis, Ctenocephalides canis, Echidnophaga gallinacea, Pulex irritans, Xenopsylla cheopis*, and the like;

*Mallophaga* insects such as *Menacanthus stramineus, Bovicola bovis*, and the like;

Anoplura insects such as *Haematopinus eurysternus, Haematopinus suis, Linognathus vituli, Solenopotes capillatus*, and the like;

Tarsonemidae such as *Phytonemus pallidus, Polyphagotarsonemus latus, Tarsonemus bilobatus*, and the like;

Eupodidae such as *Penthaleus erythrocephalus, Penthaleus major*, and the like;

Tetranychidae such as *Oligonychus shinkajii, Panonychus citri, Panonychus mori, Panonychus ulmi, Tetranychus kanzawai, Tetranychus urticae*, and the like;

Eriophiydae such as *Acaphylla theavagrans, Aceria tulipae, Aculops lycopersici, Aculops pelekassi, Aculus schlechtendali, Eriophyes chibaensis, Phyllocoptruta oleivora*, and the like;

Acaridae such as *Rhizoglyphus robini, Tyrophagus putrescentiae, Tyrophagus similis*, and the like;

Varroidae such as *Varroa jacobsoni* and the like;

Ixodidae such as *Boophilus microplus, Rhipicephalus sanguineus, Haemaphysalis longicornis, Haemophysalis flava, Haemophysalis campanulata, Ixodes ovatus, Ixodes persulcatus, Amblyomma* spp., *Dermacentor* spp., and the like;

Cheyletidae such as *Cheyletiella yasguri, Cheyletiella blakei*, and the like;

Demodicidae such as *Demodex canis, Demodex cati*, and the like;

Psoroptidae such as *Psoroptes ovis* and the like;

Sarcoptidae such as *Sarcoptes scabiei, Notoedres cati, Knemidocoptes* spp., and the like;

Crustacea such as *Armadillidium vulgare* and the like;

Gastropoda such as *Pomacea canaliculata, Achatina fulica, Meghimatium bilineatum, Limax Valentiana, Acusta despecta sieboldiana, Euhadra peliomphala*, and the like; and Nematoda such as *Prathylenchus coffeae, Prathylenchus penetrans, Prathylenchus vulnus, Globodera rostochiensis, Heterodera glycines, Meloidogyne hapla, Meloidogyne incognita, Aphelenchoides besseyi, Bursaphelenchus xylophilus*, and the like, but the present invention is not limited thereto.

Furthermore, the compound according to the present invention is also effective against pests having a developed resistance to existing pesticides such as organic phosphorous compounds, carbamate compounds, pyrethroid compounds, and the like.

Furthermore, the compound according to the present invention exerts an excellent control effect when used in combination with other agricultural/horticultural pesticides, miticides, nematocides, fungicides, herbicides, plant growth regulators, biological agricultural chemicals, or the like.

The pest control agent having the compound according to the present invention as an active ingredient has a significant control effect against the above-described harmful crops which damage lowland crops, upland crops, fruit trees, vegetables, and other crops and ornamental flowers, and therefore, the effect as a pest control agent according to the present invention can be obtained by treating the paddy field water, plant stems and leaves, or soil of the crops of lowland, upland, fruit trees, vegetables, other crops, ornamental flowers, and the like during the seasons in which the appearance of such pests is expected, or before or at the point when the pest appearance is observed.

The pest control agent having the compound according to the present invention as an active ingredient has a significant control effect against stored grain pests and the like propagated during storage of the harvest. That is, the pest control agent having the compound according to the present invention as an active ingredient may be subjected to a treatment after the harvest (post harvest) such as spray-spreading, coating, dipping, dressing, fumigation/smoking, pressurized injection, and the like with respect to the harvest or the place for storage of the harvest.

Further, the pest control agent having the compound according to the present invention as an active ingredient can be applied to plant seeds to prevent the damage caused by pests generated in the plants after seeding. That is, the pest control agent having the compound according to the present invention as an active ingredient may be subjected to a treatment such as spray-spreading, dipping, dressing, and the like on the plant seeds in an effective amount for controlling the pests as it is, as an adequate dilution with water or the like, or as a suspension to bring the compound according to the present invention into contact with the plant seeds.

The plant seeds refer to those used for breeding in agriculture by storing the nutrients for seedling germination, and examples thereof include seeds such as corn, soybeans, red beans, cotton, rice, sugar beet, wheat, barley, sunflower, tomato, cucumber, eggplant, spinach, sting beans, squash, sugarcane, tobacco, pimento, canola, and the like, seed tubers such as taro, potato, sweet potato, konjac, and the like, bulbs such as edible lily, tulips, and the like, and seed balls such as rakkyo and the like.

The pest control agent having the compound according to the present invention as an active ingredient has a significant control effect against insanitary pests such as Dipterous pests (*Culex pipiens, Culex plumosus, Musca domestica, Psychodidae, Tabanus trigonus*, and the like) Dictyoptcra pests (*Blattella germanica, Periplaneta fuliginosa, Periplaneta americana*, and the like), and other pests.

The pest control agent having the compound according to the present invention as an active ingredient has a significant control effect against wood-feeding pests such as Termidae, *Lyctus brunneus, Rhizopertha dominica*, Anobiidae, Cerambycidae, and the like, thus, the above-described wood-feeding pests can be controlled by treatment of wood, soil, buildings, and the like with the pest control agent.

The pesticide according to the present invention generally may be used after being Formulated into the shape convenient for use according to a conventional method for preparation of agricultural/horticultural chemicals. That is, the compound represented by the Formula (1) may be optionally blended with adjuvants at appropriate proportions in a suitable inert carrier, and then subjected to dissolution, separation, suspension, mixing, impregnation, adsorption, or adhesion, thereby being Formulated to a suitable form, for example, suspension concentrates, emulsifiable concentrates, soluble concentrates, wettable powder, granules, dustable powders, tablets, oils, aerosol agents, smokes, liquefied carbon dioxide Formulations, baits, resin Formulations, or the like, and then used.

The inert carrier which can be used in the present invention may be solids or liquids, and examples of the inert carrier for solids include soybean powders, grain powders, wood powders, bark powders, sawdust powders, tobacco stem powders, walnut shell powders, brans, cellulose powders, residues from plant extraction, synthetic polymers such as pulverized synthetic resins, clays (for example, kaolin, bentonite, acidic white clay), talcs (for examples, talc, pyrophyllite, etc.), silica (for examples, diatomaceous earth, sand, mica, white carbon [hydrous silica powders, synthetic high dispersity silicates called hydrous silicate, there are also products containing calcium silicate as a main component]), activated carbon, sulfur powder, pumice, calcined diatomaceous powders, pulverized bricks, fly ash, sand, inorganic mineral powders such as calcium carbonate, calcium phosphate, and the like, chemical fertilizers such as ammonium sulfate, ammonium phosphate, ammonium nitrate, urea, ammonium chloride, and the like, a compost, and others, which are used alone or as a mixture of two or more kinds thereof.

Materials which can be used as the inert carrier for liquids are selected from those having the function as a solvent, as well as those capable of dispersing the active ingredient compound with the aid of an adjuvant even if the inert carrier does not have a function as a solvent. Representative examples thereof include the carriers listed below: water, alcohols (for example, methanol, ethanol, isopropanol, butanol, ethylene glycol, and the like), ketones (for example, acetone, methyl ethyl ketone, methyl isobutyl ketone, diisobutylketone, cyclohexanone, and the like), ethers (for example, diethyl ether, dioxane, cellosolve, diisopropyl ether, tetrahydrofuran, and the like), aliphatic hydrocarbons (for example, kerosene, mineral oil, and the like), aromatic hydrocarbons (for example, benzene, toluene, xylene, solvent naphtha, alkyl naphthalene, and the like), halogenated hydrocarbons (for example, dichloromethane, chloroform, tetrachlorocarbon, chlorobenzene, and the like), esters (for example, ethyl acetate, butyl acetate, ethyl propionate, diisobutyl phthalate, dibutyl phthalate, dioctyl phthalate, and the like), amides (for example, dimethyl formamide, diethyl formamide, dimethyl acetamide, and the like), and nitriles (for example, acetonitrile, and the like), which are used alone or as mixtures of two or more kinds thereof.

Examples of the adjuvant include typical adjuvants mentioned below. These adjuvants can be used depending on purposes and used alone or in combination of two or more kinds thereof or may not be used at all in some cases.

To emulsify, disperse, dissolve and/or wet a compound as an active ingredient, a surfactant is used. Examples thereof include surfactants such as polyoxyethylene alkyl ethers, polyoxyethylene alkylaryl ethers, polyoxyethylene higher fatty acid esters, polyoxyethylene resinates, polyoxyethylene sorbitan monolaurate, polyoxyethylene sorbitan monooleate, alkylarylsulfonates, naphthalenesulfonates, lignin sulfonates, higher alcohol sulfate esters, and the like.

Furthermore, to stabilize the dispersion of a compound as an active ingredient, adhere it, and/or bind it, the following adjuvants can be used. Examples thereof include casein, gelatin, starch, methyl cellulose, carboxymethyl cellulose, gum Arabic, polyvinyl alcohols, pine oil, bran oil, bentonite, Xanthan gum, lignin sulfonates, and the like.

In order to improve the fluidity of a solid product, the following adjuvants can be used. For example, adjuvants such as waxes, stearates, alkyl phosphates, and the like can be used. Adjuvants such as naphthalenesulfonic acid condensation products, condensed phosphates, and the like may be used as a peptizer for suspendible products. As a defoaming agent, adjuvants such as silicon oils and the like can also be used.

Incidentally, the compound represented by the Formula (1) according to the present invention is stable to light, heat, oxidation, and the like. However, an anti-oxidant or an ultraviolet absorber, for example, a phenol derivative such as BHT (2,6-di-t-butyl-4-methylphenol) and BHA (butylated hydroxyanisole), a bisphenol derivative or arylamines such as phenyl-α-naphthylamine, phenyl-β-naphthylamine, condensates of phenetidine and acetone, and the like, or a stabilizer such as a benzophenone-based compound may be added in a suitable amount when necessary, whereby it is possible to obtain a composition with much stabilized effect.

The amount of the active ingredient of the compound represented by the Formula (1) according to the present invention is usually 0.5% by weight to 20% by weight for dustable powders, 5% by weight to 50% by weight for emulsifiable concentrates, 10% by weight to 90% by weight for wettable Formulations, 0.1% by weight to 20% by weight for granules, or 10% by weight to 90% by weight for flowable Formulations. The amount of the carrier in each form is usually 60% by weight to 99% by weight for dustable powders, 40% by weight to 95% by weight for emulsifiable concentrates, 10% by weight to 90% by weight for wettable powders, 80% by weight to 99% by weight for granules, or 10% by weight to 90% by weight for flowable Formulations. Further, the amount of the adjuvant is usually 0.1% by weight to 20% by weight for dustable powders, 1% by weight to 20% by weight for emulsifiable concentrates, 0.1% by weight to 20% by weight for wettable powders, 0.1% by weight to 20% by weight for granules, or 0.1% by weight to 20% by weight for flowable Formulations.

In order to control various pests, an amount effective for blight control can be applied as it is or as an adequate dilution with water or the like, or as a suspension, to the crops on which appearance of the corresponding pests is expected or to places where such occurrence is not preferable. The amount of use depends on various factors such as, for example, the purpose, the pest to be controlled, the state of plant growth, trends in pest appearance, climate, environmental conditions, Formulation, method of use, place of use, timing of use, and the like, but it is preferable to use the active ingredient in the concentration of 0.0001 ppm to 5000 ppm, and preferably 0.01 ppm to 1000 ppm. The dose that can be used per 10 a is generally in the range of 1 g to 300 g of the active ingredient The disclosure of Japanese Patent Application No. 2008-200114 is incorporated herein by reference in its entirety.

All literature, patent applications, and technical specifications cited in the present specification are herein incorporated by reference as if each such individual piece of literature, patent application, and technical specification were specifically and individually indicated to be incorporated herein by reference.

EXAMPLES

Representative Examples according to the present invention will be described with reference to the following Examples, but the present invention is not limited thereto. In the present Examples, DMF represents N,N-dimethyl formamide, THF represents tetrahydrofuran, IPE represents isopropyl ether, DMSO represents dimethyl sulfoxide, DMI represents 1,3-dimethyl-2-imidazolidinone, CDI represents carbonyldiimidazole, and PDC represents pyridinium dichromate. Further, "%" is based on mass unless specified otherwise.

Example 1

Preparation of methyl 2-(N-(2,6-dimethyl-4-(perfluoropropan-2-yl)phenyl)-2-fluoro-3-(N-methylbenzamide)benzamide)acetate (Compound No. 7-221)

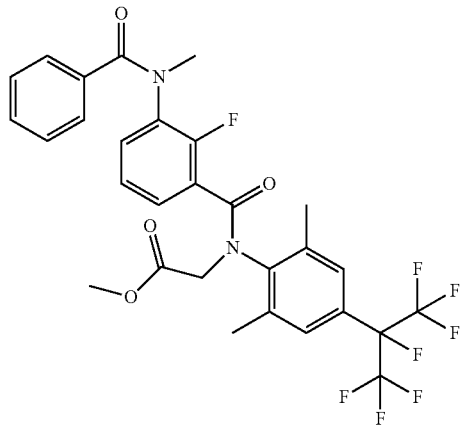 [SMILES: COC(=O)CN(C(=O)c1cccc(N(C)C(=O)c2ccccc2)c1F)c1c(C)cc(C(F)(C(F)(F)F)C(F)(F)F)cc1C]

1-1

Preparation of 2-chloro-N-(2,6-dimethyl-4-(perfluoropropan-2-yl)phenyl)-3-nitrobenzamide

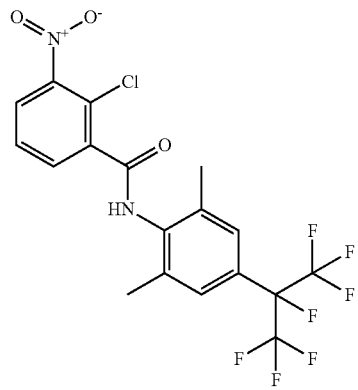 [SMILES: Cc1cc(C(F)(C(F)(F)F)C(F)(F)F)cc(C)c1NC(=O)c1cccc([N+](=O)[O-])c1Cl]

To a solution obtained by adding 2.50 g of 2-chloro-3-nitrobenzoic acid and 5 droplets of DMF to 30 ml of toluene was charged 1.62 g (13.7 mmol) of thionyl chloride, followed by heating and stirring at 80° C. for 2 hours. Then, the solvent was evaporated under reduced pressure, and the obtained crude carboxylic acid chloride was dissolved in 10 ml of THF. This was charged dropwise to a solution obtained by adding 3.24 g (11.2 mmol) of 2,6-dimethyl-4-(perfluoropropan-2-yl)aniline and 1.77 g (22.4 mmol) of pyridine to 20 ml of THF at room temperature, followed by stirring for 5 hours. Ethyl acetate and water were added to the reaction solution, a liquid separation operation was carried out, and the organic layer was collected by separation and dried over anhydrous magnesium sulfate. This solution was filtered, the filtrate was evaporated under reduced pressure, and the obtained residue was purified by silica gel column chromatography (developing solvent; hexane:ethyl acetate=4:1) to prepare 3.38 g (yield 64%) of a target compound.

$^1$H-NMR (CDCl$_3$, ppm) δ 2.42 (6H, s), 7.34 (1H, s), 7.37 (1H, s), 7.55 (1H, t, J=7.8 Hz), 7.80 (1H, dd, J=1.5 Hz, 7.8 Hz), 7.86 (1H, dd, J=1.5 Hz, 7.8 Hz), 9.58 (1H, s)

1-2

Preparation of N-(2,6-dimethyl-4-(perfluoropropan-2-yl)phenyl)-2-fluoro-3-nitrobenzamide

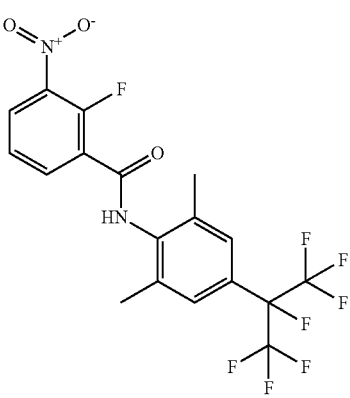

2.35 g (4.97 mmol) of 2-chloro-N-(2,6-dimethyl-4-(perfluoropropan-2-yl)phenyl)-3-nitrobenzamide and 0.870 g (15.0 mmol) of potassium fluoride (spray-dried product) were added to 25 ml of DMF dried over molecular sieves, followed by heating and stirring at 150° C. for 3 hours. After returning to room temperature, ethyl acetate and water were added to the reaction solution, a liquid separation operation was carried out, and then the organic layer was collected by separation, washed with water twice, and then dried over anhydrous magnesium sulfate. This solution was filtered, the filtrate was collected, the solvent was evaporated under reduced pressure, and the obtained residue was purified by silica gel column chromatography (developing solvent; hexane:ethyl acetate=4:1) to prepare 1.02 g (yield 45%) of a target compound.

$^1$H-NMR (CDCl$_3$, ppm) δ 2.37 (6H, s), 7.39 (2H, s), 7.48-7.53 (1H, m), 7.87 (1H, d, J=11.5 Hz), 8.23-8.28 (1H, m), 8.42-8.46 (1H, m).

1-3

Preparation of 3-amino-N-(2,6-dimethyl-4-(perfluoropropan-2-yl)phenyl)-2-fluorobenzamide

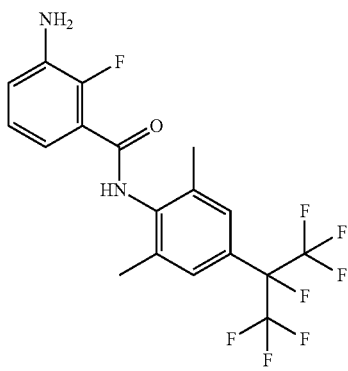 [SMILES: Cc1cc(C(F)(C(F)(F)F)C(F)(F)F)cc(C)c1NC(=O)c1cccc(N)c1F]

11.3 g (5.15 mmol) of N-(2,6-dimethyl-4-(perfluoropropan-2-yl)phenyl)-2-fluoro-3-nitrobenzamide and 14.5 g (76.5 mmol) of stannic chloride were charged to 56 ml of ethanol, and 12.5 ml of concentrated hydrochloric acid was added dropwise thereto. After stirring at 60° C. for 1.5 hours, the mixture was cooled to room temperature. The mixture was discharged to 280 ml of water, and 200 ml of acetic acid was charged thereto, followed by neutralization with sodium hydroxide. The precipitated precipitate was filtered through Celite, and then washed with ethyl acetate, and the filtrate was subjected to liquid separation. The organic layer was dried over anhydrous magnesium sulfate, and the solvent was evaporated under reduced pressure. The obtained residue was purified by silica gel column chromatography (developing solvent; hexane:ethyl acetate=5:1) to prepare 5.80 g (yield: 55%) of a target compound.

$^1$H-NMR (CDCl$_3$, ppm) δ 2.37 (6H, s), 3.90 (2H, broad-s), 6.96-7.01 (1H, m), 7.10 (1H, t, J=7.8 Hz), 7.36 (2H, s), 7.43-7.47 (1H, m), 7.86 (1H, d, J=13.2 Hz)

1-4

Preparation of N-(2,6-dimethyl-4-(perfluoropropan-2-yl)phenyl)-2-fluoro-3-(methylamino)benzamide

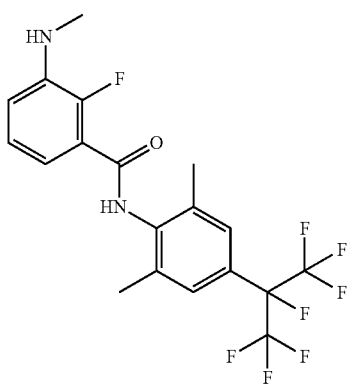 [SMILES: CNc1cccc(C(=O)Nc2c(C)cc(C(F)(C(F)(F)F)C(F)(F)F)cc2C)c1F]

5.80 g (13.6 mmol) of 3-amino-N-(2,6-dimethyl-4-(perfluoropropan-2-yl)phenyl)-2-fluorobenzamide was charged to 34.8 ml of concentrated sulfuric acid and dissolved. 17.4 ml of a 37% aqueous formaldehyde solution was added dropwise thereto over 1 hour while maintaining the internal temperature at 30° C. to 40° C. After stirring at 40° C. for 3 hours, the mixture was discharged to 200 ml of ice-water, and extracted with 100 ml of ethyl acetate three times, and the organic layer was washed with 100 ml of a 1 N aqueous sodium hydroxide solution three times and dried over anhydrous magnesium sulfate. The solvent was evaporated under reduced pressure. The obtained residue was washed with IPE to prepare 4.49 g (yield: 75%) of a target compound.

$^1$H-NMR (DMSO-d$_6$, ppm) δ 2.32 (6H, s), 2.76 (3H, d, J=4.9 Hz), 5.84 (1H, broad-s), 6.77-6.81 (2H, m), 7.10 (1H, t, J=7.8 Hz), 7.43 (2H, s), 9.90 (1H, s).

1-5

Preparation of N-(2,6-dimethyl-4-(perfluoropropan-2-yl)phenyl)-2-fluoro-3-(N-methylbenzamide)benzamide

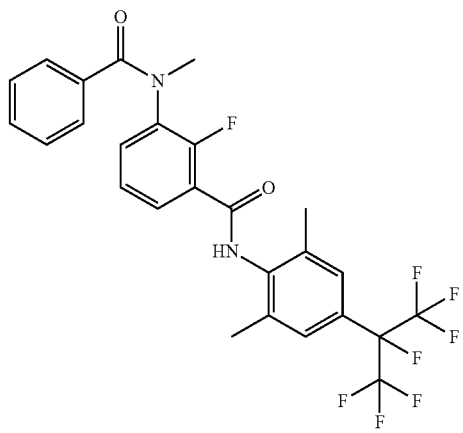 [SMILES: Cc1cc(C(F)(C(F)(F)F)C(F)(F)F)cc(C)c1NC(=O)c1cccc(N(C)C(=O)c2ccccc2)c1F]

4.49 g (10.2 mmol) of N-(2,6-dimethyl-4-(perfluoropropan-2-yl)phenyl)-2-fluoro-3-(methylamino)benzamide and 0.920 g (11.6 mmol) of pyridine were charged to 22 ml of THF, and 1.54 g (10.9 mmol) of benzoyl chloride was added thereto, followed by stirring at room temperature for 3 hours. A saturated aqueous sodium hydrogen carbonate solution was added thereto, followed by extraction with ethyl acetate, and then washing with 5% hydrochloric acid. After drying over anhydrous magnesium sulfate, the solvent was evaporated under reduced pressure and the obtained residue was washed with IPE to prepare 5.00 g (yield: 90%) of a target compound.

$^1$H-NMR (DMSO-d$_6$, ppm) δ 2.28 (6H, s), 3.36 (3H, s), 7.27-7.32 (6H, m), 7.43 (2H, s), 7.55-7.57 (2H, broad-s), 9.96 (1H, s).

1-6

Preparation of methyl 2-(N-(2,6-dimethyl-4-(perfluoropropan-2-yl)phenyl)-2-fluoro-3-(N-methylbenzamide)benzamide)acetate (Compound No. 7-221)

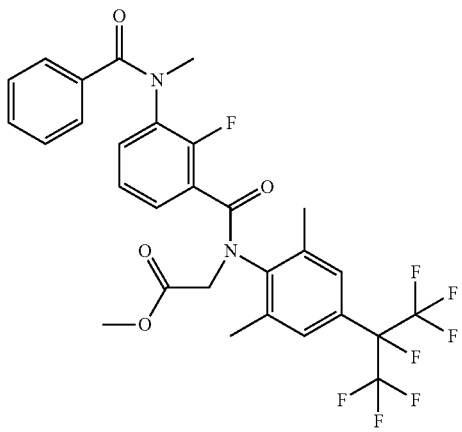 [SMILES: COC(=O)CN(C(=O)c1cccc(N(C)C(=O)c2ccccc2)c1F)c1c(C)cc(C(F)(C(F)(F)F)C(F)(F)F)cc1C]

0.240 g (6.06 mmol) of 60% sodium hydride was charged to 10 ml of DMF, and 3.00 g (5.51 mmol) of N-(2,6-dimethyl-4-(perfluoropropan-2-yl)phenyl)-2-fluoro-3-(N-methylbenzamide)benzamide dissolved in 8 ml of DMF was added dropwise thereto at room temperature. After stirring at room temperature for 2 hours, 1.86 g (12.1 mmol) of methyl bromoacetate was added thereto, followed by stirring at 60° C. for 3 hours. After cooling to room temperature, water was added thereto, followed by extraction with ethyl acetate. After drying over anhydrous magnesium sulfate, the solvent was evaporated under reduced pressure and the obtained residue was purified by column chromatography (developing solvent; hexane:ethyl acetate=10:1→7:3→1:1) to prepare 3.05 g (yield 90%) of a target compound.

$^1$H-NMR (CDCl$_3$, ppm) δ 2.37 (6H, broad-s), 3.05 (3H, s), 3.81 (3H, s), 4.25 (1H, broad-s), 4.40 (1H, broad-s), 6.80-6.89 (2H, m), 7.15-7.37 (8H, m).

Example 2

Preparation of 2-(N-(2,6-dimethyl-4-(perfluoropropan-2-yl)phenyl)-2-fluoro-3-(N-methylbenzamide)benzamide)acetic acid (Compound No. 7-222)

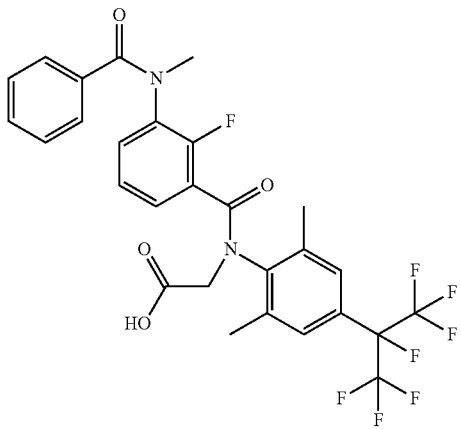 [SMILES: Cc1cc(C(F)(C(F)(F)F)C(F)(F)F)cc(C)c1N(CC(=O)O)C(=O)c1cccc(N(C)C(=O)c2ccccc2)c1F]

2.00 g (3.25 mmol) of methyl 2-(N(2,6-dimethyl-4-(perfluoropropan-2-yl)phenyl)-2-fluoro-3-(N-methylbenzamide)benzamide)acetate obtained in 1-6 of Example 1 was charged to 10 ml of methanol, and 0.520 g (13.0 mmol) of sodium hydroxide and 5 ml of water were added thereto, followed by stirring for 2 hours. The mixture was discharged to water and washed with ethyl acetate, and then the aqueous layer was adjusted to pH 1 with concentrated hydrochloric acid. After extraction with ethyl acetate, the resultant was washed with saturated brine and dried over anhydrous magnesium sulfate. The solvent was evaporated under reduced pressure to prepare 1.00 g (yield: 51%) of a target compound.

$^1$H-NMR (CDCl$_3$, ppm) δ 2.47 (6H, broad-s), 3.06 (3H, s), 4.38 (2H, broad-s), 6.81-6.89 (2H, m), 7.14-7.52 (8H, m).

The proton presumed to be indicative of the carboxylic acid was not detected.

Example 3

Preparation of N-(2,6-dimethyl-4-(perfluoropropan-2-yl)phenyl)-2-fluoro-N-(2-hydroxyethyl)-3-(N-methylbenzamide)benzamide (Compound No. 7-23)

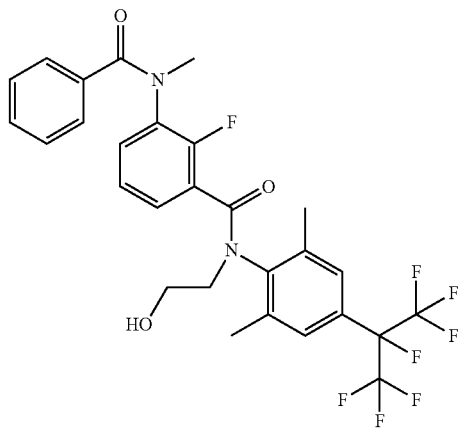 [SMILES: Cc1cc(C(F)(C(F)(F)F)C(F)(F)F)cc(C)c1N(CCO)C(=O)c1cccc(N(C)C(=O)c2ccccc2)c1F]

1.40 g (2.27 mmol) of methyl 2-(N(2,6-dimethyl-4-(perfluoropropan-2-yl)phenyl)-2-fluoro-3-(N-methylbenzamide)benzamide)acetate obtained in 1-6 of Example 1 was charged to 4 ml of ethanol, and 0.100 g (2.73 mmol) of sodium borohydride was added thereto at room temperature. After stirring at room temperature for 1 hour, 0.100 g (2.73 mmol) of sodium borohydride was added thereto, followed by stirring for 2 hours. 0.100 g (2.73 mmol) of sodium borohydride was further added thereto, followed by stirring at room temperature for 1 hour, and then water was added thereto. Table salt was added thereto, followed by extraction with ethyl acetate and drying over anhydrous magnesium sulfate. The solvent was evaporated under reduced pressure and the obtained residue was purified by silica gel column chromatography (developing solvent; hexane:ethyl acetate=7:3→1:1→1:2→0:1) to prepare 0.900 g (yield: 67%) of a target compound.

¹H-NMR (CDCl₃, ppm) δ 2.34 (6H, broad-s), 3.08 (3H, s), 3.20-3.22 (1H, m), 3.47 (1H, broad-s), 3.89 (2H, broad-s), 6.79-6.83 (1H, m), 6.88-6.89 (1H, m), 7.06-7.35 (9H, m).

Example 4

Preparation of N-(2-amino-2-oxoethyl)-N-(2,6-dimethyl-4-(perfluoropropan-2-yl)phenyl)-2-fluoro-3-(N-methylbenzamide)benzamide (Compound No. 7-220)

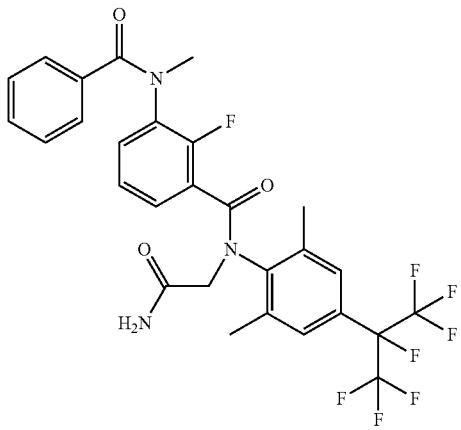 [SMILES: Cc1cc(C(F)(C(F)(F)F)C(F)(F)F)cc(C)c1N(CC(N)=O)C(=O)c1cccc(N(C)C(=O)c2ccccc2)c1F]

According to the method of 1-6 of Example 1, a target compound was prepared from N-(2,6-dimethyl-4-(perfluoropropan-2-yl)phenyl)-2-fluoro-3-(N-methylbenzamide)benzamide obtained in 1-5 of Example 1 and 2-chloroacetic acid amide.

¹H-NMR (CDCl₃, ppm) δ 2.44 (6H, broad-s), 3.13 (3H, s), 4.45 (1H, broad-s), 5.77 (1H, broad-s), 6.79-7.04 (6H, m), 7.15-7.34 (6H, m).

Example 5

Preparation of methyl 2-(N-(3((2,6-dimethyl-4-(perfluoropropan-2-yl)phenyl)(methyl)carbamoyl)phenyl)benzamide)acetate (Compound No. 6-1)

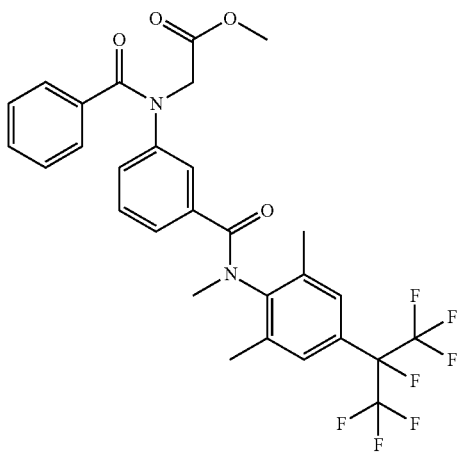 [SMILES: COC(=O)CN(C(=O)c1ccccc1)c1cccc(C(=O)N(C)c2c(C)cc(C(F)(C(F)(F)F)C(F)(F)F)cc2C)c1]

5-1

Preparation of N-(2,6-dimethyl-4-(perfluoropropan-2-yl)phenyl)-3-nitrobenzamide

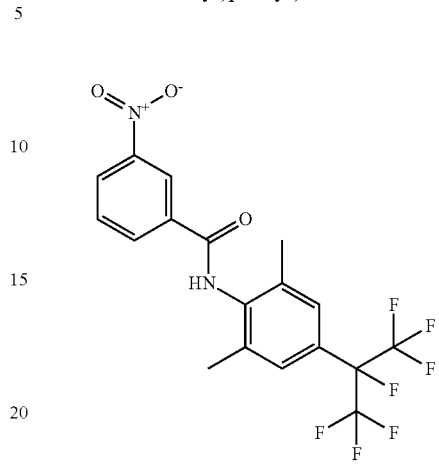

20.0 g (69.2 mmol) of 2,6-dimethyl-4-(perfluoropropan-2-yl)aniline and 11.0 g (139 mmol) of pyridine were dissolved in 100 ml of THF, and then 13.0 g of 3-nitrobenzoyl chloride dissolved in 20 ml of THF was slowly charged dropwise thereto. After stirring at room temperature for 10 hours, ethyl acetate and water were added to the reaction solution. After carrying out a liquid separation operation, the organic layer was collected by separation and dried over anhydrous magnesium sulfate. This solution was filtered, the filtrate was evaporated under reduced pressure and the obtained residue was washed with a hexane-IPE mixed solvent to prepare 26.0 g (yield 85%) of a target compound.

¹H-NMR (CDCl₃, ppm) δ 2.33 (6H, s), 7.37 (2H, s), 7.68 (1H, s), 7.72 (1H, t, J=8.1 Hz), 8.28 (1H, d, J=8.1 Hz), 8.44 (1H, dd, J=1.2 Hz, 8.1 Hz), 8.75 (1H, t, J=1.2 Hz)

5-2

Preparation of N-(2,6-dimethyl-4-(perfluoropropan-2-yl)phenyl)-N-methyl-3-nitrobenzamide

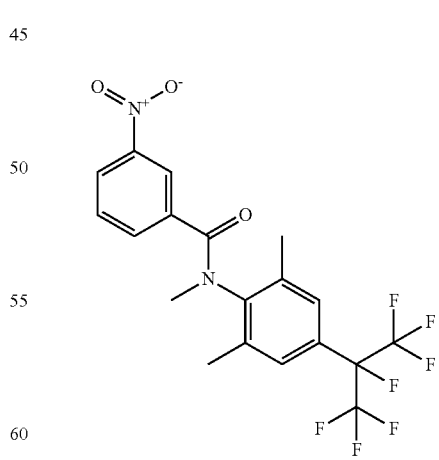

To a solution having 0.180 g of 60% sodium hydride suspended in 15 ml of THF was charged dropwise 2.00 g (4.56 mmol) of N-(2,6-dimethyl-4-(perfluoropropan-2-yl)phenyl)-3-nitrobenzamide dissolved in 5 ml of THF at room temperature. After stirring at room temperature for 30 minutes, 0.650 g of methyl iodide dissolved in 5 ml of THF was charged dropwise thereto. Then, the temperature was elevated to 50° C., followed by stirring for 4 hours, and then returning to room temperature, and ethyl acetate and water were added to the reaction solution. The organic layer was collected by separation, washed with water once, and then dried over anhydrous magnesium sulfate, and the solvent was evaporated under reduced pressure. The obtained residue was purified by silica gel column chromatography (developing solvent; hexane:ethyl acetate=6:1) to prepare 1.73 g (yield 84%) of a target compound.

$^1$H-NMR (CDCl$_3$, ppm) δ 2.31 (6H, s), 3.38 (3H, s), 7.27 (2H, s), 7.37 (1H, t, J=7.8 Hz), 7.62-7.65 (1H, m), 8.05 (1H, t, J=2.0 Hz), 8.11-8.14 (1H, m).

5-3

Preparation of 3-amino-N-(2,6-dimethyl-4-(perfluoropropan-2-yl)phenyl)-N-methylbenzamide

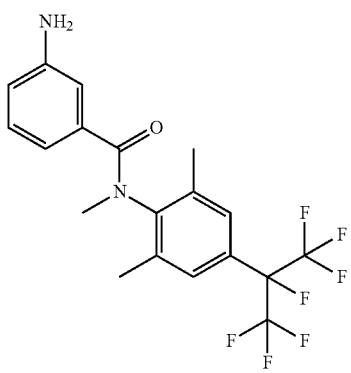 [SMILES: Cc1cc(C(F)(C(F)(F)F)C(F)(F)F)cc(C)c1N(C)C(=O)c1cccc(N)c1]

A solution obtained by adding 1.50 g (3.31 mmol) of N-(2,6-dimethyl-4-(perfluoropropan-2-yl)phenyl)-N-methyl-3-nitrobenzamide and 0.150 g of 10% palladium-carbon into 20 ml of methanol was stirred for 2 hours at a normal pressure under a hydrogen atmosphere. The catalyst was removed by filtration, and then the solvent was evaporated under reduced pressure. Then, the precipitated solid was washed with hexane to prepare 1.24 g (yield 88%) of a target compound.

$^1$H-NMR (CDCl$_3$, ppm) δ 2.27 (6H, s), 3.31 (3H, s), 3.80 (2H, broad-s), 6.40-6.43 (1H, m), 6.54-6.58 (1H, m), 6.71 (1H, t, J=2.0 Hz), 6.76-6.86 (1H, m), 7.22 (2H, s).

5-4

Preparation of 3-benzamide-N-(2,6-dimethyl-4-(perfluoropropan-2-yl)phenyl)-N-methylbenzamide

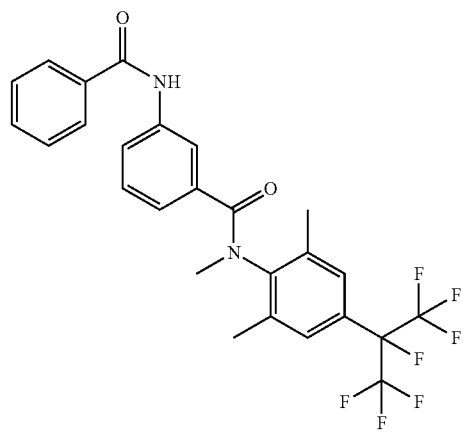 [SMILES: Cc1cc(C(F)(C(F)(F)F)C(F)(F)F)cc(C)c1N(C)C(=O)c1cccc(NC(=O)c2ccccc2)c1]

According to the method of 1-5 of Example 1, a target compound was prepared from 3-amino-N-(2,6-dimethyl-4-(perfluoropropan-2-yl)phenyl)-N-methylbenzamide and benzoyl chloride.

$^1$H-NMR (DMSO-d$_6$, ppm) δ 2.29 (6H, s), 3.24 (3H, s), 6.84 (1H, d, J=7.8 Hz), 7.12 (1H, t, J=7.8 Hz), 7.33 (2H, s), 7.50-7.64 (4H, m), 7.85-7.88 (2H, m), 7.98-8.03 (1H, m), 10.22 (1H, s).

5-5

Preparation of methyl 2-(N-(3((2,6-dimethyl-4-(perfluoropropan-2-yl)phenyl)(methyl)carbamoyl)phenyl)benzamide)acetate (Compound No. 6-1)

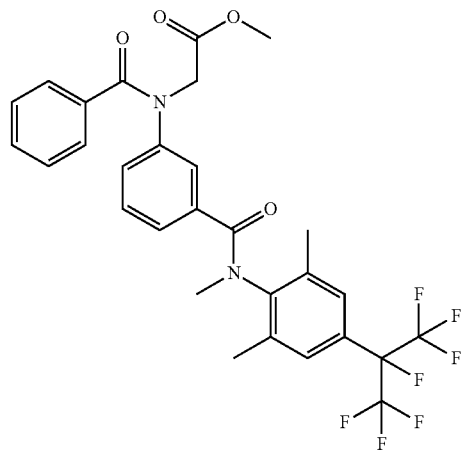 [SMILES: COC(=O)CN(C(=O)c1ccccc1)c1cccc(C(=O)N(C)c2c(C)cc(C(F)(C(F)(F)F)C(F)(F)F)cc2C)c1]

According to the method of 1-6 of Example 1, a target compound was prepared from 3-benzamide-N-(2,6-dimethyl-4-(perfluoropropan-2-yl)phenyl)-N-methylbenzamide.

¹H-NMR (CDCl₃, ppm) δ 2.18 (6H, s), 3.29 (3H, s), 3.79 (3H, s), 4.27 (2H, s), 6.92-6.94 (2H, m), 7.02-7.05 (1H, m), 7.10-7.14 (2H, m), 7.18-7.41 (6H, m).

Example 6

Preparation of 2-(N-(3-((2,6-dimethyl-4-(perfluoropropan-2-yl)phenyl)(methyl)carbamoyl)phenyl)benzamide)acetic acid (Compound No. 6-3)

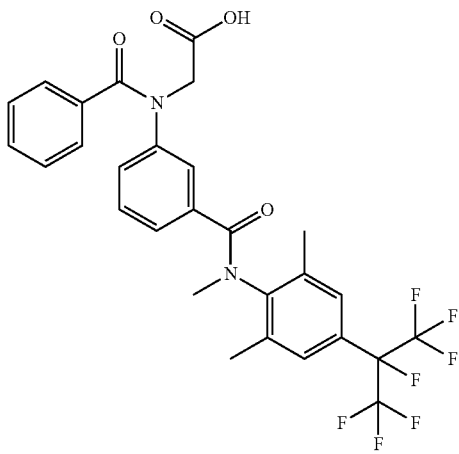 [SMILES: Cc1cc(C(F)(C(F)(F)F)C(F)(F)F)cc(C)c1N(C)C(=O)c1cccc(N(CC(=O)O)C(=O)c2ccccc2)c1]

According to the method of Example 2, a target compound was prepared from methyl 2-(N-(3((2,6-dimethyl-4-(perfluoropropan-2-yl)phenyl)(methyl)carbamoyl)phenyl)benzamide)acetate.

¹H-NMR (CDCl₃, ppm) δ 2.15 (6H, s), 3.29 (3H, s), 4.34 (2H, s), 4.70 (1H, broad-s), 6.92-6.94 (2H, m), 6.99-7.03 (1H, m), 7.10-7.28 (8H, m).

Example 7

Preparation of N-(2,6-dimethyl-4-(perfluoropropan-2-yl)phenyl)-N-methyl-3-(N-(methylthiomethyl)benzamide)benzamide (Compound No. 6-6)

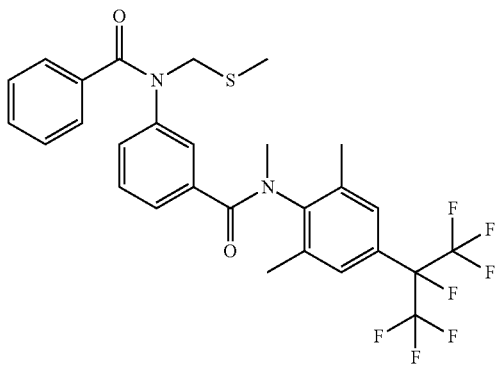 [SMILES: CSCN(C(=O)c1ccccc1)c1cccc(C(=O)N(C)c2c(C)cc(C(F)(C(F)(F)F)C(F)(F)F)cc2C)c1]

According to the method of 1-6 of Example 1, a target compound was prepared from 3-benzamide-N-(2,6-dimethyl-4-(perfluoropropan-2-yl)phenyl)-N-methylbenzamide obtained in 5-4 of Example 5 and chloromethyl methyl sulfide.

¹H-NMR (CDCl₃, ppm) δ 2.12 (3H, s), 2.18 (6H, s), 3.29 (3H, s), 4.82 (2H, s), 6.93-6.97 (2H, m), 7.03-7.05 (1H, m), 7.10-7.15 (4H, m), 7.22-7.26 (4H, m).

Example 8

Preparation of N-(2,6-dimethyl-4-(perfluoropropan-2-yl)phenyl)-N-methyl-3-(N-(methylsulfinylmethyl)benzamide)benzamide (Compound No. 6-7)

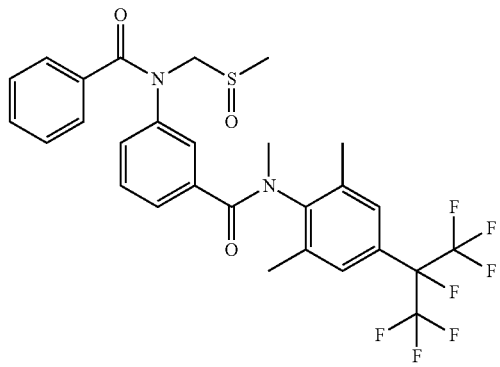 [SMILES: Cc1cc(C(F)(C(F)(F)F)C(F)(F)F)cc(C)c1N(C)C(=O)c1cccc(N(CS(C)=O)C(=O)c2ccccc2)c1]

To a solution of 0.120 g (0.200 mmol) of N-(2,6-dimethyl-4-(perfluoropropan-2-yl)phenyl)-N-methyl-3-(N-(methylthiomethyl)benzamide)benzamide obtained in Example 7 in 10 ml of dichloromethane was added 0.0440 g (0.360 mmol) of 70% metachloroperbenzoic acid, followed by stirring at room temperature for 1 hour. The reaction liquid was washed with a saturated aqueous sodium hydrogen carbonate solution and saturated brine, and dried over anhydrous magnesium sulfate. The solvent was evaporated under reduced pressure and the obtained residue was purified by silica gel column chromatography (developing solvent; hexane:ethyl acetate=1:1→0:1→ethyl acetate:methanol=10:1) to prepare 0.930 g (yield 77%) of a target compound.

¹H-NMR (CDCl₃, ppm) δ 2.18 (6H, s), 2.65 (3H, s), 3.26 (3H, s), 4.43 (1H, d, J=13.1 Hz), 5.09 (1H, d, J=13.1 Hz), 6.99-7.01 (2H, m), 7.16-7.32 (9H, m).

Example 9

Preparation of N-(2,6-dimethyl-4-(perfluoropropan-2-yl)phenyl)-N-methyl-3-(N-(methylsulfonylmethyl)benzamide)benzamide (Compound No. 6-8)

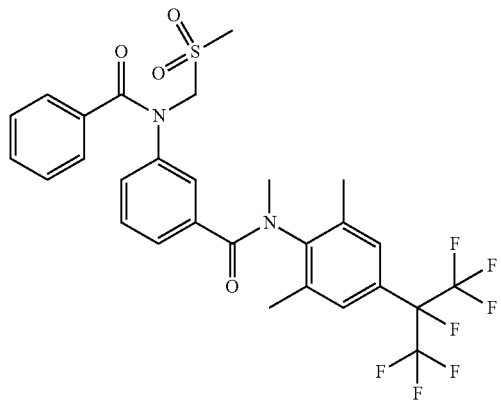 [SMILES: Cc1cc(C(F)(C(F)(F)F)C(F)(F)F)cc(C)c1N(C)C(=O)c1cccc(N(CS(C)(=O)=O)C(=O)c2ccccc2)c1]

According to the method of Example 8, 70% metachloroperbenzoic acid was used in a 3-fold molar amount with respect to N-(2,6-dimethyl-4-(perfluoropropan-2-yl)phenyl)-N-methyl-3-(N-(methylthiomethyl)benzamide)benzamide of the raw material to prepare a target compound.

¹H-NMR (CDCl₃, ppm) δ 2.18 (6H, s), 3.05 (3H, s), 3.28 (3H, s), 4.92 (2H, s), 6.99-7.01 (1H, m), 7.08-7.11 (2H, m), 7.16-7.24 (3H, m), 7.29-7.41 (5H, m).

Example 10

Preparation of N-(2,6-dimethyl-4-(perfluoropropan-2-yl)phenyl)-N-methyl-3-(N-(2-(methylthio)ethyl)benzamide)benzamide (Compound No. 5-71)

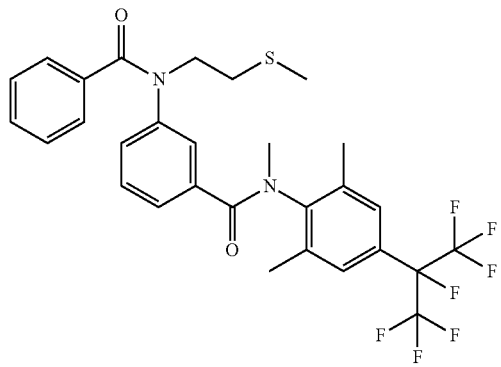 [SMILES: CSCCN(C(=O)c1ccccc1)c1cccc(C(=O)N(C)c2c(C)cc(C(F)(C(F)(F)F)C(F)(F)F)cc2C)c1]

According to the method of 1-6 of Example 1, a target compound was prepared from 3-benzamide-N-(2,6-dimethyl-4-(perfluoropropan-2-yl)phenyl)-N-methylbenzamide obtained in 5-4 of Example 5 and 2-chloroethyl methyl sulfide.

¹H-NMR (CDCl₃, ppm) δ 2.13 (6H, s), 2.18 (3H, s), 2.66 (2H, t, J=7.3 Hz), 3.27 (3H, s), 3.92 (2H, t, J=7.3 Hz), 6.90-6.96 (3H, m), 7.11-7.16 (4H, m), 7.21-7.26 (3H, m), 7.33-7.34 (1H, m).

Example 11

Preparation of N-(2,6-dimethyl-4-(perfluoropropan-2-yl)phenyl)-N-methyl-3-(N-(2-(methylsulfinyl)ethyl)benzamide)benzamide (Compound No. 5-72)

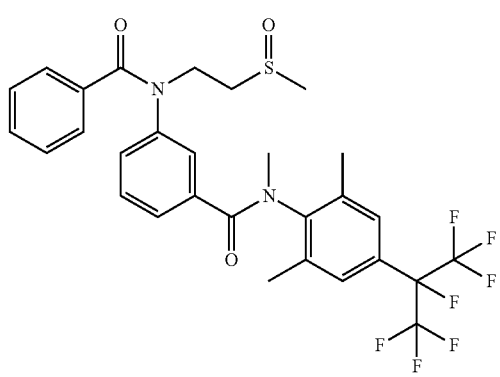 [SMILES: Cc1cc(C(F)(C(F)(F)F)C(F)(F)F)cc(C)c1N(C)C(=O)c1cccc(N(CCS(C)=O)C(=O)c2ccccc2)c1]

According to the method of Example 8, a target compound was prepared from N-(2,6-dimethyl-4-(perfluoropropan-2-yl)phenyl)-N-methyl-3-(N-(2-(methylthio)ethyl)benzamide)benzamide obtained in Example 10.

¹H-NMR (CDCl₃, ppm) δ 2.17 (6H, s), 2.66 (3H, s), 2.90-2.94 (1H, m), 3.17-3.19 (1H, m), 3.26 (3H, s), 4.00-4.02 (1H, m), 4.11-4.13 (1H, m), 6.85-6.87 m), 6.97 (1H, t, J=7.8 Hz), 7.08-7.29 (9H, m).

Example 12

Preparation of N-(2,6-dimethyl-4-(perfluoropropan-2-yl)phenyl)-N-methyl-3-(N-(2-(methylsulfonyl)ethyl)benzamide)benzamide (Compound No. 5-73)

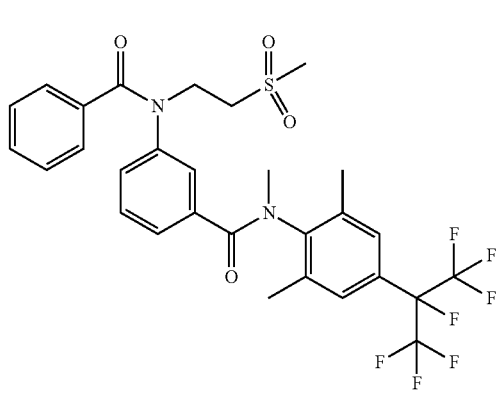 [SMILES: Cc1cc(C(F)(C(F)(F)F)C(F)(F)F)cc(C)c1N(C)C(=O)c1cccc(N(CCS(C)(=O)=O)C(=O)c2ccccc2)c1]

According to the method of Example 9, a target compound was prepared from N-(2,6-dimethyl-4-(perfluoropropan-2-yl)phenyl)-N-methyl-3-(N-(2-(methylthio)ethyl)benzamide)benzamide obtained in Example 10.

¹H-NMR (CDCl₃, ppm) δ 2.09 (6H, s), 3.03 (3H, s), 3.26 (3H, s), 3.35 (2H, t, J=7.3 Hz), 4.19 (2H, t, J=7.3 Hz), 6.85-6.87 (1H, m), 6.96 (1H, t, J=7.8 Hz), 7.06-7.07 (1H, m), 7.14-7.29 (8H, m).

Example 13

Preparation of 3-(N-(cyanomethyl)benzamide)-N-(2,6-dimethyl-4-(perfluoropropan-2-yl)phenyl)-N-methylbenzamide (Compound No. 6-18)

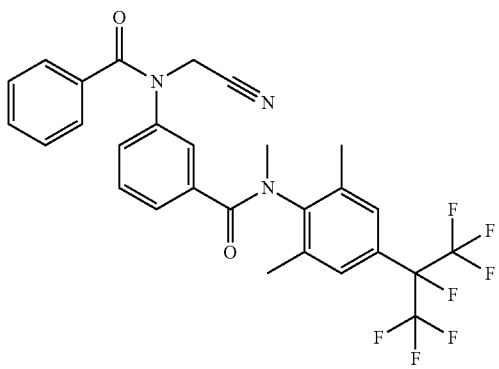 [SMILES: Cc1cc(C(F)(C(F)(F)F)C(F)(F)F)cc(C)c1N(C)C(=O)c1cccc(N(CC#N)C(=O)c2ccccc2)c1]

According to the method of 1-6 of Example 1, a target compound was prepared from 3-benzamide-N-(2,6-dimethyl-4-(perfluoropropan-2-yl)phenyl)-N-methylbenzamide obtained in 5-4 of Example 5 and chloroacetonitrile.

¹H-NMR (CDCl₃, ppm) δ 2.20 (6H, s), 3.31 (3H, s), 4.45 (2H, s), 6.92-6.94 (1H, m), 7.04-7.05 (1H, m), 7.13-7.34 (9H, m).

Example 14

Preparation of 3-(N-(2-amino-2-oxoethyl)benzamide)-N-(2,6-dimethyl-4-(perfluoropropan-2-yl)phenyl)-N-methylbenzamide (Compound No. 6-12)

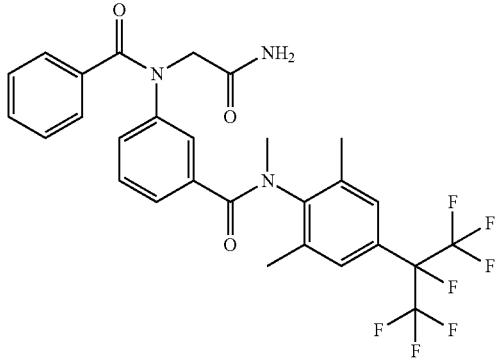 [SMILES: Cc1cc(C(F)(C(F)(F)F)C(F)(F)F)cc(C)c1N(C)C(=O)c1cccc(N(CC(N)=O)C(=O)c2ccccc2)c1]

According to the method of 1-6 of Example 1, a target compound was prepared from 3-benzamide-N-(2,6-dimethyl-4-(perfluoropropan-2-yl)phenyl)-N-methylbenzamide obtained in 5-4 of Example 5 and chloroacetic acid amide.

¹H-NMR (CDCl₃, ppm) δ 2.16 (6H, s), 3.28 (3H, s), 4.20 (2H, s), 5.50 (1H, broad-s), 6.10 (1H, broad-s), 6.94-6.95 (2H, m), 7.04-7.06 (1H, m), 7.12-7.33 (8H, m).

Example 15

Preparation of methyl 4-(N-(3-((2,6-dimethyl-4-(perfluoropropan-2-yl)phenyl)(methyl)carbamoyl)phenyl)benzamide)butanoate (Compound No. 6-13)

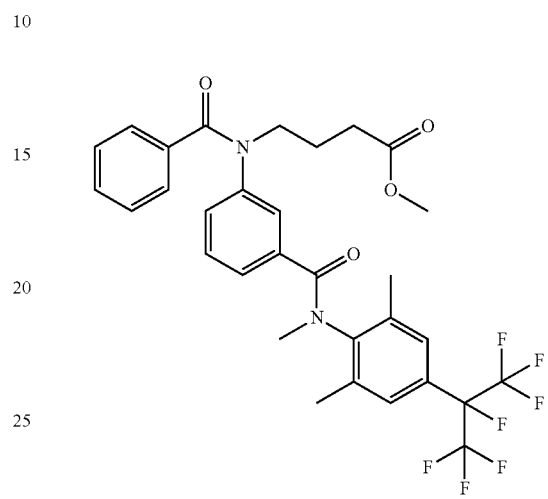

According to the method of 1-6 of Example 1, a target compound was prepared from 3-benzamide-N-(2,6-dimethyl-4-(perfluoropropan-2-yl)phenyl)-N-methylbenzamide obtained in 5-4 of Example 5 and methyl 4-iodobutyrate ester.

¹H-NMR (CDCl₃, ppm) δ 1.86-1.89 (2H, m), 2.15 (6H, s), 2.35 (2H, t, J=7.3 Hz), 3.28 (3H, s), 3.66 (3H, s), 3.78 (2H, t, J=7.3 Hz), 6.89-6.94 (3H, m), 7.11-7.12 (4H, m), 7.21-7.25 (3H, m), 7.34 (1H, broad-s).

Example 16

Preparation of 4-(N-(3-((2,6-dimethyl-4-(perfluoropropan-2-yl)phenyl)(methyl)carbamoyl)phenyl)benzamide)butanoic acid (Compound No. 6-14)

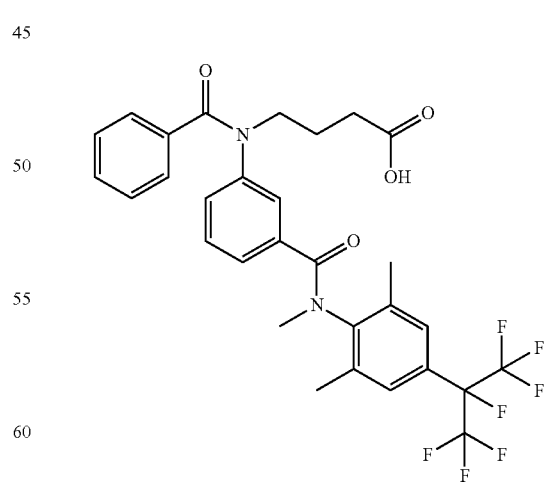

According to the method of Example 2, a target compound was prepared from methyl 4-(N-(3-((2,6-dimethyl-4-(perfluoropropan-2-yl)phenyl)(methyl)carbamoyl)phenyl)benzamide)butanoate obtained in Example 15.

¹H-NMR (CDCl₃, ppm) δ 1.85-1.87 (2H, m), 2.26 (6H, s), 2.42-2.43 (2H, m), 3.28 (3H, s), 3.83 (2H, t, J=7.3 Hz), 6.88-6.94 (3H, m), 7.09-7.14 (4H, m), 7.19-7.26 (3H, m), 7.35 (1H, broad-s).

The proton presumed to be indicative of the carboxylic acid was not detected.

Example 17

Preparation of 3-(N-(4-amino-4-oxobutyl)benzamide)-N-(2,6-dimethyl-4-(perfluoropropan-2-yl)phenyl)-N-methylbenzamide (Compound No. 6-15)

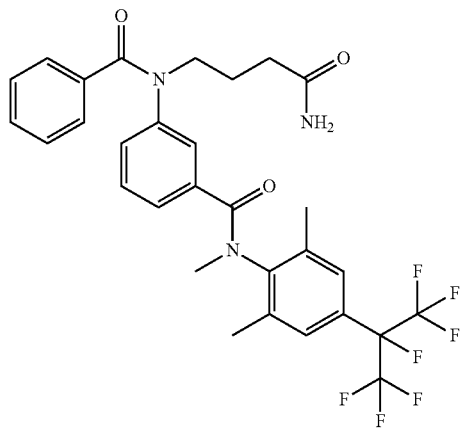 [SMILES: Cc1cc(C(F)(C(F)(F)F)C(F)(F)F)cc(C)c1N(C)C(=O)c1cccc(N(CCCC(N)=O)C(=O)c2ccccc2)c1]

0.100 g (0.163 mmol) of 4-(N-(3-((2,6-dimethyl-4-(perfluoropropan-2-yl)phenyl)(methyl)carbamoyl)phenyl)benzamide)butanoic acid obtained in Example 16 and 1 droplet of DMF were charged to 5 ml of benzene, and 0.0500 g of oxalyl chloride was added thereto, followed by stirring at 60° C. for 2 hours. After cooling to room temperature, the solvent was evaporated under reduced pressure to obtain a crude acid chloride.

To 5 ml of THF was charged 2 ml of 28% aqueous ammonia, and the acid chloride obtained above was added thereto at room temperature. After stirring at room temperature for 1 hour, ethyl acetate was charged thereto, followed by washing with a 5% aqueous hydrochloric acid solution and a saturated aqueous sodium hydrogen carbonate solution in this order. After drying over anhydrous magnesium sulfate, the solvent was evaporated under reduced pressure and the obtained residue was purified by silica gel column chromatography (developing solvent; hexane:ethyl acetate=1:1→30:1→ethyl acetate:methanol=10:1) to prepare 0.0660 g (yield: 66%) of a target compound.

¹H-NMR (CDCl₃, ppm) δ 1.86 (2H, t, J=6.8 Hz), 2.13 (6H, s), 2.25-2.30 (2H, m), 3.27 (3H, s), 3.84 (2H, t, J=6.8 Hz), 5.35 (1H, broad-s), 6.50 (1H, broad-s), 6.90-6.95 (3H, m), 7.11-7.13 (4H, m), 7.25-7.30 (3H, m), 7.34 (1H, broad-s).

Example 18

Preparation of methyl 2-(N-(3-((2,6-dimethyl-4-(perfluoropropan-2-yl)phenyl)(2-methoxy-2-oxoethyl)carbamoyl)-2-fluorophenyl)benzamide)acetate (Compound No. 8-12)

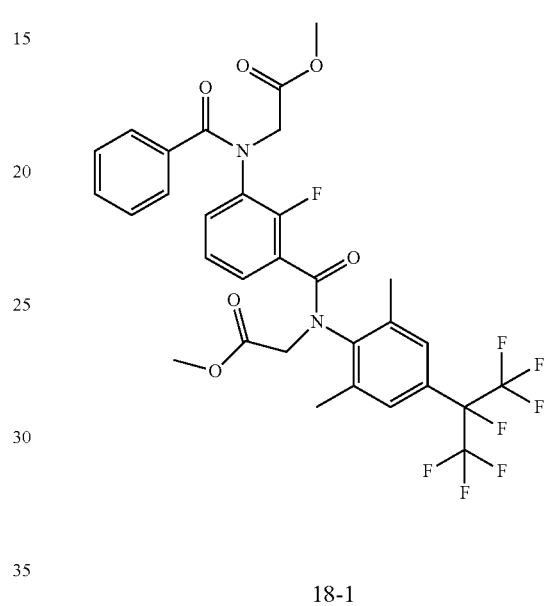

18-1

Preparation of 3-benzamide-N-(2,6-dimethyl-4-(perfluoropropan-2-yl)phenyl)-2-fluorobenzamide

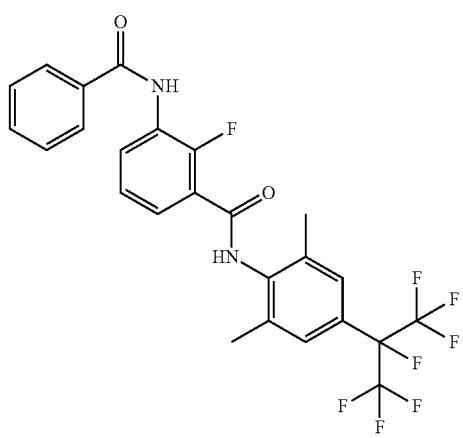 [SMILES: Cc1cc(C(F)(C(F)(F)F)C(F)(F)F)cc(C)c1NC(=O)c1cccc(NC(=O)c2ccccc2)c1F]

According to the method of 1-5 of Example 1, a target compound was prepared from 3-amino-N-(2,6-dimethyl-4-(perfluoropropan-2-yl)phenyl)-2-fluorobenzamide obtained in 1-3 of Example 1.

$^1$H-NMR (DMSO-d$_6$, ppm) δ 2.34 (6H, s), 7.37 (1H, t, J=7.8 Hz), 7.45 (2H, s), 7.53-7.65 (4H, m), 7.77-7.82 (1H, m), 8.00-8.02 (2H, m), 10.10 (1H, s), 10.29 (1H, s).

18-2

Preparation of methyl 2-(N-(3((2,6-dimethyl-4-(perfluoropropan-2-yl)phenyl)(2-methoxy-2-oxoethyl) carbamoyl)-2-fluorophenyl)benzamide)acetate (Compound No. 8-12)

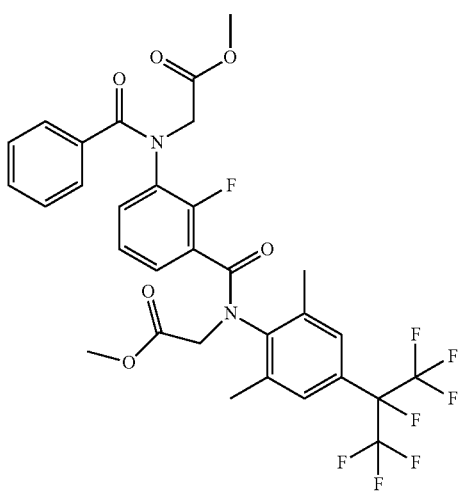 [SMILES: COC(=O)CN(C(=O)c1ccccc1)c1cccc(C(=O)N(CC(=O)OC)c2c(C)cc(C(F)(C(F)(F)F)C(F)(F)F)cc2C)c1F]

According to the method of 1-6 of Example 1, 2.2-fold molar amounts of 60% sodium hydride and 4.4-fold molar amounts of ethyl bromoacetate were used with respect to 3-benzamide-N-(2,6-dimethyl-4-(perfluoropropan-2-yl)phenyl)-2-fluorobenzamide to prepare a target compound.

$^1$H-NMR (CDCl$_3$, ppm) δ 2.50 (6H, broad-s), 3.51 (1H, s), 3.73 (3H, s), 3.81 (3H, s), 4.30 (1H, broad-s), 4.35 (1H, broad-s), 4.75 (1H, broad-s), 6.79 (1H, t, J=7.8 Hz), 7.08-7.24 (6H, m), 7.28-7.34 (3H, m).

Example 19

Preparation of 2-(N-(3((carboxymethyl)(2,6-dimethyl-4-(perfluoropropan-2-yl)phenyl)carbamoyl)-2-fluorophenyl)benzamide)acetic acid (Compound No. 8-13)

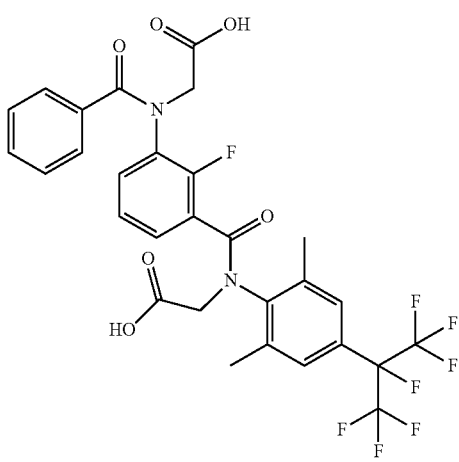 [SMILES: Cc1cc(C(F)(C(F)(F)F)C(F)(F)F)cc(C)c1N(CC(=O)O)C(=O)c1cccc(N(CC(=O)O)C(=O)c2ccccc2)c1F]

According to the method of Example 2, a target compound was prepared from methyl 2-(N-(3((2,6-dimethyl-4-(perfluoropropan-2-yl)phenyl)(2-methoxy-2-oxoethyl)carbamoyl)-2-fluorophenyl)benzamide)acetate obtained in Example 18.

$^1$H-NMR (CDCl$_3$, ppm) δ 2.18-2.38 (6H, broad-s), 4.10 (1H, broad-s), 4.32 (2H, s), 4.52 (1H, broad-s), 6.02 (2H, broad-s), 6.77 (1H, t, J=7.8 Hz), 7.03-7.41 (9H, m).

Example 20

Preparation of N-(3-amino-3-oxopropyl)-N-(3-(2,6-dimethyl-4-(perfluoropropan-2-yl)phenylcarbamoyl) phenyl)benzamide (Compound No. 1-1)

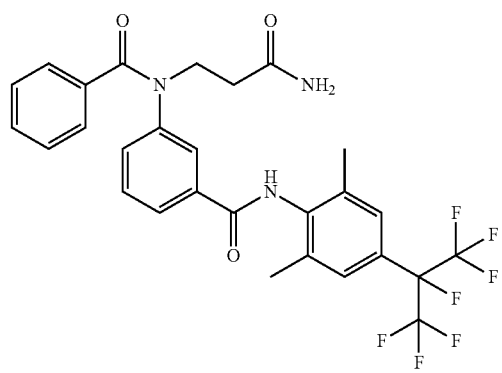 [SMILES: Cc1cc(C(F)(C(F)(F)F)C(F)(F)F)cc(C)c1NC(=O)c1cccc(N(CCC(N)=O)C(=O)c2ccccc2)c1]

20-1

Preparation of 3-amino-N-(2,6-dimethyl-4-(perfluoropropan-2-yl)phenyl)benzamide

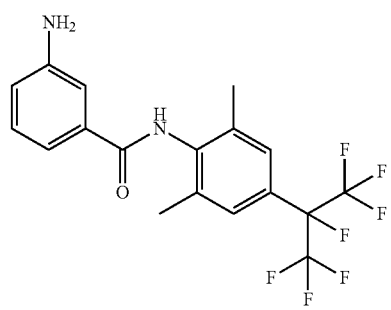 [SMILES: Cc1cc(C(F)(C(F)(F)F)C(F)(F)F)cc(C)c1NC(=O)c1cccc(N)c1]

According to the method of 1-3 of Example 1, a target compound was prepared from N-(2,6-dimethyl-4-(perfluoropropan-2-yl)phenyl)-3-nitrobenzamide obtained in 5-1 of Example 5.

$^1$H-NMR (CDCl$_3$, ppm) δ 2.34 (6H, s), 3.87 (2H, broad-s), 6.86-6.89 (1H, m), 7.20-7.35 (6H, m)

20-2

Preparation of 3-(3-amino-3-oxopropylamino)-N-(2,6-dimethyl-4-(perfluoropropan-2-yl)phenyl)benzamide (Compound No. 18-1)

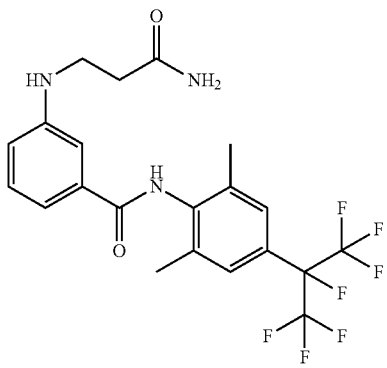 [SMILES: Cc1cc(C(F)(C(F)(F)F)C(F)(F)F)cc(C)c1NC(=O)c1cccc(NCCC(N)=O)c1]

1.00 g (2.28 mmol) of 3-amino-N-(2,6-dimethyl-4-(perfluoropropan-2-yl)phenyl)benzamide was charged to 3 ml of acetic acid, and 2.51 g (2.51 mmol) of acryl amide was added thereto, followed by stirring at 70° C. for 5 hours. After cooling to room temperature, the mixture was discharged to water, followed by neutralization with potassium carbonate. After extraction with ethyl acetate, the residue was dried over anhydrous magnesium sulfate, and the solvent was evaporated under reduced pressure. The obtained residue was purified by silica gel column chromatography (developing solvent; hexane:ethyl acetate=3:1→1:3→0:1) to prepare 0.650 g (yield 56%) of a target compound.

$^1$H-NMR (CDCl$_3$, ppm) δ 2.33 (6H, s), 2.52 (2H, t, J=5.8 Hz), 3.51 (2H, t, J=5.8 Hz), 4.45 (1H, broad-s), 5.54 (1H, broad-s), 5.73 (1H, broad-s), 6.81 (1H, d, J=8.3 Hz), 7.17-7.21 (2H, m), 7.28-7.30 (1H, m), 7.34 (2H, s), 7.54-7.59 (1H, m).

20-3

Preparation of N-(3-amino-3-oxopropyl)-N-(3-(2,6-dimethyl-4-(perfluoropropan-2-yl)phenylcarbamoyl)phenyl)benzamide (Compound No. 1-1)

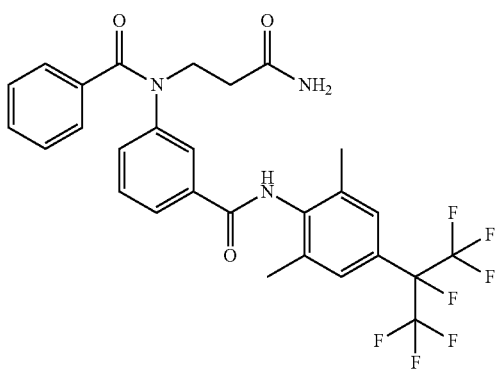 [SMILES: Cc1cc(C(F)(C(F)(F)F)C(F)(F)F)cc(C)c1NC(=O)c1cccc(N(CCC(N)=O)C(=O)c2ccccc2)c1]

According to the method of 1-5 of Example 1, a target compound was prepared from 3-(3-amino-3-oxopropylamino)-N-(2,6-dimethyl-4-(perfluoropropan-2-yl)phenyl)benzamide.

$^1$H-NMR (CDCl$_3$, ppm) δ 2.28 (6H, s), 2.71 (2H, t, J=6.8 Hz), 4.30 (2H, t, J=6.8 Hz), 5.43 (1H, broad-s), 6.17 (1H, broad-s), 7.17-7.37 (9H, m), 7.66 (1H, broad-s), 7.70-7.73 (2H, m).

Example 21

Preparation of 3-(N-(3-amino-3-oxopropyl)benzamide)-N-(2,6-dimethyl-4-(perfluoropropan-2-yl)phenyl)-2-fluorobenzamide (Compound No. 1-21)

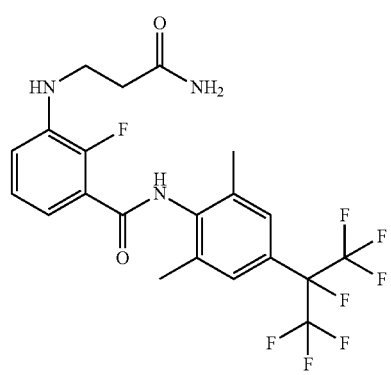 [SMILES: Cc1cc(C(F)(C(F)(F)F)C(F)(F)F)cc(C)c1NC(=O)c1cccc(NCCC(N)=O)c1F]

21-1

Preparation of 3-(3-amino-3-oxopropylamino)-N-(2,6-dimethyl-4-(perfluoropropan-2-yl)phenyl)-2-fluorobenzamide (Compound No. 18-42)

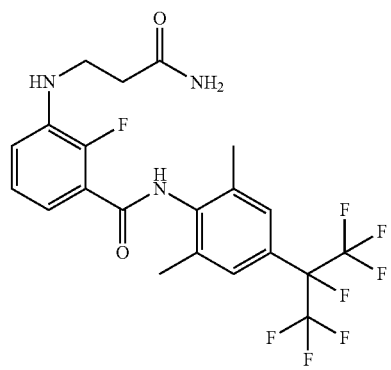 [SMILES: Cc1cc(C(F)(C(F)(F)F)C(F)(F)F)cc(C)c1NC(=O)c1cccc(NCCC(N)=O)c1F]

According to the method of 20-3 of Example 20, a target compound was prepared from 3-amino-N-(2,6-dimethyl-4-(perfluoropropan-2-yl)phenyl)-2-fluorobenzamide obtained in 1-3 of Example 1.

$^1$H-NMR (CDCl$_3$, ppm) δ 2.36 (6H, s), 2.57-2.60 (2H, m), 3.54-3.57 (2H, m), 4.64 (1H, broad-s), 5.48 (1H, broad-s), 5.61 (1H, broad-s), 6.89-6.94 (1H, m), 7.15 (1H, t, J=7.8 Hz), 7.35-7.39 (3H, m), 7.84 (1H, broad-d, J=12.7 Hz).

21-2

Preparation of 3-(N-(3-amino-3-oxopropyl)benzamide)-N-(2,6-dimethyl-4-(perfluoropropan-2-yl)phenyl)-2-fluorobenzamide (Compound No. 1-21)

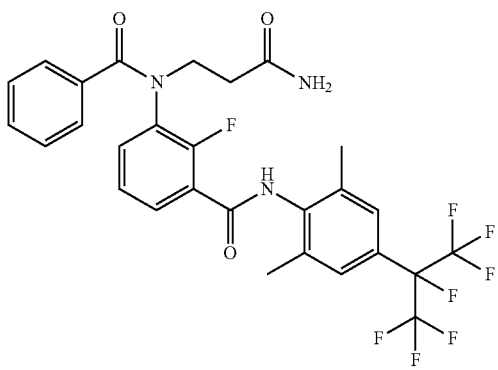 [SMILES: Cc1cc(C(F)(C(F)(F)F)C(F)(F)F)cc(C)c1NC(=O)c1cccc(N(CCC(N)=O)C(=O)c2ccccc2)c1F]

According to the method of 1-5 of Example 1, a target compound was prepared from 3-(3-amino-3-oxopropylamino)-N-(2,6-dimethyl-4-(perfluoropropan-2-yl)phenyl)-2-fluorobenzamide.

$^1$H-NMR (CDCl$_3$, ppm) δ 2.26 (6H, s), 2.60 (1H, broad-s), 2.75 (1H, broad-s), 4.22-4.23 (2H, m), 5.45 (1H, broad-s), 6.03 (1H, broad-s), 7.19-7.34 (8H, m), 7.49-7.52 (2H, m), 7.90-7.96 (1H, m).

Example 22

Preparation of 3-(N-(3-amino-3-oxopropyl)benzamide)-N-(2-bromo-4-(perfluoropropan-2-yl)-6-(trifluoromethyl)phenyl)-2-fluorobenzamide (Compound No. 1-171)

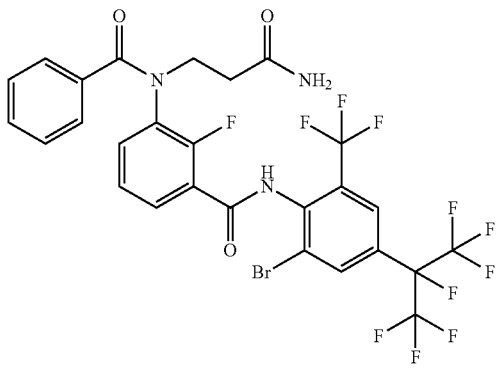 [SMILES: NC(=O)CCN(C(=O)c1ccccc1)c1cccc(C(=O)Nc2c(Br)cc(C(F)(C(F)(F)F)C(F)(F)F)cc2C(F)(F)F)c1F]

22-1

Preparation of 4-(perfluoropropan-2-yl)-2-(trifluoromethyl)aniline (Compound No. 21-2)

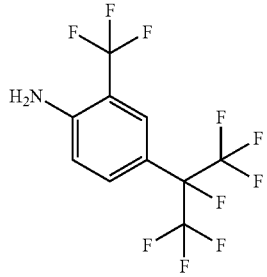 [SMILES: Nc1ccc(C(F)(C(F)(F)F)C(F)(F)F)cc1C(F)(F)F]

100 g (0.608 mol) of 2-(trifluoromethyl)aniline, 131 g (0.639 mol) of 85% sodium hydrosulfite, and 20.9 g (0.0608 mol) of tetrabutylammonium hydrogen sulfate were charged into a mixed solution of 1500 ml of ethyl acetate and 1500 ml of water, and 53.9 g (0.639 mol) of sodium hydrogen carbonate was added thereto. 198 g (0.669 mol) of heptafluoroisopropyliodide was added dropwise thereto at room temperature, followed by stirring at room temperature for 6 hours. After the liquid separation, the solvent of the organic layer was evaporated under reduced pressure, and 500 ml of ethyl acetate was charged thereto. 160 g (0.608 mol) of a 4 N hydrogen chloride/ethyl acetate solution was added dropwise thereto, followed by stirring at room temperature for 30 minutes, followed by stirring at 5° C. for 1 hour. The precipitated solid was removed by filtration, then the filtrate was washed with water and a saturated aqueous sodium hydrogen carbonate solution in this order, and then dried over anhydrous magnesium sulfate, and the solvent was evaporated under reduced pressure. The obtained residue was purified by silica gel column chromatography (developing solvent; hexane:ethyl acetate=10:1) to prepare 60.0 g (yield 30%) of a target compound.

$^1$H-NMR (CDCl$_3$, ppm) δ 4.49 (2H, broad-s), 6.81 (1H, d, J=8.3 Hz), 7.48 (1H, d, J=8.3 Hz), 7.64 (1H, s).

22-2

Preparation of 2-bromo-4-(perfluoropropan-2-yl)-6-(trifluoromethyl)aniline (Compound No. 21-9)

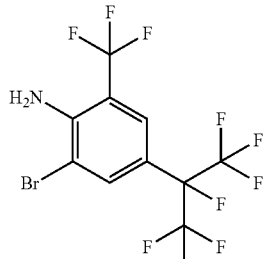

100 g (0.273 mol) of 4-(perfluoropropan-2-yl)-2-(trifluoromethyl)aniline was charged to 500 ml of DMF, and 52.1 g (0.287 mol) of N-bromosuccinimide was charged in separate portions thereto over 30 minutes. After stirring 60° C. for 2 hours, the mixture was cooled to room temperature, and the mixture was discharged to 2000 ml of water. The mixture was extracted with ethyl acetate, washed with saturated brine, and dried over anhydrous magnesium sulfate. The solvent was evaporated under reduced pressure and the obtained residue was purified by silica gel column chromatography (developing solvent; hexane:ethyl acetate=20:1) to prepare 89.0 g (yield 80%) of a target compound.

$^1$H-NMR (CDCl$_3$, ppm) δ 5.03 (2H, broad-s), 7.61 (1H, s), 7.79 (1H, s).

22-3

Preparation of N-(2-bromo-4-(perfluoropropan-2-yl)-6-(trifluoromethyl)phenyl)-2-chloro-3-nitrobenzamide (Compound No. 11-38)

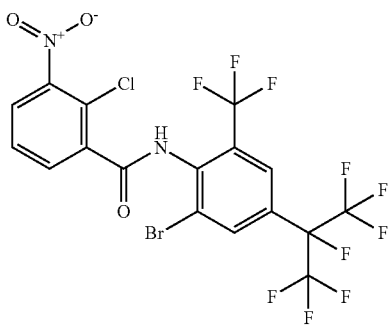 [SMILES: O=C(Nc1c(Br)cc(C(F)(C(F)(F)F)C(F)(F)F)cc1C(F)(F)F)c1cccc([N+](=O)[O-])c1Cl]

3.60 g (8.82 mmol) of 2-bromo-4-(perfluoropropan-2-yl)-6-(trifluoromethyl)aniline was charged to 20 ml of anhydrous THF, followed by cooling to −70° C. under a nitrogen atmosphere. 4.85 ml (9.70 mmol) of a 2.0 M lithium diisopropyl amide hexane solution was added dropwise thereto, and then dissolved in 5 nil of anhydrous THF, and 2.34 g (10.7 mmol) of an acid chloride prepared form 2-chloro-3-nitrobenzoic acid and thionyl chloride was added dropwise thereto, followed by stirring at −70° C. for 30 minutes and then stirring at room temperature for 30 minutes. The mixture was discharged to an aqueous ammonium chloride solution, then extracted with ethyl acetate, and dried over anhydrous magnesium sulfate. The solvent was evaporated under reduced pressure and the obtained residue was purified by silica gel column chromatography (developing solvent; hexane:ethyl acetate=10:1→8:2→3:1) to prepare 1.76 g (yield: 34%) of a target compound.

$^1$H-NMR (CDCl$_3$, ppm) δ 7.61 (1H, t, J=7.8 Hz), 7.67 (1H, broad-s), 7.93-7.97 (3H, m), 8.18 (1H, broad-s).

22-4

Preparation of N-(2-bromo-4-(perfluoropropan-2-yl)-6-(trifluoromethyl)phenyl)-2-fluoro-3-nitrobenzamide (Compound No. 11-65)

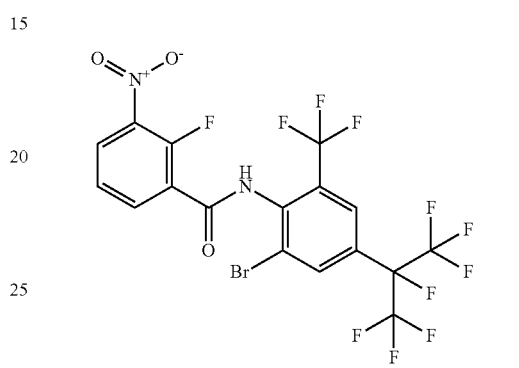

According to the method of 1-2 of Example 1, a target compound was prepared from N-(2-bromo-4-(perfluoropropan-2-yl)-6-(trifluoromethyl)phenyl)-2-chloro-3-nitrobenzamide.

$^1$H-NMR (CDCl$_3$, ppm) δ 7.53 (1H, t, J=7.3 Hz), 7.93 (1H, broad-s), 8.17-8.18 (2H, m), 8.28-8.32 (1H, m), 8.44-8.48 (1H, m).

22-5

Preparation of 3-amino-N-(2-bromo-4-(perfluoropropan-2-yl)-6-(trifluoromethyl)phenyl)-2-fluorobenzamide (Compound No. 12-37)

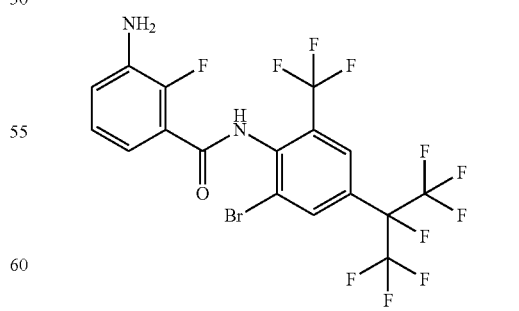

According to the method of 1-3 of Example 1, a target compound was prepared from N-(2-bromo-4-(perfluoropropan-2-yl)-6-(trifluoromethyl)phenyl)-2-fluoro-3-nitrobenzamide.

¹H-NMR (CDCl₃, ppm) δ 3.93 (2H, broad-s), 6.99-7.04 (1H, m), 7.11 (1H, t, J=7.8 Hz), 7.47-7.49 (1H, m), 7.91 (1H, s), 8.14 (1H, s), 8.28 (1H, d, J=14.6 Hz).

22-6

Preparation of 3-(3-amino-3-oxopropylamino)-N-(2-bromo-4-(perfluoropropan-2-yl)-6-(trifluoromethyl)phenyl)-2-fluorobenzamide (Compound No. 18-48)

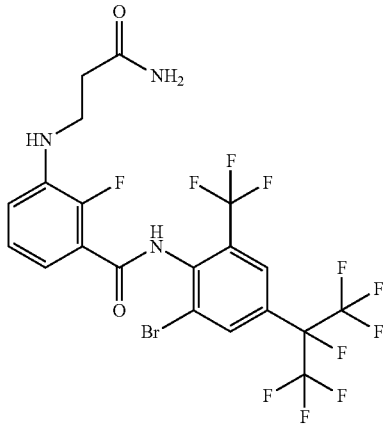 [SMILES: NC(=O)CCNc1cccc(C(=O)Nc2c(Br)cc(C(F)(C(F)(F)F)C(F)(F)F)cc2C(F)(F)F)c1F]

According to the method of 20-3 of Example 20, a target compound was prepared from 3-amino-N-(2-bromo-4-(perfluoropropan-2-yl)-6-(trifluoromethyl)phenyl)-2-fluorobenzamide.

¹H-NMR (CDCl₃, ppm) δ 2.58-2.61 (2H, m), 3.55-3.59 (2H, m), 4.60 (1H, broad-s), 5.40 (1H, broad-s), 5.60 (1H, broad-s), 6.96-6.98 (1H, m), 7.15-7.19 (1H, m), 7.39-7.43 (1H, m), 7.91 (1H, s), 8.13 (1H, s), 8.26 (1H, d, J=14.6 Hz).

22-7

Preparation of 3-(N-(3-amino-3-oxopropyl)benzamide)-N-(2-bromo-4-(perfluoropropan-2-yl)-6-(trifluoromethyl)phenyl)-2-fluorobenzamide (Compound No. 1-171)

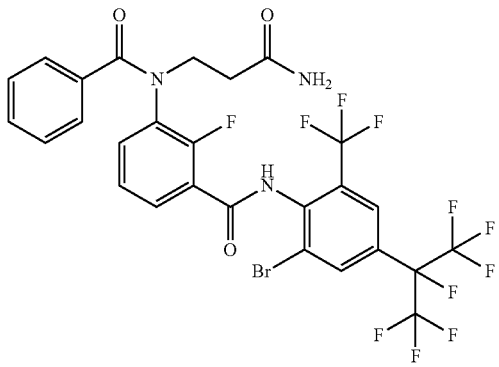 [SMILES: NC(=O)CCN(C(=O)c1ccccc1)c1cccc(C(=O)Nc2c(Br)cc(C(F)(C(F)(F)F)C(F)(F)F)cc2C(F)(F)F)c1F]

According to the method of 1-5 of Example 1, a target compound was prepared from 3-(3-amino-3-oxopropylamino)-N-(2-bromo-4-(perfluoropropan-2-yl)-6-(trifluoromethyl)phenyl)-2-fluorobenzamide.

¹H-NMR (CDCl₃, ppm) δ 2.55-2.80 (2H, m), 4.22-4.26 (2H, m), 5.45 (1H, broad-s), 6.00 (1H, broad-s), 7.21-7.30 (6H, m), 7.52-7.57 (1H, m), 7.89-8.12 (4H, m), Example 23

Preparation of 3-(N-(3-amino-3-oxopropyl)benzamide)-N-(2,6-dibromo-4-(perfluoropropan-2-yl)phenyl)-2-fluorobenzamide (Compound No. 1-163)

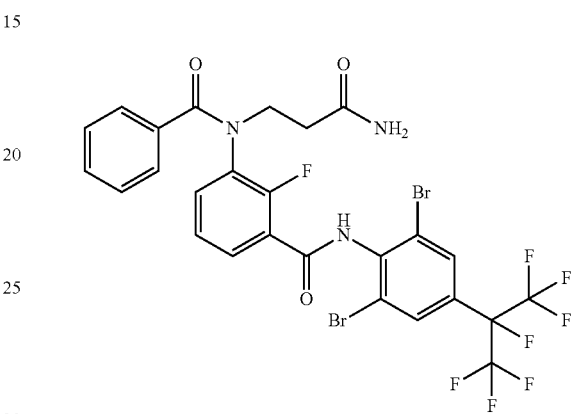

23-1

Preparation of 2,6-dibromo-4-(perfluoropropan-2-yl)aniline

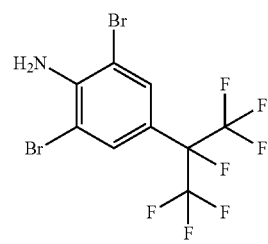 [SMILES: Nc1c(Br)cc(C(F)(C(F)(F)F)C(F)(F)F)cc1Br]

216 g (0.802 mol) of 4-(perfluoropropan-2-yl)aniline was charged to 863 ml of DMF, followed by cooling to 5° C. 285 g (1.60 mol) of N-bromosuccinimide was charged in separate portions thereto over 1 hour. The mixture was stirred at room temperature for 1 hour and stirred at 37° C. for 2 hours. The mixture was discharged to 2000 ml of water, extracted with 2000 ml of ethyl acetate, and washed with 1000 ml of saturated brine. After drying over anhydrous magnesium sulfate, the solvent was evaporated under reduced pressure. The obtained residue was purified by silica gel column chromatography (developing solvent; hexane:ethyl acetate=20:1) to prepare 304 g (yield 90%) of a target compound.

¹H-NMR (CDCl₃, ppm) δ 4.88 (2H, broad-s), 7.59 (2H, s).

23-2

Preparation of 2-chloro-N-(2,6-dibromo-4-(perfluoropropan-2-yl)phenyl)-3-nitrobenzamide (Compound No. 11-24)

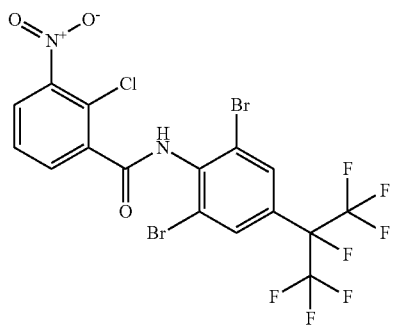 [SMILES: O=C(Nc1c(Br)cc(C(F)(C(F)(F)F)C(F)(F)F)cc1Br)c1cccc([N+](=O)[O-])c1Cl]

According to the method of 22-3 of Example 22, a target compound was prepared from 2,6-dibromo-4-(perfluoropropan-2-yl)aniline.

$^1$H-NMR (CDCl$_3$, ppm) δ 7.58 (1H, t, J=7.8 Hz), 7.66 (1H, broad-s), 7.90 (2H, s), 7.93 (1H, dd, J=1.5, 7.8 Hz), 7.98 (1H, d, J=7.8 Hz).

23-3

Preparation of N-(2,6-dibromo-4-(perfluoropropan-2-yl)phenyl)-2-fluoro-3-nitrobenzamide (Compound No. 11-51)

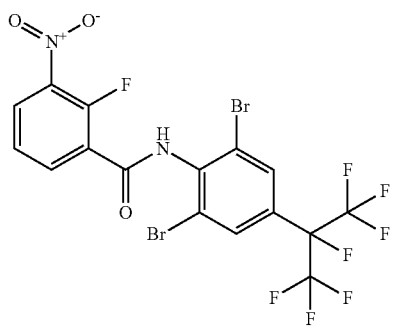 [SMILES: O=C(Nc1c(Br)cc(C(F)(C(F)(F)F)C(F)(F)F)cc1Br)c1cccc([N+](=O)[O-])c1F]

According to the method of 1-2 of Example 1, a target compound was prepared from 2-chloro-N-(2,6-dibromo-4-(perfluoropropan-2-yl)phenyl)-3-nitrobenzamide.

$^1$H-NMR (CDCl$_3$, ppm) δ 7.51-7.55 (1H, m), 7.90 (2H, s), 8.16 (1H, d, J=11.7 Hz), 8.27-8.31 (1H, m), 8.48 (1H, t, J=6.3 Hz).

23-4

Preparation of 3-amino-N-(2,6-dibromo-4-(perfluoropropan-2-yl)phenyl)-2-fluorobenzamide (Compound No. 12-26)

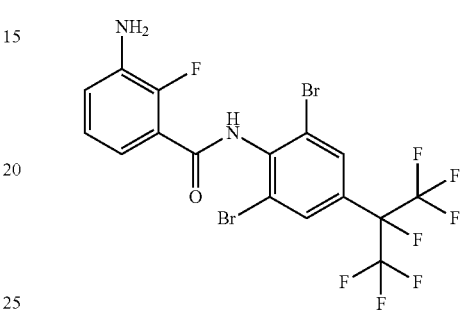

According to the method of 1-3 of Example 1, a target compound was prepared from N-(2,6-dibromo-4-(perfluoropropan-2-yl)phenyl)-2-fluoro-3-nitrobenzamide.

$^1$H-NMR (CDCl$_3$, ppm) δ 3.93 (2H, broad-s), 6.99-7.04 (1H, m), 7.11 (1H, t, J=7.8 Hz), 7.47-7.49 (1H, m), 7.91 (1H, s), 8.14 (1H, s), 8.28 (1H, d, J=14.6 Hz).

23-5

Preparation of 3-(3-amino-3-oxopropylamino)-N-(2,6-dibromo-4-(perfluoropropan-2-yl)phenyl)-2-fluorobenzamide (Compound No. 18-44)

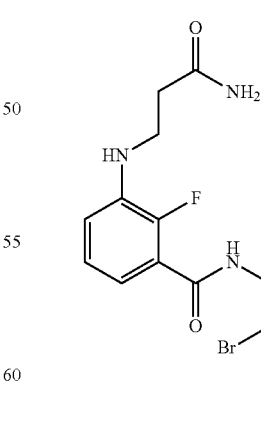

According to the method of 20-3 of Example 20, a target compound was prepared from 3-amino-N-(2,6-dibromo-4-(perfluoropropan-2-yl)phenyl)-2-fluorobenzamide.

¹H-NMR (CDCl₃, ppm) δ 2.55-2.61 (2H, m), 3.54-3.57 (2H, m), 4.60 (1H, broad-s), 5.69-5.74 (2H, m), 6.90-6.98 (1H, m), 7.16 (1H, t, J=7.8 Hz), 7.35-7.45 (1H, m), 7.87 (2H, s), 8.24 (1H, d, J=14.1 Hz).

23-6

Preparation of 3-(N-(3-amino-3-oxopropyl)benzamide)-N-(2,6-dibromo-4-(perfluoropropan-2-yl)phenyl)-2-fluorobenzamide (Compound No. 1-163)

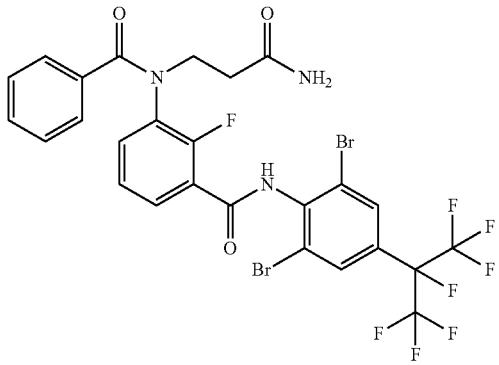 [SMILES: NC(=O)CCN(C(=O)c1ccccc1)c1cccc(C(=O)Nc2c(Br)cc(C(F)(C(F)(F)F)C(F)(F)F)cc2Br)c1F]

According to the method of 1-5 of Example 1, a target compound was prepared from 3-(3-amino-3-oxopropylamino)-N-(2,6-dibromo-4-(perfluoropropan-2-yl)phenyl)-2-fluorobenzamide ¹H-NMR (CDCl₃, ppm) δ 2.68 (1H, broad-s), 2.83 (1H, broad-s), 4.24 (2H, t, J=6.8 Hz), 5.42 (1H, broad-s), 6.02 (1H, broad-s), 7.18-7.22 (2H, m), 7.26-7.34 (4H, m), 7.55-7.56 (1H, m), 7.85 (2H, s), 7.94-8.00 (2H, m).

Example 24

Preparation of N-(2-cyanoethyl)-N-(3-(2,6-dimethyl-4-(perfluoropropan-2-yl)phenylcarbamoyl)phenyl)benzamide (Compound No. 5-8)

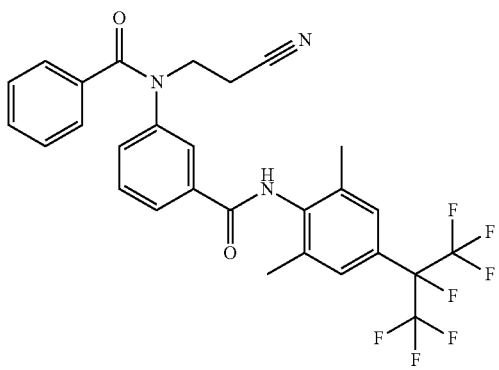 [SMILES: Cc1cc(C(F)(C(F)(F)F)C(F)(F)F)cc(C)c1NC(=O)c1cccc(N(CCC#N)C(=O)c2ccccc2)c1]

To 5 ml of DMF was added 0.300 g (2.36 mmol) of N-(3-amino-3-oxopropyl)-N-(3-(2,6-dimethyl-4-(perfluoropropan-2-yl)phenylcarbamoyl)phenyl)benzamide obtained in 20-3 of Example 20, and 1.01 g (1.73 mmol) of oxalyl chloride was added thereto under stirring, followed by stirring at room temperature for 1 hour. The reaction solution was poured into cold water for quenching, followed by extraction with ethyl acetate, then washed with a saturated aqueous sodium hydrogen carbonate solution saturated brine, and dried over anhydrous magnesium sulfate, and then the solvent was evaporated under reduced pressure. The obtained residue was purified by silica gel column chromatography (developing solvent; hexane:ethyl acetate=2:1→1:1) to prepare 0.950 g (yield 97%) of a target compound.

¹H-NMR (CDCl₃, ppm) δ 2.26 (6H, s), 2.93 (2H, t, J=6.3 Hz), 4.23 (2H, t, J=6.3 Hz), 7.20-7.37 (9H, m), 7.44-7.45 (1H, m), 7.68 (1H, s), 7.42 (1H, d, J=7.8 Hz).

Example 25

Preparation of N-(3-aminopropyl)-N-(3-(2,6-dimethyl-4-(perfluoropropan-2-yl)phenylcarbamoyl)phenyl)benzamide (Compound No. 6-20)

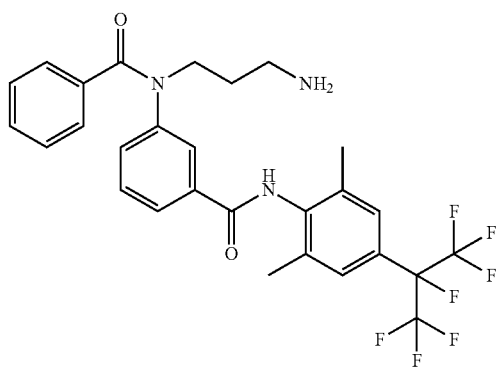 [SMILES: Cc1cc(C(F)(C(F)(F)F)C(F)(F)F)cc(C)c1NC(=O)c1cccc(N(CCCN)C(=O)c2ccccc2)c1]

To 20 ml of isoisopropanol were added 0.750 g (1.33 mmol) of N-(2-cyanoethyl)-N-(3-(2,6-dimethyl-4-(perfluoropropan-2-yl)phenylcarbamoyl)phenyl)benzamide obtained in Example 24, 0.500 g (7.93 mmol) of ammonium formate, 1.60 g (26.6 mmol) of acetic acid, and 0.200 g of 10% Pd/C, followed by stirring at room temperature for 10 hours. The catalyst was filtered, and the solution was neutralized by the addition of an aqueous sodium hydrogen carbonate solution. The solution was extracted with ethyl acetate, then washed with saturated brine, and dried over anhydrous magnesium sulfate, and then the solvent was evaporated under reduced pressure. The obtained residue was purified by silica gel column chromatography (developing solvent; ethyl acetate) to prepare 0.520 g (yield 69%) of a target compound.

¹H-NMR (CDCl₃, ppm) δ 1.83 (6H, s), 1.89 (2H, broad-s), 3.31 (2H, t, J=7.3 Hz), 4.09 (2H, t, J=7.3 Hz), 7.18-7.36 (9H, m), 7.69-7.71 (2H, m), 7.89 (1H, s). The proton presumed to be indicative of NH$_2$ was not detected.

Example 26

Preparation of methyl 3-(N-(3-(2,6-dimethyl-4-(perfluoropropan-2-yl)phenylcarbamoyl)phenyl)benzamide)propanoate (Compound No. 5-1)

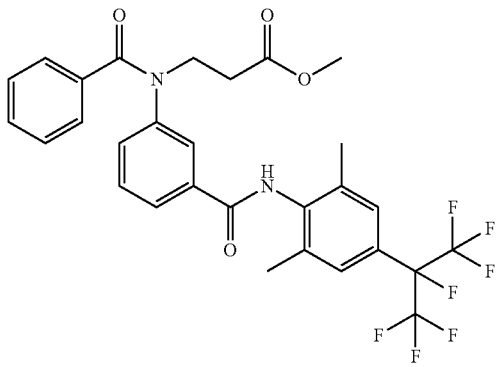 [SMILES: COC(=O)CCN(C(=O)c1ccccc1)c1cccc(C(=O)Nc2c(C)cc(C(F)(C(F)(F)F)C(F)(F)F)cc2C)c1]

26-1

Preparation of methyl 3-(3-(2,6-dimethyl-4-(perfluoropropan-2-yl)phenylcarbamoyl)phenylamino)propanoate

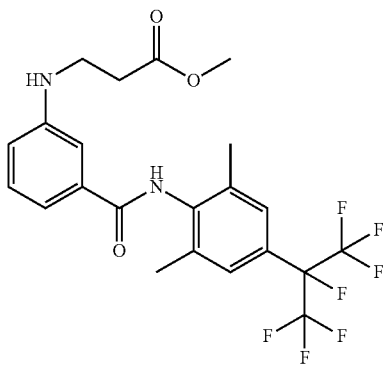 [SMILES: COC(=O)CCNc1cccc(C(=O)Nc2c(C)cc(C(F)(C(F)(F)F)C(F)(F)F)cc2C)c1]

To 30 ml of an anhydrous THF solution of 3.00 g (7.35 mmol) of 3-amino-N-(2,6-dimethyl-4-(perfluoropropan-2-yl)phenyl)benzamide obtained in 20-1 of Example 20 were added 0.760 g (8.82 mmol) of methyl acrylate and 3.69 ml (29.4 mmol) of a borane trifluoride diethyl ether complex, followed by stirring at 60° C. for 8 hours, while 0.700 g (8.13 mmol) of methyl acrylate was added thereto three times. Water was added to the reaction liquid, and the solvent was evaporated under reduced pressure. Then, the residue was dissolved in ethyl acetate. The organic layer was washed with a saturated aqueous sodium hydrogen carbonate solution and saturated brine, and then dried over anhydrous magnesium sulfate. The solvent was evaporated under reduced pressure and the obtained residue was purified by silica gel column chromatography (developing solvent; hexane:ethyl acetate=8:1) to prepare 0.100 g (yield 3%) of a target compound.

$^1$H-NMR (CDCl$_3$, ppm) δ 2.34 (6H, s), 2.63-2.67 (2H, m), 3.52 (2H, t, J=6.3 Hz), 3.71 (3H, s), 4.30 (1H, broad-s), 6.80-6.82 (1H, m), 7.15-7.19 (2H, m), 7.27-7.31 (1H, m), 7.34 (2H, s), 7.38 (1H, s).

26-2

Preparation of methyl 3-(N-(3-(2,6-dimethyl-4-(perfluoropropan-2-yl)phenylcarbamoyl)phenyl)benzamide)propanoate (Compound No. 5-1)

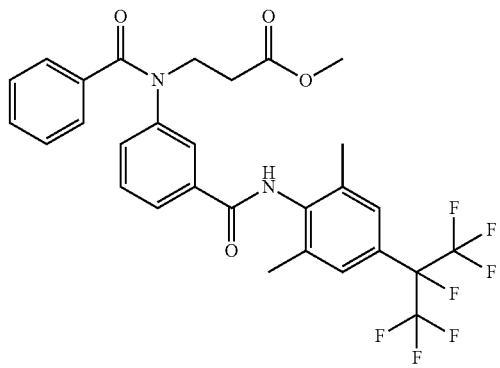 [SMILES: COC(=O)CCN(C(=O)c1ccccc1)c1cccc(C(=O)Nc2c(C)cc(C(F)(C(F)(F)F)C(F)(F)F)cc2C)c1]

According to the method of 1-5 of Example 1, a target compound was prepared from methyl 3-(3-(2,6-dimethyl-4-(perfluoropropan-2-yl)phenylcarbamoyl)phenylamino)propanoate.

$^1$H-NMR (CDCl$_3$, ppm) δ 2.27 (6H, s), 2.77 (2H, t, J=6.8 Hz), 3.61 (3H, s), 4.30 (2H, t, J=6.8 Hz), 7.18-7.34 (9H, m), 7.39-7.40 (1H, m), 7.58 (1H, s), 7.70 (1H, d, J=7.3 Hz).

Example 27

Preparation of 3-(N-(3-(2,6-dimethyl-4-(perfluoropropan-2-yl)phenylcarbamoyl)phenyl)benzamide)propanoic acid (Compound No. 5-4)

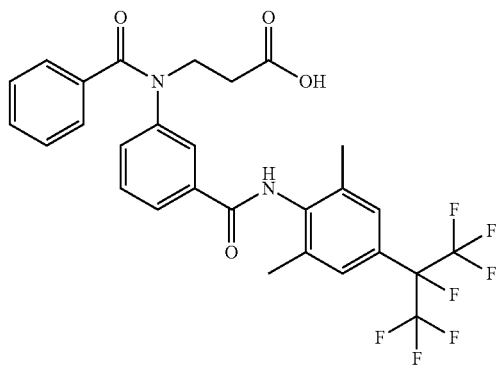 [SMILES: Cc1cc(C(F)(C(F)(F)F)C(F)(F)F)cc(C)c1NC(=O)c1cccc(N(CCC(=O)O)C(=O)c2ccccc2)c1]

According to the method of Example 2, a target compound was prepared from methyl 3-(N-(3-(2,6-dimethyl-4-(perfluoropropan-2-yl)phenylcarbamoyl)phenyl)benzamide)propanoate obtained in 26-2 of Example 26.

$^1$H-NMR (DMSO-d$_6$, ppm) δ 2.19 (6H, s), 2.57 (2H, t, J=7.3 Hz), 4.08 (2H, t, J=7.3 Hz), 7.21-7.26 (5H, m), 7.41-7.42 (4H, m), 7.73 (2H, s), 9.89 (1H, s).

The proton presumed to be indicative of the carboxylic acid was not detected.

Example 28

Preparation of tert-butyl 2-(3-(2,6-dimethyl-4-(perfluoropropan-2-yl)phenylcarbamoyl)phenyl)-14,14-dimethyl-1,5,12-trioxo-1-phenyl-13-oxa-2,6,11-triazapentadecane-10-carboxylate (Compound No. 5-15)

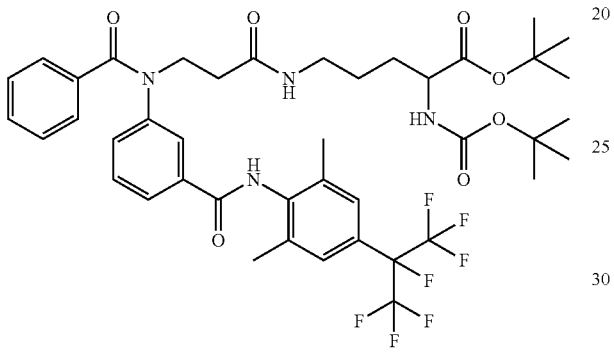

0.300 g (0.510 mmol) of 3-(N-(3-(2,6-dimethyl-4-(perfluoropropan-2-yl)phenylcarbamoyl)phenyl)benzamide) propanoic acid obtained in Example 27 and 0.1 ml of DMF were added to 10 ml of dichloromethane, and 0.0500 ml (0.620 mmol) of oxalyl chloride was added thereto, followed by stirring at 40° C. for 2 hours. The solvent was evaporated under reduced pressure and the obtained residue was added to 0.170 g (0.510 mmol) of a tert-butyl 5-amino-2-(tert-butoxycarbonylamino)pentanoate hydrochloric acid salt, and a solution of 0.150 g (1.53 mmol) of triethylamine in 10 ml of THF, followed by stirring at room temperature for 2 hours. To the reaction liquid was added ethyl acetate, and the organic layer was washed with a saturated aqueous sodium hydrogen carbonate solution and saturated brine, and then dried over anhydrous magnesium sulfate. The solvent was evaporated under reduced pressure and the obtained residue was purified by silica gel column chromatography (developing solvent; hexane:ethyl acetate=1:2) to prepare 0.450 g (yield: quantitative) of a target compound.

$^{1}$H-NMR (CDCl$_{3}$, ppm) δ 1.41-1.45 (18H, m), 1.56-1.59 (2H, m), 1.68-1.69 (1H, m), 2.04 (6H, s), 2.66-2.69 (2H, m), 3.35-3.36 (2H, m), 4.20-4.24 (1H, m), 4.25-4.29 (2H, m), 5.10-5.11 (1H, m), 6.40-6.41 (1H, m), 7.19-7.21 (3H, m), 7.24-7.29 (5H, m), 7.38-7.39 (2H, m), 7.77 (1H, s), 7.94-7.95 (1H, m).

One proton presumed to be indicative of NH was not detected.

Example 29

Preparation of a 2-amino-5-(3-(N-(3-(2,6-dimethyl-4-(perfluoropropan-2-yl)phenylcarbamoyl)phenyl)benzamide)propane amide)pentanoic acid hydrochloric acid salt (Compound No. 5-24)

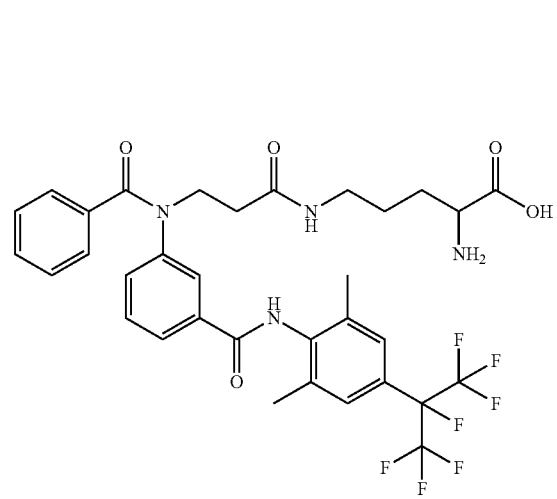 [SMILES: Cc1cc(C(F)(C(F)(F)F)C(F)(F)F)cc(C)c1NC(=O)c1cccc(N(CCC(=O)NCCCC(N)C(=O)O)C(=O)c2ccccc2)c1]

To 0.350 g (0.410 mmol) of tert-butyl 2-(3-(2,6-dimethyl-4-(perfluoropropan-2-yl)phenylcarbamoyl)phenyl)-14,14-dimethyl-1,5,12-trioxo-1-phenyl-13-oxa-2,6,11-triazapentadecane 10-carboxylate prepared in Example 28 was added 2.00 ml (8.20 mmol) of a 4 N hydrogen chloride/ethyl acetate solution, followed by stirring at room temperature for 4 hours and leaving to stand overnight. The solvent was evaporated under reduced pressure and the obtained residue was washed with IPE to prepare 0.240 g (yield 80%) of a target compound.

$^{1}$H-NMR (DMSO-d$_{6}$, ppm) δ 1.45-1.50 (2H, m), 1.50-1.52 (2H, m), 2.20 (6H, s), 2.46-2.47 (2H, m), 2.99 (2H, t, J=6.3 Hz), 4.10 (2H, t, J=7.3 Hz), 7.23-7.28 (5H, m), 7.41-7.42 (4H, m), 7.78 (2H, s), 8.15-8.16 (1H, m), 8.33-8.34 (3H, m), 10.05 (1H, s). The proton presumed to be indicative of the carboxylic acid was not detected.

Example 30

Preparation of tert-butyl 2-(tert-butoxycarbonylamino)-3-(3-(N-(3-(2,6-dimethyl-4-(perfluoropropan-2-yl)phenylcarbamoyl)phenyl)benzamide)propanoyloxy)propanoate (Compound No. 5-22)

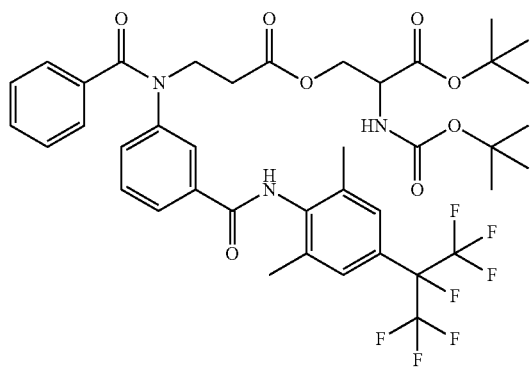 [SMILES: Cc1cc(C(F)(C(F)(F)F)C(F)(F)F)cc(C)c1NC(=O)c1cccc(N(CCC(=O)OCC(NC(=O)OC(C)(C)C)C(=O)OC(C)(C)C)C(=O)c2ccccc2)c1]

According to the method of Example 28, a target compound was prepared from 3-(N-(3-(2,6-dimethyl-4-(perfluoropropan-2-yl)phenylcarbamoyl)phenyl)benzamide)propanoic acid obtained in Example 27 and tert-butyl 2-(tert-butoxycarbonylamino)-3-hydroxypropanoate.

$^1$H-NMR (CDCl$_3$, ppm) δ 1.38 (9H, s), 1.42 (9H, s), 2.26 (6H, s), 2.77-2.78 (2H, m), 4.23-4.33 (5H, m), 5.40 (1H, m), 7.25-7.33 (8H, m), 7.39 (1H, m), 7.59 (1H, s), 7.73-7.75 (2H, m, J=3.9 Hz).

Example 31

Preparation of a 2-amino-3-(3-(N-(3-(2,6-dimethyl-4-(perfluoropropan-2-yl)phenylcarbamoyl)phenyl)benzamide)propanoyloxy)propanoic acid hydrochloric acid salt (Compound No. 5-25)

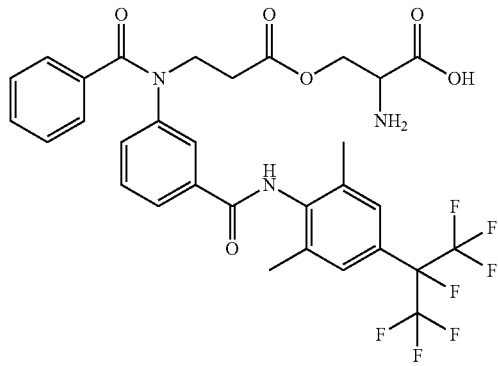 [SMILES: Cc1cc(C(F)(C(F)(F)F)C(F)(F)F)cc(C)c1NC(=O)c1cccc(N(CCC(=O)OCC(N)C(=O)O)C(=O)c2ccccc2)c1]

According to the method of Example 29, a target compound was prepared from tert-butyl 2-(tert-butoxycarbonylamino)-3-(3-(N-(3-(2,6-dimethyl-4-(perfluoropropan-2-yl)phenylcarbamoyl)phenyl)benzamide)propanoyloxy)propanoate obtained in Example 30.

$^1$H-NMR (DMSO-d$_6$, ppm) δ 2.22 (6H, s), 2.71-2.76 (2H, m), 4.13-4.19 (2H, m), 4.27-4.33 (2H, m), 4.48-4.51 (1H, m), 7.21-7.29 (5H, m), 7.40-7.43 (4H, m), 7.78-7.80 (2H, m), 8.50 (3H, broad-s), 10.07 (1H, s).

Example 32

Preparation of 3-(N-(3-(2-amino-2-oxoethylamino)-3-oxopropyl)-4-cyanobenzamide)-N-(2,6-dibromo-4-(perfluoropropan-2-yl)phenyl)-2-fluorobenzamide (Compound No. 5-31)

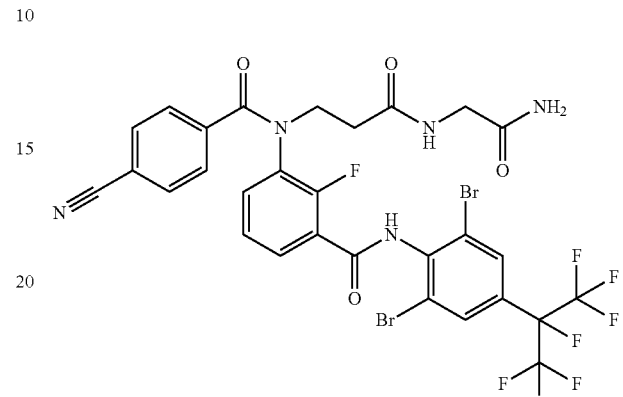

32-1

Preparation of 3-(3-(2,6-dibromo-4-(perfluoropropan-2-yl)phenylcarbamoyl)-2-fluorophenylamino)propanoic acid

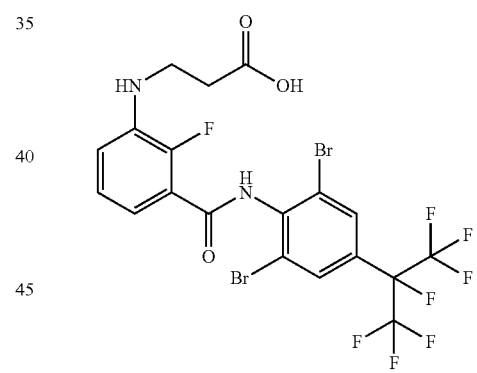

To 4.90 g (8.80 mmol) of 3-amino-N-(2,6-dibromo-4-(perfluoropropan-2-yl)phenyl)-2-fluorobenzamide obtained in 23-4 of Example 23 was added 6.50 g (90.2 mmol) of acrylic acid, followed by stirring at 60° C. for 1 hour and at 80° C. for 2 hours. To the reaction solution were added water and ethyl acetate, and the organic phase was extracted, washed with saturated brine, and dried over anhydrous magnesium sulfate, and then the solvent was evaporated under reduced pressure. Toluene was added to the residue for the purpose of removing an acrylic acid, and an operation for evaporating the solvent was repeated three times. The obtained residue was purified by silica gel column chromatography (developing solvent; hexane:ethyl acetate=3:1→2:1→1:1) to prepare 5.51 g (yield: quantitative) of a target compound.

$^1$H-NMR (CDCl$_3$, ppm) δ 2.75 (2H, t, J=6.3 Hz), 3.57 (2H, t, J=6.3 Hz), 6.92-6.97 (1H, m), 7.18-7.20 (1H, m), 7.42-7.45 (1H, m), 7.87 (2H, s), 8.19 (1H, d, J=13.7 Hz). The proton presumed to be indicative of NH and COOH was not detected.

32-2

Preparation of 3-(4-cyano-N-(3-(2,6-dibromo-4-(perfluoropropan-2-yl)phenylcarbamoyl)-2-fluorophenyl)benzamide)propanoic acid

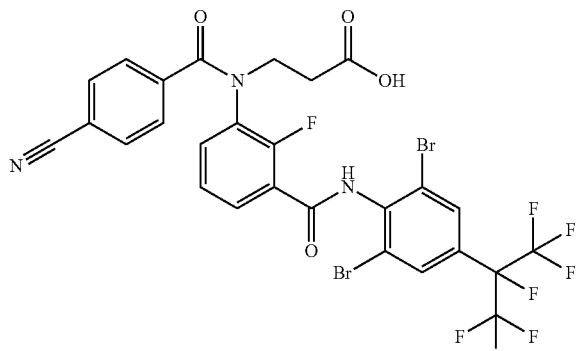

0.180 g (4.50 mmol) of sodium hydroxide was dissolved in 20 mL of water, and 1.00 g (1.59 mmol) of 3-(3-(2,6-dibromo-4-(perfluoropropan-2-yl)phenylcarbamoyl)-2-fluorophenylamino)propanoic acid and 0.530 g (3.20 mmol) of 4-cyanobenzoylchloride were added thereto, followed by stirring at room temperature for 1 day. To the reaction solution were added 4 M hydrochloric acid and ethyl acetate, the organic phase was extracted, washed with saturated brine, then dried over anhydrous magnesium sulfate, and the solvent was evaporated under reduced pressure. The obtained residue was purified by silica gel column chromatography (developing solvent; hexane:ethyl acetate=2:1→0:1) to prepare 0.430 g (yield: 36%) of a target compound.

$^1$H-NMR (CDCl$_3$+DMSO-d$_6$, ppm) δ 2.74-2.78 (2H, m), 4.20-4.22 (2H, m), 7.24 (1H, broad-d, J=4.4 Hz), 7.44-7.55 (4H, m), 7.69 (1H, broad-s), 7.87-7.90 (3H, m), 8.95 (1H, broad-d, J=4.4 Hz).

The proton presumed to be indicative of the carboxylic acid was not detected.

32-3

Preparation of 3-(N-(3-(2-amino-2-oxoethylamino)-3-oxopropyl)-4-cyanobenzamide)-N-(2,6-dibromo-4-(perfluoropropan-2-yl)phenyl)-2-fluorobenzamide (Compound No. 5-31)

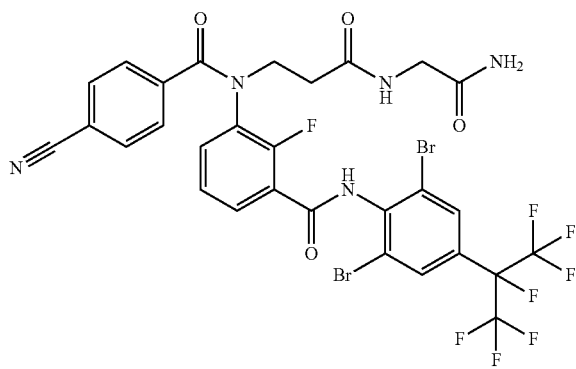 [SMILES: N#Cc1ccc(C(=O)N(CCC(=O)NCC(N)=O)c2cccc(C(=O)Nc3c(Br)cc(C(F)(C(F)(F)F)C(F)(F)F)cc3Br)c2F)cc1]

To 1 mL of DMF were added 0.120 g (0.160 mmol) of 3-(4-cyano-N-(3-(2,6-dibromo-4-(perfluoropropan-2-yl)phenylcarbamoyl)-2-fluorophenyl)benzamide)propanoic acid, 0.0260 g (0.190 mmol) of a 1-(3-dimethylaminopropyl)-3-ethylcarbodiimide hydrochloric acid salt, and 0.0250 g (0.190 mmol) of 1-hydroxybenzotriazole were added thereto under stirring, and a solution obtained by dissolving 0.0300 g (0.270 mmol) of a glycine amide hydrochloric acid salt and 0.0300 g (0.380 mmol) of triethylamine to 1 mL of DMF was slowly added dropwise thereto, followed by stirring at room temperature for 1 day. To the reaction solution were added 4 M hydrochloric acid and ethyl acetate, and the organic phase was extracted, washed with an aqueous sodium hydrogen carbonate solution and saturated brine, then dried over anhydrous magnesium sulfate. The solvent was evaporated under reduced pressure, and then the obtained residue was washed with IPE to prepare 0.0450 g (yield: 35%) of a target compound.

$^1$H-NMR (DMSO-d$_6$, ppm) δ 2.40-2.70 (2H, m), 3.56-3.58 (2H, m), 3.97 (1H, broad-s), 4.10 (1H, broad-s), 7.02 (1H, s), 7.31 (2H, broad-s), 7.45-7.47 (2H, m), 7.61 (1H, broad-s), 7.73-7.75 (3H, m), 7.95 (1H, s), 8.03 (2H, s), 8.25 (1H, broad-s).

Example 33

Preparation of 3-(3-cyano-N-(3-(hydroxyamino)-3-oxopropyl)benzamide)-N-(2,6-dibromo-4-(perfluoropropan-2-yl)phenyl)-2-fluorobenzamide (Compound No. 5-33)

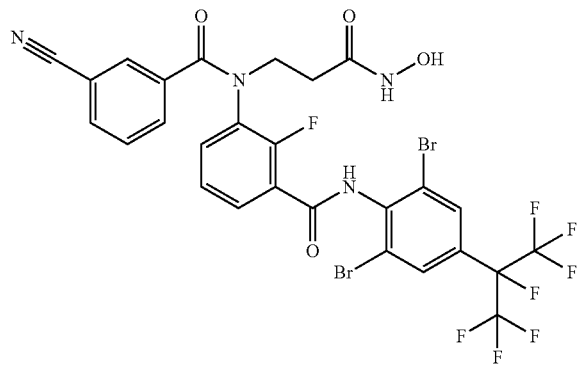 [SMILES: N#Cc1cccc(C(=O)N(CCC(=O)NO)c2cccc(C(=O)Nc3c(Br)cc(C(F)(C(F)(F)F)C(F)(F)F)cc3Br)c2F)c1]

33-1

Preparation of 3-(3-(tert-butoxyamino)-3-oxopropylamino)-N-(2,6-dibromo-4-(perfluoropropan-2-yl)phenyl)-2-fluorobenzamide

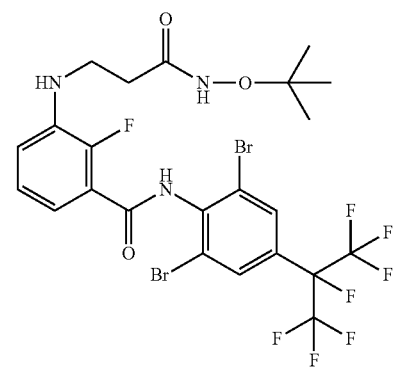 [SMILES: CC(C)(C)ONC(=O)CCNc1cccc(C(=O)Nc2c(Br)cc(C(F)(C(F)(F)F)C(F)(F)F)cc2Br)c1F]

To a solution of 3 g of 0.520 g (2.73 mmol) of a (1-(3-dimethylaminopropyl)-3-ethylcarbodiimide hydrochloric acid salt and 0.340 g (2.51 mmol) of 1-hydroxybenzotriazole in 3 g of THF was added 1.43 g (2.28 mmol) of 3-(3-(2,6-dibromo-4-(perfluoropropan-2-yl)phenylcarbamoyl)-2-fluorophenylamino)propanoic acid obtained in 32-1 of Example 32 at 0° C., followed by stirring at the same temperature 1 hour. To the reaction liquid were added 0.430 g (3.42 mmol) of a tert-butoxyamine hydrochloric acid salt and a solution of 0.370 g (3.65 mmol) of triethylamine in 3 g of THF at 0° C., followed by stirring at room temperature for 6 hours and leaving to stand overnight. To the reaction liquid were added water and ethyl acetate, and the organic layer was washed with water and saturated brine, and then dried over anhydrous magnesium sulfate. The solvent was evaporated under reduced pressure and the obtained residue was purified by silica gel column chromatography (developing solvent; dichloromethane:methanol=200:1→50:1) to prepare 0.950 g (yield 60%) of a target compound.

$^1$H-NMR (CDCl$_3$, ppm) δ 1.26 (9H, s), 2.48-2.49 (1H, m), 2.79-2.80 (1H, m), 3.58-3.59 (2H, m), 4.65 (1H, broad-s), 6.94-6.95 (1H, m), 7.16 (1H, t, J=7.8 Hz), 7.42-7.43 (1H, m), 7.69-7.70 (1H, m), 7.86 (2H, s), 8.20 (1H, d, J=14.1 Hz).

33-2

Preparation of 3-(N-(3-(tert-butoxyamino)-3-oxopropyl)-3-cyanobenzamide)-N-(2,6-dibromo-4-(perfluoropropan-2-yl)phenyl)-2-fluorobenzamide According to the method of 1-5 of Example 1, a target compound was prepared from 3-(3-(tert-butoxyamino)-3-oxopropylamino)-N-(2,6-dibromo-4-(perfluoropropan-2-yl)phenyl)-2-fluorobenzamide and 3-cyanobenzoylchloride.

$^1$H-NMR (CDCl$_3$, ppm) δ 1.20 (9H, s), 2.68-2.69 (1H, m), 2.74-2.75 (1H, m), 4.23-4.24 (2H, m), 7.29-7.33 (2H, m), 7.47-7.48 (1H, m), 7.57-7.62 (2H, m), 7.72 (1H, s), 7.85 (2H, s), 7.97-8.04 (3H, m).

33-3

Preparation of 3-(3-cyano-N-(3-(hydroxyamino)-3-oxopropyl)benzamide)-N-(2,6-dibromo-4-(perfluoropropan-2-yl)phenyl)-2-fluorobenzamide (Compound No. 5-33)

To a solution of 0.250 g (0.310 mmol) of 3-(N-(3-(tert-butoxyamino)-3-oxopropyl)-3-cyanobenzamide)-N-(2,6-dibromo-4-(perfluoropropan-2-yl)phenyl)-2-fluorobenzamide in 5 ml of dichloromethane was added 3.3 ml of trifluoroacetic acid, followed by stirring at room temperature for 7 hours, then stirring at 40° C. for 5 hours and leaving to stand overnight. The reaction liquid was further stirred at 40° C. for 12 hours, and left to stand overnight. The reaction liquid was adjusted to pH 7 by the addition of a 10% aqueous sodium hydroxide solution, and then the organic layer was washed with water and saturated brine, and then dried over anhydrous magnesium sulfate. The solvent was evaporated under reduced pressure and the obtained residue was purified by silica gel column chromatography (developing solvent; ethyl acetate→ethyl acetate:methanol=10:1) to prepare 0.130 g (yield 55%) of a target compound.

$^1$H-NMR (CDCl$_3$, ppm) δ 2.63-2.64 (2H, m), 4.20-4.21 (2H, m), 7.12-7.24 (2H, m), 7.39-7.40 (1H, m), 7.51-7.52

(3H, m), 7.69-7.70 (1H, m), 7.81 (2H, s), 7.85-7.86 (1H, m), 7.91-7.92 (1H, m), 8.31-8.32 (1H, m).

Example 34

Preparation N-(2,6-dimethyl-4-(perfluoropropan-2-yl)phenyl)-3-(N-(2-hydroxyethyl)benzamide)-N-methylbenzamide (Compound No. 5-35)

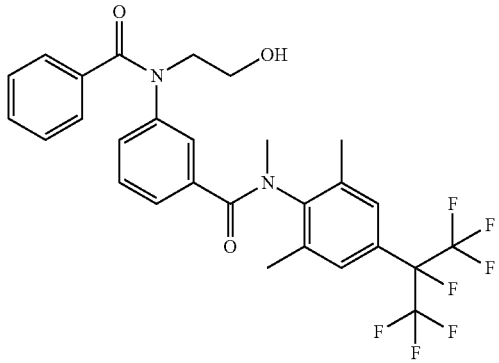 [SMILES: Cc1cc(C(F)(C(F)(F)F)C(F)(F)F)cc(C)c1N(C)C(=O)c1cccc(N(CCO)C(=O)c2ccccc2)c1]

34-1

Preparation N-(2,6-dimethyl-4-(perfluoropropan-2-yl)phenyl)-3-(2-hydroxyethylamino)-N-methylbenzamide

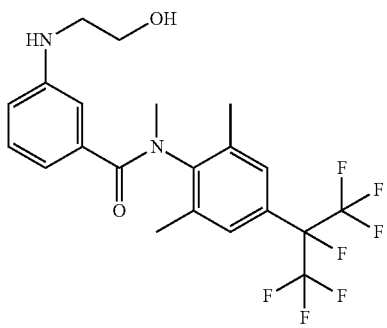 [SMILES: Cc1cc(C(F)(C(F)(F)F)C(F)(F)F)cc(C)c1N(C)C(=O)c1cccc(NCCO)c1]

A solution of 0.133 g (0.221 mmol) of methyl 2-(N-(3((2,6-dimethyl-4-(perfluoropropan-2-yl)phenyl)(methyl)carbamoyl)phenyl)benzamide)acetate obtained in 5-5 of Example 5 in 5 ml of THF was cooled to 0° C., and then 0.0213 g (0.561 mmol) of lithium aluminum hydride was added thereto, followed by stirring at 0° C. for 10 minutes. To the reaction liquid were added water and ethyl acetate, the organic phase was collected by separation, and the organic phase was washed with hydrochloric acid, a saturated aqueous sodium bicarbonate solution, and saturated brine, and dried over anhydrous sodium sulfate. The solvent was removed under reduced pressure. The obtained residue was purified by silica gel column chromatography (developing solvent; ethyl acetate) to prepare 0.0720 g (yield: 57%) of a target compound.

$^1$H-NMR (CDCl$_3$, ppm) δ 2.28 (6H, s), 2.37 (1H, s), 3.08 (2H, t, J=5.4 Hz), 3.31 (3H, s), 3.73 (2H, t, J=5.4 Hz), 3.91 (1H, broad-s), 6.53-6.57 (3H, m), 6.90 (1H, t, J=7.3 Hz), 7.23 (2H, s), 34-2

Preparation N-(2,6-dimethyl-4-(perfluoropropan-2-yl)phenyl)-3-(N-(2-hydroxyethyl)benzamide)-N-methylbenzamide (Compound No. 5-35)

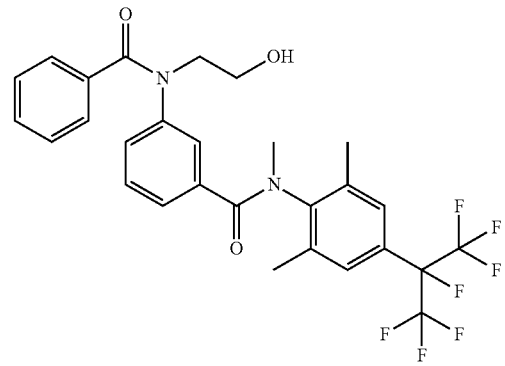 [SMILES: Cc1cc(C(F)(C(F)(F)F)C(F)(F)F)cc(C)c1N(C)C(=O)c1cccc(N(CCO)C(=O)c2ccccc2)c1]

According to the method of 1-5 of Example 1, a target compound was prepared from N-(2,6-dimethyl-4-(perfluoropropan-2-yl)phenyl)-3-(2-hydroxyethylamino)-N-methylbenzamide.

$^1$H-NMR (CDCl$_3$, ppm) δ 2.17 (6H, s), 2.90 (1H, broad-s), 3.28 (3H, s), 3.70-3.72 (2H, m), 3.85-3.92 (2H, m), 6.91-7.07 (3H, m), 7.11-7.39 (8H, m).

Example 35

N-(3-amino-3-oxopropyl)-3-benzamide-N-(2,6-dimethyl-4-(perfluoropropan-2-yl)phenyl)benzamide (Compound No. 7-1)

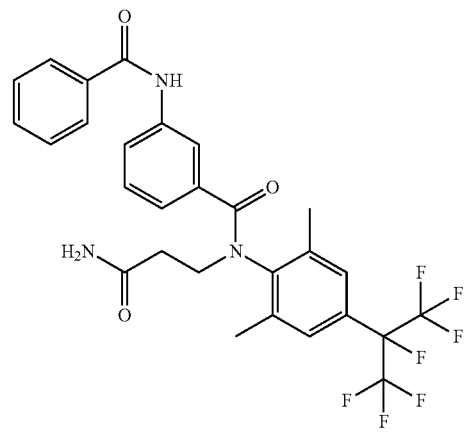 [SMILES: Cc1cc(C(F)(C(F)(F)F)C(F)(F)F)cc(C)c1N(CCC(N)=O)C(=O)c1cccc(NC(=O)c2ccccc2)c1]

35-1

Preparation of 3-(2,6-dimethyl phenylamino)propanamide

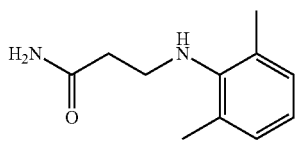

3.00 g (25.0 mmol) of 2,6-dimethyl aniline and 1.88 g (74.0 mmol) of acryl amide were charged to 10 ml of acetic acid, followed by stirring at 100° C. for 4 hours. 1.88 g (74.0 mmol) of acryl amide was further added thereto, followed by stirring for 1 hour. After cooling to room temperature, the mixture was discharged to water, neutralized with potassium carbonate, and extracted with ethyl acetate. The mixture was washed with water twice, and then dried over anhydrous magnesium sulfate, and the solvent was evaporated under reduced pressure. The obtained residue was purified by silica gel column chromatography (developing solvent; hexane:ethyl acetate=3:1→0:1) to prepare 2.64 g (yield: 55%) of a target compound.

$^1$H-NMR (CDCl$_3$, ppm) δ 2.30 (6H, s), 2.46-2.50 (2H, m), 3.25-3.26 (2H, m), 3.57 (1H, broad-s), 5.57 (1H, broad-s), 6.14 (1H, broad-s), 6.83-6.87 (1H, m), 6.99-7.10 (2H, m).

35-2

Preparation of 3-(2,6-dimethyl-4-(perfluoropropan-2-yl)phenylamino)propanamide

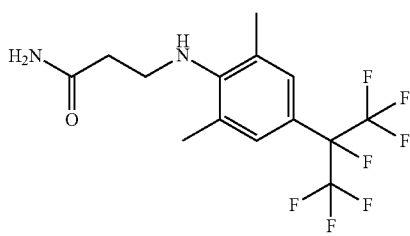 [SMILES: Cc1cc(C(F)(C(F)(F)F)C(F)(F)F)cc(C)c1NCCC(N)=O]

2.30 g (11.9 mmol) of 3-(2,6-dimethyl phenylamino)propanamide was charged to a mixed solution of 20 ml of tert-butyl methyl ether and 20 ml of water, and 2.50 g (14.3 mmol) of 85% sodium hydrosulfite and 0.400 g (1.20 mmol) of tetrabutylammonium hydrogen sulfate were added thereto, and 1.20 g (14.3 mmol) of sodium hydrogen carbonate was added thereto. Then, 4.20 g (14.3 mmol) of heptafluoroisopropyliodide was added dropwise thereto, followed by stirring at room temperature for 3 hours and performing liquid separation. The mixture was washed with a 5% aqueous hydrochloric acid solution and a saturated aqueous sodium hydrogen carbonate solution in this order, and then dried over anhydrous magnesium sulfate. The solvent was evaporated under reduced pressure, and then the obtained residue was purified by silica gel column chromatography (developing solvent; hexane:ethyl acetate=1:1→0:1) to prepare 1.25 g (yield 29%) of a target compound.

$^1$H-NMR (CDCl$_3$, ppm) δ 2.32 (6H, s), 2.47 (2H, t, J=5.9 Hz), 3.35 (2H, t, J=5.9 Hz), 5.55 (1H, broad-s), 5.69 (1H, broad-s), 7.17 (2H, s).

The proton presumed to be indicative of NH was not detected.

35-3

Preparation of N-(3-amino-3-oxopropyl)-N-(2,6-dimethyl-4-(perfluoropropan-2-yl)phenyl)-3-nitrobenzamide

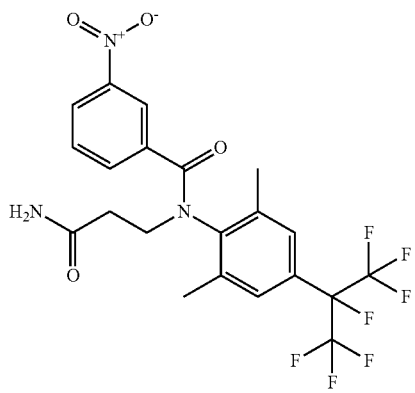 [SMILES: Cc1cc(C(F)(C(F)(F)F)C(F)(F)F)cc(C)c1N(CCC(N)=O)C(=O)c1cccc([N+](=O)[O-])c1]

According to the method of 1-1 of Example 1, a target compound was prepared from 3-(2,6-dimethyl-4-(perfluoropropan-2-yl)phenylamino)propanamide and 3-nitrobenzoyl chloride.

$^1$H-NMR (CDCl$_3$, ppm) δ 2.30 (6H, s), 2.78 (2H, t, J=7.8 Hz), 4.09 (2H, t, J=7.8 Hz), 5.50 (1H, broad-s), 6.03 (1H, broad-s), 7.27 (2H, s), 7.34-7.35 (1H, m), 7.55 (1H, dd, J=1.5, 7.8 Hz), 8.04-8.06 (1H, m), 8.13-8.16 (1H, m).

35-4

Preparation of 3-amino-N-(3-amino-3-oxopropyl)-N-(2,6-dimethyl-4-(perfluoropropan-2-yl)phenyl)benzamide (Compound No. 18-72) and methyl 3-(3-amino-N-(2,6-dimethyl-4-(perfluoropropan-2-yl)phenyl)benzamide)propanoate

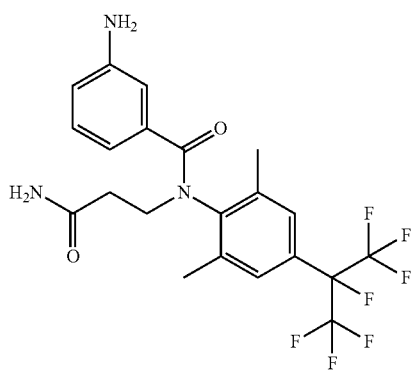

Amide body

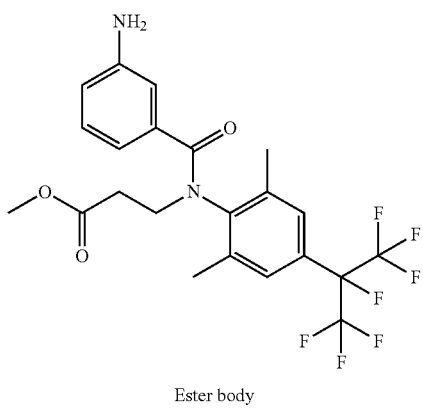

Ester body 0.300 g (0.590 mmol) of N-(3-amino-3-oxopropyl)-N-(2,6-dimethyl-4-(perfluoropropan-2-yl)phenyl)-3-nitrobenzamide and 0.550 g (2.95 mmol) of stannous chloride were charged to 5 ml of methanol, and 3 ml of concentrated hydrochloric acid was added thereto, followed by stirring at 60° C. for 30 minutes. After cooling to room temperature, ethyl acetate and water were added thereto, followed by neutralization with potassium carbonate. The solid was filtered through Celite, and then subjected to liquid separation, and dried over anhydrous magnesium sulfate. The solvent was evaporated under reduced pressure and the obtained residue was purified by silica gel column chromatography (developing solvent; hexane:ethyl acetate=1:2→ethyl acetate:methanol=10:1) to prepare 0.100 g of 3-amino-N-(3-amino-3-oxopropyl)-N-(2,6-dimethyl-4-(perfluoropropan-2-yl)phenyl) benzamide (amide product: yield: 35%) and 0.160 g of methyl 3-(3-amino-N-(2,6-dimethyl-4-(perfluoropropan-2-yl)phenyl)benzamide)propanoate (ester product: yield: 56%).

Amide Product $^1$H-NMR (CDCl$_3$, ppm) δ 2.27 (6H, s), 2.72 (2H, t, J=7.8 Hz), 3.57 (2H, broad-s), 4.03 (2H, t, J=7.8 Hz), 5.40 (H, broad-s), 6.37 (1H, broad-s), 6.38-6.41 (1H, m), 6.56-6.59 (1H, m), 6.64-6.65 (1H, m), 6.83 (1H, t, J=7.8 Hz), 7.37 (2H, s).

Ester Product $^1$H-NMR (CDCl$_3$, ppm) δ 2.27 (6H, s), 2.82 (2H, t, 1=7.3 Hz), 3.56 (2H, broad-s), 3.62 (3H, s), 4.03 (2H, t, J=7.3 Hz), 6.36-6.38 (1H, m), 6.55-6.57 (1H, m), 6.66-6.67 (1H, m), 6.81 (1H, t, J=7.8 Hz), 7.23 (2H, s).

35-5

N-(3-amino-3-oxopropyl)-3-benzamide-N-(2,6-dimethyl-4-(perfluoropropan-2-yl)phenyl)benzamide (Compound No. 7-1)

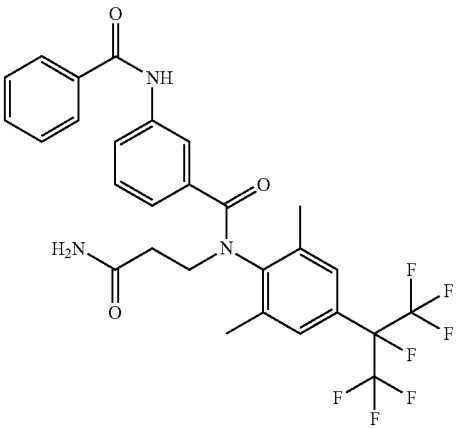 [SMILES: Cc1cc(C(F)(C(F)(F)F)C(F)(F)F)cc(C)c1N(CCC(N)=O)C(=O)c1cccc(NC(=O)c2ccccc2)c1]

According to the method of 1-5 of Example 1, a target compound was prepared from 3-amino-N-(3-amino-3-oxopropyl)-N-(2,6-dimethyl-4-(perfluoropropan-2-yl)phenyl)benzamide.

$^1$H-NMR (CDCl$_3$, ppm) δ 2.33 (6H, s), 2.72-2.74 (2H, m), 4.02 (2H, m), 6.10 (1H, broad-s), 6.78-6.80 (1H, m), 7.04 (1H, t, J=7.8 Hz), 7.21 (3H, broad-s), 7.35-7.61 (5H, m), 7.87-7.89 (2H, m), 9.80 (1H, broad-s).

Example 36

Preparation of methyl 3-(3-benzamide-N-(2,6-dimethyl-4-(perfluoropropan-2-yl)phenyl)benzamide)propanoate (Compound No. 7-6)

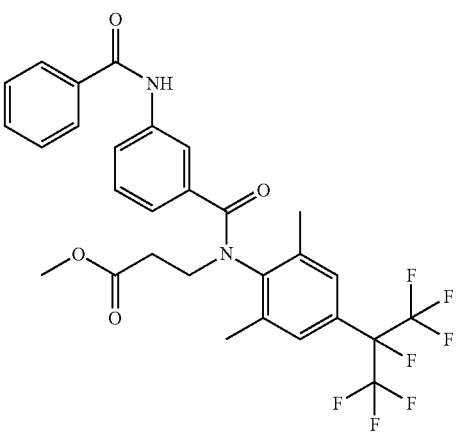 [SMILES: COC(=O)CCN(C(=O)c1cccc(NC(=O)c2ccccc2)c1)c1c(C)cc(C(F)(C(F)(F)F)C(F)(F)F)cc1C]

According to the method of 1-5 of Example 1, a target compound was prepared from methyl 3-(3-amino-N-(2,6-dimethyl-4-(perfluoropropan-2-yl)phenyl)benzamide)propanoate.

$^1$H-NMR (CDCl$_3$, ppm) δ 2.31 (6H, s), 2.84 (2H, t, J=7.8 Hz), 3.63 (3H, s), 4.07 (2H, t, J=7.8 Hz), 6.87-6.89 (1H, m), 7.10 (1H, t, J=7.8 Hz), 7.24-7.26 (2H, m), 7.46-7.58 (4H, m), 7.65-7.69 (2H, m), 7.77-7.79 (2H, m).

Example 37

Preparation of N-(3-amino-3-oxopropyl)-3-(N-(3-amino-3-oxopropyl)benzamide)-N-(2,6-dimethyl-4-(perfluoropropan-2-yl)phenyl)benzamide (Compound No. 8-1)

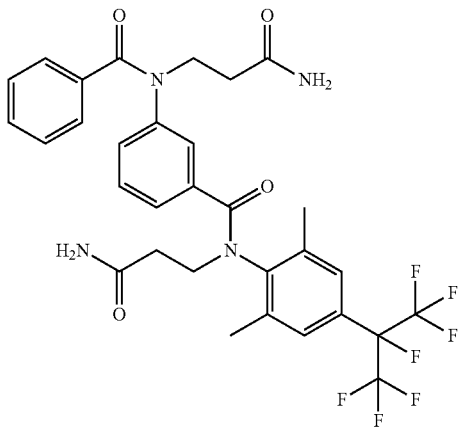 [SMILES: Cc1cc(C(F)(C(F)(F)F)C(F)(F)F)cc(C)c1N(CCC(N)=O)C(=O)c1cccc(N(CCC(N)=O)C(=O)c2ccccc2)c1]

37-1

Preparation of N-(3-amino-3-oxopropyl)-3-(3-amino-3-oxopropylamino)-N-(2,6-dimethyl-4-(perfluoropropan-2-yl)phenyl)benzamide (Compound No. 18-87)

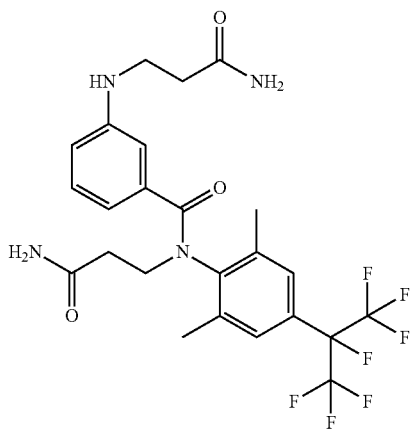 [SMILES: Cc1cc(C(F)(C(F)(F)F)C(F)(F)F)cc(C)c1N(CCC(N)=O)C(=O)c1cccc(NCCC(N)=O)c1]

According to the method of 20-2 of Example 20, a target compound was prepared from 3-amino-N-(3-amino-3-oxopropyl)-N-(2,6-dimethyl-4-(perfluoropropan-2-yl)phenyl)benzamide obtained in 35-4 of Example 35.

$^1$H-NMR (CDCl$_3$, ppm) δ 2.39-2.42 (2H, m), 2.62 (6H, s), 2.72-2.74 (2H, m), 3.19-3.20 (2H, m), 3.99-4.02 (2H, m), 4.41 (1H, broad-s), 5.80 (1H, broad-s), 5.84 (1H, broad-s), 6.41 (1H, d, J=7.8 Hz), 6.51-6.54 (2H, m), 6.84-6.88 (3H, m), 7.40 (2H, s).

37-2

Preparation of N-(3-amino-3-oxopropyl)-3-(N-(3-amino-3-oxopropyl)benzamide)-N-(2,6-dimethyl-4-(perfluoropropan-2-yl)phenyl)benzamide (Compound No. 8-1)

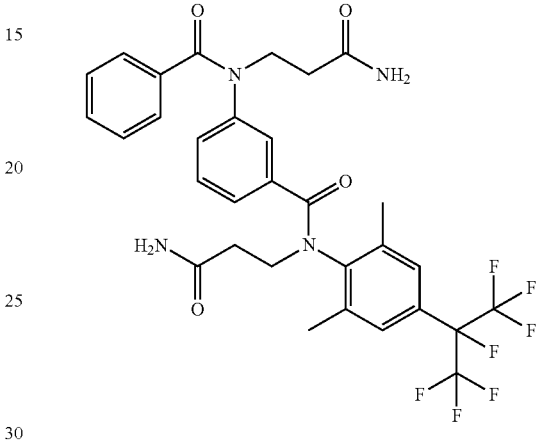

According to the method of 1-5 of Example 1, a target compound was prepared from N-(3-amino-3-oxopropyl)-3-(3-amino-3-oxopropylamino)-N-(2,6-dimethyl-4-(perfluoropropan-2-yl)phenyl)benzamide.

$^1$H-NMR (CDCl$_3$, ppm) δ 2.11 (6H, s), 2.58 (2H, t, J=6.8 Hz), 2.70 (2H, t, J=6.8 Hz), 3.96-4.05 (4H, m), 5.45 (1H, broad-s), 5.55 (1H, broad-s), 6.20 (1H, broad-s), 6.25 (1H, broad-s), 6.80-6.82 (1H, m), 6.91-6.99 (2H, m), 7.11-7.17 (5H, m), 7.22 (2H, s), 7.30-7.40 (1H, m)

Example 38

Preparation of 3-benzamide-N-(2,6-dibromo-4-(perfluoropropan-2-yl)phenyl)-2-fluoro-N-(2-(methylsulfonyl)ethyl)benzamide (Compound No. 7-169)

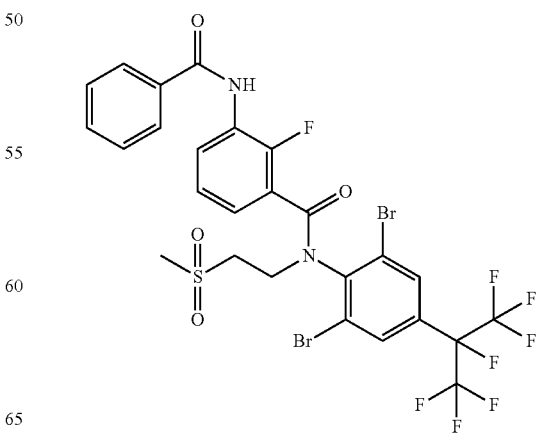

38-1

Preparation of 3-amino-N-(2,6-dibromo-4-(perfluoropropan-2-yl)phenyl)-2-fluoro-N-(2-(methylsulfonyl)ethyl)benzamide (Compound No. 20-36)

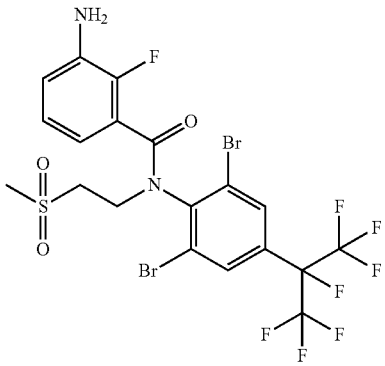 [SMILES: CS(=O)(=O)CCN(C(=O)c1cccc(N)c1F)c1c(Br)cc(C(F)(C(F)(F)F)C(F)(F)F)cc1Br]

To 0.670 g (1.20 mmol) of 3-amino-N-(2,6-dibromo-4-(perfluoropropan-2-yl)phenyl)-2-fluorobenzamide obtained in 23-4 of Example 23 was added an aqueous solution obtained by dissolving 0.550 g (5.18 mmol) of methyl vinyl sulfonate and 0.100 g (2.50 mmol) of sodium hydroxide in 2 ml of water, followed by stirring at 60° C. for 3 hours. To the reaction solution were added ethyl acetate and water, and the organic phase was extracted, then washed with saturated brine, and dried over anhydrous magnesium sulfate. Then, the solvent was evaporated under reduced pressure. The obtained residue was purified by silica gel column chromatography (developing solvent; hexane:ethyl acetate=4:1→3:1→2:1) to prepare 0.410 g (yield 52%) of a target compound.

$^1$H-NMR (CDCl$_3$, ppm) δ 3.10 (3H, s), 3.74-3.78 (4H, m), 4.18-4.22 (2H, m), 6.44-6.48 (1H, m), 6.62-6.73 (2H, m), 7.74 (2H, s).

38-2

Preparation of 3-benzamide-N-(2,6-dibromo-4-(perfluoropropan-2-yl)phenyl)-2-fluoro-N-(2-(methylsulfonyl)ethyl)benzamide (Compound No. 7-169)

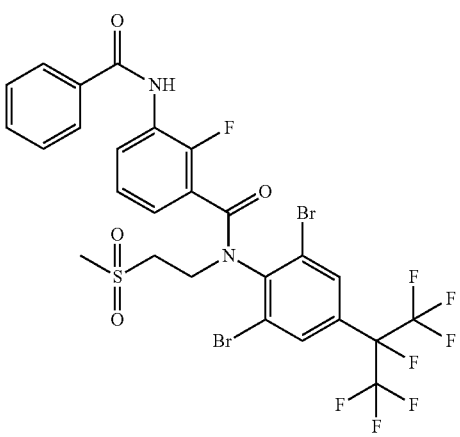 [SMILES: CS(=O)(=O)CCN(C(=O)c1cccc(NC(=O)c2ccccc2)c1F)c1c(Br)cc(C(F)(C(F)(F)F)C(F)(F)F)cc1Br]

According to the method of 1-5 of Example 1, a target compound was prepared from 3-amino-N-(2,6-dibromo-4-(perfluoropropan-2-yl)phenyl)-2-fluoro-N-(2-(methylsulfonyl)ethyl)benzamide.

$^1$H-NMR (CDCl$_3$, ppm) δ 3.10 (3H, s), 3.74-3.78 (2H, m), 4.20-4.24 (2H, m), 6.85-7.26 (2H, m), 7.51-7.60 (3H, m), 7.78 (2H, s), 7.85-7.87 (2H, m), 8.06 (1H, d, J=3.9 Hz), 8.48-8.50 (1H, m).

Example 39

Preparation of 3-(4-cyano-N-(2-sulfamoylethyl)benzamide)-N-(2,6-dibromo-4-(perfluoropropan-2-yl)phenyl)-2-fluorobenzamide (Compound No. 2-133)

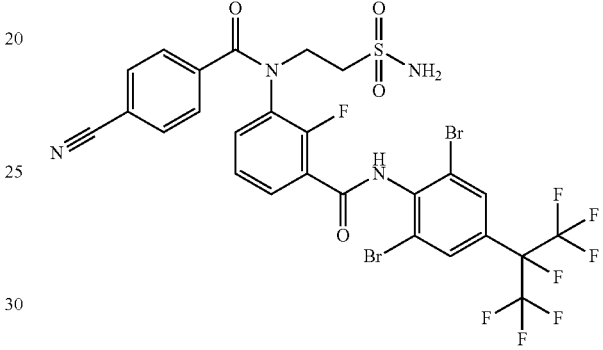

39-1

Preparation of N-tritylethenesulfonamide

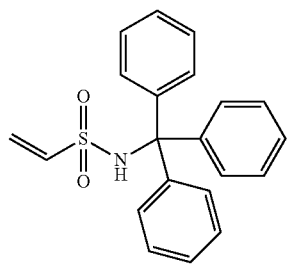 [SMILES: C=CS(=O)(=O)NC(c1ccccc1)(c1ccccc1)c1ccccc1]

To 90 of a solution of 18.1 g (111 mmol) of 2-chloroethanesulfonylchloride in dichloromethane was charged dropwise 12.4 g (122 mmol) of triethylamine at −60° C., followed by stirring at the same temperature for 30 minutes and at room temperature for 1.5 hours. The reaction liquid was cooled to −60° C., and charged dropwise to 60 g of a solution of 28.8 g (111 mmol) of tritylamine and 11.2 g (111 mmol) of triethylamine in dichloromethane, followed by stirring at the same temperature for 1.5 hours, then stirring at room temperature for 4 hours, and leaving to stand overnight. Water was added to the reaction liquid, and the organic layer was washed with water, and then dried over anhydrous magnesium sulfate. The solvent was evaporated under reduced pressure and the obtained residue was washed with ethyl acetate to prepare 25.2 g (yield 65%) of a target compound.

¹H-NMR (CDCl₃, ppm) δ 5.21-5.23 (1H, m), 5.46-5.62 (3H, m), 7.22-7.33 (9H, m), 7.43-7.55 (6H, m).

39-2

Preparation of N-(2,6-dibromo-4-(perfluoropropan-2-yl)phenyl)-2-fluoro-3-(2-sulfamoylethylamino)benzamide (Compound No. 19-44)

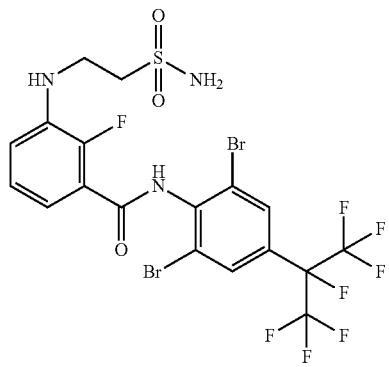 [SMILES: NS(=O)(=O)CCNc1cccc(C(=O)Nc2c(Br)cc(C(F)(C(F)(F)F)C(F)(F)F)cc2Br)c1F]

To 5 ml of an aqueous solution of 1.16 g (2.08 mmol) of 3-amino-N-(2,6-dibromo-4-(perfluoropropan-2-yl)phenyl)-2-fluorobenzamide obtained in 23-4 of Example 23 in 85% aqueous phosphoric acid solution was added 0.800 g (2.29 mmol) of N-tritylethenesulfonamide, followed by stirring at 140° C. for 20 hours. To the reaction liquid were added water and ethyl acetate, followed by adjustment to pH 7 with a 10% aqueous sodium hydroxide solution, and then the organic layer was washed with water and saturated brine, and dried over anhydrous magnesium sulfate. The solvent was evaporated under reduced pressure and the obtained residue was purified by silica gel column chromatography (developing solvent; hexane:ethyl acetate=4:1) to prepare 0.0300 g (yield 2%) of a target compound.

¹H-NMR (CDCl₃, ppm) δ 3.46 (2H, t, J=6.3 Hz), 3.77-3.81 (2H, m), 4.74 (1H, broad-s), 4.80-4.82 (2H, m), 6.92-6.96 (1H, m), 7.19 (1H, t, J=7.8 Hz), 7.44-7.49 (1H, m), 7.86 (2H, s), 8.17 (1H, d, J=13.6 Hz).

39-3

Preparation of 3-(4-cyano-N-(2-sulfamoylethyl)benzamide)-N-(2,6-dibromo-4-(perfluoropropan-2-yl)phenyl)-2-fluorobenzamide (Compound No. 2-133)

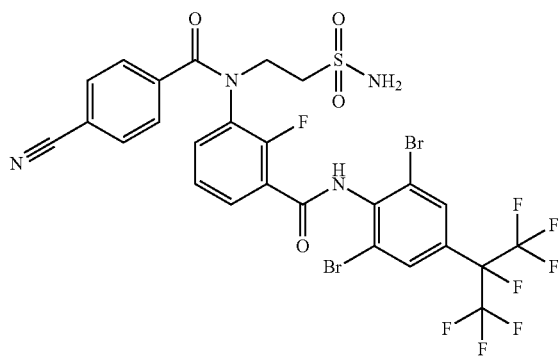 [SMILES: N#Cc1ccc(C(=O)N(CCS(N)(=O)=O)c2cccc(C(=O)Nc3c(Br)cc(C(F)(C(F)(F)F)C(F)(F)F)cc3Br)c2F)cc1]

According to the method of 1-5 of Example 1, a target compound was prepared from N-(2,6-dibromo-4-(perfluoropropan-2-yl)phenyl)-2-fluoro-3-(2-sulfamoylethylamino)benzamide and 4-cyanobenzoylchloride.

¹H-NMR (CDCl₃, ppm) δ 3.33-3.41 (2H, m), 3.97-3.99 (1H, m), 5.10-5.15 (1H, m), 5.32 (2H, broad-s), 7.22-7.24 (1H, m), 7.43 (2H, d, J=7.8 Hz), 7.53 (2H, d, J=7.8 Hz), 7.59 (1H, t, J=7.8 Hz), 7.89 (2H, s), 7.97 (1H, d, J=12.2 Hz), 8.06-8.08 (1H, m).

Example 40

Preparation of di-tert-butyl 2-((3-cyano-N-(3-(2,6-dibromo-4-(perfluoropropan-2-yl)phenylcarbamoyl)-2-fluorophenyl)benzamide)methyl)malonate (Compound No. 6-44)

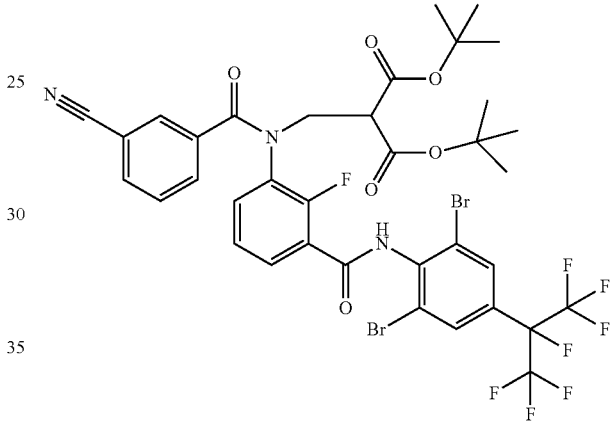

40-1

Preparation of di-tert-butyl 243-(2,6-dibromo-4-(perfluoropropan-2-yl)phenylcarbamoyl)-2-fluorophenylamino)methyl)malonate

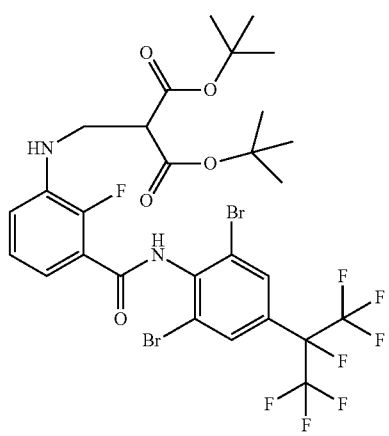 [SMILES: CC(C)(C)OC(=O)C(CNc1cccc(C(=O)Nc2c(Br)cc(C(F)(C(F)(F)F)C(F)(F)F)cc2Br)c1F)C(=O)OC(C)(C)C]

To a solution of 0.220 g (1.00 mmol) of di-tert-butyl malonate in 5 ml of acetic acid were added 0.0600 g (2.10 mmol) of paraformaldehyde, 0.0100 g (0.100 mmol) of potassium acetate, and 0.0100 g (0.0500 mmol) of copper acetate monohydrate, followed by stirring at 100° C. for 2.5 hours. To the reaction liquid was added 0.500 g (0.900 mmol) of 3-amino-N-(2,6-dibromo-4-(perfluoropropan-2-yl)phenyl)-2-fluorobenzamide obtained in 23-4 of Example 23, followed by stirring for 2.5 hours. The reaction liquid was left to stand at room temperature overnight, and then extracted with a saturated aqueous sodium hydrogen carbonate solution and ethyl acetate. The organic layer was dried over anhydrous magnesium sulfate, the solvent was evaporated under reduced pressure and the obtained residue was purified by silica gel column chromatography (developing solvent; hexane:ethyl acetate=8:1→4:1) to prepare 0.230 g (yield 32%) of a target compound.

$^1$H-NMR (CDCl$_3$, ppm) δ 1.46-1.48 (18H, m), 3.53-3.55 (1H, m), 3.70 (2H, t, J=6.3 Hz), 4.55 (1H, broad-s), 6.98-6.99 (1H, m), 7.17-7.18 (1H, m), 7.42-7.43 (1H, m), 7.86 (2H, s), 8.20-8.22 (1H, m).

40-2

Preparation of di-tert-butyl 2-((3-cyano-N-(3-(2,6-dibromo-4-(perfluoropropan-2-yl)phenylcarbamoyl)-2-fluorophenyl)benzamide)methyl)malonate (Compound No. 6-44)

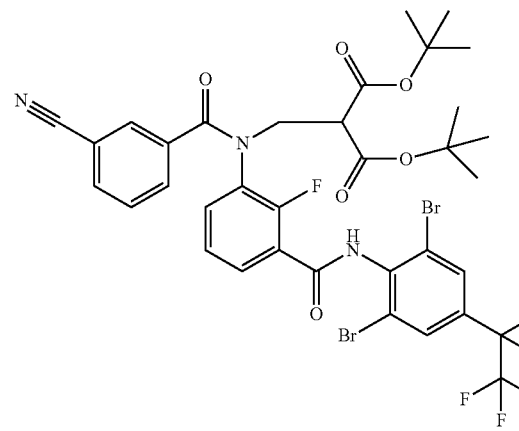

According to the method of 1-5 of Example 1, a target compound was prepared from di-tert-butyl 2-((3-(2,6-dibromo-4-(perfluoropropan-2-yl)phenylcarbamoyl)-2-fluorophenylamino)methyl)malonate and 3-cyanobenzoylchloride.

$^1$H-NMR (CDCl$_3$, ppm) δ 1.40-1.46 (18H, m), 3.78-3.79 (1H, m), 4.14-4.15 (1H, m), 4.24-4.25 (1H, m), 7.29-7.33 (2H, m), 7.44-7.45 m), 7.55-7.66 (3H, m), 7.86 (2H, s), 7.94-8.03 (2H, m).

Example 41

Preparation of N-(3-(2,6-dimethyl-4-(perfluoropropan-2-yl)phenylcarbamoyl)phenyl)-N-(3-(3-methylureido)propyl)benzamide (Compound No. 6-49)

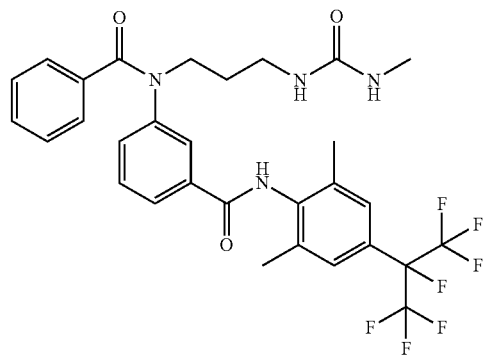 [SMILES: CNC(=O)NCCCN(C(=O)c1ccccc1)c1cccc(C(=O)Nc2c(C)cc(C(F)(C(F)(F)F)C(F)(F)F)cc2C)c1]

To a solution of 0.0200 g (0.0400 mmol) of N-(3-aminopropyl)-N-(3-(2,6-dimethyl-4-(perfluoropropan-2-yl)phenylcarbamoyl)phenyl)benzamide obtained in Example 25 in 5 ml of dichloromethane was added 0.0100 g (0.0500 mmol) of 1,1'-carbonylbis-1H-imidazole, followed by stirring at room temperature for 5.5 hours, and then 0.00300 g (0.0500 mmol) of pyridine and 0.00300 g (0.0400 mmol) of methylamine (40% methanol solution) were added thereto, followed by stirring at room temperature for 3 hours. The reaction liquid was left to stand overnight, followed by addition of water and extraction with ethyl acetate. The organic layer was washed with saturated brine, and then dried over anhydrous magnesium sulfate. The solvent was evaporated under reduced pressure and the obtained residue was purified by silica gel column chromatography (developing solvent; hexane:ethyl acetate=1:1→0:1) to prepare 0.0110 g (yield 44%) of a target compound.

$^1$H-NMR (CDCl$_3$, ppm) δ 1.78-1.79 (2H, m), 2.28 (6H, s), 2.44 (3H, d, J=4.9 Hz), 3.36-3.42 (2H, m), 4.09-4.10 (2H, m), 4.20 (1H, broad-s), 4.93 (1H, broad-s), 7.14-7.18 (2H, m), 7.21-7.23 (2H, m), 7.27-7.31 (3H, m), 7.39-7.43 (2H, m), 7.81-7.83 (1H, m), 7.87 (1H, s), 8.95 (1H, s).

Example 42

Preparation of ethyl 3-(N-(3-(2-bromo-4-(perfluorophan-2-yl)-6-(trifluoromethyl)phenylcarbamoyl)-2-fluorophenyl)-4-cyanobenzamide)propanoylcarbamate (Compound No. 5-76)

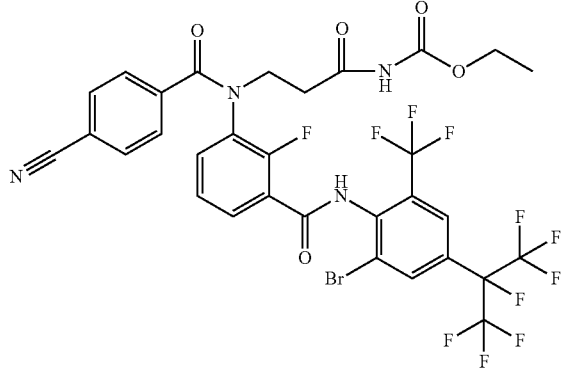 [SMILES: CCOC(=O)NC(=O)CCN(C(=O)c1ccc(C#N)cc1)c1cccc(C(=O)Nc2c(Br)cc(C(F)(C(F)(F)F)C(F)(F)F)cc2C(F)(F)F)c1F]

42-1

Preparation of 3-(N-(3-amino-3-oxopropyl)-4-cyanobenzamide)-N-(2-bromo-4-(perfluoropropan-2-yl)-6-(trifluoromethyl)phenyl)-2-fluorobenzamide (Compound No. 1-136)

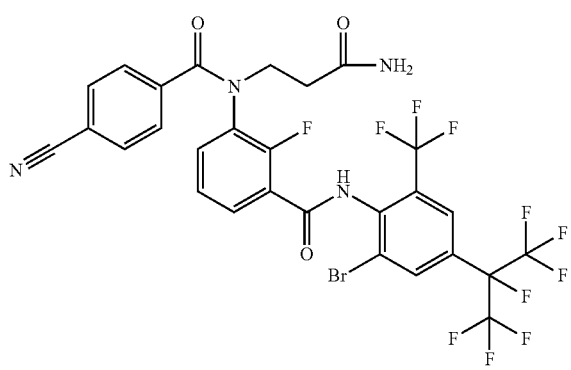 [SMILES: N#Cc1ccc(C(=O)N(CCC(N)=O)c2cccc(C(=O)Nc3c(Br)cc(C(F)(C(F)(F)F)C(F)(F)F)cc3C(F)(F)F)c2F)cc1]

According to the method of 1-5 of Example 1, a target compound was prepared from 3-(3-amino-3-oxopropylamino)-N-(2-bromo-4-(perfluoropropan-2-yl)-6-(trifluoromethyl)phenyl)-2-fluorobenzamide obtained in 22-6 of Example 22 and 4-cyanobenzoylchloride.

$^1$H-NMR (CDCl$_3$, ppm) δ 2.71 (1H, broad-s), 2.85 (1H, broad-s), 4.24 (2H, broad-t, J=6.3 Hz), 5.39 (1H, broad-s), 5.80 (1H, broad-s), 7.32 (1H, t, J=7.8 Hz), 7.42 (2H, d, J=7.8 Hz), 7.52 (2H, broad-d, J=7.8 Hz), 7.58-7.59 (1H, m), 7.91 (1H, s), 7.98-8.08 (2H, m), 8.13 (1H, s)

42-2

Preparation of ethyl 3-(N-(3-(2-bromo-4-(perfluorophen-2-yl)-6-(trifluoromethyl)phenylcarbamoyl)-2-fluorophenyl)-4-cyanobenzamide)propanoylcarbamate (Compound No. 5-76)

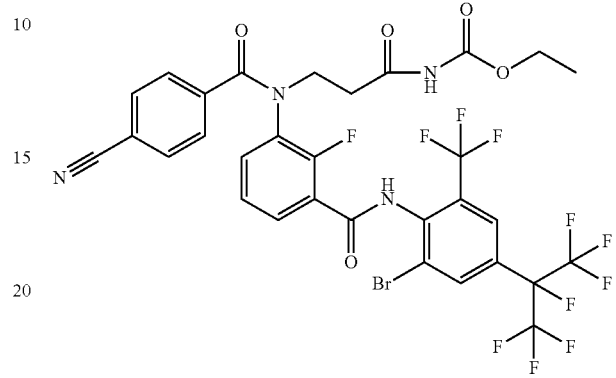

To a solution of 0.0700 g (0.0900 mmol) of 3-(N-(3-amino-3-oxopropyl)-4-cyanobenzamide)-N-(2-bromo-4-(perfluoropropan-2-yl)-6-(trifluoromethyl)phenyl)-2-fluorobenzamide in 5 ml of THF was added 0.00560 g (0.140 mmol) of sodium hydride, followed by stirring at room temperature for 1 hour, and then to the reaction liquid was added 0.0150 g (0.140 mmol) of ethyl chloroformate, followed by stirring at room temperature for 1 hour. Water was added to the reaction liquid, followed by extraction with ethyl acetate. The organic layer was washed with saturated brine, and then dried over anhydrous magnesium sulfate. The solvent was evaporated under reduced pressure and the obtained residue was purified by silica gel column chromatography (developing solvent; hexane:ethyl acetate=3:1) to prepare 0.0750 g (yield 95%) of a target compound.

$^1$H-NMR (CDCl$_3$, ppm) δ 1.24-1.30 (3H, m), 3.25 (2H, m), 3.37 (2H, m), 4.20 (1H, m), 4.35 (2H, m), 7.29 (3H, m), 7.41 (2H, m), 7.52 (2H, m), 7.91 (1H, m), 8.05 (1H, m), 8.14 (1H, m).

Example 43

Preparation of 3-(4-cyano-N-(3-hydrazinyl-3-oxopropyl)benzamide)-N-(2,6-dimethyl-4-(perfluoropropan-2-yl)phenyl)-2-fluorobenzamide (Compound No. 5-83)

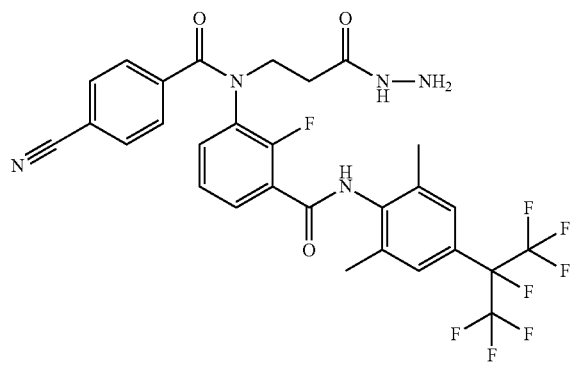 [SMILES: Cc1cc(C(F)(C(F)(F)F)C(F)(F)F)cc(C)c1NC(=O)c1cccc(N(CCC(=O)NN)C(=O)c2ccc(C#N)cc2)c1F]

43-1

Preparation of 3-(3-(2,6-dimethyl-4-(perfluoropropyl-2-yl)phenylcarbamoyl)-2-fluorophenylamino)propanoic acid

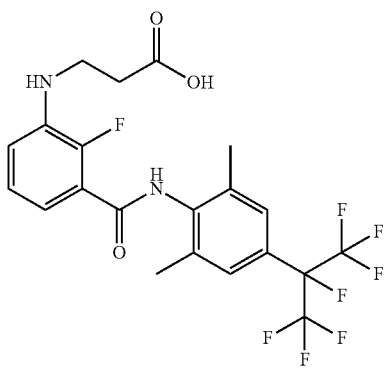

According to the method of 32-1 of Example 32, a target compound was prepared from 3-amino-N-(2,6-dimethyl-4-(perfluoropropan-2-yl)phenyl)-2-fluorobenzamide obtained in 1-3 of Example 1.

$^1$H-NMR (CDCl$_3$, ppm) δ 2.35 (6H, s), 2.68-2.76 (2H, m), 3.55 (2H, t, J=6.3 Hz), 4.43 (1H, t, J=6.3 Hz), 6.91 (1H, t, J=8.3 Hz), 7.16 (1H, t, J=7.8 Hz), 7.35-7.39 (3H, m), 7.85 (1H, d, J=12.7 Hz).

The proton presumed to be indicative of the carboxylic acid was not detected.

43-2

Preparation of ethyl 3-(3-(2,6-dimethyl-4-(perfluoropropan-2-yl)phenylcarbamoyl)-2-fluorophenylamino)propanoate

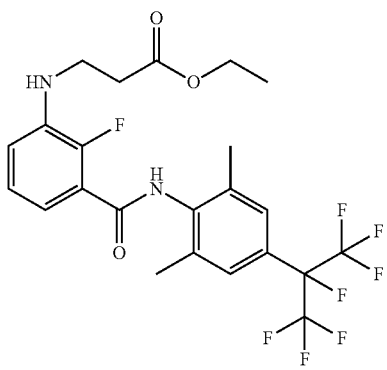 [SMILES: CCOC(=O)CCNc1cccc(C(=O)Nc2c(C)cc(C(F)(C(F)(F)F)C(F)(F)F)cc2C)c1F]

To a solution of 4.50 g (9.00 mmol) of 3-(3-(2,6-dimethyl-4-(perfluoropropyl-2-yl)phenylcarbamoyl)-2-fluorophenylamino)propanoic acid in 5 ml of THF was added 1.80 g (11.0 mmol) of 1,1'-carbonylbis 1H-imidazole, followed by stirring at room temperature for 20 minutes. To the reaction liquid was added 1.30 g (27.0 mmol) of ethanol, followed by stirring at room temperature for 4 hours, and then leaving to stand overnight at the same temperature. To the reaction liquid were added ethyl acetate and water, and the mixture was washed with saturated brine and dried over anhydrous magnesium sulfate. The solvent was evaporated under reduced pressure and the obtained residue was purified by silica gel column chromatography (developing solvent; hexane:ethyl acetate=10:1→8:1) to prepare 3.30 g (yield 68%) of a target compound.

$^1$H-NMR (CDCl$_3$, ppm) δ 1.28 (3H, t, J=7.3 Hz), 2.36 (6H, s), 2.67 (2H, t, J=6.3 Hz), 3.51-3.56 (2H, m), 4.20 (2H, q, J=7.3 Hz), 4.49 (1H, broad-s), 6.89-6.93 (1H, m), 7.16 (1H, t, J=7.8 Hz), 7.35-7.39 (3H, m), 7.81 (1H, d, J=13.1 Hz).

43-3

Preparation of ethyl 3-(4-cyano-N-(3-(2,6-dimethyl-4-(perfluoropropan-2-yl)phenylcarbamoyl)-2-fluorophenyl)benzamide)propanoate

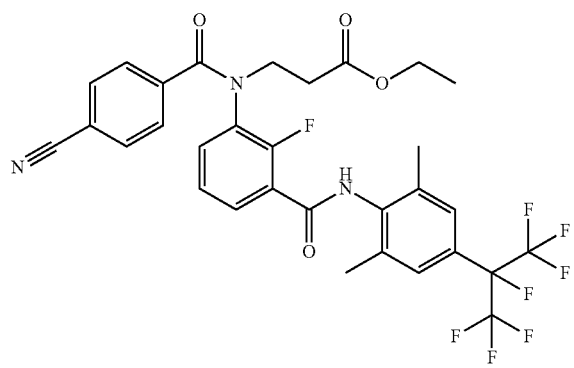 [SMILES: CCOC(=O)CCN(C(=O)c1ccc(C#N)cc1)c1cccc(C(=O)Nc2c(C)cc(C(F)(C(F)(F)F)C(F)(F)F)cc2C)c1F]

According to the method of 1-5 of Example 1, a target compound was prepared from ethyl 3-(3-(2,6-dimethyl-4-(perfluoropropan-2-yl)phenylcarbamoyl)-2-fluorophenylamino)propanoate and 4-cyanobenzoylchloride.

$^1$H-NMR (CDCl$_3$, ppm) δ 1.20 (3H, t, J=6.8 Hz), 2.28 (6H, s), 2.75-2.76 (1H, m), 2.80-2.81 (1H, m), 4.02-4.08 (2H, m), 4.24-4.25 (2H, m), 7.28-7.30 (1H, m), 7.36 (2H, s), 7.44-7.47 (3H, m), 7.51 (2H, d, J=5.8 Hz), 7.58-7.61 (1H, m), 7.99 (1H, t, J=6.8 Hz).

43-4

Preparation of 3-(4-cyano-N-(3-hydrazinyl-3-oxopropyl)benzamide)-N-(2,6-dimethyl-4-(perfluoropropan-2-yl)phenyl)-2-fluorobenzamide (Compound No. 5-83)

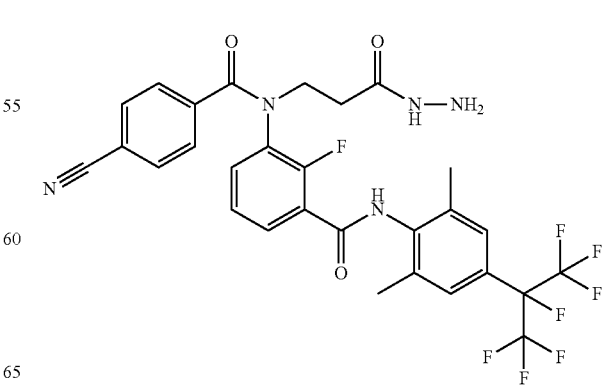

To 10 ml of 0.100 g (0.150 mmol) of ethyl 3-(4-cyano-N-(3-(2,6-dimethyl-4-(perfluoropropan-2-yl)phenylcarbamoyl)-2-fluorophenyl)benzamide)propanoate in THF was added 0.120 g (3.00 mmol) of hydrazine (80% aqueous solution), followed by stirring at 60° C. for 8 hours. The reaction liquid was concentrated, and then to the residue was added ethyl acetate, followed by washing with water and saturated brine, and drying over anhydrous magnesium sulfate. The solvent was evaporated under reduced pressure and the obtained residue was purified by silica gel column chromatography (developing solvent; hexane:ethyl acetate=1:1) to prepare 0.0270 g (yield 28%) of a target compound.

$^1$H-NMR (CDCl$_3$, ppm) δ 2.24 (6H, s), 2.65 (2H, m), 3.65 (2H, m), 4.23 (2H, m), 5.35 (1H, m), 7.26-7.53 (6H, m), 7.86-7.93 (4H, m).

Example 44

Preparation of N-(3-(2,6-dimethyl-4-(perfluoropropan-2-yl)phenylcarbamoyl)phenyl)-N-(2-hydroxyethyl)benzamide (Compound No. 5-5)

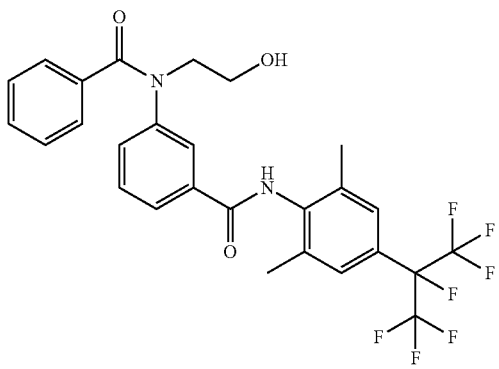 [SMILES: Cc1cc(C(F)(C(F)(F)F)C(F)(F)F)cc(C)c1NC(=O)c1cccc(N(CCO)C(=O)c2ccccc2)c1]

44-1

Preparation of ((2-iodoethoxy)methyl)benzene

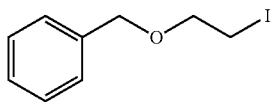 [SMILES: ICCOCc1ccccc1]

To a solution of 3.00 g (20.0 mmol) of 2-benzyloxy ethanol and 2.30 g (22.0 mmol) of triethylamine in 30 ml of dichloromethane was added 2.50 g (22.0 mmol) of mesyl chloride, followed by stirring at 0° C. for 3 hours. The precipitated solid was removed by filtration, and then the filtrate was concentrated under reduced pressure. To the obtained residue was added 30 ml of acetone, and the precipitated solid was removed by filtration. To the filtrate was added 4.50 g (30.0 mmol) of sodium iodide, followed by stirring at room temperature for 50 hours, the solid was removed by filtration, and the filtrate was concentrated under reduced pressure. The obtained residue was purified by silica gel column chromatography (developing solvent; hexane:ethyl acetate=7:1) to prepare 2.70 g (yield 52%) of a target compound.

$^1$H-NMR (CDCl$_3$, ppm) δ 3.29 (2H, t, J=6.8 Hz), 3.74 (2H, t, J=6.8 Hz), 4.58 (2H, s), 7.29-7.37 (5H, m).

44-2

Preparation of 3-benzamide-N-(2,6-dimethyl-4-(perfluoropropan-2-yl)phenyl)benzamide

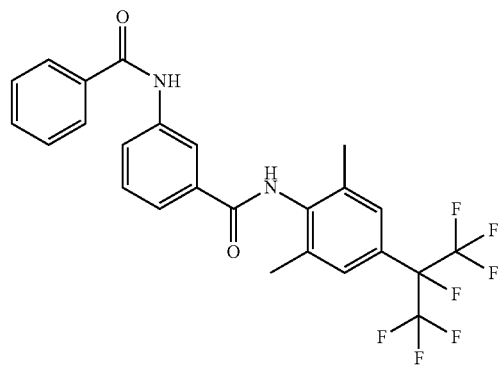 [SMILES: Cc1cc(C(F)(C(F)(F)F)C(F)(F)F)cc(C)c1NC(=O)c1cccc(NC(=O)c2ccccc2)c1]

According to the method of 1-5 of Example 1, a target compound was prepared from 3-amino-N-(2,6-dimethyl-4-(perfluoropropan-2-yl)phenyl)benzamide obtained in 20-1 of Example 20.

$^1$H-NMR (DMSO-d$_6$, ppm) δ 2.37 (6H, s), 7.34 (2H, s), 7.46-7.57 (4H, m), 7.75 (1H, d, J=7.8 Hz), 7.98-8.01 (2H, m), 8.12 (1H, d, J=7.3 Hz), 8.34 (1H, s), 8.87 (1H, s), 9.66 (1H, s).

44-3

Preparation of N-(2-(benzyloxy)ethyl)-N-(3-(2,6-dimethyl-4-(perfluoropropan-2-yl)phenylcarbamoyl)phenyl)benzamide (Compound No. 5-74)

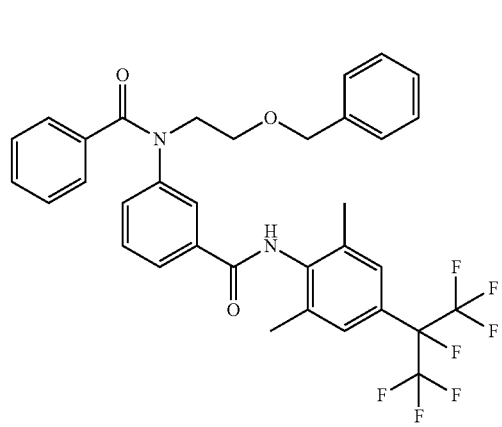 [SMILES: Cc1cc(C(F)(C(F)(F)F)C(F)(F)F)cc(C)c1NC(=O)c1cccc(N(CCOCc2ccccc2)C(=O)c2ccccc2)c1]

A solution of 0.800 g (1.50 mmol) of 3-benzamide-N-(2,6-dimethyl-4-(perfluoropropan-2-yl)phenyl)benzamide, 0.600 g (2.30 mmol) of ((2-iodoethoxy)methyl)benzene, and 0.400 g (6.80 mmol) of potassium hydroxide in 10 ml of DMSO was stirred at 100° C. for 4 hours. The solid was removed by filtration, then the filtrate was concentrated under reduced pressure, and the obtained residue was purified by silica gel column chromatography (developing solvent; hexane:ethyl acetate=7:1→5:1→3:1) to prepare 0.550 g (yield 56%) of a target compound.

¹H-NMR (CDCl₃, ppm) δ 2.29 (6H, s), 3.84 (2H, t, J=5.4 Hz), 4.03 (2H, t, J=5.4 Hz), 4.46 (2H, s), 6.80-7.79 (17H, m).

44-4

Preparation of N-(3-(2,6-dimethyl-4-(perfluoropropan-2-yl)phenylcarbamoyl)phenyl)-N-(2-hydroxyethyl)benzamide (Compound No. 5-5)

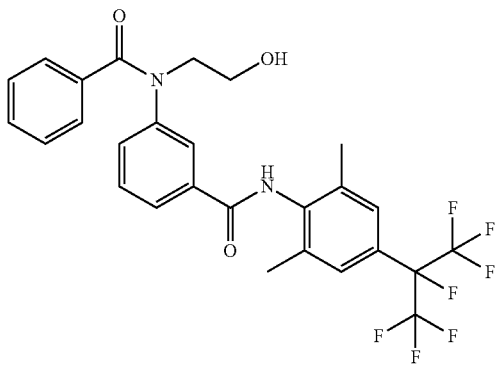 [SMILES: Cc1cc(C(F)(C(F)(F)F)C(F)(F)F)cc(C)c1NC(=O)c1cccc(N(CCO)C(=O)c2ccccc2)c1]

A solution of 0.570 g (0.880 mmol) of N-(2-(benzyloxy)ethyl)-N-(3-(2,6-dimethyl-4-(perfluoropropan-2-yl)phenylcarbamoyl)phenyl)benzamide and 10% Pd/C in 15 ml of ethanol was stirred at room temperature for 3 hours under a hydrogen gas. The catalyst was removed by filtration, then the filtrate was concentrated under reduced pressure, and the obtained residue was purified by silica gel column chromatography (developing solvent; hexane:ethyl acetate=3:1→2:1) to prepare 0.250 g (yield 51%) of a target compound.

¹H-NMR (CDCl₃, ppm) δ 2.37 (6H, s), 3.88-4.01 (5H, m), 6.95 (1H, d, J=7.8 Hz), 7.13 (1H, t, J=7.8 Hz), 7.26 (2H, s), 7.49 (2H, t, J=7.8 Hz), 7.52-7.58 (2H, m), 7.68 (1H, broad-s), 7.72 (1H, t, J=1.9 Hz), 7.77-7.79 (2H, m).

Example 45

Preparation of N-(3-(2-iodo-4-(perfluoropropan-2-yl)-6-(trifluoromethyl)phenylcarbamoyl)phenyl)-N-(3-(methylamino)-3-oxopropyl)benzamide (Compound No. 5-86)

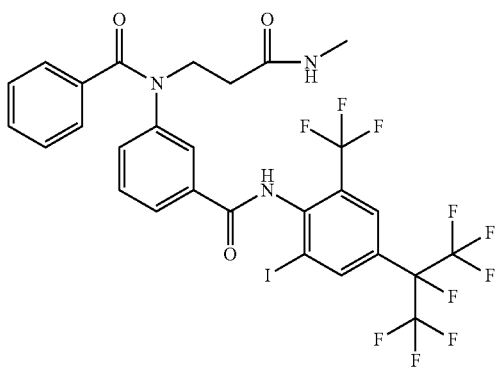 [SMILES: CNC(=O)CCN(C(=O)c1ccccc1)c1cccc(C(=O)Nc2c(I)cc(C(F)(C(F)(F)F)C(F)(F)F)cc2C(F)(F)F)c1]

45-1

Preparation of 2-iodo-4-(perfluoropropan-2-yl)-6-(trifluoromethyl)aniline (Compound No. 21-10)

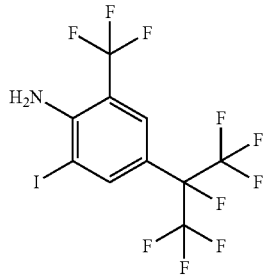 [SMILES: Nc1c(I)cc(C(F)(C(F)(F)F)C(F)(F)F)cc1C(F)(F)F]

According to the method of 22-2 of Example 22, a target compound was prepared from 4-(perfluoropropan-2-yl)-2-(trifluoromethyl)aniline obtained in 22-1 of Example 22 and N-iodosuccinimide.

¹H-NMR (CDCl₃, ppm) δ 5.04 (2H, broad-s), 7.64 (1H, s), 7.99 (1H, s).

45-2

Preparation of N-(2-iodo-4-(perfluoropropan-2-yl)-6-(trifluoromethyl)phenyl)-3-nitrobenzamide (Compound No. 11-12)

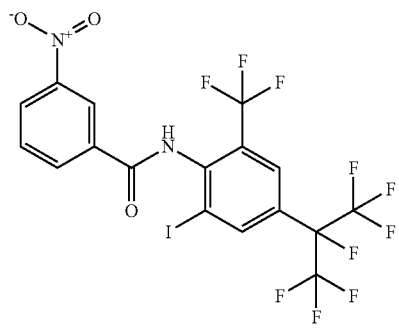

50.0 g (110 mmol) of 2-iodo-4-(perfluoropropan-2-yl)-6-(trifluoromethyl)aniline and 24.5 g (0.13 mol) of 3-nitrobenzoyl chloride were dissolved in 75 g of DMI, and reacted at an internal temperature of 100° C. to 105° C. for 8 hours. After cooling to room temperature, to the reaction liquid were added ethyl acetate and a saturated aqueous sodium bicarbonate solution, followed by liquid separation. The organic layer was washed with saturated brine, and then dried over anhydrous sodium sulfate. The solution was concentrated under reduced pressure, and the concentrated residue was purified by silica gel column chromatography (developing solvent; hexane:ethyl acetate=3:1) to prepare 52.0 g (yield 78%) of a target compound.

¹H-NMR (CDCl₃, ppm) δ 7.76-7.80 (2H, m), 7.97 (1H, s), 8.28-8.30 (1H, m), 8.37 (1H, s), 8.49-8.52 (1H, m), 8.78 (1H, s).

45-3

Preparation of 3-amino-N-(2-iodo-4-(perfluoropropan-2-yl)-6-(trifluoromethyl)phenyl)benzamide (Compound No. 12-8)

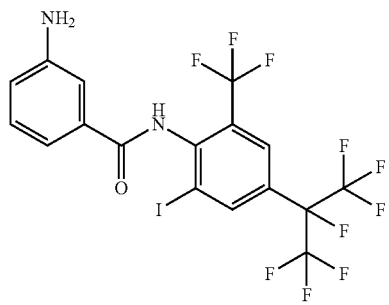 [SMILES: Nc1cccc(C(=O)Nc2c(I)cc(C(F)(C(F)(F)F)C(F)(F)F)cc2C(F)(F)F)c1]

According to the method of 1-3 of Example 1, a target compound was prepared from N-(2-iodo-4-(perfluoropropan-2-yl)-6-(trifluoromethyl)phenyl)-3-nitrobenzamide.

¹H-NMR (CDCl₃, ppm) δ 3.89 (2H, broad-s), 6.89-6.92 (1H, m), 7.23-7.32 (3H, m) 7.68 (1H, s), 7.93 (1H, s), 8.34-8.36 (1H, m).

45-4

Preparation of 3-(3-(2-iodo-4-(perfluoropropan-2-yl)-6-(trifluoromethyl)phenylcarbamoyl)phenylamino)propanoic acid

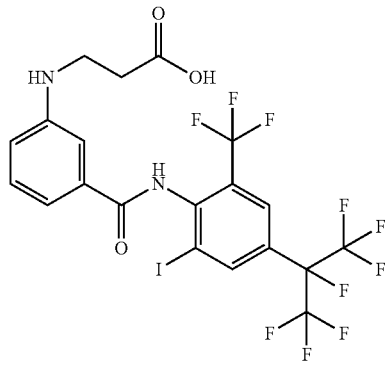 [SMILES: O=C(O)CCNc1cccc(C(=O)Nc2c(I)cc(C(F)(C(F)(F)F)C(F)(F)F)cc2C(F)(F)F)c1]

According to the method of 32-1 of Example 32, a target compound was prepared from 3-amino-N-(2-iodo-4-(perfluoropropan-2-yl)-6-(trifluoromethyl)phenyl)benzamide.

¹H-NMR (DMSO-d₆, ppm) δ 2.50-2.55 (2H, m), 3.30-3.33 (2H, m), 5.96 (1H, broad-s), 6.80-6.83 (1H, m), 7.13-7.17 (2H, m), 7.23-7.27 (1H, m), 7.95 (1H, s), 8.49 (1H, s), 10.42 (1H, s), 12.28 (1H, broad-s).

45-5

Preparation of methyl 3-(3-(2-iodo-4-(perfluoropropan-2-yl)-6-(trifluoromethyl)phenylcarbamoyl)phenylamino)propanoate

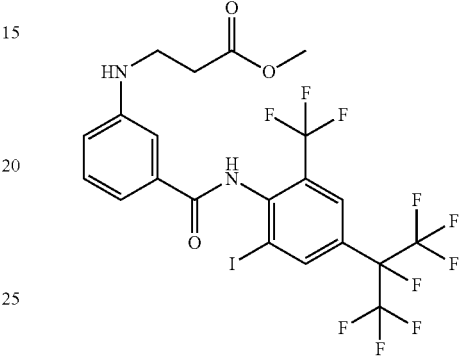

10 ml of methanol was cooled to 0° C., and 0.510 g (4.30 mmol) of thionyl chloride was added dropwise thereto, followed by stirring as it was for 10 minutes. Then, 0.690 g (1.10 mmol) of 3-(3-(2-iodo-4-(perfluoropropan-2-yl)-6-(trifluoromethyl)phenylcarbamoyl)phenylamino)propanoic acid was added thereto, followed by leaving to stand at room temperature overnight. The solvent was evaporated under reduced pressure to prepare 0.710 g (yield 97%) of a target compound.

APCI-MS m/z (M+1):661

45-6

Preparation of methyl 3-(N-(3-(2-iodo-4-(perfluoropropan-2-yl)-6-(trifluoromethyl)phenylcarbamoyl)phenyl)benzamide)propanoate (Compound No. 5-80)

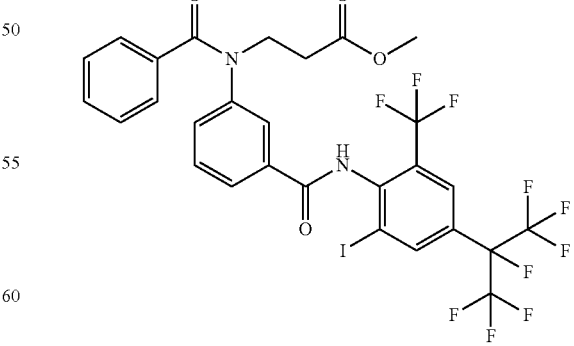

According to the method of 1-5 of Example 1, a target compound was prepared from methyl 3-(3-(2-iodo-4-(perfluoropropan-2-yl)-6-(trifluoromethyl)phenylcarbamoyl)phenylamino)propanoate.

¹H-NMR (DMSO-d₆, ppm) δ 2.66-2.70 (2H, m), 3.54 (3H, s), 4.12-4.15 (2H, m), 7.21-7.29 (5H, m), 7.45-7.47 (2H, m), 7.72 (1H, s), 7.76 OIL d, J=7.3 Hz), 7.95 (1H, s), 8.51 (1H, s), 10.59 (1H, s)

45-7

3-(N-(3-(2-iodo-4-(perfluoropropan-2-yl)-6-(trifluoromethyl)phenylcarbamoyl)phenyl)benzamide)propanoic acid (Compound No. 5-88)

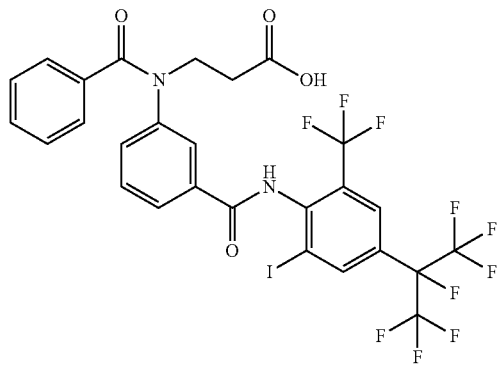 [SMILES: O=C(O)CCN(C(=O)c1ccccc1)c1cccc(C(=O)Nc2c(I)cc(C(F)(C(F)(F)F)C(F)(F)F)cc2C(F)(F)F)c1]

According to the method of Example 2, a target compound was prepared from methyl 3-(N-(3-(2-iodo-4-(perfluoropropan-2-yl)-6-(trifluoromethyl)phenylcarbamoyl)phenyl)benzamide)propanoate.

¹H-NMR (DMSO-d₆, ppm) δ 2.58-2.62 (2H, m), 4.02-4.11 (2H, m), 7.21-7.30 (5H, m), 7.46-7.49 (2H, m), 7.74-7.76 (2H, m), 7.95 (1H, s), 8.51 (1H, s), 10.6 (1H, broad-s), 12.5 (1H, broad-s)

45-8

Preparation of N-(3-(2-iodo-4-(perfluoropropan-2-yl)-6-(trifluoromethyl)phenylcarbamoyl)phenyl)-N-(3-(methylamino)-3-oxopropyl)benzamide (Compound No. 5-86)

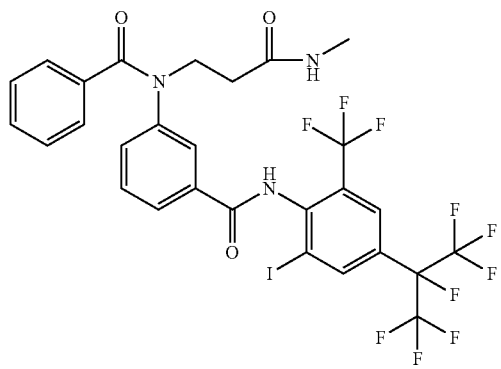 [SMILES: CNC(=O)CCN(C(=O)c1ccccc1)c1cccc(C(=O)Nc2c(I)cc(C(F)(C(F)(F)F)C(F)(F)F)cc2C(F)(F)F)c1]

According to the method of Example 28, a target compound was prepared from 3-(N-(3-(2-iodo-4-(perfluoropropan-2-yl)-6-(trifluoromethyl)phenylcarbamoyl)phenyl)benzamide)propanoic acid and methylamine (40% aqueous solution).

¹H-NMR (DMSO-d₆, ppm) δ 2.44-2.46 (2H, m), 3.33 (3H, s), 4.02-4.09 (2H, m), 7.23-7.28 (5H, m), 7.46-7.47 (2H, m), 7.68 (1H, broad-s), 7.74-7.76 (1H, m), 7.91-7.92 (1H, m), 7.95 (1H, s), 8.50 (1H, s), 10.57 (1H, s)

Example 46

Preparation of N-(3-amino-3-(hydroxyimino)propyl)-N-(3-(2,6-dimethyl-4-(perfluoropropan-2-yl)phenylcarbamoyl)phenyl)benzamide (Compound No. 5-91)

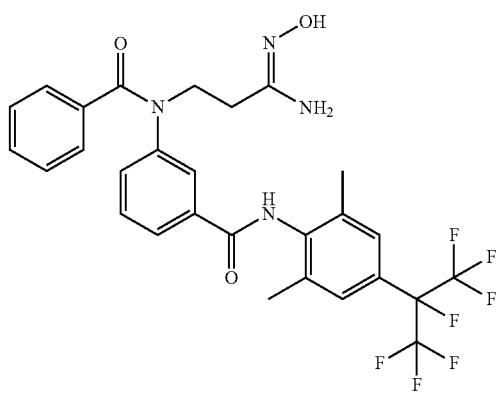 [SMILES: Cc1cc(C(F)(C(F)(F)F)C(F)(F)F)cc(C)c1NC(=O)c1cccc(N(CC/C(N)=N/O)C(=O)c2ccccc2)c1]

A solution of 0.200 g (0.350 mmol) of N-(2-cyanoethyl)-N-(3-(2,6-dimethyl-4-(perfluoropropan-2-yl)phenylcarbamoyl)phenyl)benzamide obtained in Example 24, 0.0800 g (0.800 mmol) of sodium carbonate, and 0.0500 g (0.700 mmol) of hydroxyamine-hydrate in ethanol 2 ml/water 2 ml was stirred at 80° C. for 5 hours. To the reaction liquid was added water, followed by extraction with ethyl acetate. The organic layer was dried over anhydrous sodium sulfate. The solution was evaporated under reduced pressure, the obtained residue was purified by silica gel column chromatography (developing solvent; hexane:ethyl acetate=1:1→0:1) to prepare 0.0200 g (yield 10%) of a target compound.

¹H-NMR (CDCl₃, ppm) δ 2.19 (1/2*6 H, s), 2.24 (1/2*6 H, s), 2.42 (1/2*2H, t, J=6.8

Hz), 2.67 (1/2*2H, t, J=6.8 Hz), 4.11 (1/2*2H, t, J=6.8 Hz), 4.26 (1/2*2H, t, J=6.8 Hz), 4.75 (1H, s), 5.69 (1/2*1H, broad-s), 6.30 (1/2*1H, broad-s), 7.12-7.95 (13H, m).

Example 47

Preparation of N-(4-amino-4-oxobutyl)-N-(3-(2,6-dimethyl-4-(perfluoropropan-2-yl)phenylcarbamoyl)phenyl)benzamide (Compound No. 6-16)

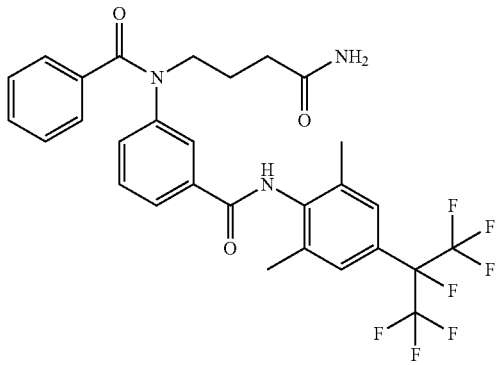 [SMILES: Cc1cc(C(F)(C(F)(F)F)C(F)(F)F)cc(C)c1NC(=O)c1cccc(N(CCCC(N)=O)C(=O)c2ccccc2)c1]

47-1

Preparation of 3-(4-amino-4-oxobutylamino)-N-(2,6-dimethyl-4-(perfluoropropan-2-yl)phenyl)benzamide

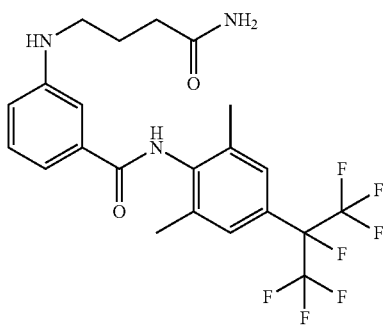 [SMILES: Cc1cc(C(F)(C(F)(F)F)C(F)(F)F)cc(C)c1NC(=O)c1cccc(NCCCC(N)=O)c1]

A solution of 0.270 g (0.470 mmol) of 3-(3-cyanopropylamino)-N-(2,6-dimethyl-4-(perfluoropropan-2-yl)phenyl)benzamide in 5 g of sulfuric acid was stirred at 100° C. for 30 minutes. To the reaction liquid was added an aqueous sodium hydrogen carbonate solution, followed by extraction with ethyl acetate. The organic layer was dried over anhydrous sodium sulfate. The solution was evaporated under reduced pressure and the obtained residue was purified by silica gel column chromatography (developing solvent; hexane:ethyl acetate=1:1→0:1) to prepare 0.18 g (yield 78%) of a target compound.

$^1$H-NMR (CDCl$_3$, ppm) δ 2.00 (2H, quintet, J=6.8 Hz), 2.35 (6H, s), 2.36 (2H, t, J=6.8 Hz), 3.26 (2H, t, J=6.8 Hz), 4.14 (1H, broad-s), 5.30 (1H, broad-s), 5.48 (1H, broad-s), 6.80 (1H, dd, J=1.5, 7.8 Hz), 7.21 (1H, d, J=7.8 Hz), 7.26-7.28 (2H, m), 7.34 (2H, s), 7.71 (1H, s).

47-2

Preparation of N-(4-amino-4-oxobutyl)-N-(3-(2,6-dimethyl-4-(perfluoropropan-2-yl)phenylcarbamoyl)phenyl)benzamide (Compound No. 6-16)

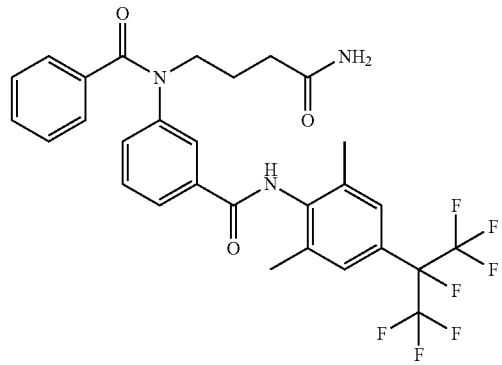 [SMILES: Cc1cc(C(F)(C(F)(F)F)C(F)(F)F)cc(C)c1NC(=O)c1cccc(N(CCCC(N)=O)C(=O)c2ccccc2)c1]

According to the method of 1-5 of Example 1, a target compound was prepared from 3-(4-amino-4-oxobutylamino)-N-(2,6-dimethyl-4-(perfluoropropan-2-yl)phenyl)benzamide.

$^1$H-NMR (CDCl$_3$, ppm) δ 2.08 (2H, quintet, J=6.8 Hz), 2.31 (6H, s), 2.40 (2H, t, J=6.8 Hz), 4.08 (2H, t, J=6.8 Hz), 5.32 (1H, broad-s), 6.02 (1H, broad-s), 7.14-7.34 (9H, m), 7.74 (1H, d, J=7.8 Hz), 7.80 (1H, s), 8.10 (1H, s).

Example 48

Preparation of N-(3-(2,6-dimethyl-4-(perfluoropropan-2-yl)phenylcarbamoyl)phenyl)-N-(2-oxoethyl)benzamide (Compound No. 6-59)

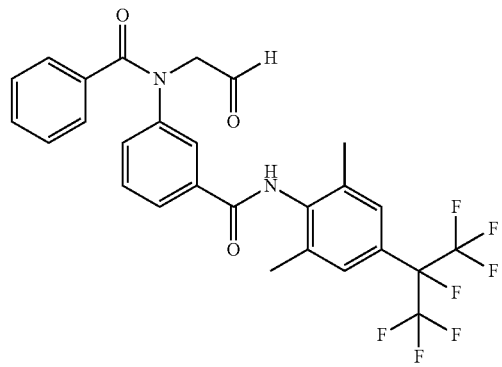 [SMILES: Cc1cc(C(F)(C(F)(F)F)C(F)(F)F)cc(C)c1NC(=O)c1cccc(N(CC=O)C(=O)c2ccccc2)c1]

A solution of 0.100 g (0.280 mmol) of N-(3-(2,6-dimethyl-4-(perfluoropropan-2-yl)phenylcarbamoyl)phenyl)-N-(2-hydroxyethyl)benzamide obtained in 44-4 of Example 44 and 0.350 g (0.900 mmol) of 98% PDC in 10 ml of dichloromethane was stirred at room temperature for 10 hours. After filtration through Celite, the filtrate was concentrated under reduced pressure, and then the obtained residue was purified by silica gel column chromatography (developing solvent; hexane:ethyl acetate=1:1→0:1) to prepare 0.0700 g (yield 44%) of a target compound.

¹H-NMR (CDCl₃, ppm) δ 2.36 (6H, s), 4.27 (2H, s), 6.97 (1H, d, J=7.8 Hz), 7.14 (1H, t, J=7.8 Hz), 7.28 (2H, s), 7.47 (2H, t, J=7.8 Hz), 7.55 (1H, t, J=7.8 Hz), 7.61 (1H, dd, J=1.5, 7.8 Hz), 7.73-7.82 (4H, m), 9.85 (1H, s).

Example 49

Preparation of N-(3-(2,6-dimethyl-4-(perfluoropropan-2-yl)phenylcarbamoyl)phenyl)-N-(3-(2-nitroguanidino)propyl)benzamide (Compound No. 6-61)

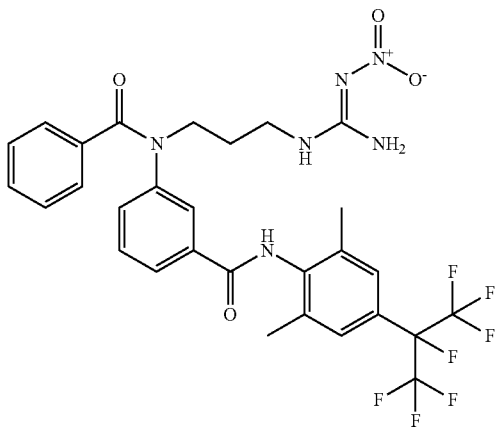 [SMILES: Cc1cc(C(F)(C(F)(F)F)C(F)(F)F)cc(C)c1NC(=O)c1cccc(N(CCCN/C(N)=N/[N+](=O)[O-])C(=O)c2ccccc2)c1]

A solution of 0.100 g (0.180 mmol) of N-(3-aminopropyl)-N-(3-(2,6-dimethyl-4-(perfluoropropan-2-yl)phenylcarbamoyl)phenyl)benzamide obtained in Example 25 and 0.0500 g (0.370 mmol) of S-methylnitrothiourea in 30 ml of ethanol was stirred at 60° C. for 5 hours. The solvent was evaporated under reduced pressure to prepare 0.0800 g (yield 67%) of a target compound.

¹H-NMR (CDCl₃, ppm) δ 1.90 (2H, broad-s), 2.02-2.07 (2H, m), 2.26 (6H, s), 3.41 (2H, q, J=6.4 Hz), 4.13 (2H, t, J=6.4 Hz), 7.16-7.82 (12H, m), 8.56 (1H, s).

Example 50

Preparation of N-(3-(2,6-dimethyl-4-(perfluoropropan-2-yl)phenylcarbamoyl)phenyl)-N-(3-(hydroxyimino)butyl)benzamide (Compound No. 5-105)

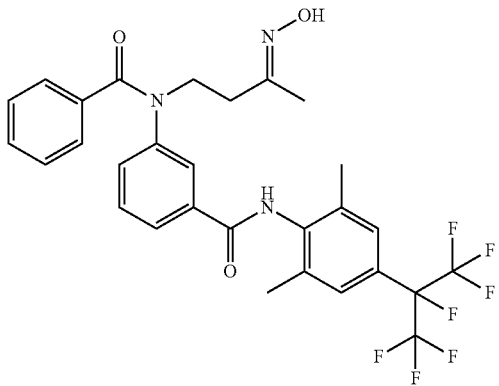 [SMILES: C/C(CCN(C(=O)c1ccccc1)c1cccc(C(=O)Nc2c(C)cc(C(F)(C(F)(F)F)C(F)(F)F)cc2C)c1)=N\O]

50-1

Preparation of N-(2,6-dimethyl-4-(perfluoropropan-2-yl)phenyl)-3-(3-oxobutylamino)benzamide

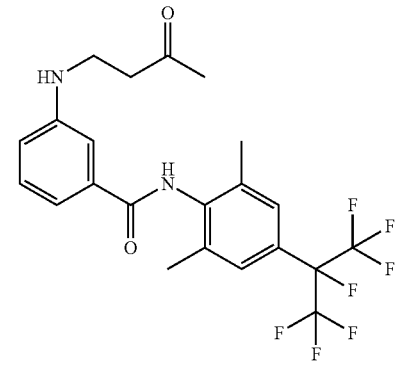 [SMILES: CC(=O)CCNc1cccc(C(=O)Nc2c(C)cc(C(F)(C(F)(F)F)C(F)(F)F)cc2C)c1]

According to the method of 20-2 of Example 20, a target compound was prepared from 3-amino-N-(2,6-dimethyl-4-(perfluoropropan-2-yl)phenyl)benzamide and 1-buten-3-one obtained in 20-1 of Example 20.

¹H-NMR (CDCl₃, ppm) δ 2.19 (3H, s), 2.35 (6H, s), 2.78 (2H, t, J=5.9 Hz), 3.48 (2H, broad-s), 4.27 (1H, broad-s), 6.78 (1H, dd, J=2.4, 7.8 Hz), 7.15-7.35 (6H, m).

50-2

Preparation of N-(3-(2,6-dimethyl-4-(perfluoropropan-2-yl)phenylcarbamoyl)phenyl)-N-(3-oxobutyl)benzamide (Compound No. 5-100)

According to the method of 1-5 of Example 1, a target compound was prepared from N-(2,6-dimethyl-4-(perfluoropropan-2-yl)phenyl)-3-(3-oxobutylamino)benzamide.

441

$^1$H-NMR (CDCl$_3$, ppm) δ 2.17 (3H, s), 2.28 (6H, s), 2.92 (2H, t, J=6.8 Hz), 4.25 (2H, t, J=6.8 Hz), 7.18-7.39 (10H, m), 7.58 (1H, s), 7.69 (1H, d, J=7.8 Hz).

50-3

Preparation of N-(3-(2,6-dimethyl-4-(perfluoropropan-2-yl)phenylcarbamoyl)phenyl)-N-(3-(hydroxyimino)butyl)benzamide (Compound No. 5-105)

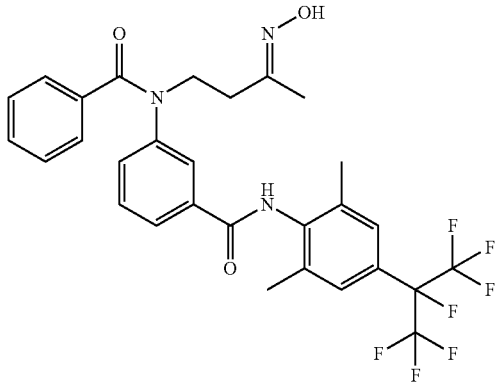 [SMILES: C/C(CCN(C(=O)c1ccccc1)c1cccc(C(=O)Nc2c(C)cc(C(F)(C(F)(F)F)C(F)(F)F)cc2C)c1)=N\O]

According to the method of Example 46, a target compound was prepared from N-(3-(2,6-dimethyl-4-(perfluoropropan-2-yl)phenylcarbamoyl)phenyl)-N-(3-oxobutyl)benzamide.

$^1$H-NMR (CDCl$_3$, ppm) δ 1.82 (3/4*3 H, s), 1.92 (1/4*3 H, s), 2.24 (3/4*6 H, s), 2.26 (1/4*6 H, s), 2.58 (3/4*2H, t, J=6.8 Hz), 2.78 (1/4*2H, t, J=6.8 Hz), 4.21 (2H, t, J=6.8 Hz), 7.18-7.71 (13H, m).

Example 51

Preparation of N-(2-bromo-4-(perfluoropropan-2-yl)-6-(trifluoromethyl)phenyl)-2-fluoro-3-(methylamino)benzamide (Compound No. 13-40)

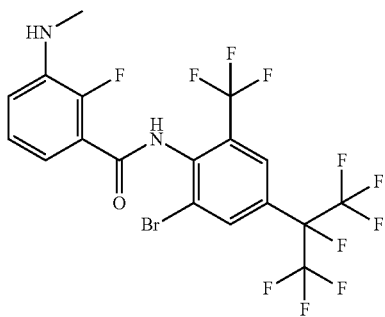 [SMILES: CNc1cccc(C(=O)Nc2c(Br)cc(C(F)(C(F)(F)F)C(F)(F)F)cc2C(F)(F)F)c1F]

0.930 g (1.71 mmol) of 3-amino-N-(2-bromo-4-(perfluoropropan-2-yl)-6-(trifluoromethyl)phenyl)-2-fluorobenzamide obtained in 22-5 of Example 22 was added to 5 ml of concentrated sulfuric acid, and 10 ml of a 37% aqueous formaldehyde solution was charged dropwise thereto at 40° C. The reaction liquid was poured into ice-water, adjusted to pH 10 with an aqueous sodium hydroxide solution, and extracted by the addition of ethyl acetate. The organic layer was washed with a 20% aqueous sodium hydroxide solution and saturated brine, and then dried over anhydrous magnesium sulfate. The solvent was evaporated under reduced pressure and the obtained residue was purified by silica gel column chromatography (developing solvent; hexane:ethyl acetate=8:1) to prepare 0.690 g (yield 72%) of a target compound.

$^1$H-NMR (CDCl$_3$, ppm) δ 2.94 (3H, s), 4.14 (1H, broad-s), 6.88-6.93 (1H, m), 7.18 (1H, t, J=7.8 Hz), 7.37-7.41 (1H, m), 7.90 (1H, s), 8.13 (1H, s), 8.27 (1H, d, J=14.6 Hz).

Example 52

Preparation of 3-amino-N-(2,6-diiodo-4-(perfluoropropan-2-yl)phenyl)-2-fluorobenzamide (Compound No. 12-27)

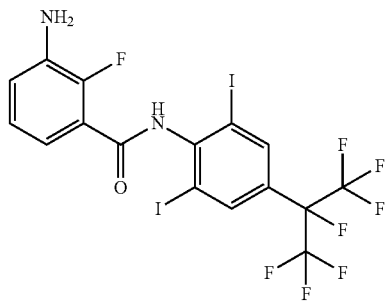 [SMILES: Nc1cccc(C(=O)Nc2c(I)cc(C(F)(C(F)(F)F)C(F)(F)F)cc2I)c1F]

52-1

Preparation of 4-(perfluoropropan-2-yl)aniline

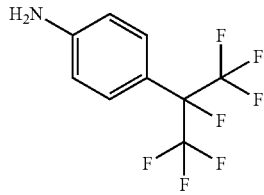 [SMILES: Nc1ccc(C(F)(C(F)(F)F)C(F)(F)F)cc1]

100 g (1.02 mol) of aniline, 230 g (1.12 mol) of 85% sodium hydrosulfite, and 35.1 g (0.100 mol) of tetrabutylammonium hydrogen sulfate were charged to a mixed solution of 1500 ml of t-butyl methyl ether and 1500 ml of water, and 94.7 g (1.12 mol) of sodium hydrogen carbonate was added thereto. 350 g (1.12 mol) of heptafluoroisopropyl iodide was added dropwise thereto at room temperature, followed by stirring at room temperature for 6 hours. After the liquid separation, the organic layer was washed with 1 N hydrochloric acid, water, and a saturated aqueous sodium hydrogen carbonate solution, and then dried over anhydrous sodium sulfate. The solvent was evaporated under reduced pressure, and 500 ml of ethyl acetate was charged thereto. 255 g (1.02 mol) of a 4 M hydrogen chloride/ethyl acetate solution was added dropwise thereto, followed by stirring at room temperature for 30 minutes and at 5° C. for 1 hour. The precipitated solid was separated by filtration, and the solid was charged to 1000 ml of ethyl acetate, and adjusted to pH 8 to 9 by the addition of a saturated aqueous sodium hydrogen carbonate solution at 20° C. or lower, and subjected to liquid separation. The organic layer was dried over anhydrous sodium sulfate, and then the solvent was evaporated under reduced pressure to prepare 188 g (yield 71%) of a target compound.

$^1$H-NMR (CDCl$_3$, ppm) δ 3.92 (2H, broad-s), 6.69-6.74 (2H, m), 7.35 (2H, d, J=9.3 Hz).

52-2

Preparation of 2,6-diiodo-4-(perfluoropropan-2-yl)aniline

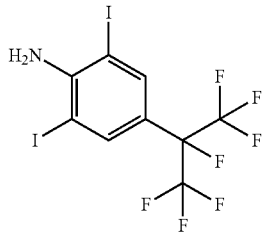 [SMILES: Nc1c(I)cc(C(F)(C(F)(F)F)C(F)(F)F)cc1I]

To a solution of 5.74 g (22.0 mmol) of 4-(perfluoropropan-2-yl)aniline in 50 ml of ethanol was added 2.16 g (22.0 mmol) of concentrated sulfuric acid at 5° C. The reaction liquid was warmed to room temperature, and 10.0 g (44.0 mmol) of N-iodosuccinimide was added thereto, followed by stirring for 3 hours. The reaction liquid was poured into a saturated aqueous sodium hydrogen carbonate solution for neutralization. The precipitated crystals were filtered, washed with water, and then dried to prepare 9.00 g (yield 80%) of a target compound.

$^1$H-NMR (CDCl$_3$, ppm) δ 4.95 (2H, broad-s), 7.79 (2H, s).

52-3

Preparation of 2-chloro-N-(2,6-diiodo-4-(perfluoropropan-2-yl)phenyl)-3-nitrobenzamide (Compound No. 11-25)

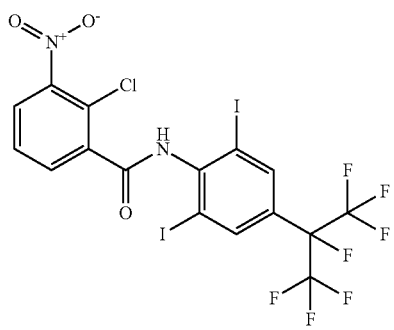 [SMILES: O=C(Nc1c(I)cc(C(F)(C(F)(F)F)C(F)(F)F)cc1I)c1cccc([N+](=O)[O-])c1Cl]

To a solution of 40.0 g (78.0 mmol) of 2,6-diiodo-4-(perfluoropropan-2-yl)aniline in 100 ml of DMI was added 20.6 g (94.0 mmol) of 2-chloro-3-nitrobenzoyl chloride, followed by stirring at 135° C. for 3 hours. After cooling to room temperature, the reaction liquid was poured into 1000 ml of water. After extraction with the addition of 1000 ml of ethyl acetate, the organic layer was washed with water, and then dried over anhydrous magnesium sulfate. The solvent was evaporated under reduced pressure and the obtained residue was washed with hexane to prepare 56.2 g (yield 99%) of a target compound.

$^1$H-NMR (CDCl$_3$, ppm) δ 7.58 (1H, t, J=8.3 Hz), 7.70 (1H, d, J=3.4 Hz), 7.93 (1H, dd, J=1.5, 6.3 Hz), 8.08-8.10 (1H, m), 8.13 (2H, s).

52-4

Preparation of N-(2,6-diiodo-4-(perfluoropropan-2-yl)phenyl)-2-fluoro-3-nitrobenzamide (Compound No. 11-52)

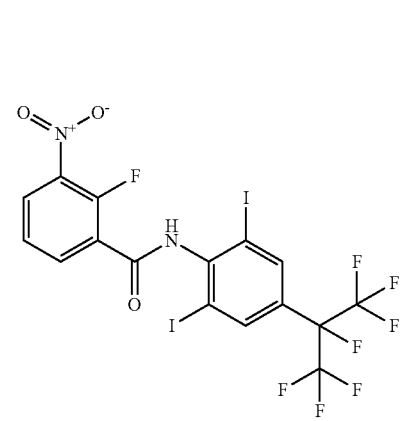 [SMILES: O=C(Nc1c(I)cc(C(F)(C(F)(F)F)C(F)(F)F)cc1I)c1cccc([N+](=O)[O-])c1F]

According to the method of 1-2 of Example 1, a target compound was prepared from 2-chloro-N-(2,6-diiodo-4-(perfluoropropan-2-yl)phenyl)-3-nitrobenzamide.

$^1$H-NMR (CDCl$_3$, ppm) δ 7.52-7.55 (1H, m), 8.12-8.18 (3H, m), 8.29-8.32 (1H, m), 8.48-8.51 (1H, m).

52-5

Preparation of 3-amino-N-(2,6-diiodo-4-(perfluoropropan-2-yl)phenyl)-2-fluorobenzamide (Compound No. 12-27)

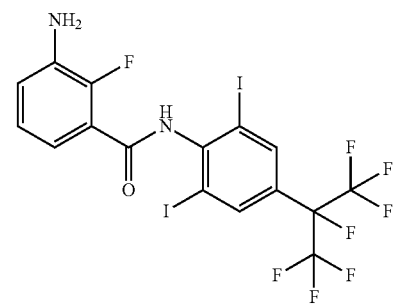 [SMILES: Nc1cccc(C(=O)Nc2c(I)cc(C(F)(C(F)(F)F)C(F)(F)F)cc2I)c1F]

According to the method of 1-3 of Example 1, a target compound was prepared from N-(2,6-diiodo-4-(perfluoropropan-2-yl)phenyl)-2-fluoro-3-nitrobenzamide.

$^1$H-NMR (CDCl$_3$, ppm) δ 3.93 (2H, broad-s), 6.99-7.04 (1H, m), 7.08 (1H, t, J=7.8

Hz), 7.39-7.43 (1H, m), 8.10 (2H, s), 8.72 (1H, d, J=11.2 Hz).

Example 53

Preparation of -(2,6-dibromo-4-(perfluorobutan-2-yl)phenyl)-2-fluoro-3-(methylamino)benzamide (Compound No. 13-32)

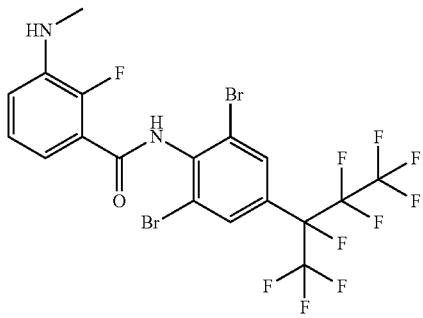 [SMILES: CNc1cccc(C(=O)Nc2c(Br)cc(C(F)(C(F)(F)F)C(F)(F)C(F)(F)F)cc2Br)c1F]

53-1

Preparation of 4-(perfluorobutan-2-yl)aniline

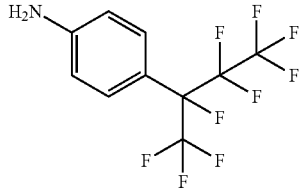 [SMILES: Nc1ccc(C(F)(C(F)(F)F)C(F)(F)C(F)(F)F)cc1]

4.90 g (52.6 mmol) of aniline, 10.1 g (58.0 mmol) of 85% sodium hydrosulfite, and 1.90 g (5.77 mmol) of tetrabutylammonium hydrogen sulfate were charged to a mixed solution of 150 ml of t-butyl methyl ether and 150 ml of water using a light-shield reaction vessel, and 4.84 g (57.6 mmol) of sodium hydrogen carbonate was added thereto. 20.0 g (57.8 mmol) of nonafluoro-s-butyliodide was added dropwise thereto at room temperature, followed by stirring at room temperature for 5 hours. The organic phase was collected by separation, washed with 2 mol/L of an aqueous hydrochloric acid solution twice, and then washed with saturated brine, an aqueous sodium hydrogen carbonate solution, and saturated brine. The organic layer was dried over anhydrous magnesium sulfate, and then the solvent was evaporated under reduced pressure to prepare 8.32 g (yield 51%) of a target compound.

$^1$H-NMR (CDCl$_3$, ppm) δ 3.92 (2H, broad-s), 6.72 (2H, d, J=8.8 Hz), 7.34 (2H, d, J=8.8 Hz).

53-2

Preparation of 2,6-dibromo-4-(perfluorobutan-2-yl)aniline

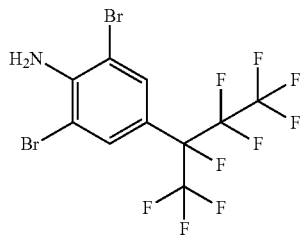 [SMILES: Nc1c(Br)cc(C(F)(C(F)(F)F)C(F)(F)C(F)(F)F)cc1Br]

According to the method of 23-1 of Example 23, a target compound was prepared from 4-(perfluorobutan-2-yl)aniline.

$^1$H-NMR (CDCl$_3$, ppm) δ 4.89 (2H, broad-s), 7.57 (2H, s).

53-3

Preparation of 2-chloro-N-(2,6-dibromo-4-(perfluorobutan-2-yl)phenyl)-3-nitrobenzamide (Compound No. 11-29)

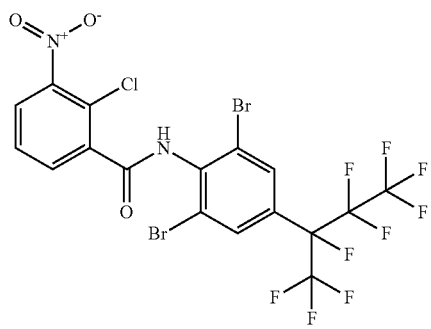 [SMILES: O=C(Nc1c(Br)cc(C(F)(C(F)(F)F)C(F)(F)C(F)(F)F)cc1Br)c1cccc([N+](=O)[O-])c1Cl]

To 27 ml of DMI were added 9.90 g (21.1 mmol) of 2,6-dibromo-4-(perfluorobutan-2-yl)aniline and 4.60 g (20.9 mmol) of 2-chloro-3-nitrobenzoyl chloride, followed by stirring at 140° C. for 4 hours. To the reaction solution were added water and ethyl acetate, and the organic phase was extracted, washed with 1 mol/L of an aqueous sodium hydroxide solution and saturated brine, and dried over anhydrous magnesium sulfate. Then, the solvent was evaporated under reduced pressure. The obtained residue was purified by silica gel column chromatography (developing solvent; hexane:ethyl acetate=20:1→10:1→5:1→3:1) to prepare 5.44 g (yield 40%) of a target compound.

¹H-NMR (CDCl₃, ppm) δ 7.52-7.61 (2H, m), 7.89 (2H, s), 7.94 (1H, dd, J=1.5, 8.3 Hz), 7.99 (1H, d, J=7.8 Hz).

53-4

Preparation of N-(2,6-dibromo-4-(perfluorobutan-2-yl)phenyl)-2-fluoro-3-nitrobenzamide (Compound No. 11-56)

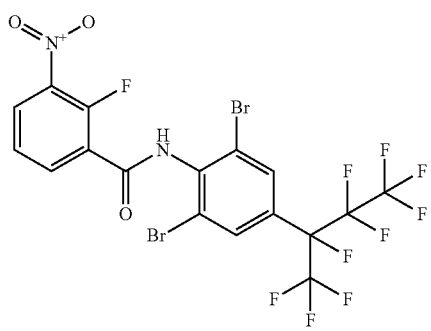

To 108 ml of DMSO were added 5.44 g (8.34 mmol) of 2-chloro-N-(2,6-dibromo-4-(perfluorobutan-2-yl)phenyl)-3-nitrobenzamide and 4.90 g (84.3 mmol) of potassium fluoride (spray-dried product), followed by stirring at 145° C. for 2 hours. The reaction solution was poured into ice-water to precipitate crystals, and the obtained crystals were filtered and washed with hexane. The obtained crystals were purified by silica gel column chromatography (developing solvent; hexane:ethyl acetate=5:1) to prepare 2.42 g (yield 46%) of a target compound.

¹H-NMR (CDCl₃, ppm) δ 7.53-7.54 (1H, m), 7.89 (2H, s), 8.17 (1H, d, J=12.2 Hz), 8.29-8.30 (1H, m), 8.48-8.49 (1H, m).

53-5

Preparation of 3-amino-N-(2,6-dibromo-4-(perfluorobutan-2-yl)phenyl)-2-fluorobenzamide (Compound No. 12-30)

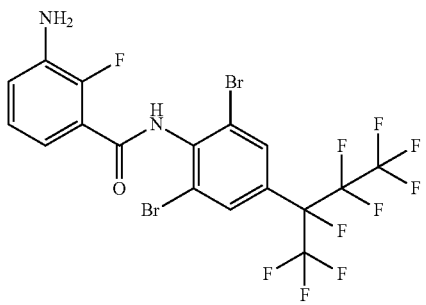 [SMILES: Nc1cccc(C(=O)Nc2c(Br)cc(C(F)(C(F)(F)F)C(F)(F)C(F)(F)F)cc2Br)c1F]

According to the method of 1-3 of Example 1, a target compound was prepared from N-(2,6-dibromo-4-(perfluorobutan-2-yl)phenyl)-2-fluoro-3-nitrobenzamide.

¹H-NMR (CDCl₃, ppm) δ 3.92 (2H, broad-s), 6.99-7.04 (1H, m), 7.11-7.12 (1H, m), 7.48-7.52 (1H, m), 7.86 (2H, s), 8.22 (1H, d, J=14.1 Hz).

53-6

Preparation of N-(2,6-dibromo-4-(perfluorobutan-2-yl)phenyl)-2-fluoro-3-(methylamino)benzamide (Compound No. 13-32)

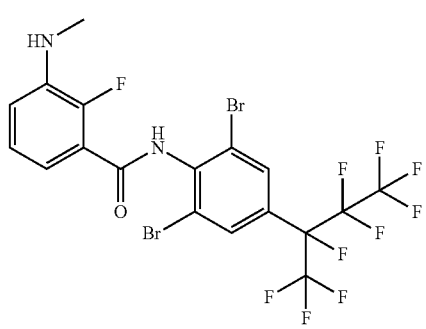 [SMILES: CNc1cccc(C(=O)Nc2c(Br)cc(C(F)(C(F)(F)F)C(F)(F)C(F)(F)F)cc2Br)c1F]

According to the method of Example 51, a target compound was prepared from 3-amino-N-(2,6-dibromo-4-(perfluorobutan-2-yl)phenyl)-2-fluorobenzamide.

¹H-NMR (CDCl₃, ppm) δ 2.95 (3H, s), 4.14 (1H, broad-s), 6.91-6.92 (1H, m), 7.17-7.21 (1H, m), 7.39-7.43 (1H, m), 7.85 (2H, s), 8.21 (1H, d, J=14.1 Hz).

Example 54

Preparation of 3-amino-N-(2-bromo-6-(perfluoroethyl)-4-(perfluoropropan-2-yl)phenyl)-2-fluorobenzamide (Compound No. 12-46)

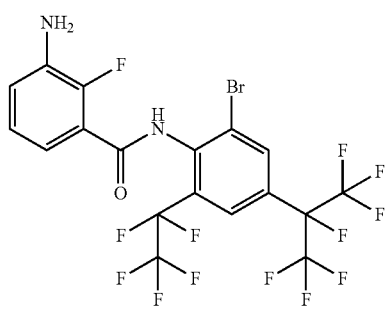 [SMILES: Nc1cccc(C(=O)Nc2c(Br)cc(C(F)(C(F)(F)F)C(F)(F)F)cc2C(F)(F)C(F)(F)F)c1F]

54-1

Preparation of 2-(perfluoroethyl)-4-(perfluoropropan-2-yl)aniline (Compound No. 21-4)

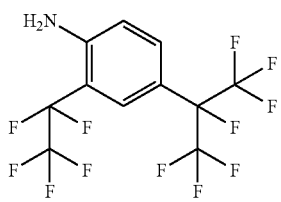 [SMILES: Nc1ccc(C(F)(C(F)(F)F)C(F)(F)F)cc1C(F)(F)C(F)(F)F]

According to the method of 22-1 of Example 22, a target compound was prepared from 4-(perfluoropropan-2-yl)aniline obtained in Example 52-1 and 1,1,2,2,2-pentafluoroethyliodide.

$^1$H-NMR (CDCl$_3$, ppm) δ 4.56 (2H, broad-s), 6.79 (1H, d, J=8.8 Hz), 7.47 (1H, d, J=8.8 Hz), 7.53 (1H, s).

54-2

Preparation of 2-bromo-6-(perfluoroethyl)-4-(perfluoropropan-2-yl)aniline (Compound No. 21-19)

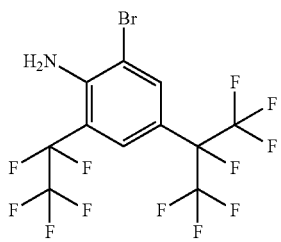 [SMILES: Nc1c(Br)cc(C(F)(C(F)(F)F)C(F)(F)F)cc1C(F)(F)C(F)(F)F]

According to the method of 22-2 of Example 22, a target compound was prepared from 2-(perfluoroethyl)-4-(perfluoropropan-2-yl)aniline.

$^1$H-NMR (CDCl$_3$, ppm) δ 5.14 (2H, broad-s), 7.58 (1H, s), 7.81 (1H, s).

54-3

Preparation of N-(2-bromo-6-(perfluoroethyl)-4-(perfluoropropan-2-yl)phenyl)-2-chloro-3-nitrobenzamide (Compound No. 11-48)

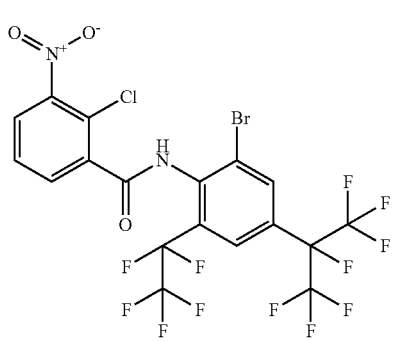 [SMILES: O=C(Nc1c(Br)cc(C(F)(C(F)(F)F)C(F)(F)F)cc1C(F)(F)C(F)(F)F)c1cccc([N+](=O)[O-])c1Cl]

According to the method of 53-3 of Example 53, a target compound was prepared from 2-bromo-6-(perfluoroethyl)-4-(perfluoropropan-2-yl)aniline.

$^1$H-NMR (CDCl$_3$, ppm) δ 7.56-7.61 (1H, m), 7.73 (1H, s), 7.88 (1H, d, J=1.5 Hz), 7.92-7.98 (2H, m), 8.21 (1H, s).

54-4

Preparation of N-(2-bromo-6-(perfluoroethyl)-4-(perfluoropropan-2-yl)phenyl)-2-fluoro-3-nitrobenzamide (Compound No. 11-75)

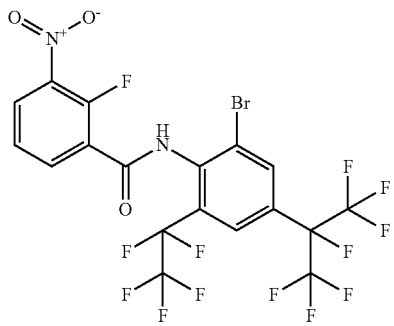 [SMILES: O=C(Nc1c(Br)cc(C(F)(C(F)(F)F)C(F)(F)F)cc1C(F)(F)C(F)(F)F)c1cccc([N+](=O)[O-])c1F]

According to the method of 1-2 of Example 1, a target compound was prepared from N-(2-bromo-6-(perfluoroethyl)-4-(perfluoropropan-2-yl)phenyl)-2-chloro-3-nitrobenzamide.

APCI-MS m/z (M+1):626

54-5

Preparation of 3-amino-N-(2-bromo-6-(perfluoroethyl)-4-(perfluoropropan-2-yl)phenyl)-2-fluorobenzamide (Compound No. 12-46)

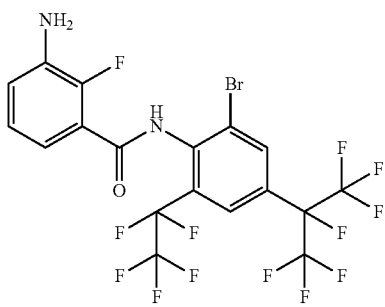 [SMILES: Nc1cccc(C(=O)Nc2c(Br)cc(C(F)(C(F)(F)F)C(F)(F)F)cc2C(F)(F)C(F)(F)F)c1F]

According to the method of 1-3 of Example 1, a target compound was prepared from N-(2-bromo-6-(perfluoroethyl)-4-(perfluoropropan-2-yl)phenyl)-2-fluoro-3-nitrobenzamide.

$^1$H-NMR (CDCl$_3$, ppm) δ 3.92 (2H, broad-s), 6.99-7.04 (1H, m), 7.05-7.18 (1H, m), 7.46-7.51 (1H, m), 7.85 (1H, broad-s), 8.17 (1H, broad-s), 8.34 (1H, d, J=15.1 Hz).

Example 55

Preparation of N-(2-bromo-4-(perfluoropropan-2-yl)-6-(trifluoromethyl)phenyl)-6-(methylamino)picolinamide (Compound No. 15-68)

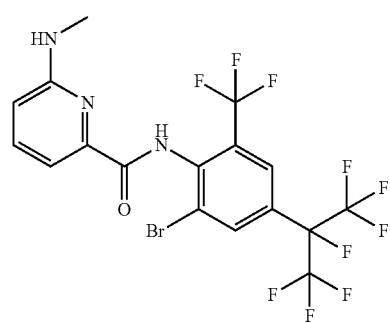 [SMILES: CNc1cccc(C(=O)Nc2c(Br)cc(C(F)(C(F)(F)F)C(F)(F)F)cc2C(F)(F)F)n1]

55-1

Preparation of N-(2-bromo-4-(perfluoropropan-2-yl)-6-(trifluoromethyl)phenyl)-6-chloropicoline amide (Compound No. 14-6)

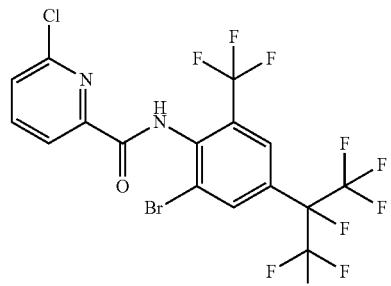

According to the method of 22-3 of Example 22, a target compound was prepared from 2-chloropyridine-6-carboxylic acid, 2-chloropyridine-6-carboxylic acid chloride prepared from thionyl chloride, and 2-bromo-4-(perfluoropropan-2-yl)-6-(trifluoromethyl)aniline obtained in 22-2 of Example 22.

$^1$H-NMR (CDCl$_3$, ppm) δ 7.59 (1H, d, J=7.3 Hz), 7.90-7.93 (2H, m), 8.14 (1H, s), 8.20-8.24 (1H, m), 9.60 (1H, s).

55-2

Preparation of N-(2-bromo-4-(perfluoropropan-2-yl)-6-(trifluoromethyl)phenyl)-6-(methylamino)picolinamide (Compound No. 15-68)

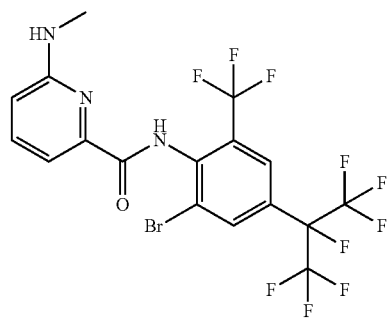 [SMILES: CNc1cccc(C(=O)Nc2c(Br)cc(C(F)(C(F)(F)F)C(F)(F)F)cc2C(F)(F)F)n1]

To a solution of 0.100 g (0.180 mmol) of N-(2-bromo-4-(perfluoropropan-2-yl)-6-(trifluoromethyl)phenyl)-6-chloropicoline amide in 5 ml of 1,4-dioxane were added 0.00600 g (0.0360 mmol) of copper sulfate and 0.140 g (1.80 mmol) of a 40% aqueous methylamine solution, followed by stirring at an oil bath temperature 80° C. for 3 hours under an enclosed condition. The reaction liquid was returned to room temperature and opened, and water and ethyl acetate were added thereto. The organic layer was washed with water, saturated brine, and dried over anhydrous magnesium sulfate. The solvent was evaporated under reduced pressure and the obtained residue was purified by silica gel column chromatography (developing solvent; hexane:ethyl acetate=2:1) to prepare 0.0700 g (yield 69%) of a target compound.

¹H-NMR (CDCl₃, ppm) δ 2.64 (3H, s), 3.79 (1H, broad-s), 7.56-7.60 (1H, m), 7.87-7.93 (2H, m), 8.14-8.15 (1H, m), 8.20-8.23 (1H, m), 9.60 (1H, s).

Example 56

Preparation of N-(2-bromo-4-(perfluoropropan-2-yl)-6-(trifluoromethyl)phenyl)-2-(methylamino)thiazole-4-carboxamide (Compound No. 17-42)

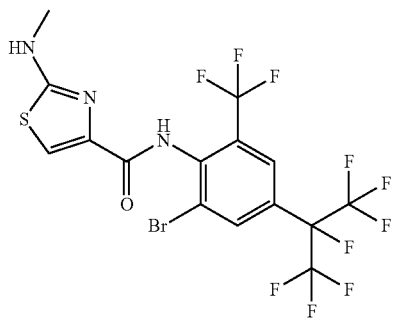 [SMILES: CNc1nc(C(=O)Nc2c(Br)cc(C(F)(C(F)(F)F)C(F)(F)F)cc2C(F)(F)F)cs1]

56-1

Preparation of 2-aminothiazole-4-carboxylic acid

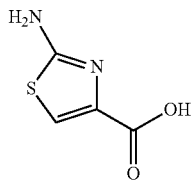

To 40 ml of an aqueous solution of 4.00 g (23.2 mmol) of ethyl 2-aminothiazole-4-carboxylate was added 1.86 g (46.5 mmol) of sodium hydroxide, followed by stirring at room temperature for 5 hours. To the reaction liquid was added concentrated hydrochloric acid to adjust to pH 1, and the precipitated crystals were collected by filtration to prepare 2.84 g (yield 85%) of a target compound.

¹H-NMR (CDCl₃, ppm) δ 7.18 (2H, broad-s), 7.38 (1H, s).
The proton presumed to be indicative of carboxylic acid was not detected.

56-2

Preparation of 2-chlorothiazole-4-carboxylic acid

To a solution of 2.84 g (19.7 mmol) of 2-aminothiazole-4-carboxylic acid in 30 ml of 1,4-dioxane was added 50 ml of concentrated hydrochloric acid, followed by cooling to 0° C., and 10 ml of an aqueous solution of 2.04 g (29.6 mmol) of sodium nitrite was charged dropwise thereto at 0° C. to 5° C. The reaction liquid was stirred at 0° C. for 2 hours, and then 2.93 g (29.6 mmol) of copper chloride was charged in separate portions thereto. The reaction liquid was returned to room temperature, followed by stirring for 8 hours. To the reaction liquid were added water and ethyl acetate, followed by extraction with ethyl acetate four times. The organic layer was washed with saturated brine, and then dried over anhydrous magnesium sulfate. The solvent was evaporated under reduced pressure to prepare 1.77 g (yield 55%) of a target compound.

¹H-NMR (DMSO-d₆, ppm) δ 8.41 (1H, s).
The proton presumed to be indicative of carboxylic acid was not detected.

56-3

Preparation of N-(2-bromo-4-(perfluoropropan-2-yl)-6-(trifluoromethyl)phenyl)-2-chlorothiazole-4-carboxamide (Compound No. 16-6)

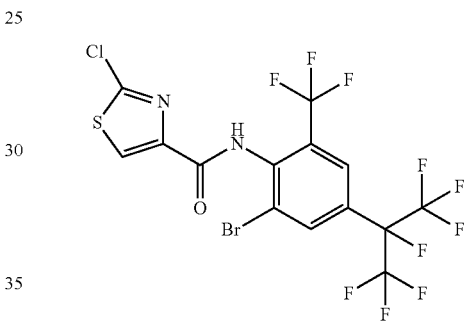

According to the method of 53-3 of Example 53, a target compound was prepared from 2-chlorothiazole-4-carboxylic acid, 2-chlorothiazole-4-carbonylchloride prepared from thionyl chloride, and 2-bromo-4-(perfluoropropan-2-yl)-6-(trifluoromethyl)aniline obtained in 22-2 of Example 22.

¹H-NMR (CDCl₃, ppm) δ 7.91 (1H, s), 8.13 (1H, s), 8.19 (1H, s), 8.82 (1H, s).

56-4

Preparation of N-(2-bromo-4-(perfluoropropan-2-yl)-6-(trifluoromethyl)phenyl)-2-(methylamino)thiazole-4-carboxamide (Compound No. 17-42)

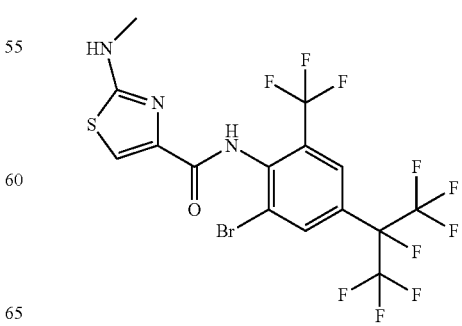

According to the method of 55-2 of Example 55, a target compound was prepared from N-(2-bromo-4-(perfluoropropan-2-yl)-6-(trifluoromethyl)phenyl)-2-chlorothiazole-4-carboxamide.

$^1$H-NMR (CDCl$_3$, ppm) δ 3.03 (3H, s), 5.11-5.12 (1H, m), 7.50 (1H, s), 7.88 (1H, s), 8.11 (1H, s), 8.99 (1H, s).

Example 57

Preparation of 2-fluoro-N-(2-iodo-4-(perfluorobutan-2-yl)-6-(trifluoromethyl)phenyl)-3-(methylamino)benzamide (Compound No. 13-44)

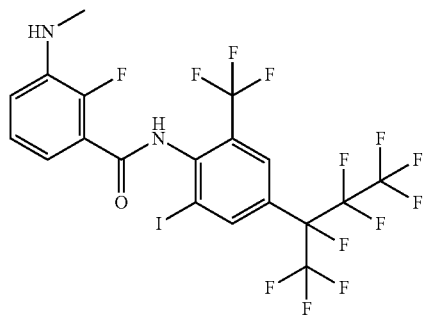 [SMILES: CNc1cccc(C(=O)Nc2c(I)cc(C(F)(C(F)(F)F)C(F)(F)C(F)(F)F)cc2C(F)(F)F)c1F]

57-1

Preparation of 4-(perfluorobutan-2-yl)-2-(trifluoromethyl)aniline (Compound No. 21-3)

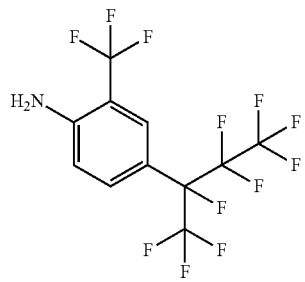 [SMILES: Nc1ccc(C(F)(C(F)(F)F)C(F)(F)C(F)(F)F)cc1C(F)(F)F]

According to the method of 22-1 of Example 22, a target compound was prepared from 2-(trifluoromethyl)aniline and nonafluoro-s-butyliodide under the light-shielding condition.

$^1$H-NMR (CDCl$_3$, ppm) δ 4.49 (2H, broad-s), 6.81 (1H, d, J=8.8 Hz), 7.47 (1H, d, J=8.8 Hz), 7.61 (1H, s).

57-2

Preparation of 2-iodo-4-(perfluorobutan-2-yl)-6-(trifluoromethyl)aniline (Compound No. 21-14)

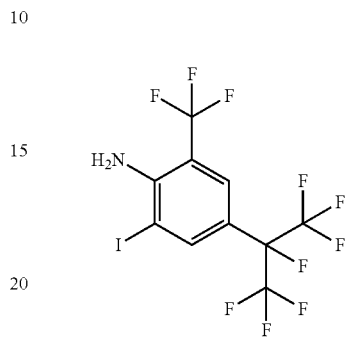

To 100 mL of ethanol was added 17.0 g (44.8 mmol) of 4-(perfluorobutan-2-yl)-2-(trifluoromethyl)aniline, and 5.28 g (53.8 mmol) of concentrated sulfuric acid and 12.6 g (55.8 mmol) of N-iodosuccinimide were added thereto under ice-cooling, followed by stirring at room temperature for 1 hour and 30 minutes and at 40° C. for 4 hours. The reaction solution was neutralized by adding a 4 N aqueous sodium hydroxide solution to the reaction solution, then ethyl acetate was added thereto, and the organic phase was extracted. The organic phase was washed with saturated brine and dried over anhydrous magnesium sulfate, and then the solvent was evaporated under reduced pressure. The obtained residue was purified by silica gel column chromatography (developing solvent; hexane:ethyl acetate=10:1) to prepare 14.6 g (yield 65%) of a target compound.

$^1$H-NMR (CDCl$_3$, ppm) δ 5.04 (2H, broad-s), 7.62 (1H, s), 7.97 (1H, s).

57-3

Preparation of 2-chloro-N-(2-iodo-4-(perfluorobutan-2-yl)-6-(trifluoromethyl)phenyl)-3-nitrobenzamide (Compound No. 11-43)

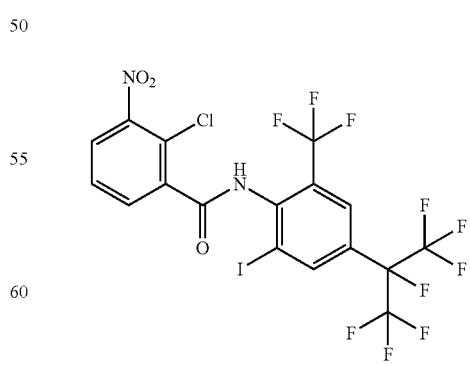

According to the method of 53-3 of Example 53, a target compound was prepared from 2-iodo-4-(perfluorobutan-2-yl)-6-(trifluoromethyl)aniline.

¹H-NMR (CDCl₃, ppm) δ 7.60-7.61 (1H, m), 7.77 (1H, s), 7.89-7.96 (2H, m), 8.03-8.04 (1H, m), 8.38 (1H, s).

57-4

Preparation of 2-fluoro-N-(2-iodo-4-(perfluorobutan-2-yl)-6-(trifluoromethyl)phenyl)-3-nitrobenzamide (Compound No. 11-70)

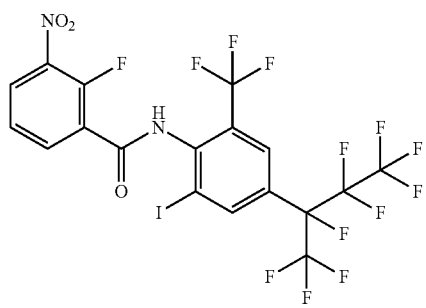

According to the method of 1-2 of Example 1, a target compound was prepared from 2-chloro-N-(2-iodo-4-(perfluorobutan-2-yl)-6-(trifluoromethyl)phenyl)-3-nitrobenzamide.

¹H-NMR (CDCl₃, ppm) δ 7.53-7.54 (1H, m), 7.95 (1H, s), 8.24-8.32 (2H, m), 8.36 (1H, s), 8.44-8.48 (1H, m).

57-5

Preparation of 3-amino-2-fluoro-N-(2-iodo-4-(perfluorobutan-2-yl)-6-(trifluoromethyl)phenyl)benzamide (Compound No. 12-41)

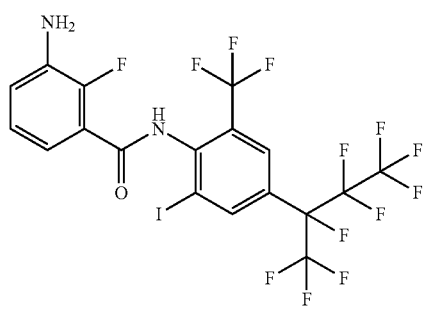 [SMILES: O=C(Nc1c(I)cc(C(F)(C(F)(F)F)C(F)(F)C(F)(F)F)cc1C(F)(F)F)c1cccc([N+](=O)[O-])c1F]

According to the method of 1-3 of Example 1, a target compound was prepared from 2-fluoro-N-(2-iodo-4-(perfluorobutan-2-yl)-6-(trifluoromethyl)phenyl)-3-nitrobenzamide.

¹H-NMR (CDCl₃, ppm) δ 3.93 (2H, broad-s), 7.02-7.03 (1H, m), 7.11-7.13 (1H, m), 7.47-7.51 (1H, m), 7.92 (1H, s), 8.31-8.34 (2H, m).

57-6

Preparation of 2-fluoro-N-(2-iodo-4-(perfluorobutan-2-yl)-6-(trifluoromethyl)phenyl)-3-(methylamino)benzamide (Compound No. 13-44)

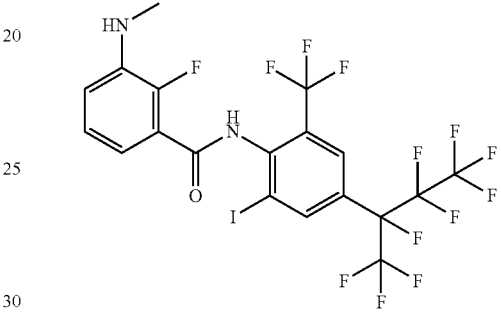

According to the method of Example 51, a target compound was prepared from 3-amino-2-fluoro-N-(2-iodo-4-(perfluorobutan-2-yl)-6-(trifluoromethyl)phenyl)benzamide.

¹H-NMR (CDCl₃, ppm) δ 2.95-2.96 (3H, m), 4.15 (1H, broad-s), 6.91-6.93 (1H, m), 7.19-7.20 (1H, m), 7.38-7.42 (1H, m), 7.92 (1H, s), 8.32 (1H, d, J=14.1 Hz), 8.34 (1H, s).

Example 58

Preparation of N-(2-chloro-4-(perfluoropropan-2-yl)-6-(trifluoromethyl)phenyl)-4-cyano-3-(methylamino)benzamide (Compound No. 13-85)

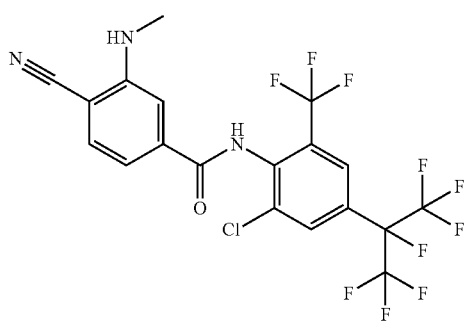 [SMILES: CNc1cc(C(=O)Nc2c(Cl)cc(C(F)(C(F)(F)F)C(F)(F)F)cc2C(F)(F)F)ccc1C#N]

58-1

Preparation of 2-chloro-4-(perfluoropropan-2-yl)-6-(trifluoromethyl)aniline (Compound No. 21-8)

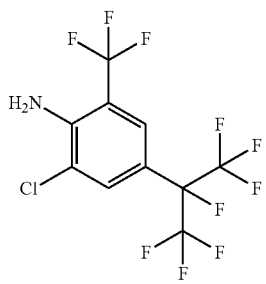 [SMILES: Nc1c(Cl)cc(C(F)(C(F)(F)F)C(F)(F)F)cc1C(F)(F)F]

According to the method of 22-2 of Example 22, a target compound was prepared from 4-(perfluoropropan-2-yl)-2-(trifluoromethyl)aniline obtained in 22-1 of Example 22 and N-chlorosuccinimide.

$^1$H-NMR (CDCl$_3$, ppm) δ 4.97 (2H, broad-s), 7.57 (1H, s), 7.64 (1H, s).

58-2

Preparation of N-(2-chloro-4-(perfluoropropan-2-yl)-6-(trifluoromethyl)phenyl)-4-iodo-3-nitrobenzamide (Compound No. 11-100)

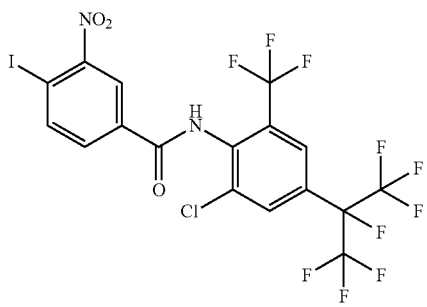

According to the method of 22-3 of Example 22, a target compound was prepared from 4-iodo-3-nitrobenzoic acid, 4-iodo-3-nitrobenzoyl chloride prepared from thionyl chloride, and 2-chloro-4-(perfluoropropan-2-yl)-6-(trifluoromethyl)aniline.

$^1$H-NMR (CDCl$_3$, ppm) δ 7.52-7.81 (2H, m), 7.89 (1H, s), 8.00 (1H, s), 8.25 (1H, d, J=8.3 Hz), 8.38 (1H, d, J=1.9 Hz).

58-3

Preparation of 3-amino-N-(2-chloro-4-(perfluoropropan-2-yl)-6-(trifluoromethyl)phenyl)-4-iodobenzamide (Compound No. 12-63)

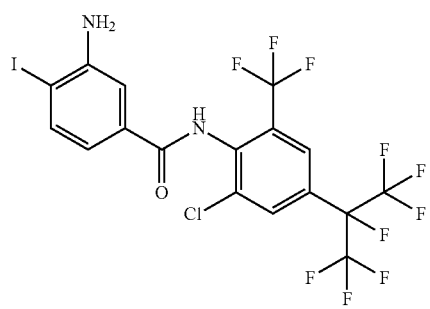 [SMILES: O=C(Nc1c(Cl)cc(C(F)(C(F)(F)F)C(F)(F)F)cc1C(F)(F)F)c1ccc(I)c([N+](=O)[O-])c1]

According to the method of 1-3 of Example 1, a target compound was prepared from N-(2-chloro-4-(perfluoropropan-2-yl)-6-(trifluoromethyl)phenyl)-4-iodo-3-nitrobenzamide.

$^1$H-NMR (CDCl$_3$, ppm) δ 4.35 (2H, s), 6.92 (1H, dd, J=1.9, 8.3 Hz), 7.29 (1H, d, J=1.9 Hz), 7.60 (1H, s), 7.79 (1H, d, J=8.3 Hz), 7.86 (1H, s), 7.97 (1H, s).

58-4

Preparation of N-(2-chloro-4-(perfluoropropan-2-yl)-6-(trifluoromethyl)phenyl)-4-iodo-3-(methylamino)benzamide (Compound No. 13-68)

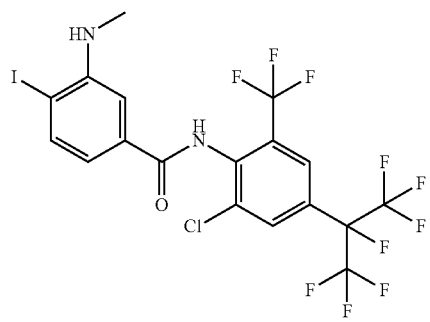 [SMILES: CNc1cc(C(=O)Nc2c(Cl)cc(C(F)(C(F)(F)F)C(F)(F)F)cc2C(F)(F)F)ccc1I]

According to the method of Example 51, a target compound was prepared from 3-amino-N-(2-chloro-4-(perfluoropropan-2-yl)-6-(trifluoromethyl)phenyl)-4-iodobenzamide.

¹H-NMR (CDCl₃, ppm) δ 2.97 (3H, s), 4.46 (1H, broad-s), 6.89 (1H, dd, J=1.9, 8.3 Hz), 7.07 (1H, d, J=1.9 Hz), 7.65 (1H, s), 7.80 (1H, d, J=8.3 Hz), 7.86 (1H, s), 7.97 (1H, s).

58-5

Preparation of N-(2-chloro-4-(perfluoropropan-2-yl)-6-(trifluoromethyl)phenyl)-4-cyano-3-(methylamino)benzamide (Compound No. 13-85)

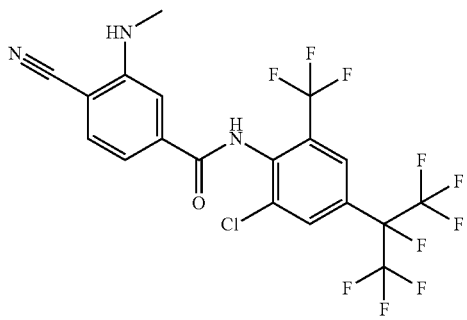

To 10 mL of DMF were added 0.350 g (0.560 mmol) of N-(2-chloro-4-(perfluoropropan-2-yl)-6-(trifluoromethyl)phenyl)-4-iodo-3-(methylamino)benzamide and 0.200 g (2.25 mmol) of copper (I) cyanide, followed by stirring at 140° C. for 1 hour and 30 minutes. A saturated aqueous sodium thiosulfate solution was poured into the reaction solution to quench the reaction, and the organic layer was collected by separation with ethyl acetate and washed with saturated brine. The organic layer was dried over anhydrous magnesium sulfate, and then the solvent was evaporated under reduced pressure. The obtained residue was purified by silica gel column chromatography (developing solvent; hexane:ethyl acetate=5:1→3:1) to prepare 0.250 g (yield 86%) of a target compound.

¹H-NMR (CDCl₃, ppm) δ 3.01 (1/2*3 H, s), 3.03 (1/2*3 H, s), 4.89 (1/2*1H, s), 4.90 (1/2*1H, s), 7.80 (1H, dd, J=1.5, 8.3 Hz), 7.21-7.22 (1H, m), 7.54 (1H, d, J=8.3 Hz), 7.67 (1H, s), 7.88 (1H, s), 7.99 (1H, s).

Example 59

Preparation of 3-amino-N-(2-bromo-4-(perfluoropropan-2-yl)-6-(trifluoromethyl)phenyl)-4-cyano-2-fluorobenzamide (Compound No. 12-94)

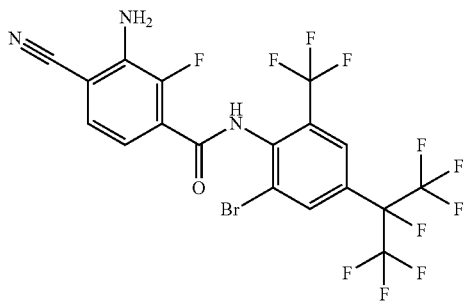

59-1

Preparation of N-(2-bromo-4-(perfluoropropan-2-yl)-6-(trifluoromethyl)phenyl)-4-cyano-2,3-difluorobenzamide

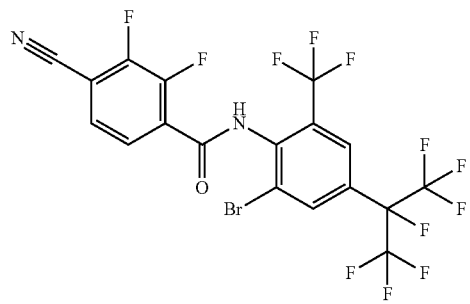 [SMILES: N#Cc1ccc(C(=O)Nc2c(Br)cc(C(F)(C(F)(F)F)C(F)(F)F)cc2C(F)(F)F)c(F)c1F]

To a solution of 0.840 g (4.59 mmol) of 4-cyano-2,3-difluorobenzoic acid in 10 ml of dichloromethane were added one drop of DMF and 0.470 ml (5.51 mmol) of oxalyl chloride, followed by stirring at room temperature for 1 hour. The solvent was evaporated under reduced pressure and the obtained 4-cyano-2,3-difluorobenzoyl chloride was added to a solution of 1.56 g (3.83 mmol) of 2-bromo-4-(perfluoropropan-2-yl)-6-(trifluoromethyl)aniline obtained in 22-2 of Example 22 in 5 ml of DMI, followed by stirring at 130° C. for 5 hours. To the reaction liquid were added water and ethyl acetate, and the organic layer was washed with a saturated aqueous sodium hydrogen carbonate solution and saturated brine, and then dried over anhydrous magnesium sulfate. The solvent was evaporated under reduced pressure and the obtained residue was purified by silica gel column chromatography (developing solvent; hexane:ethyl acetate=1:0→10:1) to prepare 0.58 g (yield 27%) of a target compound.

¹H-NMR (CDCl₃, ppm) δ 7.52-7.62 (1H, m), 7.92-7.94 (1H, m), 8.02-8.06 (1H, m), 8.13-8.16 (2H, m).

59-2

Preparation of 3-amino-N-(2-bromo-4-(perfluoropropan-2-yl)-6-(trifluoromethyl)phenyl)-4-cyano-2-fluorobenzamide (Compound No. 12-94)

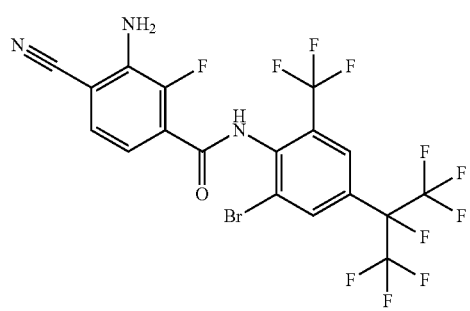 [SMILES: N#Cc1ccc(C(=O)Nc2c(Br)cc(C(F)(C(F)(F)F)C(F)(F)F)cc2C(F)(F)F)c(F)c1N]

To a solution of N-(2-bromo-4-(perfluoropropan-2-yl)-6-(trifluoromethyl)phenyl)-4-cyano-2,3-difluorobenzamide in 5 ml of DMSO was added 49.0 mg of ammonium carbonate, followed by stirring at 100° C. for 5 hours. To the reaction liquid were added water and ethyl acetate, and the organic layer was washed with water, and then dried over anhydrous magnesium sulfate. The solvent was evaporated under reduced pressure and the obtained residue was purified by silica gel column chromatography (developing solvent; hexane:ethyl acetate=8:1→4:1) to prepare 0.30 g (yield 51%) of a target compound.

$^1$H-NMR (CDCl$_3$, ppm) δ 4.71 (2H, broad-s), 7.35-7.39 (1H, m), 7.40-7.44 (1H, m), 7.92 (1H, s), 8.12-8.15 (2H, m).

Example 60

Preparation of 3-amino-N-(2,6-diiodo-4-(perfluorobutan-2-yl)phenyl)benzamide (Compound No. 12-3)

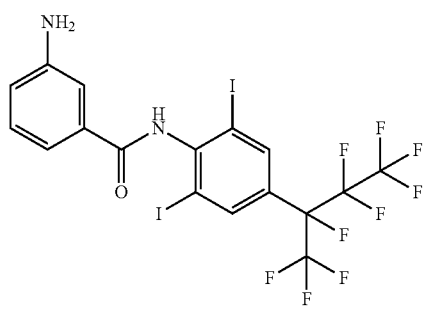

60-1

Preparation of 2,6-diiodo-4-(perfluorobutan-2-yl)aniline

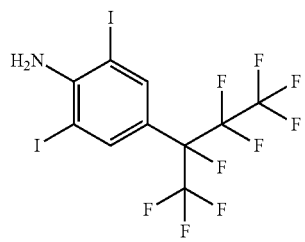 [SMILES: Nc1c(I)cc(C(F)(C(F)(F)F)C(F)(F)C(F)(F)F)cc1I]

According to the method of 52-2 of Example 52, a target compound was prepared from 4-(perfluorobutan-2-yl)aniline obtained in 53-1 of Example 53.

$^1$H-NMR (CDCl$_3$, ppm) δ 4.95 (2H, broad-s), 7.78 (2H, s).

60-2

Preparation of N-(2,6-diiodo-4-(perfluorobutan-2-yl)phenyl)-3-nitrobenzamide (Compound No. 11-4)

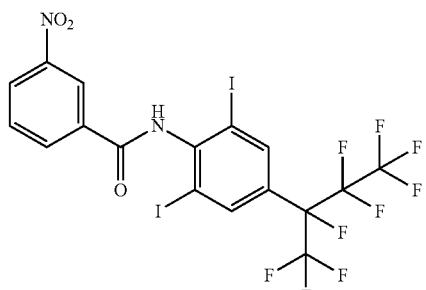

According to the method of 53-3 of Example 53, a target compound was prepared from 2,6-diiodo-4-(perfluorobutan-2-yl)aniline and 3-nitrobenzoyl chloride.

$^1$H-NMR (CDCl$_3$, ppm) δ 7.74 (1H, t, J=8.0 Hz), 8.11 (2H, s), 8.42 (1H, d, J=7.6 Hz), 8.46 (1H, d, J=8.4 Hz), 8.90 (1H, d, J=12.4 Hz), 8.92 (1H, s).

60-3

Preparation of 3-amino-N-(2,6-diiodo-4-(perfluorobutan-2-yl)phenyl)benzamide (Compound No. 12-3)

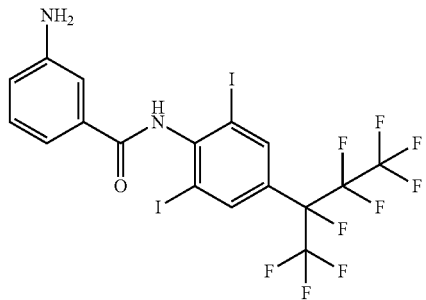 [SMILES: Nc1cccc(C(=O)Nc2c(I)cc(C(F)(C(F)(F)F)C(F)(F)C(F)(F)F)cc2I)c1]

According to the method of 1-3 of Example 1, a target compound was prepared from N-(2,6-diiodo-4-(perfluorobutan-2-yl)phenyl)-3-nitrobenzamide.

$^1$H-NMR (CDCl$_3$, ppm) δ 5.39 (2H, broad-s), 6.89-6.93 (1H, m), 7.29-7.31 (3H, m), 7.68 (1H, s), 8.08 (2H, s).

Example 61

Preparation of 3-amino-N-(2-bromo-4-(perfluoropropan-2-yl)-6-(trifluoromethoxy)phenyl)-2-fluorobenzamide (Compound No. 12-33)

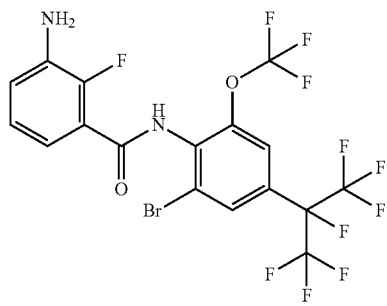 [SMILES: Nc1cccc(C(=O)Nc2c(Br)cc(C(F)(C(F)(F)F)C(F)(F)F)cc2OC(F)(F)F)c1F]

61-1

Preparation of 4-(perfluoropropan-2-yl)-2-(trifluoromethoxy)aniline

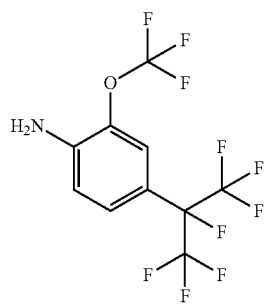 [SMILES: Nc1ccc(C(F)(C(F)(F)F)C(F)(F)F)cc1OC(F)(F)F]

According to the method of 22-1 of Example 22, a target compound was prepared from 2-trifluoromethoxy aniline.

$^1$H-NMR (CDCl$_3$, ppm) δ 4.19 (2H, broad-s), 6.86 (1H, d, J=8.8 Hz), 7.30 (1H, d, J=8.8 Hz), 7.36 (1H, s).

61-2

Preparation of 2-bromo-4-(perfluoropropan-2-yl)-6-(trifluoromethoxy)aniline

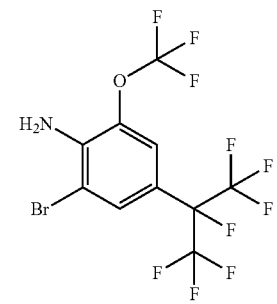 [SMILES: Nc1c(Br)cc(C(F)(C(F)(F)F)C(F)(F)F)cc1OC(F)(F)F]

According to the method of 22-2 of Example 22, a target compound was prepared from 4-(perfluoropropan-2-yl)-2-(trifluoromethoxy)aniline.

$^1$H-NMR (CDCl$_3$, ppm) δ 4.65 (2H, broad-s), 7.33 (1H, s), 7.71 (1H, s).

61-3

Preparation of N-(2-bromo-4-(perfluoropropan-2-yl)-6-(trifluoromethoxy)phenyl)-2-chloro-3-nitrobenzamide (Compound No. 11-33)

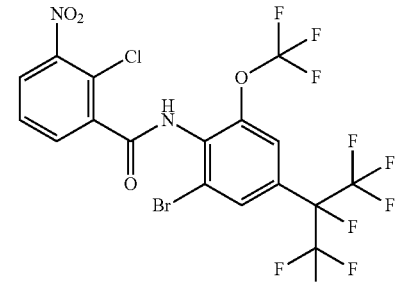

According to the method of 22-3 of Example 22, a target compound was prepared from 2-bromo-4-(perfluoropropan-2-yl)-6-(trifluoromethoxy)aniline ¹H-NMR (CDCl₃, ppm) δ 7.49-7.61 (3H, m), 7.80-7.96 (3H, m).

61-4

Preparation of N-(2-bromo-4-(perfluoropropan-2-yl)-6-(trifluoromethoxy)phenyl)-2-fluoro-3-nitrobenzamide (Compound No. 11-60)

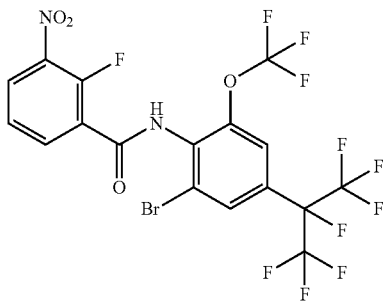 [SMILES: O=C(Nc1c(Br)cc(C(F)(C(F)(F)F)C(F)(F)F)cc1OC(F)(F)F)c1cccc([N+](=O)[O-])c1F]

According to the method of 1-2 of Example 1, a target compound was prepared from N-(2-bromo-4-(perfluoropropan-2-yl)-6-(trifluoromethoxy)phenyl)-2-chloro-3-nitrobenzamide.

¹H-NMR (CDCl₃, ppm) δ 7.53 (1H, t, J=7.8 Hz), 7.60 (1H, broad-s), 7.89 (1H, d, J=1.5 Hz), 8.07 (1H, broad-d, J=12.7 Hz), 8.29-8.30 (1H, m), 8.43-8.47 (1H, m).

61-5

Preparation of 3-amino-N-(2-bromo-4-(perfluoropropan-2-yl)-6-(trifluoromethoxy)phenyl)-2-fluorobenzamide (Compound No. 12-33)

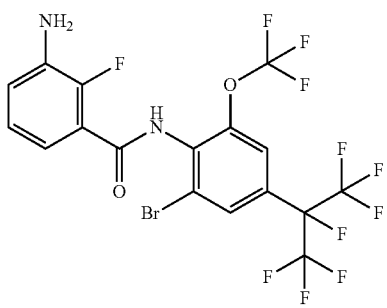 [SMILES: Nc1cccc(C(=O)Nc2c(Br)cc(C(F)(C(F)(F)F)C(F)(F)F)cc2OC(F)(F)F)c1F]

According to the method of 1-3 of Example 1, a target compound was prepared from N-(2-bromo-4-(perfluoropropan-2-yl)-6-(trifluoromethoxy)phenyl)-2-fluoro-3-nitrobenzamide.

¹H-NMR (CDCl₃, ppm) δ 3.92 (2H, broad-s), 6.99-7.04 (1H, m), 7.11 (1H, t, J=7.8 Hz), 7.45-7.49 (1H, m), 7.57 (1H, broad-s), 7.87 (1H, d, J=2.0 Hz), 8.14 (1H, d, J=14.2 Hz).

Example 62

Preparation of 3-amino-N-(2-bromo-4-(perfluoropropan-2-yl)-6-(trifluoromethyl)phenyl)-4-fluorobenzamide (Compound No. 12-53)

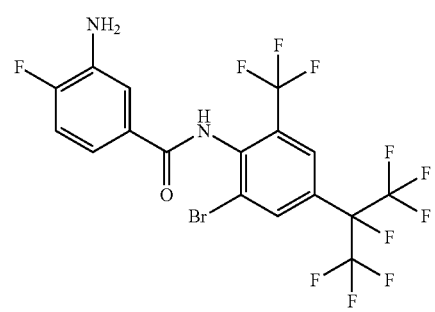 [SMILES: O=C(Nc1c(Br)cc(C(F)(C(F)(F)F)C(F)(F)F)cc1C(F)(F)F)c1ccc(F)c([N+](=O)[O-])c1]

62-1

Preparation of N-(2-bromo-4-(perfluoropropan-2-yl)-6-(trifluoromethyl)phenyl)-4-fluoro-3-nitrobenzamide (Compound No. 11-84)

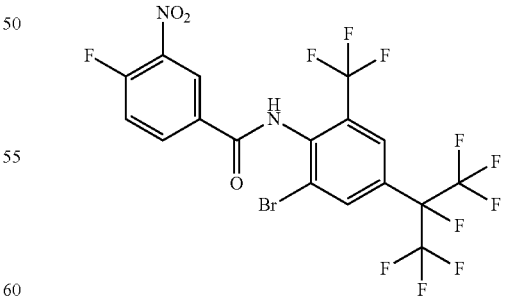

According to the method of 22-3 of Example 22, target compound was prepared from 4-fluoro-3-nitrobenzoic acid, 4-fluoro-3-nitrobenzoyl chloride prepared from thionyl chloride, and 2-bromo-4-(perfluoropropan-2-yl)-6-(trifluoromethyl)aniline obtained in 22-2 of Example 22.

¹H-NMR (CDCl₃, ppm) δ 7.47-7.50 (1H, m), 7.92 (2H, d, J=5.9 Hz), 8.16 (1H, s), 8.23-8.28 (1H, m), 8.65-8.67 (1H, m).

62-2

Preparation of 3-amino-N-(2-bromo-4-(perfluoropropan-2-yl)-6-(trifluoromethyl)phenyl)-4-fluorobenzamide (Compound No. 12-53)

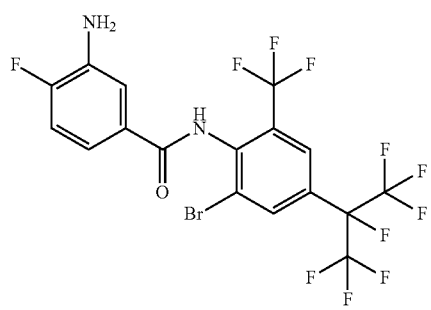

According to the method of 1-3 of Example 1, a target compound was prepared from N-(2-bromo-4-(perfluoropropan-2-yl)-6-(trifluoromethyl)phenyl)-4-fluoro-3-nitrobenzamide.
APCI-MS m/z (M+1):546

Example 63

Preparation of 2-fluoro-N-(2-iodo-4-(perfluoropropan-2-yl)-6-(trifluoromethyl)phenyl)-3-(methylamino)benzamide (Compound No. 13-41)

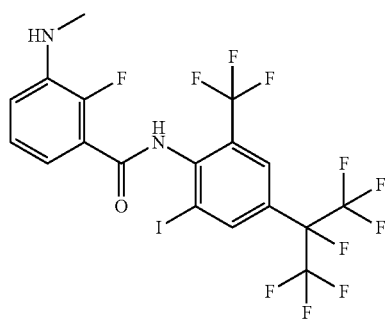 [SMILES: CNc1cccc(C(=O)Nc2c(I)cc(C(F)(C(F)(F)F)C(F)(F)F)cc2C(F)(F)F)c1F]

63-1

Preparation of 2-chloro-N-(2-iodo-4-(perfluoropropan-2-yl)-6-(trifluoromethyl)phenyl)-3-nitrobenzamide (Compound No. 11-39)

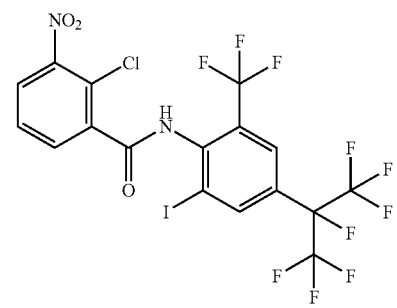

According to the method of 53-3 of Example 53, a target compound was prepared from 2-iodo-4-(perfluoropropan-2-yl)-6-(trifluoromethyl)aniline obtained in 45-1 of Example 45 and 2-chloro-3-nitrobenzoyl chloride.

¹H-NMR (CDCl₃, ppm) δ 7.60 (1H, t, J=7.8 Hz), 7.76 (1H, s), 7.94 (1H, dd, J=1.5, 7.8 Hz), 7.97 (1H, s), 8.03 (1H, dd, J=1.5, 7.8 Hz), 8.39 (1H, s).

63-2

Preparation of 2-fluoro-N-(2-iodo-4-(perfluoropropan-2-yl)-6-(trifluoromethyl)phenyl)-3-nitrobenzamide (Compound No. 11-66)

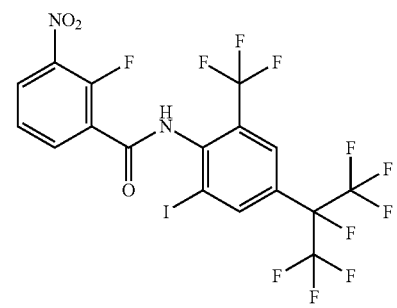 [SMILES: O=C(Nc1c(I)cc(C(F)(C(F)(F)F)C(F)(F)F)cc1C(F)(F)F)c1cccc([N+](=O)[O-])c1Cl]

According to the method of 1-2 of Example 1, a target compound was prepared from 2-chloro-N-(2-iodo-4-(perfluoropropan-2-yl)-6-(trifluoromethyl)phenyl)-3-nitrobenzamide.

¹H-NMR (CDCl₃, ppm) δ 7.51-7.55 (1H, m), 7.97 (1H, s), 8.23 (1H, d, J=12.2 Hz), 8.28-8.32 (1H, m), 8.37 (1H, s), 8.44-8.48 (1H, m).

63-3

Preparation of 3-amino-2-fluoro-N-(2-iodo-4-(perfluoropropan-2-yl)-6-(trifluoromethyl)phenyl)benzamide (Compound No. 12-38)

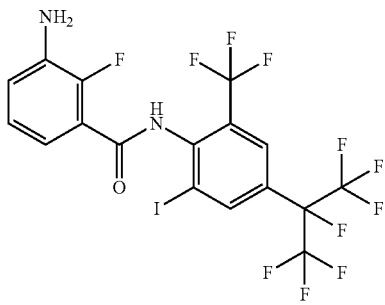

According to the method of 1-3 of Example 1, a target compound was prepared from 2-fluoro-N-(2-iodo-4-(perfluoropropan-2-yl)-6-(trifluoromethyl)phenyl)-3-nitrobenzamide.

¹H-NMR (CDCl₃, ppm) δ 3.92 (2H, broad-s), 7.02-7.04 (1H, m), 7.11 (1H, t, J=7.8 Hz), 7.47-7.52 (1H, m), 7.94 (1H, s), 8.30-8.35 (2H, m).

63-4

Preparation of 2-fluoro-N-(2-iodo-4-(perfluoropropan-2-yl)-6-(trifluoromethyl)phenyl)-3-(methylamino)benzamide (Compound No. 13-41)

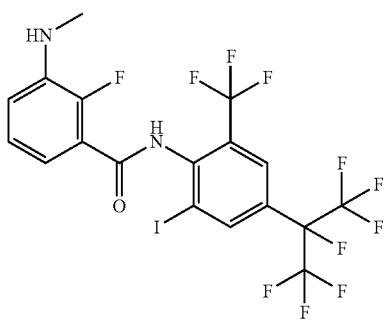 [SMILES: CNc1cccc(C(=O)Nc2c(I)cc(C(F)(C(F)(F)F)C(F)(F)F)cc2C(F)(F)F)c1F]

According to the method of Example 51, a target compound was prepared from 3-amino-2-fluoro-N-(2-iodo-4-(perfluoropropan-2-yl)-6-(trifluoromethyl)phenyl)benzamide.

¹H-NMR (CDCl₃, ppm) δ 2.95 (3H, s), 4.15 (1H, broad-s), 6.90 (1H, t, J=8.2 Hz), 7.19 (1H, t, J=7.8 Hz), 7.40 (1H, t, J=7.8 Hz), 7.92 (1H, s), 8.30 (1H, s), 8.34 (1H, s).

Example 64

Preparation of 3-amino-N-(2-bromo-4-(perfluoropropan-2-yl)-6-(trifluoromethyl)phenyl)-N-methylbenzamide (Compound No. 12-107)

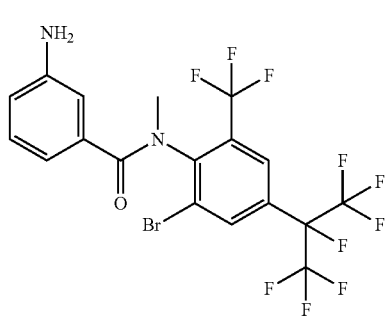 [SMILES: CN(C(=O)c1cccc(N)c1)c1c(Br)cc(C(F)(C(F)(F)F)C(F)(F)F)cc1C(F)(F)F]

64-1

Preparation of N-(2-bromo-4-(perfluoropropan-2-yl)-6-(trifluoromethyl)phenyl)-3-nitrobenzamide (Compound No. 11-11)

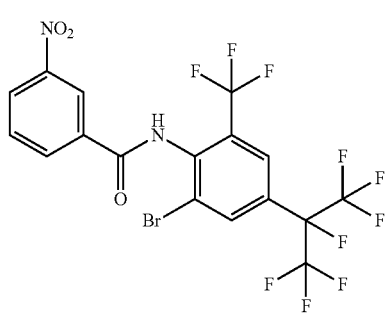 [SMILES: O=C(Nc1c(Br)cc(C(F)(C(F)(F)F)C(F)(F)F)cc1C(F)(F)F)c1cccc([N+](=O)[O-])c1]

According to the method of 53-3 of Example 53, a target compound was prepared from 2-bromo-4-(perfluoropropan-2-yl)-6-(trifluoromethyl)aniline obtained in 22-2 of Example 22 and 3-nitrobenzoyl chloride.

¹H-NMR (CDCl₃, ppm) δ 7.75-7.79 (2H, m), 7.94 (1H, s), 8.17 (1H, d, J=1.0 Hz), 8.28 (1H, dd, J=1.5, 7.8 Hz), 8.48-8.51 (1H, m), 8.76-8.77 (1H, m).

64-2

Preparation of N-(2-bromo-4-(perfluoropropan-2-yl)-6-(trifluoromethyl)phenyl)-N-methyl-3-nitrobenzamide (Compound No. 11-136)

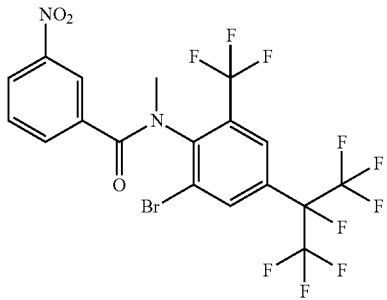

To a solution of 1.50 g (2.69 mmol) of N-(2-bromo-4-(perfluoropropan-2-yl)-6-(trifluoromethyl)phenyl)-3-nitrobenzamide in 20 ml of DMF was added 0.160 g (4.04 mmol) of sodium hydride (60% in oil), followed by stirring at room temperature for 10 minutes, and then 0.840 ml (13.5 mmol) of methyl iodide was added thereto, followed by stirring at the same temperature for 2 hours. To the reaction liquid were added water and ethyl acetate, and the organic layer was washed with water and saturated brine, and then dried over anhydrous magnesium sulfate. The solvent was evaporated under reduced pressure and the obtained residue was purified by NH silica gel column chromatography (developing solvent; hexane:ethyl acetate=20:1) to prepare 1.42 g (yield 93%) of a target compound.

¹H-NMR (CDCl₃, ppm) δ 3.28 (1/2*3 H, s), 3.44 (1/2*3 H, s), 7.41 (1/2*1H, t, J=7.8 Hz), 7.71-7.76 (2/2*1H, m), 7.84 (1/2*1H, s), 7.93-7.95 (1/2*1H, m), 7.98 (1/2*1H, s), 8.07-8.09 (2/2*1H, m), 8.14-8.16 (1/2*1H, m), 8.19 (1/2*1H, s), 8.39-8.41 (1/2*1H, m), 8.45-8.46 (1/2*1H, m).

64-3

Preparation of 3-amino-N-(2-bromo-4-(perfluoropropan-2-yl)-6-(trifluoromethyl)phenyl)-N-methylbenzamide (Compound No. 12-107)

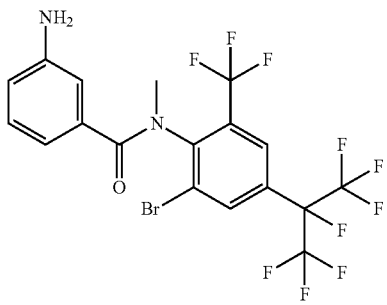

According to the method of 1-3 of Example 1, a target compound was prepared from N-(2-bromo-4-(perfluoropropan-2-yl)-6-(trifluoromethyl)phenyl)-N-methyl-3-nitrobenzamide.

¹H-NMR (CDCl₃, ppm) δ 3.24 (3/4*3 H, s), 3.37 (1/4*3 H, s), 3.80 (2H, broad-s), 6.47 (1/4*1H, d, J=7.8 Hz), 6.54-6.57 (1/4*1H, m), 6.78-6.84 (5/4*1H, m), 6.86 (3/4*1H, t, J=2.0 Hz), 6.96 (3/4*1H, d, J=7.8 Hz), 7.23-7.27 (3/4*1H, m), 7.79 (1/4*1H, s), 7.94 (3/4*1H, s), 8.00 (1/4*1H, s), 8.15 (3/4*1H, s).

Example 65

Preparation of 3-amino-N-(2-bromo-4-(perfluoroethyl)-6-(trifluoromethyl)phenyl)benzamide (Compound No. 12-5)

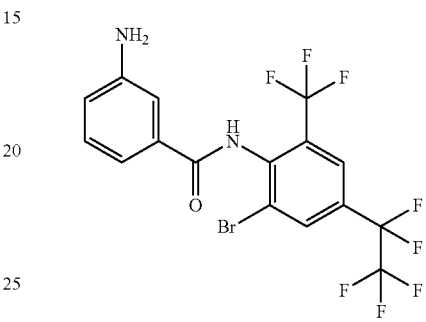

65-1

Preparation of 4-(perfluoroethyl)-2-(trifluoromethyl)aniline (Compound No. 21-1)

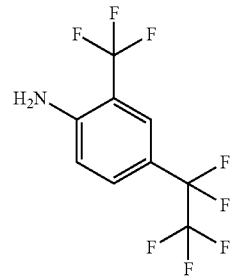 [SMILES: Nc1ccc(C(F)(F)C(F)(F)F)cc1C(F)(F)F]

To 40 ml of an aqueous solution of 7.04 g (40.4 mmol) of 85% sodium hydrosulfite and 3.40 g (40.4 mmol) of sodium hydrogen carbonate were added 13.6 g (33.7 mmol) of 2-(trifluoromethyl)aniline and 40 ml of DMF. To this reaction liquid was added 50 ml of a solution of 11.2 g (45.5 mmol) of 1,1,2,2,2-pentafluoroethyl iodide in DMF (DMF was cooled to −30° C., and 1,1,2,2,2-pentafluoroethyl iodide was dissolved therein), and charged to an autoclave, followed by stirring at 110° C. for 9 hours. After leaving to stand at room temperature overnight, water and ethyl acetate were added to the reaction mixture, followed by extraction with ethyl acetate. The organic layer was washed with water, a saturated aqueous sodium hydrogen carbonate solution, and saturated brine. The organic layer was dried over anhydrous sodium sulfate, then the solvent was evaporated under reduced pressure, and the obtained residue was purified by silica gel column chromatography (developing solvent; hexane:ethyl acetate=10:1→5:1) to prepare 1.95 g (yield 21%) of a target compound.

¹H-NMR (CDCl₃, ppm) δ 4.53 (2H, broad-s), 6.81 (1H, d, J=8.3 Hz), 7.48 (1H, d, J=8.3 Hz), 7.63 (1H, broad-s).

65-2

Preparation of 2-bromo-4-(perfluoroethyl)-6-(trifluoromethyl)aniline (Compound No. 21-6)

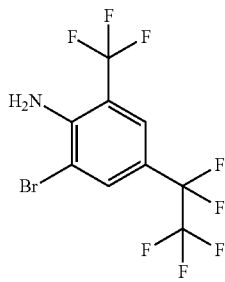 [SMILES: Nc1c(Br)cc(C(F)(F)C(F)(F)F)cc1C(F)(F)F]

According to the method of 22-2 of Example 22, a target compound was prepared from 4-(perfluoroethyl)-2-(trifluoromethyl)aniline.

¹H-NMR (CDCl₃, ppm) δ 5.08 (2H, broad-s), 7.62 (1H, s), 7.80 (1H, s).

65-3

Preparation of N-(2-bromo-4-(perfluoroethyl)-6-(trifluoromethyl)phenyl)-3-nitrobenzamide (Compound No. 11-8)

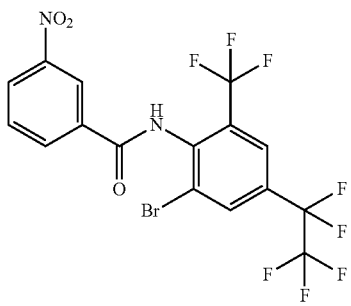 [SMILES: O=C(Nc1c(Br)cc(C(F)(F)C(F)(F)F)cc1C(F)(F)F)c1cccc([N+](=O)[O-])c1]

To a solution of 2.50 g (6.99 mmol) of 2-bromo-4-(perfluoroethyl)-6-(trifluoromethyl)aniline in 20 ml of pyridine was added 2.72 g (14.7 mmol) of 3-nitrobenzoyl chloride, followed by stirring at 100° C. for 12 hours. To the reaction liquid were added water and ethyl acetate, followed by extraction with ethyl acetate. The organic layer was washed with 1 M hydrochloric acid, a saturated aqueous sodium hydrogen carbonate solution, and saturated brine. The organic layer was dried over anhydrous sodium sulfate, and then the solvent was evaporated under reduced pressure. To the obtained residue were added THF and an aqueous sodium hydroxide solution, followed by stirring at room temperature for 8 hours. The reaction liquid was extracted/dried in the manner as described above, and the solvent was evaporated under reduced pressure. The obtained residue was purified by silica gel column chromatography (developing solvent; hexane:ethyl acetate=7:1→5:1) to prepare 0.202 g (yield 6%) of a target compound.

¹H-NMR (CDCl₃, ppm) δ 7.75 (1H, s), 7.78 (1H, t, J=7.8 Hz), 7.94 (1H, s), 8.17 (1H, s), 8.29-8.30 (1H, m), 8.50-8.52 (1H, m), 8.78 (1H, t, J=2.0 Hz).

65-4

Preparation of 3-amino-N-(2-bromo-4-(perfluoroethyl)-6-(trifluoromethyl)phenyl)benzamide (Compound No. 12-5)

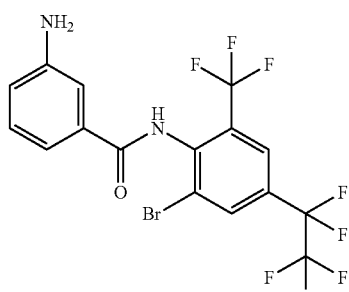

According to the method of 1-3 of Example 1, a target compound was prepared from N-(2-bromo-4-(perfluoroethyl)-6-(trifluoromethyl)phenyl)-3-nitrobenzamide.

¹H-NMR (CDCl₃, ppm) δ 3.89 (2H, broad-s), 6.90-6.92 (1H, m), 7.23-7.32 (3H, m), 7.64 (1H, s), 7.90 (1H, s), 8.13 (1H, s).

Example 66

Preparation of 3-amino-N-(2-bromo-4-(perfluoropropan-2-yl)-6-(trifluoromethyl)phenyl)-4-cyanobenzamide (Compound No. 12-79)

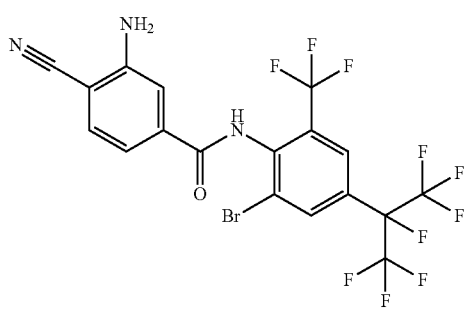 [SMILES: N#Cc1ccc(C(=O)Nc2c(Br)cc(C(F)(C(F)(F)F)C(F)(F)F)cc2C(F)(F)F)cc1N]

66-1

Preparation of N-(2-bromo-4-(perfluoropropan-2-yl)-6-(trifluoromethyl)phenyl)-4-cyano-3-nitrobenzamide (Compound No. 11-122)

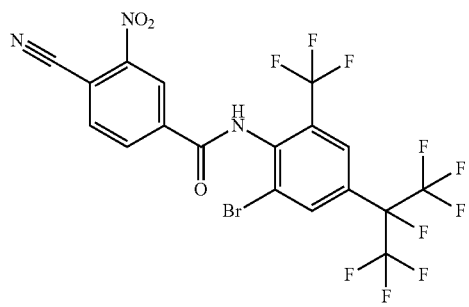

To a solution of 0.500 g (0.870 mmol) of N-(2-bromo-4-(perfluoropropan-2-yl)-6-(trifluoromethyl)phenyl)-4-fluoro-3-nitrobenzamide obtained in 62-1 of Example 62 in 5 ml of DMF was added 0.0639 g (1.31 mmol) of sodium cyanide, followed by stirring at room temperature for 10 hours. To the reaction liquid were added water and ethyl acetate, followed by extraction with ethyl acetate. The organic layer was washed with a 10% aqueous sodium hydroxide solution and saturated brine. The organic layer was dried over anhydrous sodium sulfate, and then the solvent was evaporated under reduced pressure. The obtained residue was purified by silica gel column chromatography to prepare 0.0500 g (yield 10%) of a target compound.

$^1$H-NMR (CDCl$_3$, ppm) δ 7.80 (1H, s), 7.96 (1H, s), 8.12-8.14 (1H, m), 8.18 (1H, s), 8.36 (1H, dd, J=2.0, 8.3 Hz), 8.84 (1H, d, J=1.5 Hz).

66-2

Preparation of 3-amino-N-(2-bromo-4-(perfluoropropan-2-yl)-6-(trifluoromethyl)phenyl)-4-cyanobenzamide (Compound No. 12-79)

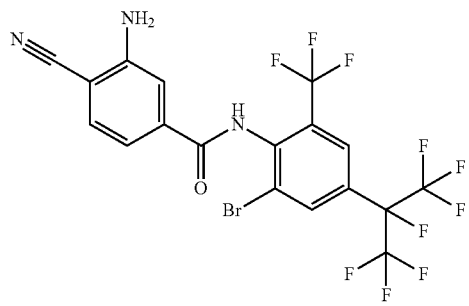 [SMILES: N#Cc1ccc(C(=O)Nc2c(Br)cc(C(F)(C(F)(F)F)C(F)(F)F)cc2C(F)(F)F)cc1[N+](=O)[O-]]

According to the method of 1-3 of Example 1, a target compound was prepared from N-(2-bromo-4-(perfluoropropan-2-yl)-6-(trifluoromethyl)phenyl)-4-cyano-3-nitrobenzamide.

$^1$H-NMR (CDCl$_3$, ppm) δ 4.68 (2H, broad-s), 7.18 (1H, dd, J=1.9, 8.3 Hz), 7.29 (1H, s), 7.52-7.55 (1H, m), 7.68 (1H, s), 7.92 (1H, s), 8.14 (1H, d, J=1.5 Hz).

Next, Preparation Examples in which the compound according to the present invention is contained as an active ingredient will be shown, but the present invention is not limited thereto. Further, in Preparation Examples, parts represent parts by weight.

Preparation Example 1

20 parts of the compound represented by the Formula (1) according to the present invention, 10 parts of polyoxyethylene styrylphenyl ether, and 70 parts of xylene were mixed uniformly to obtain an emulsion.

Preparation Example 2

10 parts of the compound represented by the Formula (1) according to the present invention, 2 parts of sodium lauryl sulfate, 2 parts of dialkyl sulfosuccinate, 1 part of a β-naphthalene sulfonic acid formalin condensate sodium salt, and 85 parts of diatomaceous earth were stirred and mixed uniformly to obtain wettable powders.

Preparation Example 3

0.3 parts of the compound represented by the Formula (1) according to the present invention and 0.3 parts of white carbon were mixed uniformly, and 99.2 parts of clay and 0.2 parts of DRILESS A (manufactured by Sankyo Agro Co., Ltd.) were added thereto, followed by pulverizing and mixing uniformly, thereby obtaining dustable powders.

Preparation Example 4

3 parts of the compound represented by the Formula (1) according to the present invention, 1.5 parts of a polyoxyethylene/polyoxypropylene condensate, 3 parts of carboxymethyl cellulose, 64.8 parts of clay, and 27.7 parts of talc were pulverized and mixed uniformly, and water was added thereto, followed by kneading, granulating, and drying, thereby obtaining granules.

Preparation Example 5

10 parts of the compound represented by the Formula (1) according to the present invention, 3 parts of a β-naphthalene sulfonic acid formalin condensate sodium salt, 1 part of tristyrylphenol, 5 parts of propylene glycol, 0.5 parts of a silicon-based defoaming agent, and 33.5 parts of water were sufficiently stirred and mixed, and then 0.3 parts of xanthan gum and 46.7 parts of water were mixed therewith, followed by stirring and mixing again, thereby obtaining a flowable Formulation.

Preparation Example 6

20 parts of the compound represented by the Formula (1) according to the present invention, 6 parts of a naphthalene sulfonic acid formaldehyde condensate metal salt, 1 part of dialkylsulfosuccinate metal salt, and 73 parts of calcium carbonate were pulverized and mixed uniformly, and water was added thereto, followed by kneading, granulating, and drying, thereby obtaining water dispersible granules.

Furthermore, Test Examples are shown below in order to clarify that the compound represented by the Formula (1) according to the present invention has an excellent pesticidal activity, but the present invention is not limited thereto.

Test Example 1

Pesticidal Test Against *Spodoptera litura*

A piece of a cabbage leaf was immersed for 30 seconds in a chemical solution in which a test compound had been diluted at a predetermined concentration, and air-dried, and then put into a 7 cm polyethylene cup having a filter paper laid on the bottom thereof, and 2-stage larvae of *Spodoptera litura* were released. They were left to stand in a thermostatic chamber at 25° C., and the numbers of the living pests and the dead pests were examined after 6 days. The test was carried out with five larvae per group in two replicates.

As a result, the compounds of the following Compound Nos. showed a pesticidal rate of 70% or more at 100 ppm.

1-1, 1-16, 1-21, 1-36, 1-62, 1-63, 1-64, 1-65, 1-82, 1-95, 1-96, 1-99, 1-100, 1-101, 1-103, 1-104, 1-105, 1-115, 1-116, 1-117, 1-118, 1-132, 1-133, 1-134, 1-136, 1-137, 1-138, 1-139, 1-151, 1-152, 1-154, 1-163, 1-164, 1-167, 1-168, 1-169, 1-171, 1-172, 1-173, 1-175, 1-176, 1-177, 1-179, 1-180, 1-183, 1-184, 1-185, 1-187, 1-188, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-220, 1-221, 1-222, 1-223, 1-224, 1-225, 1-226, 1-227, 1-231, 1-232, 1-233, 1-234, 1-235, 1-236, 1-237, 1-239, 1-241, 1-242, 2-133, 3-133, 3-163, 3-164, 3-197, 5-1, 5-8, 5-10, 5-11, 5-12, 5-14, 5-15, 5-16, 5-17, 5-18, 5-19, 5-20, 5-21, 5-22, 5-25, 5-27, 5-29, 5-31, 5-32, 5-33, 5-34, 5-35, 5-36, 5-37, 5-71, 5-72, 5-73, 5-76, 5-77, 5-78, 5-79, 5-80, 5-81, 5-82, 5-83, 5-84, 5-86, 5-87, 5-88, 5-89, 5-91, 5-92, 5-93, 5-94, 5-95, 5-96, 5-98, 5-99, 5-100, 5-101, 5-102, 5-103, 5-104, 5-105, 5-107, 5-108, 5-109, 5-111, 5-112, 5-128, 6-1, 6-5, 6-6, 6-7, 6-8, 6-9, 6-10, 6-12, 6-15, 6-16, 6-18, 6-20, 6-43, 6-44, 6-45, 6-49, 6-53, 6-55, 6-59, 6-61, 6-62, 6-64, 6-68, 6-69, 7-1, 7-220, 7-221, 7-222, 7-226, 8-12, 9-12

Test Example 2

Pesticidal Test Against *Plutella xylostella*

A piece of a cabbage leaf was immersed for 30 seconds in a chemical solution in which a test compound had been diluted at a predetermined concentration, and air-dried, and then put into a 7 cm polyethylene cup having a filter paper laid on the bottom thereof, and 3-stage larvae of *Plutella xylostella* were released. They were left to stand in a thermostatic chamber at 25° C., and the numbers of the living pests and the dead pests were examined after 6 days. The test was carried out with five larvae per group in two replicates.

As a result, the compounds of the following Compound Nos. showed a pesticidal rate of 70% or more at 100 ppm.

1-1, 1-16, 1-21, 1-36, 1-62, 1-63, 1-64, 1-65, 1-82, 1-95, 1-96, 1-99, 1-100, 1-101, 1-103, 1-104, 1-105, 1-115, 1-116, 1-117, 1-118, 1-132, 1-133, 1-134, 1-136, 1-137, 1-138, 1-139, 1-151, 1-152, 1-154, 1-163, 1-164, 1-167, 1-168, 1-169, 1-171, 1-172, 1-173, 1-175, 1-176, 1-177, 1-179, 1-180, 1-183, 1-184, 1-185, 1-187, 1-188, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-220, 1-221, 1-222, 1-223, 1-224, 1-225, 1-226, 1-227, 1-231, 1-232, 1-233, 1-234, 1-235, 1-236, 1-237, 1-238, 1-239, 1-240, 1-241, 1-242, 2-133, 3-133, 3-163, 3-164, 3-197, 5-1, 5-4, 5-8, 5-10, 5-11, 5-12, 5-14, 5-15, 5-16, 5-17, 5-18, 5-19, 5-20, 5-21, 5-22, 5-25, 5-27, 5-29, 5-30, 5-31, 5-32, 5-33, 5-34, 5-35, 5-36, 5-37, 5-71, 5-72, 5-73, 5-76, 5-77, 5-78, 5-79, 5-80, 5-81, 5-82, 5-83, 5-84, 5-85, 5-86, 5-87, 5-88, 5-89, 5-90, 5-91, 5-92, 5-93, 5-94, 5-95, 5-96, 5-97, 5-98, 5-99, 5-100, 5-101, 5-102, 5-103, 5-104, 5-105, 5-107, 5-108, 5-109, 5-111, 5-112, 5-128, 6-1, 6-5, 6-6, 6-7, 6-8, 6-9, 6-10, 6-12, 6-13, 6-15, 6-16, 6-18, 6-20, 6-43, 6-44, 6-45, 6-46, 6-47, 6-49, 6-50, 6-52, 6-53, 6-55, 6-56, 6-57, 6-58, 6-59, 6-60, 6-64, 6-68, 6-69, 7-1, 7-6, 7-22, 7-23, 7-169, 7-220, 7-221, 7-222, 7-226, 8-12, 8-13, 9-12

Test Example 3

Pesticidal Test of Penetration Migration against *Spodoptera litura*

A root portion of a radish seedling was immersed for 2 days in a chemical solution in which a test compound had been diluted at a predetermined concentration, then the leaf was cut and put into a 7 cm polyethylene cup having a filter paper laid on the bottom thereof, and 2-stage larvae of *Spodoptera litura* were released. They were left to stand in a thermostatic chamber at 25° C., and the numbers of the living pests and the dead pests were examined after 3 days. The test was carried out with five larvae per group in two replicates.

As a result, the compounds of the following Compound Nos. showed a pesticidal rate of 70% or more at 1 ppm.

1-16, 1-21, 1-36, 1-62, 1-63, 1-64, 1-65, 1-82, 1-95, 1-96, 1-97, 1-99, 1-100, 1-101, 1-103, 1-104, 1-105, 1-115, 1-116, 1-117, 1-118, 1-132, 1-133, 1-134, 1-136, 1-137, 1-138, 1-139, 1-151, 1-152, 1-154, 1-163, 1-164, 1-167, 1-168, 1-169, 1-171, 1-172, 1-173, 1-175, 1-176, 1-177, 1-179, 1-180, 1-184, 1-185, 1-187, 1-188, 1-195, 1-196, 1-197, 1-198, 1-199, 1-202, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-225, 1-226, 1-227, 1-231, 1-232, 1-233, 1-234, 1-235, 1-236, 1-241, 1-242, 2-133, 3-133, 3-163, 3-164, 3-197, 5-33, 5-34, 5-76, 5-77, 5-78, 5-79, 5-82, 5-86, 5-92, 5-96, 5-99, 5-101, 5-103, 5-104

Test Example 4

Pesticidal Test Against *Musca domestica*

1 ml of an acetone solution in which a test compound had been diluted at a predetermined concentration was added dropwise to a petri dish having a diameter of 9 cm, and air-dried, and then the female adults of *Musca domestica* were released and the petri dish was capped. They were left to stand in a thermostatic chamber at 25° C., and the numbers of the living pests and the dead pests were examined after 1 day. The test was carried out with five larvae per group in two replicates.

As a result, the compounds of the following Compound Nos. showed a pesticidal rate of 70% or more at 1000 ppm.

1-65, 1-82, 1-104, 1-116, 1-117, 1-118, 1-136, 1-151, 1-152, 1-175, 1-176, 1-177, 1-183, 1-184, 1-187, 1-195, 1-220, 1-221, 1-222, 1-234, 1-235, 1-239, 1-241, 1-242, 5-8, 5-76, 5-77, 5-78, 5-79, 5-80, 5-81, 5-82, 5-86, 5-87, 5-89, 5-92, 5-93, 5-95, 5-96, 5-99, 5-100, 5-101, 5-104, 5-105, 5-112, 6-16, 6-43, 6-44, 6-45, 6-54, 6-55

Test Example 5

Pesticidal Test against *Blattella germanica*

1 ml of an acetone solution in which a test compound had been diluted at a predetermined concentration was added dropwise to a petri dish having a diameter of 9 cm, and air-dried, and then the male adults of *Blattella germanica* were released and the petri dish was capped. They were left to stand in a thermostatic chamber at 25° C., and the numbers of the living pests and the dead pests were examined after 1 day. The test was carried out with five larvae per group in two replicates.

As a result, the compounds of the following Compound Nos. showed a pesticidal rate of 70% or more at 1000 ppm.
1-118, 1-133, 1-136, 1-152, 1-168, 1-171, 1-183, 1-196, 1-221, 1-223, 1-225, 1-232, 6-53

Test Example 6

Pesticidal Test Against *Culexpipiens molestus*

1 ml of an acetone solution in which a test compound had been diluted at a predetermined concentration was added dropwise to a petri dish having a diameter of 9 cm, and air-dried, and then the adults of *Culexpipiens molestus* were released and the petri dish was capped. They were left to stand in a thermostatic chamber at 25° C., and the numbers of the living pests and the dead pests were examined after 1 day of treatment. The test was carried out with five larvae per group in two replicates.

As a result, the compound of the following Compound No. showed a pesticidal rate of 70% or more at 1000 ppm.
1-136

Test Example 7

Pesticidal Test Against *Coplolermes formosanus*

20 µl of an acetone solution in which a test compound had been prepared at a predetermined concentration was added dropwise to the filter paper having a diameter of 2.6 mm included in a polypropylene tube, and air-dried, and then 20 µl of water was added thereto. *Coptotermes formosanus* was released and the tube was capped. They were left to stand in a thermostatic chamber at 28° C., and the numbers of the living pests and the dead pests were examined after 5 days of treatment. The test was carried out with ten larvae per group in two replicates.

As a result, the compounds of the following Compound Nos. showed a pesticidal rate of 70% or more at 30 ppm.
1-136

Industrial Applicability

According to the present invention, it became possible to provide a novel amide derivative. The amide derivative shows a significant effect for a pest control activity, and has a high industrial applicability.

The invention claimed is:
1. A compound represented by the following Formula (6d):

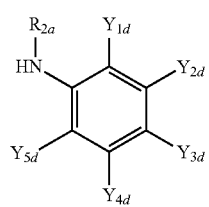

Formula (6d)

wherein $Y_{5d}$ represents a C1-C3 haloalkyl group;
$Y_{1d}$ represents a hydrogen atom, a halogen atom, a C1-C4 haloalkyl group, a C1-C4 haloalkoxy group, or a C1-C4 haloalkylsulfinyl group;
$Y_{3d}$ represents a C2-C6 haloalkyl group;
$Y_{2d}$ and $Y_{4d}$ each independently represent a hydrogen atom, a halogen atom, or a C1-C4 alkyl group;
$R_{2a}$ represents a hydrogen atom or a C1-C4 alkyl group; and
in a case where $Y_{1d}$ represents a hydrogen atom, $R_{2a}$ represents a C1-C4 alkyl group.

2. A compound represented by the following Formula (6a):

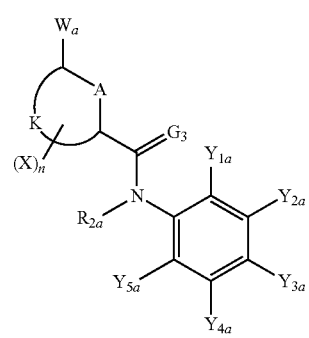

Formula (6a)

wherein
A represents a carbon atom, an oxygen atom, a nitrogen atom, an oxidized nitrogen atom or a sulfur atom;
K represents a non-metal atom group necessary for forming a cyclic linking group derived from benzene, pyridine, pyridine-N-oxide or thiazole, in combination with A and two carbon atoms to which A bonds;
X represents a hydrogen atom or a halogen atom, and when there are two or more X's, each X may be the same as or different from each other;
n represents an integer of from 0 to 4;
$G_3$ represents an oxygen atom or a sulfur atom;
$R_{2a}$ represents a hydrogen atom, a C1-C4 alkyl group, or a group represented by -L-D;
wherein, L represents —C($M_1$)($M_2$)-, —C($M_1$)($M_2$)-C($M_3$)($M_4$)-, —C($M_1$)($M_2$)-C($M_3$)($M_4$)-C($M_5$)($M_6$)-, or —C($M_1$)($M_2$)-C($M_3$)($M_4$)-C($M_5$)($M_6$)-C($M_7$)($M_8$)-;
$M_1$ to $M_8$ each independently represent a hydrogen atom, a halogen atom, a cyano group, a carboxy group, a hydroxy group, a carbamoyl group, or a C1-C4 alkyl group which may have a substituent;
D represents —C(=O)O$U_1$, —C(=O)$U_2$, —C(=O)N$U_3U_4$, —N$U_5$C(=O)$U_6$, —S—$U_7$, —S(=O)$U_8$, —S(=O)(=O)$U_9$, —S(=O)(=O)N$U_{10}U_{11}$, —O$U_{12}$, —N$U_{13}U_{14}$, —C(=N$U_{15}$)$U_{16}$, —N$U_{17}$—C(=N$U_{18}$)$U_{19}$, or —C≡N;
$U_1$ to $U_{19}$ each independently represent a hydrogen atom, a hydroxy group, an amino group, a cyano group, a nitro group, a C1-C6 alkyl group which may have a substituent, a C2-C7 alkoxycarbonyl group, a C2-C7 haloalkoxycarbonyl group, a C2-C7 alkylcarbonyl group, a C1-C3 alkylamino group, a phenyl group, or a heterocyclic group;
wherein $U_3$ and $U_4$, $U_5$ and $U_6$, $U_{10}$ and $U_{11}$, $U_{12}$ and L, $U_{13}$ and $U_{14}$, $U_{15}$ and $U_{16}$, and from $U_{17}$ to $U_{19}$ may be linked with each other to form a saturated heterocyclic group;
$W_a$ represents a nitro group, an amino group, or —NH—$R_{1a}$;

$R_{1a}$ represents a hydrogen atom, a C1-C4 alkyl group, or a group represented by -L-D, wherein L and D have the same definitions as L and D, respectively, in $R_{2a}$;

at least one of $R_{1a}$ and $R_{2a}$ represents a group represented by -L-D;

$Y_{1a}$ and $Y_{5a}$ each independently represent a halogen atom, a C1-C6 haloalkoxy group, or a C1-C3 haloalkyl group;

in a case where K forms a benzene ring together with A and two carbon atoms to which A bonds, all X's represent hydrogen atoms, $R_{2a}$ represents a hydrogen atom, and $Y_{3a}$ represents a C3 perfluoroalkyl group, $Y_{5a}$ represents a C1-C3 haloalkyl group;

$Y_{2a}$ and $Y_{4a}$ each independently represent a hydrogen atom, a halogen atom, or a C1-C4 alkyl group; and $Y_{3a}$ represents a C2-C5 haloalkyl group.

3. A compound represented by the following Formula (6c):

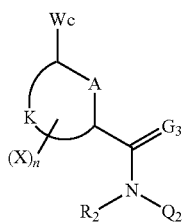

Formula (6c)

wherein A represents a carbon atom, an oxygen atom, a nitrogen atom, an oxidized nitrogen atom or a sulfur atom;

K represents a non-metal atom group necessary for forming a cyclic linking group derived from benzene, pyridine, pyridine-N-oxide or thiazole, in combination with A and two carbon atoms to which A bonds;

X represents a hydrogen atom or a halogen atom, and when there are two or more X's, each X may be the same as or different from each other;

n represents an integer of from 0 to 3;

$G_3$ represents an oxygen atom or a sulfur atom;

$R_2$ represents a hydrogen atom, a C1-C4 alkyl group, or a group represented by -L-D;

wherein L represents —C($M_1$)($M_2$)-, —C($M_1$)($M_2$)C($M_3$)($M_4$)-, —C($M_1$)($M_2$)-C($M_3$)($M_4$)-C($M_5$)($M_6$)-, or —C($M_1$)($M_2$)-C($M_3$)($M_4$)-C($M_5$)($M_6$)-C($M_7$)($M_8$)-;

$M_1$ to $M_8$ each independently represent a hydrogen atom, a halogen atom, a cyano group, a carboxy group, a hydroxy group, a carbamoyl group, or a C1-C4 alkyl group which may have a substituent;

D represents —C(=O)O$U_1$, —C(=O)$U_2$, —C(=O)N$U_3U_4$, —N$U_5$C(=O)$U_6$, —S—$U_7$, —S(=O)$U_8$, —S(=O)(=O)$U_9$, —S(=O)(=O)N$U_{10}U_{11}$, —O$U_{12}$, —N$U_{13}U_{14}$, —C(=N$U_{15}$)$U_{16}$, —N$U_{17}$—C(=N$U_{18}$)$U_{19}$, or —C≡N;

$U_1$ to $U_{19}$ each independently represent a hydrogen atom, a hydroxy group, an amino group, a cyano group, a nitro group, a C1-C6 alkyl group which may have a substituent, a C2-C7 alkoxycarbonyl group, a C2-C7 haloalkoxycarbonyl group, a C2-C7 alkylcarbonyl group, a C1-C3 alkylamino group, a phenyl group, or a heterocyclic group;

wherein $U_3$ and $U_4$, $U_5$ and $U_6$, $U_{10}$ and $U_{11}$, $U_{12}$ and L, $U_{13}$ and $U_{14}$, $U_{15}$ and $U_{16}$, and $U_{17}$ to $U_{19}$ may be linked with each other to form a saturated heterocyclic group;

$Q_2$ represents a phenyl group which may have a substituent or a heterocyclic group which may have a substituent;

the substituent of a phenyl group which may have a substituent and a heterocyclic group which may have a substituent represents one or more substituents selected from a group consisting of:

a halogen atom, a C1-C6 alkyl group, a C1-C6 haloalkyl group, a C1-C6 haloalkoxy group, a C1-C6 haloalkylthio group, a C1-C6 haloalkylsulfinyl group, and a C1-C6 haloalkylsulfonyl group, and when there are two or more substituents, the substituents may be the same as or different from each other, Wc represents —NH—C($M_1$)($M_2$)-C($M_3$)($M_4$)-D;

$M_1$, $M_2$, $M_3$, $M_4$, and D have the same definitions as $M_1$, $M_2$, $M_3$, $M_4$, and D, respectively, in $R_2$.

* * * * *